United States Patent
Seo et al.

(10) Patent No.: US 11,950,497 B2
(45) Date of Patent: Apr. 2, 2024

(54) LIGHT-EMITTING ELEMENT, DISPLAY DEVICE, ELECTRONIC DEVICE, ORGANIC COMPOUND, AND LIGHTING DEVICE

(71) Applicant: SEMICONDUCTOR ENERGY LABORATORY CO., LTD., Atsugi (JP)

(72) Inventors: Satoshi Seo, Kanagawa (JP); Nobuharu Ohsawa, Kanagawa (JP); Takuya Haruyama, Kanagawa (JP); Anna Tada, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 615 days.

(21) Appl. No.: 16/977,612

(22) PCT Filed: Feb. 21, 2019

(86) PCT No.: PCT/IB2019/051403
§ 371 (c)(1),
(2) Date: Sep. 2, 2020

(87) PCT Pub. No.: WO2019/171197
PCT Pub. Date: Sep. 12, 2019

(65) Prior Publication Data
US 2021/0043840 A1    Feb. 11, 2021

(30) Foreign Application Priority Data

Mar. 7, 2018 (JP) ................. 2018-040387
Jul. 11, 2018 (JP) ................. 2018-131250
Nov. 30, 2018 (JP) ................. 2018-224768

(51) Int. Cl.
*H10K 85/60* (2023.01)
*C07C 211/61* (2006.01)
(Continued)

(52) U.S. Cl.
CPC .......... *H10K 85/633* (2023.02); *C07C 211/61* (2013.01); *C07F 7/081* (2013.01);
(Continued)

(58) Field of Classification Search
CPC .... H10K 85/633; H10K 85/40; H10K 85/791; H10K 50/11; H10K 59/1213;
(Continued)

(56) References Cited

U.S. PATENT DOCUMENTS

| | | |
|---|---|---|
| 5,759,444 A | 6/1998 | Enokida et al. |
| 6,376,107 B1 | 4/2002 | Heuer et al. |

(Continued)

FOREIGN PATENT DOCUMENTS

| | | |
|---|---|---|
| CN | 101142169 A | 3/2008 |
| CN | 105514288 A | 4/2016 |

(Continued)

OTHER PUBLICATIONS

Figueira-Duarte, T. M., & Mullen, K. (2011). Pyrene-based materials for organic electronics. Chemical reviews, 111(11), 7260-7314. (Year: 2011).*

(Continued)

*Primary Examiner* — Dawn L Garrett
(74) *Attorney, Agent, or Firm* — Fish & Richardson P.C.

(57) ABSTRACT

A light-emitting element with high emission efficiency and high reliability is provided.
The light-emitting element includes a host material and a guest material in a light-emitting layer. The host material has a function of converting triplet excitation energy into light emission and the guest material emits fluorescence. The molecular structure of the guest material is a structure including a luminophore and protecting groups, and five or more protecting groups are included in one molecule of the guest material. The introduction of the protecting groups (Continued)

into the molecule inhibits energy transfer of triplet excitation energy by the Dexter mechanism from the host material to the guest material. As the protecting group, an alkyl group or a branched-chain alkyl group is used.

30 Claims, 167 Drawing Sheets

(51) Int. Cl.
  *C07F 7/08* (2006.01)
  *C09K 11/06* (2006.01)
  *H10K 50/11* (2023.01)
  *H10K 59/121* (2023.01)
  *H10K 85/00* (2023.01)
  *H10K 85/40* (2023.01)
  *H10K 101/00* (2023.01)
  *H10K 101/10* (2023.01)
  *H10K 101/20* (2023.01)

(52) U.S. Cl.
  CPC .............. *C09K 11/06* (2013.01); *H10K 85/40* (2023.02); *H10K 85/791* (2023.02); *C07C 2601/14* (2017.05); *C07C 2603/24* (2017.05); *C09K 2211/1007* (2013.01); *C09K 2211/1011* (2013.01); *C09K 2211/1014* (2013.01); *H10K 50/11* (2023.02); *H10K 59/1213* (2023.02); *H10K 85/615* (2023.02); *H10K 2101/10* (2023.02); *H10K 2101/20* (2023.02); *H10K 2101/27* (2023.02)

(58) Field of Classification Search
  CPC ............. H10K 85/615; H10K 2101/10; H10K 2101/20; H10K 2101/27; H10K 85/657; H10K 59/00; H10K 85/631; C07C 211/61; C07C 2601/14; C07C 2603/24; C07F 7/081; C07F 7/0805; C07F 7/10; C09K 11/06; C09K 2211/1007; C09K 2211/1011; C09K 2211/1014; Y02P 20/55; C07D 471/04; G02B 5/20; H05B 33/20
  See application file for complete search history.

(56) References Cited

U.S. PATENT DOCUMENTS

| | | | |
|---|---|---|---|
| 6,863,997 B2 | 3/2005 | Thompson et al. |
| 6,869,695 B2 | 3/2005 | Thompson et al. |
| 6,951,694 B2 | 10/2005 | Thompson. et al. |
| 7,175,922 B2 | 2/2007 | Jarikov et al. |
| 7,183,010 B2 | 2/2007 | Jarikov |
| 7,332,857 B2 | 2/2008 | Seo et al. |
| 7,553,557 B2 | 6/2009 | Thompson et al. |
| 7,572,522 B2 | 8/2009 | Seo et al. |
| 7,597,967 B2 | 10/2009 | Kondakova et al. |
| 7,816,017 B2 | 10/2010 | Funahashi et al. |
| 7,943,925 B2 | 5/2011 | Yamazaki |
| 7,993,760 B2 | 8/2011 | Komori et al. |
| 8,034,465 B2 | 10/2011 | Liao et al. |
| 8,058,478 B2 | 11/2011 | Funahashi et al. |
| 8,247,086 B2 | 8/2012 | Inoue et al. |
| 8,274,214 B2 | 9/2012 | Ikeda et al. |
| 8,476,823 B2 | 7/2013 | Kuma et al. |
| 8,729,310 B2 | 5/2014 | Osaka et al. |
| 8,766,249 B2 | 7/2014 | Sawada et al. |
| 8,803,134 B2 | 8/2014 | Inoue et al. |
| 8,853,680 B2 | 10/2014 | Yamazaki et al. |
| 8,963,127 B2 | 2/2015 | Pieh et al. |
| 8,981,355 B2 | 3/2015 | Seo |
| 8,993,129 B2 | 3/2015 | Endo et al. |
| 8,994,263 B2 | 3/2015 | Shitagaki et al. |
| 9,054,317 B2 | 6/2015 | Monkman et al. |
| 9,159,942 B2 | 10/2015 | Seo et al. |
| 9,175,213 B2 | 11/2015 | Seo et al. |
| 9,356,250 B2 | 5/2016 | Ohsawa et al. |
| 9,362,517 B2 | 6/2016 | Ohsawa et al. |
| 9,515,279 B2 | 12/2016 | Ishisone et al. |
| 9,604,928 B2 | 3/2017 | Shitagaki et al. |
| 9,634,279 B2 | 4/2017 | Seo et al. |
| 10,347,851 B2 | 7/2019 | Lennartz et al. |
| 10,367,160 B2 | 7/2019 | Seo et al. |
| 10,439,005 B2 | 10/2019 | Ishisone et al. |
| 2003/0175553 A1 | 9/2003 | Thompson et al. |
| 2004/0253478 A1 | 12/2004 | Thompson et al. |
| 2005/0048310 A1 | 3/2005 | Cocchi et al. |
| 2005/0221116 A1 | 10/2005 | Cocchi et al. |
| 2006/0134464 A1 | 6/2006 | Nariyuki |
| 2006/0186376 A1 | 8/2006 | Yamamoto et al. |
| 2006/0202190 A1 | 9/2006 | Funahashi |
| 2006/0210830 A1 | 9/2006 | Funahashi et al. |
| 2006/0228577 A1 | 10/2006 | Nagara |
| 2007/0007884 A1 | 1/2007 | Iwanaga et al. |
| 2007/0090756 A1 | 4/2007 | Okada et al. |
| 2007/0244320 A1 | 10/2007 | Inoue et al. |
| 2007/0252511 A1 | 11/2007 | Funahashi |
| 2008/0160345 A1 | 7/2008 | Inoue et al. |
| 2008/0286604 A1 | 11/2008 | Inoue et al. |
| 2009/0166563 A1 | 7/2009 | Yokoyama et al. |
| 2010/0052527 A1 | 3/2010 | Ikeda et al. |
| 2010/0145044 A1 | 6/2010 | Inoue et al. |
| 2010/0301318 A1 | 12/2010 | Kuma et al. |
| 2011/0001146 A1 | 1/2011 | Yamazaki et al. |
| 2011/0034733 A1 | 2/2011 | Funahashi et al. |
| 2011/0127503 A1 | 6/2011 | Takahashi et al. |
| 2011/0210316 A1 | 9/2011 | Kadoma et al. |
| 2011/0215714 A1 | 9/2011 | Seo et al. |
| 2012/0098417 A1 | 4/2012 | Inoue et al. |
| 2012/0205632 A1 | 8/2012 | Shitagaki et al. |
| 2012/0205687 A1 | 8/2012 | Yamazaki et al. |
| 2012/0206035 A1 | 8/2012 | Shitagaki et al. |
| 2012/0217486 A1 | 8/2012 | Takemura et al. |
| 2012/0217487 A1 | 8/2012 | Yamazaki et al. |
| 2012/0235127 A1 | 9/2012 | Takasu et al. |
| 2012/0242219 A1 | 9/2012 | Seo et al. |
| 2012/0248421 A1 | 10/2012 | Yamazaki et al. |
| 2012/0248968 A1 | 10/2012 | Ogiwara et al. |
| 2012/0256535 A1 | 10/2012 | Seo et al. |
| 2012/0263648 A1 | 10/2012 | Shapiro et al. |
| 2013/0048964 A1 | 2/2013 | Takeda et al. |
| 2013/0056720 A1 | 3/2013 | Kim et al. |
| 2013/0207088 A1 | 8/2013 | Seo |
| 2013/0270531 A1 | 10/2013 | Seo et al. |
| 2013/0277653 A1 | 10/2013 | Osaka et al. |
| 2013/0277655 A1 | 10/2013 | Seo et al. |
| 2013/0277656 A1 | 10/2013 | Seo et al. |
| 2013/0292656 A1 | 11/2013 | Seo et al. |
| 2013/0306945 A1 | 11/2013 | Seo |
| 2014/0014930 A1 | 1/2014 | Hirose et al. |
| 2014/0034925 A1 | 2/2014 | Osaka et al. |
| 2014/0034926 A1 | 2/2014 | Matsubara et al. |
| 2014/0034927 A1 | 2/2014 | Seo et al. |
| 2014/0034930 A1 | 2/2014 | Seo et al. |
| 2014/0034931 A1 | 2/2014 | Inoue et al. |
| 2014/0034932 A1 | 2/2014 | Seo et al. |
| 2014/0048784 A1 | 2/2014 | Inoue et al. |
| 2014/0061604 A1 | 3/2014 | Seo et al. |
| 2014/0103329 A1 | 4/2014 | Ogiwara et al. |
| 2014/0336379 A1 | 11/2014 | Adachi et al. |
| 2015/0069352 A1 | 3/2015 | Kim et al. |
| 2016/0028022 A1 | 1/2016 | Seo et al. |
| 2016/0056401 A1 | 2/2016 | Lee et al. |
| 2016/0064684 A1 | 3/2016 | Seo et al. |
| 2016/0093823 A1 | 3/2016 | Seo et al. |
| 2016/0104847 A1* | 4/2016 | Xia .................. H10K 85/346 252/301.16 |
| 2016/0104855 A1 | 4/2016 | Ohsawa et al. |
| 2016/0172602 A1* | 6/2016 | Ogiwara ................ C09K 11/06 252/301.16 |
| 2016/0172605 A1 | 6/2016 | Seo et al. |
| 2016/0190500 A1 | 6/2016 | Watabe et al. |

(56) References Cited

U.S. PATENT DOCUMENTS

| | | |
|---|---|---|
| 2016/0248031 A1 | 8/2016 | Seo |
| 2016/0248032 A1 | 8/2016 | Seo et al. |
| 2016/0268513 A1 | 9/2016 | Ishisone et al. |
| 2016/0268534 A1 | 9/2016 | Hosoumi et al. |
| 2016/0315274 A1 | 10/2016 | Lennartz et al. |
| 2016/0343949 A1 | 11/2016 | Seo et al. |
| 2016/0343954 A1 | 11/2016 | Seo et al. |
| 2016/0351833 A1 | 12/2016 | Hosoumi et al. |
| 2017/0012207 A1 | 1/2017 | Seo et al. |
| 2017/0133617 A1 | 5/2017 | Seo et al. |
| 2017/0271610 A1 | 9/2017 | Takahashi |
| 2017/0324054 A1 | 11/2017 | Ishisone et al. |
| 2017/0324055 A1 | 11/2017 | Ishisone et al. |
| 2019/0040314 A1 | 2/2019 | Ito et al. |
| 2019/0140027 A1 | 5/2019 | Ishisone et al. |
| 2019/0173038 A1 | 6/2019 | Seo et al. |
| 2019/0280236 A1 | 9/2019 | Tabata et al. |
| 2020/0044165 A1 | 2/2020 | Lennartz et al. |
| 2020/0083460 A1* | 3/2020 | Duan ................ H10K 85/6572 |
| 2021/0057667 A1 | 2/2021 | Ohsawa et al. |

FOREIGN PATENT DOCUMENTS

| | | |
|---|---|---|
| CN | 105993083 A | 10/2016 |
| EP | 1202608 A | 5/2002 |
| EP | 1860096 A | 11/2007 |
| EP | 2312667 A | 4/2011 |
| EP | 3084855 A | 10/2016 |
| JP | 2686418 | 12/1997 |
| JP | 2002-256168 A | 9/2002 |
| JP | 2005-514754 | 5/2005 |
| JP | 2006-256979 A | 9/2006 |
| JP | 2008-288344 A | 11/2008 |
| JP | 2011-213643 A | 10/2011 |
| JP | 2014-045179 A | 3/2014 |
| JP | 2016-027606 A | 2/2016 |
| JP | 2017-502516 | 1/2017 |
| KR | 2007-0110362 A | 11/2007 |
| KR | 2016-0043505 A | 4/2016 |
| KR | 2016-0100961 A | 8/2016 |
| TW | 200643138 | 12/2006 |
| TW | 201537801 | 10/2015 |
| WO | WO-2000/070655 | 11/2000 |
| WO | WO-2003/059015 | 7/2003 |
| WO | WO-2006/098080 | 9/2006 |
| WO | WO-2010/013780 | 2/2010 |
| WO | WO-2015/091716 | 6/2015 |
| WO | WO-2015/198988 | 12/2015 |
| WO | WO-2017/170812 | 10/2017 |
| WO | WO-2018/097153 | 5/2018 |

OTHER PUBLICATIONS

Kim, H. G., Kim, K. H., Moon, C. K., & Kim, J. J. (2017). Harnessing triplet excited states by fluorescent dopant utilizing codoped phosphorescent dopant in exciplex host for efficient fluorescent organic light emitting diodes. Advanced Optical Materials, 5(3), 1600749. (Year: 2017).*

Song, W., Lee, H. L., & Lee, J. Y. (2017). High triplet energy exciplex hosts for deep blue phosphorescent organic light-emitting diodes. Journal of Materials Chemistry C, 5(24), 5923-5929 (Year: 2017).*

Itano.K et al., "Exciplex formation at the organic solid-state interface: Yellow emission in organic light-emitting diodes using green-fluorescent tris(8-quinolinolato)aluminum and hole-transporting molecular materials with low ionization potentials", Appl. Phys. Lett. (Applied Physics Letters), Feb. 9, 1998, vol. 72, No. 6, pp. 636-638.

Endo.A et al., "Efficient Up-Conversion of Triplet Excitons Into a Singlet State and Its Application for Organic Light Emitting Diodes", Appl. Phys. Lett. (Applied Physics Letters), Feb. 24, 2011, vol. 98, No. 8, pp. 083302-1-083302-3.

Kondakova.M et al., "High-efficiency, low-voltage phosphorescent organic light-emitting diode devices with mixed host", J. Appl. Phys. (Journal of Applied Physics), Nov. 4, 2008, vol. 104, pp. 094501-1-094501-17.

Hino.Y et al., "Red Phosphorescent Organic Light-Emitting Diodes Using Mixture System of Small-Molecule and Polymer Host", Jpn. J. Appl. Phys. (Japanese Journal of Applied Physics), Apr. 21, 2005, vol. 44, No. 4B, pp. 2790-2794.

Su.S et al., "RGB Phosphorescent Organic Light-Emitting Diodes by Using Host Materials with Heterocyclic Cores:Effect of Nitrogen Atom Orientations", Chem. Mater. (Chemistry of Materials), 2011, vol. 23, No. 2, pp. 274-284.

Fujita.M et al., "Reduction of operating voltage in organic light-emitting diode by corrugated photonic crystal structure", Appl. Phys. Lett. (Applied Physics Letters), Dec. 6, 2004, vol. 85, No. 23, pp. 5769-5771.

Tsuboyama.A et al., "Homoleptic Cyclometalated Iridium Complexes with Highly Efficient Red Phosphorescence and Application to Organic Light-Emitting Diode", J. Am. Chem. Soc. (Journal of the American Chemical Society), 2003, vol. 125, No. 42, pp. 12971-12979.

Yoshida.K et al., "High efficiency reverse intersystem crossing of exciplex states", The 71st Autumn Meeting of the Japan Society of Applied Physics and Related Societies, 2010, p. 319, The Japan Society of Applied Physics.

Goushi.K et al., "Delayed fluorescence organic light-emitting diodes based on exciplex", The 59th Spring Meeting of the Japan Society of Applied Physics and Related Societies Preliminary Drafts, 2012, p. 251.

Nakagawa.T et al., "Electroluminescence based on thermally activated delayed fluorescence generated by a spirobifluorene donor-acceptor structure", Chemical Communications, Apr. 17, 2012, vol. 48, No. 77, pp. 9580-9582, RSC Publishing.

Yokoyama.D et al., "Dual efficiency enhancement by delayed fluorescence and dipole orientation in high-efficiency fluorescent organic light-emitting diodes", Appl. Phys. Lett. (Applied Physics Letters), Sep. 22, 2011, vol. 99, No. 12, pp. 1-4, AIP Publishing.

Mehes.G et al., "Thermally Activated Delayed Fluorescence and its Application for OLED", The 2nd PHOENICS International Symposium, Mar. 5, 2012.

Sajoto.T et al., "Temperature Dependence of Blue Phosphorescent Cyclometalated Ir(III) Complexes", J. Am. Chem. Soc. (Journal of the American Chemical Society), Jun. 18, 2009, vol. 131, No. 28, pp. 9813-9822.

Gong.X et al., "Phosphorescence from iridium complexes doped into polymer blends", J. Appl. Phys. (Journal of Applied Physics), Feb. 1, 2004, vol. 95, No. 3, pp. 948-953.

Lee.J et al., "Stabilizing the efficiency of phosphorescent organic light-emitting diodes", SPIE Newsroom, Apr. 21, 2008, pp. 1-3.

D'Andrade.B et al., "High-efficiency yellow double-doped organic light-emitting devices based on phosphor-sensitized fluorescence", Appl. Phys. Lett. (Applied Physics Letters), Aug. 13, 2001, vol. 79, No. 7, pp. 1045-1047.

Cheng.G et al., "Improved efficiency for white organic light-emitting devices based on phosphor sensitized fluorescence", Appl. Phys. Lett. (Applied Physics Letters), Feb. 20, 2006, vol. 88, No. 8, pp. 083512-1-083512-3.

Kanno.H et al., "White organic light-emitting device based on a compound fluorescent phosphor-sensitized-fluorescent emission layer", Appl. Phys. Lett. (Applied Physics Letters), Oct. 2, 2006, vol. 89, No. 14, pp. 143516-1-143516-3.

Matsumoto.N et al., "Exciplex Formations between Tris(8-hydoxyquinolate)aluminum and Hole Transport Materials and Their Photoluminescence and Electroluminescence Characteristics", J. Phys. Chem. C (The Journal of Physical Chemistry C), May 22, 2008, vol. 112, No. 20, pp. 7735-7741.

Yersin.H et al., Highly Efficient OLEDs with Phosphorescent Materials, 2008, pp. 1-97,283-309, Wiley-VCH Verlag Gmbh & Co.

Tokito.S et al., "Improvement in performance by doping", Organic EL Display, Aug. 20, 2004, pp. 67-99, Ohmsha.

Jeon.W et al., "Ideal host and guest system in phosphorescent OLEDs", Organic Electronics, 2009, vol. 10, pp. 240-246, Elsevier.

(56) References Cited

OTHER PUBLICATIONS

Rausch.A et al., "Matrix Effects on the Triplet State of the OLED Emitter Ir(4,6-dFppy)2(pic)(Flrpic):Investigations by High-Resolution Optical Spectroscopy", Inorg. Chem. (Inorganic Chemistry), 2009, vol. 48, No. 5, pp. 1928-1937.

Zhao.Q et al., "Synthesis and Photophysical, Electrochemical, and Electrophosphorescent Properties of a Series of Iridium(III) Complexes Based on Quinoline Derivatives and Different β-Diketonate Ligands", Organometallic, Jun. 14, 2006, vol. 25, No. 15, pp. 3631-3638.

Park.Y et al., "Efficient triplet harvesting by fluorescent molecules through exciplexes for high efficiency organic light-emitting diodes", Appl. Phys. Lett. (Applied Physics Letters), Apr. 18, 2013, vol. 102, No. 15, pp. 153306-1-153306-5.

Nakanotani.H et al., "High-efficiency organic light-emitting diodes with fluorescent emitters", Nature Communications, May 30, 2014, vol. 5, pp. 4016-1-4016-7.

Noda.H et al., "Excited state engineering for efficient reverse intersystem crossing", Science Advances, Jul. 22, 2018, vol. 4, No. 6, p. 6910.

Baldo.M et al., "High-Efficiency Fluorescent Organic Light-Emitting Devices Using a Phosphorescent Sensitizer", Nature, Feb. 17, 2000, vol. 403, No. 6771, pp. 750-753.

International Search Report (Application No. PCT/IB2019/051403) dated May 28, 2019.

Written Opinion (Application No. PCT/IB2019/051403) dated May 28, 2019.

German Office Action (Application No. 112019001181.2) dated Jan. 3, 2024.

Zhou.D et al., "Host to Guest Energy Transfer Mechanism in Phosphorescent and Flourescent Organic Light-Emitting Devices Utilizing Exciplex-Forming Hosts", J. Phys. Chem. C (The Journal of Physical Chemistry C), Sep. 24, 2014, vol. 118, No. 41, pp. 24006-24012, American Chemical Society.

Kim.J et al., "Study of Sequential Dexter Energy Transfer in High Efficient Phosphorescent White Organic Light-Emitting Diodes with Single Emissive Layer", Sci. Rep. (Scientific Reports), Nov. 12, 2014, vol. 4, No. 7009, pp. 1-6, Nature.

Xu.D et al., "Organic light-emitting diode with liquid emitting layer", Appl. Phys. Lett. (Applied Physics Letters), Aug. 6, 2009, vol. 95, No. 5, pp. 053304-1-053304-3.

Zhang. D et al., "Highly efficient blue thermally activated delayed fluorescent OLEDs with record-low driving voltages utilizing high triplet energy hosts with small singlet-triplet splittings", Chem. Sci. (Chemical Science), Feb. 12, 2016, vol. 7, No. 5, pp. 3355-3363.

Tokito.S et al., "Phosphorescent Organic Light-emitting Devices: Triplet Energy Management", Electrochemistry, 2008, vol. 76, No. 1, pp. 24-31.

Fukuda.T et al., "Transient characteristics of organic light-emitting diodes with efficient energy transfer in emitting material", Thin Solid Films, Jul. 9, 2009, vol. 518, No. 2, pp. 567-570.

\* cited by examiner (a)

(b)

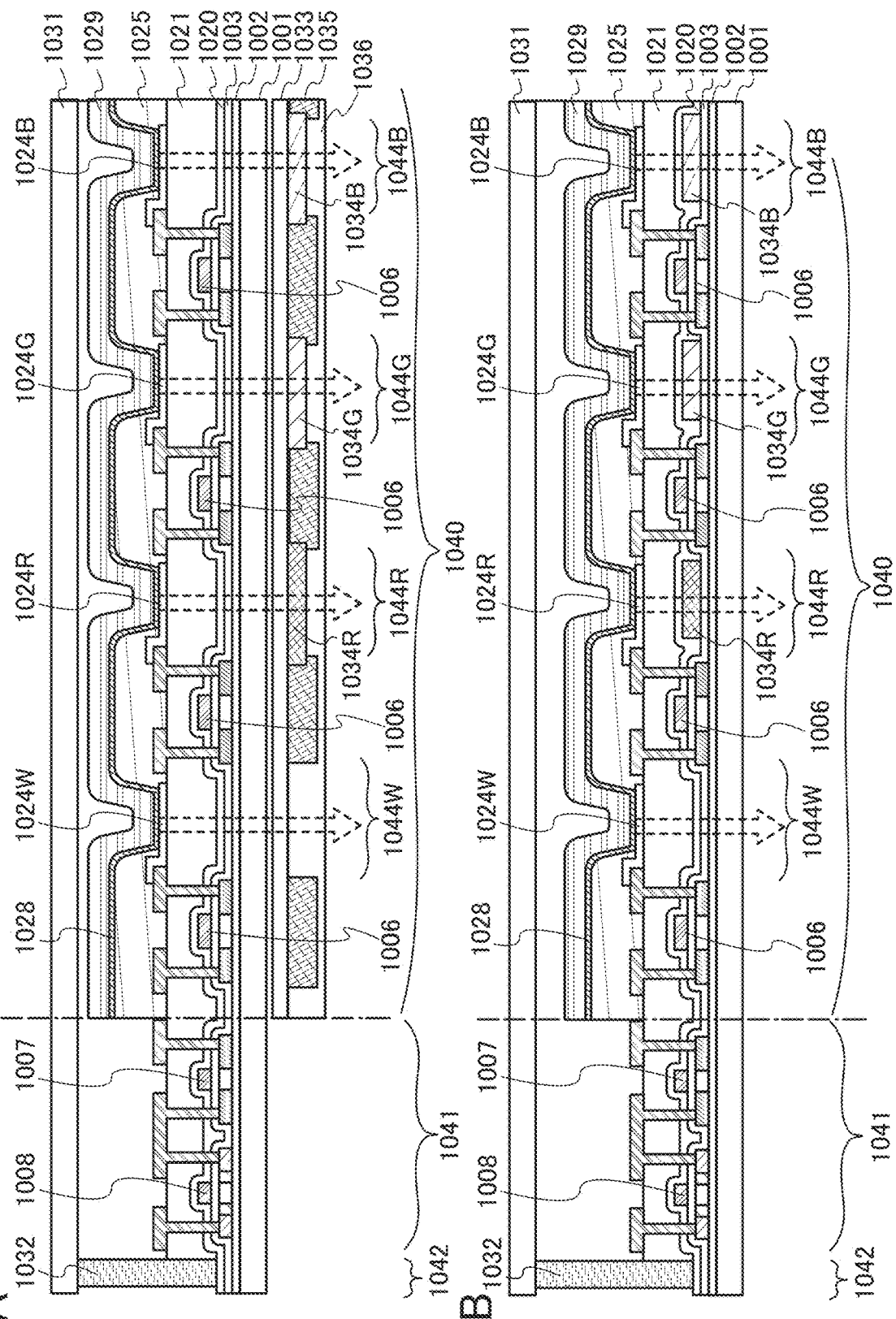

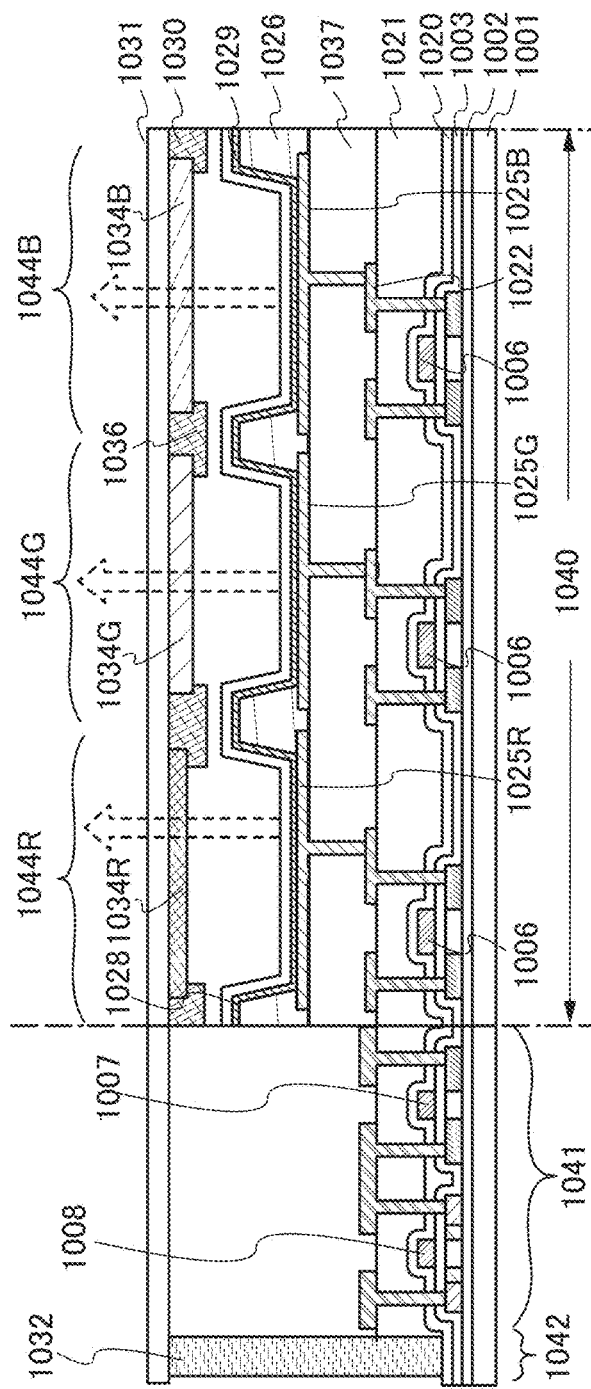
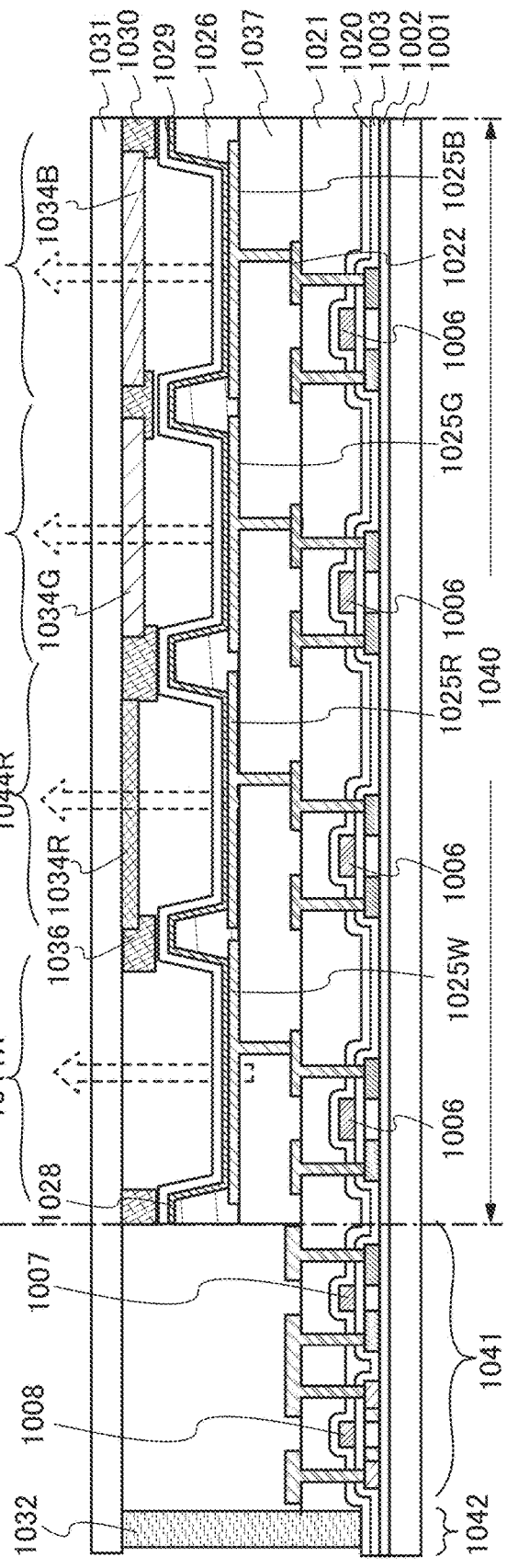
FIG. 10A
FIG. 10B

| Light-emitting element | External quantum efficiency (%) (1000 cd/m$^2$) |
|---|---|
| Element 4 | 17.4 |
| Element 8 | 22.0 |
| Comparative element 17 | 17.9 |
| Comparative element 21 | 16.1 |
| Comparative element 25 | 16.5 |
| Comparative element 29 | 19.0 |

LIGHT-EMITTING ELEMENT, DISPLAY DEVICE, ELECTRONIC DEVICE, ORGANIC COMPOUND, AND LIGHTING DEVICE

CROSS REFERENCE TO RELATED APPLICATIONS

This application is a U.S. National Phase Application under 35 U.S.C. § 371 of International Application PCT/M2019/051403, filed on Feb. 21, 2019, which is incorporated by reference and claims the benefit of foreign priority applications filed in Japan on Mar. 7, 2018, as Application No. 2018-040387, on Jul. 11, 2018, as Application No. 2018-131250, and on Nov. 30, 2018, as Application No. 2018-224768.

TECHNICAL FIELD

One embodiment of the present invention relates to a light-emitting element, an organic compound, or a display device, an electronic device, and a lighting device each including the light-emitting element.

Note that one embodiment of the present invention is not limited to the above technical field. The technical field of one embodiment of the invention disclosed in this specification and the like relates to an object, a method, or a manufacturing method. Alternatively, one embodiment of the present invention relates to a process, a machine, manufacture, or a composition of matter. Accordingly, specific examples of the technical field of one embodiment of the present invention disclosed in this specification include a semiconductor device, a display device, a liquid crystal display device, a light-emitting apparatus, a lighting device, a power storage device, a memory device, a driving method thereof, and a manufacturing method thereof.

BACKGROUND ART

In recent years, research and development have been extensively conducted on light-emitting elements utilizing electroluminescence (EL). The basic structure of these light-emitting elements is a structure in which a layer containing a light-emitting substance (an EL layer) is interposed between a pair of electrodes. By application of a voltage between the electrodes of this element, light emission from the light-emitting substance can be obtained.

Since the above light-emitting element is a self-luminous type, a display device using this has advantages such as high visibility, no necessity of a backlight, and low power consumption. The display device also has advantages in that it can be manufactured to be thin and lightweight and has high response speed, for example.

In the case where an organic compound is used as a light-emitting substance and an EL layer containing the light-emitting organic compound is provided between a pair of electrodes in a light-emitting element (e.g., an organic EL element), application of a voltage between the pair of electrodes causes injection of electrons from a cathode and holes from an anode into the light-emitting EL layer and thus a current flows. By recombination of the injected electrons and holes, the light-emitting organic compound is brought into an excited state, and light emission can be obtained from the excited light-emitting organic compound.

The types of excited states formed by an organic compound are a singlet excited state ($S^*$) and a triplet excited state ($T^*$); light emission from the singlet excited state is referred to as fluorescence, and light emission from the triplet excited state is referred to as phosphorescence. The statistical formation ratio of them in the light-emitting element is $S^*:T^*=1:3$. For this reason, a light-emitting element using a compound that emits phosphorescence (phosphorescent material) can have higher emission efficiency than a light-emitting element using a compound that emits fluorescence (fluorescent material). Therefore, light-emitting elements using phosphorescent materials capable of converting energy of the triplet excited state into light emission have been actively developed in recent years.

Among light-emitting elements using phosphorescent materials, a light-emitting element that emits blue light in particular has not yet been put into practical use because it is difficult to develop a stable compound having a high triplet excitation energy level. For this reason, the development of a light-emitting element using a fluorescent material, which is more stable, has been conducted and a technique for improving the emission efficiency of a light-emitting element using a fluorescent material (fluorescent element) has been searched.

As a material capable of converting part or all of energy of the triplet excited state into light emission, a thermally activated delayed fluorescent (Thermally Activated Delayed Fluorescence: TADF) material is known in addition to a phosphorescent material. In a thermally activated delayed fluorescent material, a singlet excited state is generated from a triplet excited state by reverse intersystem crossing, and the singlet excited state is converted into light emission.

In order to improve the emission efficiency of a light-emitting element using a thermally activated delayed fluorescent material, not only efficient generation of a singlet excited state from a triplet excited state but also efficient light emission from a singlet excited state, that is, high fluorescence quantum yield, is important in a thermally activated delayed fluorescent material. It is, however, difficult to design a light-emitting material that simultaneously meets these two.

Then, a method in which in a light-emitting element containing a thermally activated delayed fluorescent material and a fluorescent material, singlet excitation energy of the thermally activated delayed fluorescent material is transferred to the fluorescent material and light emission is obtained from the fluorescent material has been proposed (see Patent Document 1).

REFERENCE

Patent Document

[Patent Document 1] Japanese Published Patent Application No. 2014-45179

Non-Patent Document

[Non-Patent Document 1] Hiroki Noda et al., "SCIENCE ADVANCES", 2018, vol. 4, no. 6, eaao6910

SUMMARY OF THE INVENTION

Problems to be Solved by the Invention

As described above, the efficiency of a fluorescent element is improved as follows, for example: in a light-emitting layer containing a host material and a guest material, triplet excitons of the host material are converted into singlet excitons, and then, singlet excitation energy is transferred to a fluorescent material, which is the guest material. However, the process where the triplet excitation energy of the host material is converted into the singlet excitation energy and a process where the triplet excitation energy is deactivated conflict with each other. Therefore, the triplet excitation energy of the host material is not sufficiently converted into the singlet excitation energy in some cases. In the case where a fluorescent material is used as a guest material of a light-emitting layer of a light-emitting device, a possible pathway where the triplet excitation energy is deactivated, for example, is a deactivation pathway where the triplet excitation energy of a host material is transferred to the lowest triplet excitation energy level ($T_1$ level) of the fluorescent material. The energy transfer in the deactivation pathway does not contribute to light emission, which might decrease the emission efficiency of a fluorescent device. This deactivation pathway can be inhibited by reducing the guest material concentration; however, in this case, the rate of energy transfer from the host material to a singlet excited state of the guest material is also decreased, so that quenching due to a degraded material and an impurity is likely to occur. Therefore, the luminance of the light-emitting device is likely to decrease, leading to a decrease in reliability.

In order to improve the emission efficiency and reliability of a fluorescent element, it is preferred that triplet excitation energy in a light-emitting layer be efficiently converted into singlet excitation energy and the triplet excitation energy be efficiently transferred as singlet excitation energy to a fluorescent material. Hence, it is required to develop a method and a material for generating a singlet excited state of a guest material from a triplet excited state of a host material to further improve the emission efficiency and reliability of a light-emitting element.

An object of one embodiment of the present invention is to, in a host material and a guest material of a light-emitting layer of a light-emitting device, inhibit transfer of the triplet excitation energy of the host material to the $T_1$ level of the guest material and convert the triplet excitation energy of the host material into the singlet excitation energy of the guest material efficiently, so as to improve the fluorescence efficiency and reliability of the light-emitting device.

Another object of one embodiment of the present invention is to provide a light-emitting element with reduced power consumption. Another object of one embodiment of the present invention is to provide a novel light-emitting element. Another object of one embodiment of the present invention is to provide a novel light-emitting apparatus. Another object of one embodiment of the present invention is to provide a novel display device. Another object of one embodiment of the present invention is to provide a novel organic compound.

Note that the description of the above objects does not disturb the existence of other objects. In one embodiment of the present invention, there is no need to achieve all of these objects. Objects other than those described above are apparent from the description of the specification and the like and objects other than those described above can be derived from the description of the specification and the like.

Means for Solving the Problems

As described above, the development of a method for efficiently converting triplet excitation energy into light emission in a light-emitting element that emits fluorescence is required. Thus, it is necessary to improve energy transfer efficiency between materials used in a light-emitting layer. This needs inhibition of the transfer of triplet excitation energy by the Dexter mechanism between an energy donor and an energy acceptor.

Thus, one embodiment of the present invention is a light-emitting element including a light-emitting layer between a pair of electrodes. The light-emitting layer contains a first material having a function of converting triplet excitation energy into light emission and a second material having a function of converting singlet excitation energy into light emission; the second material contains a luminophore and five or more protecting groups; the luminophore is a condensed aromatic ring or a condensed heteroaromatic ring; the five or more protecting groups each independently have any one of an alkyl group having 1 to 10 carbon atoms, a substituted or unsubstituted cycloalkyl group having 3 to 10 carbon atoms, and a trialkylsilyl group having 3 to 12 carbon atoms; and light emission is obtained from the second material.

In the above structure, it is preferable that at least four of the five protecting groups be each independently any one of an alkyl group having 3 to 10 carbon atoms, a substituted or unsubstituted cycloalkyl group having 3 to 10 carbon atoms, and a trialkylsilyl group having 3 to 12 carbon atoms.

Another embodiment of the present invention is a light-emitting element including a light-emitting layer between a pair of electrodes. The light-emitting layer contains a first material having a function of converting triplet excitation energy into light emission and a second material having a function of converting singlet excitation energy into light emission; the second material contains a luminophore and at least four protecting groups; the luminophore is a condensed aromatic ring or a condensed heteroaromatic ring; the four protecting groups are not directly bonded to the condensed aromatic ring or the condensed heteroaromatic ring; the four protecting groups each independently have any one of an alkyl group having 3 to 10 carbon atoms, a substituted or unsubstituted cycloalkyl group having 3 to 10 carbon atoms, and a trialkylsilyl group having 3 to 12 carbon atoms; and light emission is obtained from the second material.

Another embodiment of the present invention is a light-emitting element including a light-emitting layer between a pair of electrodes. The light-emitting layer contains a first material having a function of converting triplet excitation energy into light emission and a second material having a function of converting singlet excitation energy into light emission; the second material contains a luminophore and two or more diarylamino groups; the luminophore is a condensed aromatic ring or a condensed heteroaromatic ring; the condensed aromatic ring or the condensed heteroaromatic ring is bonded to the two or more diarylamino groups; aryl groups in the two or more diarylamino groups each independently have at least one protecting group; the protecting groups each independently have any one of an alkyl group having 3 to 10 carbon atoms, a substituted or unsubstituted cycloalkyl group having 3 to 10 carbon atoms, and a trialkylsilyl group having 3 to 12 carbon atoms; and light emission is obtained from the second material.

Another embodiment of the present invention is a light-emitting element including a light-emitting layer between a pair of electrodes. The light-emitting layer contains a first material having a function of converting triplet excitation energy into light emission and a second material having a function of converting singlet excitation energy into light emission; the second material contains a luminophore and two or more diarylamino groups; the luminophore is a condensed aromatic ring or a condensed heteroaromatic ring; the condensed aromatic ring or the condensed heteroaromatic ring is bonded to the two or more diarylamino groups; aryl groups in the two or more diarylamino groups each independently have at least two protecting groups; the protecting groups each independently have any one of a branched-chain alkyl group having 3 to 10 carbon atoms, a substituted or unsubstituted cycloalkyl group having 3 to 10 carbon atoms, and a trialkylsilyl group having 3 to 12 carbon atoms; and light emission is obtained from the second material.

In the above structure, the diarylamino group is preferably a diphenylamino group.

In the above structure, the alkyl group is preferably a branched-chain alkyl group.

Another embodiment of the present invention is a light-emitting element including a light-emitting layer between a pair of electrodes. The light-emitting layer contains a first material having a function of converting triplet excitation energy into light emission and a second material having a function of converting singlet excitation energy into light emission; the second material contains a luminophore and a plurality of protecting groups; the luminophore is a condensed aromatic ring or a condensed heteroaromatic ring; at least one of atoms of the plurality of protecting groups is positioned directly on one plane of the condensed aromatic ring or the condensed heteroaromatic ring and at least one of atoms of the plurality of protecting groups is positioned directly on the other plane of the condensed aromatic ring or the condensed heteroaromatic ring; and light emission is obtained from the second material.

Another embodiment of the present invention is a light-emitting element including a light-emitting layer between a pair of electrodes. The light-emitting layer contains a first material having a function of converting triplet excitation energy into light emission and a second material having a function of converting singlet excitation energy into light emission; the second material contains a luminophore and two or more diarylamino groups; the luminophore is a condensed aromatic ring or a condensed heteroaromatic ring; the condensed aromatic ring or the condensed heteroaromatic ring is bonded to the two or more diphenylamino groups; phenyl groups in the two or more diphenylamino groups each independently have protecting group at the 3-position and the 5-position; the protecting groups each independently have any one of an alkyl group having 3 to 10 carbon atoms, a substituted or unsubstituted cycloalkyl group having 3 to 10 carbon atoms, and a trialkylsilyl group having 3 to 12 carbon atoms; and light emission is obtained from the second material.

In the above structure, the alkyl group is preferably a branched-chain alkyl group.

In the above structure, the branched-chain alkyl group preferably has quaternary carbon.

In the above structure, the condensed aromatic ring or the condensed heteroaromatic ring preferably contains any one of naphthalene, anthracene, fluorene, chrysene, triphenylene, pyrene, tetracene, perylene, coumarin, quinacridone, and naphthobisbenzofuran.

In the above structure, the first material preferably includes a first organic compound and a second organic compound, and the first organic compound and the second organic compound preferably form an exciplex. The first organic compound preferably emits phosphorescence.

In the above structure, the first material preferably emits phosphorescence.

In the above structure, the emission spectrum of the first material preferably overlaps with an absorption band on the longest wavelength side of the absorption spectrum of the second material.

In the above structure, the concentration of the second material in the light-emitting layer is preferably higher than or equal to 2 wt % and lower than or equal to 30 wt %.

Another embodiment of the present invention is an organic compound represented by General Formula (G1) or (G2) shown below.

[Chemical Formula 1]

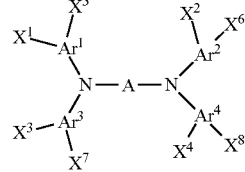

(G1)

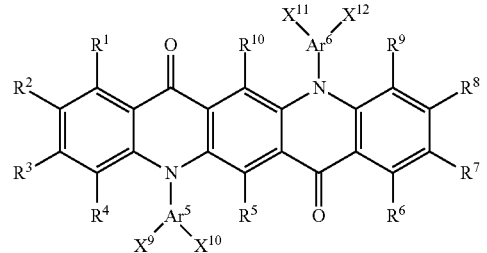

(G2)

In General Formulae (G1) and (G2), A represents a substituted or unsubstituted condensed aromatic ring having 10 to 30 carbon atoms or a substituted or unsubstituted condensed heteroaromatic ring having 10 to 30 carbon atoms, $Ar^1$ to $Ar^6$ each independently represent a substituted or unsubstituted aromatic hydrocarbon group having 6 to 13 carbon atoms, $X^1$ to $X^{12}$ each independently represent any one of a branched-chain alkyl group having 3 to 10 carbon atoms, a substituted or unsubstituted cycloalkyl group having 3 to 10 carbon atoms, and a trialkylsilyl group having 3 to 12 carbon atoms, and $R^1$ to $R^{10}$ each independently represent any one of hydrogen, an alkyl group having 3 to 10 carbon atoms, a substituted or unsubstituted cycloalkyl group having 3 to 10 carbon atoms, and a trialkylsilyl group having 3 to 12 carbon atoms.

In the above structure, the organic compound is preferably an organic compound represented by General Formula (G3) or (G4) shown below.

[Chemical Formula 2]

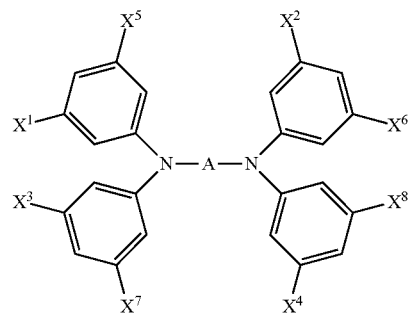

(G3)

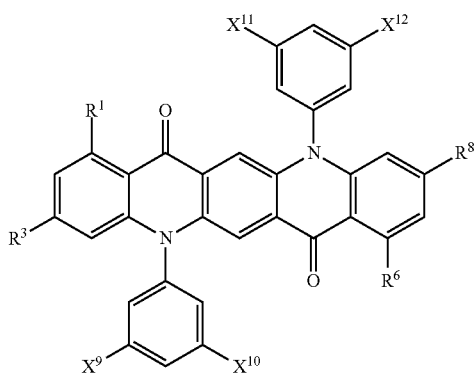

(G4)

In General Formulae (G3) and (G4), A represents a substituted or unsubstituted condensed aromatic ring having 10 to 30 carbon atoms or a substituted or unsubstituted condensed heteroaromatic ring having 10 to 30 carbon atoms, $X^1$ to $X^{12}$ each independently represent any one of a branched-chain alkyl group having 3 to 10 carbon atoms, a substituted or unsubstituted cycloalkyl group having 3 to 10 carbon atoms, and a trialkylsilyl group having 3 to 12 carbon atoms, and $R^1$, $R^3$, $R^6$, and $R^8$ each independently represent any one of hydrogen, an alkyl group having 3 to 10 carbon atoms, a substituted or unsubstituted cycloalkyl group having 3 to 10 carbon atoms, and a trialkylsilyl group having 3 to 12 carbon atoms.

In the above structure, the organic compound is preferably an organic compound represented by General Formula (G5) shown below.

[Chemical Formula 3]

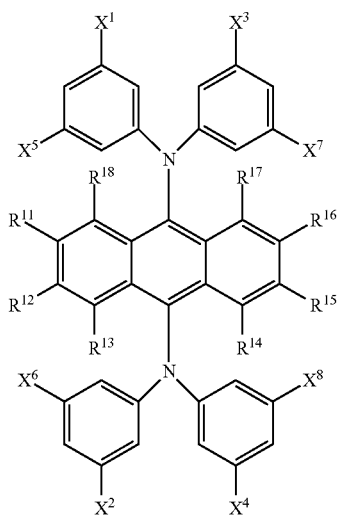

(G5)

In General Formula (G5), $X^1$ to $X^8$ each independently represent any one of a branched-chain alkyl group having 3 to 10 carbon atoms, a substituted or unsubstituted cycloalkyl group having 3 to 10 carbon atoms, and a trialkylsilyl group having 3 to 12 carbon atoms, and $R^{11}$ to $R^{18}$ each independently represent any one of hydrogen, an alkyl group having 3 to 10 carbon atoms, a substituted or unsubstituted cycloalkyl group having 3 to 10 carbon atoms, a trialkylsilyl group having 3 to 12 carbon atoms, and a substituted or unsubstituted aryl group having 6 to 25 carbon atoms.

In the above structure, the alkyl group is preferably a branched-chain alkyl group.

In the above structure, the branched-chain alkyl preferably has quaternary carbon.

In the above structure, the organic compound is preferably an organic compound represented by any one of General Formulae (102) to (104), (221), (222), (225), (229), (250), (254), (257), (261), and (264) shown below.

[Chemical Formula 4]

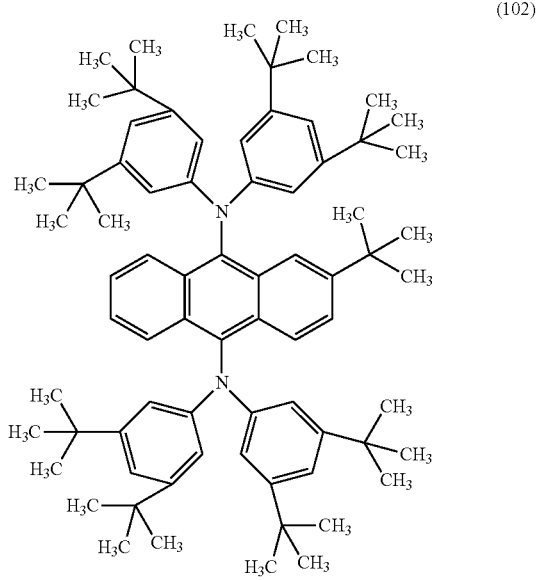

(102)

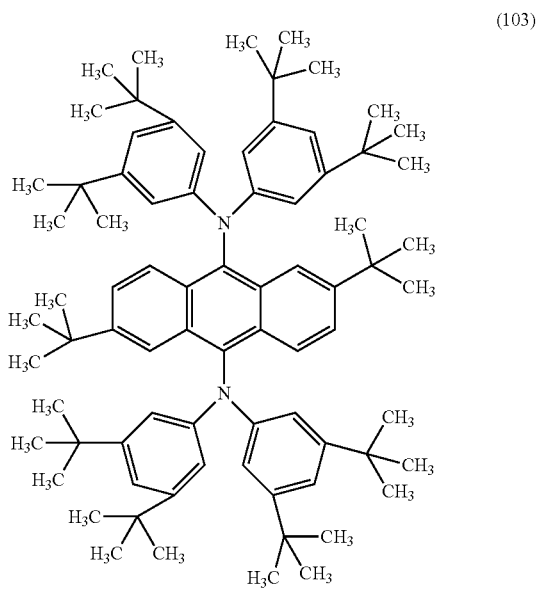

(103)

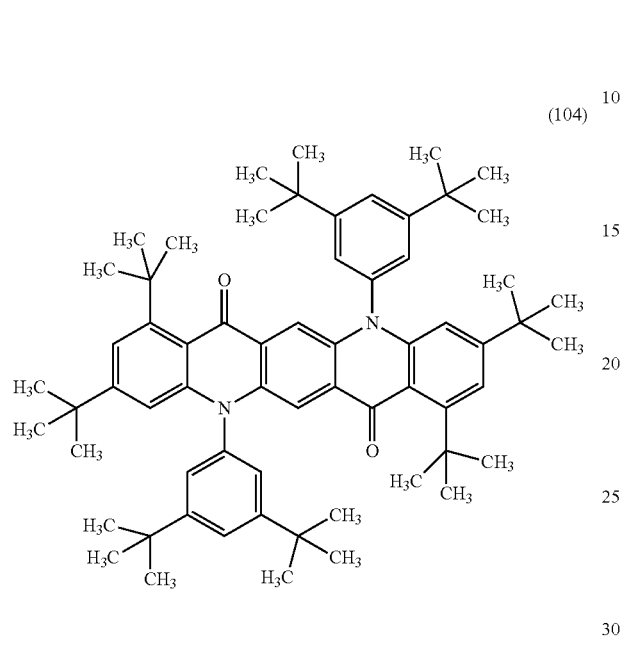
(104)
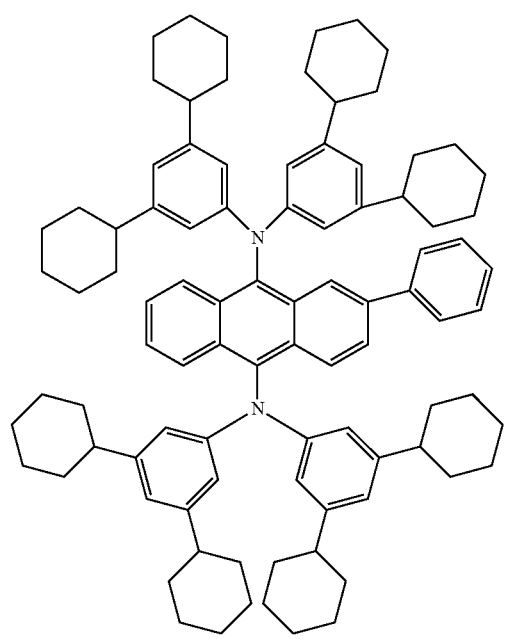
(222)
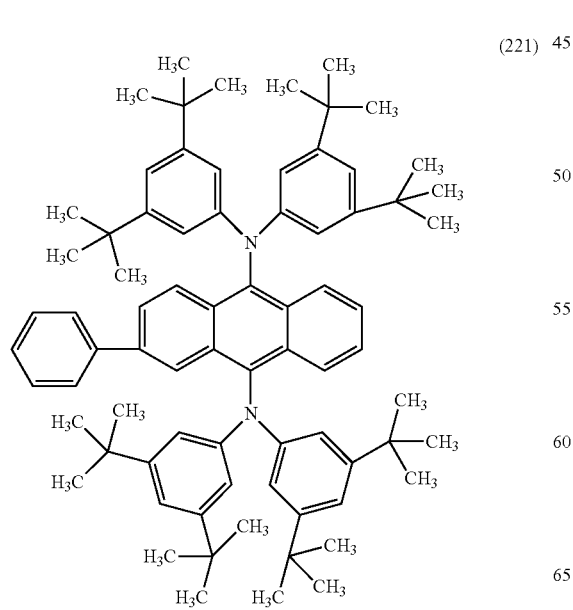
(221)
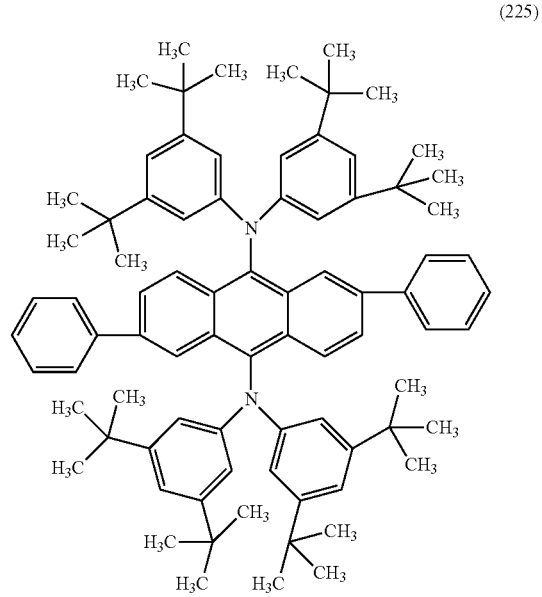
(225)

[Chemical Formula 5]
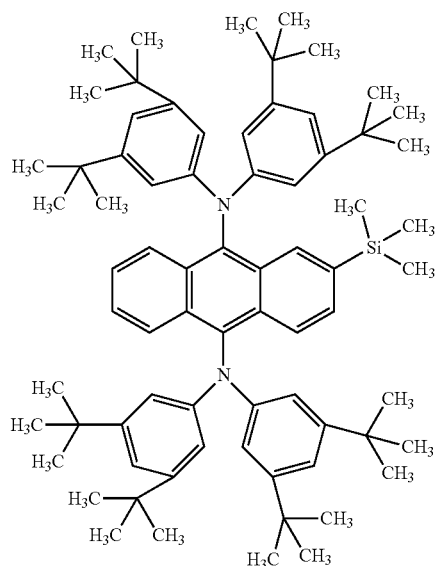
(229)
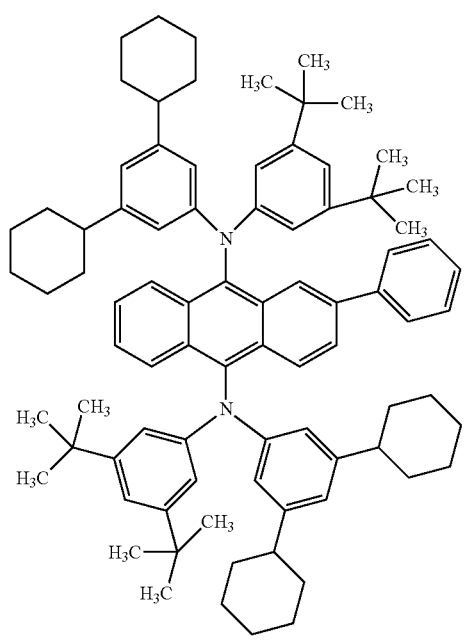
(250)
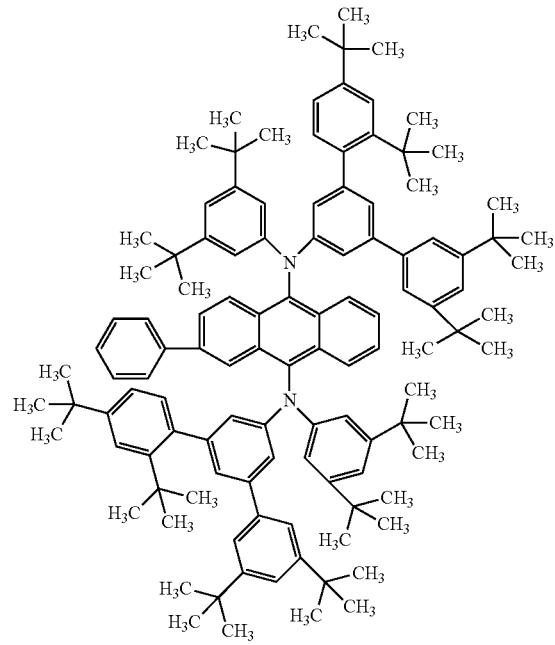
(254)
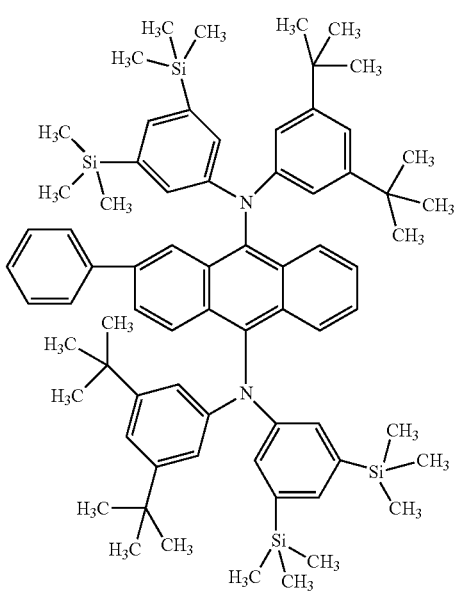
(257)

[Chemical Formula 6]

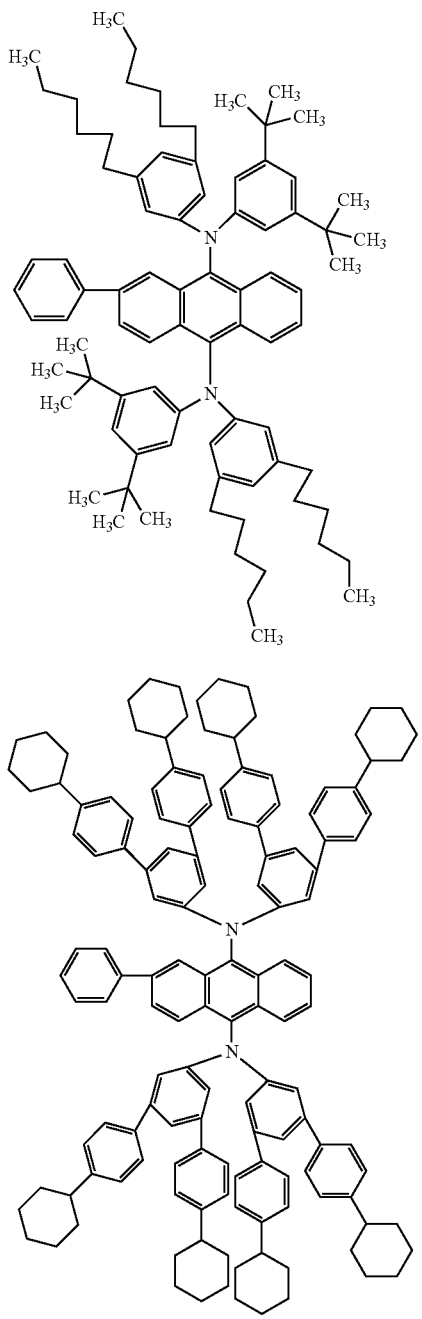

(261)

(264)

Another embodiment of the present invention is a light-emitting element including any one or a plurality of the above organic compounds.

Another embodiment of the present invention is a display device including the light-emitting element having any of the above structures and at least one of a color filter and a transistor. Another embodiment of the present invention is an electronic device including the display device and at least one of a housing and a touch sensor. Another embodiment of the present invention is a lighting device including the light-emitting element having any of the above structures and at least one of a housing and a touch sensor. The category of one embodiment of the present invention includes not only a light-emitting apparatus including a light-emitting element but also an electronic device including a light-emitting apparatus. Accordingly, a light-emitting apparatus in this specification refers to an image display device or a light source (including a lighting device). In some cases, the light-emitting (display) apparatus is included in a display module in which a connector, for example, an FPC (Flexible Printed Circuit) or a TCP (Tape Carrier Package), is connected to a light-emitting apparatus, a display module in which a printed wiring board is provided on the tip of a TCP, or a display module in which an IC (integrated circuit) is directly mounted on a light-emitting element by a COG (Chip On Glass) method.

Effect of the Invention

According to one embodiment of the present invention, a light-emitting element with high emission efficiency can be provided. According to another embodiment of the present invention, a light-emitting element with high reliability can be provided. According to another embodiment of the present invention, a light-emitting element with reduced power consumption can be provided. According to another embodiment of the present invention, a novel light-emitting element can be provided. According to another embodiment of the present invention, a novel light-emitting apparatus can be provided. According to another embodiment of the present invention, a novel display device can be provided. According to another embodiment of the present invention, a novel organic compound can be provided.

Note that the description of these effects does not disturb the existence of other effects. In one embodiment of the present invention, there is no need to achieve all of these effects. Other effects are apparent from the description of the specification, drawings, claims, and the like and other effects can be derived from the description of the specification, drawings, claims, and the like.

BRIEF DESCRIPTION OF THE DRAWINGS

FIGS. 9A and 9B Schematic cross-sectional views illustrating display devices of embodiments of the present invention.

FIGS. 10A and 10B Schematic cross-sectional views illustrating display devices of embodiments of the present invention.

Figure 120:
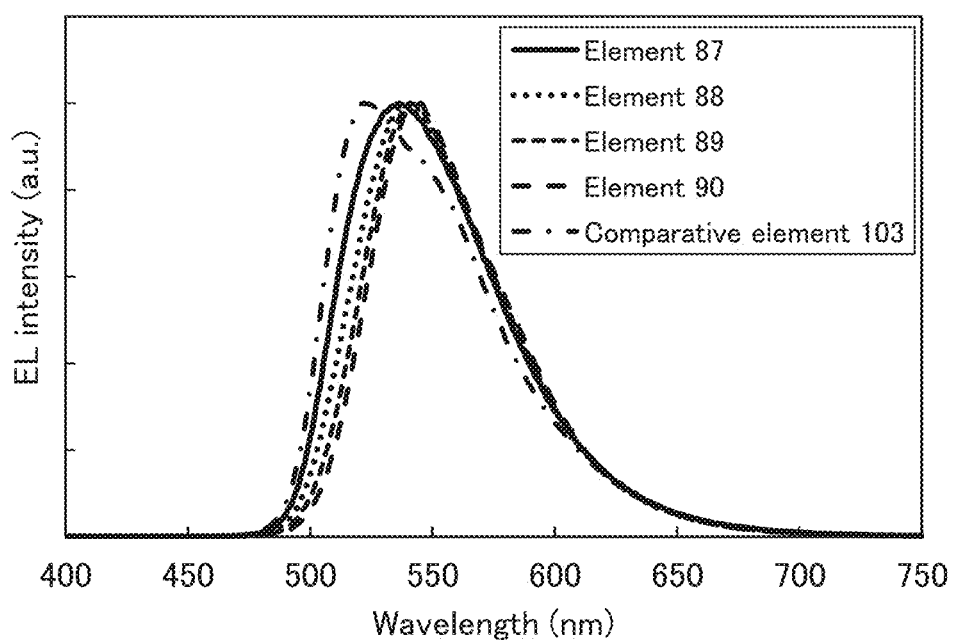

FIG. 120 A diagram showing electroluminescence spectra of light-emitting elements in Example.

Figure 121:
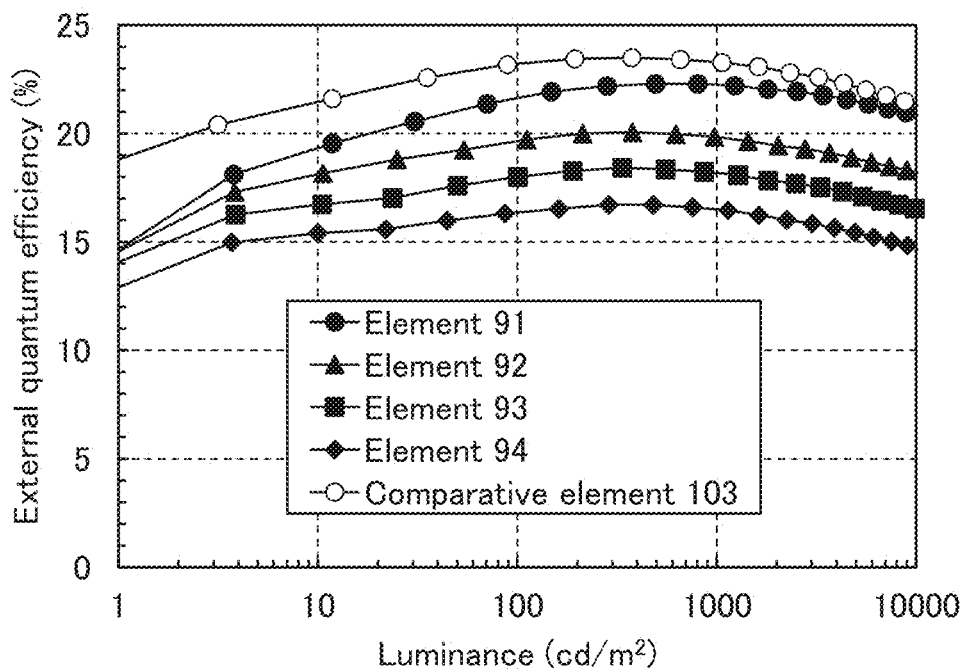

FIG. 121 A diagram showing external quantum efficiency-luminance characteristics of light-emitting elements in Example.

Figure 122:
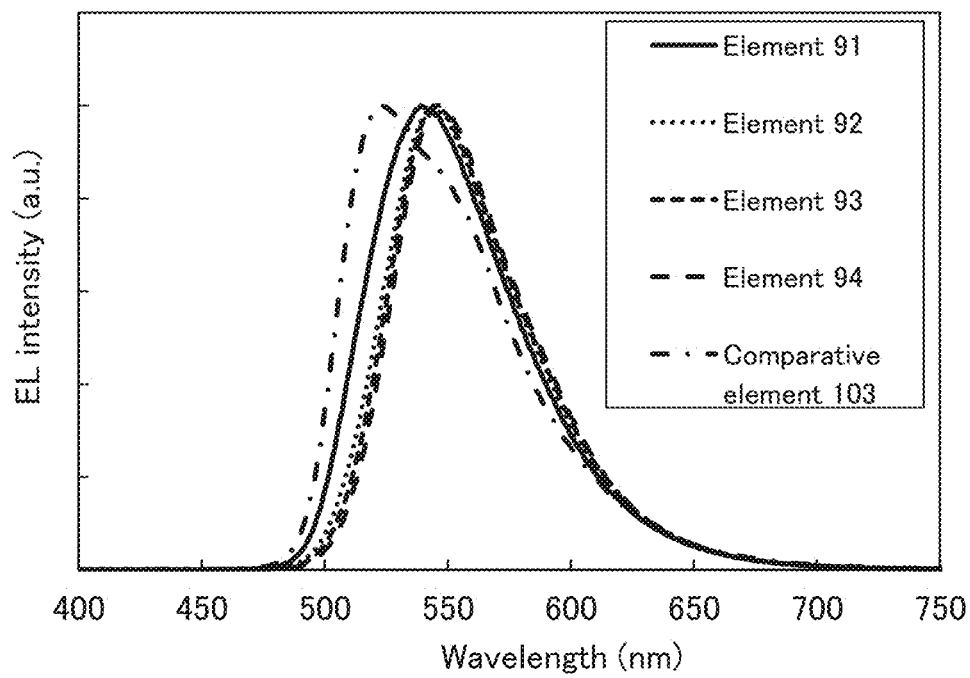

FIG. 122 A diagram showing electroluminescence spectra of light-emitting elements in Example.

Figure 123:
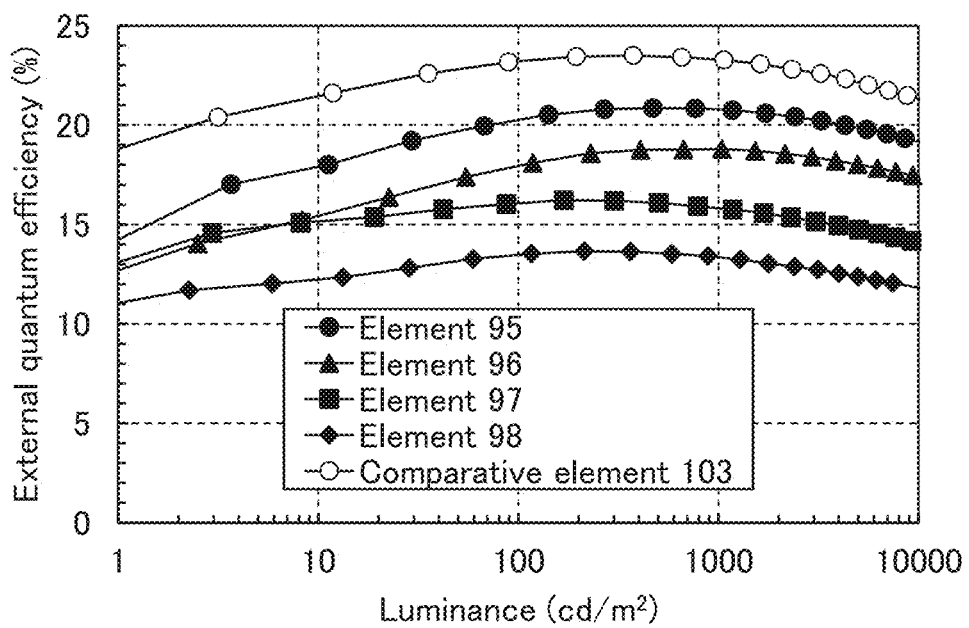

FIG. 123 A diagram showing external quantum efficiency-luminance characteristics of light-emitting elements in Example.

Figure 124:
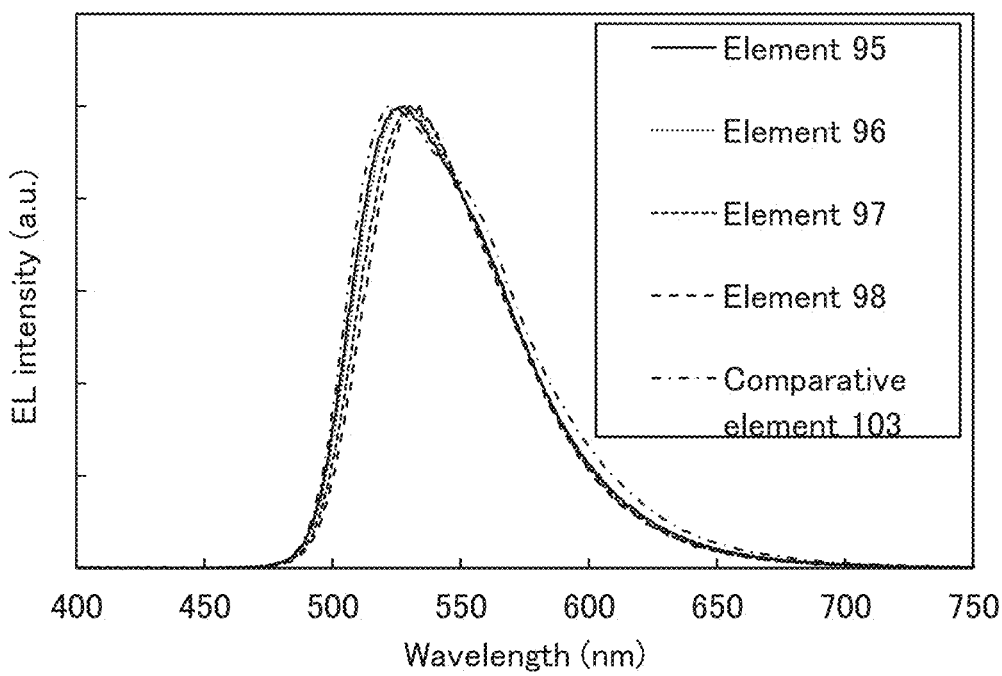

FIG. 124 A diagram showing electroluminescence spectra of light-emitting elements in Example.

Figure 125:
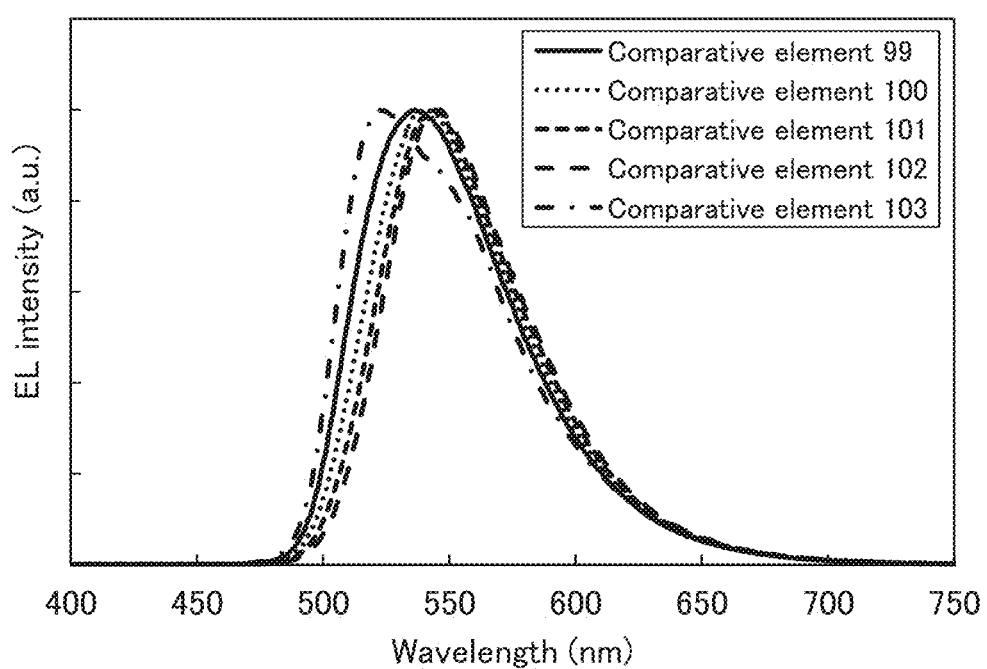

FIG. 125 A diagram showing electroluminescence spectra of comparative light-emitting elements in Example.

Figure 126:
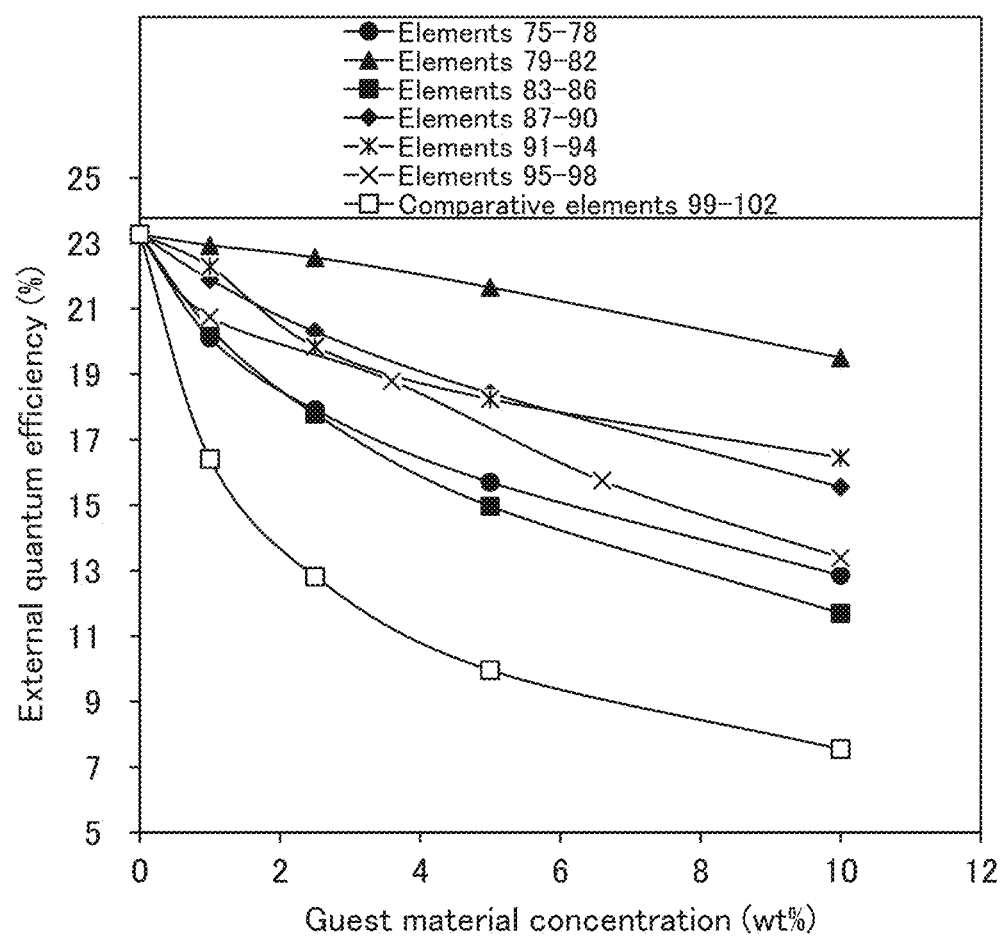

FIG. 126 A diagram showing the relation between external quantum efficiency and guest material concentration in Example.

Figure 127:
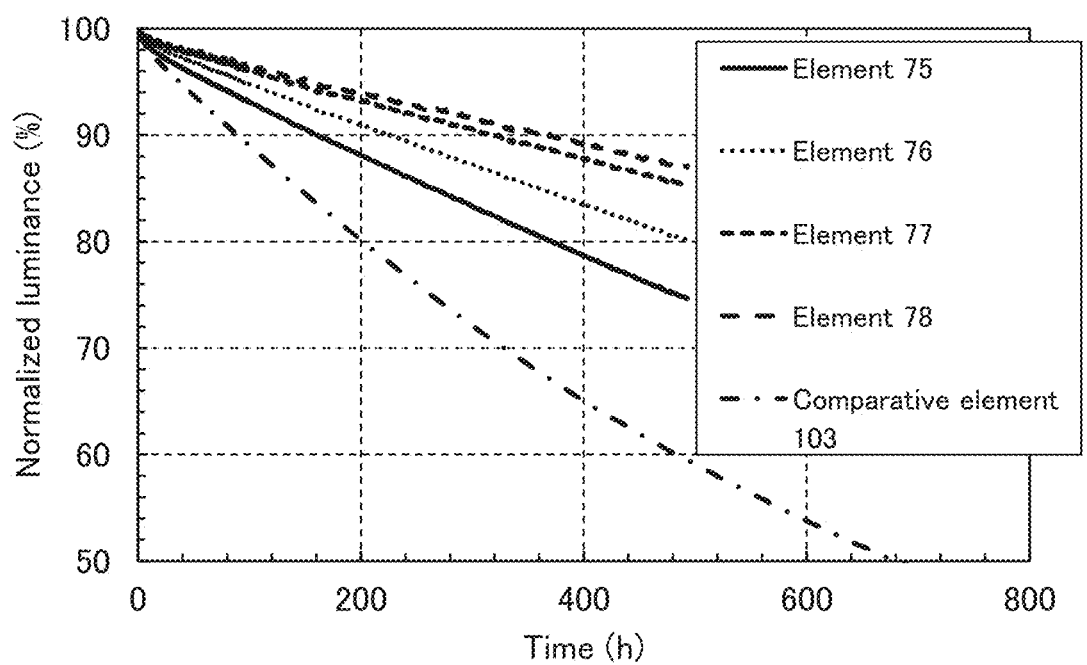

FIG. 127 A diagram showing reliability measurement results of light-emitting elements in Example.

Figure 128:
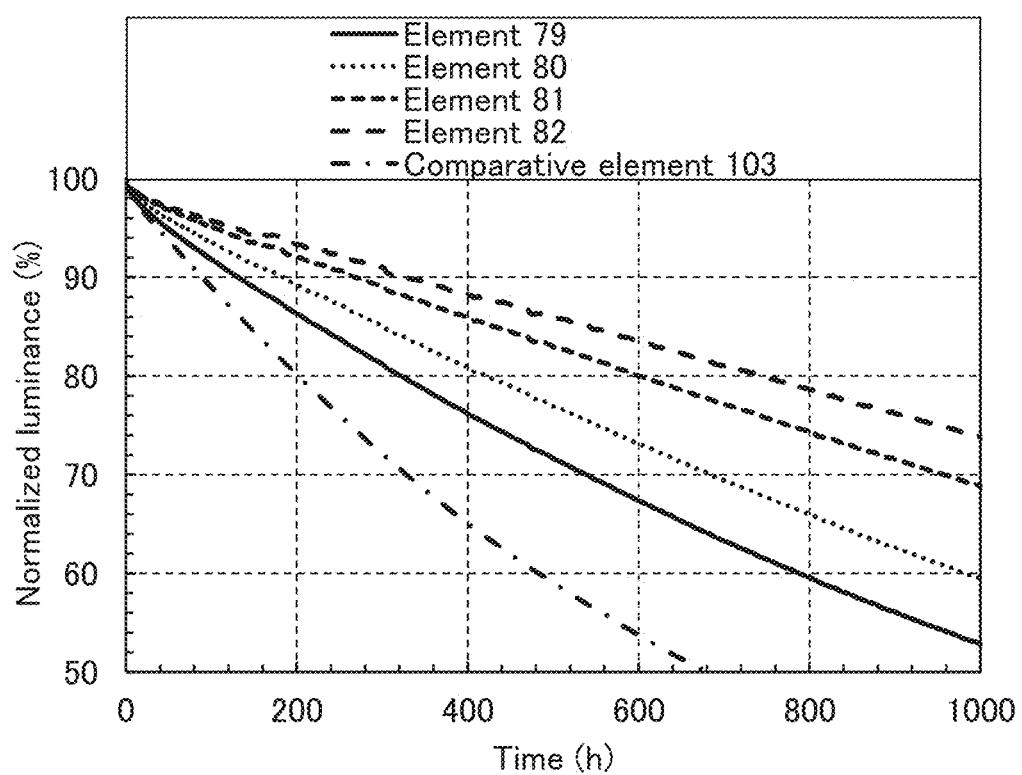

FIG. 128 A diagram showing reliability measurement results of light-emitting elements in Example.

Figure 129:
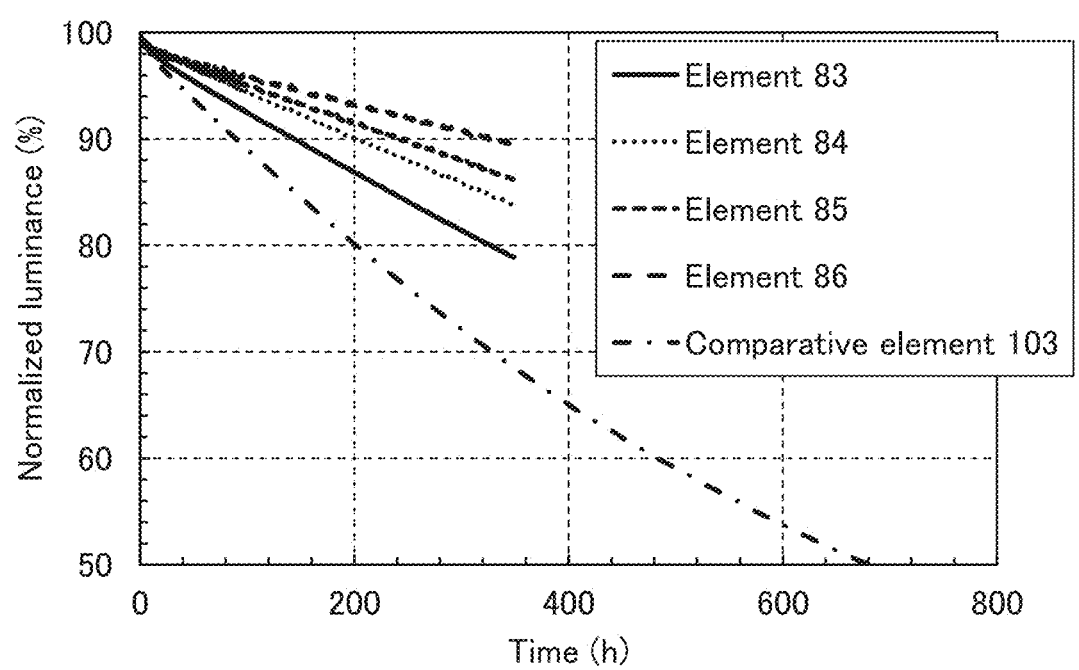

FIG. 129 A diagram showing reliability measurement results of light-emitting elements in Example.

Figure 130:
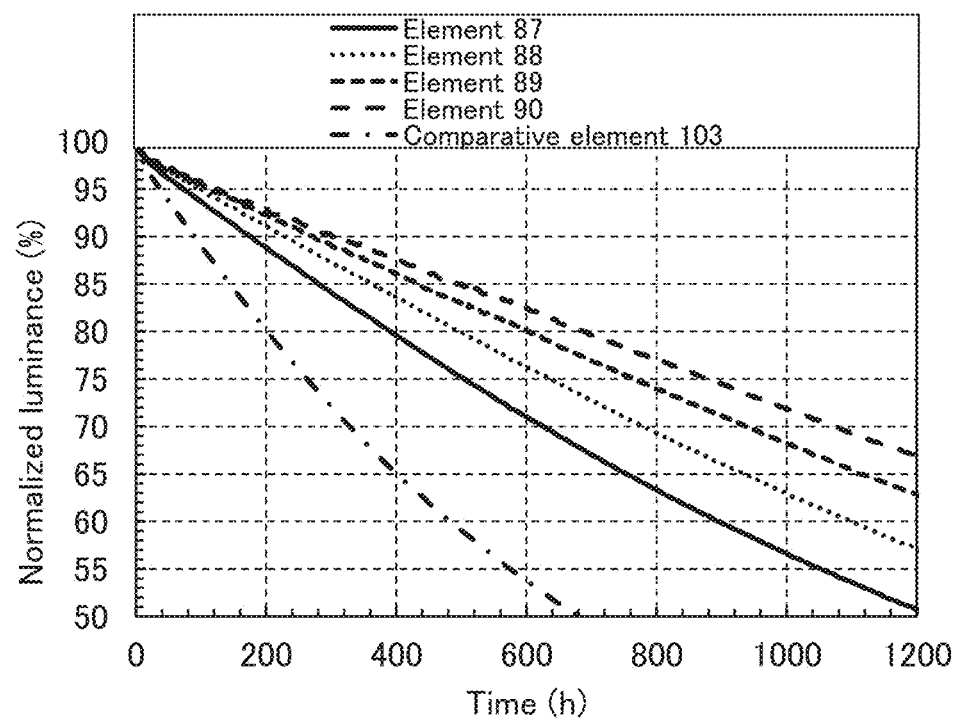

FIG. 130 A diagram showing reliability measurement results of light-emitting elements in Example.

Figure 131:
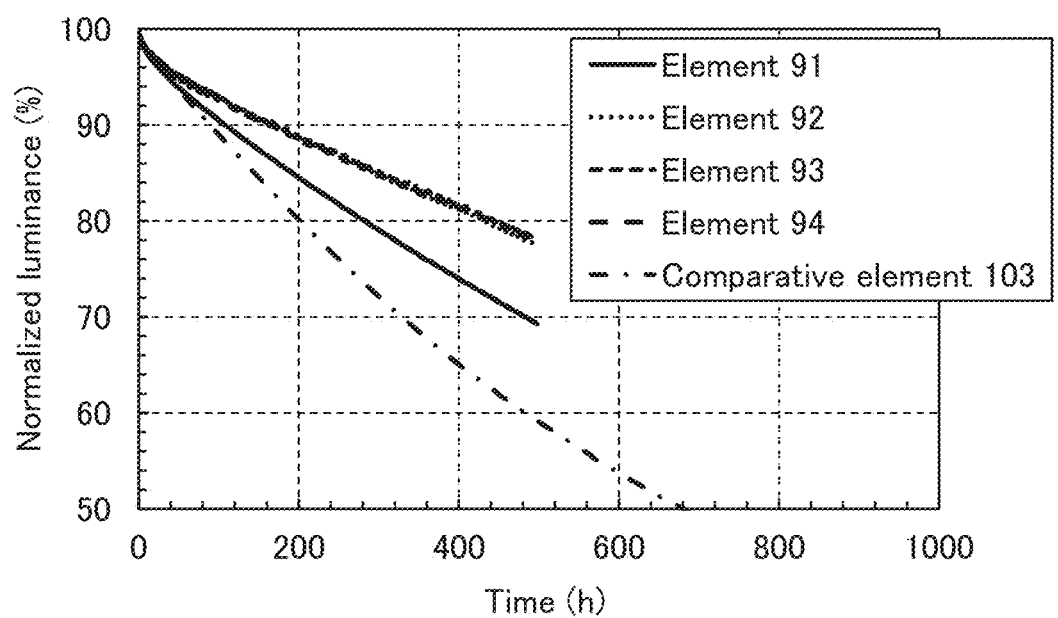

FIG. 131 A diagram showing reliability measurement results of light-emitting elements in Example.

Figure 132:
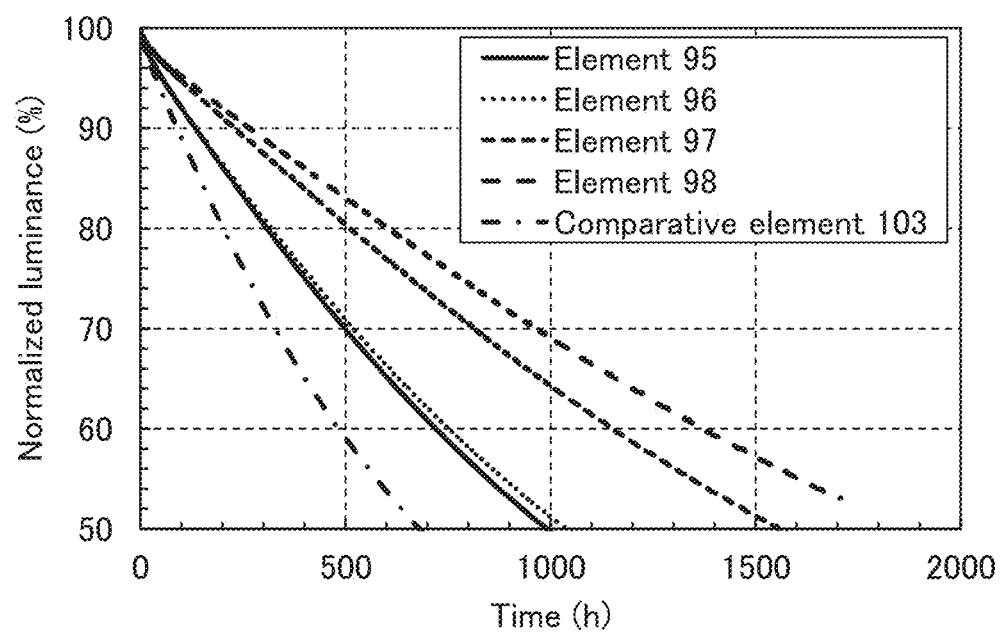

FIG. 132 A diagram showing reliability measurement results of light-emitting elements in Example.

Figure 133:
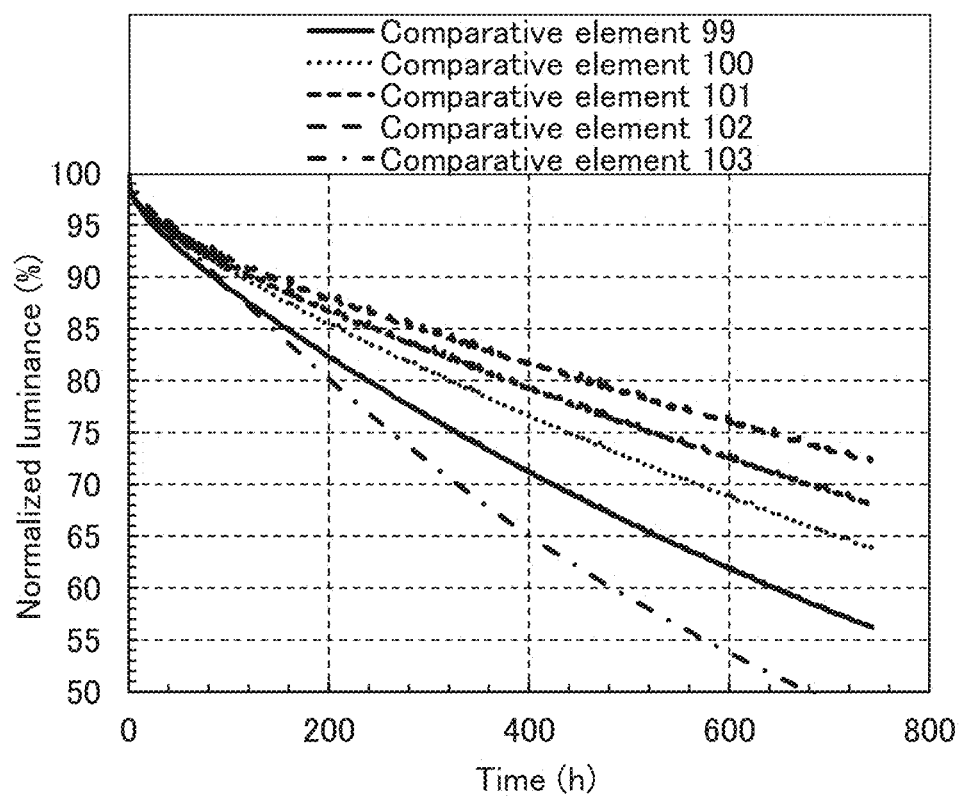

FIG. 133 A diagram showing reliability measurement results of comparative light-emitting elements in Example.

Figure 134:
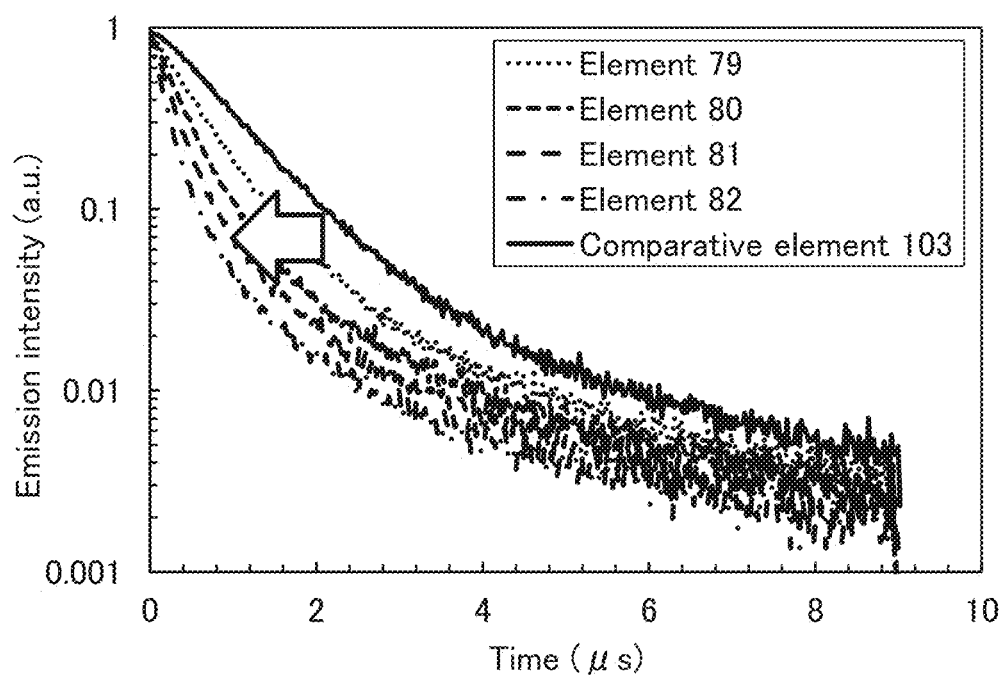

FIG. 134 A diagram showing emission lifetime measurement results of light-emitting elements in Example.

Figure 135:
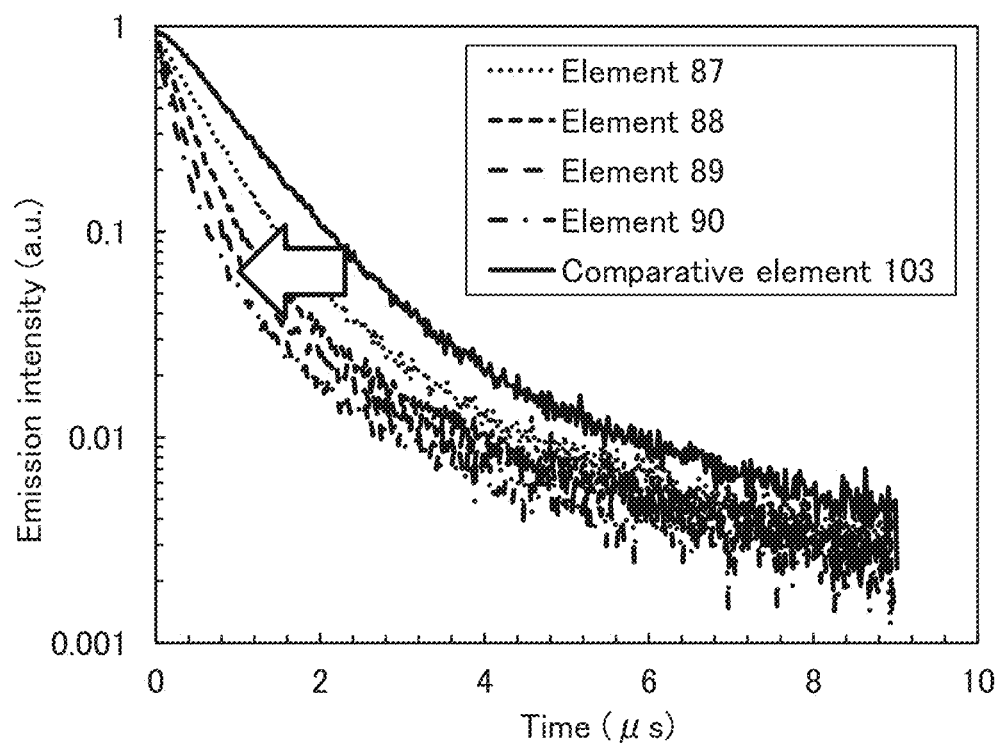

FIG. 135 A diagram showing emission lifetime measurement results of light-emitting elements in Example.

Figure 136:
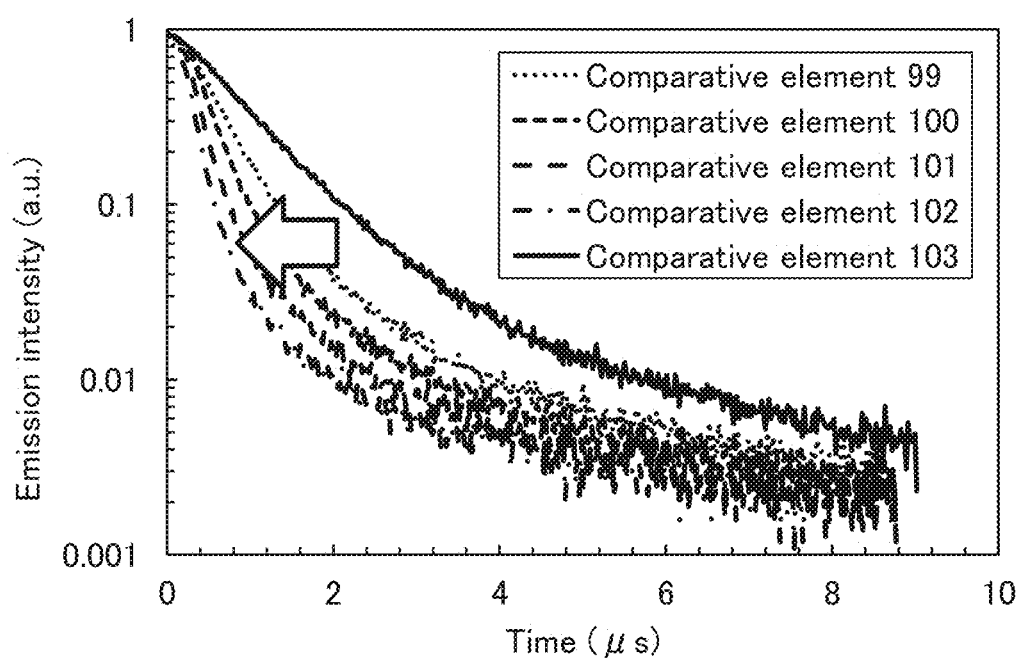

FIG. 136 A diagram showing emission lifetime measurement results of comparative light-emitting elements in Example.

Figure 137:
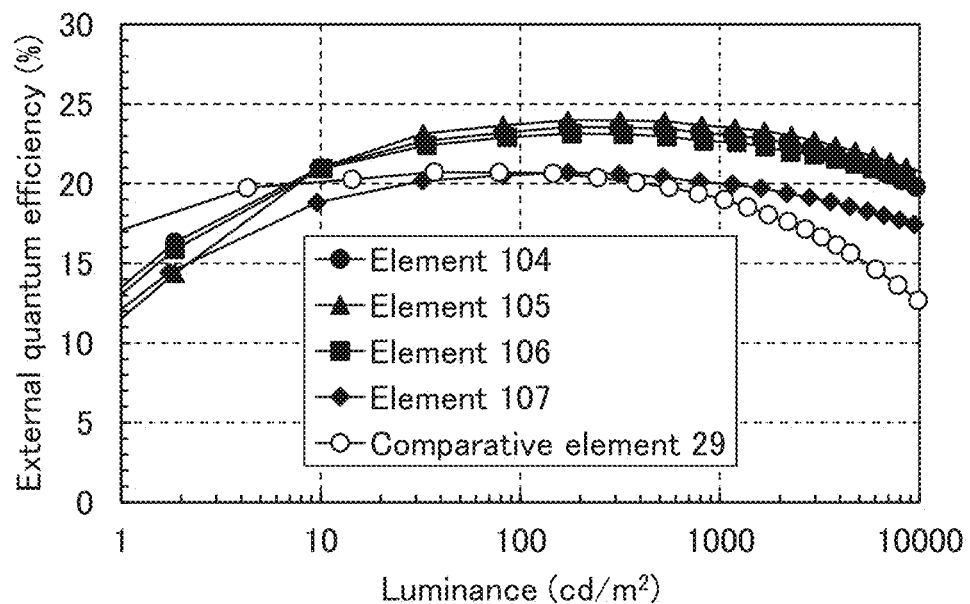

FIG. 137 A diagram showing external quantum efficiency-luminance characteristics of light-emitting elements in Example.

Figure 138:
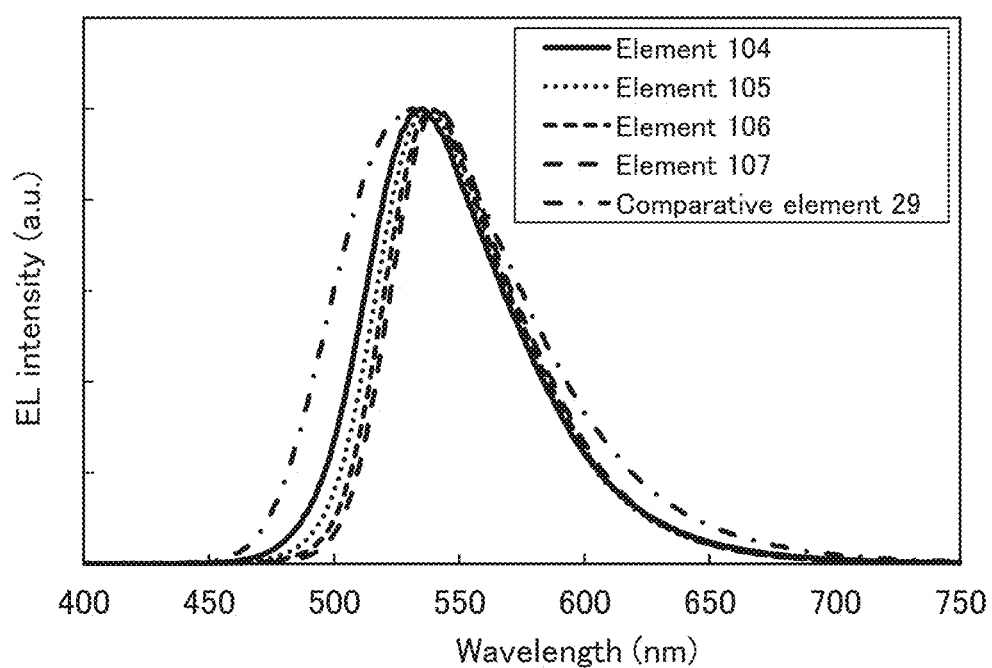

FIG. 138 A diagram showing electroluminescence spectra of light-emitting elements in Example.

Figure 139:
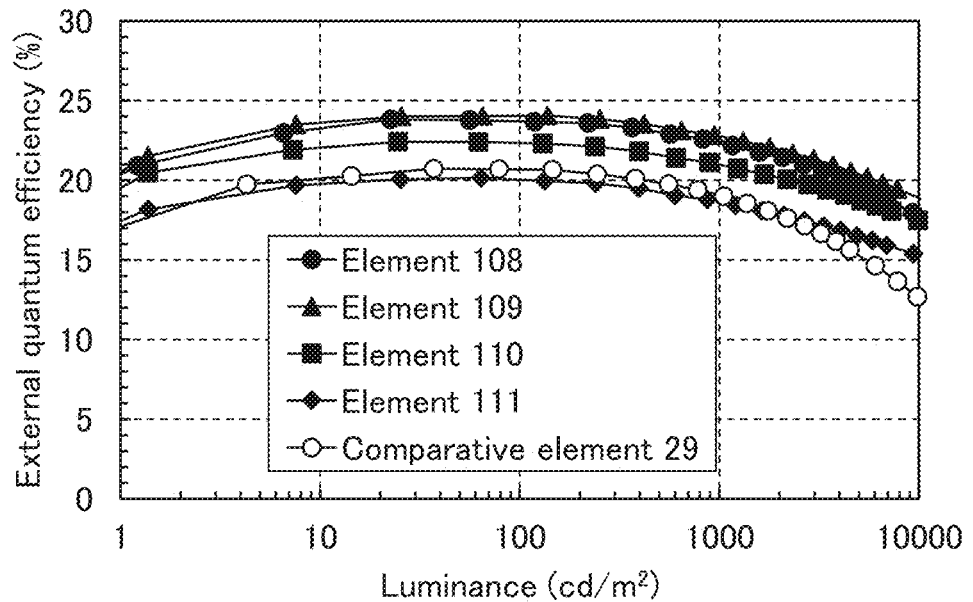

FIG. 139 A diagram showing external quantum efficiency-luminance characteristics of light-emitting elements in Example.

Figure 140:
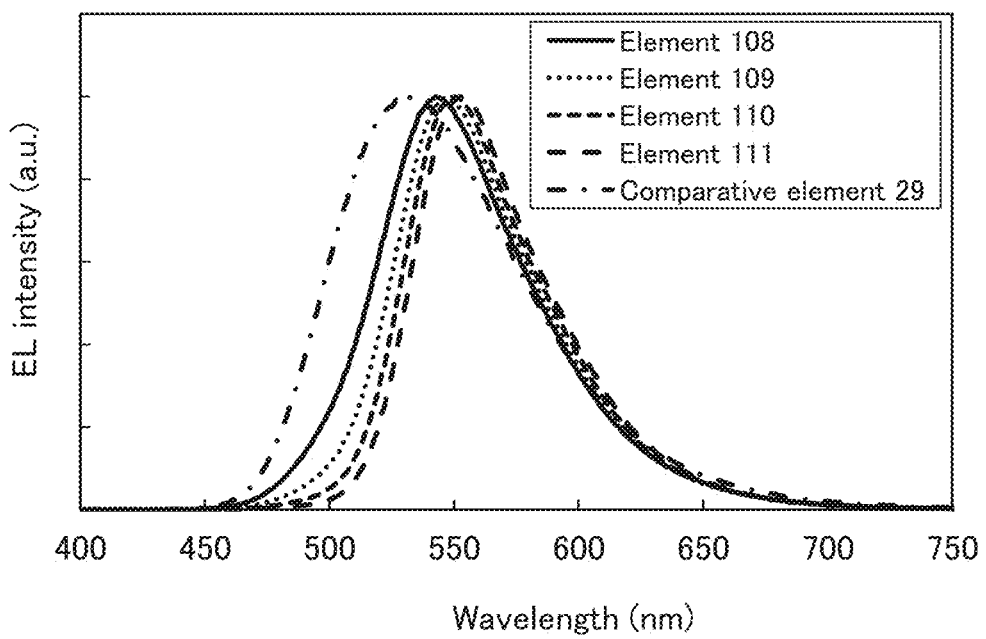

FIG. 140 A diagram showing electroluminescence spectra of light-emitting elements in Example.

Figure 141:
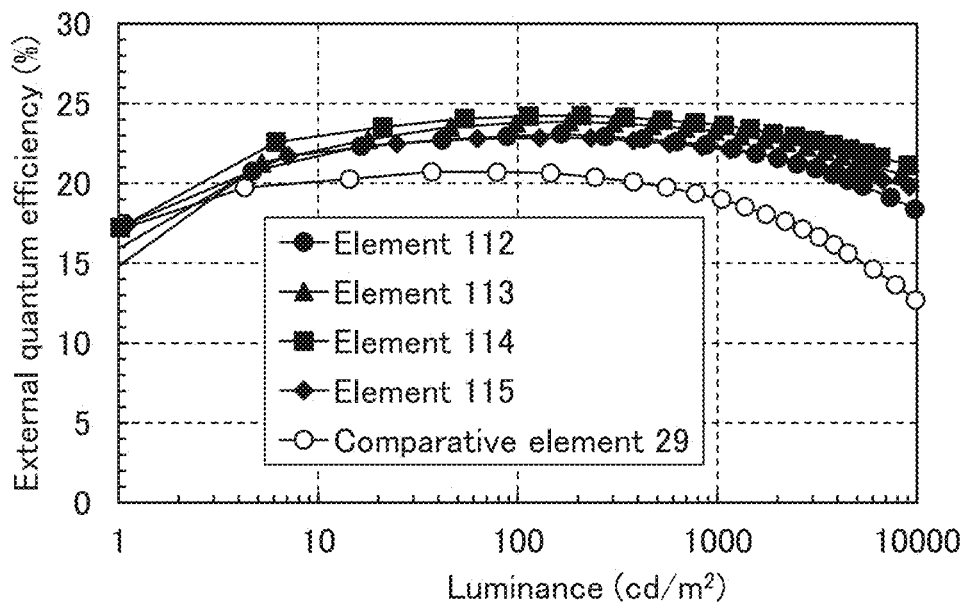

FIG. 141 A diagram showing external quantum efficiency-luminance characteristics of light-emitting elements in Example.

Figure 142:
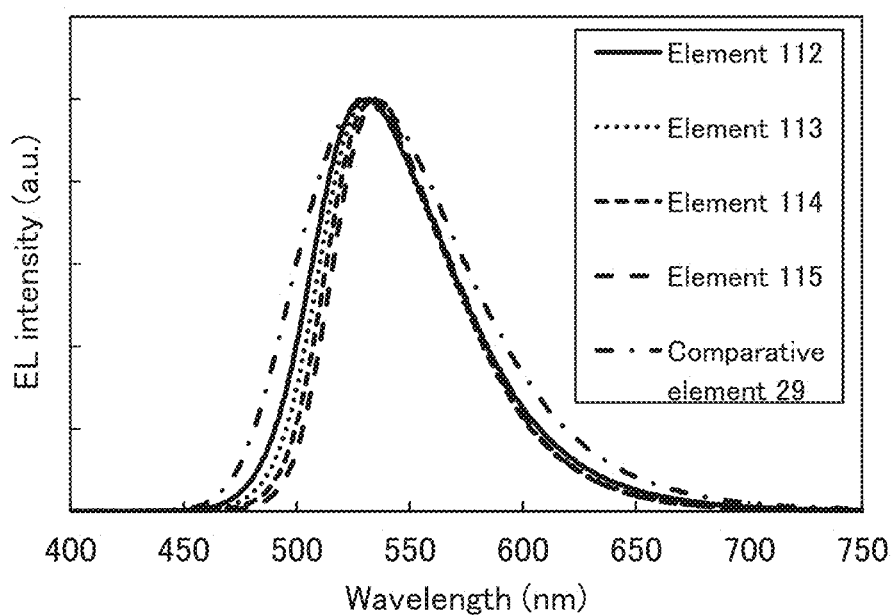

FIG. 142 A diagram showing electroluminescence spectra of light-emitting elements in Example.

Figure 143:
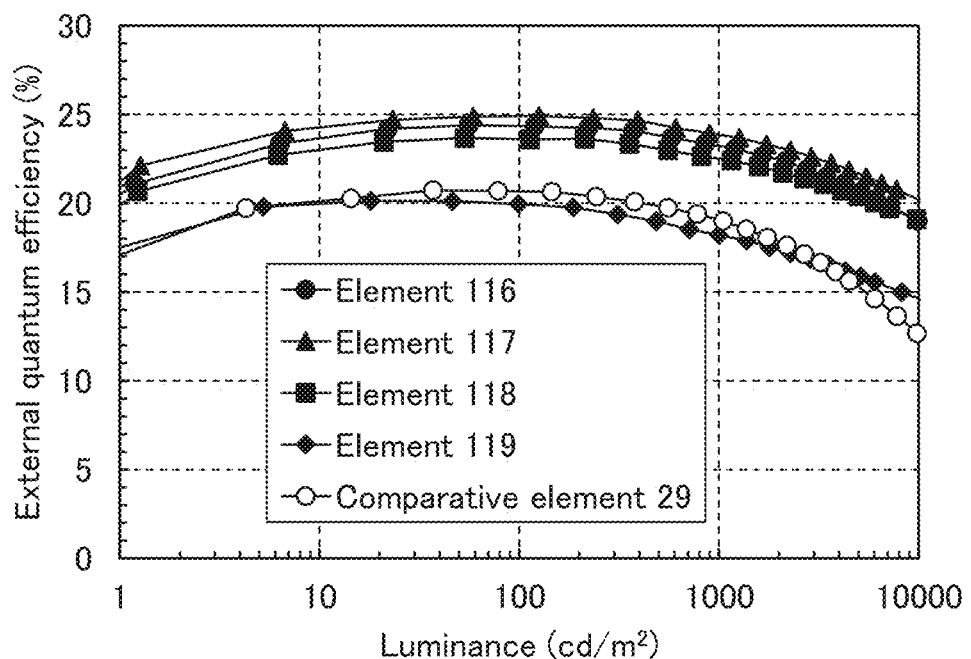

FIG. 143 A diagram showing external quantum efficiency-luminance characteristics of light-emitting elements in Example.

Figure 144:
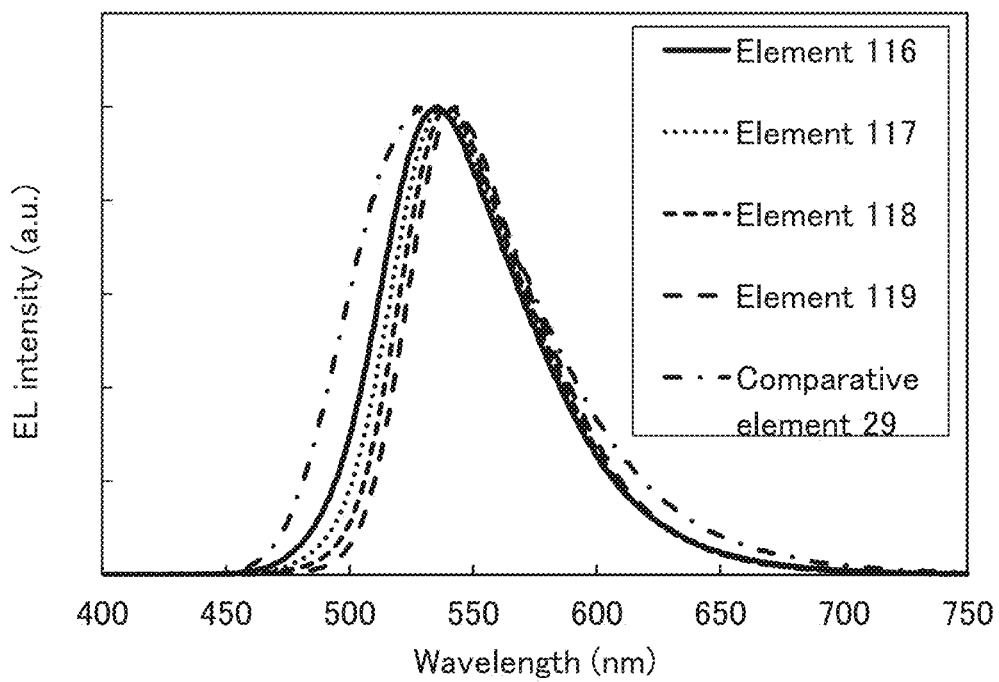

FIG. 144 A diagram showing electroluminescence spectra of light-emitting elements in Example.

Figure 145:
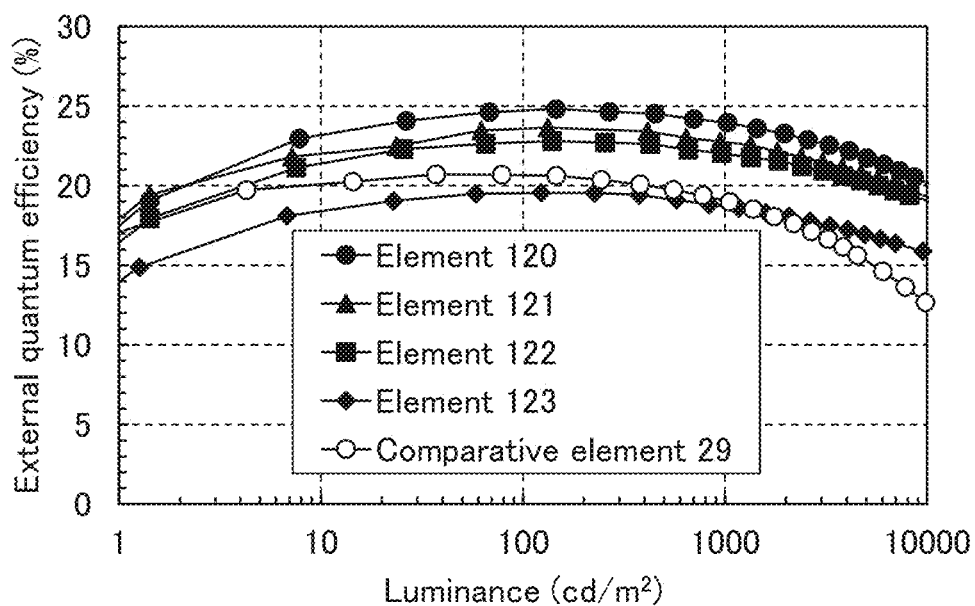

FIG. 145 A diagram showing external quantum efficiency-luminance characteristics of light-emitting elements in Example.

Figure 146:
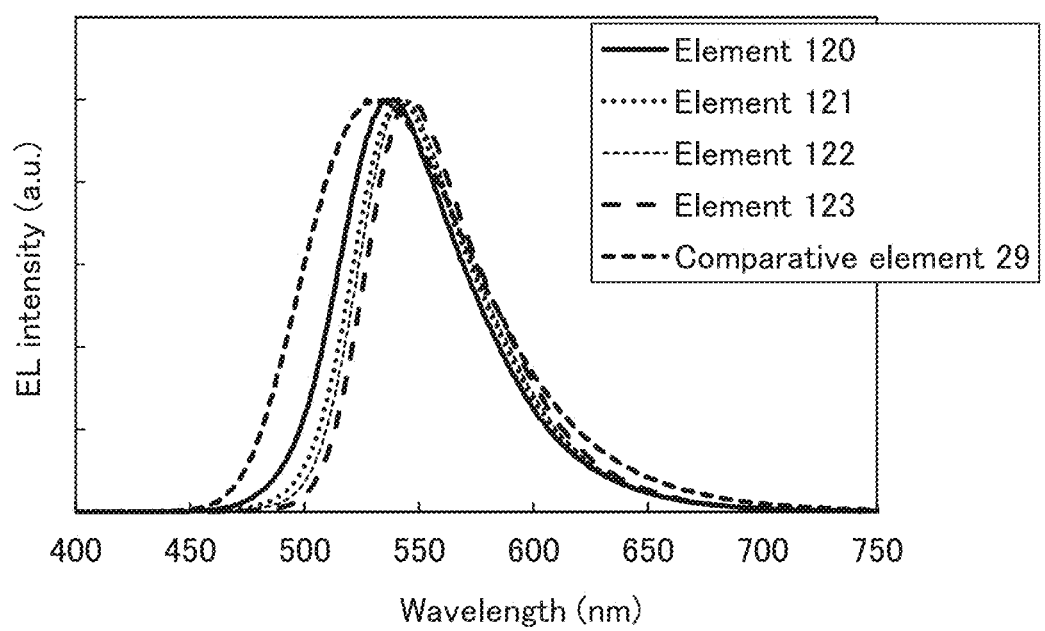

FIG. 146 A diagram showing electroluminescence spectra of light-emitting elements in Example.

Figure 147:
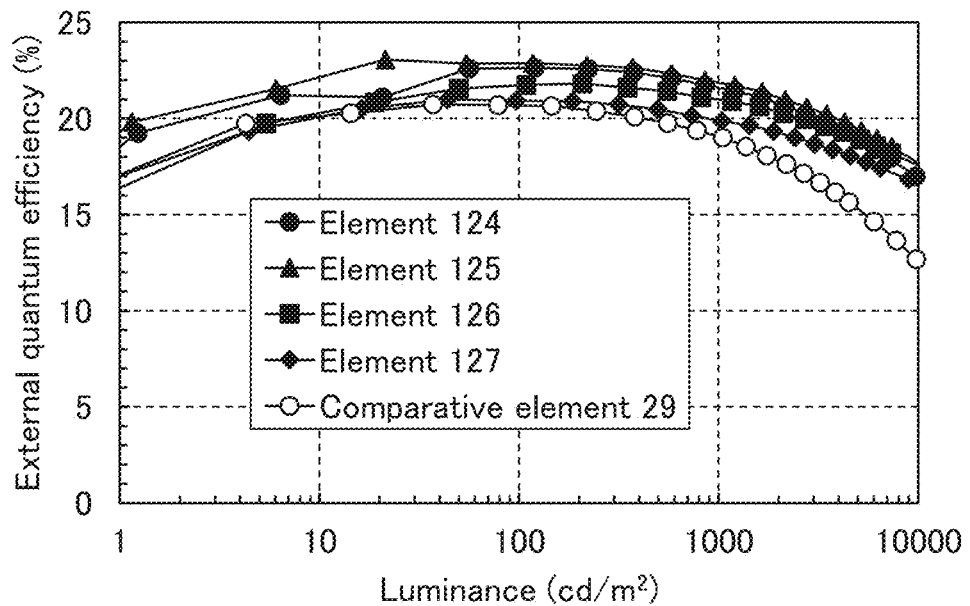

FIG. 147 A diagram showing external quantum efficiency-luminance characteristics of light-emitting elements in Example.

Figure 148:
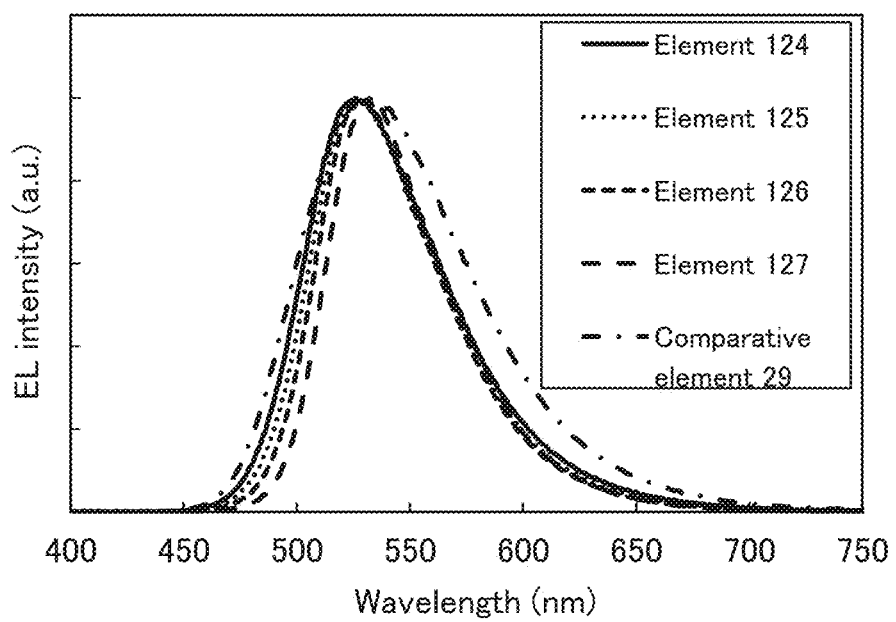

FIG. 148 A diagram showing electroluminescence spectra of light-emitting elements in Example.

Figure 149:
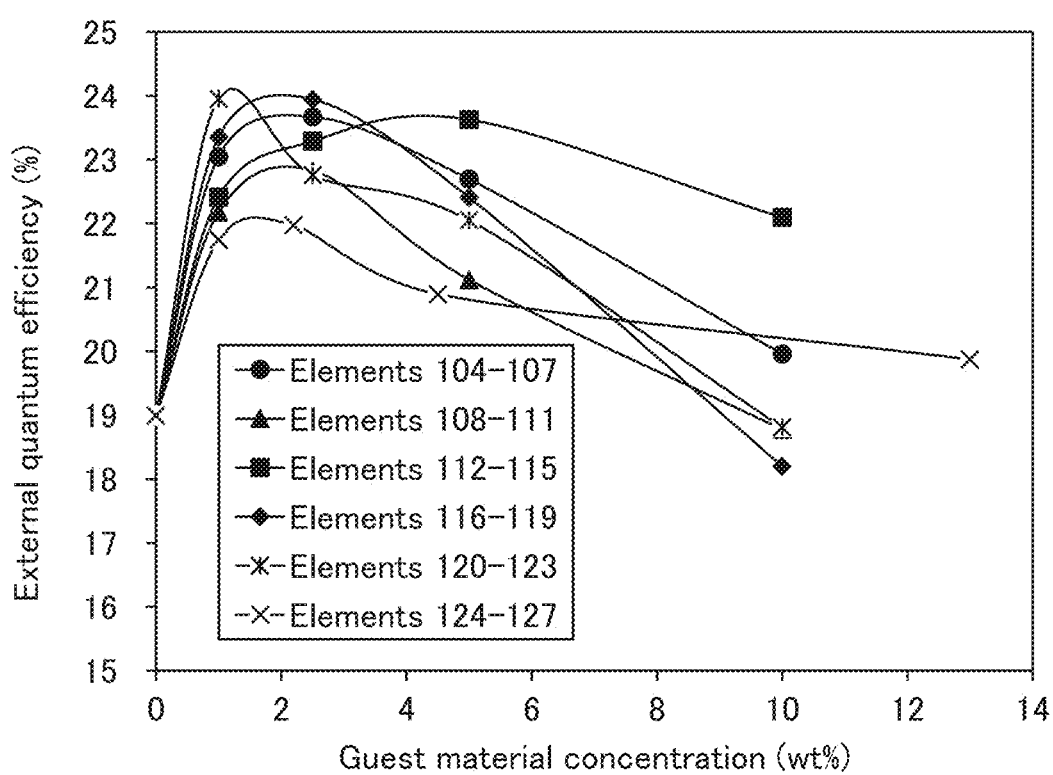

FIG. 149 A diagram showing the relation between external quantum efficiency and guest material concentration in Example.

Figure 150:
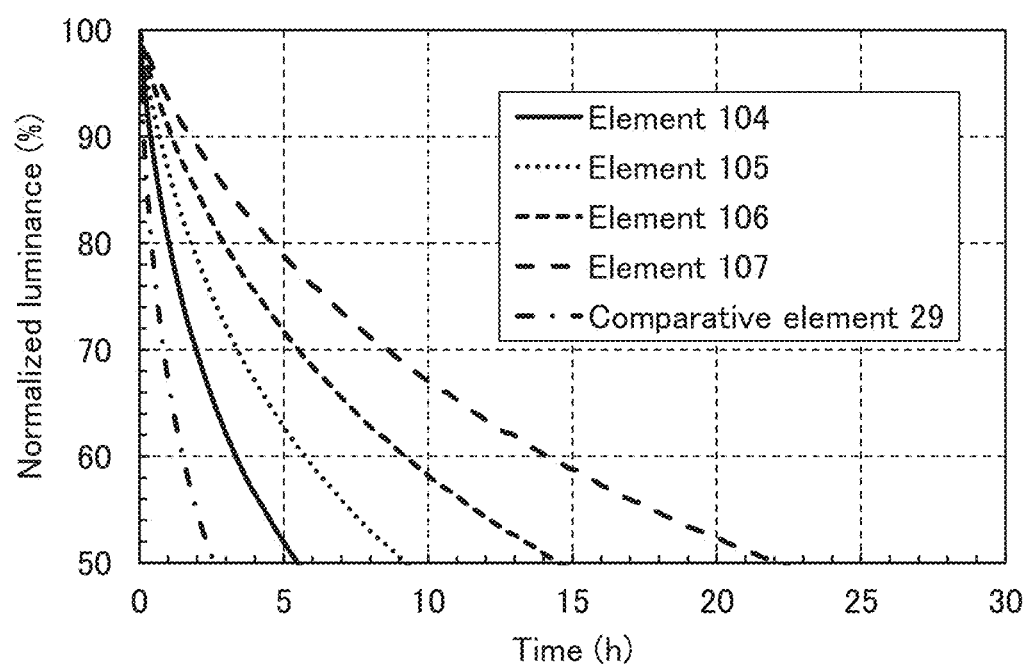

FIG. 150 A diagram showing reliability measurement results of light-emitting elements in Example.

Figure 151:
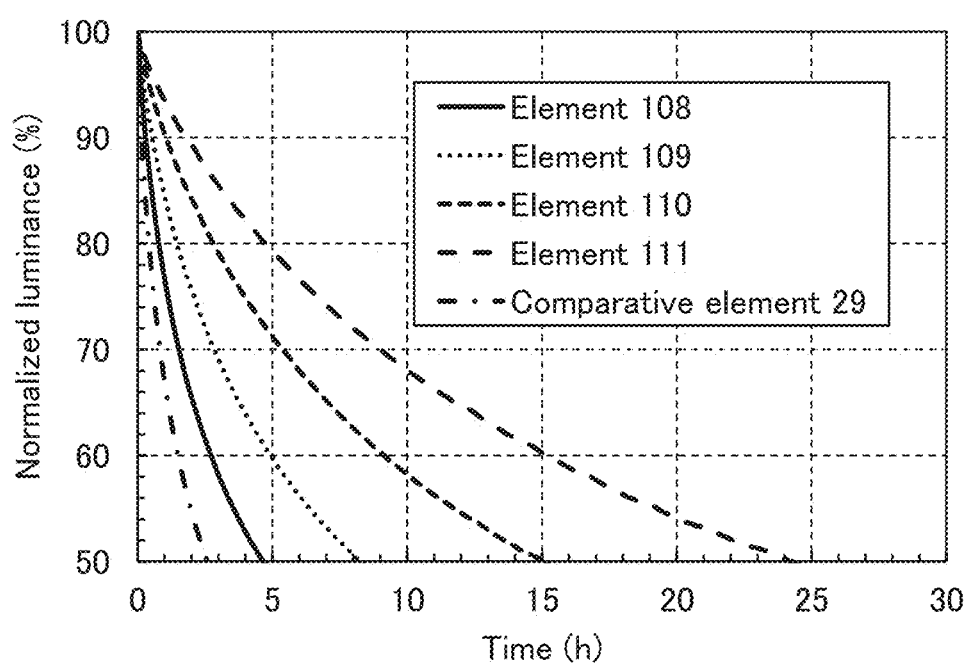

FIG. 151 A diagram showing reliability measurement results of light-emitting elements in Example.

Figure 152:
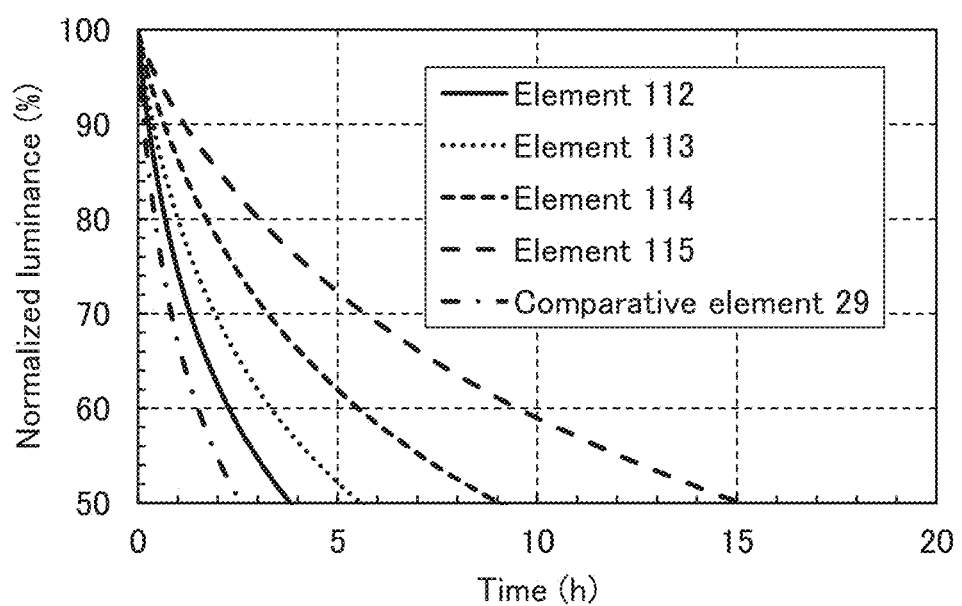

FIG. 152 A diagram showing reliability measurement results of light-emitting elements in Example.

Figure 153:
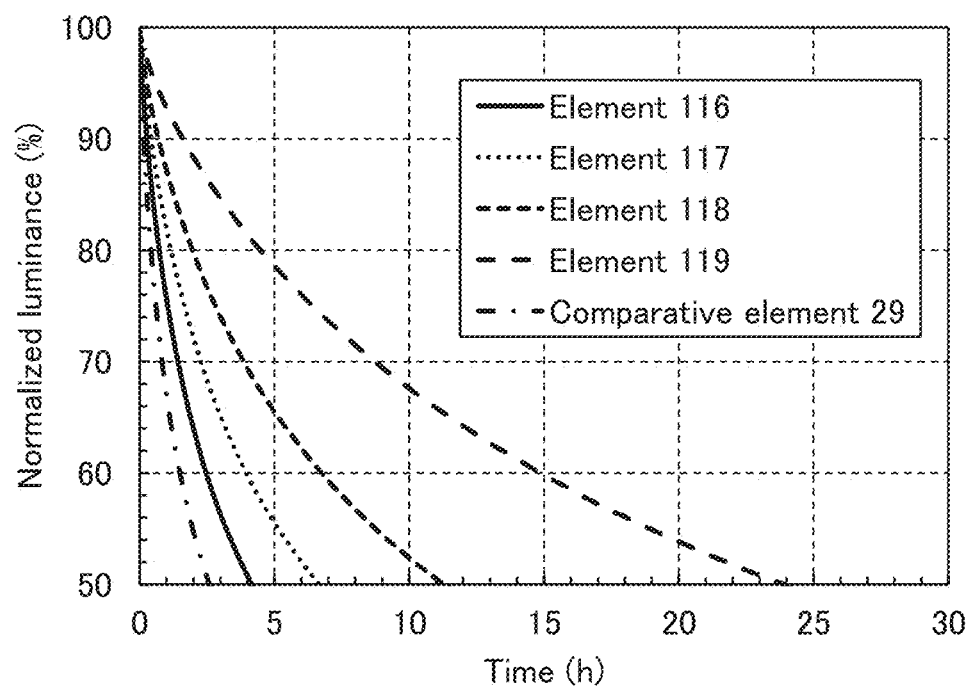

FIG. 153 A diagram showing reliability measurement results of light-emitting elements in Example.

Figure 154:
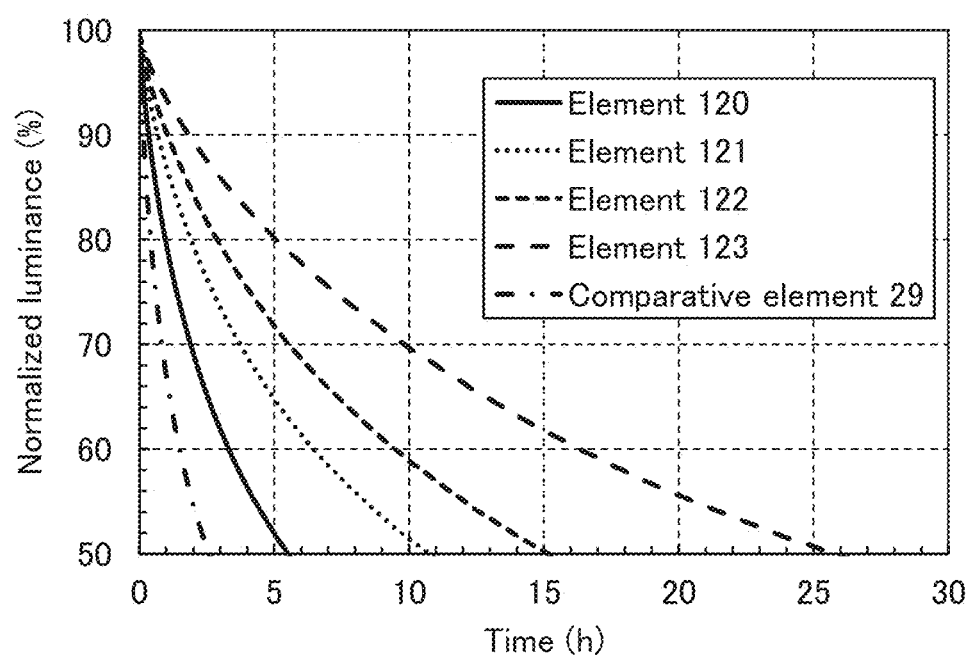

FIG. 154 A diagram showing reliability measurement results of light-emitting elements in Example.

Figure 155:
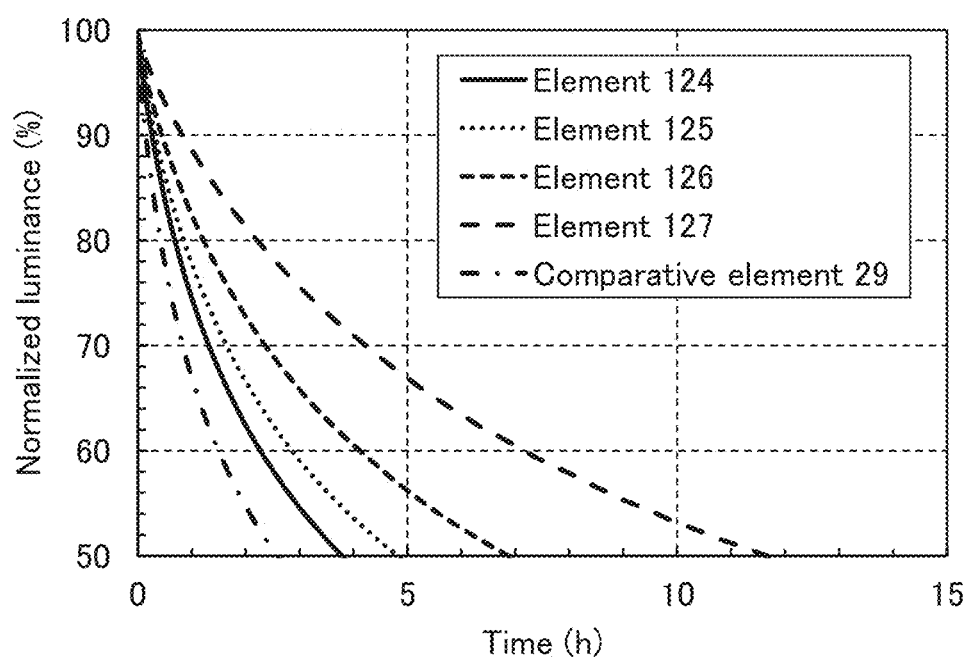

FIG. 155 A diagram showing reliability measurement results of light-emitting elements in Example.

Figure 156:
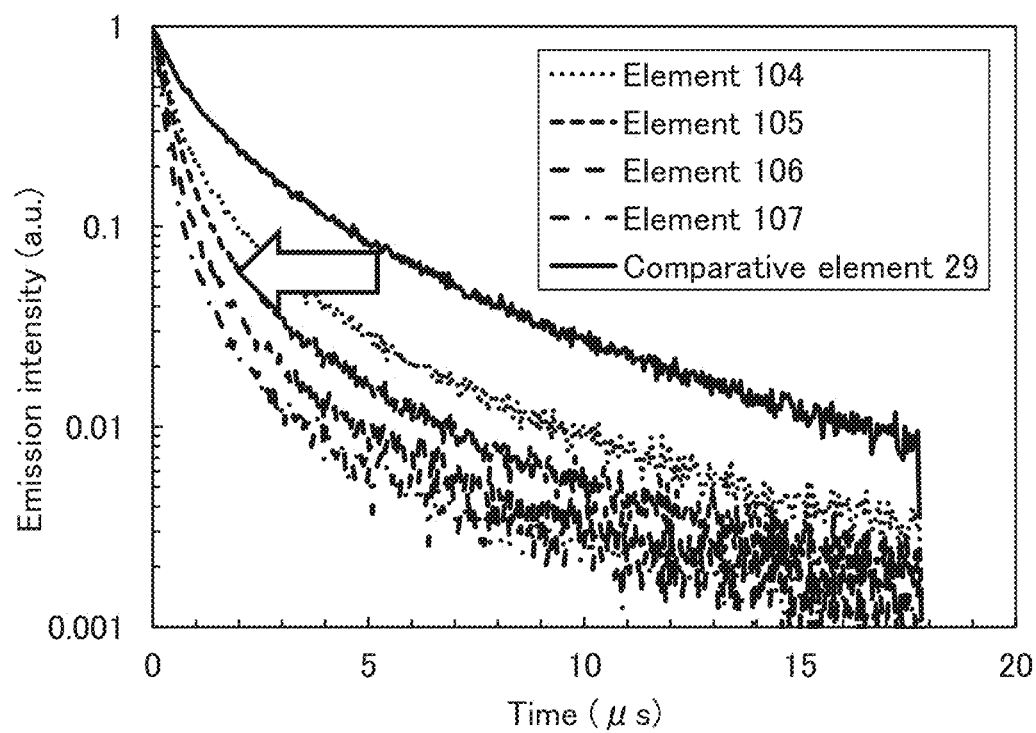

FIG. 156 A diagram showing emission lifetime measurement results of light-emitting elements in Example.

Figure 157:
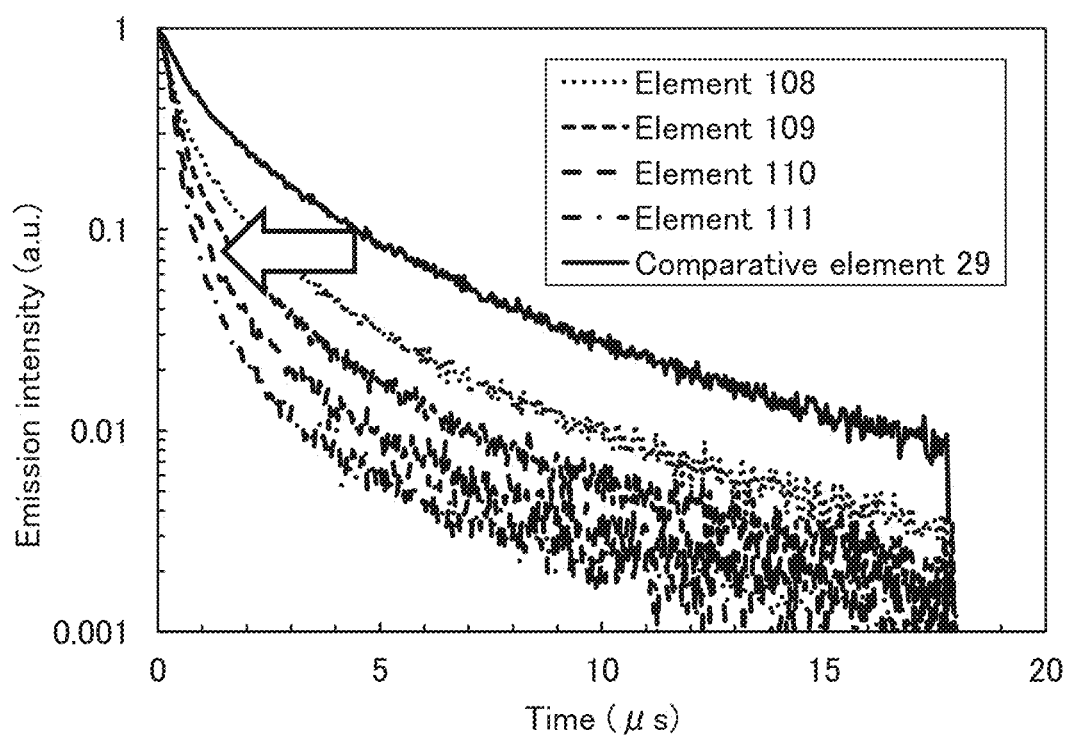

FIG. 157 A diagram showing emission lifetime measurement results of light-emitting elements in Example.

Figure 158:
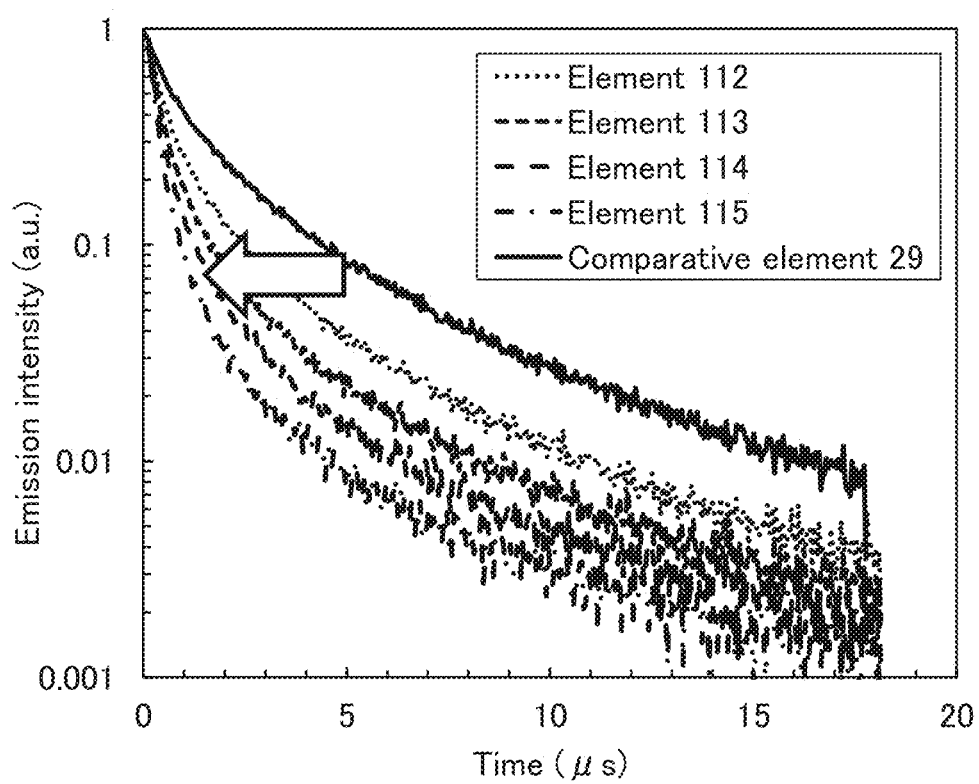

FIG. 158 A diagram showing emission lifetime measurement results of light-emitting elements in Example.

Figure 159:
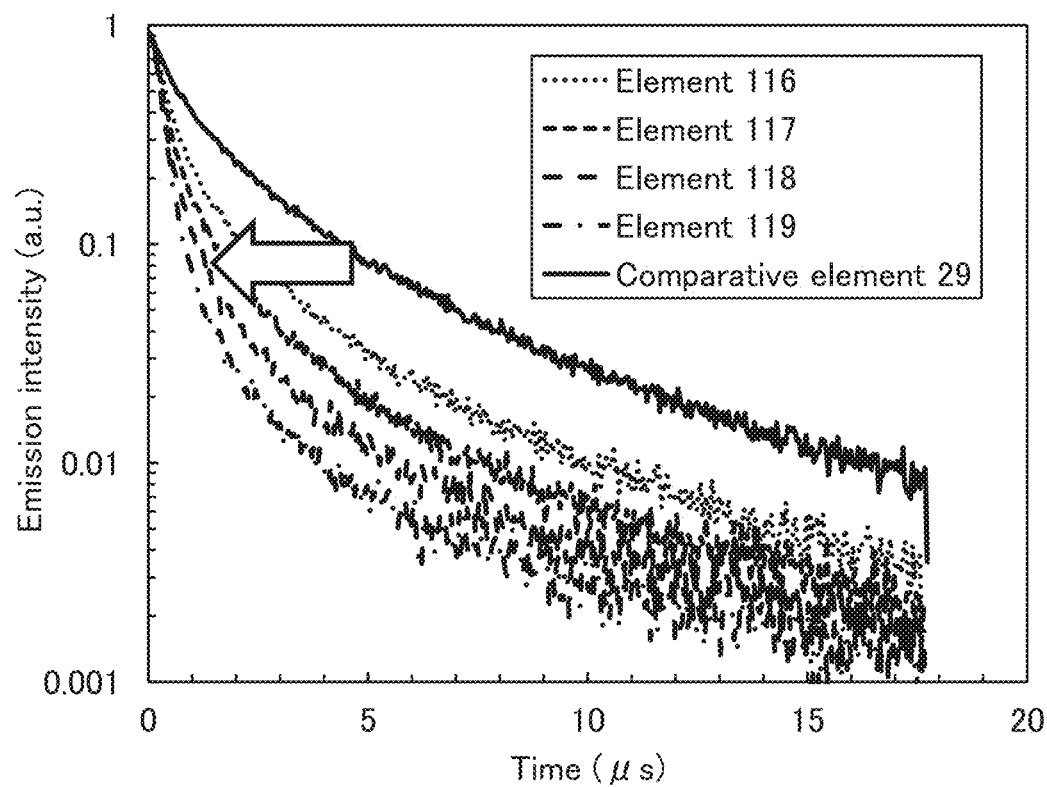

FIG. 159 A diagram showing emission lifetime measurement results of light-emitting elements in Example.

Figure 160:
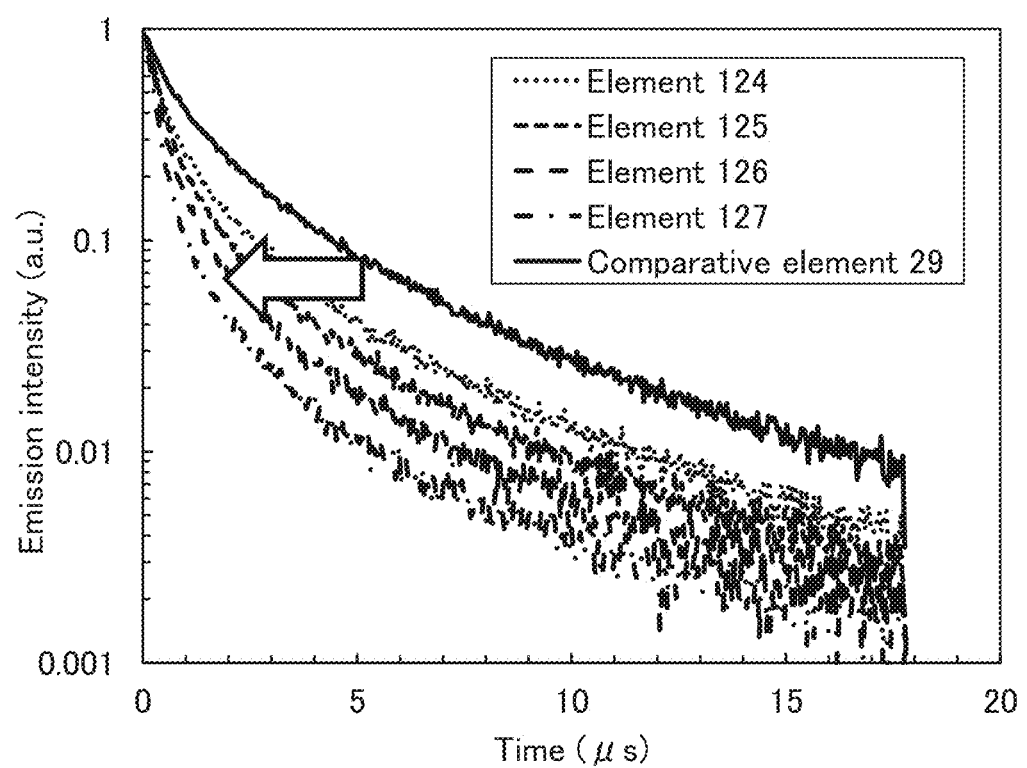

FIG. 160 A diagram showing emission lifetime measurement results of light-emitting elements in Example.

Figure 161:
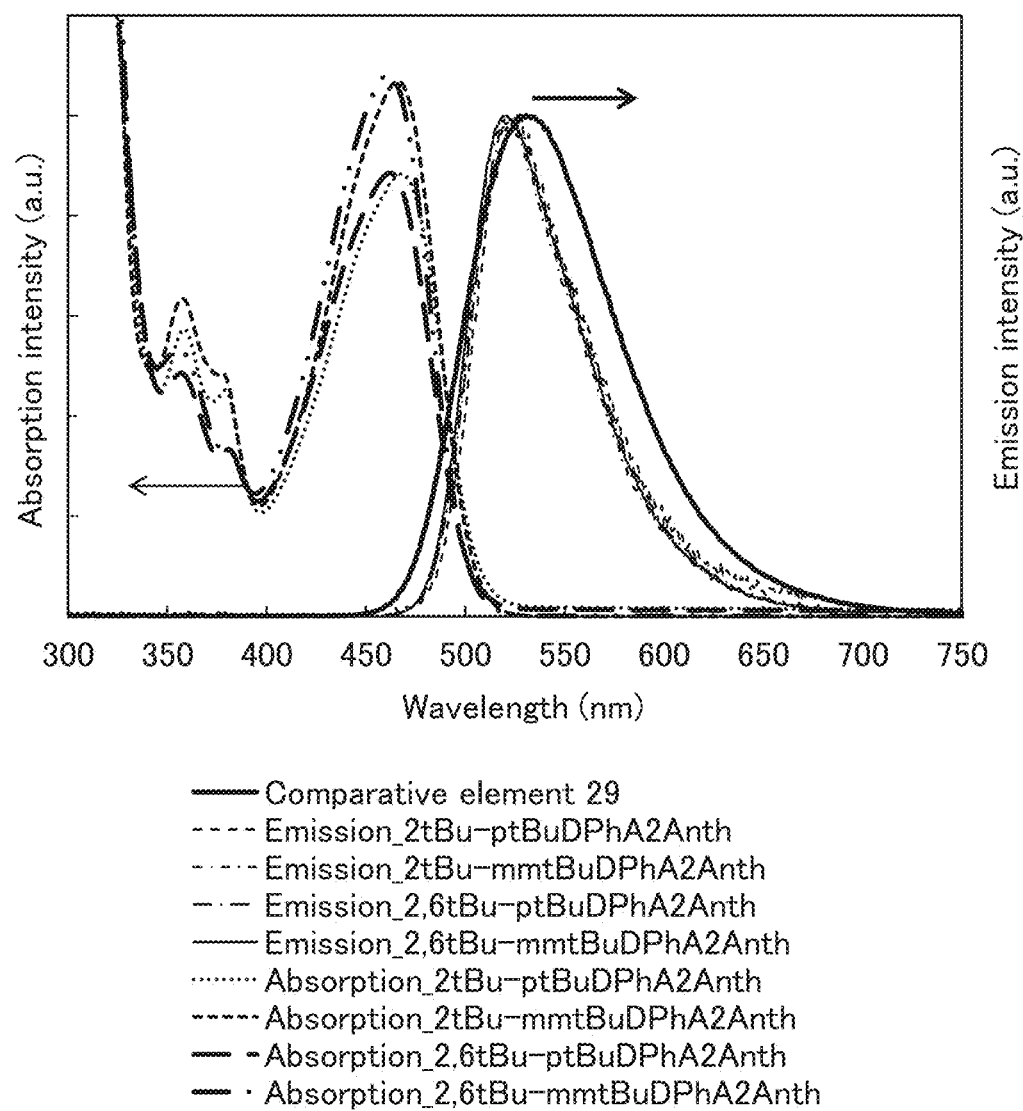

FIG. 161 A diagram showing the relation between energy donor emission and guest material absorption in Example.

Figure 162:
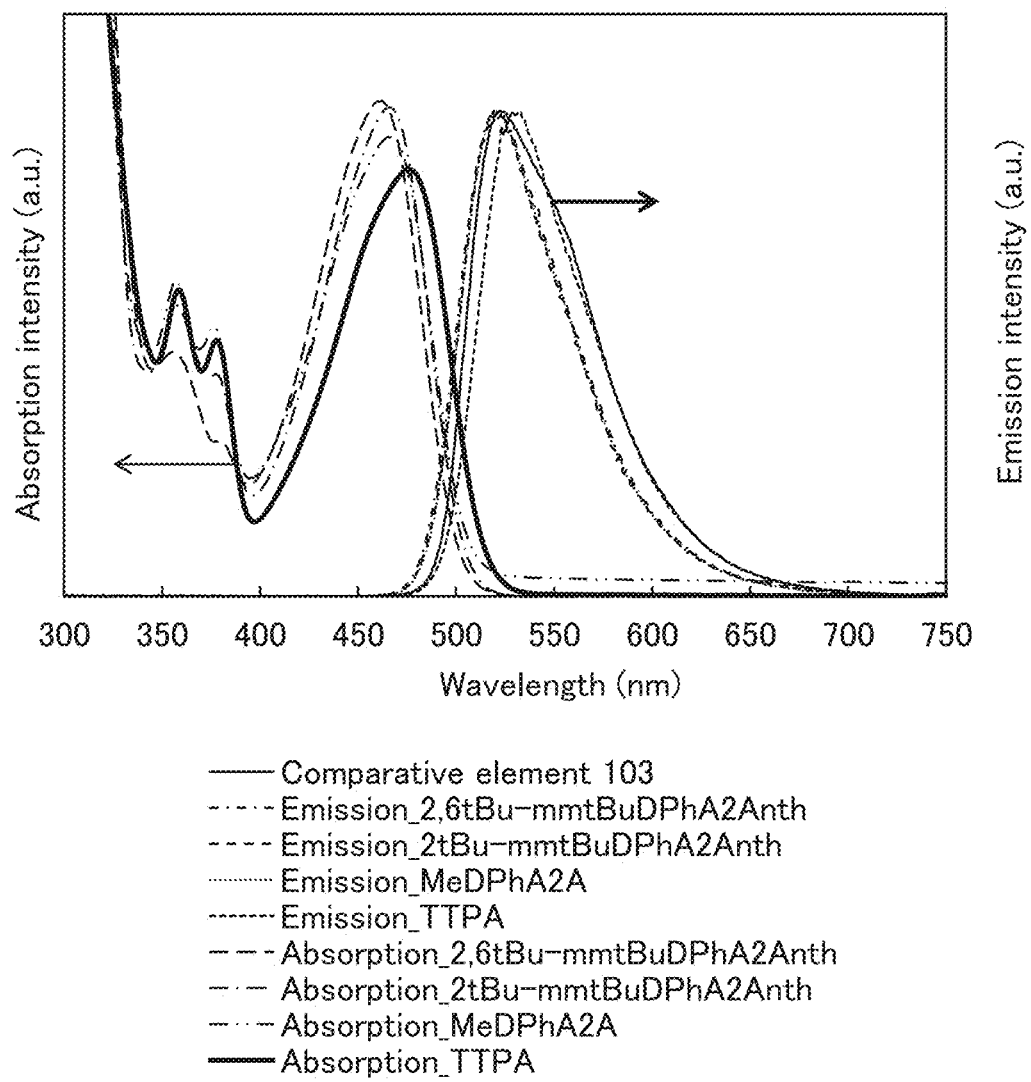

FIG. 162 A diagram showing the relation between energy donor emission and guest material absorption in Example.

Figure 163:
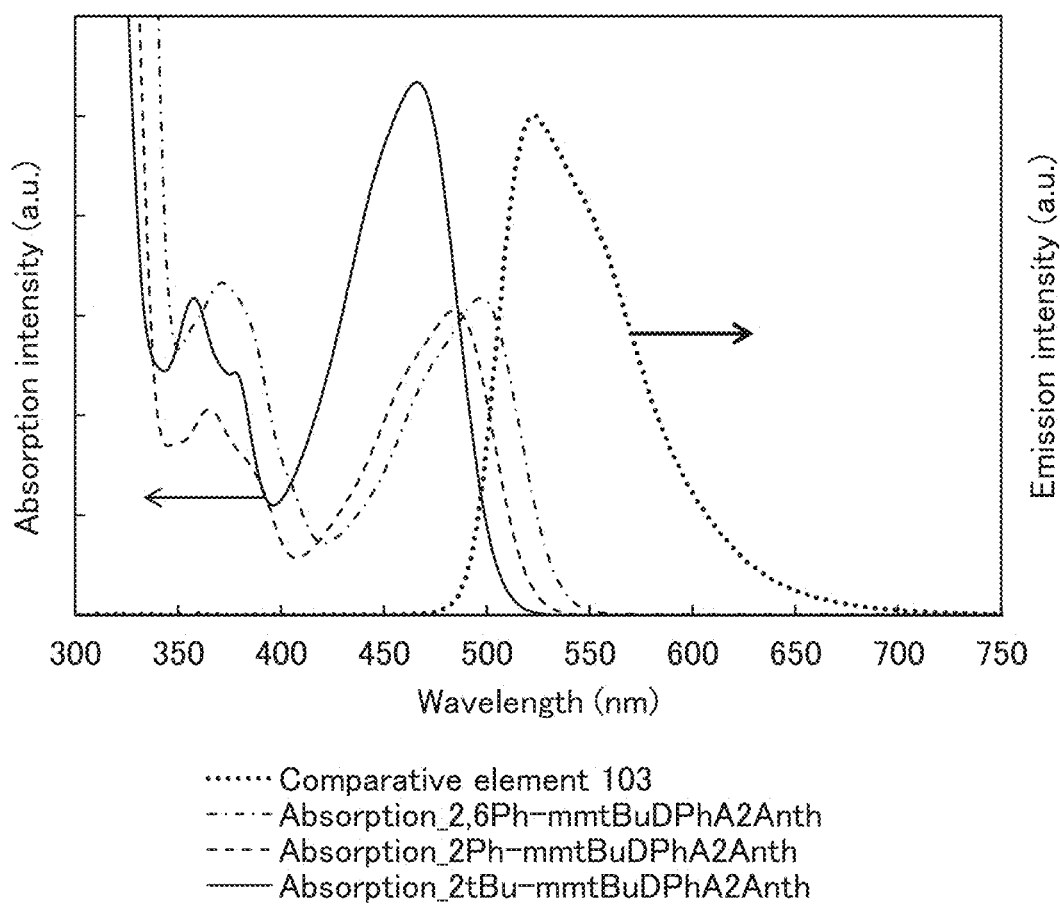

FIG. 163 A diagram showing the relation between energy donor emission and guest material absorption in Example.

Figure 164A:
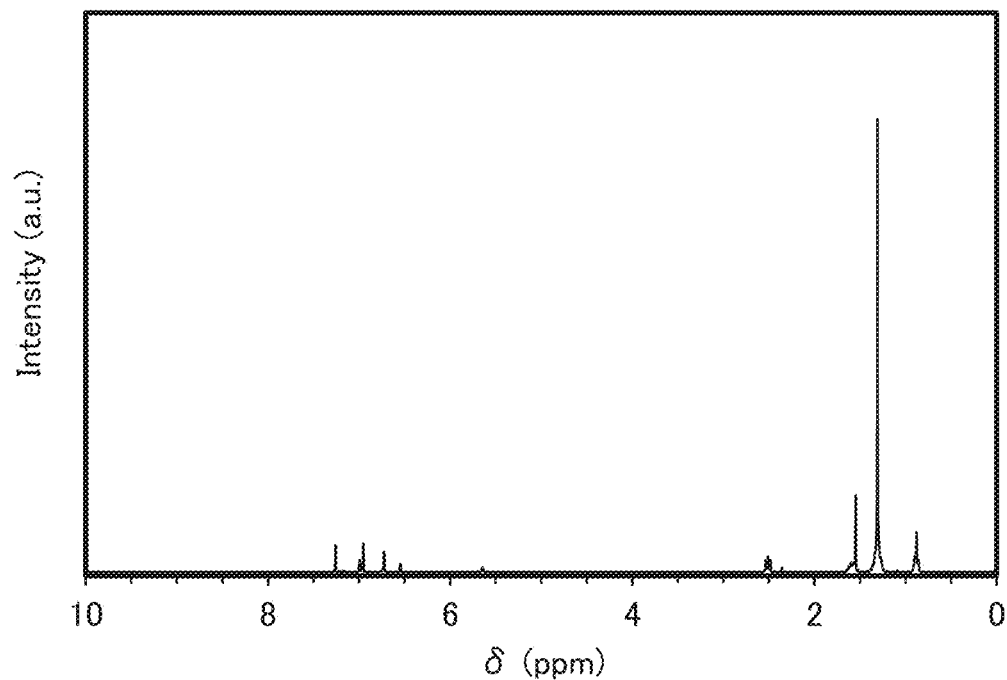
Figure 164B:
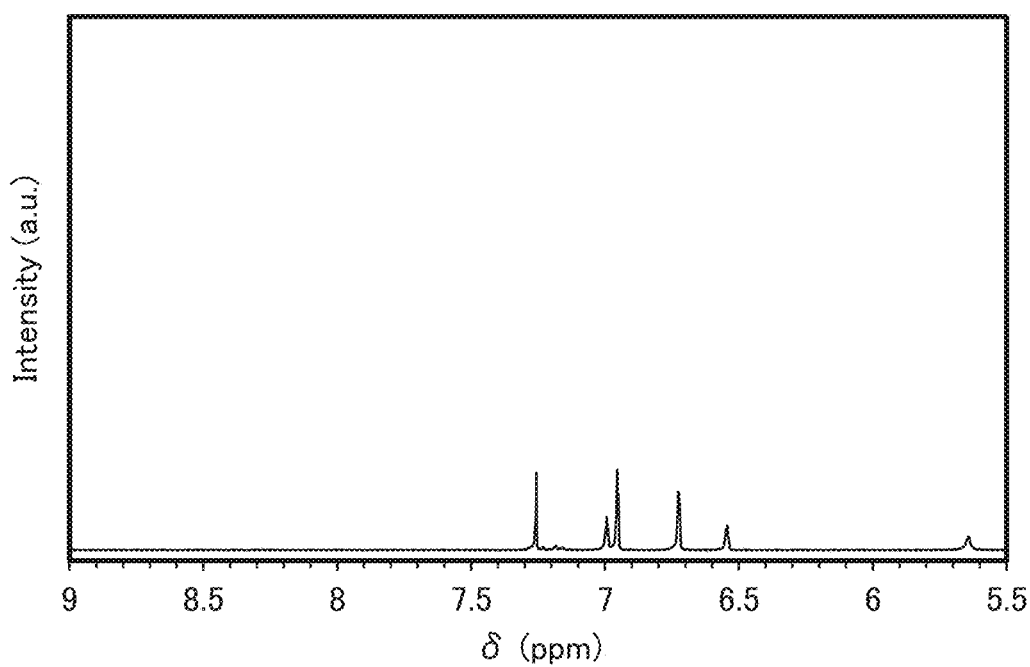

FIGS. 164A and 164B Diagrams showing NMR charts of a compound in Example.

Figure 165:
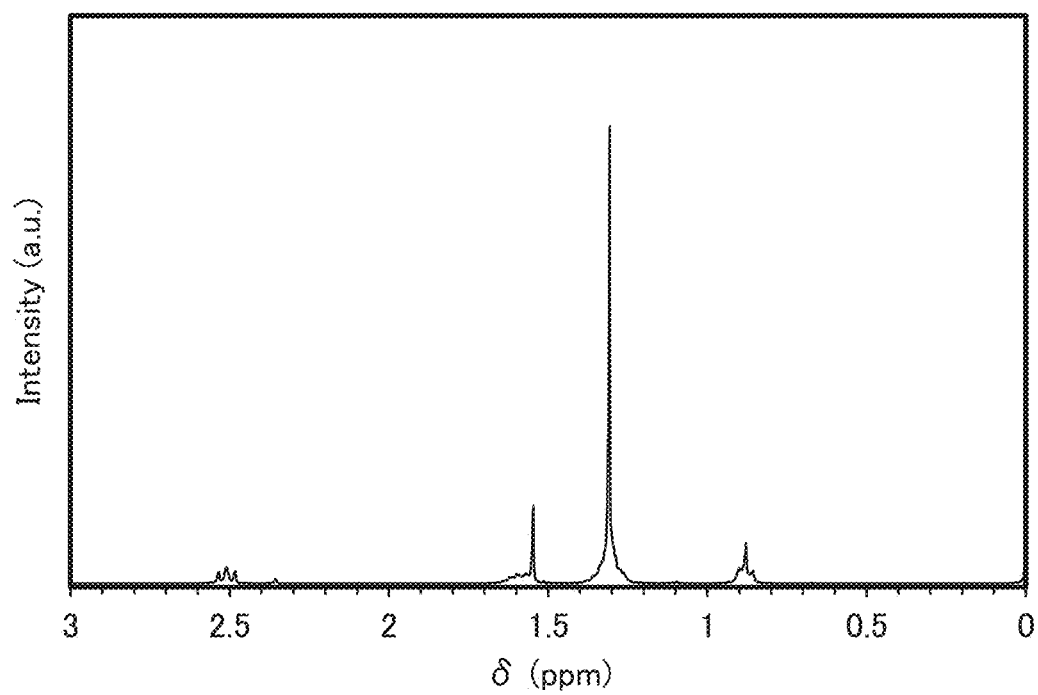

FIG. 165 A diagram showing an NMR chart of a compound in Example.

Figure 166A:
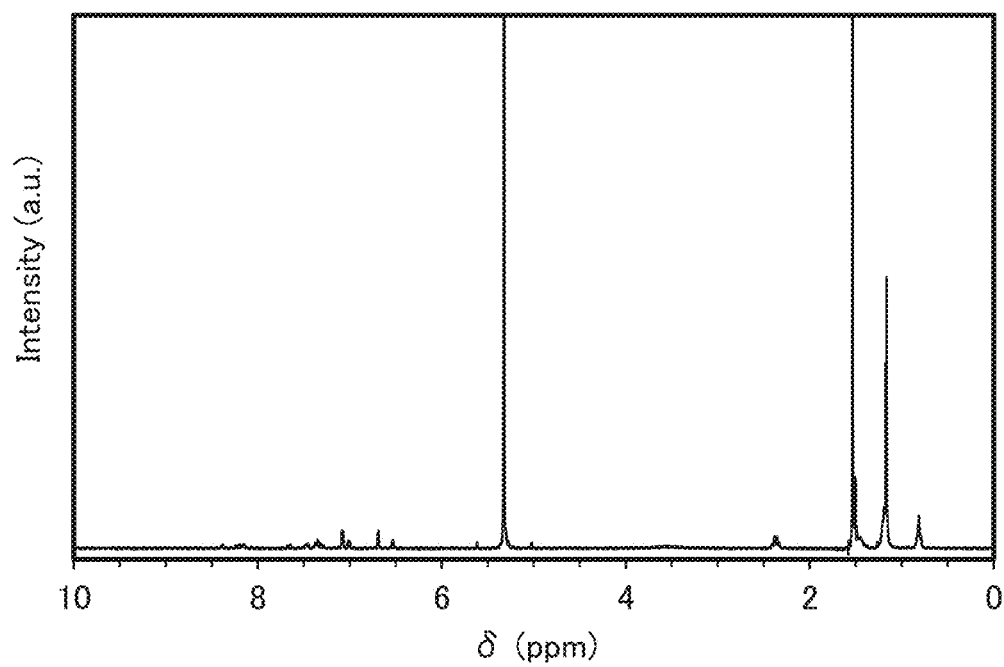
Figure 166B:
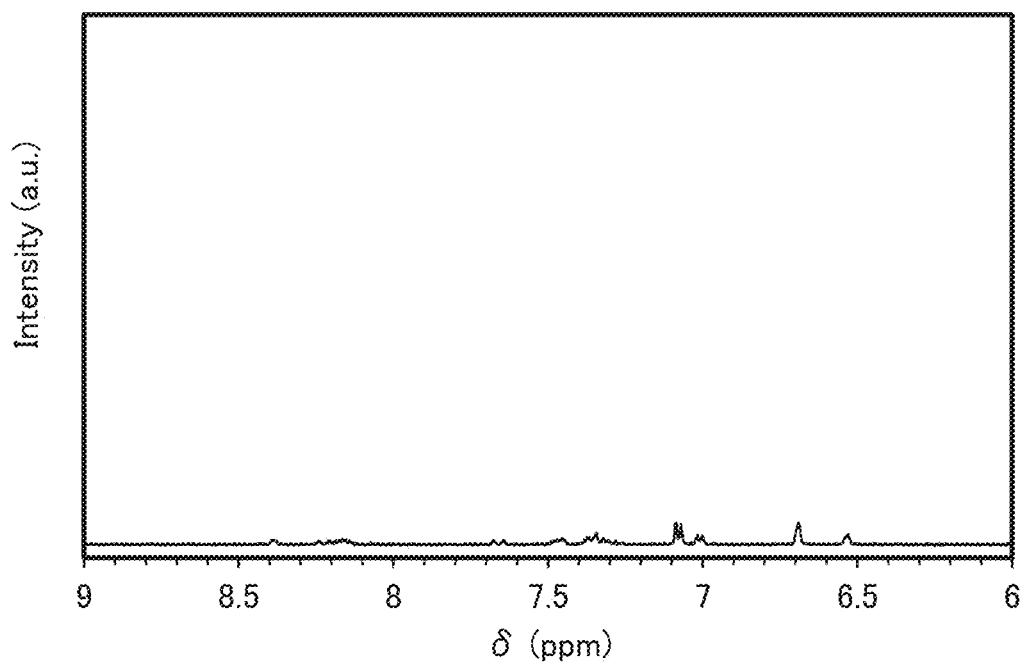

FIGS. 166A and 166B Diagrams showing NMR charts of a compound in Example.

Figure 167:
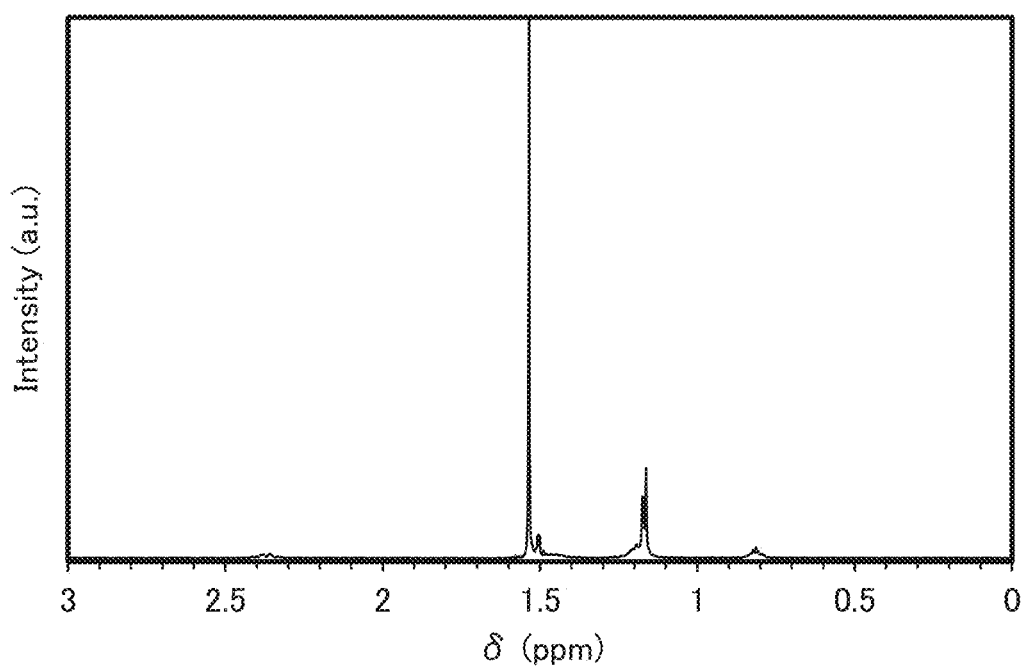

FIG. 167 A diagram showing an NMR chart of a compound in Example.

Figure 168:
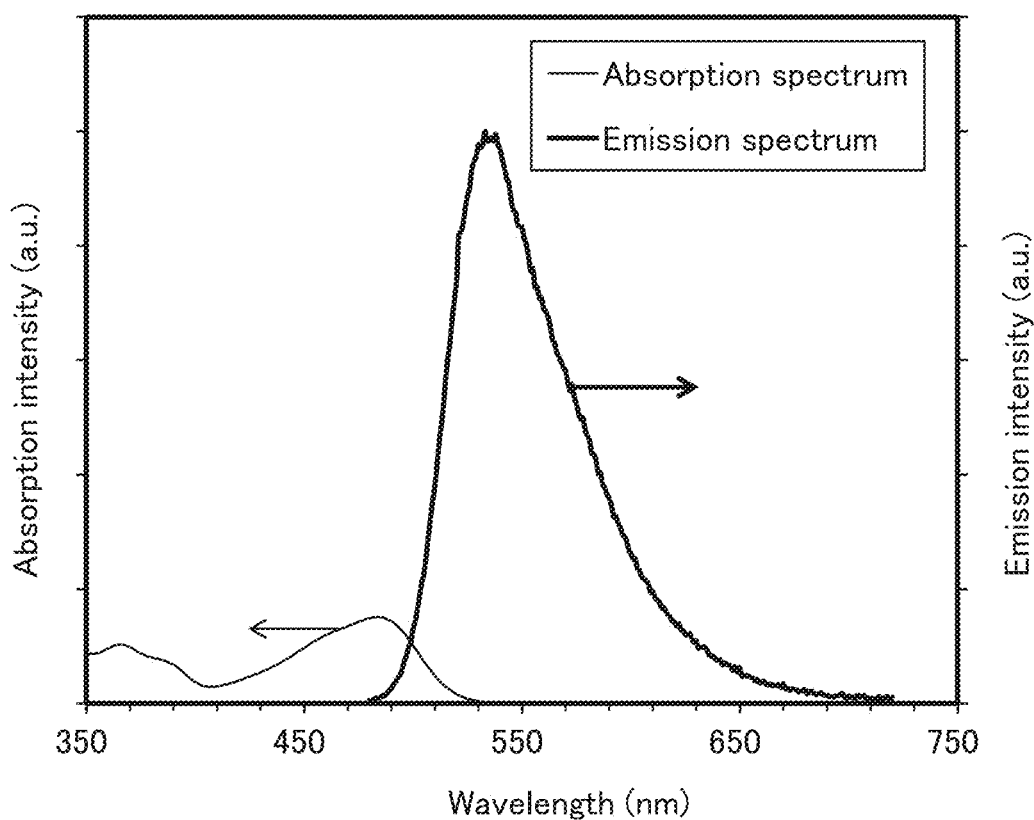

FIG. 168 A diagram showing absorption and emission spectra of a compound in Example.

Figure 169:
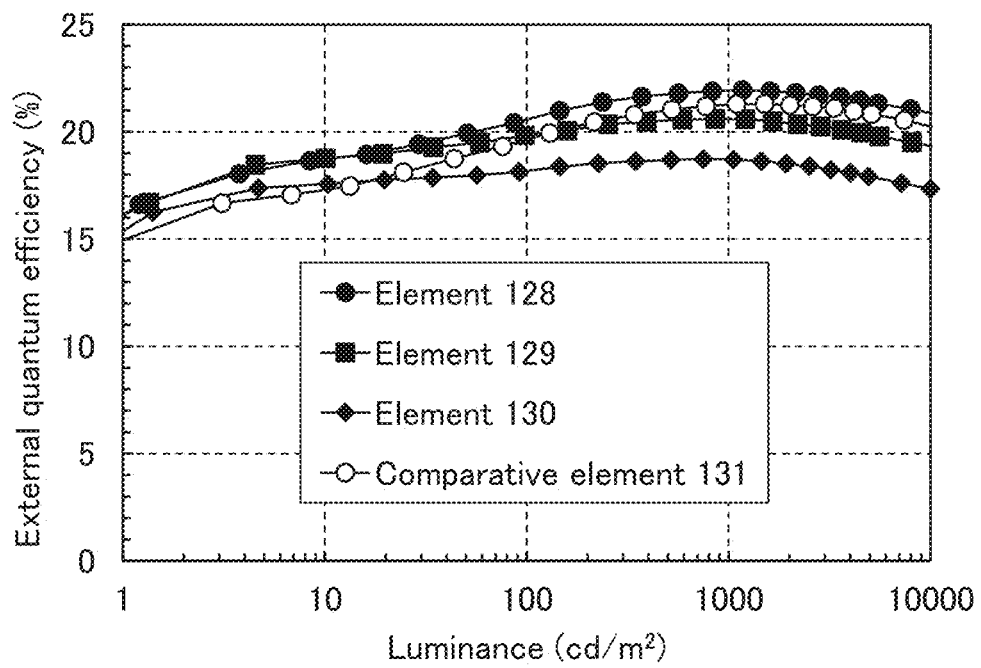

FIG. 169 A diagram showing external quantum efficiency-luminance characteristics of light-emitting elements in Example.

Figure 170:
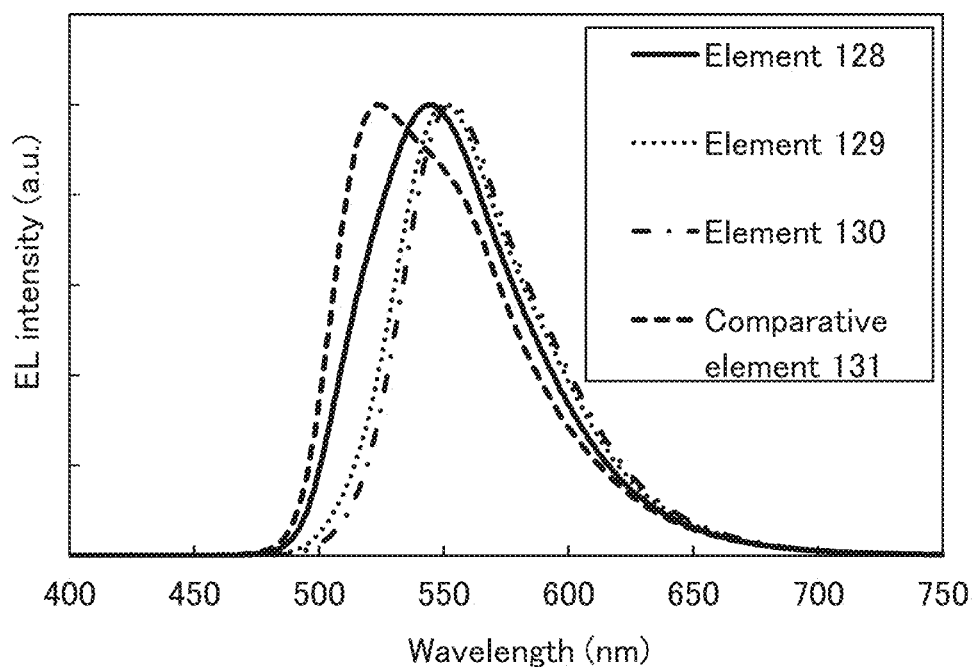

FIG. 170 A diagram showing electroluminescence spectra of light-emitting elements in Example.

Figure 171:
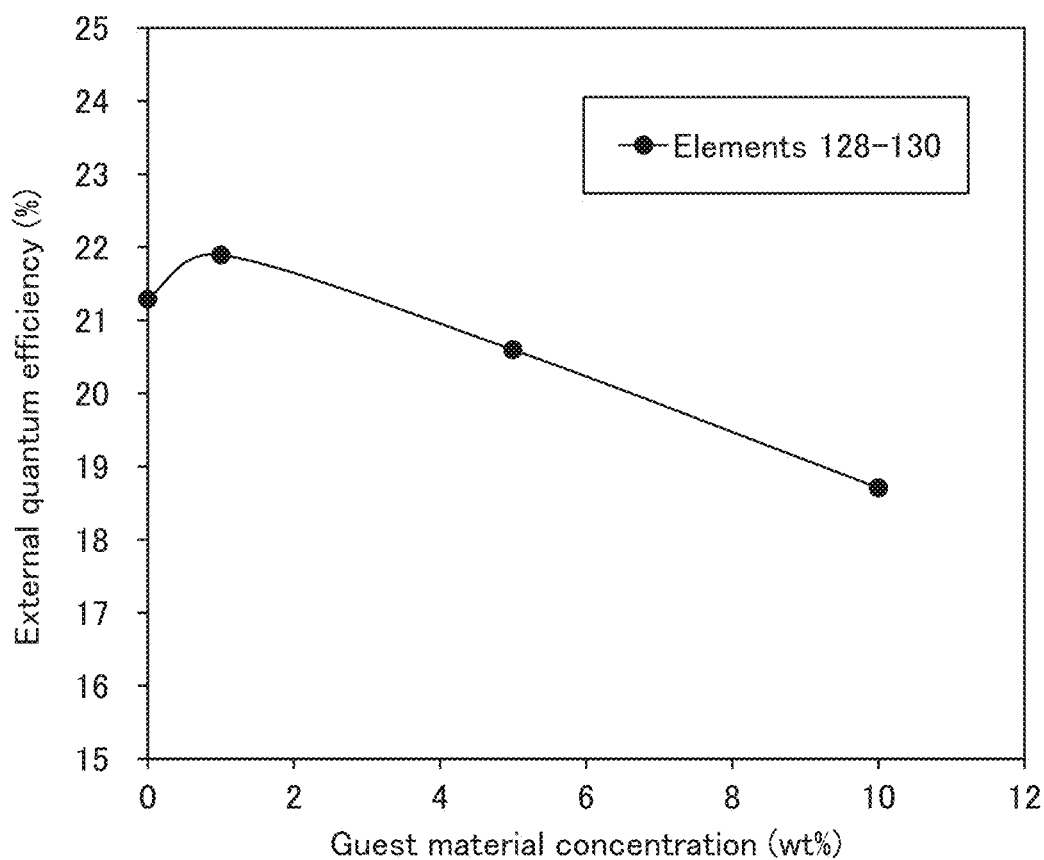

FIG. 171 A diagram showing the relation between external quantum efficiency and guest material concentration in Example.

Figure 172:
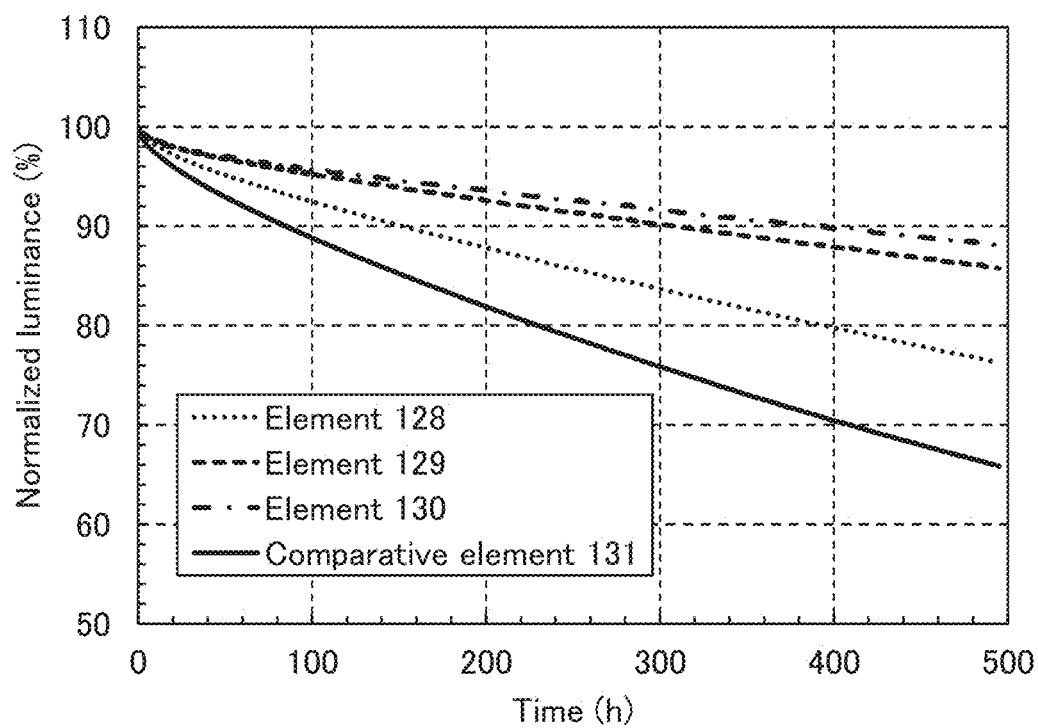

FIG. 172 A diagram showing the reliability measurement results of light-emitting elements in Example.

Figure 173:
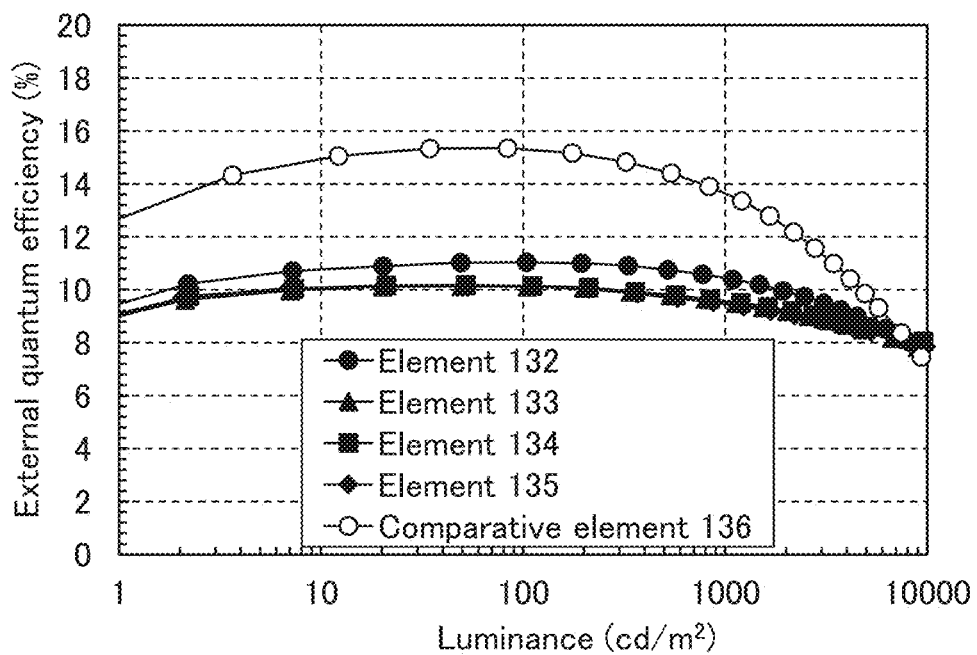

FIG. 173 A diagram showing external quantum efficiency-luminance characteristics of light-emitting elements in Example.

Figure 174:
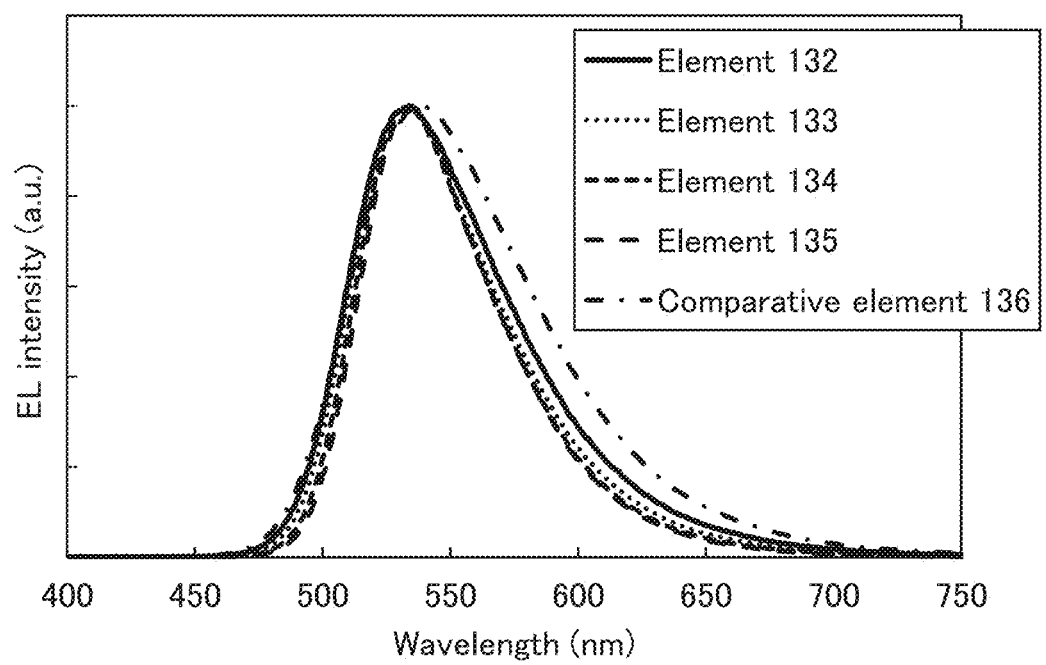

FIG. 174 A diagram showing electroluminescence spectra of light-emitting elements in Example.

Figure 175:
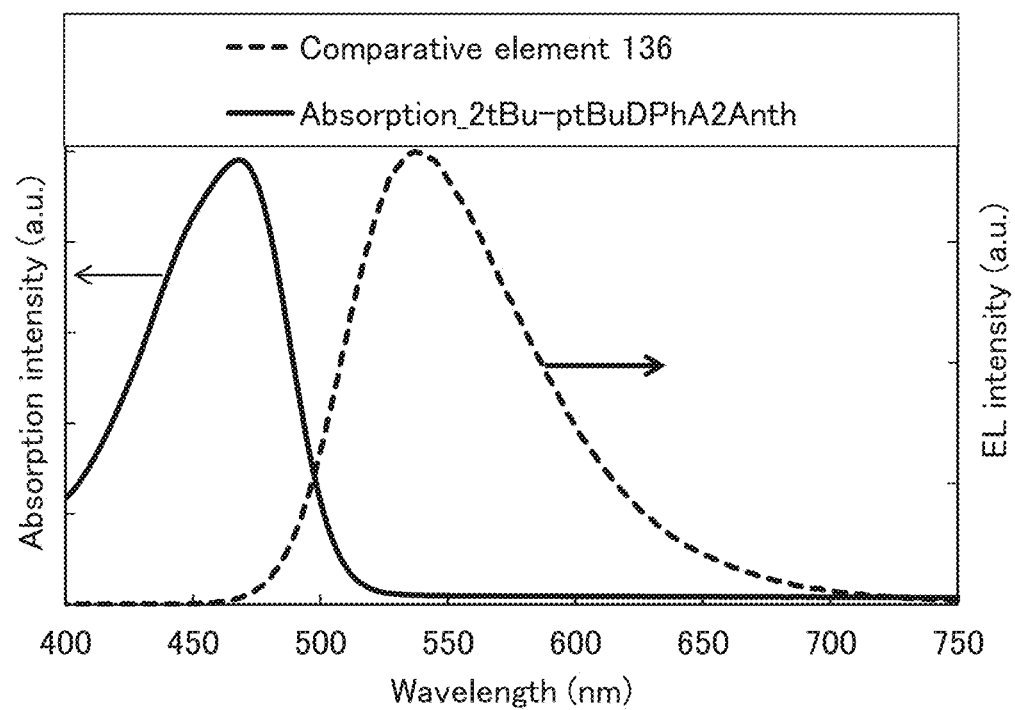

FIG. 175 A diagram showing the relation between energy donor emission and guest material absorption.

Figure 176:
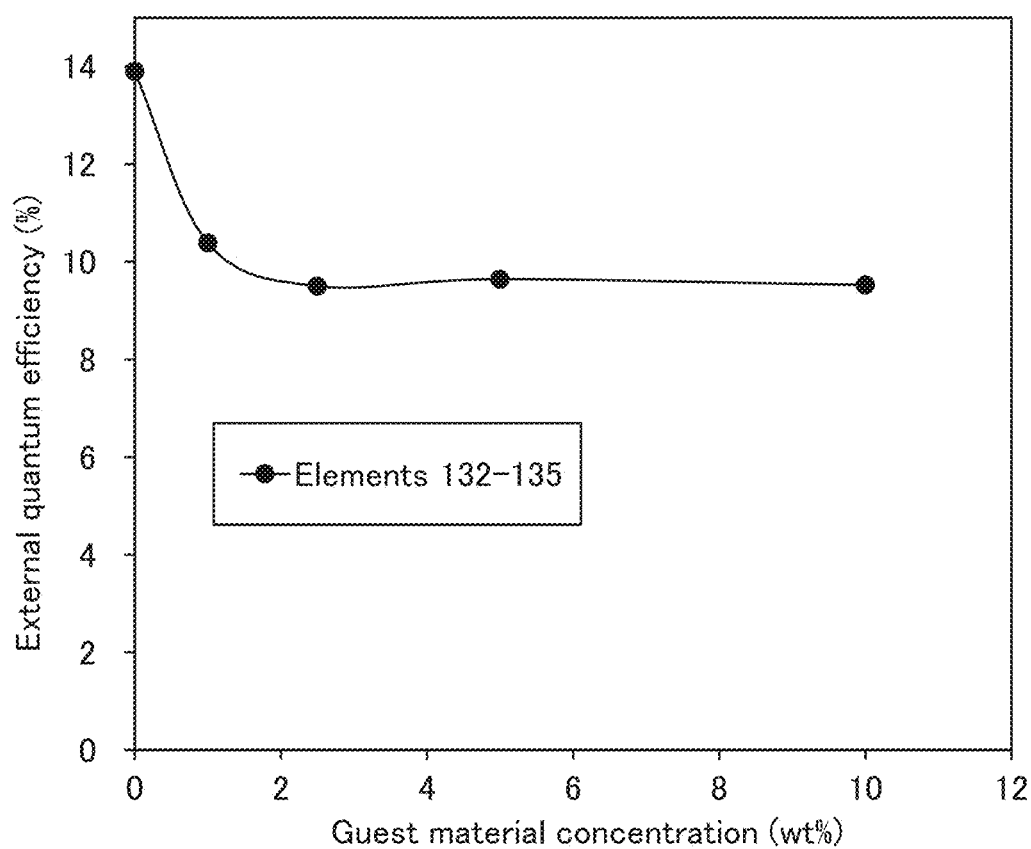

FIG. 176 A diagram showing the relation between external quantum efficiency and guest material concentration in Example.

Figure 177:
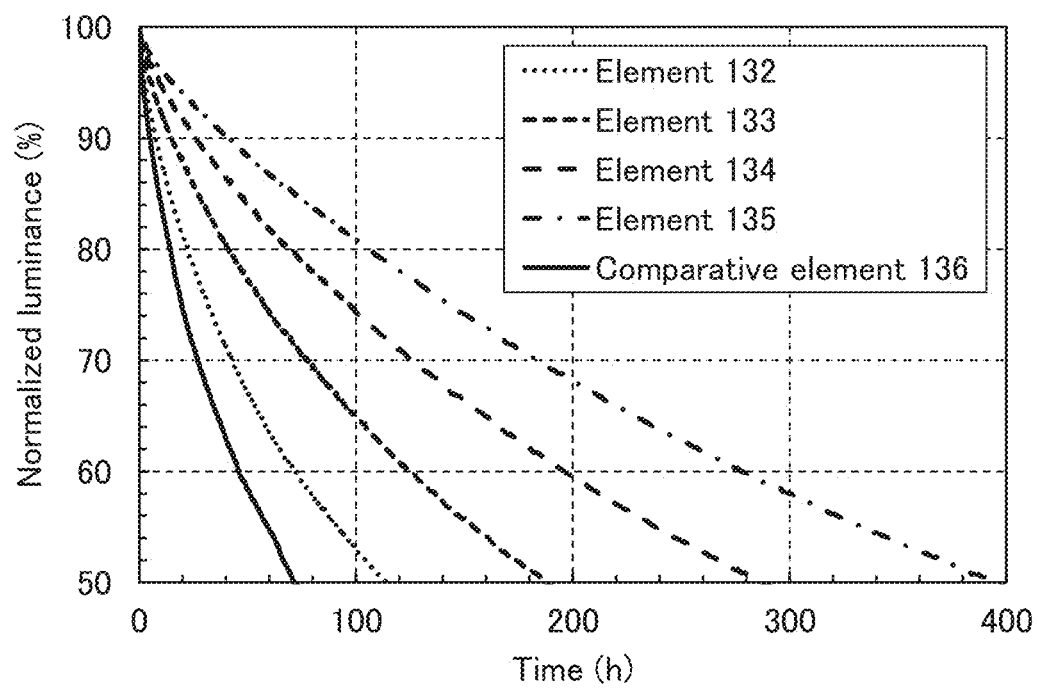

FIG. 177 A diagram showing reliability measurement results of light-emitting elements in Example.

Figure 178:
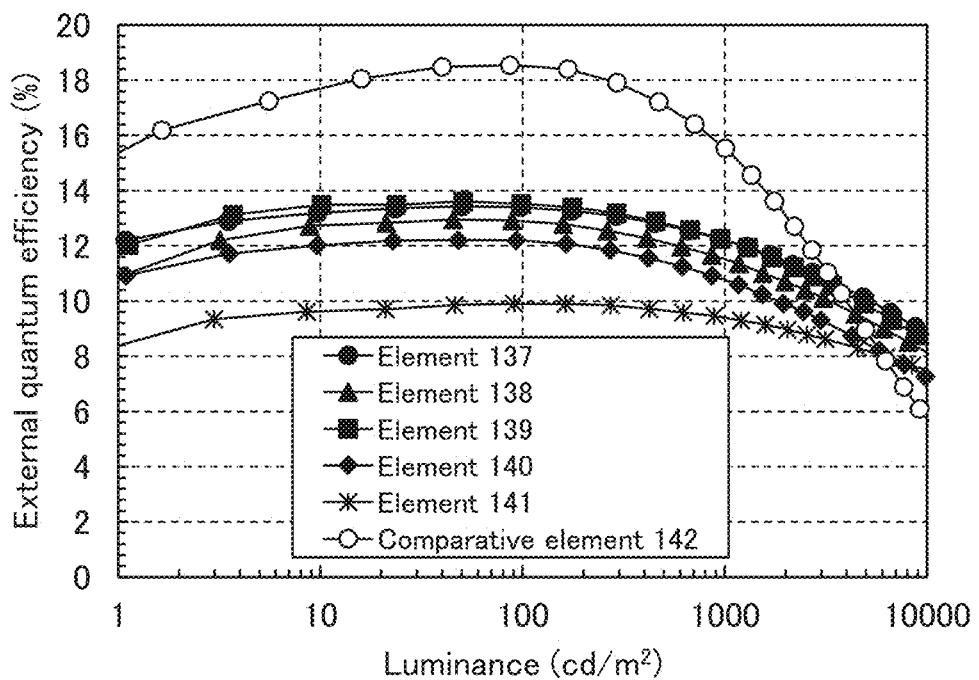

FIG. 178 A diagram showing external quantum efficiency-luminance characteristics of light-emitting elements in Example.

Figure 179:
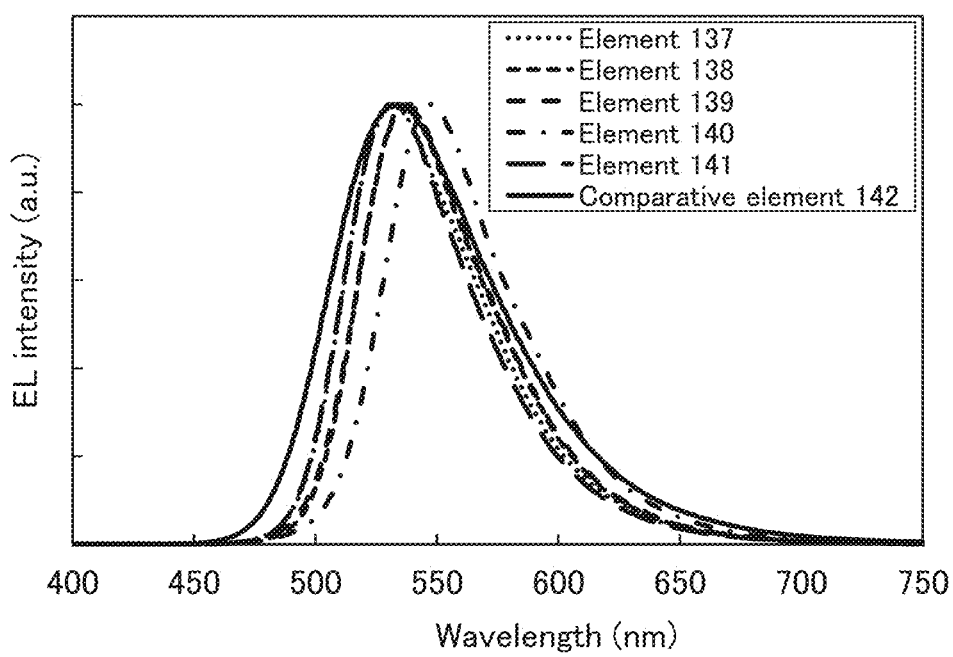

FIG. 179 A diagram showing electroluminescence spectra of light-emitting elements in Example.

Figure 180:
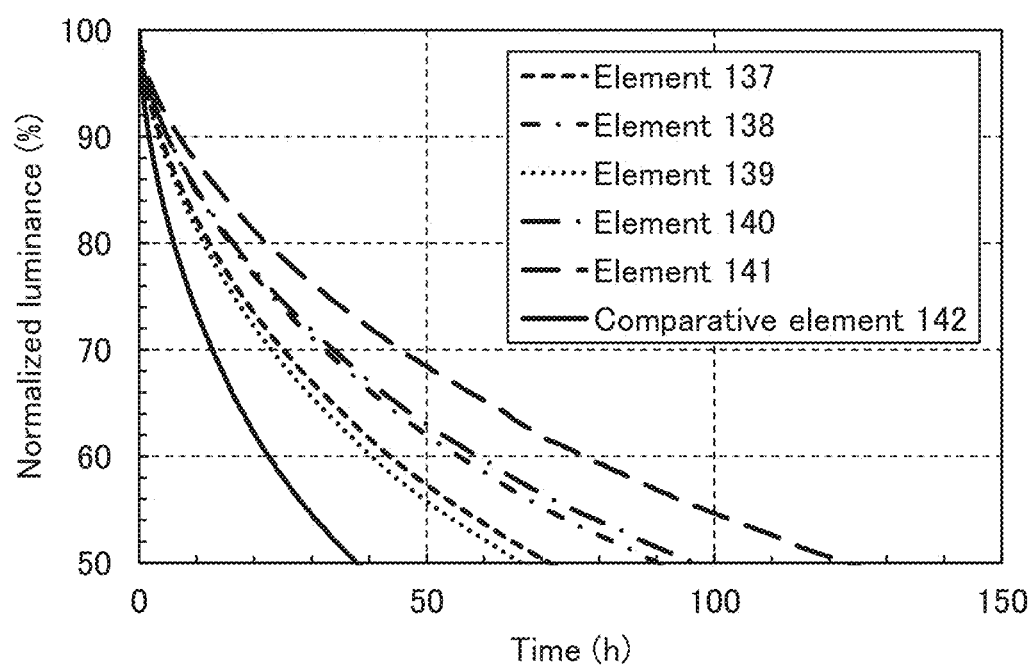

FIG. 180 A diagram showing reliability measurement results of light-emitting elements in Example.

Figure 181:
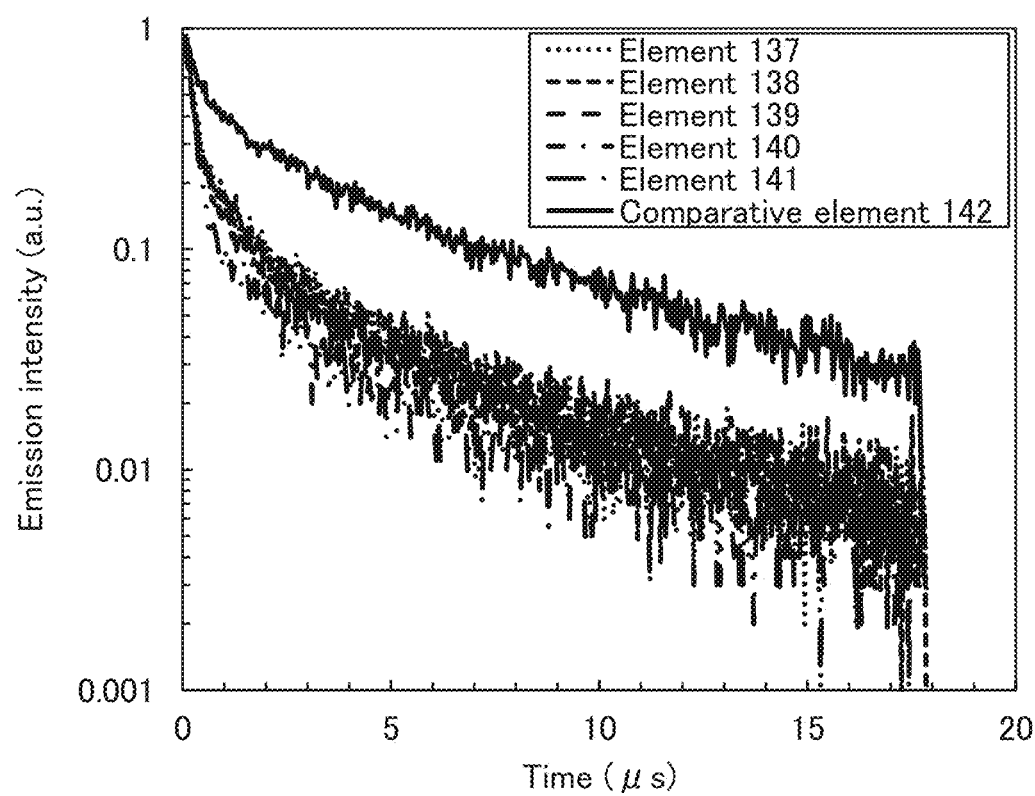

FIG. 181 A diagram showing emission lifetime measurement results of light-emitting elements in Example.

Figure 182:
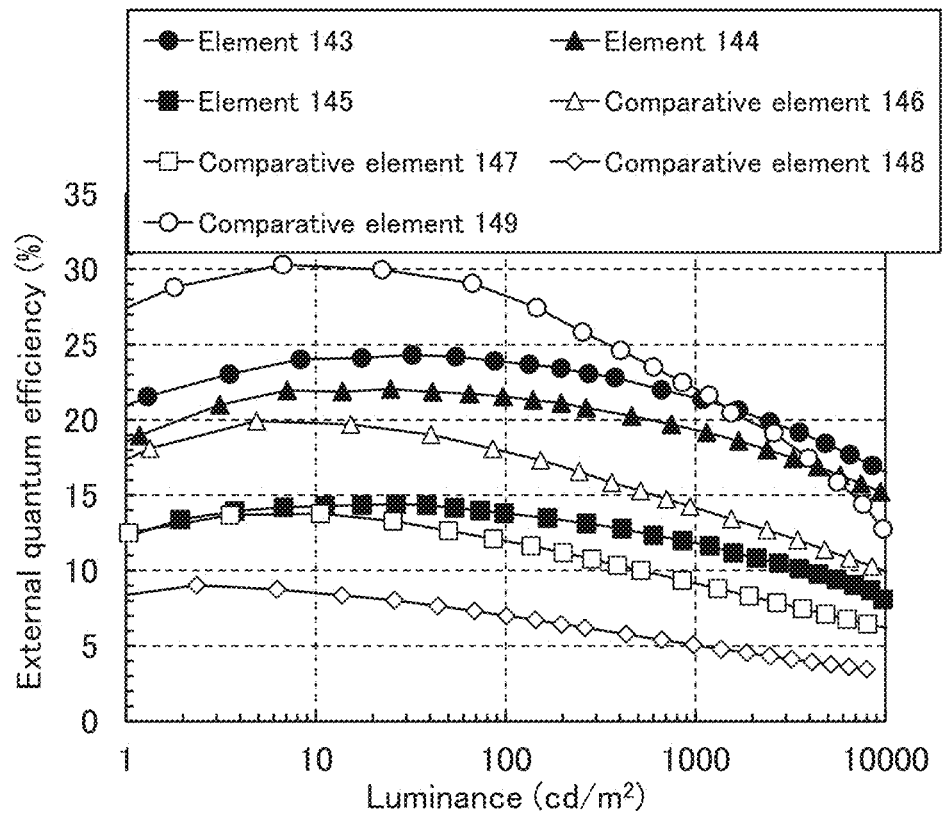

FIG. 182 A diagram showing external quantum efficiency-luminance characteristics of light-emitting elements in Example.

Figure 183:
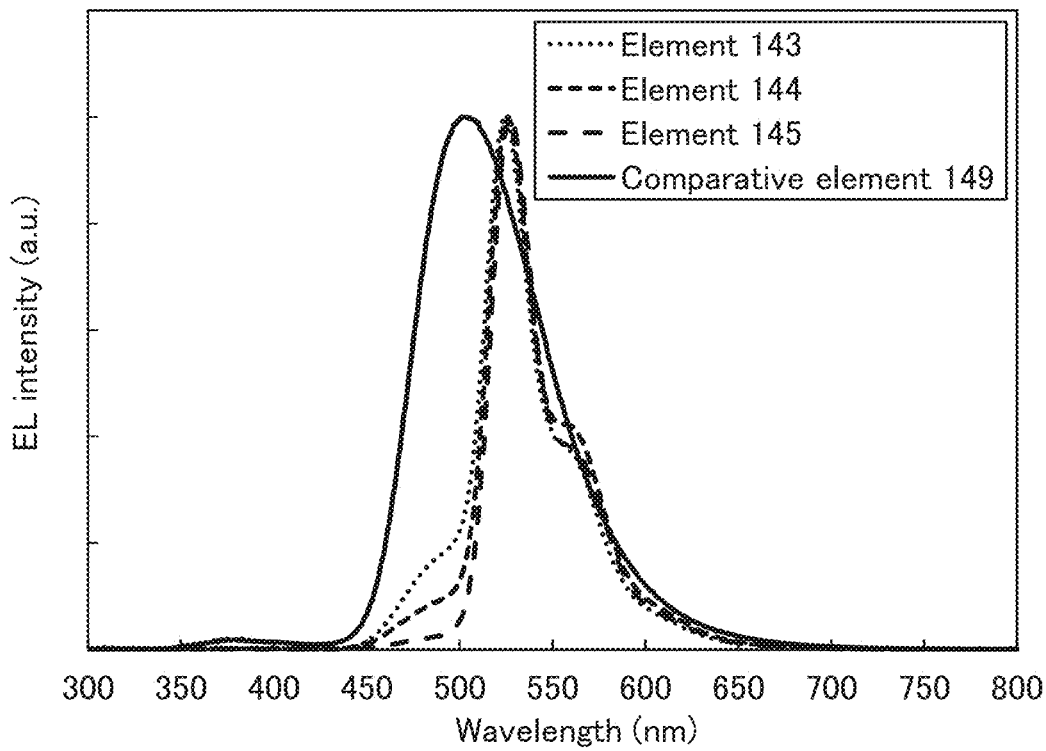

FIG. 183 A diagram showing electroluminescence spectra of light-emitting elements in Example.

Figure 184:
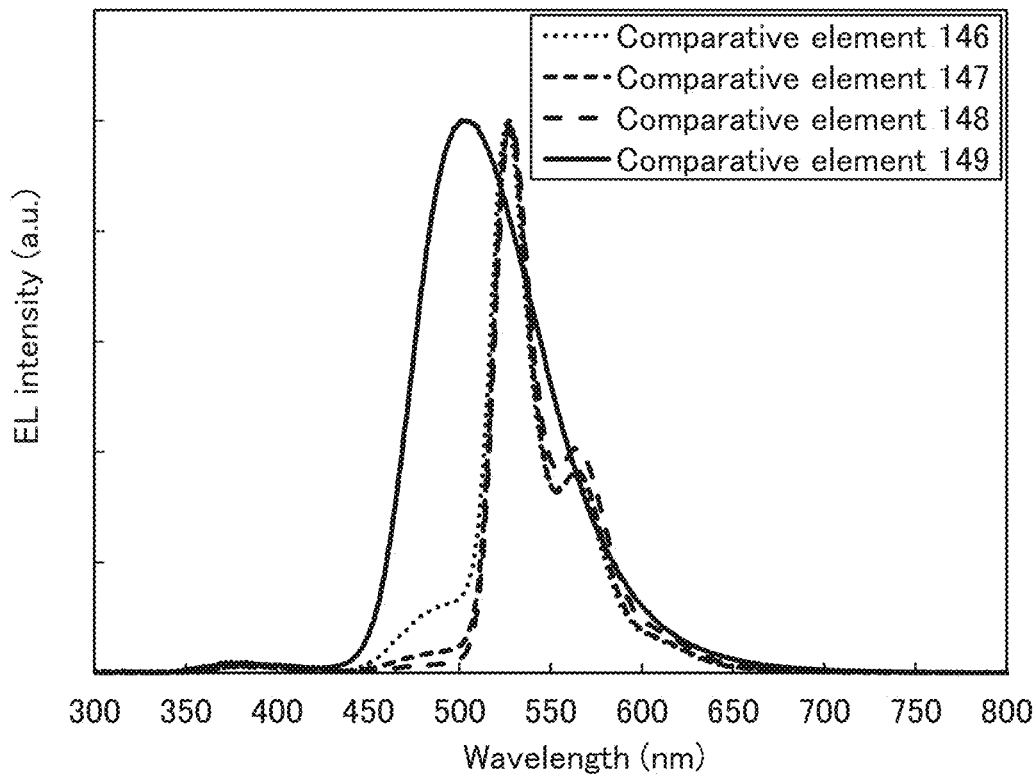

FIG. 184 A diagram showing electroluminescence spectra of light-emitting elements in Example.

Figure 185:
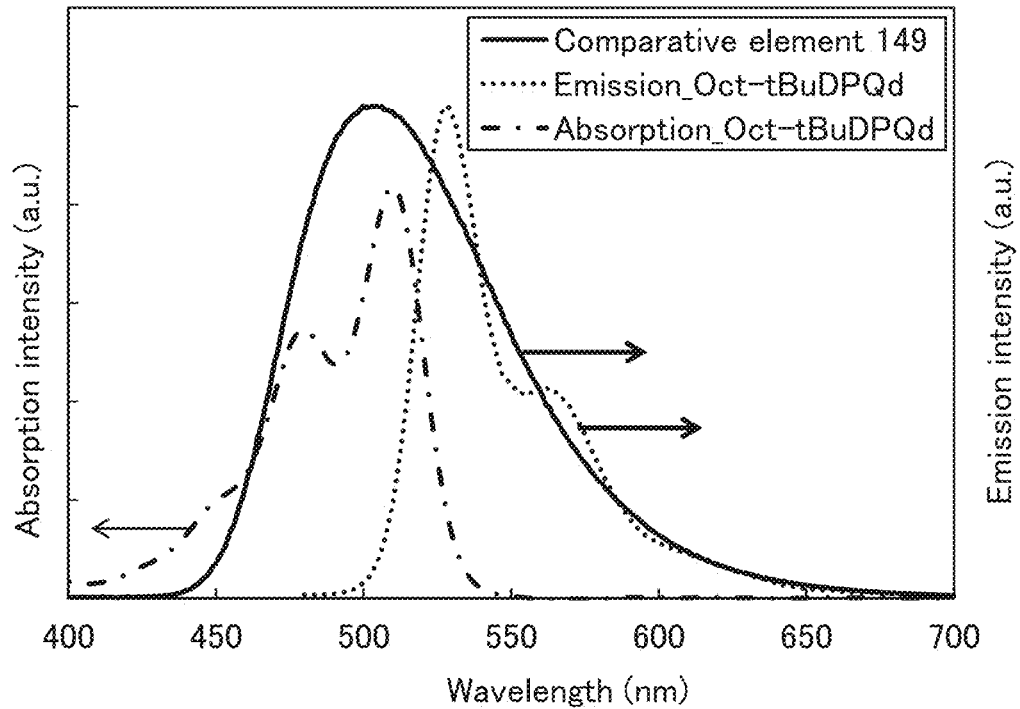

FIG. 185 A diagram showing the relation between energy donor emission and guest material absorption in Example.

Figure 186:
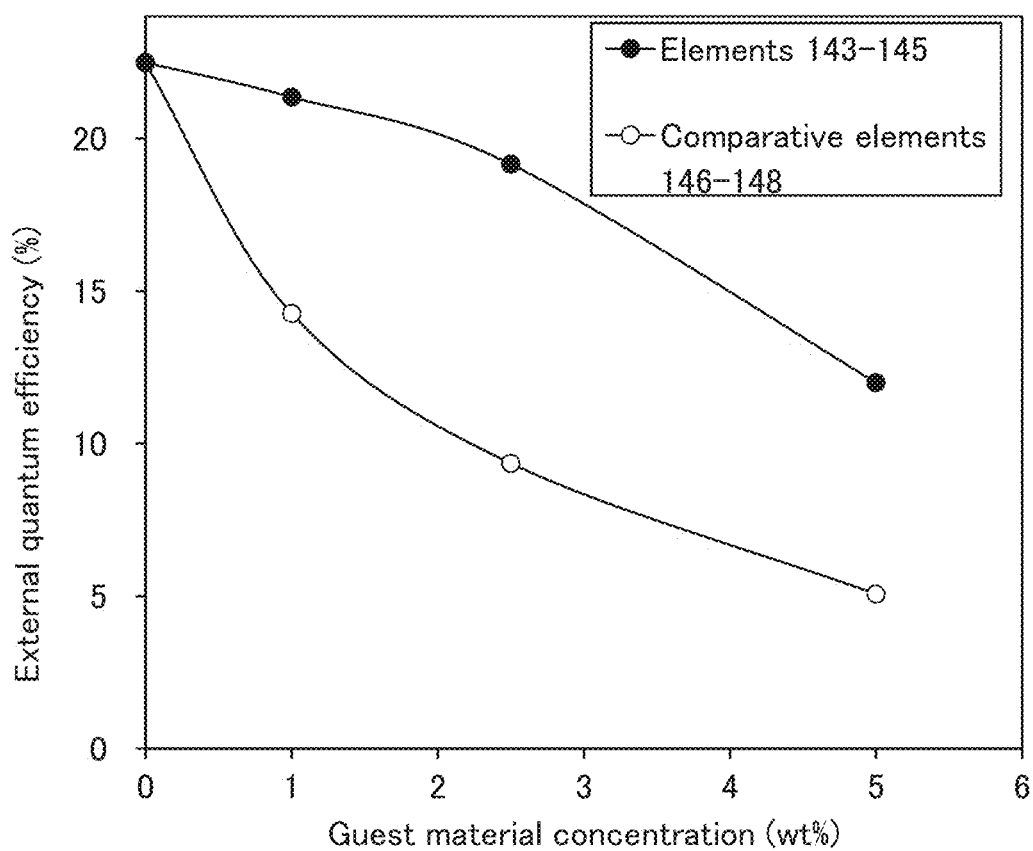

FIG. 186 A diagram showing the relation between external quantum efficiency and guest material concentration in Example.

MODE FOR CARRYING OUT THE INVENTION

Embodiments of the present invention are described in detail below with reference to drawings. Note that the present invention is not limited to the following description, and the modes and details of the present invention can be modified in various ways without departing from the spirit and scope of the present invention. Accordingly, the present invention should not be interpreted as being limited to the description of the embodiments below.

Note that the position, size, range, or the like of each structure illustrated in the drawings and the like do not represent the actual position, size, range, or the like in some cases for easy understanding. Therefore, the disclosed invention is not necessarily limited to the position, size, range, or the like disclosed in drawings and the like.

In this specification and the like, the ordinal numbers such as first and second are used for convenience, and do not denote the order of steps or the stacking order of layers in some cases. Therefore, for example, description can be made even when "first" is replaced with "second", "third", or the like, as appropriate. In addition, the ordinal numbers in this specification and the like do not correspond to the ordinal numbers which are used to specify one embodiment of the present invention in some cases.

In describing structures of the invention in this specification and the like with reference to drawings, common numerals are used for the same components in different drawings in some cases.

Moreover, in this specification and the like, the term "film" and the term "layer" can be interchanged with each other. For example, the term "conductive layer" can be changed into the term "conductive film" in some cases. For another example, the term "insulating film" can be changed into the term "insulating layer" in some cases.

In this specification and the like, a singlet excited state (S*) refers to a singlet state having excitation energy. An S1 level means the lowest level of the singlet excitation energy level, that is, the excitation energy level of the lowest singlet excited state (S1 state). A triplet excited state (T*) refers to a triplet state having excitation energy. A T1 level means the lowest level of the triplet excitation energy level, that is, the excitation energy level of the lowest triplet excited state (T1 state). Note that in this specification and the like, simple expressions singlet excited state and singlet excitation energy level mean the S1 state and the S1 level, respectively, in some cases. In addition, expressions triplet excited state and triplet excitation energy level mean the T1 state and the T1 level, respectively, in some cases.

In this specification and the like, a fluorescent material refers to a compound that supplies light emission in the visible light region when the relaxation from the singlet excited state to the ground state occurs. A phosphorescent material refers to a compound that supplies light emission in the visible light region at room temperature when the relaxation from the triplet excited state to the ground state occurs. In other words, a phosphorescent material refers to one of compounds that can convert triplet excitation energy into visible light.

Note that in this specification and the like, room temperature refers to a temperature in the range of higher than or equal to 0° C. and lower than or equal to 40° C.

In this specification and the like, a wavelength range of blue is greater than or equal to 400 nm and less than 490 nm, and blue light has at least one emission spectrum peak in that wavelength range. A wavelength range of green is greater than or equal to 490 nm and less than 580 nm, and green light has at least one emission spectrum peak in that wavelength range. A wavelength range of red is greater than or equal to 580 nm and less than or equal to 680 nm, and red light has at least one emission spectrum peak in that wavelength range.

Embodiment 1

In this embodiment, a light-emitting element of one embodiment of the present invention will be described below with reference to FIG. 1 to FIG. 6.

<Structure Example of Light-Emitting Element>

First, the structure of the light-emitting element of one embodiment of the present invention will be described below with reference to FIG. 1.

Figure 1A:
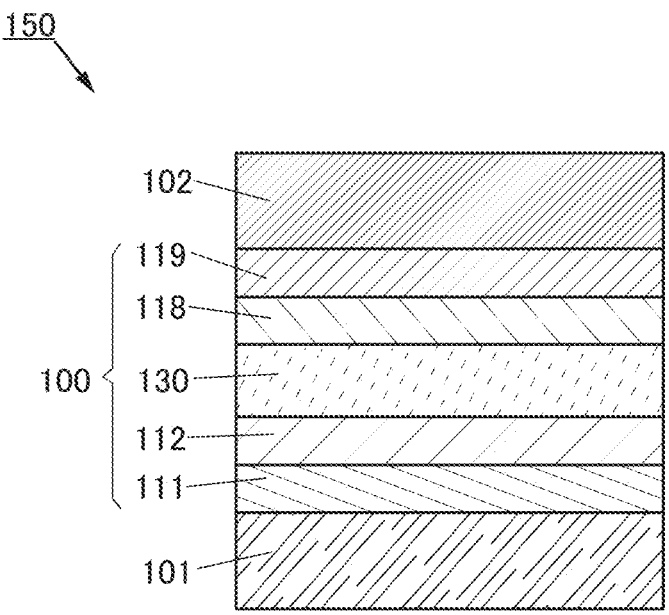
FIGS. 1A to 1C Schematic cross-sectional views of a light-emitting layer of a light-emitting element of one embodiment of the present invention and a diagram showing the correlation between energy levels.

FIG. 1(A) is a schematic cross-sectional view of a light-emitting element 150 of one embodiment of the present invention.

The light-emitting element 150 includes a pair of electrodes (an electrode 101 and an electrode 102) and an EL layer 100 provided between the pair of electrodes. The EL layer 100 includes at least a light-emitting layer 130.

The EL layer 100 illustrated in FIG. 1(A) includes functional layers such as a hole-injection layer 111, a hole-transport layer 112, an electron-transport layer 118, and an electron-injection layer 119, in addition to the light-emitting layer 130.

Note that in this embodiment, although description is given assuming that the electrode 101 and the electrode 102 of the pair of electrodes serve as an anode and a cathode, respectively, the structure of the light-emitting element 150 is not limited thereto. That is, the electrode 101 may serve as a cathode, the electrode 102 may serve as an anode, and the stacking order of layers between the electrodes may be reversed. In other words, the hole-injection layer 111, the hole-transport layer 112, the light-emitting layer 130, the electron-transport layer 118, and the electron-injection layer 119 may be stacked in this order from the anode side.

The structure of the EL layer 100 is not limited to the structure illustrated in FIG. 1(A), as long as at least one selected from the hole-injection layer 111, the hole-transport layer 112, the electron-transport layer 118, and the electron-injection layer 119 is included. Alternatively, the EL layer 100 may have a structure including a functional layer which has a function of lowering a hole- or electron-injection barrier, improving a hole- or electron-transport property, inhibiting a hole- or electron-transport property, inhibiting a quenching phenomenon by an electrode, or the like. Note that the functional layers may each be a single layer or have a structure in which a plurality of layers are stacked.

<Light Emission Mechanism of Light-Emitting Element>

Next, the light emission mechanism of the light-emitting layer 130 will be described below.

In the light-emitting element 150 of one embodiment of the present invention, voltage application between the pair of electrodes (the electrode 101 and the electrode 102) allows electrons and holes to be injected from the cathode and the anode, respectively, into the EL layer 100 and thus a current flows. The ratio (hereinafter, exciton generation probability) of singlet excitons to triplet excitons which are generated by recombination of carriers (electrons and holes) is 1:3 according to the statistically obtained probability. In other words, the generation probability of singlet excitons is 25% and the generation probability of triplet excitons is 75%; thus, it is important to make the triplet excitons contribute to light emission in order to improve the emission efficiency of the light-emitting element. For this reason, a material that has a function of converting triplet excitation energy into light emission is preferably used for the light-emitting layer 130.

As the material that has a function of converting triplet excitation energy into light emission, a compound that can emit phosphorescence (hereinafter, also referred to as a phosphorescent material) can be given. A phosphorescent material in this specification and the like is a compound that exhibits phosphorescence and exhibits no fluorescence at a temperature in a range of higher than or equal to a low temperature (e.g., 77 K) and lower than or equal to room temperature (i.e., higher than or equal to 77 K and lower than or equal to 313 K). The phosphorescent material preferably contains a metal element with large spin-orbit interaction, specifically a transition metal element. It is particularly preferable that a platinum group element (ruthenium (Ru), rhodium (Rh), palladium (Pd), osmium (Os), iridium (Ir), or platinum (Pt)) be contained, especially iridium be contained because the transition probability relating to direct transition between a singlet ground state and a triplet excited state can be increased.

As the material that has a function of converting triplet excitation energy into light emission, a TADF material is given. Note that the TADF material is a material having a small difference between the S1 level and the T1 level and having a function of converting triplet excitation energy into singlet excitation energy by reverse intersystem crossing. Thus, it is possible to upconvert triplet excitation energy into singlet excitation energy (reverse intersystem crossing) using a little thermal energy and efficiently generate a singlet excited state. An exciplex whose excited state is formed by two kinds of substances has an extremely small difference between the S1 level and the T1 level and functions as a TADF material that can convert triplet excitation energy into singlet excitation energy.

Note that a phosphorescent spectrum observed at a low temperature (e.g., 10 K) is used for an index of the T1 level. When the level of energy with a wavelength of the line obtained by extrapolating a tangent to the fluorescent spectrum at room temperature or a low temperature at a tail on the short wavelength side is the S1 level and the level of energy with a wavelength of the line obtained by extrapolating a tangent to the phosphorescent spectrum at a tail on the short wavelength side is the T1 level, the difference between S1 and T1 of the TADF material is preferably less than or equal to 0.2 eV.

An example of a material having a function of converting triplet excitation energy into light emission is a nano-structure of a transition metal compound having a perovskite structure. In particular, a nano-structure of a metal-halide perovskite is preferable. The nano-structure is preferably a nanoparticle or a nanorod.

Figure 1B:
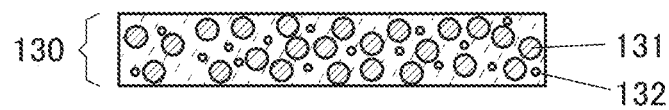
Figure 1C:
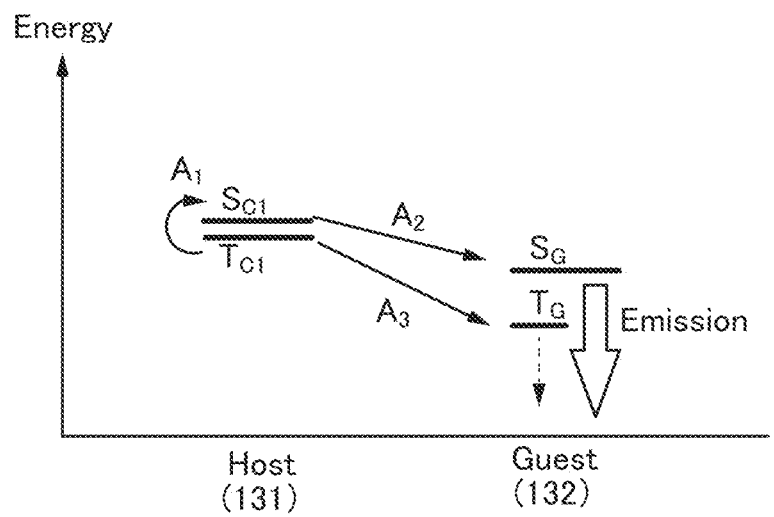

FIG. 1(B) is a schematic cross-sectional view illustrating the light-emitting layer 130 of the light-emitting element of one embodiment of the present invention. In one embodiment of the present invention, the light-emitting layer 130 contains a compound 131 and a compound 132. The compound 131 has a function of converting triplet excitation energy into light emission and the compound 132 has a function of converting singlet excitation energy into light emission. A fluorescent material has high stability, so that a fluorescent material is preferably used as the compound 132 in order to obtain a light-emitting element with high reliability. The compound 131 has a function of converting triplet excitation energy into light emission; thus, it is preferred that carrier recombination occur in the compound 131 in order to obtain a light-emitting element with high emission efficiency. Therefore, it is preferred that both the singlet excitation energy and the triplet excitation energy of excitons generated by carrier recombination in the compound 131 be finally transferred to the singlet excited state of the compound 132, and the compound 132 emit light. In the light-emitting layer 130, the compound 131 is an energy donor, and the compound 132 is an energy acceptor. In FIG. 1(C), the light-emitting layer 130 is a fluorescent layer containing the compound 131 as a host material and the compound 132 as a guest material. That is, in FIG. 1(C), the host material serves as an energy donor, and the guest material serves as an energy acceptor. In addition, light emission originating from the compound 132, which is a guest material, can be obtained from the light-emitting layer 130.

Structure Example 1 of Light-Emitting Layer

FIG. 1(C) shows an example of the correlation between energy levels in the light-emitting layer of the light-emitting element of one embodiment of the present invention. In this structure example, the case where a TADF material is used as the compound 131 is described.

FIG. 1(C) shows the correlation between the energy levels of the compound 131 and the compound 132 in the light-emitting layer 130. The following explains what terms and numerals in FIG. 1(C) represent.

Host (131): the compound 131
Guest (132): the compound 132
$T_{C1}$: the T1 level of the compound 131
$S_{C1}$: the S1 level of the compound 131
$S_G$: the S1 level of the compound 132
$T_G$: the T1 level of the compound 132

Here, the triplet excitation energy of the compound 131 generated by current excitation is focused on. The compound 131 has a TADF property. Therefore, the compound 131 has a function of converting triplet excitation energy into singlet excitation energy by upconversion (Route $A_1$ in FIG. 1(C)). The singlet excitation energy of the compound 131 can be rapidly transferred to the compound 132 (Route $A_2$ in FIG. 1(C)). At this time, $S_{C1} \geq S_G$ is preferable. Specifically, when the level of energy with a wavelength of the line obtained by extrapolating a tangent to the fluorescent spectrum of the compound 131 at a tail on the short wavelength side is $S_{C1}$ and the level of energy with a wavelength of the absorption edge of the absorption spectrum of the compound 132 is $S_G$, $S_{C1} \geq S_G$ is preferable.

The triplet excitation energy generated in the compound 131 is transferred to the S1 level of the compound 132, which is a guest material, through Route $A_1$ and Route $A_2$ described above and the compound 132 emits light, whereby the emission efficiency of the light-emitting element can be improved. In Route $A_2$, the compound 131 serves as an energy donor and the compound 132 serves as an energy acceptor.

Here, in the light-emitting layer 130, the compound 131 and the compound 132 are mixed. Thus, a process where the triplet excitation energy of the compound 131 is converted into the triplet excitation energy of the compound 132 (Route $A_3$ in FIG. 1(C)) can be caused conflicting with Route $A_1$ and Route $A_2$ described above. Since the compound 132 is a fluorescent material, the triplet excitation energy of the compound 132 does not contribute to light emission. That is, when the energy transfer through Route $A_3$ occurs, the emission efficiency of the light-emitting element decreases. Note that in practice, the energy is not directly transferred from $T_{C1}$ to $T_G$ (Route $A_3$), but can pass through a pathway where $T_{C1}$ is once transferred to the triplet excited state at a level higher than $T_G$ of the compound 132 and then the triplet excited state is converted into $T_G$ by internal conversion; the process is omitted in the drawing. Hereinafter, the same applies to all undesired thermal deactivation processes, that is, all the deactivation processes to $T_G$ in this specification.

As mechanisms of the intermolecular energy transfer, the Förster mechanism (dipole-dipole interaction) and the Dexter mechanism (electron exchange interaction) are known. Since the compound 132, which is an energy acceptor, is a fluorescent material, the Dexter mechanism is dominant as the mechanism of energy transfer through Route $A_3$. In general, the Dexter mechanism occurs significantly when the distance between the compound 131, which is an energy donor, and the compound 132, which is an energy acceptor, is less than or equal to 1 nm. Therefore, to inhibit Route $A_3$, it is important that the host material and the guest material, that is, the energy donor and the energy acceptor be made away from each other.

Note that since direct transition from a singlet ground state to a triplet excited state in the compound 132 is forbidden, energy transfer from the singlet excitation energy level ($S_{C1}$) of the compound 131 to the triplet excitation energy level ($T_G$) of the compound 132 is unlikely to be a main energy transfer process, and thus is not illustrated.

$T_G$ in FIG. 1(C) is an energy level derived from a luminophore in the energy acceptor in many cases. Therefore, specifically, to inhibit Route $A_3$, it is important that the energy donor and the luminophore of the energy acceptor be made away from each other. A general method for making the energy donor and the luminophore of the energy acceptor away from each other is to lower the concentration of the energy acceptor in a mixed film of these compounds. However, lowering the concentration of the energy acceptor in the mixed film inhibits not only energy transfer based on the Dexter mechanism from the energy donor to the energy acceptor but also energy transfer based on the Förster mechanism from the energy donor to the energy acceptor. In that case, a problem such as a decrease in the emission efficiency and reliability of the light-emitting element is caused because Route $A_2$ is based on the Förster mechanism.

In view of the above, the present inventors have found that the use of a fluorescent material having protecting groups, as an energy acceptor, for keeping a distance from the energy donor can inhibit the above-described decrease in the emission efficiency.

<Concept of Fluorescent Material Having Protecting Groups>

Figure 2A:
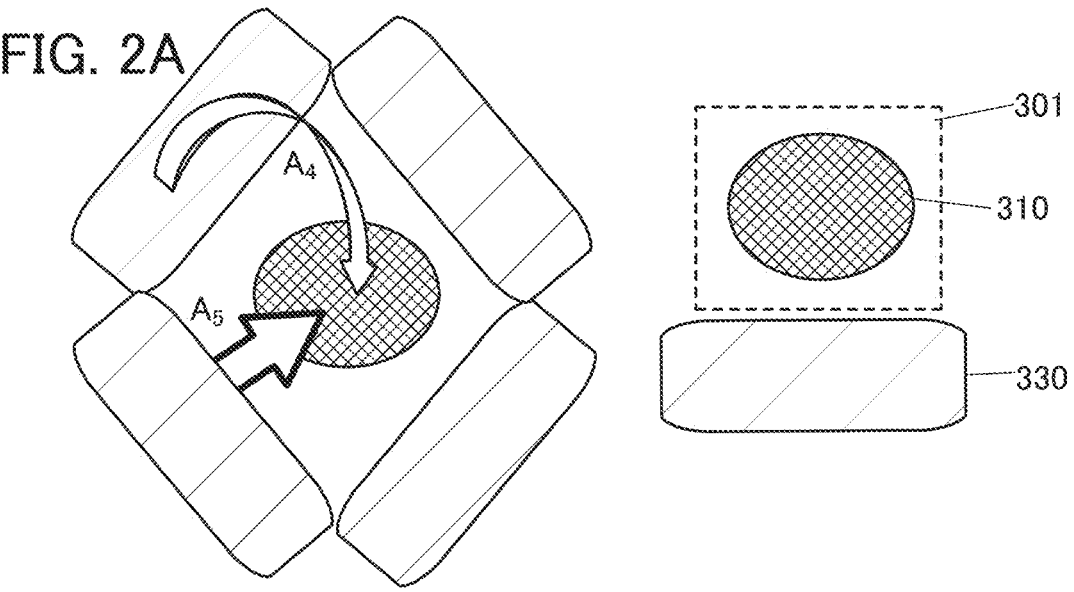
FIGS. 2A and 2B Conceptual diagrams of a conventional guest material and a guest material used for a light-emitting element of one embodiment of the present invention.
Figure 2B:
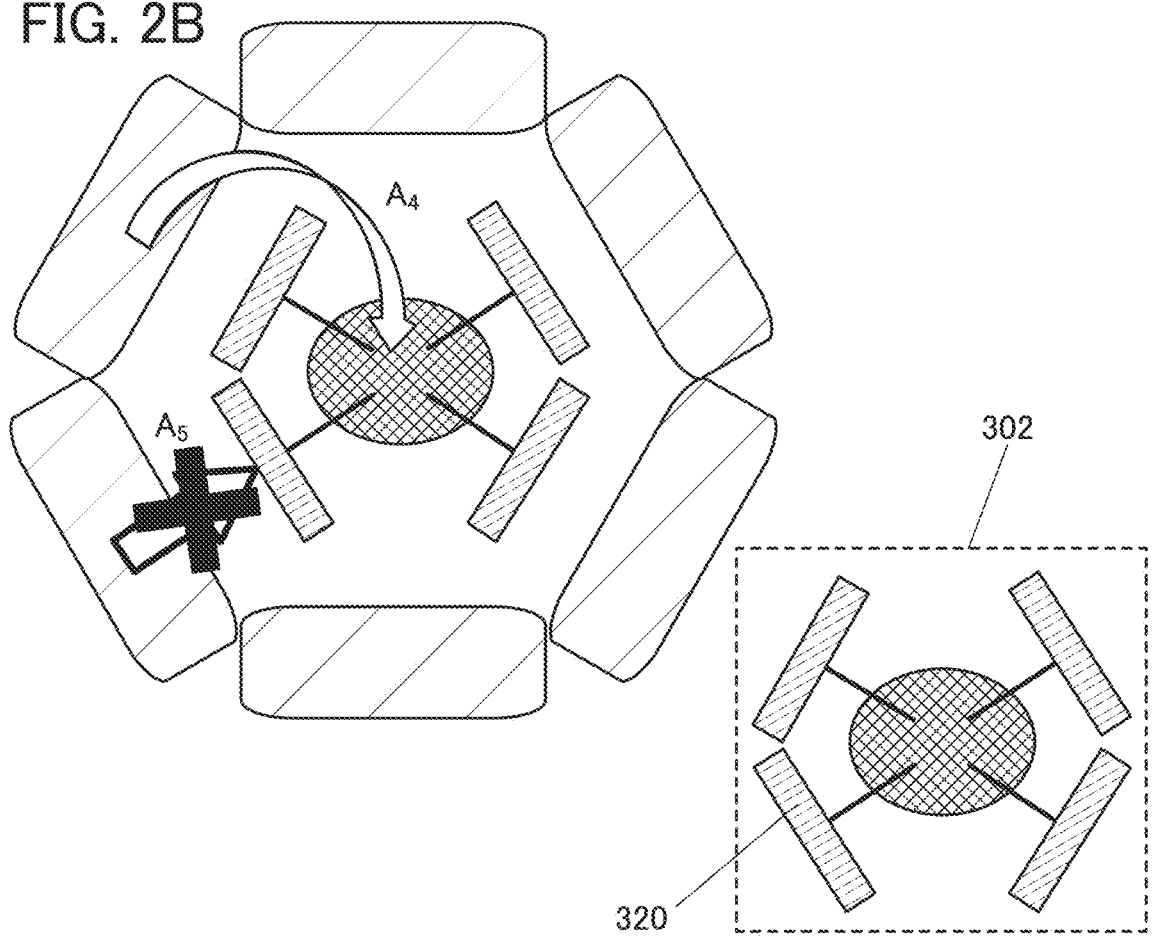

FIG. 2(A) is a conceptual diagram illustrating the case where a typical fluorescent material having no protecting group is dispersed as a guest material to a host material. FIG. 2(B) is a conceptual diagram illustrating the case where the fluorescent material having protecting groups, which is used for the light-emitting element of one embodiment of the present invention, is dispersed as a guest material to a host material. The host material and the guest material may be replaced with an energy donor and an energy acceptor, respectively. Here, the protecting groups have a function of making a luminophore and the host material away from each other. In FIG. 2(A), a guest material 301 includes a luminophore 310. The guest material 301 serves as an energy acceptor. In FIG. 2(B), a guest material 302 includes the luminophore 310 and protecting groups 320. In FIGS. 2(A) and 2(B), the guest material 301 and the guest material 302 are surrounded by host materials 330. Since the luminophore is close to the host materials in FIG. 2(A), both energy transfer by the Förster mechanism (Route $A_4$ in FIGS. 2(A) and 2(B)) and energy transfer by the Dexter mechanism (Route $A_5$ in FIGS. 2(A) and 2(B)) can occur as the energy transfer from the host materials 330 to the guest material 301. When the guest material is a fluorescent material, energy transfer of triplet excitation energy by the Dexter mechanism from the host material to the guest material is caused, and the triplet excited state of the guest material is generated, non-radiative decay of the triplet excitation energy is caused, contributing to a reduction in the emission efficiency.

In contrast, the guest material 302 in FIG. 2(B) has the protecting groups 320. Thus, the luminophore 310 and each of the host materials 330 can be kept away from each other. This inhibits energy transfer by the Dexter mechanism (Route $A_5$).

Here, in order that the guest material 302 emits light, the guest material 302 needs to receive energy from the host materials 330 by the Förster mechanism because the Dexter mechanism is inhibited. In other words, it is preferred that energy transfer by the Förster mechanism be efficiently utilized while energy transfer by the Dexter mechanism is inhibited. It is known that energy transfer by the Förster mechanism is also affected by the distance between a host material and a guest material. In general, the Dexter mechanism is dominant when the distance between the host material 330 and the guest material 302 is less than or equal to 1 nm, and the Förster mechanism is dominant when the distance therebetween is greater than or equal to 1 nm and less than or equal to 10 nm. Energy transfer is generally less likely to occur when the distance between the host material 330 and the guest material 302 is greater than or equal to 10 nm. Here, the distance between the host material 330 and the guest material 302 can be rephrased as the distance between the host material 330 and the luminophore 310.

Thus, the protecting groups 320 preferably extend within a range from 1 nm to 10 nm from the luminophore 310. A range from 1 nm to 5 nm is more preferable. With such a structure, energy transfer by the Förster mechanism from the host material 330 to the guest material 302 can be efficiently utilized while energy transfer by the Dexter mechanism is inhibited. Thus, the light-emitting element with high emission efficiency can be fabricated.

Furthermore, in order to improve the efficiency of energy transfer (increase the energy transfer rate) by the Förster mechanism, the concentration of the guest material 301 or the guest material 302 with respect to the host material 330 is preferably increased. However, as the concentration of the guest material is increased, the rate of energy transfer by the Dexter mechanism is usually increased, resulting in a decrease in emission efficiency. It is thus difficult to increase the concentration of the guest material. As a fluorescent element using a material having a function of converting triplet excitation energy into light emission as a host material, a light-emitting element having a small guest material concentration of lower than or equal to 1 wt % has been reported.

In contrast, in the light-emitting element of one embodiment of the present invention, a guest material in which a luminophore has protecting groups is used for a light-emitting layer. Therefore, energy transfer by the Förster mechanism can be efficiently utilized while inhibiting energy transfer by the Dexter mechanism; thus, the concentration of the guest material, which is an energy acceptor, can be increased. As a result, increasing the rate of energy transfer by the Förster mechanism and inhibiting energy transfer by the Dexter mechanism, which are originally conflicting phenomena, can be concurrently caused. As the rate of energy transfer by the Förster mechanism is increased, the excitation lifetime of the energy acceptor in the light-emitting layer becomes shorter; thus, the reliability of the light-emitting element can be improved. The concentration of the guest material with respect to the host material is preferably higher than or equal to 2 wt % and lower than or equal to 30 wt %, more preferably higher than or equal to 5 wt % and lower than or equal to 20 wt %, still more preferably higher than or equal to 5 wt % and lower than or equal to 15 wt %. With such a structure, the rate of energy transfer by the Förster mechanism can be increased; thus, a light-emitting element with high emission efficiency can be obtained. In addition, the use of a material having a function of converting triplet excitation energy into light emission as a host material allows fabrication of a fluorescent element having emission efficiency as high as that of a phosphorescent element. Since the emission efficiency can be improved using a fluorescent material having high stability, a light-emitting element with high reliability can be fabricated. Note that the above-described concentration is concentration when a light-emitting material is mainly used as the guest material and a material other than the guest material is used as the host material of the light-emitting layer.

In particular, the effect of the light-emitting element of one embodiment of the present invention is not only an increase in reliability owing to the use of a fluorescent material with high stability. The energy transfer described above always conflicts with a quenching process due to the influence of a degraded material and an impurity. As the quenching rate constant of the quenching process increases over time, the proportion of light emission from the light-emitting element decreases. That is, the luminance of the light-emitting element deteriorates. However, as described above, the rate of energy transfer by the Förster mechanism can be increased compared with a conventional light-emitting element while the energy transfer by the Dexter mechanism is inhibited in one embodiment of the present invention; thus, the influence of conflict with the quenching process can be reduced, so that the lifetime of the element can be increased.

Here, the luminophore refers to an atomic group (skeleton) that causes light emission in a fluorescent material. The luminophore generally has a π bond and preferably contains an aromatic ring, more preferably a condensed aromatic ring or a condensed heteroaromatic ring. As another embodiment, the luminophore can be regarded as an atomic group (skeleton) having an aromatic ring having a transition dipole vector on a ring plane. In the case where one fluorescent material has a plurality of condensed aromatic rings or condensed heteroaromatic rings, a skeleton having the lowest S1 level among the plurality of condensed aromatic rings or condensed heteroaromatic rings is considered as a luminophore of the fluorescent material in some cases. In other cases, a skeleton having an absorption edge on the longest wavelength side among the plurality of condensed aromatic rings or condensed heteroaromatic rings may be considered as the luminophore of the fluorescent material. The luminophore of the fluorescent material can be presumed from the shapes of the emission spectra of the plurality of condensed aromatic rings or condensed heteroaromatic rings in some cases.

Examples of the condensed aromatic ring or the condensed heteroaromatic ring have a phenanthrene skeleton, a stilbene skeleton, an acridone skeleton, a phenoxazine skeleton, and a phenothiazine skeleton. Specifically, a fluorescent material having any of a naphthalene skeleton, an anthracene skeleton, a fluorene skeleton, a chrysene skeleton, a triphenylene skeleton, a tetracene skeleton, a pyrene skeleton, a perylene skeleton, a coumarin skeleton, a quinacridone skeleton, and a naphthobisbenzofuran skeleton is preferred because of its high fluorescence quantum yield.

Substituents used as the protecting groups need to have a triplet excitation energy level higher than the T1 levels of the luminophore and the host material. Thus, a saturated hydrocarbon group is preferably used. That is because a substituent having no π bond has a high triplet excitation energy level. In addition, a substituent having no π bond does not have a sufficient function of transporting carriers (electrons or holes). Thus, a saturated hydrocarbon group can make the luminophore and the host material away from each other with substantially no influence on the excited state or the carrier-transport property of the host material. In an organic compound including a substituent having no π bond and a substituent having a π-conjugated system, frontier orbitals {HOMO (Highest Occupied Molecular Orbital) and LUMO (Lowest Unoccupied Molecular Orbital)} are present on the side of the substituent having a π-conjugated system in many cases; in particular, the luminophore tends to have frontier orbitals. As described later, the overlap of the HOMOs of the energy donor and the energy acceptor and the overlap of the LUMOs of the energy donor and the energy acceptor are important for energy transfer by the Dexter mechanism. Therefore, the use of saturated hydrocarbon groups as the protecting groups enables a large distance between the frontier orbitals of the host material, which is an energy donor, and the frontier orbitals of the guest material, which is an energy acceptor, and thus, energy transfer by the Dexter mechanism can be inhibited.

A specific example of the protecting group is an alkyl group having 1 to 10 carbon atoms. In addition, the protecting group is preferably a bulky substituent because it needs to make the luminophore and the host material away from each other. Thus, an alkyl group having 3 to 10 carbon atoms, a substituted or unsubstituted cycloalkyl group having 3 to 10 carbon atoms, or a trialkylsilyl group having 3 to 10 carbon atoms can be favorably used. In particular, the alkyl group is preferably a bulky branched-chain alkyl group. Furthermore, it is particularly preferred that the substituent have quaternary carbon to be a bulky substituent.

One luminophore preferably has five or more protecting groups. With such a structure, the luminophore can be entirely covered with the protecting groups, so that the distance between the host material and the luminophore can be appropriately adjusted. In FIG. 2(B), the protecting groups are directly bonded to the luminophore; however, the protecting groups are preferably not directly bonded to the luminophore. For example, the protecting groups may each be bonded to the luminophore via a substituent with a valence of 2 or more, such as an arylene group or an amino group. Bonding of each of the protecting groups to the luminophore via the substituent can effectively make the luminophore away from the host material. Thus, in the case where the protecting groups are not directly bonded to the luminophore, four or more protecting groups for one luminophore can effectively inhibit energy transfer by the Dexter mechanism.

Furthermore, the substituent with a valence of 2 or more that bonds the luminophore and each of the protecting groups is preferably a substituent having a π-conjugated system. With such a structure, the physical properties of the guest material, such as the emission color, the HOMO level, and the glass transition point, can be adjusted. Note that the protecting groups are preferably positioned on the outermost side when the molecular structure is seen around the luminophore.

<Examples of Fluorescent Material Having Protecting Groups and its Molecular Structure>

Here, the structure of N,N'-[(2-tert-butylanthracene)-9,10-diyl]-N,N'-bis(3,5-di-tert-butylphenyl)amine (abbreviation: 2tBu-mmtBuDPhA2Anth), a fluorescent material that is represented by Structural Formula (102) shown below and can be used for the light-emitting element of one embodiment of the present invention, is shown. In 2tBu-mmtBuDPhA2Anth, an anthracene ring is a luminophore and tertiary butyl (tBu) groups serve as protecting groups.

[Chemical Formula 7]

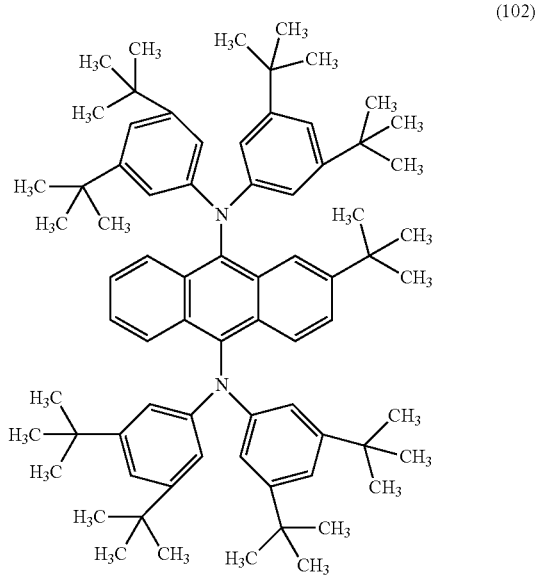

(102)

Figure 3A:
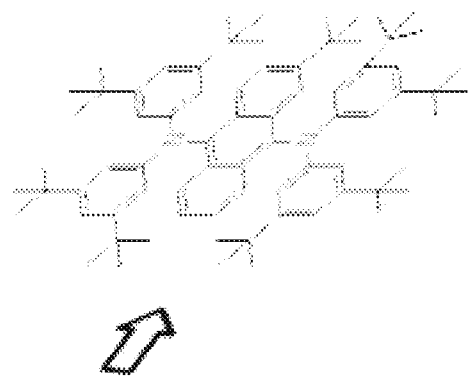
FIGS. 3A and 3B A structural formula and a ball-and-stick image of a guest material used in a light-emitting element of one embodiment of the present invention.
Figure 3B:
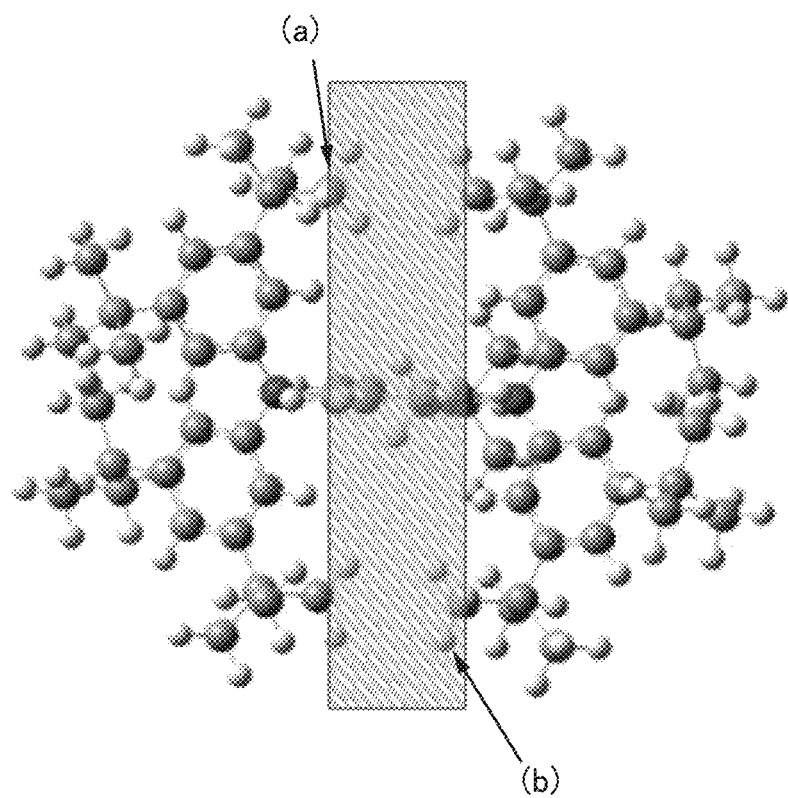

FIG. 3(B) shows a ball-and-stick model image of 2tBu-mmtBuDPhA2Anth described above. Note that FIG. 3(B) shows the state where 2tBu-mmtBuDPhA2Anth is seen from the direction of the arrow in FIG. 3(A) (the direction parallel to the anthracene ring plane). The hatched portion in FIG. 3(B) represents an overhead portion of the plane of the anthracene ring, which is a luminophore, and the overhead portion includes a region overlapping with tBu groups, which are protecting groups. For example, in FIG. 3(B), an atom denoted by the arrow (a) is a carbon atom of the tBu group overlapping with the hatched portion, and an atom denoted by the arrow (b) is a hydrogen atom of the tBu group overlapping with the hatched portion. That is, in 2tBu-mmtBuDPhA2Anth, atoms included in protecting groups are positioned directly on one plane of the luminophore, and atoms included in protecting groups are also positioned directly on the other plane. With such a structure, even in the state where a guest material is dispersed into a host material, the anthracene ring, which is a luminophore, and the host material can be away from each other in the horizontal direction and the vertical direction of the anthracene ring, leading to inhibition of energy transfer by the Dexter mechanism.

In addition, for example, when the transition related to energy transfer is transition between HOMO and LUMO, the overlap of the HOMOs of the host material and the guest material and the overlap of LUMOs of the host material and the guest material are important for energy transfer by the Dexter mechanism. The overlap of the HOMOs of both of the materials and the overlap of LUMOs thereof significantly cause the Dexter mechanism. Therefore, it is important to prevent the overlap of the HOMOs of both of the materials and the overlap of LUMOs thereof to inhibit the Dexter mechanism. That is, it is important that the distance between the skeleton related to the excited state and the host material be large. In a fluorescent material, both HOMO and LUMO are included in the luminophore in many cases. For example, in the case where the HOMO and LUMO of a guest material extend above and below the luminophore plane (above and below the anthracene ring in 2tBu-mmtBuDPhA2Anth), it is important that the upper and lower planes of the luminophore be covered with protecting groups.

In a condensed aromatic ring and a condensed heteroaromatic ring serving as a luminophore, such as a pyrene ring and an anthracene ring, a transition dipole vector exists on the ring plane. Thus, in FIG. 3(B), 2tBu-mmtBuDPhA2Anth preferably includes a region overlapping with a tBu group, which is a protecting group, on a plane where a transition dipole vector exists, that is, directly on the plane of the anthracene ring. Specifically, at least one of atoms of a plurality of protecting groups (tBu groups in FIGS. 3(A) and 3(B)) is positioned directly on one plane of a condensed aromatic ring or a condensed heteroaromatic ring (an anthracene ring in FIGS. 3(A) and 3(B)), and at least one of atoms of the plurality of protecting groups is positioned directly on the other plane of the condensed aromatic ring or the condensed heteroaromatic ring. With such a structure, even in the state where a guest material is dispersed in a host material, the luminophore and the host material can be away from each other, leading to inhibition of energy transfer by the Dexter mechanism. Furthermore, protecting groups such as tBu groups are preferably positioned to cover a luminophore such as an anthracene ring.

Structure Example 2 of Light-Emitting Layer

Figure 4A:
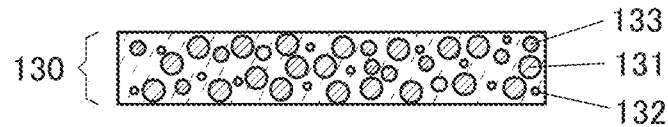
FIGS. 4A to 4D A schematic cross-sectional view of a light-emitting layer of a light-emitting element of one embodiment of the present invention and diagrams illustrating the correlation between energy levels.
Figure 4B:
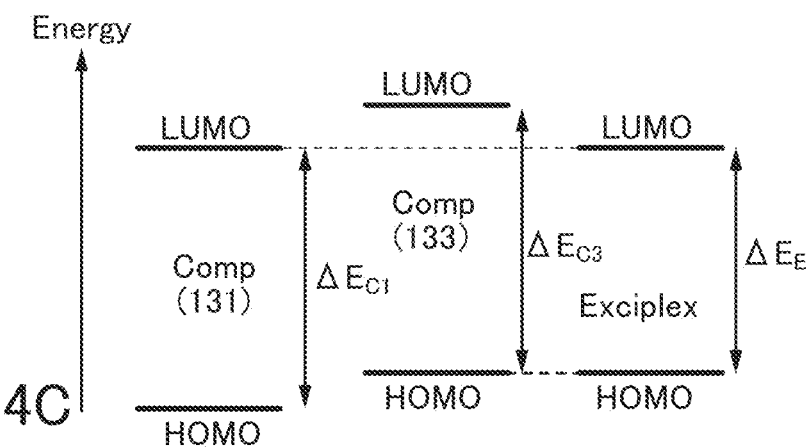
Figure 4C:
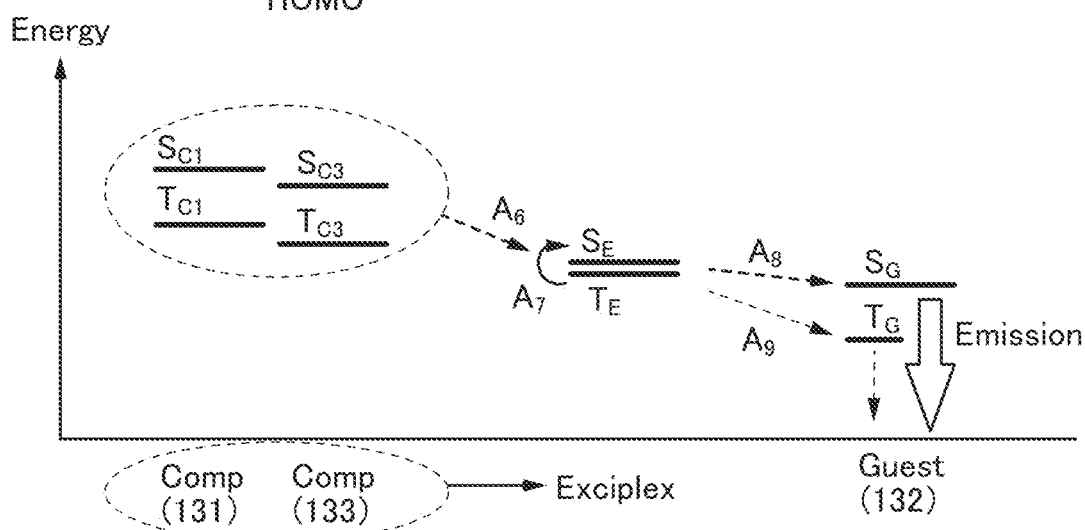

FIG. 4(C) shows an example of the correlation between energy levels in the light-emitting layer 130 of the light-emitting element 150 of one embodiment of the present invention. The light-emitting layer 130 illustrated in FIG. 4(A) contains the compound 131, the compound 132, and also a compound 133. In one embodiment of the present invention, the compound 132 is preferably a fluorescent material. In this structure example, the compound 131 and the compound 133 form an exciplex in combination.

Although it is acceptable as long as the compound 131 and the compound 133, in combination, can form an exciplex, it is further preferable that one of them be a compound having a function of transporting holes (a hole-transport property) and the other be a compound having a function of transporting electrons (an electron-transport property). In that case, a donor-acceptor exciplex is easily formed; thus, efficient formation of an exciplex is possible. In the case where the combination of the compound 131 and the compound 133 is a combination of a compound having a hole-transport property and a compound having an electron-transport property, the carrier balance can be easily controlled by the mixture ratio. Specifically, the ratio of the compound having a hole-transport property to the compound having an electron-transport property is preferably within a range of 1:9 to 9:1 (weight ratio). Since the carrier balance can be easily controlled with the structure, a carrier recombination region can also be controlled easily.

For the combination of host materials for forming an exciplex efficiently, it is preferred that the HOMO level of one of the compound 131 and the compound 133 be higher than the HOMO level of the other and the LUMO level of the one of the compounds be higher than the LUMO level of the other. Note that the HOMO level of the compound 131 may be equivalent to the HOMO level of the compound 133, or the LUMO level of the compound 131 may be equivalent to the LUMO level of the compound 133.

Note that the LUMO levels and the HOMO levels of the compounds can be derived from the electrochemical characteristics (reduction potentials and oxidation potentials) of the compounds that are measured by cyclic voltammetry (CV) measurement.

When the compound 131 has a hole-transport property and the compound 133 has an electron-transport property, for example, it is preferable that the HOMO level of the compound 131 be higher than the HOMO level of the compound 133 and that the LUMO level of the compound 131 be higher than the LUMO level of the compound 133, as in an energy band diagram in FIG. 4(B). Such a correlation between energy levels is suitable because holes and electrons, which are carriers injected from the pair of electrodes (the electrode 101 and the electrode 102), are easily injected into the compound 131 and the compound 133, respectively.

As for expressions and reference numerals in FIG. 4(B), Comp (131) represents the compound 131, Comp (133) represents the compound 133, $\Delta E_{C1}$ represents the energy difference between the LUMO level and the HOMO level of the compound 131, $\Delta E_{C3}$ represents the energy difference between the LUMO level and the HOMO level of the compound 132, and $\Delta E_E$ represents the energy difference between the LUMO level of the compound 133 and the HOMO level of the compound 131.

The exciplex formed by the compound 131 and the compound 133 is an exciplex that has HOMO of the molecular orbital in the compound 131 and LUMO of the molecular orbital in the compound 133. The excitation energy of the exciplex substantially corresponds to the energy difference ($\Delta E_E$) between the LUMO level of the compound 133 and the HOMO level of the compound 131, which is smaller than the energy difference ($\Delta E_{C1}$) between the LUMO level and the HOMO level of the compound 131 and the energy difference ($\Delta E_{C3}$) between the LUMO level and the HOMO level of the compound 133. Thus, when the compound 131 and the compound 133 form an exciplex, an excited state can be formed with lower excitation energy. Having lower excitation energy, the exciplex can form a stable excited state.

FIG. 4(C) shows the correlation between the energy levels of the compound 131, the compound 132, and the compound 133 in the light-emitting layer 130. The following explains what terms and numerals in FIG. 4(C) represent.

Comp (131): the compound 131
Comp (133): the compound 133
Guest (132): the compound 132
$S_{C1}$: the S1 level of the compound 131
$T_{C1}$: the T1 level of the compound 131
$S_{C3}$: the S1 level of the compound 133
$T_{C3}$: the S1 level of the compound 133
$T_G$: the T1 level of the compound 132
$S_E$: the S1 level of the exciplex
$T_E$: the T1 level of the exciplex In the light-emitting element of one embodiment of the present invention, the compound 131 and the compound 133 contained in the light-emitting layer 130 form the exciplex.

The S1 level ($S_E$) of the exciplex and the T1 level ($T_E$) of the exciplex are energy levels adjacent to each other (see Route $A_6$ in FIG. 4(C)).

Because the excitation energy levels ($S_E$ and $T_E$) of the exciplex are lower than the S1 levels ($S_E$) and $S_{C3}$) of the substances (the compound 131 and the compound 133) that form an exciplex, an excited state can be formed with lower excitation energy. Accordingly, the driving voltage of the light-emitting element 150 can be reduced.

Since the S1 level ($S_E$) and the T1 level ($T_E$) of the exciplex are adjacent to each other, reverse intersystem crossing occurs easily; the exciplex has a TADF property. Thus, the exciplex has a function of converting triplet excitation energy into singlet excitation energy by upconversion (Route $A_7$ in FIG. 4(C)). The singlet excitation energy of the exciplex can be rapidly transferred to the compound 132 (Route $A_8$ in FIG. 4(C)). At this time, $S_E \geq S_G$ is preferable. In Route $A_8$, the exciplex serves as an energy donor, and the compound 132 serves as an energy acceptor. Specifically, when the level of energy with a wavelength of the line obtained by extrapolating a tangent to the fluorescent spectrum of the exciplex at a tail on the short wavelength side is $S_E$ and the level of energy with a wavelength of the absorption edge of the absorption spectrum of the compound 132 is $S_G$, $S_E \geq S_G$ is preferable.

Note that in order to improve the TADF property, it is preferred that the T1 levels of both of the compound 131 and the compound 133, that is, $T_{C1}$ and $T_{C3}$ be higher than or equal to $T_E$. As the index for them, the emission peak wavelengths of the phosphorescent spectra of the compound 131 and the compound 133 on the shortest wavelength side are each preferably less than or equal to the maximum emission peak wavelength of the exciplex. When the level of energy with a wavelength of the line obtained by extrapolating a tangent to the fluorescent spectrum of the exciplex at a tail on the short wavelength side is $S_E$ and the levels of energies with wavelengths of the lines obtained by extrapolating tangents to the phosphorescent spectra of the compound 131 and the compound 133 at a tail on the short wavelength side are $T_{C1}$ and $T_{C3}$, respectively, $S_E - T_{C1} \leq 0.2$ eV and $S_E - T_{C3} \leq 0.2$ eV are preferable.

Triplet excitation energy generated in the light-emitting layer 130 is transferred through Route $A_6$ and from the S1 level of the exciplex to the S1 level of the guest material (Route $A_8$), which allows light emission of the guest material. Thus, the use of a combination of materials that form an exciplex in the light-emitting layer 130 can improve the emission efficiency of the fluorescent element.

In the light-emitting element of one embodiment of the present invention, a guest material in which a luminophore has protecting groups is used as the compound 132. Such a structure can inhibit energy transfer by the Dexter mechanism that is represented by Route $A_9$ as described above, leading to inhibition of deactivation of triplet excitation energy. Thus, a fluorescent element with high emission efficiency can be obtained.

The above-described processes through Routes $A_6$ to $A_8$ are sometimes referred to as ExSET (Exciplex-Singlet Energy Transfer) or ExEF (Exciplex-Enhanced Fluorescence) in this specification and the like. In other words, in the light-emitting layer 130, excitation energy is supplied from the exciplex to the fluorescent material.

Structure Example 3 of Light-Emitting Layer

In this structure example, the case where a phosphorescent material is used as the compound 133 of the light-emitting element utilizing ExEF described above is described. That is, the case where a phosphorescent material is used as one of compounds that form an exciplex is described.

In this structure example, a compound containing a heavy atom is used as one of compounds that form an exciplex. Thus, intersystem crossing between a singlet state and a triplet state is promoted. Thus, an exciplex in which the triplet excited state can be transferred to the singlet ground state (i.e., that can exhibit phosphorescence) can be formed. In this case, unlike in the case of a typical exciplex, the triplet excitation energy level ($T_E$) of the exciplex is the level of an energy donor; thus, $T_E$ is preferably higher than or equal to the singlet excitation energy level ($S_G$) of the compound 132, which is a light-emitting material. Specifically, when the level of energy with a wavelength of the line obtained by extrapolating a tangent to the emission spectrum of the exciplex containing a heavy atom at a tail on the short wavelength side is $T_E$ and the level of energy with a wavelength of the absorption edge of the absorption spectrum of the compound 132 is $S_G$, $T_E \geq S_G$ is preferable.

With such an energy level correlation, the triplet excitation energy of the formed exciplex can be transferred from the triplet excitation energy level ($T_E$) of the exciplex to the singlet excitation energy level ($S_G$) of the compound 132. Note that it is difficult to clearly distinguish fluorescence and phosphorescence from each other in an emission spectrum in some cases because the S1 level ($S_E$) and the T1 level ($T_E$) of the exciplex are energy levels adjacent to each other. In that case, fluorescence and phosphorescence can be sometimes distinguished from each other by the emission lifetime.

Note that the phosphorescent material used in the above structure preferably contains a heavy atom such as Ir, Pt, Os, Ru, or Pd. In contrast, in this structure example, a phosphorescent material serves as an energy donor; thus, the quantum yield can be either high or low. That is, energy transfer from the triplet excitation energy level of the exciplex to the singlet excitation energy level of the guest material is acceptable as long as it is allowable transition. The energy transfer from the phosphorescent material or the exciplex formed using a phosphorescent material to the guest material is preferred, in which case energy transfer from the triplet excitation energy level of the energy donor to the singlet excitation energy level of the guest material (energy acceptor) is allowable transition. Thus, without through the process of Route $A_7$ in FIG. 4(C), the triplet excitation energy of the exciplex can be transferred to the S1 level ($S_G$) of the guest material through the process of Route $A_8$. That is, triplet excitation energy and singlet excitation energy can be transferred to the S1 level of the guest material only through the process of Route $A_6$ and Route $A_8$. In Route $A_8$, the exciplex serves as an energy donor, and the compound 132 serves as an energy acceptor.

In the light-emitting element of one embodiment of the present invention, a guest material in which a luminophore has protecting groups is used as the compound 132. Such a structure can inhibit energy transfer by the Dexter mechanism that is represented by Route $A_9$ as described above, leading to inhibition of deactivation of triplet excitation energy. Thus, a fluorescent element with high emission efficiency can be obtained.

Structure Example 4 of Light-Emitting Layer

In this structure example, the case where a material having a TADF property is used as the compound 133 of the light-emitting element utilizing ExEF described above will be described with reference to FIG. 4(D).

Figure 4D:
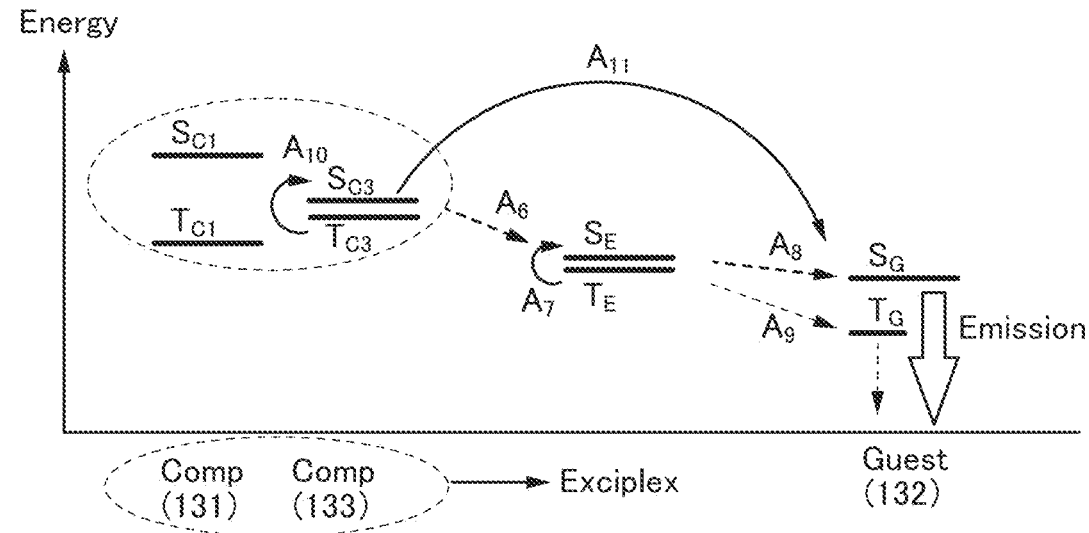

Since the compound 133 is the TADF material, the compound 133 that does not form an exciplex has a function of converting triplet excitation energy into singlet excitation energy by upconversion (Route $A_{10}$ in FIG. 4(D)). The singlet excitation energy of the compound 133 can be rapidly transferred to the compound 132 (Route $A_{11}$ in FIG. 4(D)). At this time, $S_{C3} \geq S_G$ is preferable.

As described in the above structure example of the light-emitting layer, the light-emitting element of one embodiment of the present invention has a pathway where the triplet excitation energy is transferred to the compound 132, which is a guest material, through Route $A_6$ to Route $A_8$ in FIG. 4(D) and a pathway where the triplet excitation energy is transferred to the compound 132 through Route $A_{10}$ and Route $A_{11}$ in FIG. 4(D). A plurality of pathways through each of which the triplet excitation energy is transferred to the fluorescent material can further improve the emission efficiency. In Route $A_8$, the exciplex serves as an energy donor, and the compound 132 serves as an energy acceptor. In Route $A_{11}$, the compound 133 serves as an energy donor and the compound 132 serves as an energy acceptor.

In this structure example, the exciplex and the compound 133 serve as energy donors, and the compound 132 serves as an energy acceptor.

Structure Example 5 of Light-Emitting Layer

Figure 5A:
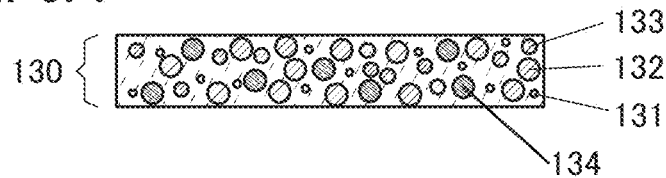
FIGS. 5A to 5C A schematic cross-sectional view of a light-emitting layer of a light-emitting element of one embodiment of the present invention and diagrams illustrating the correlation between energy levels.

FIG. 5(A) shows the light-emitting layer 130 containing four kinds of materials. The light-emitting layer 130 in FIG. 5(A) contains the compound 131, the compound 132, the compound 133, and a compound 134. In one embodiment of the present invention, the compound 133 has a function of converting triplet excitation energy into light emission. In this structure example, the case where the compound 133 is a phosphorescent material is described. The compound 132 is a guest material that emits fluorescence. The compound 131 is an organic compound that forms an exciplex together with the compound 134.

Figure 5B:
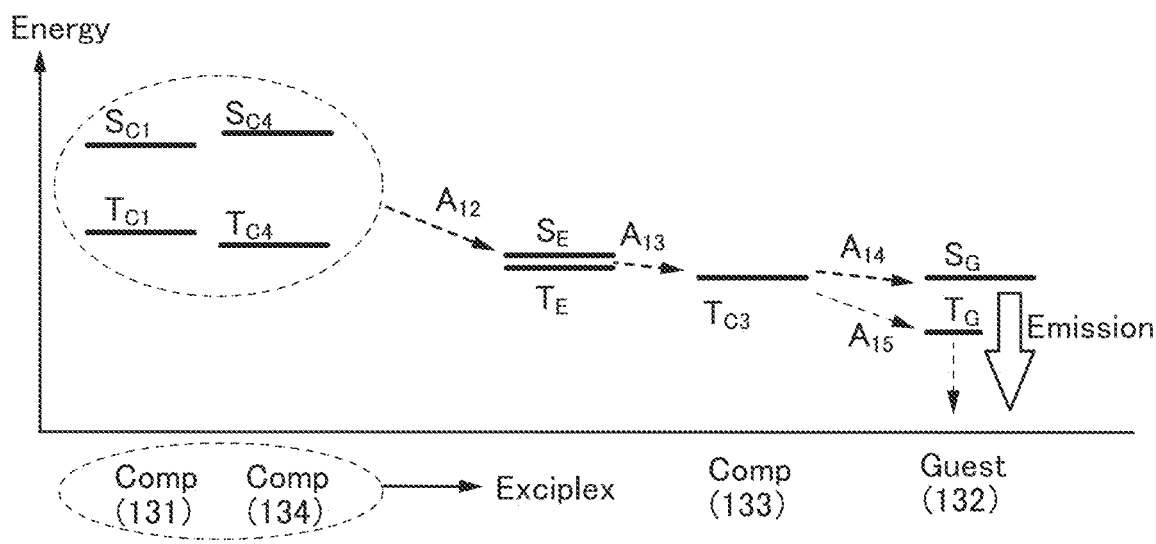

FIG. 5(B) shows the correlation between the energy levels of the compound 131, the compound 132, the compound 133, and the compound 134 in the light-emitting layer 130. The following explains what terms and signs in FIG. 5(B) represent, and the other terms and signs are the same as the terms and the signs in FIG. 4(B).

$S_{C4}$: the S1 level of the compound 134
$T_{C4}$: the T1 level of the compound 134

In the light-emitting element of one embodiment of the present invention described in this structure example, the compound 131 and the compound 134 contained in the light-emitting layer 130 form the exciplex. The S1 level ($S_E$) of the exciplex and the T1 level ($T_E$) of the exciplex are energy levels adjacent to each other (see Route $A_{12}$ in FIG. 5(B)).

As described above, when the exciplex formed through the above process loses excitation energy, the two substances forming the exciplex individually behave as the original separate substances.

Because the excitation energy levels ($S_E$ and $T_E$) of the exciplex are lower than the S1 levels ($S_{C1}$ and $S_{C4}$) of the substances (the compound 131 and the compound 134) that form an exciplex, an excited state can be formed with lower excitation energy. Accordingly, the driving voltage of the light-emitting element 150 can be reduced.

Here, when the compound 133 is a phosphorescent material, intersystem crossing between a singlet state and a triplet state is allowed. Hence, both the singlet excitation energy and the triplet excitation energy of the exciplex are rapidly transferred to the compound 133 (Route $A_{13}$). At this time, $T_E \geq T_{C3}$ is preferable. In addition, the triplet excitation energy of the compound 133 can be efficiently converted into the singlet excitation energy of the compound 132 (Route $A_{14}$). Here, $T_E \geq T_{C3} \geq S_G$ as shown in FIG. 5(B) is preferable, in which case the excitation energy of the compound 133 is efficiently transferred as the singlet excitation energy to the compound 132, which is the guest material. Specifically, when the level of energy with a wavelength of the line obtained by extrapolating a tangent to the phosphorescent spectrum of the compound 133 at a tail on the short wavelength side is $T_{C3}$ and the level of energy with a wavelength of the absorption edge of the absorption spectrum of the compound 132 is $S_G$, $T_{C3} \geq S_G$ is preferable. In Route $A_{14}$, the compound 133 serves as an energy donor and the compound 132 serves as an energy acceptor.

Although it is acceptable as long as the compound 131 and the compound 134, in combination, can form an exciplex, it is further preferable that one of them be a compound having a hole-transport property and the other be a compound having an electron-transport property.

For the combination of materials for forming an exciplex efficiently, it is preferred that the HOMO level of one of the compound 131 and the compound 134 be higher than the HOMO level of the other and the LUMO level of the one of the compounds be higher than the LUMO level of the other.

Furthermore, the correlation between the energy levels of the compound 131 and the compound 134 is not limited to that shown in FIG. 5(B). That is, the singlet excitation energy level ($S_{C1}$) of the compound 131 may be higher or lower than the singlet excitation energy level ($S_{C4}$) of the compound 134. The triplet excitation energy level ($T_{C1}$) of the compound 131 may be higher or lower than the triplet excitation energy level ($T_{C4}$) of the compound 134.

In the light-emitting element of one embodiment of the present invention, the compound 131 preferably has a π-electron deficient skeleton. Such a composition lowers the LUMO level of the compound 131, which is suitable for forming an exciplex.

In the light-emitting element of one embodiment of the present invention, the compound 131 preferably has a π-electron rich skeleton. Such a composition increases the HOMO level of the compound 131, which is suitable for forming an exciplex.

In the light-emitting element of one embodiment of the present invention, a guest material in which a luminophore has protecting groups is used as the compound 132. Such a structure can inhibit energy transfer by the Dexter mechanism that is represented by Route $A_{15}$ as described above, leading to inhibition of deactivation of triplet excitation energy. Thus, a fluorescent element with high emission efficiency can be obtained. In addition, the concentration of the compound 133, which is an energy donor, can be increased. As a result, increasing the rate of energy transfer by the Förster mechanism and inhibiting energy transfer by the Dexter mechanism, which are originally conflicting phenomena, can be concurrently caused. As the rate of energy transfer by the Förster mechanism is increased, the excitation lifetime of the energy acceptor in the light-emitting layer becomes shorter; thus, the reliability of the light-emitting element can be improved. When the compound 133, which is an energy donor, is added to the light-emitting layer, the concentration of the compound 133 with respect to the host material is preferably higher than or equal to 2 wt % and lower than or equal to 50 wt %, more preferably higher than or equal to 5 wt % and lower than or equal to 30 wt %, still more preferably higher than or equal to 5 wt % and lower than or equal to 20 wt %. With such a structure, the rate of energy transfer by the Förster mechanism can be increased; thus, a light-emitting element with high emission efficiency can be obtained.

Note that the above-described processes through Routes $A_{12}$ and $A_{13}$ may be referred to as ExTET (Exciplex-Triplet Energy Transfer) in this specification and the like. In other words, in the light-emitting layer 130, excitation energy is supplied from the exciplex to the compound 133. Thus, this structure example can be referred to as a structure in which a fluorescent material having protecting groups is mixed to a light-emitting layer capable of utilizing ExTET.

Structure Example 6 of Light-Emitting Layer

In this structure example, the case where a material having a TADF property is used as the compound 134 described in Structure example 5 of light-emitting layer described above will be described.

Figure 5C:
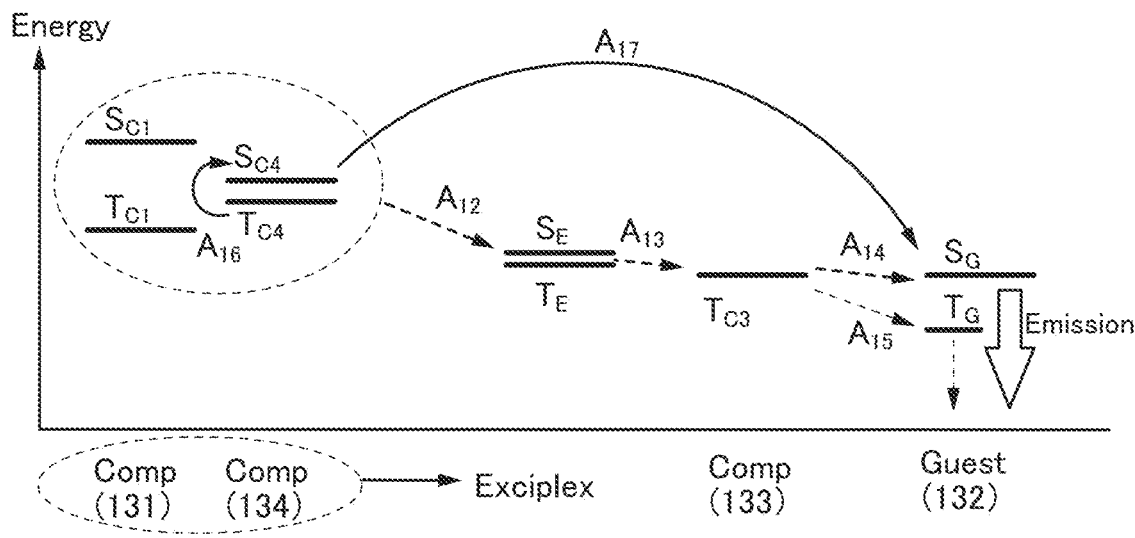

FIG. 5(C) shows the light-emitting layer 130 containing four kinds of materials. The light-emitting layer 130 in FIG. 5(C) contains the compound 131, the compound 132, the compound 133, and a compound 134. In one embodiment of the present invention, the compound 133 has a function of converting triplet excitation energy into light emission. The compound 132 is a guest material that emits fluorescence. The compound 131 is an organic compound that forms an exciplex together with the compound 134.

Here, since the compound 134 is the TADF material, the compound 134 that does not form an exciplex has a function of converting triplet excitation energy into singlet excitation energy by upconversion (Route $A_{16}$ in FIG. 5(C)). The singlet excitation energy of the compound 134 can be rapidly transferred to the compound 132 (Route $A_{17}$ in FIG. 5(C)). At this time, $S_{C4} S_G$ is preferable. Specifically, when the level of energy with a wavelength of the line obtained by extrapolating a tangent to the fluorescent spectrum of the compound 134 at a tail on the short wavelength side is $S_{C4}$ and the level of energy with a wavelength of the absorption edge of the absorption spectrum of the compound 132 is $S_G$, $S_{C4} \geq S_G$ is preferable.

As described in the above structure example of the light-emitting layer, the light-emitting element of one embodiment of the present invention has a pathway where the triplet excitation energy is transferred to the compound 132, which is a guest material, through Route $A_{12}$ to Route $A_{14}$ in FIG. 5(B) and a pathway where the triplet excitation energy is transferred to the compound 132 through Route $A_{16}$ and Route $A_{17}$ in FIG. 5(C). A plurality of pathways through each of which the triplet excitation energy is transferred to the fluorescent material can further improve the emission efficiency. In Route $A_{14}$, the compound 133 serves as an energy donor, and the compound 132 serves as an energy acceptor. In Route $A_{17}$, the compound 134 serves as an energy donor and the compound 132 serves as an energy acceptor.

Structure Example 7 of Light-Emitting Layer

Figure 6A:
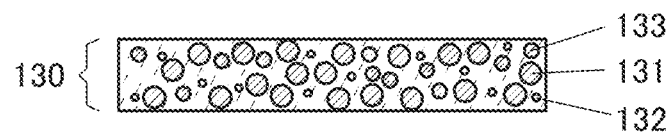
FIGS. 6A to 6C A schematic cross-sectional view of a light-emitting layer of a light-emitting element of one embodiment of the present invention and diagrams illustrating the correlation between energy levels.
Figure 6B:
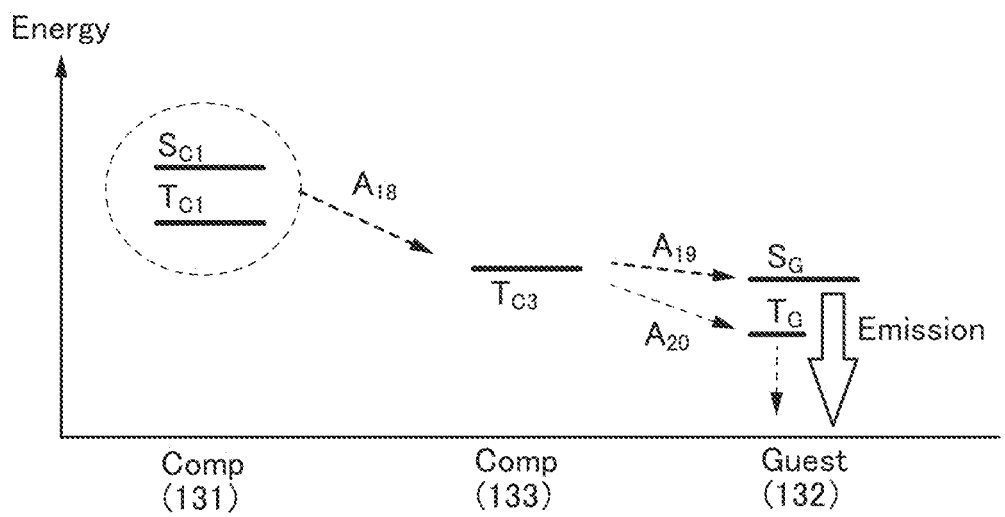

FIG. 6(B) shows an example of the correlation between energy levels in the light-emitting layer 130 of the light-emitting element 150 of one embodiment of the present invention. The light-emitting layer 130 illustrated in FIG.

6(A) contains the compound 131, the compound 132, and also the compound 133. In one embodiment of the present invention, the compound 132 is a fluorescent material having protecting groups. The compound 133 has a function of converting triplet excitation energy into light emission. In this structure example, the case where the compound 133 is a phosphorescent material is described.

The following explains what terms and numerals in FIG. 6(B) and FIG. 6(C) described later represent.
Comp (131): the compound 131
Comp (133): the compound 133
Guest (132): the compound 132
$S_{C1}$: the S1 level of the compound 131
$T_{C1}$: the T1 level of the compound 131
$T_{C3}$: the T1 level of the compound 133
$T_G$: the T1 level of the compound 132
$S_G$: the S1 level of the compound 132

In the light-emitting element of one embodiment of the present invention, when carrier recombination mainly occurs in the compound 131 contained in the light-emitting layer 130, singlet excitons and triplet excitons are generated. Since the compound 133 is a phosphorescent material, selecting materials that have a relation of $T_{C3} \leq T_{C1}$ allows both the singlet excitation energy and triplet excitation energy generated in the compound 131 to be transferred to the $T_{C3}$ level of the compound 133 (Route $A_{18}$ in FIG. 6(B)). Some of the carriers can be recombined in the compound 133.

Note that the phosphorescent material used in the above structure preferably contains a heavy atom such as Ir, Pt, Os, Ru, or Pd. In contrast, also in this structure example, a phosphorescent material serves as an energy donor as described above; thus, the quantum yield can be either high or low. A phosphorescent material is preferably used as the compound 133, in which case energy transfer from the triplet excitation energy level of the energy donor to the singlet excitation energy level of the guest material (energy acceptor) is allowable transition. Thus, the triplet excitation energy of the compound 133 can be transferred to the S1 level ($S_G$) of the guest material through the process of Route $A_{19}$. In Route $A_{19}$, the compound 133 serves as an energy donor and the compound 132 serves as an energy acceptor. In that case, $T_{C3} \geq S_G$ is preferable because the excitation energy of the compound 133 is efficiently transferred to the singlet excited state of the compound 132, which is a guest material. Specifically, when the level of energy with a wavelength of the line obtained by extrapolating a tangent to the phosphorescent spectrum of the compound 133 at a tail on the short wavelength side is $T_{C3}$ and the level of energy with a wavelength of the absorption edge of the absorption spectrum of the compound 132 is $S_G$, $T_{C3} \geq S_G$ is preferable.

In the light-emitting element of one embodiment of the present invention, a guest material in which a luminophore has protecting groups is used as the compound 132. Such a structure can inhibit energy transfer by the Dexter mechanism that is represented by Route $A_{20}$ as described above, leading to inhibition of deactivation of triplet excitation energy. Thus, a fluorescent element with high emission efficiency can be obtained.

Structure Example 8 of Light-Emitting Layer

Figure 6C:
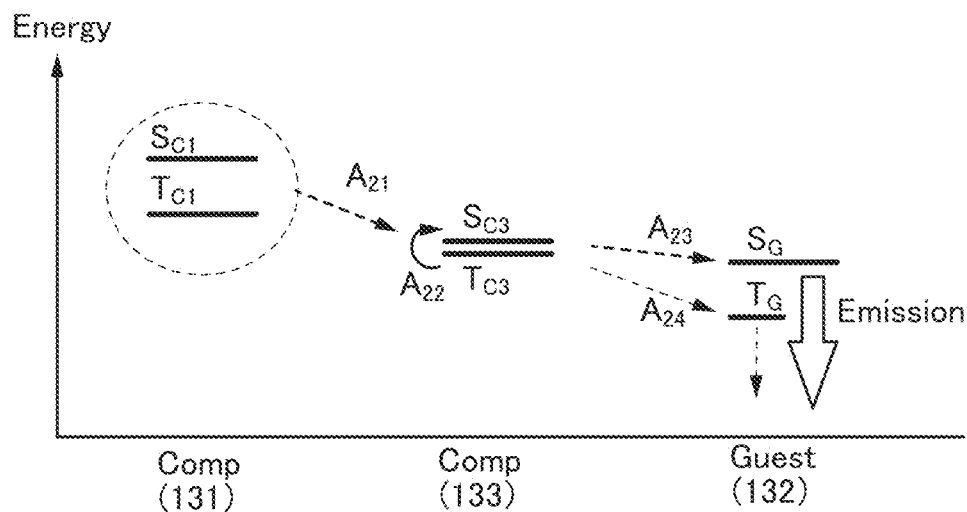

FIG. 6(C) shows an example of the correlation between energy levels in the light-emitting layer 130 of the light-emitting element 150 of one embodiment of the present invention. The light-emitting layer 130 illustrated in FIG. 6(C) contains the compound 131, the compound 132, and also the compound 133. In one embodiment of the present invention, the compound 132 is a fluorescent material having protecting groups. The compound 133 has a function of converting triplet excitation energy into light emission. In this structure example, the case where the compound 133 is a compound having a TADF property is described.

The following explains what terms and signs in FIG. 6(C) represent, and the other terms and signs are the same as the terms and the signs in FIG. 6(B).
$S_{C3}$: the S1 level of the compound 133

In the light-emitting element of one embodiment of the present invention, when carrier recombination mainly occurs in the compound 131 contained in the light-emitting layer 130, singlet excitons and triplet excitons are generated. Selecting materials that have a relation of $S_{C3}\ S_{C1}$ and $T_{C3} \leq T_{C1}$ allows both the singlet excitation energy and triplet excitation energy generated in the compound 131 to be transferred to the $S_{C3}$ and $T_{C3}$ levels of the compound 133 (Route $A_{21}$ in FIG. 6(C)). Some of the carriers can be recombined in the compound 133.

The compound 134 is a TADF material and thus has a function of converting triplet excitation energy into singlet excitation energy by upconversion (Route $A_{22}$ in FIG. 6(C)). The singlet excitation energy of the compound 133 can be rapidly transferred to the compound 132 (Route $A_{23}$ in FIG. 6(C)). At this time, $S_{C3} \geq S_G$ is preferable. Specifically, when the level of energy with a wavelength of the line obtained by extrapolating a tangent to the fluorescent spectrum of the compound 133 at a tail on the short wavelength side is $S_{C3}$ and the level of energy with a wavelength of the absorption edge of the absorption spectrum of the compound 132 is $S_G$, $S_{C3} \geq S_G$ is preferable. Through the processes through Route $A_{21}$ to Route $A_{23}$, triplet excitation energy in the light-emitting layer 130 can be converted into fluorescence of the compound 132. In Route $A_{23}$, the compound 133 serves as an energy donor and the compound 132 serves as an energy acceptor.

In the light-emitting element of one embodiment of the present invention, a guest material in which a luminophore has protecting groups is used as the compound 132. Such a structure can inhibit energy transfer by the Dexter mechanism that is represented by Route $A_{24}$ as described above, leading to inhibition of deactivation of triplet excitation energy. Thus, a fluorescent element with high emission efficiency can be obtained.

<Energy Transfer Mechanism>

Here, the Förster mechanism and the Dexter mechanism will be described. Here, as for supply of excitation energy from a first material in an excited state to a second material in a ground state, an intermolecular energy transfer process between the first material and the second material is described; the same can be applied to the case where one of them is an exciplex.

<<Förster Mechanism>>

In the Förster mechanism, energy transfer does not require direct contact between molecules and energy is transferred through a resonant phenomenon of dipolar oscillation between a first material and a second material. By the resonant phenomenon of dipolar oscillation, the first material provides energy to the second material, and thus, the first material in an excited state is brought into a ground state and the second material in a ground state is brought into an excited state. Note that the rate constant $k_{h^* \to g}$ of the Förster mechanism is expressed by Formula (1).

[Formula 1]

$$k_{h^* \to g} = \frac{9000c^4 K^2 \phi \ln 10}{128\pi^5 n^4 N \tau R^6} \int \frac{f'_h(v)\varepsilon_g(v)}{v^4} dv \qquad (1)$$

In Formula (1), v denotes a frequency, $f'_h(v)$ denotes a normalized emission spectrum of the first material (a fluorescent spectrum in the case where energy transfer from a singlet excited state is discussed, or a phosphorescent spectrum in the case where energy transfer from a triplet excited state is discussed), $\varepsilon_g(v)$ denotes a molar absorption coefficient of the second material, N denotes Avogadro's number, n denotes a refractive index of a medium, R denotes an intermolecular distance between the first material and the second material, τ denotes a measured lifetime of an excited state (fluorescence lifetime or phosphorescence lifetime), c denotes the speed of light, ϕ denotes a luminescence quantum yield (a fluorescence quantum yield in the case where energy transfer from a singlet excited state is discussed, or a phosphorescence quantum yield in the case where energy transfer from a triplet excited state is discussed), and $K^2$ denotes a coefficient (0 to 4) of orientation of a transition dipole moment between the first material and the second material. Note that $K^2 = 2/3$ in random orientation.

In the case where the first material is used as the energy donor and the second material is used as the energy acceptor and the emission colors of the first material and the second material are close to each other, the overlap between $f'_h(v)$ and $\varepsilon_g(v)$ decreases according to Formula (1) shown above ($\varepsilon_g(v)$ exists on the longer wavelength side than the emission spectrum of the second material); thus, $k_{h^* \to g}$ decreases. However, in the light-emitting element of one embodiment of the present invention, the energy donor concentration in the light-emitting layer can be increased as mentioned above, so that the value of R in Formula (1) can be increased, which inhibits a decrease in $k_{h^* \to g}$. Thus, a fluorescent material having an emission color close to that of the energy donor can be used as a light-emitting material of the light-emitting element of one embodiment of the present invention. Note that the light-emitting element of one embodiment of the present invention can also use an energy donor and an energy acceptor that have different emission colors.

<<Dexter Mechanism>>

In the Dexter mechanism, the first material and the second material are close to a contact effective range where their orbitals overlap, and the first material in an excited state and the second material in a ground state exchange their electrons, which leads to energy transfer. Note that the rate constant $k_{h^* \to g}$ of the Dexter mechanism is expressed by Formula (2).

[Formula 2]

$$k_{h^* \to g} = \left(\frac{2\pi}{h}\right) K^2 \exp\left(-\frac{2R}{L}\right) \int f'_h(v)\varepsilon'_g(v) dv \qquad (2)$$

In Formula (2), h denotes a Planck constant, K denotes a constant having an energy dimension, v denotes a frequency, $f'_h(v)$ denotes a normalized emission spectrum of the first material (the fluorescent spectrum in the case where energy transfer from a singlet excited state is discussed, or the phosphorescent spectrum in the case where energy transfer from a triplet excited state is discussed), $\varepsilon'_g(v)$ denotes a normalized absorption spectrum of the second material, L denotes an effective molecular radius, and R denotes an intermolecular distance between the first material and the second material.

Here, the efficiency $\phi_{ET}$ of energy transfer from the first material to the second material is expressed by Formula (3). $k_r$ denotes a rate constant of a light-emission process (fluorescence in the case where energy transfer from a singlet excited state is discussed, or phosphorescence in the case where energy transfer from a triplet excited state is discussed) of the first material, $k_n$ denotes a rate constant of a non-light-emission process (thermal deactivation or intersystem crossing) of the second material, and τ denotes a measured lifetime of an excited state of the first material.

[Formula 3]

$$\phi_{ET} = \frac{k_{h^* \to g}}{k_r + k_n + k_{h^* \to g}} = \frac{k_{h^* \to g}}{\left(\frac{1}{\tau}\right) + k_{h^* \to g}} \qquad (3)$$

According to Formula (3), it is found that the energy transfer efficiency $\phi_{ET}$ can be increased by increasing the rate constant $k_{h^* \to g}$ of energy transfer so that another competing rate constant $k_r + k_n (= 1/\tau)$ becomes relatively small.

<<Concept for Promoting Energy Transfer>>

First, energy transfer by the Förster mechanism is considered. When Formula (1) is substituted into Formula (3), τ can be eliminated. Thus, in the case of the Förster mechanism, the energy transfer efficiency $\phi_{ET}$ does not depend on the lifetime r of the excited state of the first material. Furthermore, it can be said that high energy transfer efficiency $\phi_{ET}$ is obtained when the emission quantum yield ϕ is high.

Furthermore, it is preferred that the emission spectrum of the first material largely overlap with the absorption spectrum of the second material (absorption corresponding to transition from a singlet ground state to a singlet excited state). Moreover, it is preferable that the molar absorption coefficient of the second material be also high. This means that the emission spectrum of the first material overlaps with the absorption band of the second material which is on the longest wavelength side. Note that since direct transition from the singlet ground state to the triplet excited state of the second material is forbidden, the molar absorption coefficient of the second material in the triplet excited state can be ignored. Thus, a process of energy transfer from an excited state of the first material to a triplet excited state of the second material by the Förster mechanism can be ignored, and only a process of energy transfer to a singlet excited state of the second material is considered.

The rate of energy transfer by the Förster mechanism is inversely proportional to the 6th power of the intermolecular distance R between the first material and the second material, according to Formula (1). As described above, when R is less than or equal to 1 nm, energy transfer by the Dexter mechanism is dominant. Therefore, to increase the rate of energy transfer by the Förster mechanism while inhibiting energy transfer by the Dexter mechanism, the intermolecular distance is preferably greater than or equal to 1 nm and less than or equal to 10 nm. This requires the above protecting groups to be not too bulky; thus, the number of carbon atoms of the protecting groups is preferably 3 to 10.

Next, energy transfer by the Dexter mechanism is considered. According to Formula (2), in order to increase the rate constant $k_{h^* \to g}$, it is found that the emission spectrum of the first material (the fluorescent spectrum in the case where energy transfer from a singlet excited state is discussed, or the phosphorescent spectrum in the case where energy transfer from a triplet excited state is discussed) preferably largely overlaps with the absorption spectrum of the second material (absorption corresponding to transition from a singlet ground state to a singlet excited state). Therefore, the energy transfer efficiency can be optimized by making the emission spectrum of the first material overlap with the absorption band of the second material which is on the longest wavelength side.

When Formula (2) is substituted into Formula (3), it is found that the energy transfer efficiency $\phi_{ET}$ in the Dexter mechanism depends on $\tau$. Since the Dexter mechanism is a process of energy transfer based on the electron exchange, as well as the energy transfer from the singlet excited state of the first material to the singlet excited state of the second material, energy transfer from the triplet excited state of the first material to the triplet excited state of the second material occurs.

In the light-emitting element of one embodiment of the present invention in which the second material is a fluorescent material, the efficiency of energy transfer to the triplet excited state of the second material is preferably low. That is, the efficiency of energy transfer based on the Dexter mechanism from the first material to the second material is preferably low and the efficiency of energy transfer based on the Förster mechanism from the first material to the second material is preferably high.

As described above, the energy transfer efficiency in the Förster mechanism does not depend on the lifetime $\tau$ of the excited state of the first material. In contrast, the energy transfer efficiency in the Dexter mechanism depends on the excitation lifetime $\tau$ of the first material; to reduce the energy transfer efficiency in the Dexter mechanism, the excitation lifetime $\tau$ of the first material is preferably short.

Thus, in one embodiment of the present invention, an exciplex, a phosphorescent material, or a TADF material is used as the first material. These materials each have a function of converting triplet excitation energy into light emission. The energy transfer efficiency of the Förster mechanism depends on the emission quantum yield of the energy donor; thus, the excitation energy of the first material capable of converting the triplet excited state energy into light emission, such as a phosphorescent material, an exciplex, or a TADF material, can be transferred to the second material by the Förster mechanism. Meanwhile, with the structure of one embodiment of the present invention, reverse intersystem crossing from the triplet excited state to the singlet excited state of the first material (exciplex or TADF material) can be promoted, and the excitation lifetime $\tau$ of the triplet excited state of the first material can be short. Furthermore, transition from the triplet excited state to the singlet ground state of the first material (phosphorescent material or exciplex using a phosphorescent material) can be promoted, and the excitation lifetime $\tau$ of the triplet excited state of the first material can be short. As a result, the energy transfer efficiency from the triplet excited state of the first material to the triplet excited state of the fluorescent material (second material) in the Dexter mechanism can be reduced.

In the light-emitting element of one embodiment of the present invention, a fluorescent material having protecting groups is used as the second material, as described above. Therefore, the intermolecular distance between the first material and the second material can be large. In the light-emitting element of one embodiment of the present invention, a material having a function of converting triplet excitation energy into light emission is used as the first material, and a fluorescent material having protecting groups is used as the second material, whereby the efficiency of energy transfer by the Dexter mechanism can be reduced. As a result, non-radiative decay of the triplet excitation energy in the light-emitting layer 130 can be inhibited, and a light-emitting element with high emission efficiency can be provided.

<Material>

Next, components of a light-emitting element of one embodiment of the present invention will be described in detail below.

<<Light-Emitting Layer>>

Materials that can be used for the light-emitting layer 130 will be described below. In the light-emitting layer of the light-emitting element of one embodiment of the present invention, an energy acceptor having a function of converting triplet excitation energy into light emission and an energy donor having a luminophore and protecting groups are used. Examples of the material having a function of converting triplet excitation energy into light emission include a TADF material, an exciplex, and a phosphorescent material.

Examples of the luminophore included in the compound 132 serving as an energy acceptor have a phenanthrene skeleton, a stilbene skeleton, an acridone skeleton, a phenoxazine skeleton, and a phenothiazine skeleton. Specifically, a fluorescent material having any of a naphthalene skeleton, an anthracene skeleton, a fluorene skeleton, a chrysene skeleton, a triphenylene skeleton, a tetracene skeleton, a pyrene skeleton, a perylene skeleton, a coumarin skeleton, a quinacridone skeleton, and a naphthobisbenzofuran skeleton is preferred because of its high fluorescence quantum yield.

The protecting group is preferably an alkyl group having 1 to 10 carbon atoms, a cycloalkyl group having 3 to 10 carbon atoms, a branched-chain alkyl group having 3 to 10 carbon atoms, or a trialkylsilyl group having 3 to 12 carbon atoms.

Examples of an alkyl group having 1 to 10 carbon atoms include a methyl group, an ethyl group, a propyl group, a pentyl group, and a hexyl group, and a branched-chain alkyl group having 3 to 10 carbon atoms, which is described later, is particularly preferred. Note that the alkyl group is not limited thereto.

Examples of a cycloalkyl group having 3 to 10 carbon atoms include a cyclopropyl group, a cyclobutyl group, a cyclohexyl group, a norbornyl group, and an adamantyl group. The cycloalkyl group is not limited thereto. In the case where the cycloalkyl group has a substituent, examples of the substituent include an alkyl group having 1 to 7 carbon atoms, such as a methyl group, an ethyl group, a propyl group, an isopropyl group, a butyl group, an isobutyl group, a sec-butyl group, a tert-butyl group, a pentyl group, or a hexyl group, a cycloalkyl group having 5 to 7 carbon atoms, such as a cyclopentyl group, a cyclohexyl group, a cycloheptyl group, or a 8,9,10-trinorbornanyl group, and an aryl group having 6 to 12 carbon atoms, such as a phenyl group, a naphthyl group, or a biphenyl group.

Examples of a branched-chain alkyl group having 3 to 10 carbon atoms include an isopropyl group, a sec-butyl group, an isobutyl group, a tert-butyl group, an isopentyl group, a sec-pentyl group, a tert-pentyl group, a neopentyl group, an isohexyl group, a 3-methylpentyl group, a 2-methylpentyl group, a 2-ethylbutyl group, a 1,2-dimethylbutyl group, and a 2,3-dimethylbutyl group. The branched-chain alkyl group is not limited thereto.

Examples of a trialkylsilyl group having 3 to 12 carbon atoms include a trimethylsilyl group, a triethylsilyl group, and a tert-butyl dimethylsilyl group. The trialkylsilyl group is not limited thereto.

In the molecular structure of the energy acceptor, it is preferred that two or more diarylamino groups be bonded to a luminophore and aryl groups of the diarylamino groups each have at least one protecting group. It is further preferred that at least two protecting groups be bonded to each of the aryl groups. This is because a larger number of protecting groups more effectively inhibit energy transfer by the Dexter mechanism in the case where the guest material is used for the light-emitting layer. To inhibit an increase in molecular weight and keep the sublimation property, the diarylamino groups are preferably diphenylamino groups. Note that a structure in which the luminophore and the diarylamino group are bonded to each other through a nitrogen atom of the diarylamino group is preferable.

Furthermore, when two or more diarylamino groups are bonded to a luminophore, a fluorescent material whose emission color can be adjusted and which has high quantum yield can be obtained. The diarylamino groups are preferably bonded to the luminophore at symmetric positions. With such a structure, the fluorescent material can have high quantum yield.

The protecting groups may be introduced to the luminophore via the aryl groups of the diarylamino groups, not directly introduced to the luminophore. Such a structure is preferred because the protecting groups can be arranged to cover the luminophore, allowing the host material and the luminophore to be away from each other from any direction. In the case where the protecting groups are not directly bonded to the luminophore, four or more protecting groups are preferably introduced to one luminophore.

Furthermore, it is preferred that at least one of atoms of the plurality of protecting groups be positioned directly on one plane of the luminophore, that is, the condensed aromatic ring or the condensed heteroaromatic ring, and at least one of atoms of the plurality of protecting groups be positioned directly on the other plane of the condensed aromatic ring or the condensed heteroaromatic ring, as illustrated in FIG. 3. As a specific method, the following structure is given. That is, the condensed aromatic ring or the condensed heteroaromatic ring, which is a luminophore, is bonded to two or more diphenylamino groups, and the phenyl groups of the two or more diphenylamino groups each independently have protecting groups at the 3-position and the 5-position.

Such a structure enables a steric configuration in which the protecting groups at the 3-position and the 5-position of the phenyl groups are positioned directly on the condensed aromatic ring or the condensed heteroaromatic ring, which is a luminophore, as shown in FIG. 3. As a result, the upper and lower planes of the condensed aromatic ring or the condensed heteroaromatic ring can be efficiently covered, inhibiting energy transfer by the Dexter mechanism.

As the energy acceptor material described above, the organic compound represented by General Formula (G1) or (G2) shown below can be favorably used.

[Chemical Formula 8]

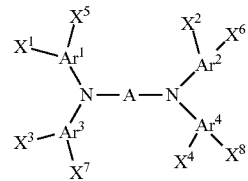
(G1)

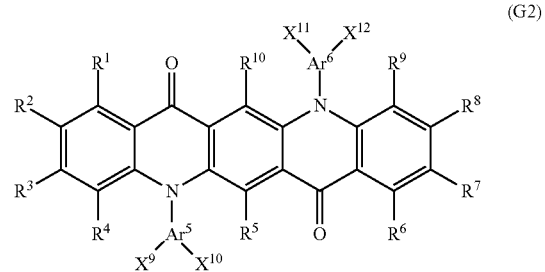
(G2)

In General Formulae (G1) and (G2), A represents a substituted or unsubstituted condensed aromatic ring having 10 to 30 carbon atoms or a substituted or unsubstituted condensed heteroaromatic ring having 10 to 30 carbon atoms, $Ar^1$ to $Ar^6$ each independently represent a substituted or unsubstituted aromatic hydrocarbon group having 6 to 13 carbon atoms, $X^1$ to $X^{12}$ each independently represent any one of a branched-chain alkyl group having 3 to 10 carbon atoms, a substituted or unsubstituted cycloalkyl group having 3 to 10 carbon atoms, and a trialkylsilyl group having 3 to 10 carbon atoms, and $R^1$ to $R^{10}$ each independently represent any one of hydrogen, an alkyl group having 3 to 10 carbon atoms, a substituted or unsubstituted cycloalkyl group having 3 to 10 carbon atoms, and a trialkylsilyl group having 3 to 12 carbon atoms.

Examples of an aromatic hydrocarbon group having 6 to 13 carbon atoms include a phenyl group, a biphenyl group, a naphthyl group, and a fluorenyl group. Note that the aromatic hydrocarbon group is not limited thereto. In the case where the aromatic hydrocarbon group has a substituent, examples of the substituent include an alkyl group having 1 to 7 carbon atoms, such as a methyl group, an ethyl group, a propyl group, an isopropyl group, a butyl group, an isobutyl group, a sec-butyl group, a tert-butyl group, a pentyl group, or a hexyl group, a cycloalkyl group having 5 to 7 carbon atoms, such as a cyclopentyl group, a cyclohexyl group, a cycloheptyl group, or an 8,9,10-trinorbornanyl group, and an aryl group having 6 to 12 carbon atoms, such as a phenyl group, a naphthyl group, or a biphenyl group.

In General Formula (G1), the substituted or unsubstituted condensed aromatic ring having 10 to 30 carbon atoms or the substituted or unsubstituted condensed heteroaromatic ring having 10 to 30 carbon atoms represents the luminophore; any of the above skeletons can be used. In General Formulae (G1) and (G2), $X^1$ to $X^{12}$ represent protecting groups.

In General Formula (G2), the protecting groups are bonded to a quinacridone skeleton, which is a luminophore, via aromatic hydrocarbon groups. With this structure, the protecting groups can be arranged to cover the luminophore; thus, energy transfer by the Dexter mechanism can be inhibited. Note that any of the protecting groups may be directly bonded to the luminophore.

As the energy acceptor material, an organic compound represented by General Formula (G3) or (G4) can be favorably used.

[Chemical Formula 9]

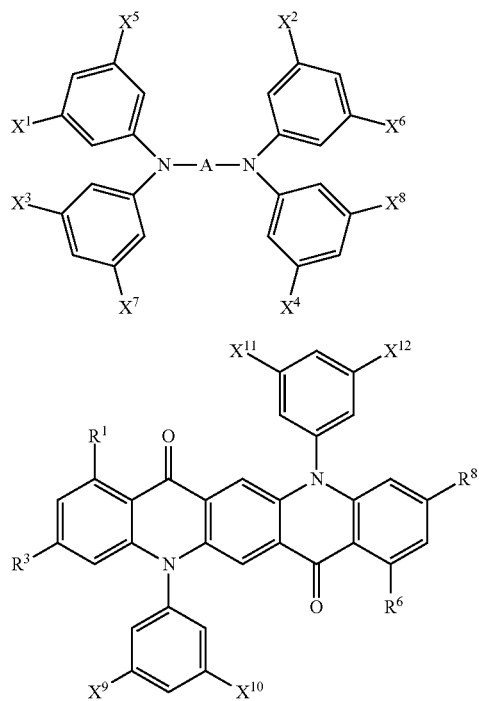

[Chemical Formula 10]

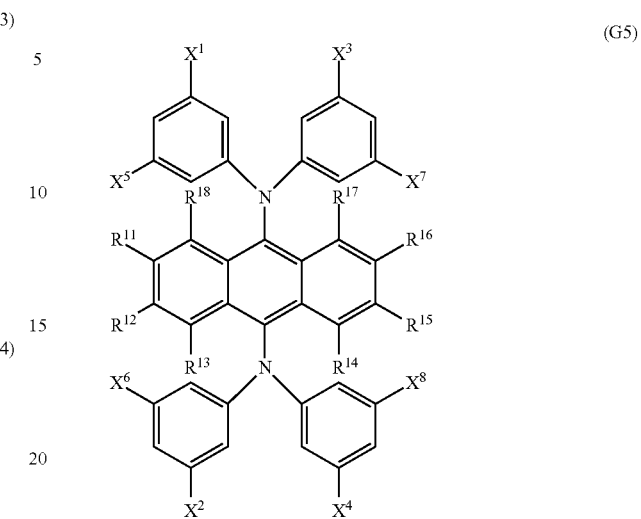

In General Formulae (G3) and (G4), A represents a substituted or unsubstituted condensed aromatic ring having 10 to 30 carbon atoms or a substituted or unsubstituted condensed heteroaromatic ring having 10 to 30 carbon atoms, and $X^1$ to $X^{12}$ each independently represent any one of a branched-chain alkyl group having 3 to 10 carbon atoms, a substituted or unsubstituted cycloalkyl group having 3 to 10 carbon atoms, and a trialkylsilyl group having 3 to 10 carbon atoms. $R^1$ $R^3$, $R^6$, and $R^8$ each independently represent any one of hydrogen, an alkyl group having 3 to 10 carbon atoms, a substituted or unsubstituted cycloalkyl group having 3 to 10 carbon atoms, and a trialkylsilyl group having 3 to 12 carbon atoms.

The protecting groups are each preferably bonded to the luminophore via a phenylene group. With this structure, the protecting groups can be arranged to cover the luminophore; thus, energy transfer by the Dexter mechanism can be inhibited. In the case where the protecting groups are each bonded to the luminophore via a phenylene group and two protecting groups are bonded to the phenylene group, the two protecting groups are preferably bonded to the phenylene group at meta-positions as shown in General Formulae (G3) and (G4). With such a structure, the luminophore can be efficiently covered; thus, energy transfer by the Dexter mechanism can be inhibited. An example of the organic compound represented by General Formula (G3) is 2tBu-mmtBuDPhA2Anth described above. That is, in one embodiment of the present invention, General Formula (G3) is particularly preferred as an example.

As the energy acceptor material, an organic compound represented by General Formula (G5) shown below can be favorably used.

In General Formula (G5), $X^1$ to $X^8$ each independently represent any one of a branched-chain alkyl group having 3 to 10 carbon atoms, a substituted or unsubstituted cycloalkyl group having 3 to 10 carbon atoms, and a trialkylsilyl group having 3 to 10 carbon atoms, and $R^{11}$ to $R^{18}$ each independently represent any one of hydrogen, a branched-chain alkyl group having 3 to 10 carbon atoms, a substituted or unsubstituted cycloalkyl group having 3 to 10 carbon atoms, a trialkylsilyl group having 3 to 10 carbon atoms, and a substituted or unsubstituted aryl group having 6 to 25 carbon atoms.

Examples of the aryl group having 6 to 25 carbon atoms include a phenyl group, a naphthyl group, a biphenyl group, a fluorenyl group, and a spirofluorenyl group. Note that an aryl group having 6 to 25 carbon atoms is not limited thereto. In the case where the aryl group has a substituent, examples of the substituent include the alkyl group having 1 to 10 carbon atoms, the branched-chain alkyl group having 3 to 10 carbon atoms, the substituted or unsubstituted cycloalkyl group having 3 to 10 carbon atoms, and the trialkylsilyl group having 3 to 10 carbon atoms, which are described above.

An anthracene compound has a high emission quantum yield and a small area of the luminophore; therefore, the upper and lower planes of anthracene can be efficiently covered with the protecting groups. An example of the organic compound represented by General Formula (G5) is 2tBu-mmtBuDPhA2Anth described above.

Examples of the compounds represented by General Formulae (G1) to (G5) are shown by Structural Formulae (102) to (105) and (200) to (284) below. Note that the compounds represented by General Formulae (G1) to (G5) are not limited thereto. The compounds represented by Structural Formulae (102) to (105) and (200) to (284) can be favorably used as a guest material of the light-emitting element of one embodiment of the present invention. Note that the guest material is not limited thereto.

[Chemical Formula 11]
(102)
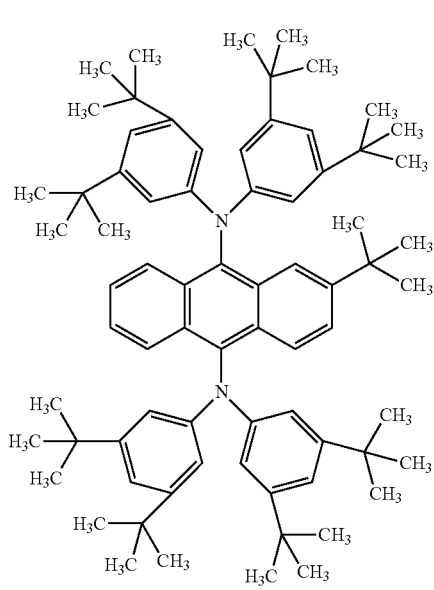
(103)
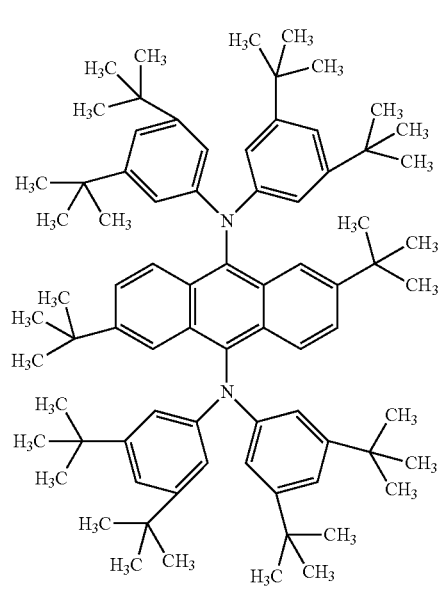
(104)
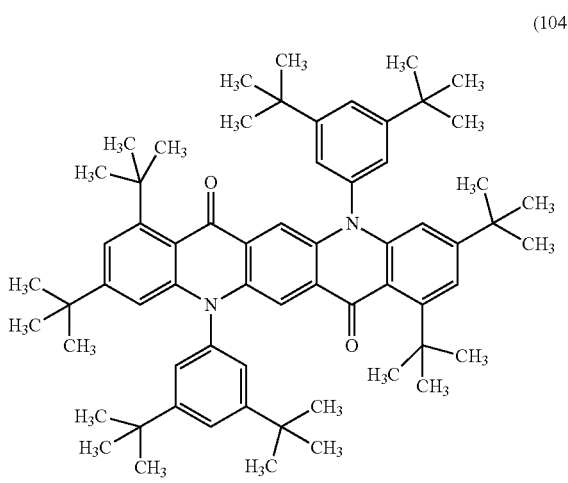
(105)
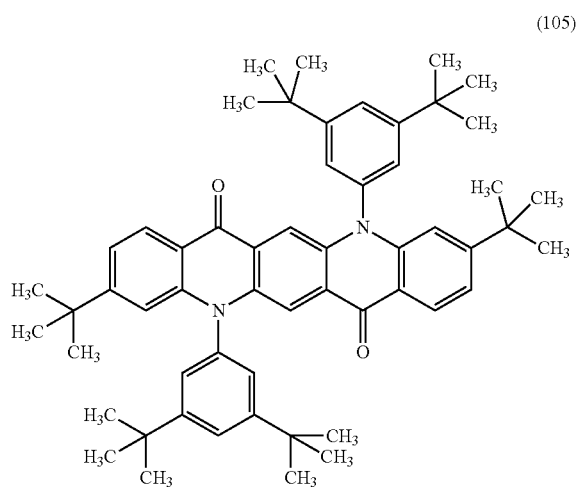

[Chemical Formula 12]
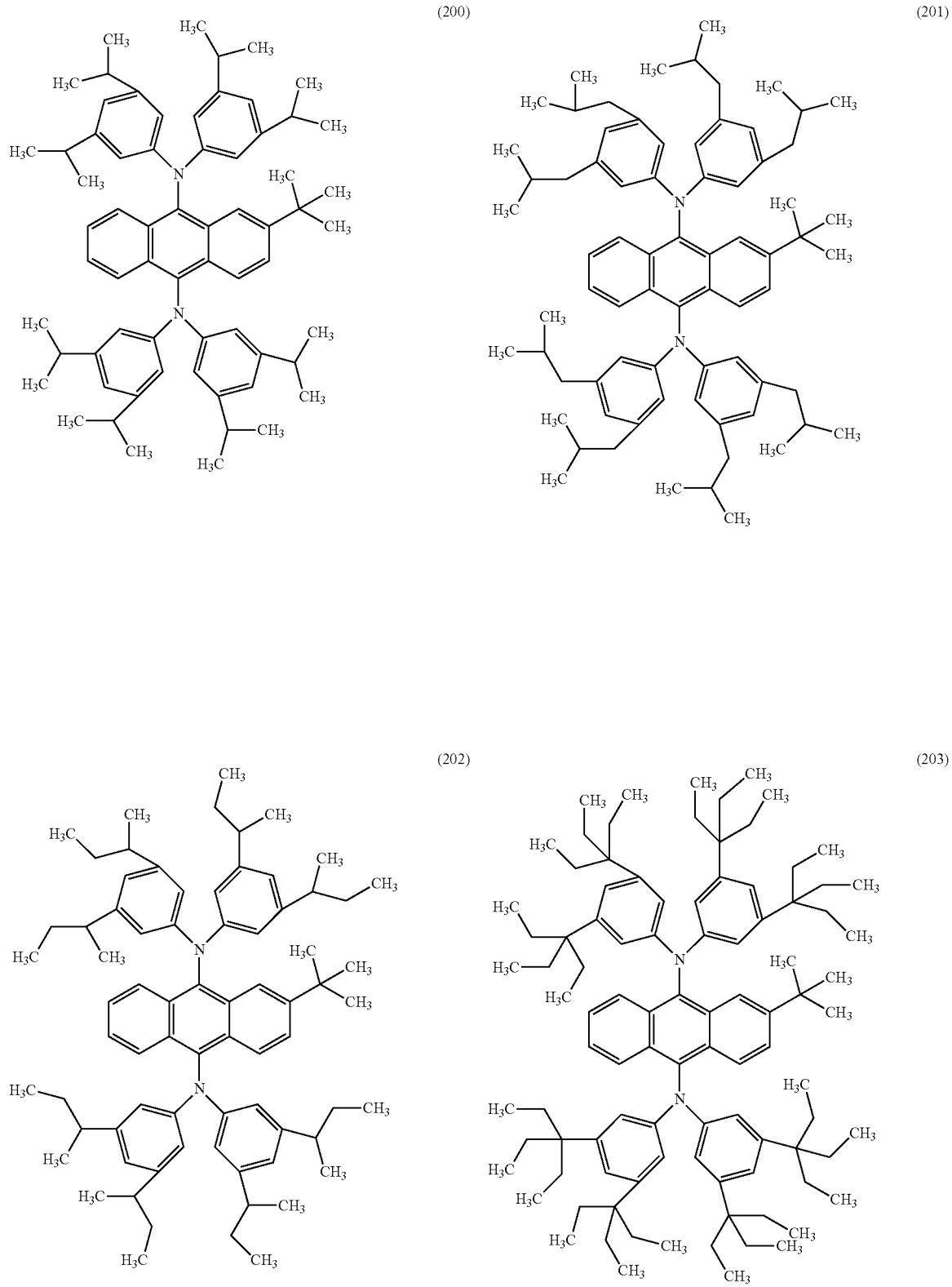

[Chemical Formula 13]
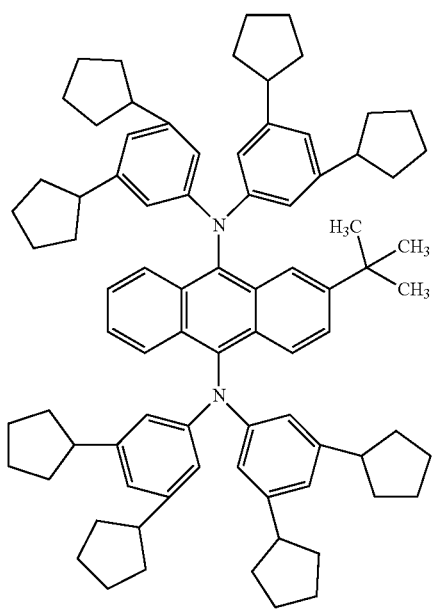
(204)
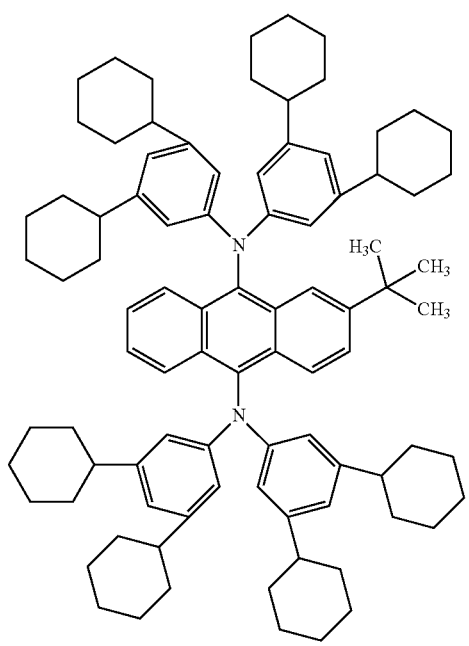
(205)
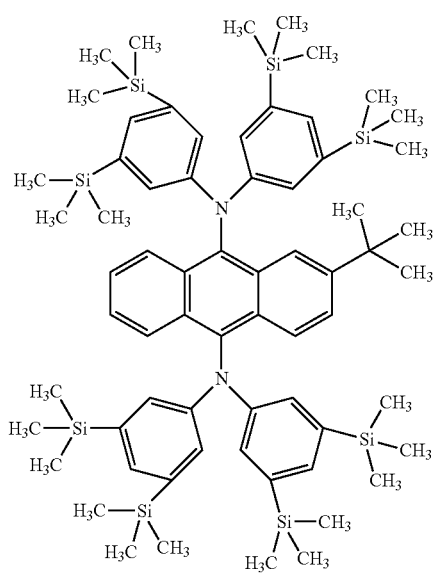
(206)
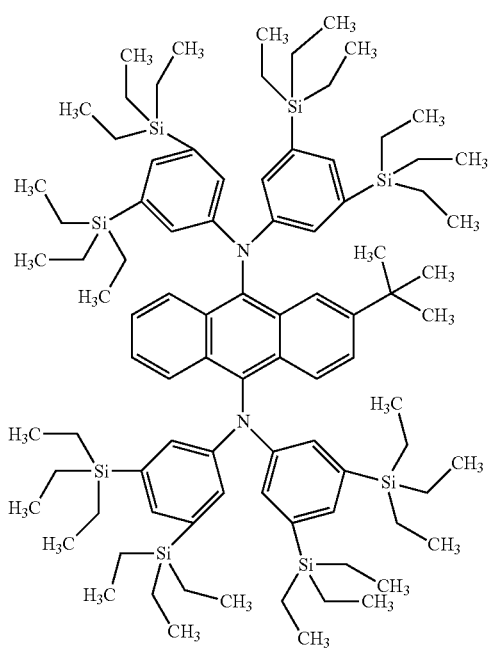
(207)

[Chemical Formula 14]
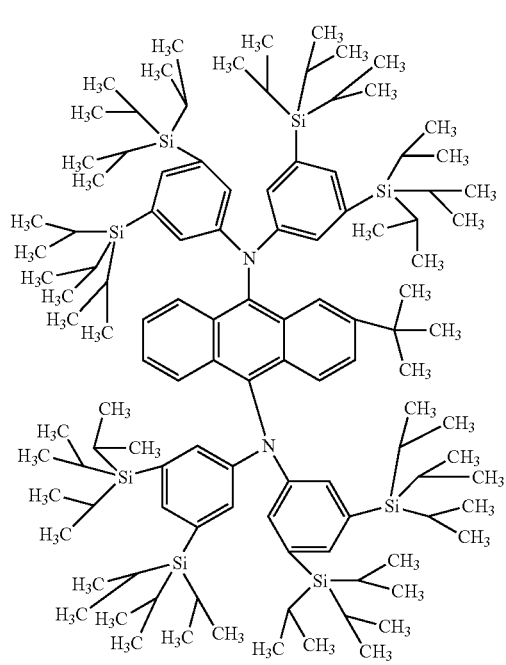
(208)
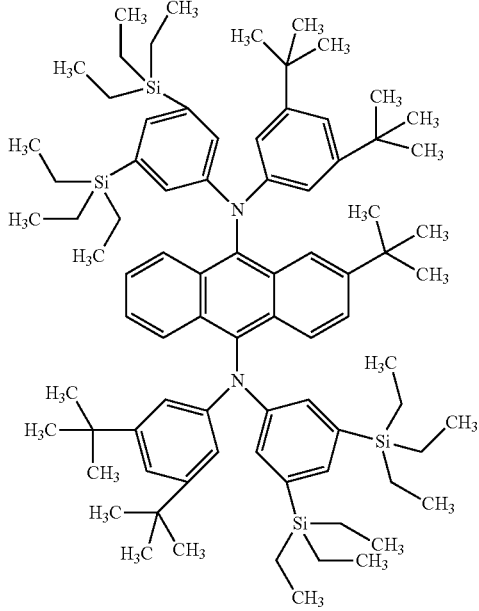
(209)
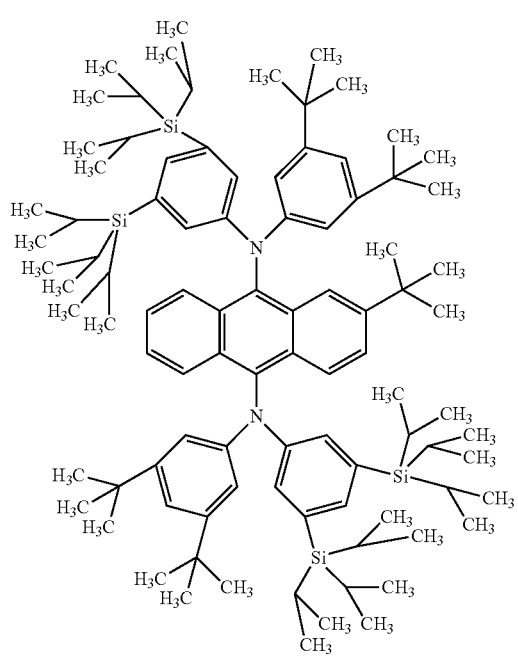
(210)
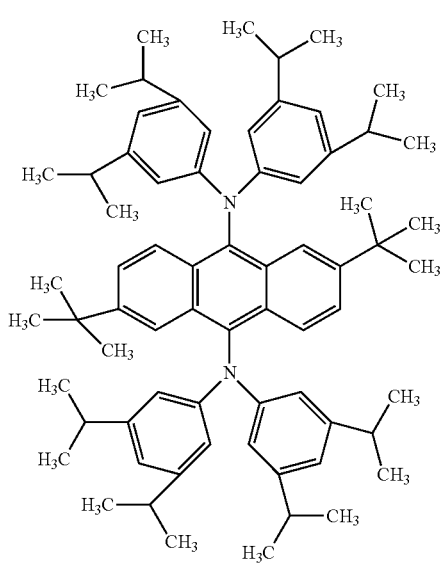
(211)

[Chemical Formula 15]
(212) 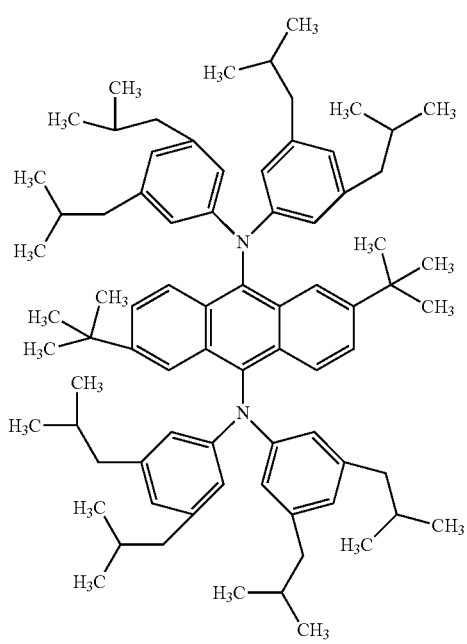
(213) 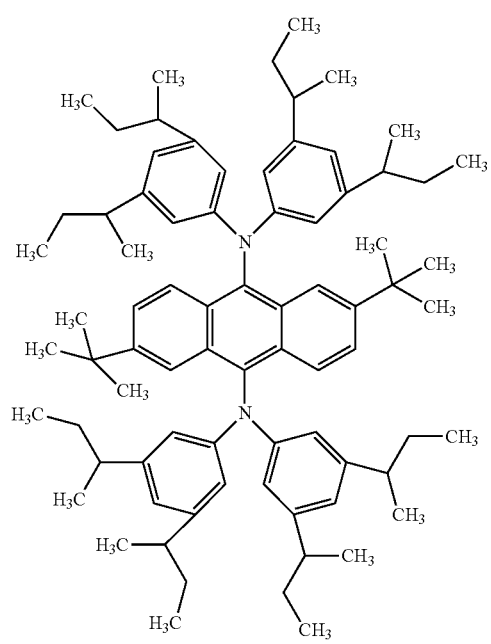
(214) 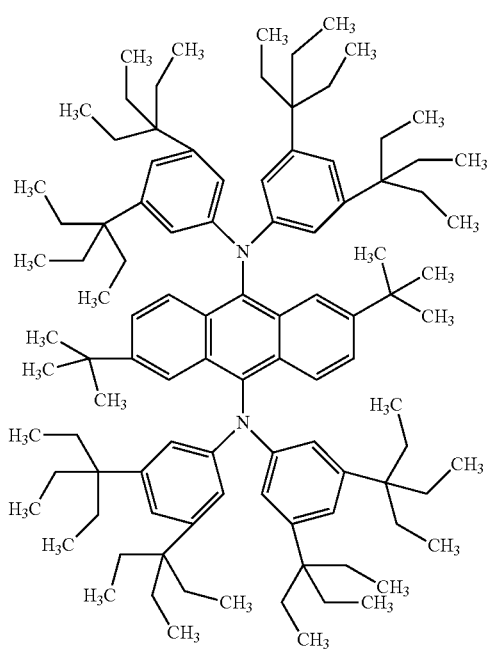
(215) 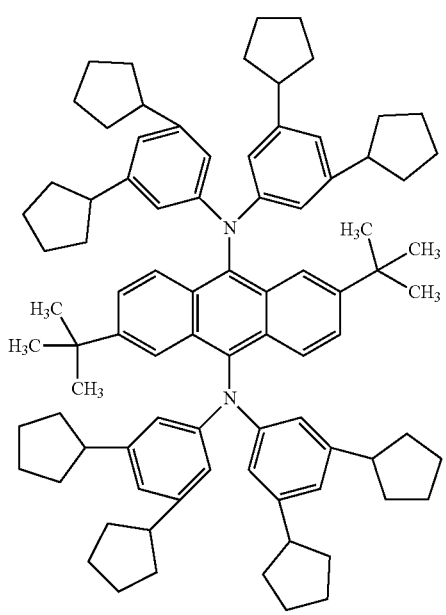

[Chemical Formula 16]
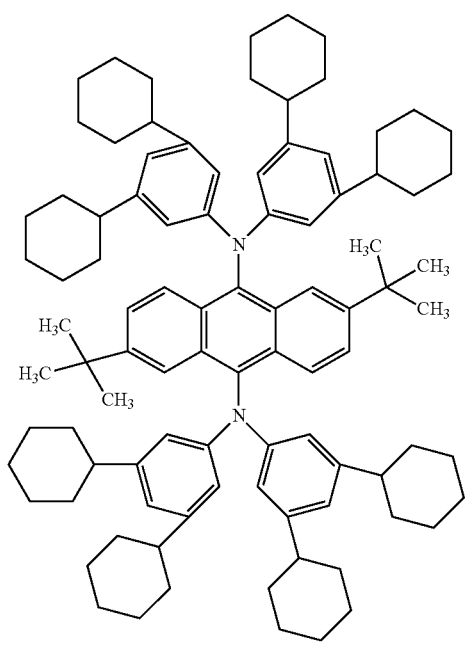
(216)
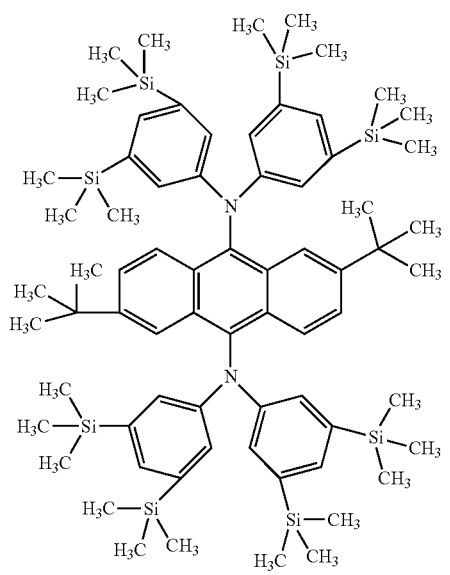
(217)
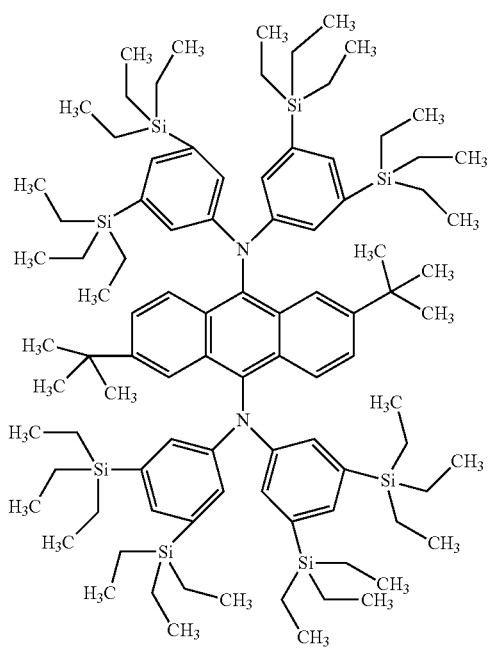
(218)
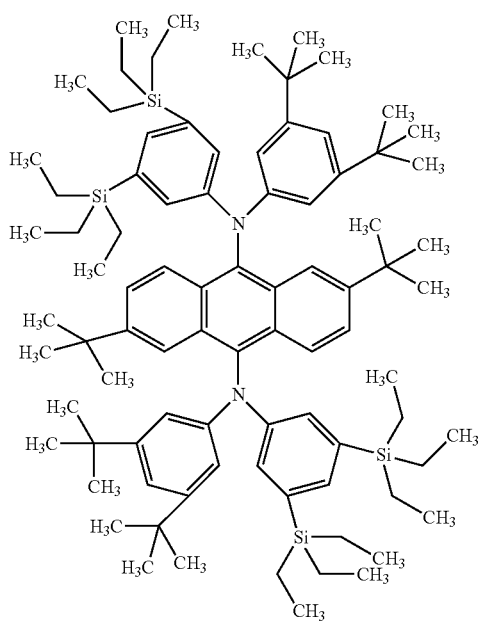
(219)

[Chemical Formula 17]
-continued
(220)
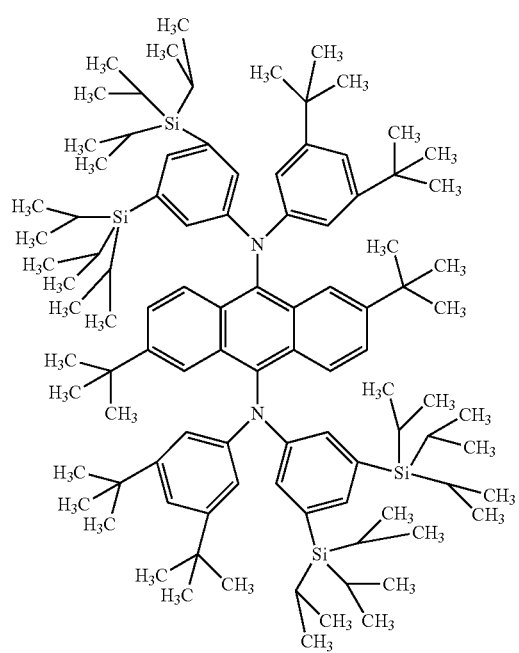
(221)
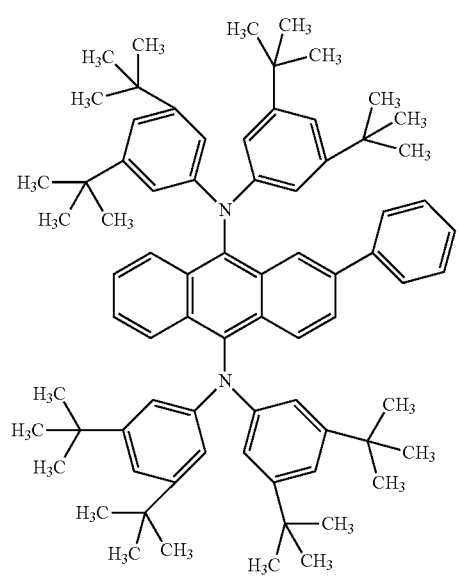
(222)
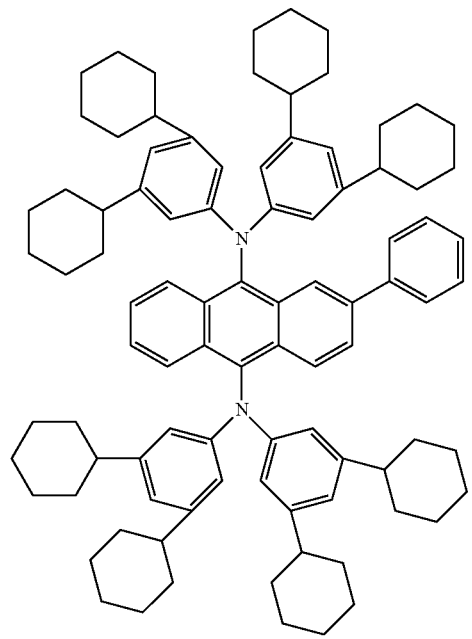
(223)
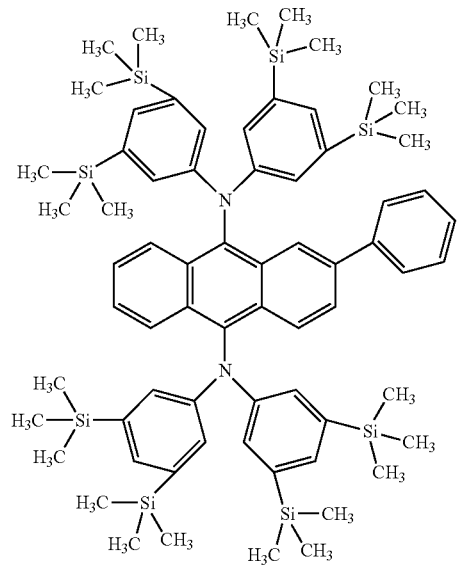

[Chemical Formula 18]
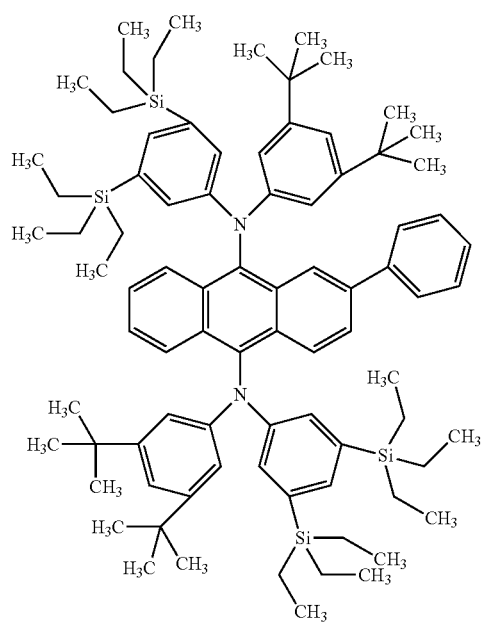
(224)
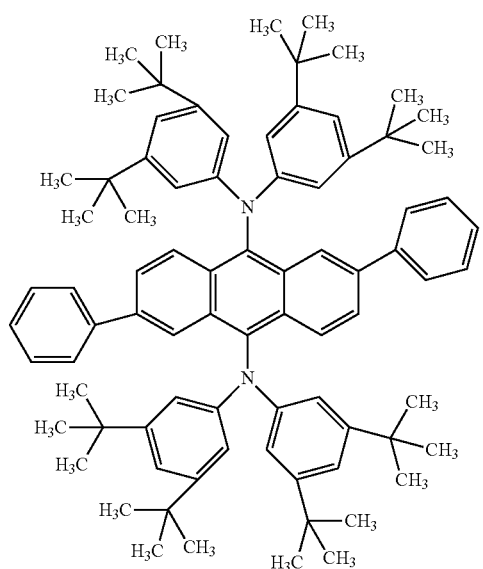
(225)
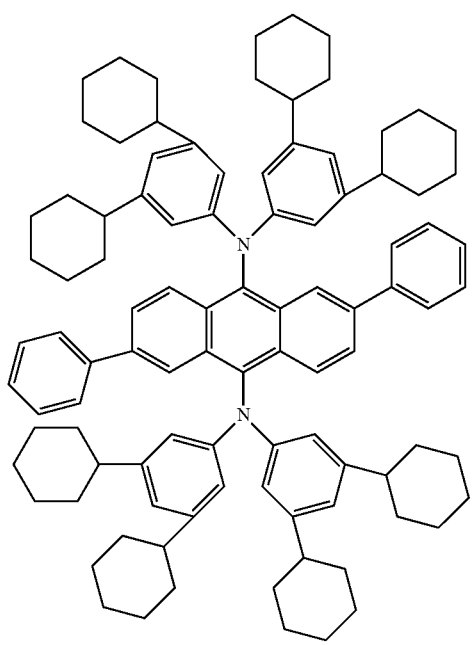
(226)
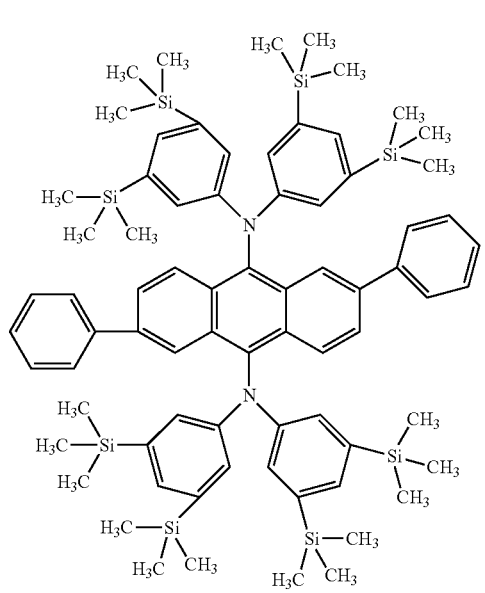
(227)

[Chemical Formula 19]
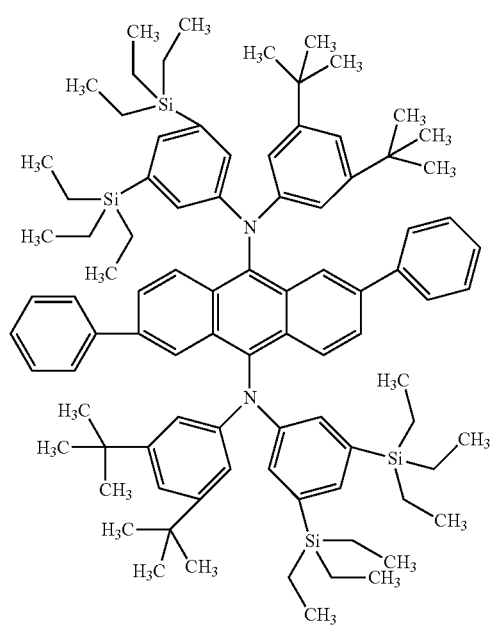
(228)
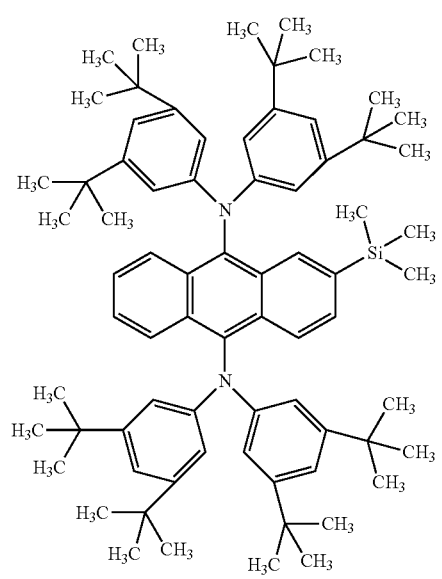
(229)
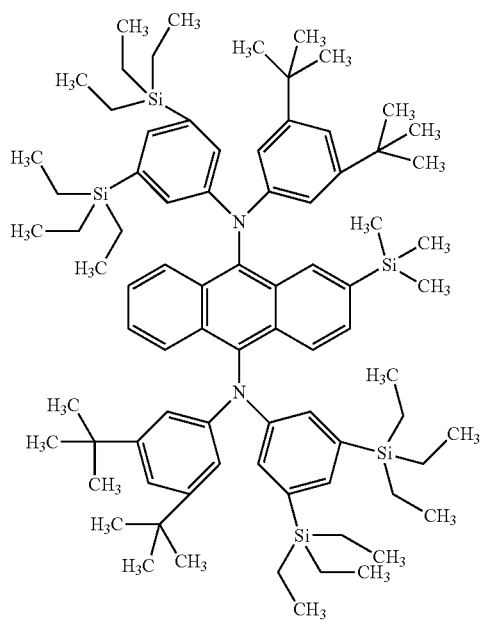
(230)
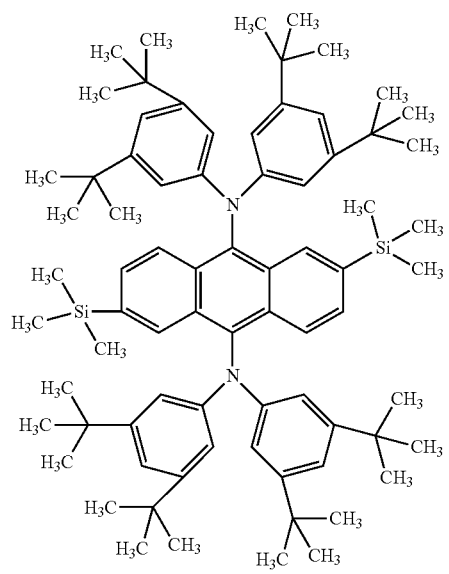
(231)

[Chemical Formula 20]
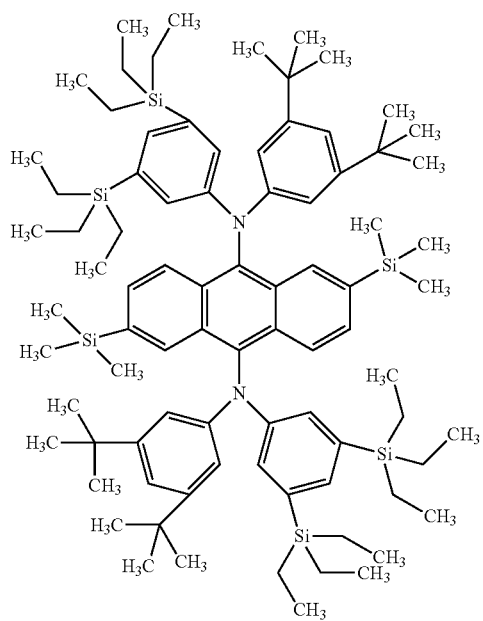
(232)
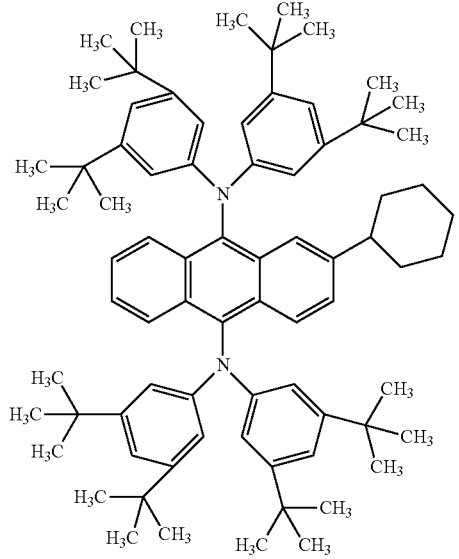
(233)
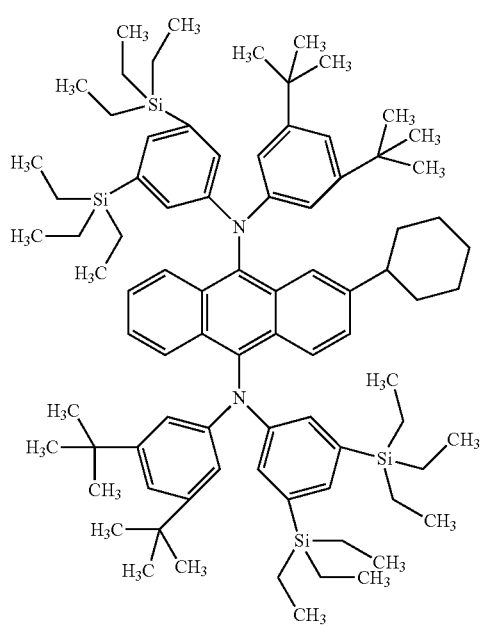
(234)
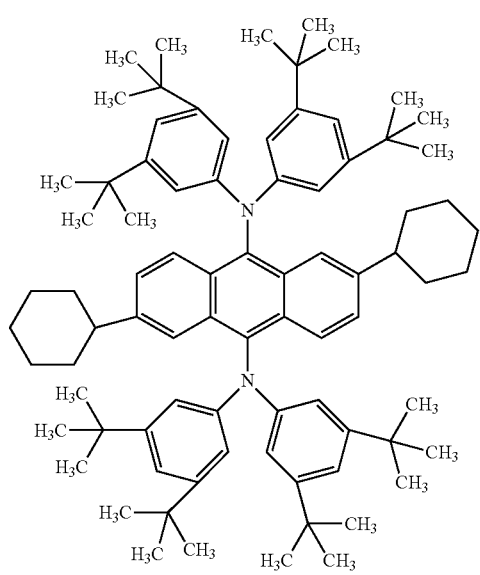
(235)

[Chemical Formula 21]
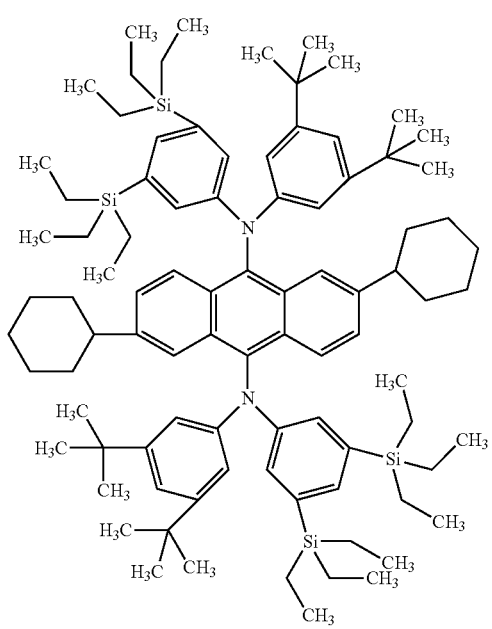
(236)
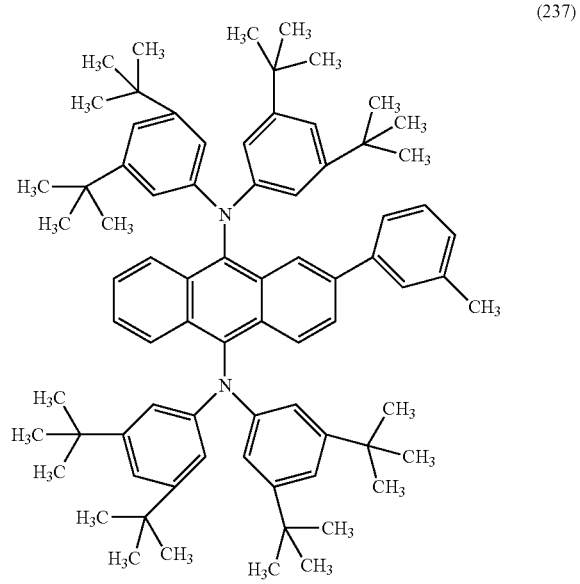
(237)
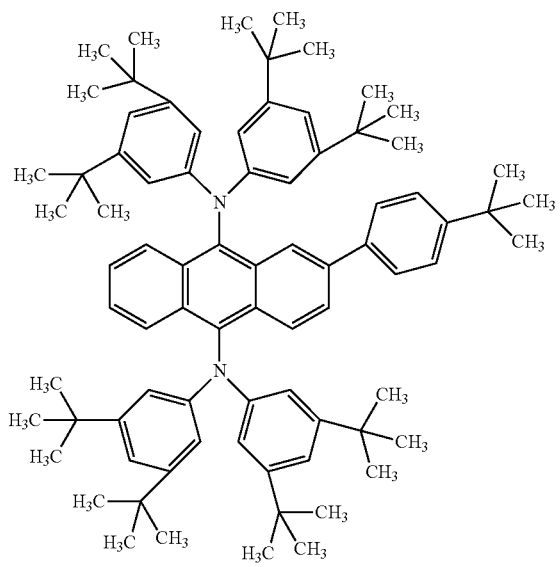
(238)
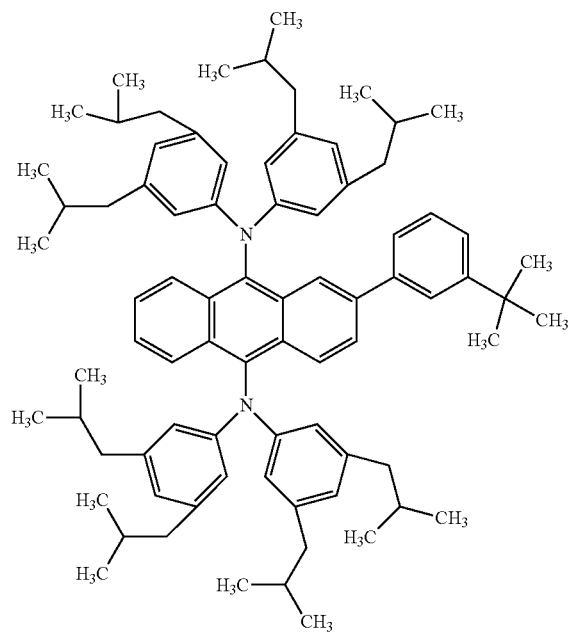
(239)

(240)
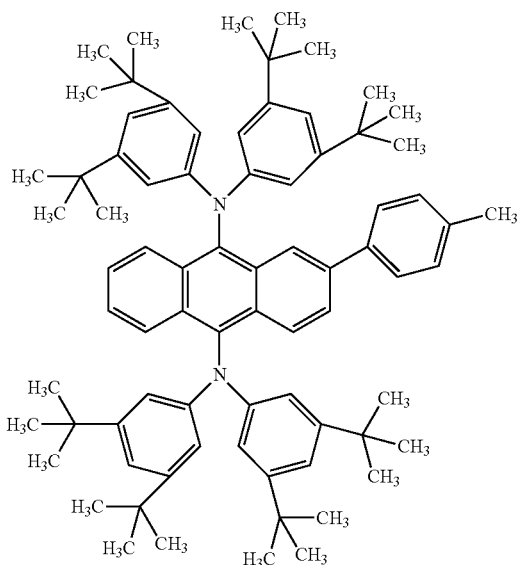
(241)
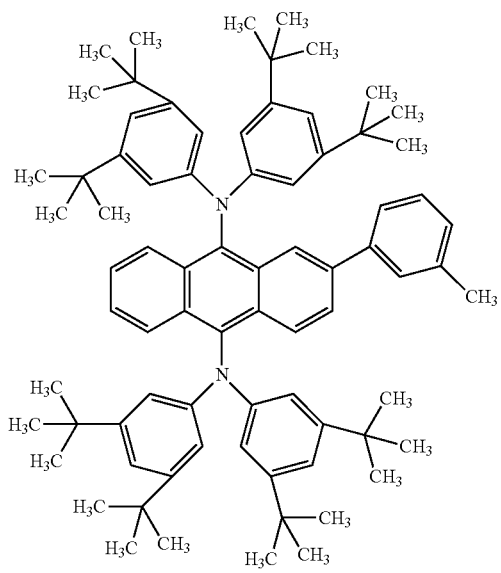
[Chemical Formula 22]
(242)
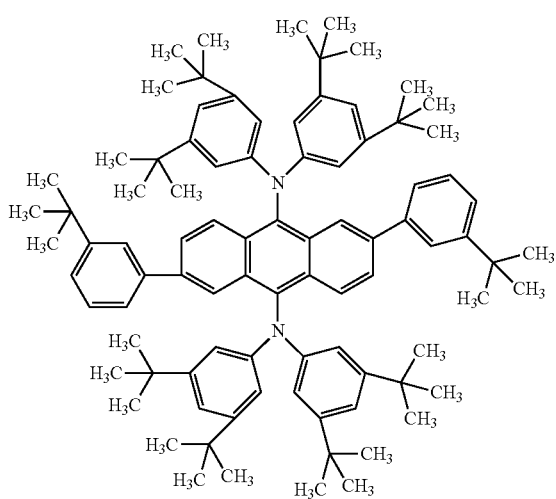
(243)
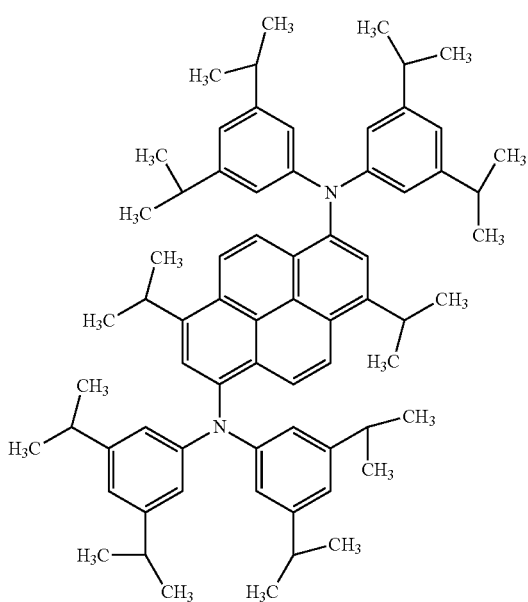

(244)
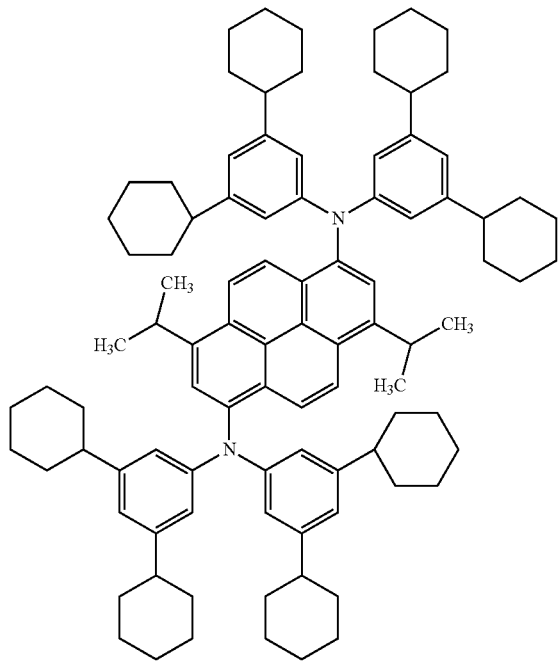
(245)
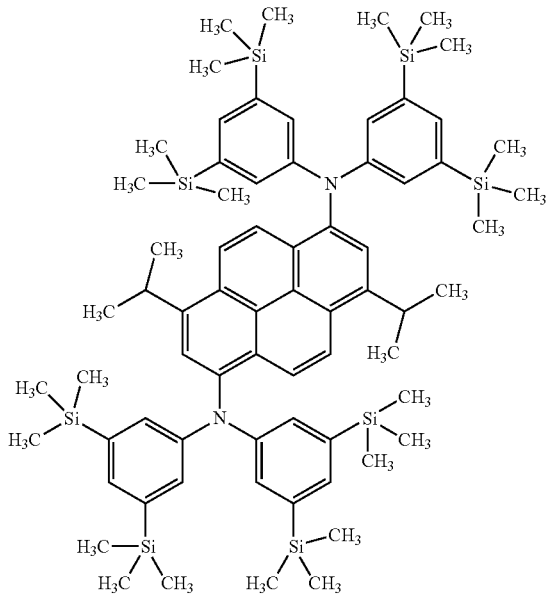
[Chemical Formula 23]
(246)
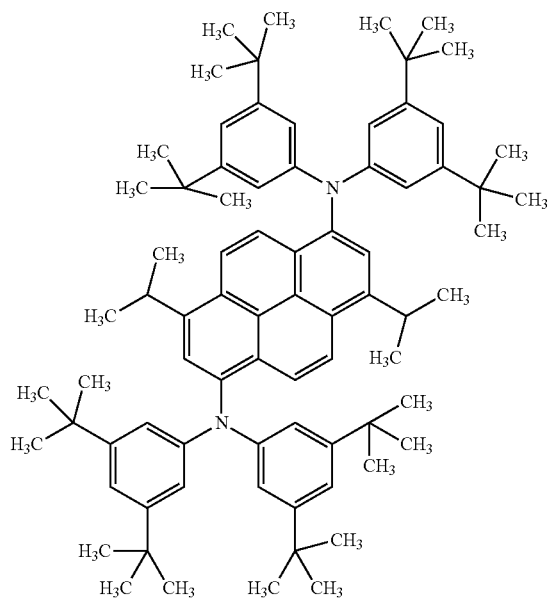
(247)
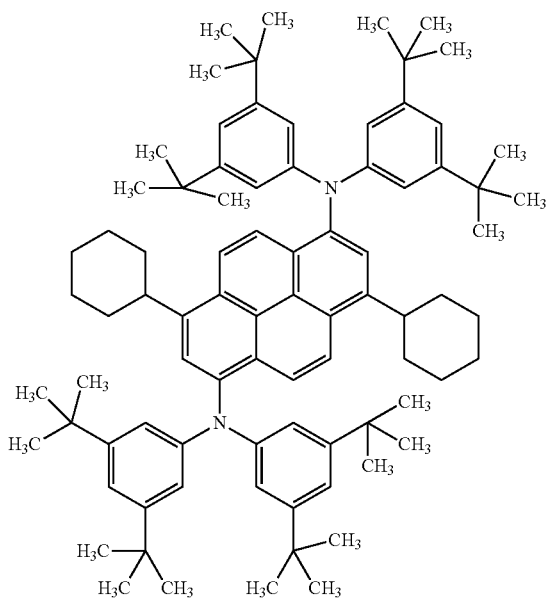

(248)
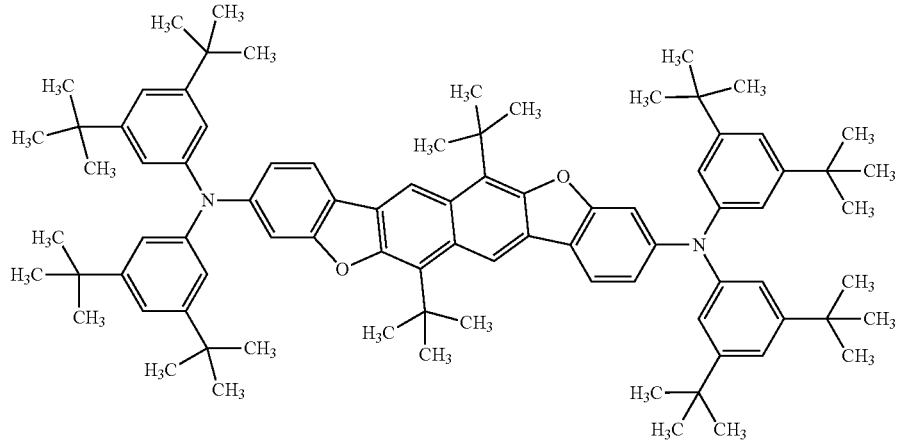
(249)
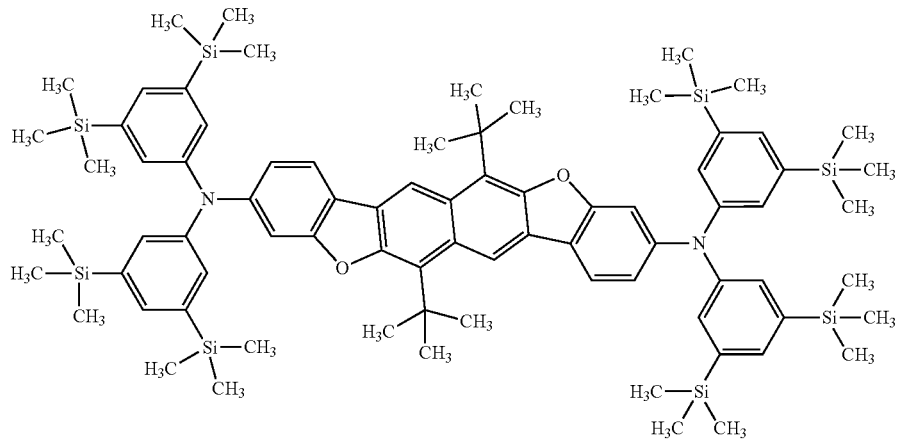
[Chemical Formula 24]
(250)
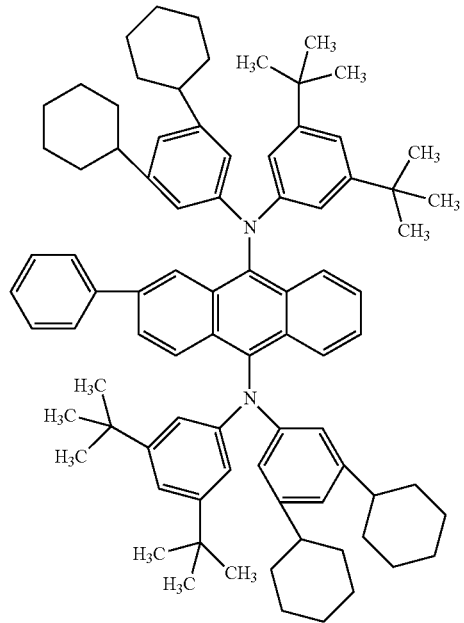
(251)
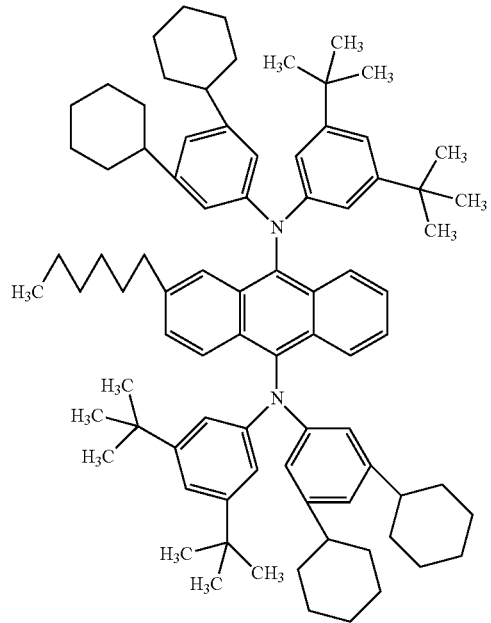

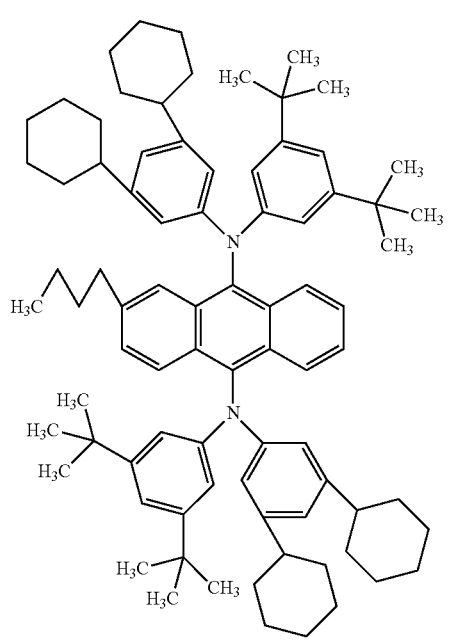
(252)
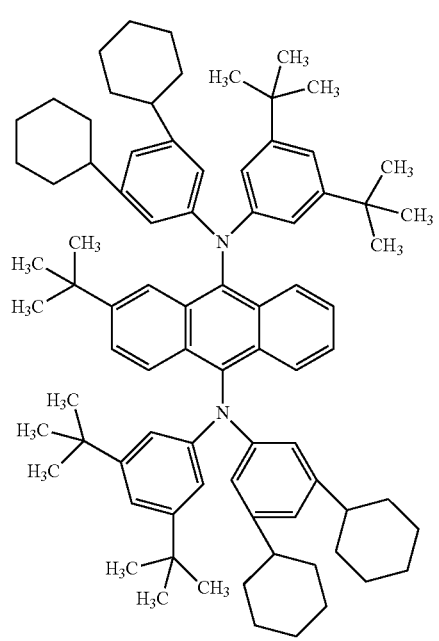
(253)
[Chemical Formula 25]
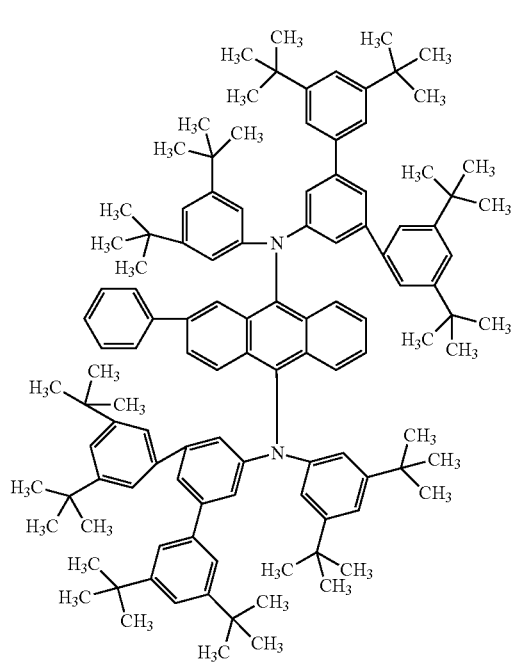
(254)
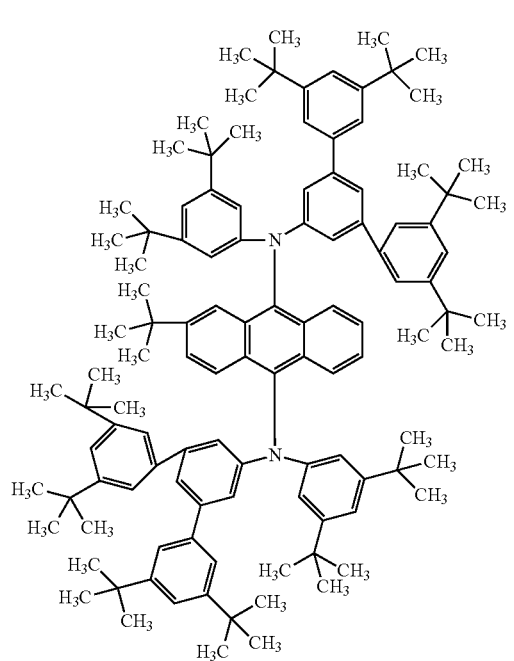
(255)

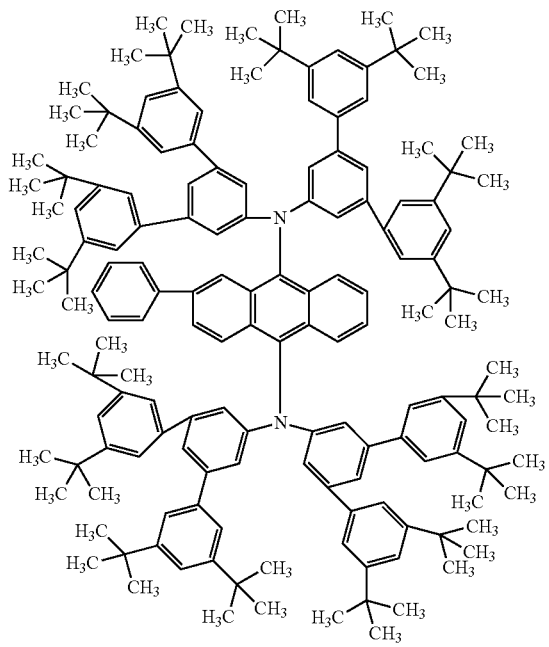
(256)
[Chemical Formula 26]
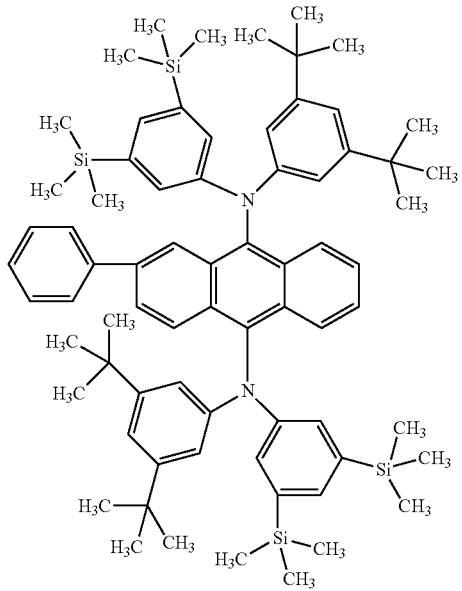
(257)
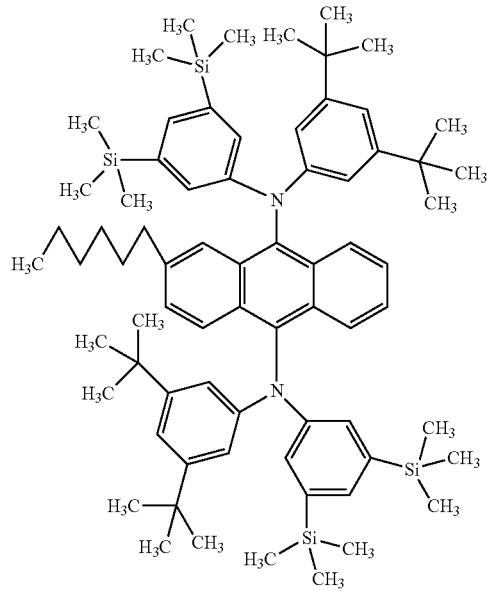
(258)

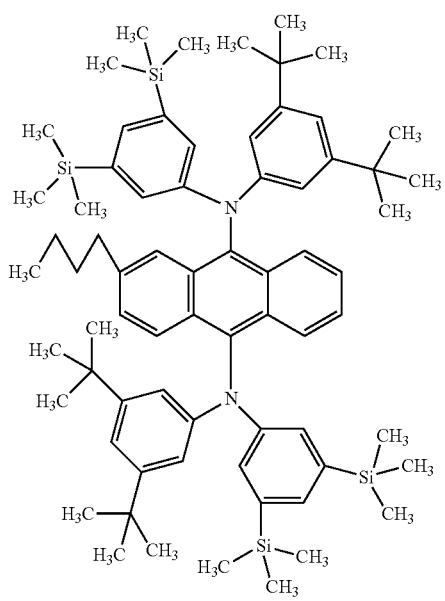 (259)
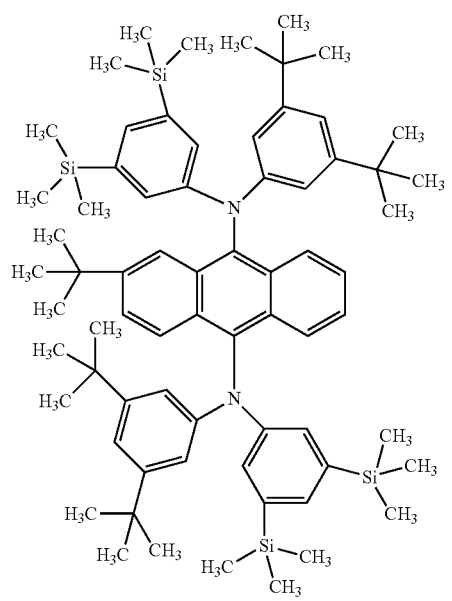 (260)
[Chemical Formula 27]
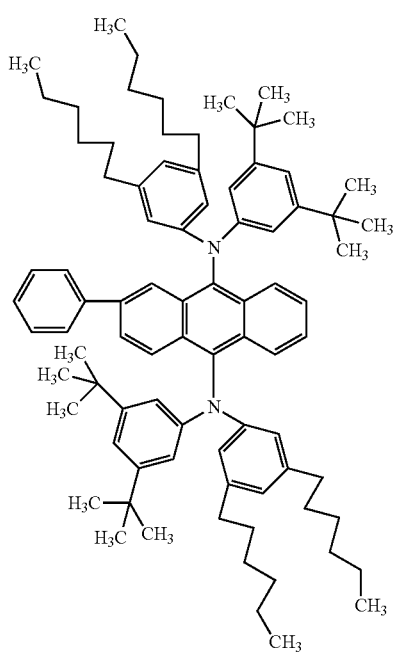 (261)
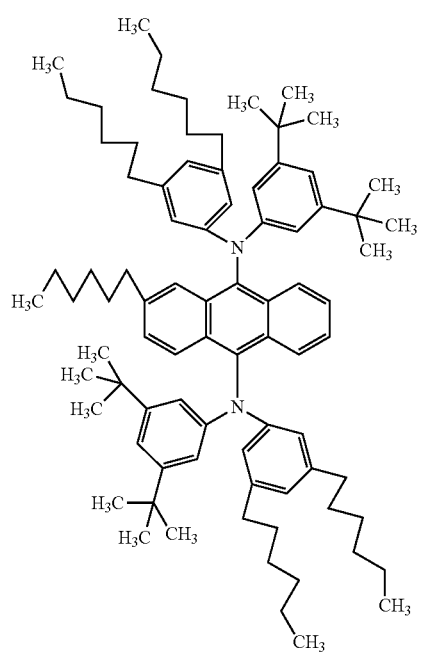 (262)

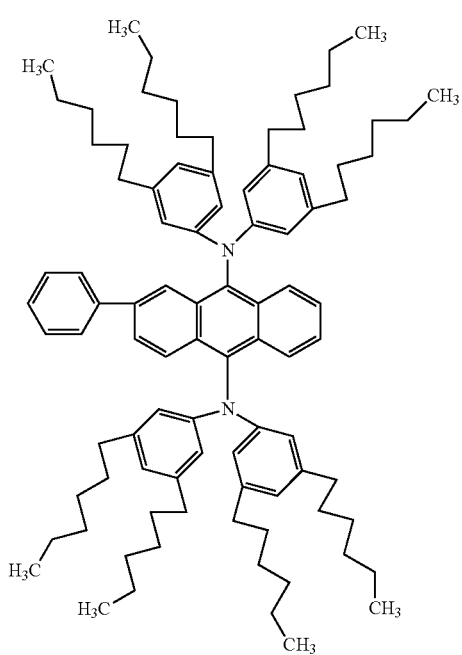 (262)
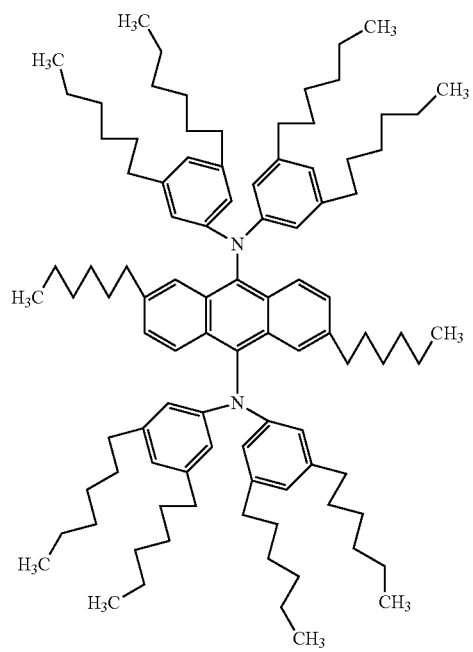 (263)
[Chemical Formula 28]
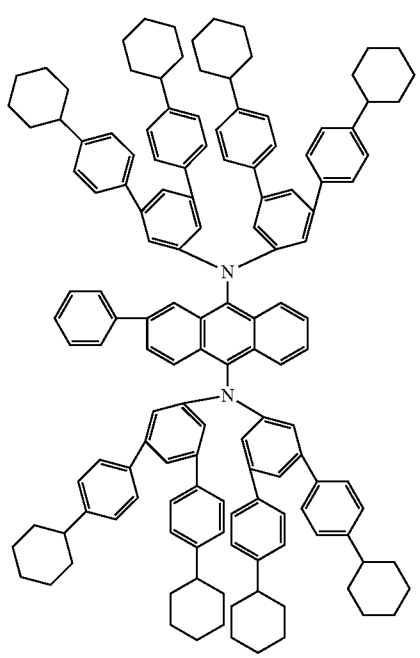 (264)
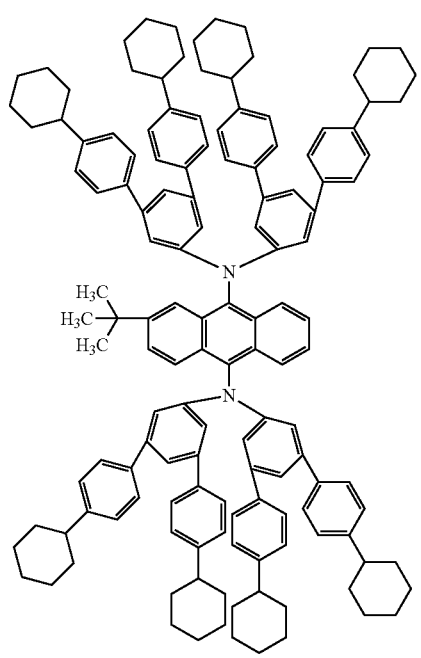 (265)

(267)
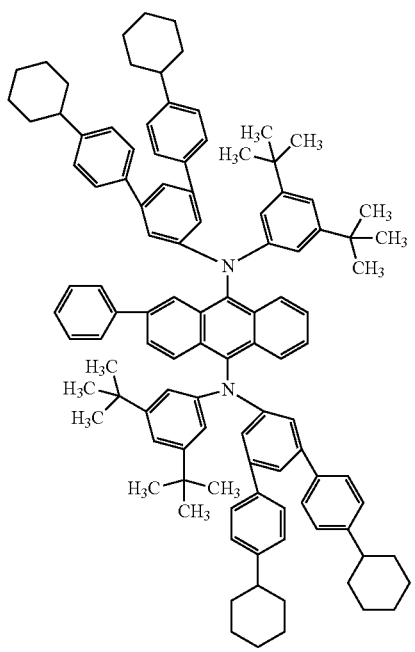
(268)
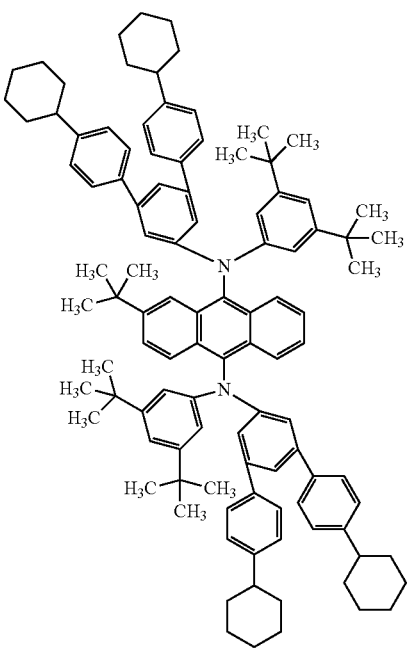
[Chemical Formula 29]
(269)
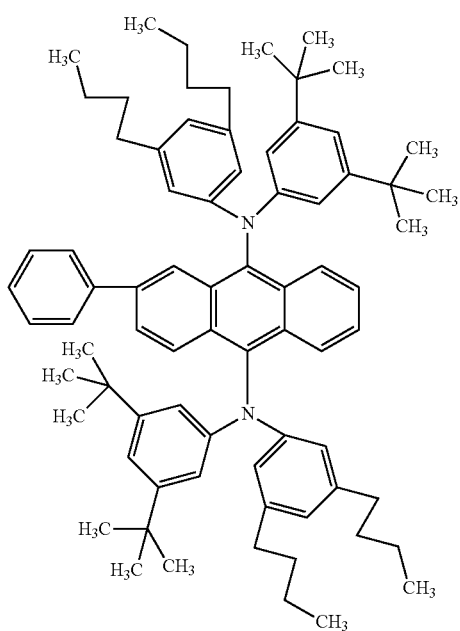
(270)
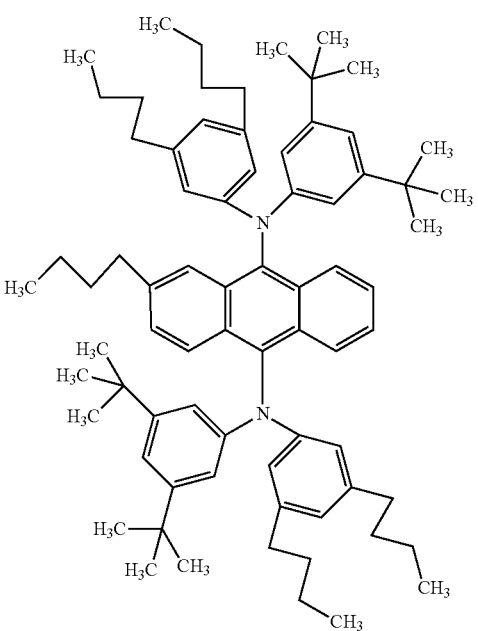

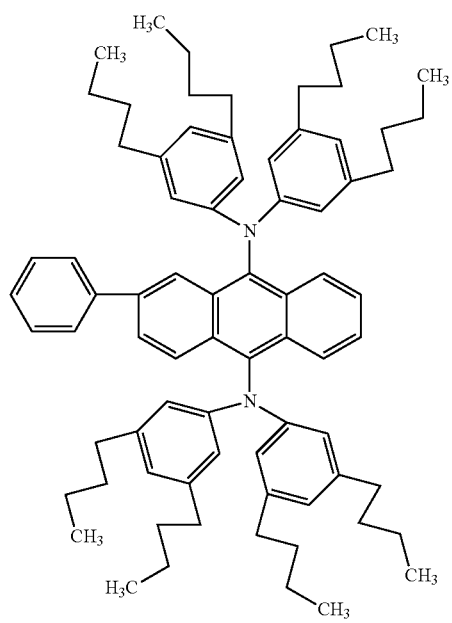
(271)
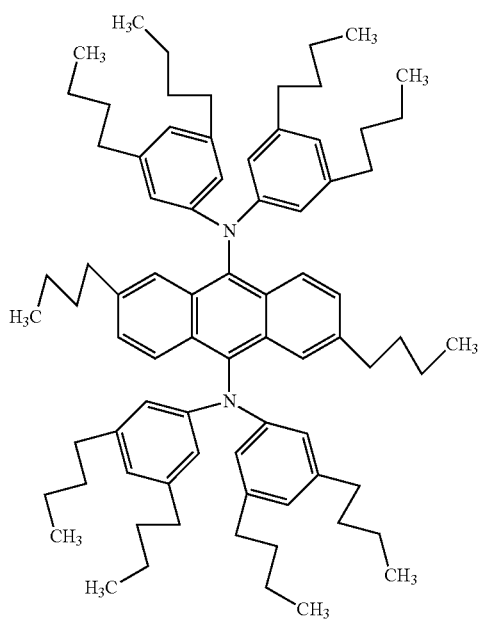
(272)
[Chemical Formula 30]
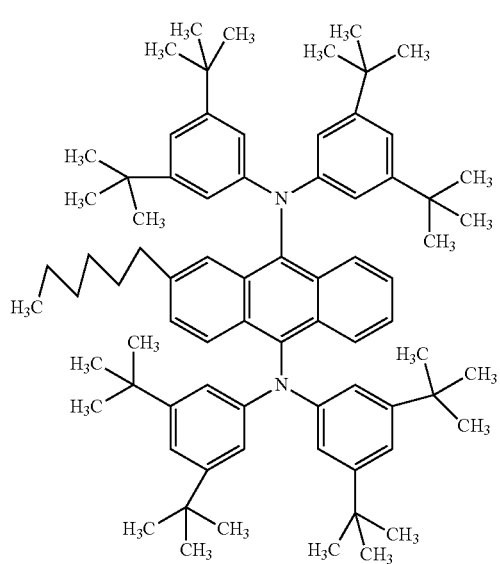
(273)
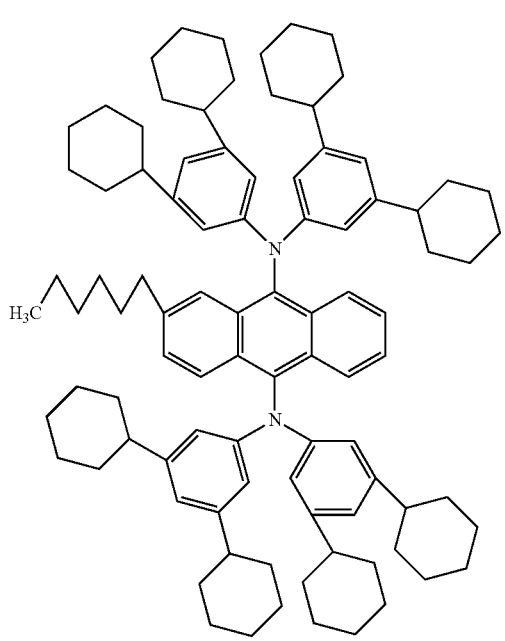
(274)

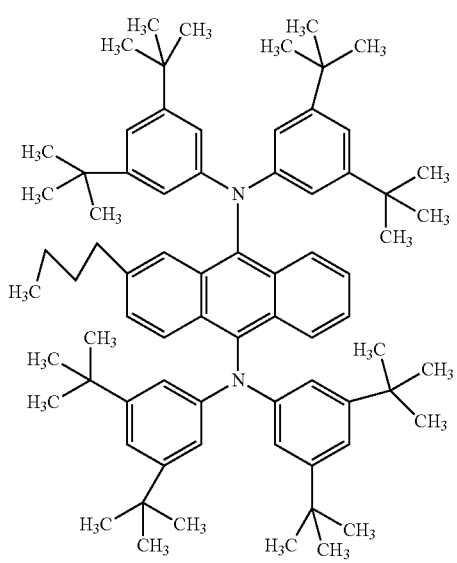 (275)
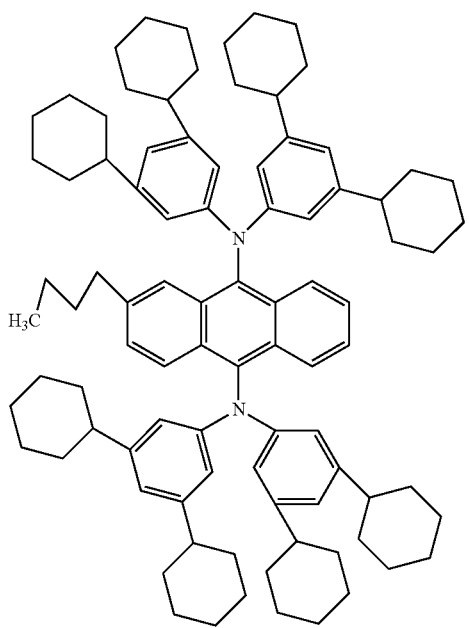 (276)
[Chemical Formula 31]
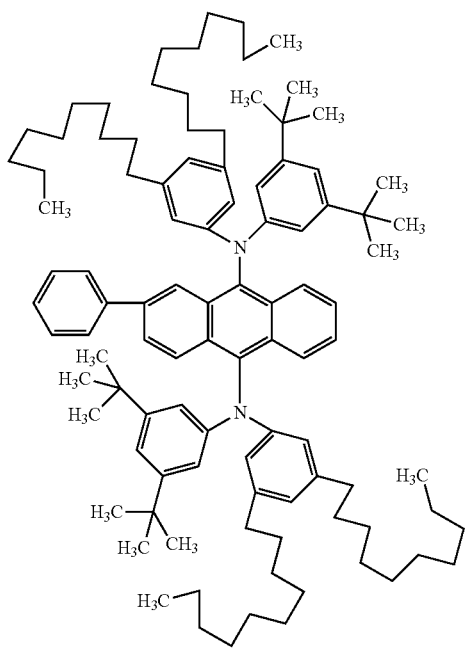 (277)
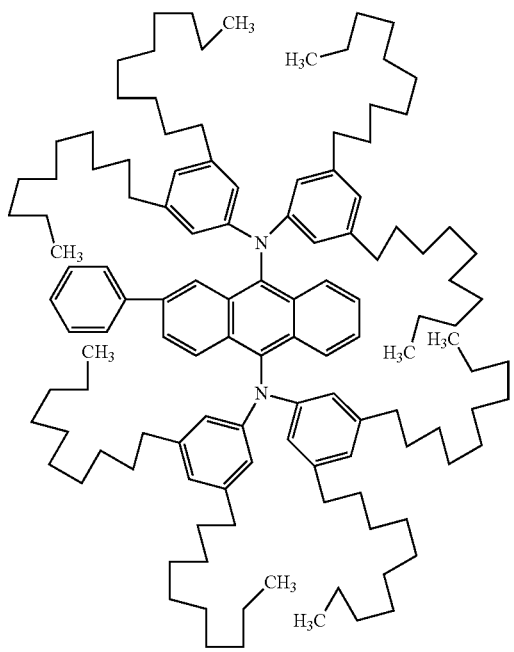 (278)

(279)
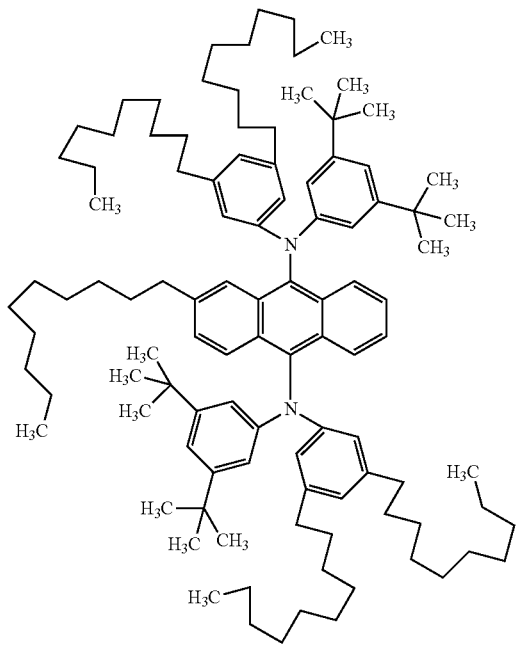
(280)
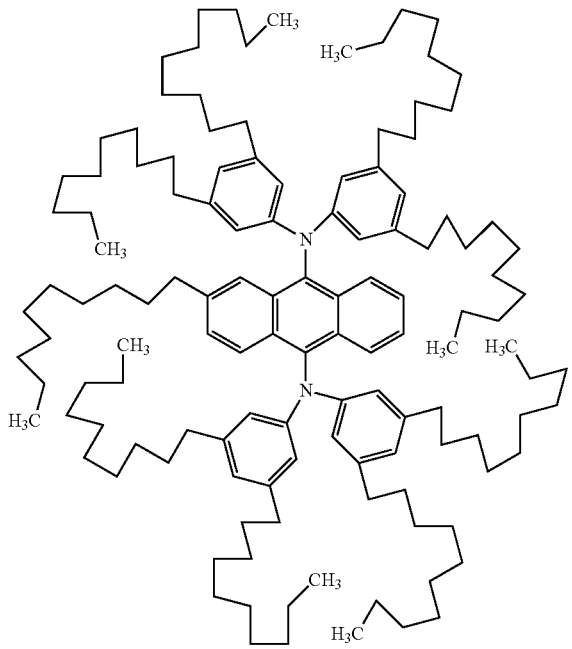
[Chemical Formula 32]
(281)
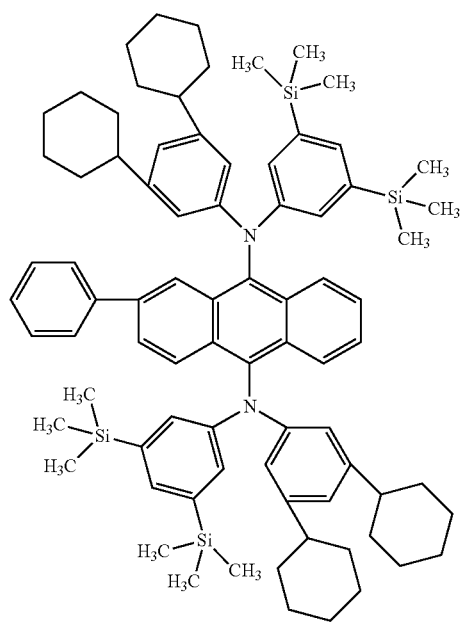
(282)
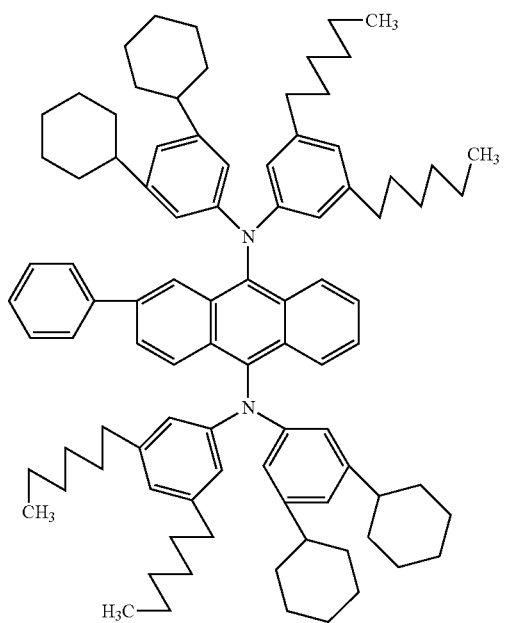

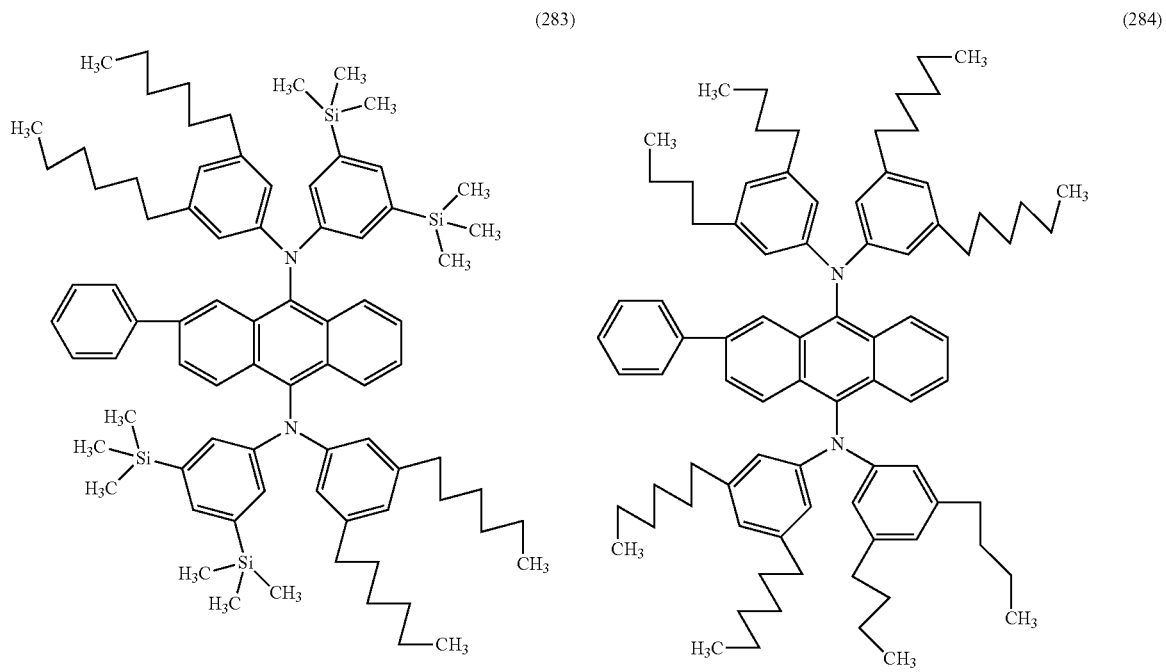

Examples of materials that can be favorably used as a guest material of the light-emitting element of one embodiment of the present invention are shown by Structural Formulae (100) and (101). Note that the guest material is not limited thereto.

[Chemical Formula 33]

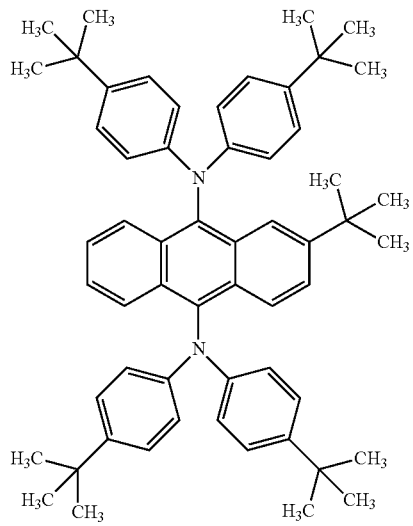

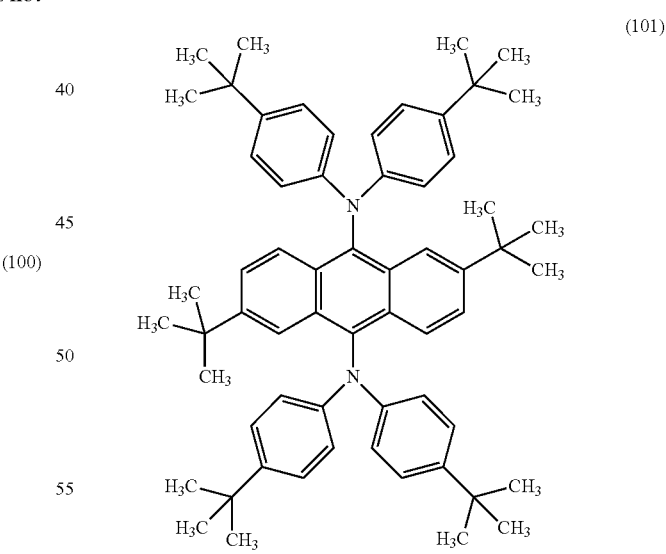

When the compound 133 serves as an energy donor, a TADF material can be used, for example. The energy difference between the S1 level and the T1 level of the compound 133 is preferably small, and specifically, greater than 0 eV and less than or equal to 0.2 eV.

In the case where the compound 133 is a TADF material, the compound 133 preferably has a skeleton having a hole-transport property and a skeleton having an electron-transport property. Alternatively, the compound 133 preferably has a π-electron rich skeleton or an aromatic amine skeleton, and a π-electron deficient skeleton. In that case, a donor-acceptor excited state is easily formed in a molecule. Furthermore, to increase both the donor property and the acceptor property in the molecule of the compound 133, the skeleton having an electron-transport property and the skeleton having a hole-transport property are preferably directly bonded to each other. Alternatively, the π-electron deficient skeleton is preferably directly bonded to the π-electron rich skeleton or the aromatic amine skeleton. By improving both the donor property and the acceptor property in the molecule, an overlap between a region where the HOMO is distributed and a region where the LUMO is distributed in the compound 133 can be small, and the energy difference between the singlet excitation energy level and the triplet excitation energy level of the compound 133 can be small. Moreover, the triplet excitation energy level of the compound 133 can be kept high.

In the case where a TADF material is composed of one kind of material, the following materials can be used, for example.

First, a fullerene, a derivative thereof, an acridine derivative such as proflavine, eosin, and the like can be given. Furthermore, a metal-containing porphyrin containing magnesium (Mg), zinc (Zn), cadmium (Cd), tin (Sn), platinum (Pt), indium (In), palladium (Pd), or the like can be given. Examples of the metal-containing porphyrin include a protoporphyrin-tin fluoride complex ($SnF_2$(Proto IX)), a mesoporphyrin-tin fluoride complex ($SnF_2$(Meso IX)), a hematoporphyrin-tin fluoride complex ($SnF_2$(Hemato IX)), a coproporphyrin tetramethyl ester-tin fluoride complex ($SnF_2$(Copro III-4Me)), an octaethylporphyrin-tin fluoride complex ($SnF_2$(OEP)), an etioporphyrin-tin fluoride complex ($SnF_2$(Etio I)), and an octaethylporphyrin-platinum chloride complex ($PtCl_2$OEP).

[Chemical Formula 34]

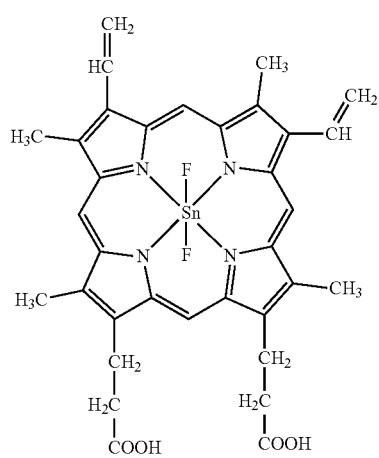

SnF₂(Proto IX)

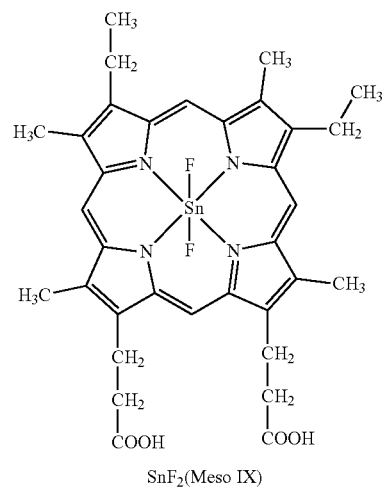

SnF₂(Meso IX)

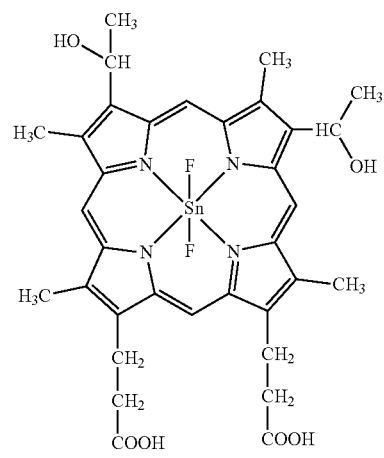

SnF₂(Hemato IX)

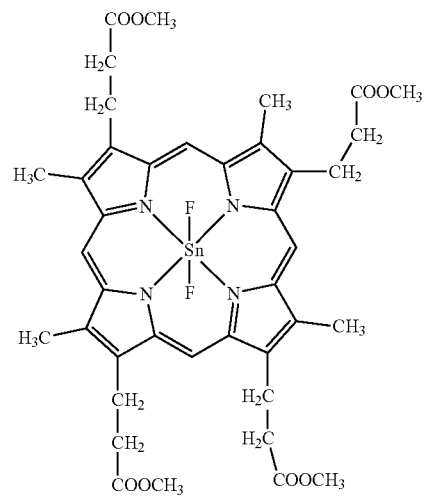

SnF₂(Copro III-4Me)

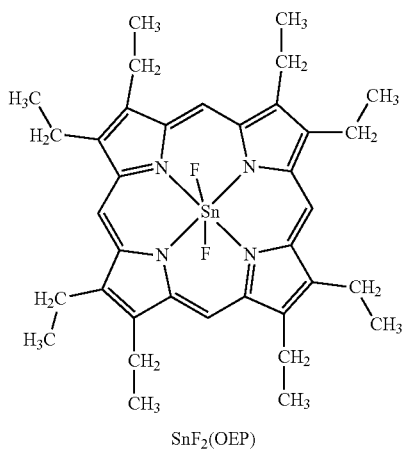

SnF₂(OEP)

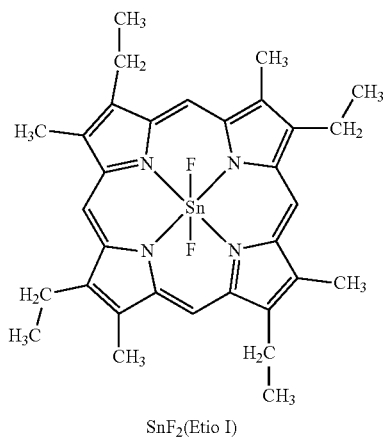

SnF₂(Etio I)

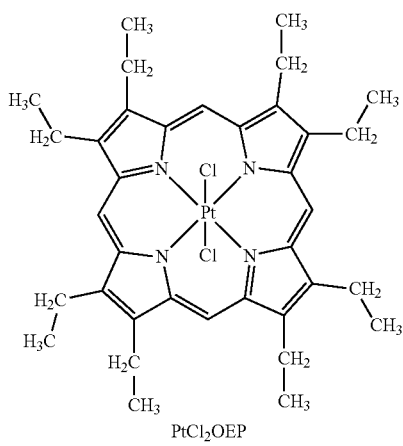

PtCl₂OEP

As the thermally activated delayed fluorescent material composed of one kind of material, a heterocyclic compound having one or both of a π-electron rich heteroaromatic skeleton and a π-electron deficient heteroaromatic skeleton can also be used. Specific examples include 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(1 OH-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), 10-phenyl-10H,10'H-spiro[acridin-9,9'-anthracen]-10'-one (abbreviation: ACRSA), 4-(9'-phenyl-3,3'-bi-9H-carbazol-9-yl)benzofuro[3,2-d]pyrimidine (abbreviation: 4PCCzBfpm), 4-[4-(9'-phenyl-3,3'-bi-9H-carbazol-9-yl)phenyl]benzofuro[3,2-d]pyrimidine (abbreviation: 4PCCzPBfpm), and 9-[3-(4,6-diphenyl-1,3,5-triazin-2-yl)phenyl]-9'-phenyl-2,3'-bi-9H-carbazole (abbreviation: mPCCzPTzn-02). The heterocyclic compound is preferable because of its high electron-transport property and hole-transport property due to the π-electron rich heteroaromatic ring and the π-electron deficient heteroaromatic ring contained therein. Among skeletons having the π-electron deficient heteroaromatic ring, a pyridine skeleton, a diazine skeleton (a pyrimidine skeleton, a pyrazine skeleton, or a pyridazine skeleton) and a triazine skeleton are particularly preferable because of their high stability and reliability. In particular, a benzofuropyrimidine skeleton, a benzothienopyrimidine skeleton, a benzofuropyrazine skeleton, and a benzothienopyrazine skeleton are preferable because of their high acceptor properties and reliability. Among skeletons having the π-electron rich type heteroaromatic ring, an acridine skeleton, a phenoxazine skeleton, a phenothiazine skeleton, a furan skeleton, a thiophene skeleton, and a pyrrole skeleton have stability and high reliability; therefore, at least one of these skeletons is preferably included. Note that as a furan skeleton, a dibenzofuran skeleton is preferable, and as a thiophene skeleton, a dibenzothiophene skeleton is preferable. Furthermore, as a pyrrole skeleton, an indole skeleton, a carbazole skeleton, a bicarbazole skeleton, or a 3-(9-phenyl-9H-carbazol-3-yl)-9H-carbazole skeleton is particularly preferable. Note that a substance in which the π-electron rich type heteroaromatic ring is directly bonded to the π-electron deficient type heteroaromatic ring is particularly preferred because the donor property of the π-electron rich type heteroaromatic ring and the acceptor property of the π-electron deficient type heteroaromatic ring are both intense and the difference between the level of the singlet excited state and the level of the triplet excited state becomes small. Note that an aromatic ring to which an electron-withdrawing group such as a cyano group is bonded may be used instead of the π-electron deficient heteroaromatic ring. As a π-electron rich skeleton, an aromatic amine skeleton, a phenazine skeleton, or the like can be used. As a π-electron deficient skeleton, a xanthene skeleton, a thioxanthene dioxide skeleton, an oxadiazole skeleton, a triazole skeleton, an imidazole skeleton, an anthraquinone skeleton, a boron-containing skeleton such as phenylborane or boranthrene, an aromatic ring or a heteroaromatic ring having a nitrile group or a cyano group, such as benzonitrile or cyanobenzene, a carbonyl skeleton such as benzophenone, a phosphine oxide skeleton, a sulfone skeleton, or the like can be used. As described above, a π-electron deficient skeleton and a π-electron rich skeleton can be used instead of at least one of the π-electron deficient heteroaromatic ring and the π-electron rich heteroaromatic ring.

[Chemical Formula 35]
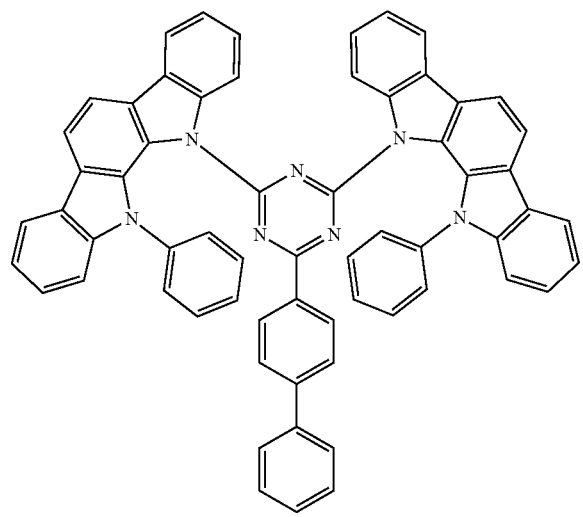
PIC-TRZ
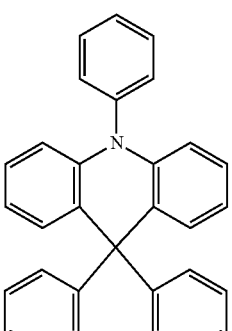
ACRSA
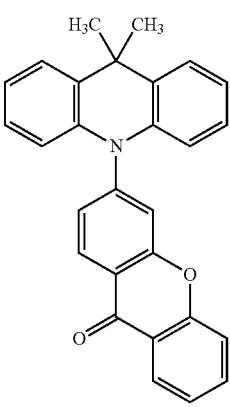
ACRXTN
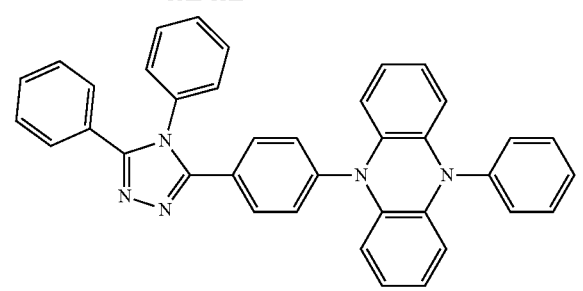
PXZ-TRZ
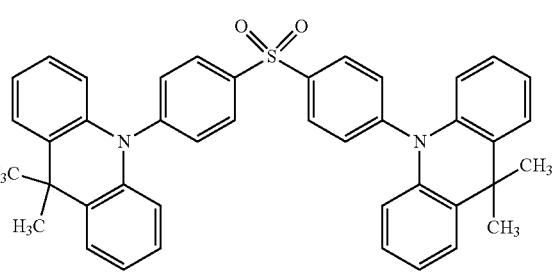
DMAC-DPS
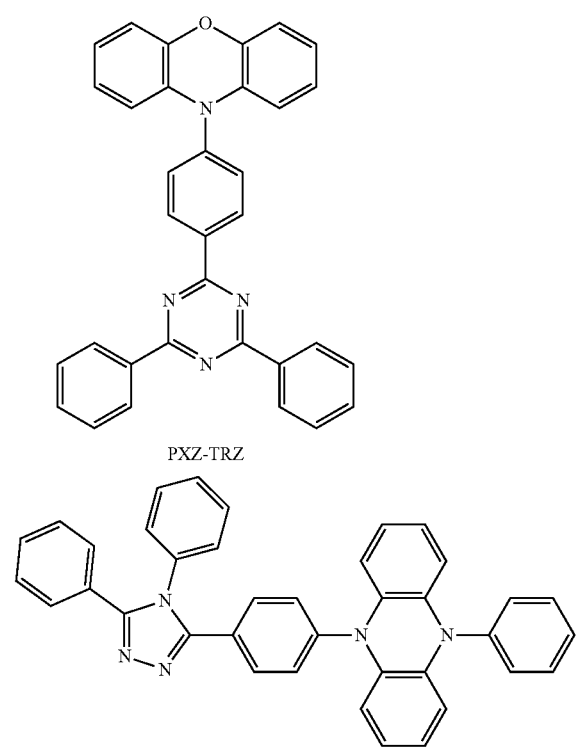
PPZ-3TPT
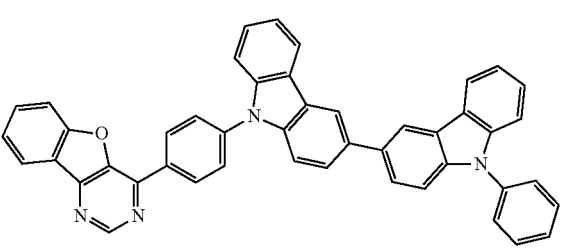
4PCCzPBfpm
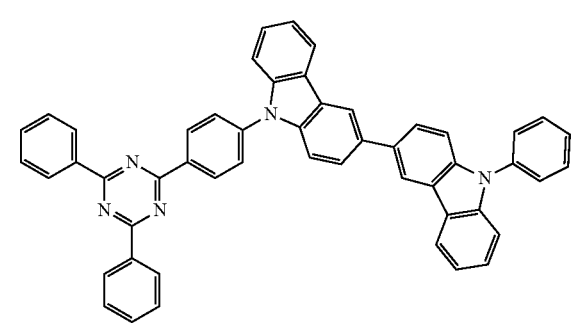
PCCzPTzn
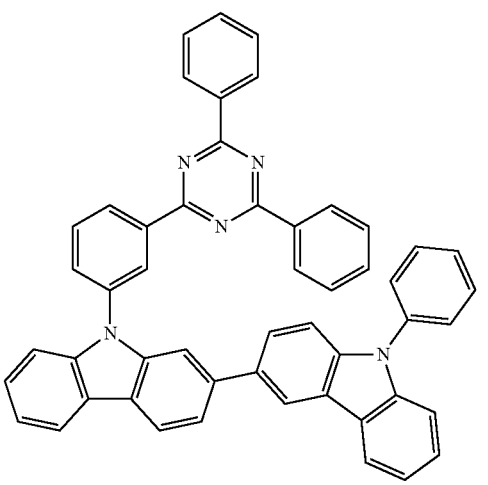
mPCCzPTzn-02

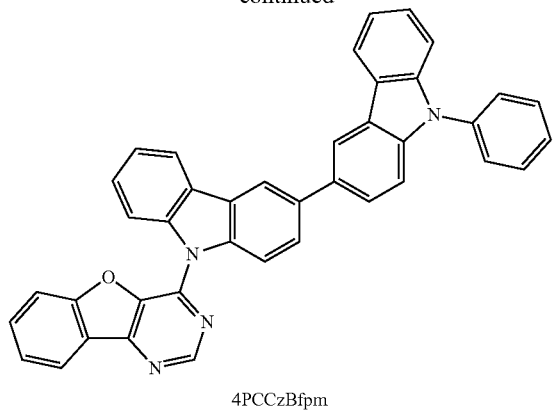

4PCCzBfpm

In the case where the compound 133 does not have a function of converting triplet excitation energy into light emission, a combination of the compound 131 and the compound 133 or the compound 131 and the compound 134 is preferably, but is not particularly limited to, a combination that forms an exciplex. It is preferred that one have a function of transporting electrons and the other have a function of transporting holes. Furthermore, it is preferred that one have a π-electron deficient heteroaromatic ring skeleton and the other have a π-electron rich heteroaromatic ring skeleton.

Examples of the organic compound 131 include, in addition to a zinc- or aluminum-based metal complex, an oxadiazole derivative, a triazole derivative, a benzimidazole derivative, a quinoxaline derivative, a dibenzoquinoxaline derivative, a dibenzothiophene derivative, a dibenzofuran derivative, a pyrimidine derivative, a triazine derivative, a pyridine derivative, a bipyridine derivative, and a phenanthroline derivative. Other examples include an aromatic amine and a carbazole derivative.

In addition, the following hole-transport materials and electron-transport materials can be used.

As the hole-transport material, a material having a property of transporting more holes than electrons can be used, and a material having a hole mobility of $1\times10^{-6}$ cm$^2$Ns or higher is preferable. Specifically, an aromatic amine, a carbazole derivative, an aromatic hydrocarbon, a stilbene derivative, or the like can be used. Furthermore, the hole-transport material may be a high molecular compound.

Examples of the aromatic amine compound, which is a material having a high hole-transport property, include N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenyl aminophenyl)-N-phenyl amino]benzene (abbreviation: DPA3B).

Specific examples of the carbazole derivative include 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Other examples of the carbazole derivative include 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene.

Moreover, examples of the aromatic hydrocarbon include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Besides, pentacene, coronene, and the like can be used. Thus, the use of the aromatic hydrocarbon having a hole mobility of $1\times10^{-6}$ cm$^2$/Vs or higher and having 14 carbon atoms to 42 carbon atoms is further preferable.

The aromatic hydrocarbon may have a vinyl skeleton. Examples of the aromatic hydrocarbon having a vinyl group include 4,4'-bis(2,2-diphenylvinyl)biphenyl (abbreviation: DPVBi) and 9,10-bis[4-(2,2-diphenylvinyl)phenyl]anthracene (abbreviation: DPVPA).

It is also possible to use high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD).

As the material having a high hole-transport property, the following aromatic amine compounds can be used for example: 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4"-tris(carbazol-9-yl)triphenylamine (abbreviation: TCTA), 4,4',4"-tris[N-(1-naphthyl)-N-phenylamino]triphenylamine (abbreviation: 1'-TNATA), 4,4',4"-tris(N,N'-diphenylamino)triphenylamine (abbreviation: TDATA), 4,4',4"-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N-phenyl-N-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2[N-(4-diphenylaminophenyl)-N-phenylamino]spiro-9,9'-bifluorene (abbreviation: DPASF), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9- phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N,N'-triphenyl-N,N,N'-tris(9-phenylcarbazol-3-yl)benzene-1,3,5-triamine (abbreviation: PCA3B), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 9,9-dimethyl-N-phenyl-N-[4-(9-phenyl-9H-carbazol-3-yl)phenyl]-fluoren-2-amine (abbreviation: PCBAF), N-phenyl-N-[4-(9-phenyl-9H-carbazol-3-yl)phenyl]-spiro-9,9'-bifluoren-2-amine (abbreviation: PCBASF), 2[N-(9-phenylcarbazol-3-yl)-N-phenylamino]spiro-9,9'-bifluorene (abbreviation: PCASF), 2,7-bis[N-(4-diphenylaminophenyl)-N-phenylamino]-spiro-9,9'-bifluorene (abbreviation: DPA2SF), N-[4-(9H-carbazol-9-yl)phenyl]-N-(4-phenyl)phenylaniline (abbreviation: YGA1BP), and N,N'-bis[4-(carbazol-9-yl)phenyl]-N,N'-diphenyl-9,9-dimethylfluorene-2,7-diamine (abbreviation: YGA2F). It is also possible to use an amine compound, a carbazole compound, a thiophene compound, a furan compound, a fluorene compound, a triphenylene compound, a phenanthrene compound, or the like such as 3-[4-(1-naphthyl)-phenyl]-9-phenyl-9H-carbazole (abbreviation: PCPN), 3-[4-(9-phenanthryl)-phenyl]-9-phenyl-9H-carbazole (abbreviation: PCPPn), 3,3'-bis(9-phenyl-9H-carbazole) (abbreviation: PCCP), 1,3-bis(N-carbazolyl)benzene (abbreviation: mCP), 3,6-bis(3,5-diphenylphenyl)-9-phenylcarbazole (abbreviation: CzTP), 4-{3-[3-(9-phenyl-9H-fluoren-9-yl)phenyl]phenyl}dibenzofuran (abbreviation: mmDBFFLBi-II), 4,4',4"-(benzene-1,3,5-triyl)tri(dibenzofuran) (abbreviation: DBF3P-II), 1,3,5-tri(dibenzothiophen-4-yl)-benzene (abbreviation: DBT3P-II), 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), or 4-[3-(triphenylen-2-yl)phenyl]dibenzothiophene (abbreviation: mDBTPTp-II). The substances described here are mainly substances having a hole mobility of $1 \times 10^{-6}$ cm$^2$/Vs or higher. Note that other substances may also be used as long as they have a property of transporting more holes than electrons.

A material having a property of transporting more electrons than holes can be used as the electron-transport material, and a material having an electron mobility of $1 \times 10^{-6}$ cm$^2$/Vs or higher is preferable. A π-electron deficient type heteroaromatic compound such as a nitrogen-containing heteroaromatic compound, a metal complex, or the like can be used as the material that easily accepts electrons (the material having an electron-transport property). Specifically, metal complexes having a quinoline ligand, a benzoquinoline ligand, an oxazole ligand, and a thiazole ligand; an oxadiazole derivative; a triazole derivative; a phenanthroline derivative; a pyridine derivative; a bipyridine derivative; a pyrimidine derivative; and the like are given.

Specific examples include metal complexes having a quinoline skeleton or a benzoquinoline skeleton, such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), and bis(8-quinolinolato)zinc(II) (abbreviation: Znq). Alternatively, a metal complex having an oxazole-based or thiazole-based ligand, such as bis[2-(2-benzoxazolyl)phenolato]zinc(II) (abbreviation: ZnPBO) or bis[2-(2-benzothiazolyl)phenolato]zinc(II) (abbreviation: ZnBTZ), or the like can also be used. Furthermore, other than the metal complexes, it is possible to use a heterocyclic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), bathophenanthroline (abbreviation: BPhen), 2,9-bis(naphthalen-2-yl)-4,7-diphenyl-1,10-phenanthroline (abbreviation: NBPhen), or bathocuproine (abbreviation: BCP); a heterocyclic compound having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), or 4,6-bis[3-(9H-carbazol-9-yl)phenyl]pyrimidine (abbreviation: 4,6mCzP2Pm); a heterocyclic compound having a triazine skeleton, such as 2-{4[3-(N-phenyl-9H-carbazol-3-yl)-9H-carbazol-9-yl]phenyl}-4,6-diphenyl-1,3,5-triazine (abbreviation: PCCzPTzn); a heterocyclic compound having a pyridine skeleton, such as 3,5-bis[3-(9H-carbazol-9-yl)phenyl]pyridine (abbreviation: 35DCzPPy), or 1,3,5-tri[3-(3-pyridyl)phenyl]benzene (abbreviation: TmPyPB); or a heteroaromatic compound such as 4,4'-bis(5-methylbenzoxazol-2-yl)stilbene (abbreviation: BzOs). Furthermore, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used. The substances described here are mainly substances having an electron mobility of $1 \times 10^{-6}$ cm$^2$/Vs or higher. Note that other substances may also be used as long as they have a property of transporting more electrons than holes.

As the compound 133 or the compound 134, a material that can form an exciplex together with the compound 131 is preferable. Specifically, the above-described hole-transport material and electron-transport material can be used. In that case, it is preferred that the compound 131 and the compound 133, the compound 131 and the compound 134, and the compound 132 (fluorescent material) be selected so that the emission peak of the exciplex formed by the compound 131 and the compound 133 or the compound 131 and the compound 134 overlaps with an absorption band on the longest wavelength side (low energy side) of the compound 132 (fluorescent material). This makes it possible to provide a light-emitting element with drastically improved emission efficiency.

A phosphorescent material can be used as the compound 133. As the phosphorescent material, an iridium-, rhodium-, or platinum-based organometallic complex or a metal complex can be given. A platinum complex or organoiridium complex having a porphyrin ligand can be given; among them, for example, an organoiridium complex such as an iridium-based ortho-metalated complex is preferable. Examples of an ortho-metalated ligand include a 4H-triazole ligand, a 1H-triazole ligand, an imidazole ligand, a pyridine ligand, a pyrimidine ligand, a pyrazine ligand, and an isoquinoline ligand. In this case, the compound 133 (phosphorescent material) has an absorption band of triplet MLCT (Metal to Ligand Charge Transfer) transition. It is preferred that the compound 133 and the compound 132 (fluorescent material) be selected so that the emission peak of the compound 133 overlaps with an absorption band on the longest wavelength side (low energy side) of the compound 132 (fluorescent material). This makes it possible to provide a light-emitting element with drastically improved emission efficiency. Even in the case where the compound 133 is a phosphorescent material, it may form an exciplex together with the compound 131. When an exciplex is formed, the phosphorescent material does not need to emit light at room temperature and emits light at room temperature after an exciplex is formed. In this case, for example, $Ir(ppz)_3$ can be used as the phosphorescent material.

Examples of the substance that has an emission peak in blue or green include organometallic iridium complexes having a 4H-triazole skeleton, such as tris {2-[5-(2-methylphenyl)-4-(2,6-dimethylphenyl)-4H-1,2,4-triazol-3-yl-κ/$N^2$]phenyl-κC}iridium(III) (abbreviation: $Ir(mpptz-dmp)_3$), tris(5-methyl-3,4-diphenyl-4H-1,2,4-triazolato)iridium(III) (abbreviation: $Ir(Mptz)_3$), tris[4-(3-biphenyl)-5-isopropyl-3-phenyl-4H-1,2,4-triazolato]iridium(III) (abbreviation: $Ir(iPrptz-3b)_3$), and tris[3-(5-biphenyl)-5-isopropyl-4-phenyl-4H-1,2,4-triazolato]iridium(III) (abbreviation: $Ir(iPr5btz)_3$); organometallic iridium complexes having a 1H-triazole skeleton, such as tris[3-methyl-1-(2-methylphenyl)-5-phenyl-1H-1,2,4-triazolato]iridium(III) (abbreviation: $Ir(Mptz1-mp)_3$) and tris(1-methyl-5-phenyl-3-propyl-1H-1,2,4-triazolato)iridium(III) (abbreviation: $Ir(Prptz1-Me)_3$); organometallic iridium complexes having an imidazole skeleton, such as fac-tris[1-(2,6-diisopropylphenyl)-2-phenyl-1H-imidazole]iridium(III) (abbreviation: $Ir(iPrpmi)_3$) and tris[3-(2,6-dimethylphenyl)-7-methylimidazo[1,2-f] phenanthridinato]iridium(III) (abbreviation: $Ir(dmpimpt-Me)_3$); and organometallic iridium complexes in which a phenylpyridine derivative having an electron-withdrawing group is a ligand, such as bis[2-(4',6'-difluorophenyOpyridinato-$N,C^2$']iridium(III) tetrakis(1-pyrazolyl)borate (abbreviation: FIr6), bis[2-(4',6'-difluorophenyl)pyridinato-$N,C^2$'] iridium(III) picolinate (abbreviation: Flrpic), bis{2-[3',5'-bis (trifluoromethyl)phenyl]pyridinato-$N,C^{2'}$}iridium(III) picolinate (abbreviation: $Ir(CF_3ppy)_2(pic)$), and bis[2-(4',6'-difluorophenyl)pyridinato-$N,C^{2'}$]iridium(III) acetylacetonate (abbreviation: FIr(acac)). Among the materials given above, the organometallic iridium complexes having a nitrogen-containing five-membered heterocyclic skeleton, such as a 4H-triazole skeleton, a 1H-triazole skeleton, or an imidazole skeleton have high triplet excitation energy, reliability, and emission efficiency and are thus especially preferable.

Examples of the substance that has an emission peak in green or yellow include organometallic iridium complexes having a pyrimidine skeleton, such as tris(4-methyl-6-phenylpyrimidinato)iridium(III) (abbreviation: $Ir(mppm)_3$), tris (4-t-butyl-6-phenylpyrimidinato)iridium(III) (abbreviation: $Ir(tBuppm)_3$), (acetylacetonato)bis(6-methyl-4-phenylpyrimidinato)iridium(III) (abbreviation: $Ir(mppm)_2(acac)$), (acetylacetonato)bis(6-tert-butyl-4-phenylpyrimidinato) iridium(III) (abbreviation: $Ir(tBuppm)_2(acac)$), (acetylacetonato)bis[4-(2-norbornyl)-6-phenylpyrimidinato]iridium(III) (abbreviation: $Ir(nbppm)_2(acac)$), (acetylacetonato)bis[5-methyl-6-(2-methylphenyl)-4-phenylpyrimidinato]iridium (III) (abbreviation: $Ir(mpmppm)_2(acac)$), (acetylacetonato) bis{4,6-dimethyl-2-[6-(2,6-dimethylphenyl)-4-pyrimidinyl-κ$N^3$]phenyl-κC}iridium(III) (abbreviation: $Ir(dmppm-dmp)_2(acac)$), and (acetylacetonato)bis(4,6-diphenylpyrimidinato)iridium(III) (abbreviation: $Ir(dppm)_2(acac)$); organometallic iridium complexes having a pyrazine skeleton, such as (acetylacetonato)bis(3,5-dimethyl-2-phenylpyrazinato)iridium(III) (abbreviation: $Ir(mppr-Me)_2(acac)$) and (acetylacetonato)bis(5-isopropyl-3-methyl-2-phenylpyrazinato)iridium(III) (abbreviation: $Ir(mppr-iPr)_2(acac)$); organometallic iridium complexes having a pyridine skeleton, such as tris(2-phenylpyridinato-$N,C^{2'}$)iridium(III) (abbreviation: $Ir(ppy)_3$), bis(2-phenylpyridinato-$N,C^{2'}$)iridium(III) acetylacetonate (abbreviation: $Ir(ppy)_2(acac)$), bis(benzo[h]quinolinato)iridium(III) acetylacetonate (abbreviation: $Ir(bzq)_2(acac)$), tris(benzo[h] quinolinato)iridium(III) (abbreviation: $Ir(bzq)_3$), tris(2-phenylquinolinato-$N,C^{2'}$)iridium(III) (abbreviation: $Ir(pq)_3$), and bis(2-phenylquinolinato-$N,C^{2'}$)iridium(III) acetylacetonate (abbreviation: $Ir(pq)_2(acac)$); organometallic iridium complexes such as bis(2,4-diphenyl-1,3-oxazolato-$N,C^{2'}$) iridium(III) acetylacetonate (abbreviation: $Ir(dpo)_2(acac)$), bis{2-[4'-(perfluorophenyl)phenyl]pyridinato-N, $C^{2'}$}iridium(III) acetylacetonate (abbreviation: $Ir(p-PF-ph)_2(acac)$), and bis(2-phenylbenzothiazolato-$N,C^{2'}$)iridium(III) acetylacetonate (abbreviation: $Ir(bt)_2(acac)$); and a rare earth metal complex such as tris(acetylacetonato) (monophenanthroline)terbium(III) (abbreviation: $Tb(acac)_3$ (Phen)). Among the materials given above, the organometallic iridium complexes having a pyrimidine skeleton have distinctively high reliability and emission efficiency and are thus especially preferable.

Examples of the substance that has an emission peak in yellow or red include organometallic iridium complexes having a pyrimidine skeleton, such as (diisobutyrylmethanato)bis[4,6-bis(3-methylphenyl)pyrimidinato]iridium(III) (abbreviation: $Ir(5mdppm)_2(dibm)$), bis[4,6-bis(3-methylphenyl)pyrimidinato](dipivaloylmethanato)iridium(III) (abbreviation: $Ir(5mdppm)_2(dpm)$), and bis[4,6-di(naphthalen-1-yl)pyrimidinato](dipivaloylmethanato)iridium(III) (abbreviation: $Ir(dlnpm)_2(dpm)$); organometallic iridium complexes having a pyrazine skeleton, such as (acetylacetonato)bis(2,3,5-triphenylpyrazinato)iridium(III) (abbreviation: $Ir(tppr)_2(acac)$), bis(2,3,5-triphenylpyrazinato)(dipivaloylmethanato)iridium(III) (abbreviation: $Ir(tppr)_2(dpm)$), and (acetylacetonato)bis[2,3-bis(4-fluorophenyl) quinoxalinato]iridium(III) (abbreviation: $Ir(Fdpq)_2(acac)$); organometallic iridium complexes having a pyridine skeleton, such as tris(1-phenylisoquinolinato-$N,C^{2'}$)iridium(III) (abbreviation: $Ir(piq)_3$) and bis(1-phenylisoquinolinato-N, $C^{2'}$)iridium(III) acetylacetonate (abbreviation: $Ir(piq)_2(acac)$); a platinum complex such as 2,3,7,8,12,13,17,18-octaethyl-21H,23H-porphyrin platinum(II) (abbreviation: PtOEP); and rare earth metal complexes such as tris(1,3-diphenyl-1,3-propanedionato) (monophenanthroline)europium(III) (abbreviation: $Eu(DBM)_3(Phen)$) and tris[1-(2-thenoyl)-3,3,3-trifluoroacetonato] (monophenanthroline) europium(III) (abbreviation: $Eu(TTA)_3(Phen)$).

Among the materials given above, the organometallic iridium complexes having a pyrimidine skeleton have distinctively high reliability and emission efficiency and are thus especially preferable. Furthermore, the organometallic iridium complexes having a pyrazine skeleton can emit red light with favorable chromaticity.

Examples of a material that can be used as the above-described energy donor include metal-halide perovskites. The metal-halide perovskites can be represented by any of General Formulae (g1) to (g3) below.

(SA)MX$_3$: (g1)

(LA)$_2$(SA)$_{n-1}$M$_n$X$_{3n+1}$: (g2)

(PA)(SA)$_{n-1}$M$_n$X3$_{n+1}$: (g3)

In the above general formulae, M represents a divalent metal ion, and X represents a halogen ion.

As the divalent metal ion, specifically, a divalent cation of lead, tin, or the like is used.

As the halogen ion, specifically, an anion of chlorine, bromine, iodine, fluorine, or the like is used.

Note that n represents an integer of 1 to 10. In the case where n is larger than 10 in General Formula (g2) or General Formula (g3), the properties are close to those of the metal-halide perovskite represented by General Formula (g1).

In addition, LA is an ammonium ion represented by R$^{30}$—NH$_3^+$.

In the ammonium ion represented by the general formula R$^{30}$—NH$_3^+$, R$^{30}$ represents any one of an alkyl group, an aryl group, and a heteroaryl group each having 2 to 20 carbon atoms or a group in which any one of an alkyl group, an aryl group, and a heteroaryl group each having 2 to 20 carbon atoms is combined with an alkylene group and a vinylene group each having 1 to 12 carbon atoms and an arylene group and a heteroarylene group each having 6 to 13 carbon atoms. In the latter case, a plurality of alkylene groups, arylene groups, and heteroarylene groups may be coupled, and a plurality of groups of the same kind may be used. In the case where a plurality of alkylene groups, vinylene groups, arylene groups, and heteroarylene groups are coupled, the total number of alkylene groups, vinylene groups, arylene groups, and heteroarylene groups is preferably smaller than or equal to 35.

Furthermore, SA is represented by a monovalent metal ion or R$^{31}$—NH$_3^+$, and R$^{31}$ represents an alkyl group having 1 to 6 carbon atoms.

Moreover, PA represents NH$_3^+$—R$^{32}$—NH$_3^+$, NH$_3^+$—R$^{33}$—R$^{34}$—R$^{35}$—NH$_3^+$, or a part or whole of branched polyethyleneimine including ammonium cations, and the valence of this portion is +2. Note that charges are roughly in balance in the general formula.

Here, charges of the metal-halide perovskite are not necessarily in balance strictly in every portion of the material in the above formula as long as the neutrality is roughly maintained in the material as a whole. In some cases, other ions such as a free ammonium ion, a free halogen ion, or an impurity ion exist locally in the material and neutralize the charges. In addition, in some cases, the neutrality is not maintained locally also at a surface of a particle or a film, a crystal grain boundary, or the like; thus, the neutrality is not necessarily maintained in every location.

Note that in the above formula (g2), (LA) can be any of substances represented by General Formulae (a-1) to (a-11) and General Formulae (b-1) to (b-6) shown below, for example.

[Chemical Formula 36]

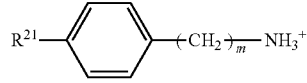
(a-1)

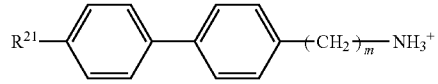
(a-2)

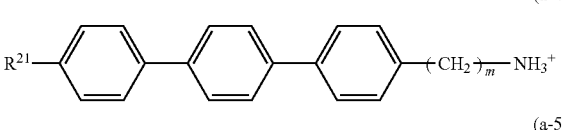
(a-3)

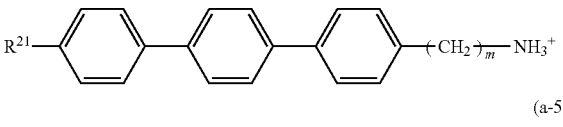
(a-4)

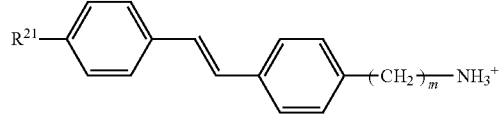
(a-5)

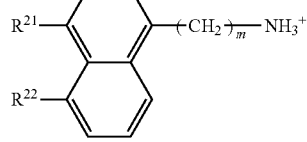
(a-6)

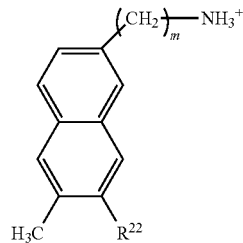
(a-7)

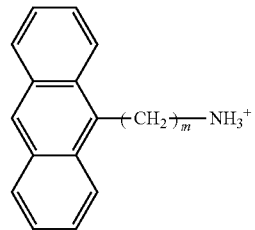
(a-8)

(a-9)

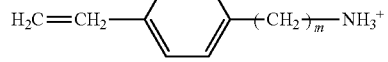
(a-10)

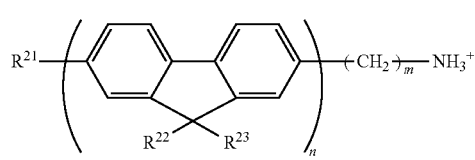
(a-11)

[Chemical Formula 37]

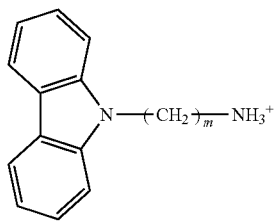
(b-1)

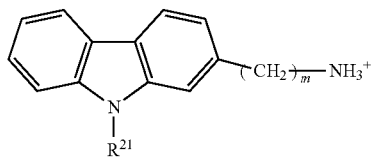
(b-2)

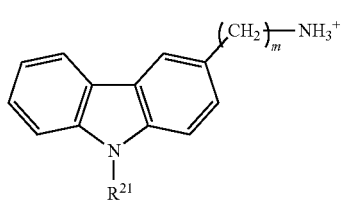
(b-3)

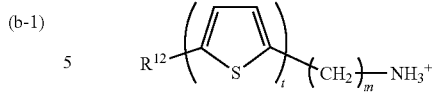
(b-4)

(b-5)

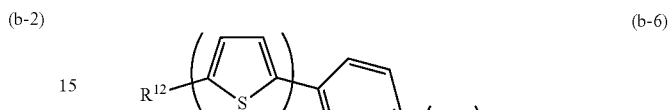
(b-6)

Furthermore, (PA) in General Formula (g3) typically represents any of substances represented by General Formulae (c-1), (c-2), and (d) shown below or a part or whole of branched polyethyleneimine including ammonium cations, and has a valence of +2. These polymers may neutralize charges over a plurality of unit cells. Alternatively, one charge of each of two different polymer molecules may neutralize charges of one unit cell.

[Chemical Formula 38]

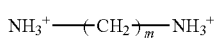
(c-1)

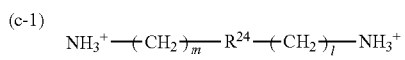
(c-2)

[Chemical Formula 39]

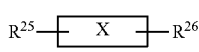
(d)

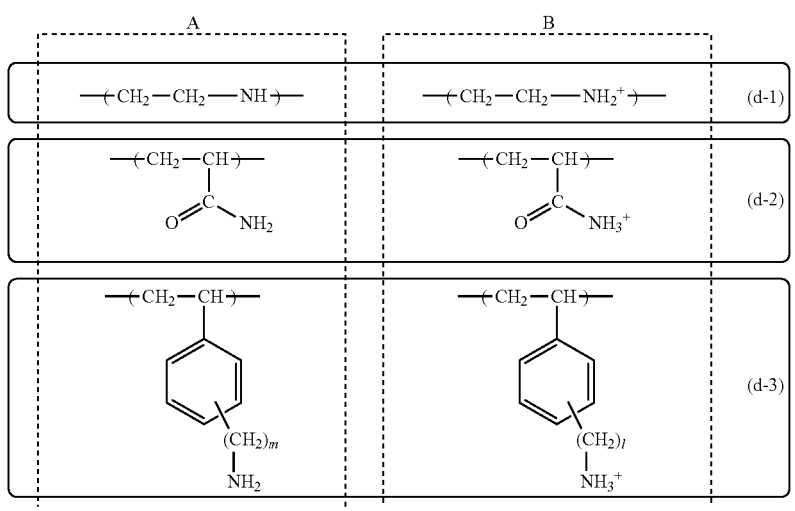

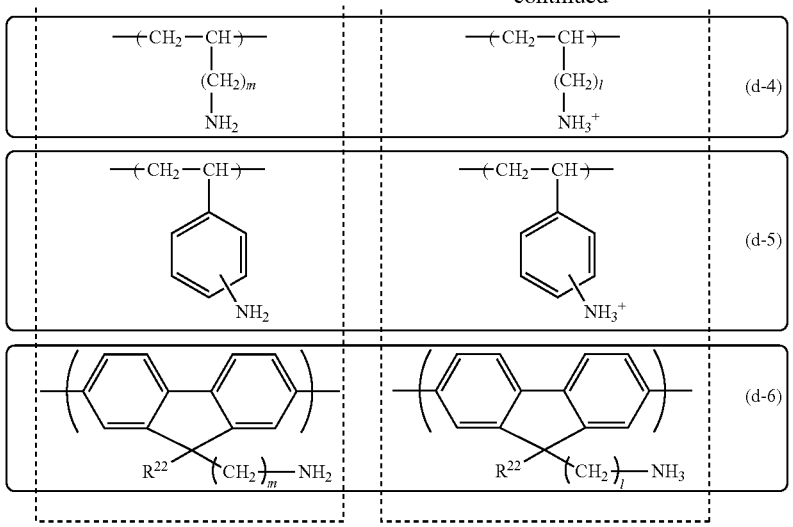

Note that in the above general formulae, $R^{20}$ represents an alkyl group having 2 to 18 carbon atoms, $R^{21}$, $R^{22}$, and $R^{23}$ represent hydrogen or an alkyl group having 1 to 18 carbon atoms, and $R^{24}$ represents any of Structural Formulae and General Formulae ($R^{24}$-1) to ($R^{24}$-14) shown below. Furthermore, $R^{25}$ and $R^{26}$ each independently represent hydrogen or an alkyl group having 1 to 6 carbon atoms. In addition, X has a combination of monomer units A and B represented by any of (d-1) to (d-6) shown above, and represents a structure including u A and v B. Note that the arrangement order of A and B is not limited. Furthermore, m and/are each independently an integer of 0 to 12, and t is an integer of 1 to 18. In addition, u is an integer of 0 to 17, v is an integer of 1 to 18, and u+v is an integer of 1 to 18.

[Chemical Formula 40]

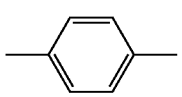

($R^{24}$-1)

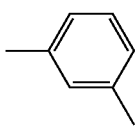

($R^{24}$-2)

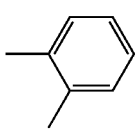

($R^{24}$-3)

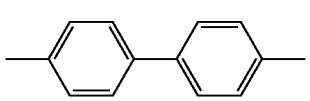

($R^{24}$-4)

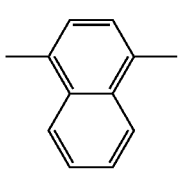

($R^{24}$-5)

-continued

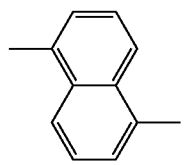

($R^{24}$-6)

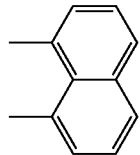

($R^{24}$-7)

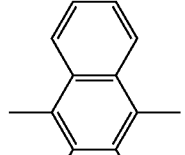

($R^{24}$-8)

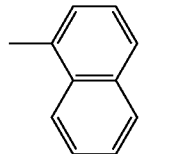

($R^{24}$-9)

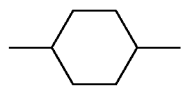

($R^{24}$-10)

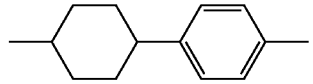

($R^{24}$-11)

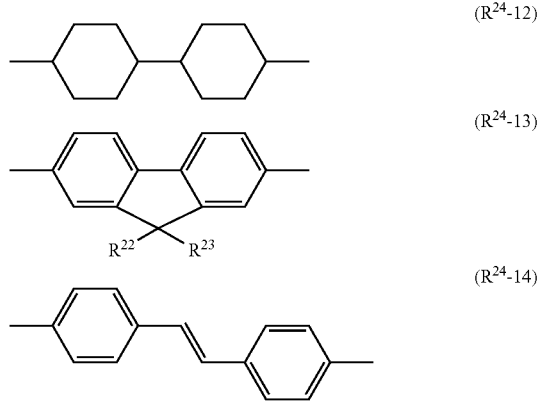

(R24-12)

(R24-13)

(R24-14)

Note that these are examples, and the substances that can be used as (LA) and (PA) are not limited thereto.

In the metal-halide perovskite having a three-dimensional structure including the composition (SA)MX$_3$ represented by General Formula (g1), regular octahedral structures in each of which a metal atom M is placed at the center and halogen atoms are placed at six vertexes are three-dimensionally arranged by sharing the halogen atoms at the vertexes, so that a skeleton is formed. This regular octahedral structure unit including a halogen atom at each vertex is referred to as a perovskite unit. There are a zero-dimensional structure body in which a perovskite unit exists in isolation, a linear structure body in which perovskite units are one-dimensionally coupled with a halogen atom at the vertex, a sheet-shaped structure body in which perovskite units are two-dimensionally coupled, a structure body in which perovskite units are three-dimensionally coupled, and a complicated two-dimensional structure body formed of a stack of a plurality of sheet-shaped structure bodies in each of which perovskite units are two-dimensionally coupled. There is a more complicated structure body. All of these structure bodies having a perovskite unit are collectively defined as a metal-halide perovskite.

The light-emitting layer 130 can be formed of two or more layers. For example, in the case where the light-emitting layer 130 is formed by stacking a first light-emitting layer and a second light-emitting layer in this order from the hole-transport layer side, a substance having a hole-transport property is used as the host material of the first light-emitting layer and a substance having an electron-transport property is used as the host material of the second light-emitting layer.

The light-emitting layer 130 may contain a material (a compound 135) other than the compound 131, the compound 132, the compound 133, and the compound 134. In that case, in order for the compound 131 and the compound 133 (or the compound 134) to efficiently form an exciplex, it is preferable that the HOMO level of one of the compound 131 and the compound 133 (or the compound 134) be the highest HOMO level of the materials in the light-emitting layer 130, and that the LUMO level of the other be the lowest LUMO level of the materials in the light-emitting layer 130. With such an energy level correlation, the reaction for forming an exciplex by the compound 131 and the compound 135 can be inhibited.

In the case where, for example, the compound 131 has a hole-transport property and the compound 133 (or the compound 134) has an electron-transport property, the HOMO level of the compound 131 is preferably higher than the HOMO level of the compound 133 and the HOMO level of the compound 135, and the LUMO level of the compound 133 is preferably lower than the LUMO level of the compound 131 and the LUMO level of the compound 135. In this case, the LUMO level of the compound 135 may be higher or lower than the LUMO level of the compound 131. Furthermore, the HOMO level of the compound 135 may be higher or lower than the HOMO level of the compound 133.

Although there is no particular limitation on a material (the compound 135) that can be used in the light-emitting layer 130, for example, metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: BPhen), bathocuproine (abbreviation: BCP), and 9-[4-(5-phenyl-1,3,4-oxadiazol-2-yl)phenyl]-9H-carbazole (abbreviation: CO11); and aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4,4'-bis[N-(spiro-9,9'-bifluoren-2-yl)-N-phenylamino]biphenyl (abbreviation: BSPB) can be given. Other examples include condensed polycyclic aromatic compounds such as anthracene derivatives, phenanthrene derivatives, pyrene derivatives, chrysene derivatives, and dibenzo[g,p]chrysene derivatives, and specific examples include 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N, 9-diphenyl-N-(9,10-diphenyl-2-anthryl)-9H-carbazol-3-amine (abbreviation: 2PCAPA), 6,12-dimethoxy-5,11-diphenylchrysene, N,N,N',N',N'',N'',N''',N'''-octaphenyldibenzo[g,p]chrysene-2,7,10,15-tetraamine (abbreviation: DBC1), 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), and 1,3,5-tri(1-pyrenyl)benzene (abbreviation: TPB3). One or more substances having a wider energy gap than the compound 131 and the compound 132 are selected from these and known substances.

<<Pair of Electrodes>>

The electrode 101 and the electrode 102 have functions of injecting holes and electrons into the light-emitting layer 130. The electrode 101 and the electrode 102 can be formed using a metal, an alloy, a conductive compound, a mixture or a stack thereof, or the like. As the metal, aluminum (Al) is a typical example; besides, a transition metal such as silver (Ag), tungsten, chromium, molybdenum, copper, or titanium, an alkali metal such as lithium (Li) or cesium, or a Group 2 metal such as calcium or magnesium (Mg) can be used. As the transition metal, a rare earth metal such as ytterbium (Yb) may be used. An alloy containing the above metal can be used as the alloy, and MgAg, AlLi, and the like can be given, for example. As the conductive compound, for example, metal oxides such as indium tin oxide (hereinafter ITO), indium tin oxide containing silicon or silicon oxide (abbreviation: ITSO), indium zinc oxide, and indium oxide containing tungsten and zinc can be given. It is also possible to use an inorganic carbon-based material such as graphene as the conductive compound.

As described above, one or both of the electrode 101 and the electrode 102 may be formed by stacking two or more of these materials.

Light emission obtained from the light-emitting layer 130 is extracted through one or both of the electrode 101 and the electrode 102. Therefore, at least one of the electrode 101 and the electrode 102 has a function of transmitting visible light. As the conductive material having a function of transmitting light, a conductive material having a visible light transmittance of higher than or equal to 40% and lower than or equal to 100%, preferably higher than or equal to 60% and lower than or equal to 100%, and a resistivity of lower than or equal to $1\times10^{-2}$ Ω·cm can be given. The electrode through which light is extracted may be formed using a conductive material having a function of transmitting light and a function of reflecting light. An example of the conductive material is a conductive material having a visible light reflectivity higher than or equal to 20% and lower than or equal to 80%, preferably higher than or equal to 40% and lower than or equal to 70%, and a resistivity lower than or equal to $1\times10^{-2}$ Ω·cm. In the case where a material with low light transmittance, such as metal or alloy, is used for the electrode through which light is extracted, one or both of the electrode 101 and the electrode 102 are formed to a thickness that is thin enough to transmit visible light (e.g., a thickness of 1 nm to 10 nm).

Note that in this specification and the like, for the electrode having a function of transmitting light, a material that has a function of transmitting visible light and has conductivity is used, and examples include, in addition to the above-described oxide conductor layer typified by an ITO, an oxide semiconductor layer and an organic conductor layer containing an organic substance. As the organic conductor layer containing an organic substance, for example, a layer containing a composite material in which an organic compound and an electron donor (donor) are mixed, a layer containing a composite material in which an organic compound and an electron acceptor (acceptor) are mixed, and the like can be given. The resistivity of the transparent conductive layer is preferably lower than or equal to $1\times10^5$ Ω·cm, and further preferably lower than or equal to $1\times10^4$ Ω·cm.

As the method for forming the electrode 101 and the electrode 102, a sputtering method, an evaporation method, a printing method, a coating method, an MBE (Molecular Beam Epitaxy) method, a CVD method, a pulsed laser deposition method, an ALD (Atomic Layer Deposition) method, or the like can be used as appropriate.

<<Hole-Injection Layer>>

The hole-injection layer 111 has a function of reducing a barrier for hole injection from one of the pair of electrodes (the electrode 101 or the electrode 102) to promote hole injection and is formed using a transition metal oxide, a phthalocyanine derivative, an aromatic amine, or the like, for example. Examples of the transition metal oxide include molybdenum oxide, vanadium oxide, ruthenium oxide, tungsten oxide, and manganese oxide. Examples of the phthalocyanine derivative include phthalocyanine and metal phthalocyanine. Examples of the aromatic amine include a benzidine derivative and a phenylenediamine derivative. It is also possible to use a high molecular compound such as polythiophene or polyaniline; a typical example thereof is poly(ethylenedioxythiophene)/poly(styrenesulfonic acid), which is self-doped polythiophene.

As the hole-injection layer 111, a layer containing a composite material of a hole-transport material and a material having a property of accepting electrons from the hole-transport material can also be used. Alternatively, a stack of a layer containing a material having an electron-accepting property and a layer containing a hole-transport material may also be used. In a steady state or in the presence of an electric field, a charge can be transferred between these materials. Examples of the material having an electron-accepting property include organic acceptors such as a quinodimethane derivative, a chloranil derivative, and a hexaazatriphenylene derivative. A specific example is a compound having an electron-withdrawing group (in particular, a cyano group or a halogen group such as a fluoro group), such as 7,7,8,8-tetracyano-2,3,5,6-tetrafluoroquinodimethane (abbreviation: F4-TCNQ), chloranil, 2,3,6,7,10,11-hexacyano-1,4,5,8,9,12-hexaazatriphenylene (abbreviation: HAT-CN), and 1,3,4,5,7,8-hexafluorotetracyanonaphthoquinodimethane (abbreviation: F6-TCNNQ). A compound in which electron-withdrawing groups are bonded to a condensed aromatic ring having a plurality of hetero atoms, such as HAT-CN, is particularly preferable because it is thermally stable. A [3]radialene derivative including an electron-withdrawing group (in particular, a cyano group or a halogen group such as a fluoro group) has a very high electron-accepting property and thus is preferred; specific examples include α,α',α''-1,2,3-cyclopropanetriylidenetris[4-cyano-2,3,5,6-tetrafluorobenzeneacetonitrile], α,α',α''-1,2,3-cyclopropanetriylidenetris[2,6-dichloro-3,5-difluoro-4-(trifluoromethyl)benzeneacetonitrile], and α,α',α''-1,2,3-cyclopropanetriylidenetris[2,3,4,5,6-pentafluorobenzeneacetonitrile]. Alternatively, a transition metal oxide such as an oxide of metal from Group 4 to Group 8 can be used. Specifically, vanadium oxide, niobium oxide, tantalum oxide, chromium oxide, molybdenum oxide, tungsten oxide, manganese oxide, rhenium oxide, or the like can be used. In particular, molybdenum oxide is preferable because of stability in the air, a low hygroscopic property, and easiness of handling.

As the hole-transport material, a material having a property of transporting more holes than electrons can be used, and a material having a hole mobility of $1\times10^{-6}$ cm$^2$/Vs or higher is preferable. Specifically, the aromatic amines and the carbazole derivatives given as the hole-transport material that can be used in the light-emitting layer 130 can be used. Alternatively, the aromatic hydrocarbons, the stilbene derivatives, and the like can be used. Furthermore, the hole-transport material may be a high molecular compound.

Examples of the aromatic hydrocarbon include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl) phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Besides, pentacene, coronene, and the like can be used. Thus, the use of the aromatic hydrocarbon having a hole mobility of $1\times10^{-6}$ cm$^2$/Vs or higher and having 14 carbon atoms to 42 carbon atoms is further preferable.

The aromatic hydrocarbon may have a vinyl skeleton. Examples of the aromatic hydrocarbon having a vinyl group include 4,4'-bis(2,2-diphenylvinyl)biphenyl (abbreviation: DPVBi) and 9,10-bis[4-(2,2-diphenylvinyl)phenyl]anthracene (abbreviation: DPVPA).

It is also possible to use high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD).

<<Hole-Transport Layer>>

The hole-transport layer 112 is a layer containing a hole-transport material and can be formed using any of the materials given as examples of the materials of the hole-injection layer 111. In order that the hole-transport layer 112 has a function of transporting holes injected into the hole-injection layer 111 to the light-emitting layer 130, the hole-transport layer 112 preferably has the HOMO level equal or close to the HOMO level of the hole-injection layer 111.

As the hole-transport material, the material given as an example of the material of the hole-injection layer 111 can be used. A substance having a hole mobility of $1\times10^{-6}$ cm$^2$/Vs or higher is preferred. Note that other substances may also be used as long as they have a property of transporting more holes than electrons. The layer containing a substance having a high hole-transport property is not limited to a single layer, and two or more layers containing the aforementioned substances may be stacked.

<<Electron-Transport Layer>>

The electron-transport layer 118 has a function of transporting, to the light-emitting layer 130, electrons injected from the other of the pair of electrodes (the electrode 101 or the electrode 102) through the electron-injection layer 119. A material having a property of transporting more electrons than holes can be used as the electron-transport material, and a material having an electron mobility of $1\times10^{-6}$ cm$^2$/Vs or higher is preferable. As a compound that easily accepts electrons (a material having an electron-transport property), a π-electron deficient heteroaromatic compound such as a nitrogen-containing heteroaromatic compound or a metal complex can be used, for example. Specifically, the metal complex having a quinoline ligand, a benzoquinoline ligand, an oxazole ligand, or a thiazole ligand, which is given as the electron-transport material that can be used in the light-emitting layer 130, can be given. Furthermore, an oxadiazole derivative, a triazole derivative, a phenanthroline derivative, a pyridine derivative, a bipyridine derivative, a pyrimidine derivative, and the like can be given. A substance having an electron mobility of $1\times10^{-6}$ cm$^2$/Vs or higher is preferable. Note that other substances may also be used for the electron-transport layer as long as they have a property of transporting more electrons than holes. The electron-transport layer 118 is not limited to a single layer, and two or more layers containing the aforementioned substances may be stacked.

A layer that controls transfer of electron carriers may be provided between the electron-transport layer 118 and the light-emitting layer 130. The layer that controls transfer of electron carriers is a layer in which a small amount of a substance having a high electron-trapping property is added to the above-described material having a high electron-transport property, and is capable of adjusting carrier balance by inhibiting transfer of electron carriers. Such a structure is very effective in preventing a problem (such as a reduction in element lifetime) caused when electrons pass through the light-emitting layer.

<<Electron-Injection Layer>>

The electron-injection layer 119 has a function of reducing a barrier for electron injection from the electrode 102 to promote electron injection, and a Group 1 metal, a Group 2 metal, or an oxide, a halide, a carbonate, or the like of them can be used, for example. Alternatively, a composite material of the electron-transport material described above and a material having a property of donating electrons thereto can be used. Examples of the material having an electron-donating property include a Group 1 metal, a Group 2 metal, and an oxide of them. Specifically, an alkali metal, an alkaline earth metal, or a compound thereof, such as lithium fluoride (LiF), sodium fluoride (NaF), cesium fluoride (CsF), calcium fluoride (CaF$_2$), or lithium oxide (LiO$_x$), can be used. Alternatively, a rare earth metal compound such as erbium fluoride (ErF$_3$) can be used. Electride may also be used for the electron-injection layer 119. Examples of the electride include a substance in which electrons are added at high concentration to a mixed oxide of calcium and aluminum. The substance that can be used for the electron-transport layer 118 can be used for the electron-injection layer 119.

A composite material in which an organic compound and an electron donor (donor) are mixed may also be used for the electron-injection layer 119. Such a composite material is excellent in an electron-injection property and an electron-transport property because electrons are generated in the organic compound by the electron donor. In this case, the organic compound is preferably a material that is excellent in transporting the generated electrons; specifically, the above-described substances contained in the electron-transport layer 118 (the metal complexes, heteroaromatic compounds, and the like) can be used, for example. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like are given as examples. In addition, an alkali metal oxide or an alkaline earth metal oxide is preferable, and examples include lithium oxide, calcium oxide, and barium oxide. A Lewis base such as magnesium oxide can also be used. An organic compound such as tetrathiafulvalene (abbreviation: TTF) can also be used.

Note that the light-emitting layer, the hole-injection layer, the hole-transport layer, the electron-transport layer, and the electron-injection layer described above can each be formed by a method such as an evaporation method (including a vacuum evaporation method), an inkjet method, a coating method, a nozzle printing method, or gravure printing. Other than the above-described materials, an inorganic compound such as a quantum dot or a high molecular compound (an oligomer, a dendrimer, a polymer, or the like) may be used in the light-emitting layer, the hole-injection layer, the hole-transport layer, the electron-transport layer, and the electron-injection layer described above.

As the quantum dot, a colloidal quantum dot, an alloyed quantum dot, a core-shell quantum dot, a core quantum dot, or the like may be used. Moreover, a quantum dot containing an element group of Group 2 and Group 16, Group 13 and Group 15, Group 13 and Group 17, Group 11 and Group 17, or Group 14 and Group 15 may be used. Alternatively, a quantum dot containing an element such as cadmium (Cd), selenium (Se), zinc (Zn), sulfur (S), phosphorus (P), indium (In), tellurium (Te), lead (Pb), gallium (Ga), arsenic (As), or aluminum (Al) may be used.

As the liquid medium used for the wet process, an organic solvent of ketones such as methyl ethyl ketone and cyclohexanone; fatty acid esters such as ethyl acetate; halogenated hydrocarbons such as dichlorobenzene; aromatic hydrocarbons such as toluene, xylene, mesitylene, and cyclohexylbenzene; aliphatic hydrocarbons such as cyclohexane, decalin, and dodecane; dimethylformamide (DMF); dimethyl sulfoxide (DMSO); or the like can be used.

Examples of the high molecular compound that can be used for the light-emitting layer include a polyphenylenevinylene (PPV) derivative such as poly[2-methoxy-5-(2-ethylhexyloxy)-1,4-phenylenevinylene] (abbreviation: MEH-PPV) or poly(2,5-dioctyl-1,4-phenylenevinylene); a polyfluorene derivative such as poly(9,9-di-n-octylfluorenyl-2,7-diyl) (abbreviation: PF8), poly[(9,9-di-n-octylfluorenyl-2,7-diyl)-alt-(benzo[2,1,3]thiadiazole-4,8-diyl)] (abbreviation: F8BT), poly[(9,9-di-n-octylfluorenyl-2,7-diyl)-alt-(2,2'-bithiophene-5,5'-diyl)] (abbreviation: F8T2), poly[(9,9-dioctyl-2,7-divinylenefluorenylene)-alt-(9,10-anthracene)], or poly[(9,9-dihexylfluorene-2,7-diyl)-alt-(2,5-dimethyl-1,4-phenylene)]; a polyalkylthiophene (PAT) derivative such as poly(3-hexylthiophene-2,5-diyl) (abbreviation: P3HT); and a polyphenylene derivative. These high molecular compounds and high molecular compounds such as PVK, poly(2-vinylnaphthalene), and poly[bis(4-phenyl) (2,4,6-trimethylphenyl)amine] (abbreviation: PTAA) may be doped with a light-emitting compound and used for the light-emitting layer. As the light-emitting compound, the above-described light-emitting compound can be used.

<<Substrate>>

A light-emitting element of one embodiment of the present invention is formed over a substrate of glass, plastic, or the like. As for the order of forming layers over the substrate, layers may be sequentially stacked from the electrode 101 side or sequentially stacked from the electrode 102 side.

For the substrate over which the light-emitting element of one embodiment of the present invention can be formed, glass, quartz, plastic, or the like can be used, for example. Furthermore, a flexible substrate can be used. The flexible substrate is a substrate that can be bent (is flexible), such as a plastic substrate made of polycarbonate or polyarylate, for example. Furthermore, a film, an inorganic vapor deposition film, or the like can be used. Another material may be used as long as the substrate functions as a support in a fabrication process of the light-emitting elements or the optical elements. Another material having a function of protecting the light-emitting elements or the optical elements may be used.

In one embodiment of the present invention, a light-emitting element can be formed using any of a variety of substrates, for example. The type of substrate is not limited particularly. Examples of the substrate include a semiconductor substrate (e.g., a single-crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, cellulose nanofiber (CNF) and paper which include a fibrous material, and a base material film. Examples of the glass substrate include barium borosilicate glass, aluminoborosilicate glass, and soda lime glass. Examples of the flexible substrate, the attachment film, the base material film, and the like are as follows. Examples of the flexible substrate, the attachment film, the base material film, and the like include substrates of plastics typified by polyethylene terephthalate (PET), polyethylene naphthalate (PEN), polyether sulfone (PES), and polytetrafluoroethylene (PTFE). Another example is a resin such as acrylic. Furthermore, polypropylene, polyester, polyvinyl fluoride, and polyvinyl chloride can be given as examples. Other examples are polyamide, polyimide, aramid, epoxy, an inorganic vapor deposition film, and paper.

Furthermore, a flexible substrate may be used as the substrate and the light-emitting element may be formed directly on the flexible substrate. Alternatively, a separation layer may be provided between the substrate and the light-emitting element. The separation layer can be used when part or the whole of a light-emitting element formed thereover is separated from the substrate and transferred onto another substrate. In such a case, the light-emitting element can be transferred to a substrate having low heat resistance or a flexible substrate as well. For the above separation layer, a stacked structure of inorganic films, which are a tungsten film and a silicon oxide film, or a structure in which a resin film of polyimide or the like is formed over a substrate can be used, for example.

In other words, after the light-emitting element is formed using a substrate, the light-emitting element may be transferred to and arranged over another substrate. Examples of the substrate to which the light-emitting element is transferred include, in addition to the above substrates, a cellophane substrate, a stone substrate, a wood substrate, a cloth substrate (including a natural fiber (silk, cotton, or hemp), a synthetic fiber (nylon, polyurethane, or polyester), a regenerated fiber (acetate, cupro, rayon, or regenerated polyester), and the like), a leather substrate, and a rubber substrate. With the use of such a substrate, a light-emitting element with high durability, a light-emitting element with high heat resistance, a light-emitting element with reduced weight, or a light-emitting element with reduced thickness can be obtained.

The light-emitting element 150 may be formed over an electrode electrically connected to a field-effect transistor (FET), for example, that is formed over the above-described substrate. Accordingly, an active matrix display device in which the FET controls the driving of the light-emitting element can be fabricated.

The structure described in this embodiment can be used in appropriate combination with the other embodiments.

Embodiment 2

In this embodiment, examples of a method for synthesizing an organic compound that can be favorably used for the light-emitting element of one embodiment of the present invention will be described giving the organic compounds represented by General Formulae (G1) and (G2) as an example.

<Method for Synthesizing Organic Compound Represented by General Formula (G1)>

The organic compound represented by General Formula (G1) shown above can be synthesized by a synthesis method using a variety of reactions. For example, the organic compound can be synthesized by Synthesis Schemes (S-1) and (S-2) shown below. A compound 1, an arylamine (compound 2), and an arylamine (compound 3) are coupled, whereby a diamine compound (compound 4) is obtained.

Next, the diamine compound (compound 4), halogenated aryl (compound 5), and halogenated aryl (compound 6) are coupled, whereby the organic compound represented by General Formula (G1) can be obtained.

[Chemical Formula 41]

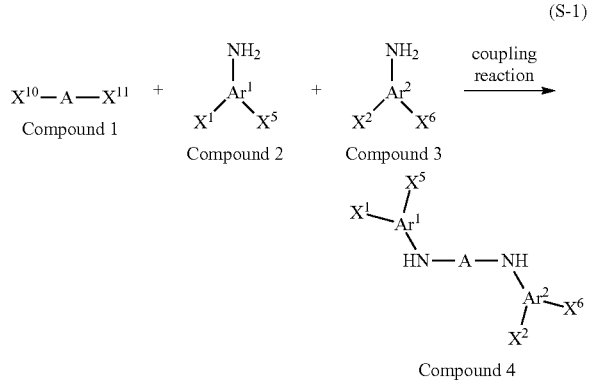

[Chemical Formula 42]

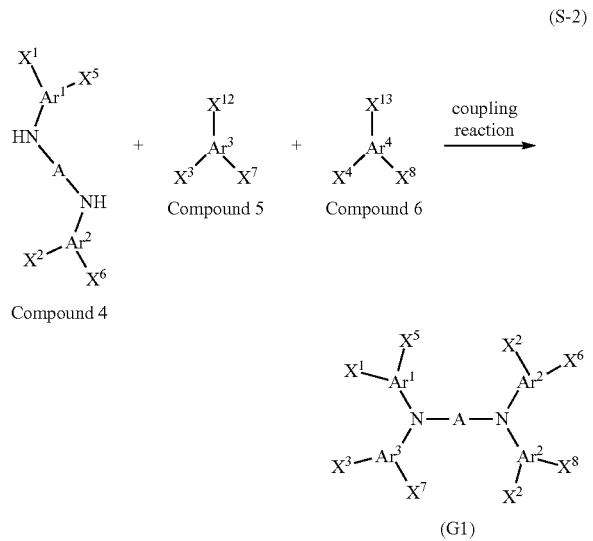

In Synthesis Schemes (S-1) and (S-2) shown above, A represents a substituted or unsubstituted condensed aromatic ring having 10 to 30 carbon atoms or a substituted or unsubstituted condensed heteroaromatic ring having 10 to 30 carbon atoms, $Ar^1$ to $Ar^4$ each independently represent a substituted or unsubstituted aromatic hydrocarbon group having 6 to 13 carbon atoms, $X^1$ to $X^8$ each independently represent any one of an alkyl group having 3 to 10 carbon atoms, a substituted or unsubstituted cycloalkyl group having 3 to 10 carbon atoms, and a trialkylsilyl group having 3 to 12 carbon atoms. Examples of the condensed aromatic ring or condensed heteroaromatic ring include chrysene, phenanthrene, stilbene, acridone, phenoxazine, and phenothiazine. In particular, anthracene, pyrene, coumarin, quinacridone, perylene, tetracene, and naphthobisbenzofuran are preferable.

In the case where a Buchwald-Hartwig reaction using a palladium catalyst is performed in Synthesis Schemes (S-1) and (S-2) shown above, $X^{10}$ to $X^{13}$ each represent a halogen group or a triflate group, and the halogen is preferably iodine, bromine, or chlorine. In the reaction, a palladium compound such as bis(dibenzylideneacetone)palladium(0) or palladium(II) acetate and a ligand such as tri(tert-butyl)phosphine, tri(n-hexyl)phosphine, tricyclohexylphosphine, di(1-adamantyl)-n-butylphosphine, or 2-dicyclohexylphosphino-2',6'-dimethoxy-1,1'-biphenyl can be used. In addition, an organic base such as sodium tert-butoxide, an inorganic base such as potassium carbonate, cesium carbonate, sodium carbonate, or the like can be used. Furthermore, toluene, xylene, mesitylene, benzene, tetrahydrofuran, dioxane, or the like can be used as a solvent. Reagents that can be used in the reaction are not limited thereto.

The reaction performed in Synthesis Schemes (S-1) and (S-2) shown above is not limited to the Buchwald-Hartwig reaction. A Migita-Kosugi-Stille coupling reaction using an organotin compound, a coupling reaction using a Grignard reagent, an Ullmann reaction using copper or a copper compound, or the like can be used.

In the case where the compound 2 and the compound 3 have different structures in Synthesis Scheme (S-1) shown above, it is preferred that the compound 1 and the compound 2 be reacted first to form a coupling product and then the obtained coupling product and the compound 3 be reacted. In the case where the compound 1 is reacted with the compound 2 and the compound 3 in different stages, it is preferred that the compound 1 be a dihalogen compound and $X^{10}$ and $X^{11}$ be different halogens and selectively subjected to amination reactions one by one.

Furthermore, in the case where the compound 5 and the compound 6 have different structures in Synthesis Scheme (S-2), it is preferred that the compound 4 and the compound 5 be reacted first to form a coupling product and then the obtained coupling product and the compound 6 be reacted.

<Method for Synthesizing Organic Compound Represented by General Formula (G2)>

The organic compound represented by General Formula (G2) can be synthesized by utilizing a variety of organic reactions. Two kinds of methods are shown below as examples.

The first method consists of Synthesis Schemes (S-3) to (S-8) below. In the first step, a condensation reaction of an aniline compound (compound 7) and a 1,4-cyclohexadiene-1,4-dicarboxylic acid compound (compound 8) gives an amine compound (compound 9). The step is shown in Scheme (S-3). Note that in the case where two aniline compounds (compounds 7) having the same substituent are condensed and an amino group having the same substituent is introduced in one step, the reaction is preferably performed with two equivalents of the aniline compound (compound 7). In that case, an object can be obtained even when a carbonyl group of the compound 8 does not have reaction selectivity.

Next, a condensation reaction of the amine compound (compound 9) and an aniline derivative (compound 10)

gives a 1,4-cyclohexadiene compound (compound 11). The step for obtaining the compound 11 is shown in Scheme (S-4).

Then, the 1,4-cyclohexadiene compound (compound 11) is oxidized in the air, whereby a terephthalic acid compound (compound 12) can be obtained. The step for obtaining the compound 12 is shown in Scheme (S-5).

Next, a ring of the terephthalic acid compound (compound 12) is fused using acid, whereby a quinacridone compound (compound 13) can be obtained. The step for obtaining the compound 13 is shown in Scheme (S-6).

Then, the quinacridone compound (compound 13) and a halogenated aryl (compound 14) are coupled, whereby a quinacridone compound (compound 15) can be obtained. The step for obtaining the compound 15 is shown in Scheme (S-7). Note that in the case where two halogenated aryls (compounds 8) having the same substituent can be coupled and an amino group having the same substituent is introduced in one step, the reaction is preferably performed with two equivalents of the halogenated aryl (compound 14). In that case, an object can be obtained even when an amino group of the compound 14 does not have reaction selectivity.

Then, the quinacridone compound (compound 15) and a halogenated aryl (compound 16) are coupled, whereby the organic compound represented by General Formula (G2) shown above can be obtained. The step is shown in Scheme (S-8).

[Chemical Formula 43]

(S-3)

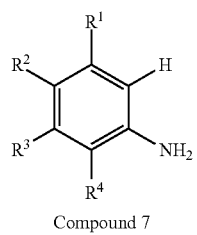

Compound 7

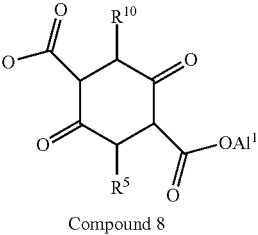

Compound 8

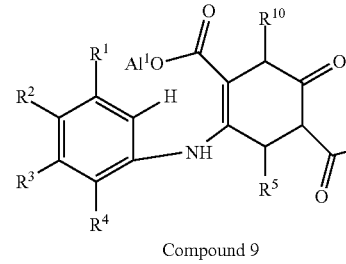

Compound 9

(S-4)

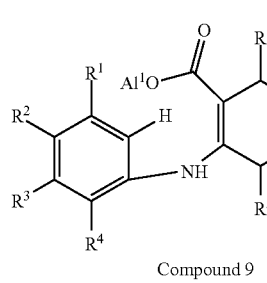

Compound 9

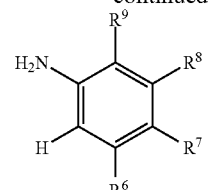

Compound 10

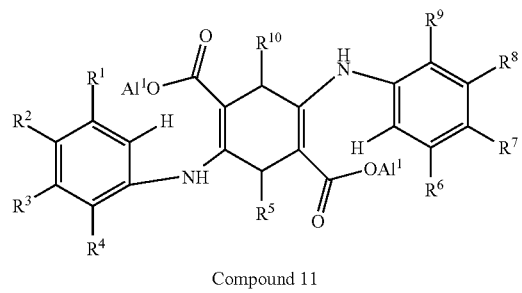

Compound 11

(S-5)

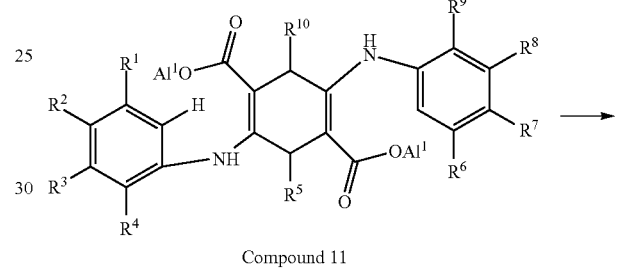

Compound 11

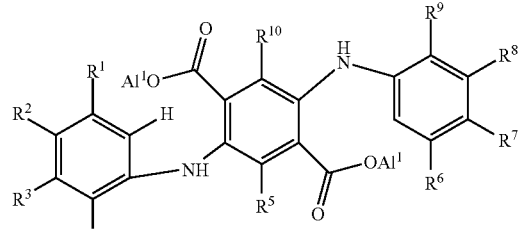

Compound 12

[Chemical Formula 44]

(S-6)

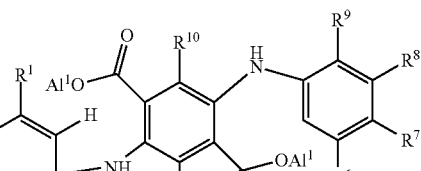

Compound 12

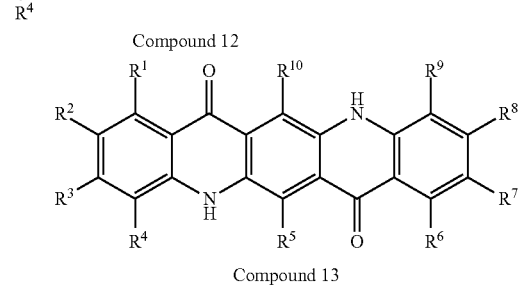

Compound 13

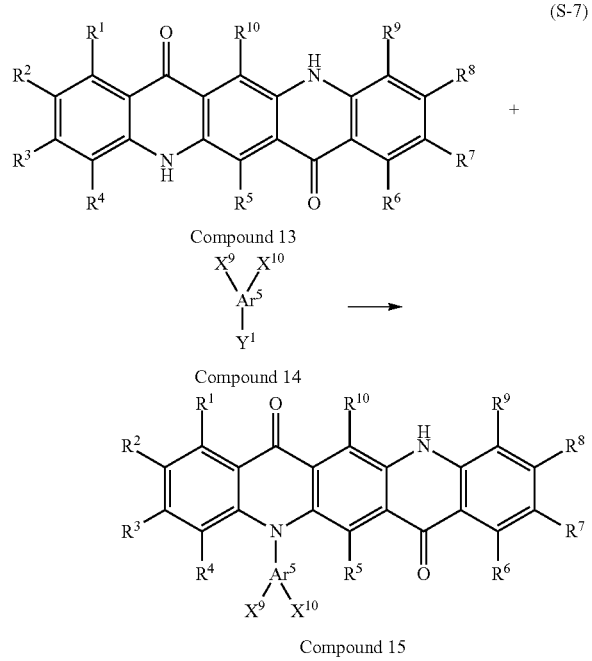

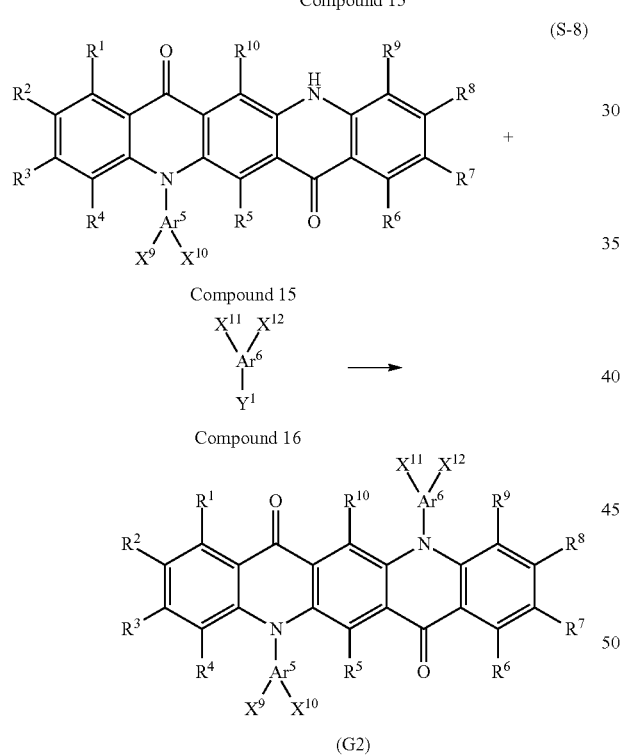

equivalents of the halogenated aryl (compound 14). In that case, an object can be obtained even when an amino group of the compound 12 does not have reaction selectivity.

Next, the diamine compound (compound 17) and the halogenated aryl (compound 16) are coupled, whereby a diamine compound (compound 18) can be obtained. The step for obtaining the compound 18 is shown in Scheme (S-10).

Finally, a ring of the diamine compound (compound 18) is fused using acid, whereby the organic compound represented by General Formula (G2) shown above can be obtained. The step is shown in Scheme (S-11). Note that in the annelation reaction, hydrogen at the ortho position of $Ar^5$ or $Ar^6$ may be reacted and an isomer of the organic compound represented by General Formula (G2) shown above may be generated.

The diamine compound (compound 18) having a symmetrical structure is used in Scheme (S-11), whereby the organic compound represented by General Formula (G2) shown above can be synthesized.

[Chemical Formula 45]

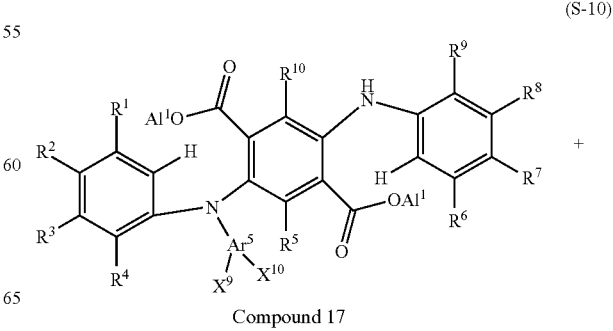

The second method consists of Synthesis Schemes (S-3) to (S-5) and Synthesis Schemes (S-9), (S-10), and (S-11) below. The description of (S-3) to (S-5) is as described above. The terephthalic acid compound (compound 12) and the halogenated aryl (compound 14) are coupled, whereby a diamine compound (compound 17) can be obtained. The step for obtaining the compound 17 is shown in Scheme (S-9). Note that in the case where two halogenated aryl molecules having the same substituent can be coupled and an amino group having the same substituent is introduced in one step, the reaction is preferably performed with two

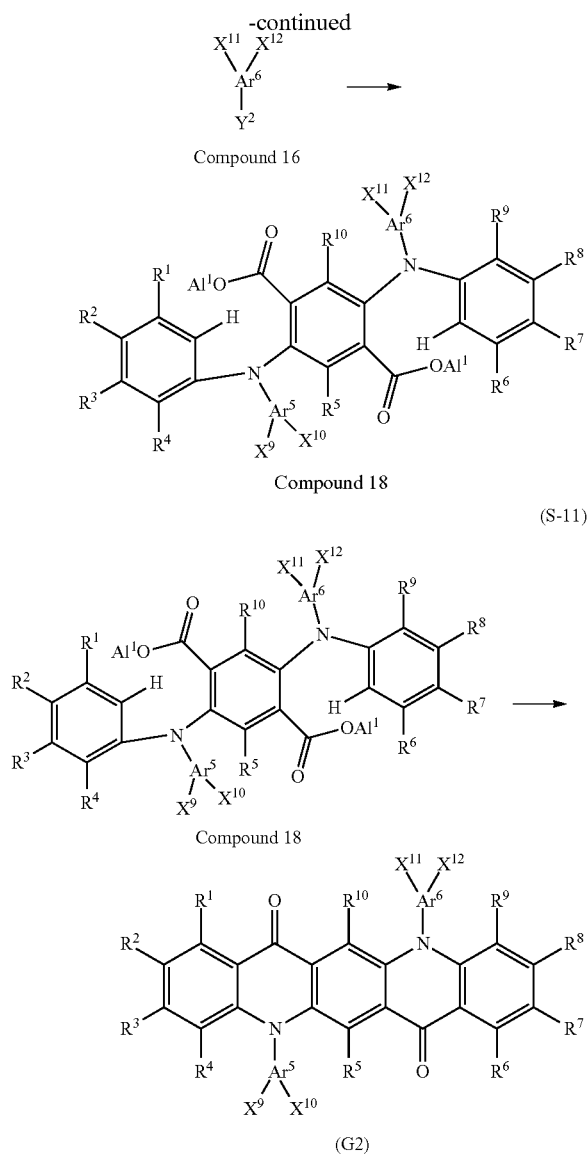

In Synthesis Schemes (S-3) to (S-6) and (S-9) to (S-11), $Al^1$ represents an alkyl group such as a methyl group.

In Synthesis Schemes (S-7) to (S-10), $Y^1$ and $Y^2$ each represent chlorine, bromine, iodine, or a triflate group.

In Synthesis Schemes (S-7) to (S-10), the Ullmann reaction is preferably performed because the reaction can proceed at high temperatures and an objective compound can be obtained in a relatively high yield. In the reaction, copper or a copper compound can be used as a reagent, and an inorganic base such as potassium carbonate or sodium hydride can be used as a base. Examples of the solvent that can be used in the reaction include 2,2,6,6-tetramethyl-3,5-heptanedione, 1,3-dimethyl-3,4,5,6-tetrahydro-2(1R)pyrimidinone (DMPU), toluene, xylene, and benzene. In the Ullmann reaction, the objective substance can be obtained in a shorter time and in a higher yield when the reaction temperature is 100° C. or higher; therefore, it is preferable to use 2,2,6,6-tetramethyl-3,5-heptanedione, DMPU, or xylene, which has high boiling temperatures. A reaction temperature of 150° C. or higher is further preferred, and accordingly, DMPU is further preferably used. Reagents that can be used in the reaction are not limited to the above-described reagents.

In Synthesis Schemes (S-7) to (S-10), the Buchwald-Hartwig reaction using a palladium catalyst can be performed. In the reaction, a palladium compound such as bis(dibenzylideneacetone)palladium(0), palladium(II) acetate, [1,1-bis(diphenylphosphino)ferrocene]palladium (II) dichloride, tetrakis(triphenylphosphine)palladium(0), or allylpalladium(II) chloride (dimer) and a ligand such as tri(tert-butyl)phosphine, tri(n-hexyl)phosphine, tricyclohexylphosphine, di(1-adamantyl)-n-butylphosphine, 2-dicyclohexylphosphino-2',6'-dimethoxybiphenyl, tri(ortho-tolyl)phosphine, or (S)-(6,6'-dimethoxybiphenyl-2,2'-diyl)bis (diisopropylphosphine) (abbreviation: cBRIDP (registered trademark)) can be used, for example. In the reaction, an organic base such as sodium tert-butoxide, an inorganic base such as potassium carbonate, cesium carbonate, or sodium carbonate, or the like can be used. In the reaction, toluene, xylene, benzene, tetrahydrofuran, dioxane, or the like can be used as a solvent. Reagents that can be used in the reaction are not limited to the above-described reagents.

The method for synthesizing the organic compound represented by General Formula (G2) of the present invention is not limited to Synthesis Schemes (S-1) to (S-11).

Specific examples of $R^1$ to $R^{10}$ substituted at the quinacridone skeleton include an n-propyl group, an isopropyl group, an n-butyl group, an isobutyl group, a tert-butyl group, a cyclopropyl group, a cyclobutyl group, a cyclopentyl group, a cyclohexyl group, a trimethylsilyl group, a triethylsilyl group, and a tributylsilyl group.

Specific examples of $Ar^5$ at which $X^9$ and $X^{10}$ are substituted and $Ar^6$ at which $X^{11}$ and $X^{12}$ are substituted include a 2-isopropylphenyl group, a 2-butylphenyl group, a 2-isobutylphenyl group, a 2-tert-butylphenyl group, a 2-isopropylphenyl group, a 2-butylphenyl group, a 3-propylphenyl group, a 3-isobutylphenyl group, a 3-tert-butylphenyl group, a 4-propylphenyl group, a 4-isopropylphenyl group, a 4-butylphenyl group, a 4-isobutylphenyl group, a 4-tert-butylphenyl group, a 3,5-dipropylphenyl group, a 3,5-diisopropylphenyl group, a 3,5-dibutylphenyl group, a 3,5-diisobutylphenyl group, a (3,5-di-tert-butyl)phenyl group, a 1,3-dipropylphenyl group, a 1,3-di-isopropylphenyl group, a 1,3-dibutylphenyl group, a 1,3-di-isobutylphenyl group, a (1,3-di-tert-butyl)phenyl group, a 1,3,5-triisopropylphenyl group, a (1,3,5-tri-tert-butyl)phenyl group, and a 4-cyclohexylphenyl group.

The above is the description of the methods for synthesizing the organic compounds which are embodiments of the present invention and are represented by General Formula (G1) and General Formula (G2); however, the present invention is not limited thereto and the synthesis may be performed by another synthesis method.

Embodiment 3

In this embodiment, a light-emitting element having a structure different from the structure of the light-emitting element described in Embodiment 1 will be described below with reference to FIG. 7. Note that in FIG. 7, a portion having a function similar to that of a portion denoted by a reference numeral shown in FIG. 1(A) is represented by the same hatch pattern and the reference numeral is omitted in some cases. In addition, common reference numerals are used for portions having similar functions, and a detailed description thereof is omitted in some cases.

Structure Example 2 of Light-Emitting Element

Figure 7:
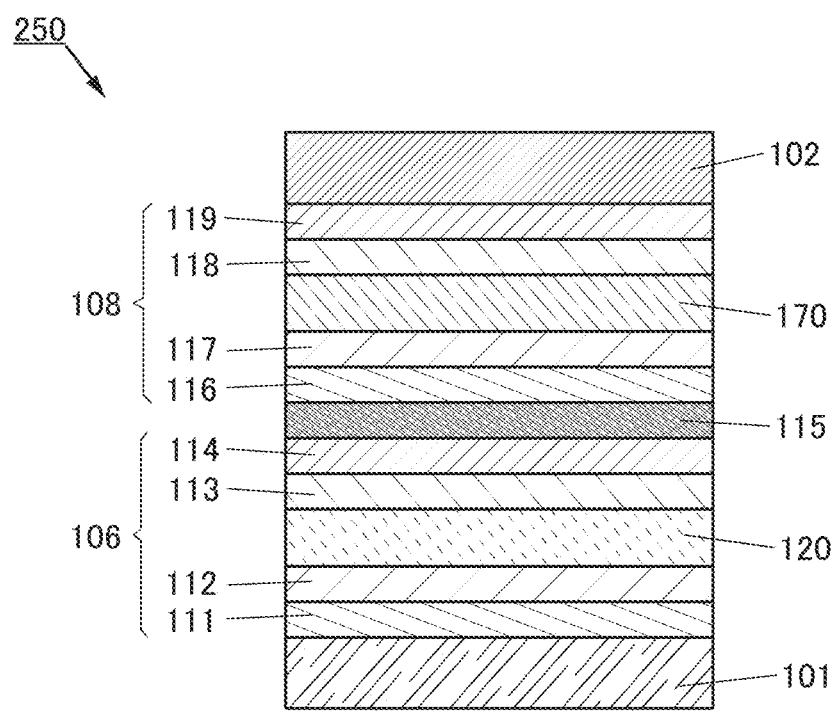
FIG. 7 A schematic cross-sectional view of a light-emitting element of one embodiment of the present invention.

FIG. 7 is a schematic cross-sectional view of a light-emitting element 250.

The light-emitting element 250 illustrated in FIG. 7 includes a plurality of light-emitting units (a light-emitting unit 106 and a light-emitting unit 108) between a pair of electrodes (the electrode 101 and the electrode 102). Any one of the plurality of light-emitting units preferably has a structure similar to that of the EL layer 100 illustrated in FIG. 1(A). That is, the light-emitting element 150 illustrated in FIG. 1(A) includes one light-emitting unit, while the light-emitting element 250 includes a plurality of light-emitting units. Note that the electrode 101 functions as an anode and the electrode 102 functions as a cathode in the light-emitting element 250 in the following description; however, the functions of the electrodes may be reversed as the structure of the light-emitting element 250.

Moreover, in the light-emitting element 250 illustrated in FIG. 7, the light-emitting unit 106 and the light-emitting unit 108 are stacked, and a charge-generation layer 115 is provided between the light-emitting unit 106 and the light-emitting unit 108. Note that the light-emitting unit 106 and the light-emitting unit 108 may have the same structure or different structures. For example, it is preferable to use a structure similar to that of the EL layer 100 for the light-emitting unit 108.

The light-emitting element 250 includes a light-emitting layer 120 and a light-emitting layer 170. The light-emitting unit 106 includes the hole-injection layer 111, the hole-transport layer 112, an electron-transport layer 113, and an electron-injection layer 114 in addition to the light-emitting layer 120. The light-emitting unit 108 includes a hole-injection layer 116, a hole-transport layer 117, the electron-transport layer 118, and the electron-injection layer 119 in addition to the light-emitting layer 170.

In the light-emitting element 250, any layer of each of the light-emitting unit 106 and the light-emitting unit 108 contains the compound of one embodiment of the present invention. Note that the layer containing the compound is preferably the light-emitting layer 120 or the light-emitting layer 170.

The charge-generation layer 115 may have either a structure in which a substance having an acceptor property, which is an electron acceptor, is added to a hole-transport material or a structure in which a substance having a donor property, which is an electron donor, is added to an electron-transport material. Alternatively, both of these structures may be stacked.

In the case where the charge-generation layer 115 contains a composite material of an organic compound and a substance having an acceptor property, the composite material that can be used for the hole-injection layer 111 described in Embodiment 1 is used as the composite material. As the organic compound, a variety of compounds such as an aromatic amine compound, a carbazole compound, an aromatic hydrocarbon, and a high molecular compound (an oligomer, a dendrimer, a polymer, or the like) can be used. Note that a substance having a hole mobility of $1 \times 10^{-6}$ cm$^2$/Vs or higher is preferably used as the organic compound. However, other substances may also be used as long as they have a property of transporting more holes than electrons. Since the composite material of an organic compound and a substance having an acceptor property has excellent carrier-injection and carrier-transport properties, low-voltage driving or low-current driving can be achieved. Note that in the case where a surface of a light-emitting unit on the anode side is in contact with the charge-generation layer 115, the charge-generation layer 115 can also serve as a hole-injection layer or a hole-transport layer of the light-emitting unit; thus, a structure in which a hole-injection layer or a hole-transport layer is not provided in the light-emitting unit may be employed. Alternatively, in the case where a surface of a light-emitting unit on the cathode side is in contact with the charge-generation layer 115, the charge-generation layer 115 can also serve as an electron-injection layer or an electron-transport layer of the light-emitting unit; thus, a structure in which an electron-injection layer or an electron-transport layer is not provided in the light-emitting unit may be employed.

Note that the charge-generation layer 115 may have a stacked-layer structure combining a layer containing the composite material of an organic compound and a substance having an acceptor property and a layer formed of another material. For example, a layer containing the composite material of an organic compound and a substance having an acceptor property and a layer containing one compound selected from electron-donating substances and a compound having a high electron-transport property may be combined. Moreover, a layer containing the composite material of an organic compound and a substance having an acceptor property and a layer containing a transparent conductive film may be combined.

Note that the charge-generation layer 115 sandwiched between the light-emitting unit 106 and the light-emitting unit 108 injects electrons into one of the light-emitting units and injects holes into the other of the light-emitting units when voltage is applied to the electrode 101 and the electrode 102. For example, in FIG. 7, the charge-generation layer 115 injects electrons into the light-emitting unit 106 and injects holes into the light-emitting unit 108 when voltage is applied such that the potential of the electrode 101 is higher than the potential of the electrode 102.

Note that in terms of outcoupling efficiency, the charge-generation layer 115 preferably has a property of transmitting visible light (specifically, the transmittance of visible light through the charge-generation layer 115 is higher than or equal to 40%). Moreover, the charge-generation layer 115 functions even when it has lower conductivity than the pair of electrodes (the electrode 101 and the electrode 102).

Forming the charge-generation layer 115 using the above-described materials can inhibit an increase in driving voltage in the case where the light-emitting layers are stacked.

The light-emitting element having two light-emitting units has been described with reference to FIG. 7; however, a light-emitting element in which three or more light-emitting units are stacked can be similarly employed. When a plurality of light-emitting units partitioned by the charge-generation layer are arranged between a pair of electrodes as in the light-emitting element 250, it is possible to achieve a light-emitting element that can emit high-luminance light with the current density kept low and has a long lifetime. Moreover, a light-emitting element having low power consumption can be achieved.

Note that in each of the above-described structures, the emission colors of the guest materials used for the light-emitting unit 106 and the light-emitting unit 108 may be the same or different from each other. In the case where guest materials having a function of emitting light of the same color are used for the light-emitting unit 106 and the light-emitting unit 108, the light-emitting element 250 can exhibit high emission luminance at a small current value, which is preferable. In the case where guest materials having a function of emitting light of different colors are used for the light-emitting unit 106 and the light-emitting unit 108, the light-emitting element 250 can exhibit multi-color light emission, which is preferable. In this case, with the use of a plurality of light-emitting materials with different emission wavelengths in one or both of the light-emitting layer 120 and the light-emitting layer 170, the light-emitting element 250 emits light obtained by synthesizing light emission having different emission peaks; thus, its emission spectrum has at least two maximum values.

The above structure is also suitable for obtaining white light emission. When the light-emitting layer 120 and the light-emitting layer 170 emit light of complementary colors, white light emission can be obtained. It is particularly favorable to select the guest materials so that white light emission with high color rendering properties or light emission of at least red, green, and blue can be obtained.

One or both of the light-emitting layer 120 and the light-emitting layer 170 preferably have the structure of the light-emitting layer 130 described in Embodiment 1. With such a structure, a light-emitting element with favorable emission efficiency and favorable reliability can be obtained. The guest material contained in the light-emitting layer 130 is a fluorescent material. Thus, when one or both of the light-emitting layer 120 and the light-emitting layer 170 have the structure of the light-emitting layer 130 described in Embodiment 1, a light-emitting element with high efficiency and high reliability can be obtained.

In the case of a light-emitting element in which three or more light-emitting units are stacked, the emission colors of guest materials used in the light-emitting units may be the same or different from each other. In the case where a plurality of light-emitting units that exhibit the same emission color are included, the emission color of the plurality of light-emitting units can have higher emission luminance at a smaller current value than another color. Such a structure can be suitably used for adjustment of emission colors. The structure is particularly suitable when guest materials that exhibit different emission colors with different luminous efficiencies are used. For example, when three layers of light-emitting units are included, the intensity of fluorescence and phosphorescence can be adjusted with two layers of light-emitting units that contain a fluorescent material for the same color and one layer of a light-emitting unit that contains a phosphorescent material that exhibits a different emission color from that of the fluorescent material. That is, the intensity of emitted light of each color can be adjusted with the number of light-emitting units.

In the case of the light-emitting element including two layers of fluorescent units and one layer of a phosphorescent unit, it is preferable to use a light-emitting element including the two layers of the light-emitting units including a blue fluorescent material and the one layer of the light-emitting unit including a yellow phosphorescent material; a light-emitting element including the two layers of the light-emitting units including a blue fluorescent material and the one layer of the light-emitting unit including a red phosphorescent material and a green phosphorescent material; or a light-emitting element including the two layers of the light-emitting units including a blue fluorescent material and the one layer of the light-emitting unit including a red phosphorescent material, a yellow phosphorescent material, and a green phosphorescent material, in which case white light emission can be obtained efficiently. Thus, the light-emitting element of one embodiment of the present invention can be combined with a phosphorescent unit, as appropriate.

The above phosphorescent units exhibit an emission color other than blue. The structure of the light-emitting layer 130 described in Embodiment 1 can be used for the light-emitting units of a color other than blue. In this case, the light-emitting units of a color other than blue contains a fluorescent material. For example, it is possible to use a light-emitting element including two layers of the light-emitting units including a blue fluorescent material and one layer of the light-emitting unit including a yellow fluorescent material; a light-emitting element including two layers of the light-emitting units including a blue fluorescent material and one layer of the light-emitting unit including a red fluorescent material and a green fluorescent material; or a light-emitting element including two layers of the light-emitting units including a blue fluorescent material and one layer of the light-emitting unit including a red fluorescent material, a yellow fluorescent material, and a green fluorescent material. In that case, when a light-emitting unit that emits light of a color other than blue and the above-described light-emitting unit are combined as the light-emitting unit of the light-emitting element, a structure in which the structure of the light-emitting layer 130 described in Embodiment 1 is used for light-emitting units of red, green, and yellow can be employed. This structure is preferable because white light emission can be efficiently obtained. In that case, the following materials can be used for the light-emitting layer of the blue fluorescent unit. The relation between the T1 level of the host material and the T1 level of the guest material of the light-emitting layer of the blue fluorescent unit is, preferably, the T1 level of the host material <the T1 level of the guest material, in which case high efficiency owing to triplet-triplet annihilation (TTA) can be expected. Needless to say, the structure of the light-emitting layer 130 described in Embodiment 1 may be used for the blue fluorescent unit.

At least one of the light-emitting layer 120 and the light-emitting layer 170 may further be divided into layers and the divided layers may contain different light-emitting materials. That is, at least one of the light-emitting layer 120 and the light-emitting layer 170 can consist of two or more layers. For example, in the case where the light-emitting layer is formed by stacking a first light-emitting layer and a second light-emitting layer in this order from the hole-transport layer side, the first light-emitting layer is formed using a material having a hole-transport property as the host material and the second light-emitting layer is formed using a material having an electron-transport property as the host material. In this case, the light-emitting materials contained in the first light-emitting layer and the second light-emitting layer may be the same or different, and may have functions of exhibiting light emission of the same color or exhibiting light emission of different colors. White light emission with high color rendering properties that is formed of three primary colors or four or more emission colors can also be obtained by using a plurality of light-emitting materials having functions of exhibiting light emission of different colors.

Note that the hole-transport material, electron-transport material, and phosphorescent material described in Embodiment 1 can be used in appropriate combination for the phosphorescent unit described in Embodiment 3.

There is no particular limitation on the host material and guest material used for the light-emitting layer of the blue fluorescent unit, and the following materials can be given as examples.

As the guest material, a pyrene derivative, a perylene derivative, or the like can be used, and for example, the following materials can be used.

Specifically, N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9-phenyl-9H-fluoren-9-yl)phenyl]-N,N'-bis(4-tert-butylphenyl)pyrene-1,6-diamine (abbreviation: 1,6tBu-FLPAPrn), N,N'-bis[4-(9-phenyl-9H-fluoren-9-yl)phenyl]-N,N'-diphenyl-3,8-dicyclohexylpyrene-1,6-diamine (abbreviation: ch-1,6FLPAPrn), 5,10,15,20-tetraphenylbisbenzo[5,6]indeno[1,2,3-cd:1',2',3'-lm]perylene, and the like are given.

Examples of the host material include condensed polycyclic aromatic compounds such as anthracene derivatives, phenanthrene derivatives, pyrene derivatives, chrysene derivatives, and dibenzo[g,p]chrysene derivatives, and specific examples include metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: BPhen), bathocuproine (abbreviation: BCP), and 9-[4-(5-phenyl-1,3,4-oxadiazol-2-yl)phenyl]-9H-carbazole (abbreviation: CO11); and aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4,4'-bis[N-(spiro-9,9'-bifluoren-2-yl)-N-phenylamino]biphenyl (abbreviation: BSPB). Other examples include condensed polycyclic aromatic compounds such as anthracene derivatives, phenanthrene derivatives, pyrene derivatives, chrysene derivatives, and dibenzo[g,p]chrysene derivatives, and specific examples include 9,10-diphenylanthracene (abbreviation: DPAnth), N,N'-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 7-[4-(10-phenyl-9-anthryl)phenyl]-7H-dibenzo[c,g]carbazole (abbreviation: cgDBCzPA), 6,12-dimethoxy-5,11-diphenylchrysene, N,N,N',N',N'',N'',N''',N'''-octaphenyldibenzo[g,p]chrysene-2,7,10,15-tetraamine (abbreviation: DBC1), 9-phenyl-3-[4-(10-phenyl-9-anthryl)phenyl]-9H-carbazole (abbreviation: PCzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyOdiphenanthrene (abbreviation: DPNS), 9,9'-(stilbene-4,4'-diyl)diphenanthrene (abbreviation: DPNS2), and 1,3,5-tri(1-pyrenyl)benzene (abbreviation: TPB3). One or more substances having a wider energy gap than the guest material are selected from these and known substances.

Note that this embodiment can be combined as appropriate with any of the other embodiments.

Embodiment 4

In this embodiment, a light-emitting apparatus including the light-emitting element described in Embodiment 1 and Embodiment 3 will be described with reference to FIG. 8(A) and FIG. 8(B).

Figure 8A:
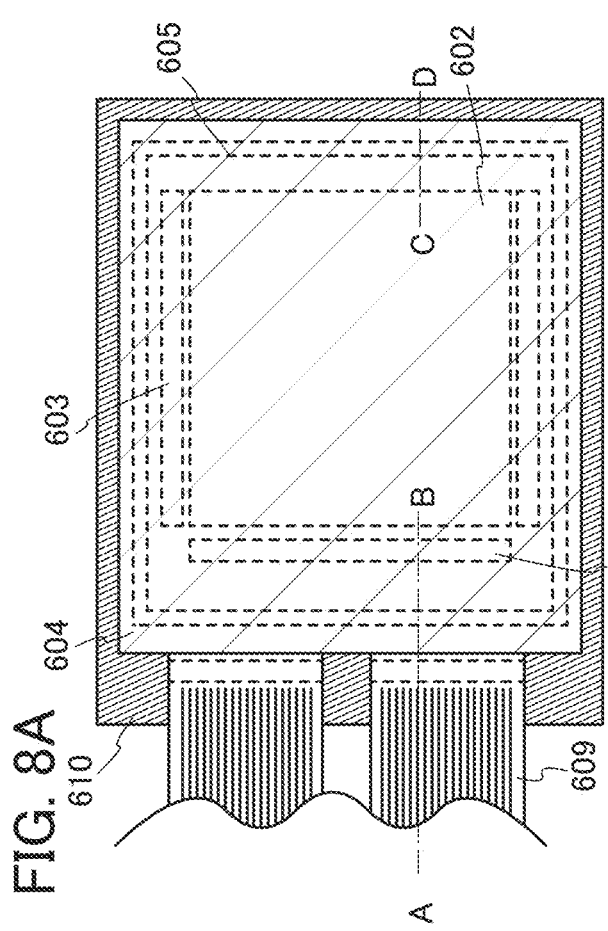
FIGS. 8A and 8B A top view and a schematic cross-sectional view illustrating a display device of one embodiment of the present invention.
Figure 8B:
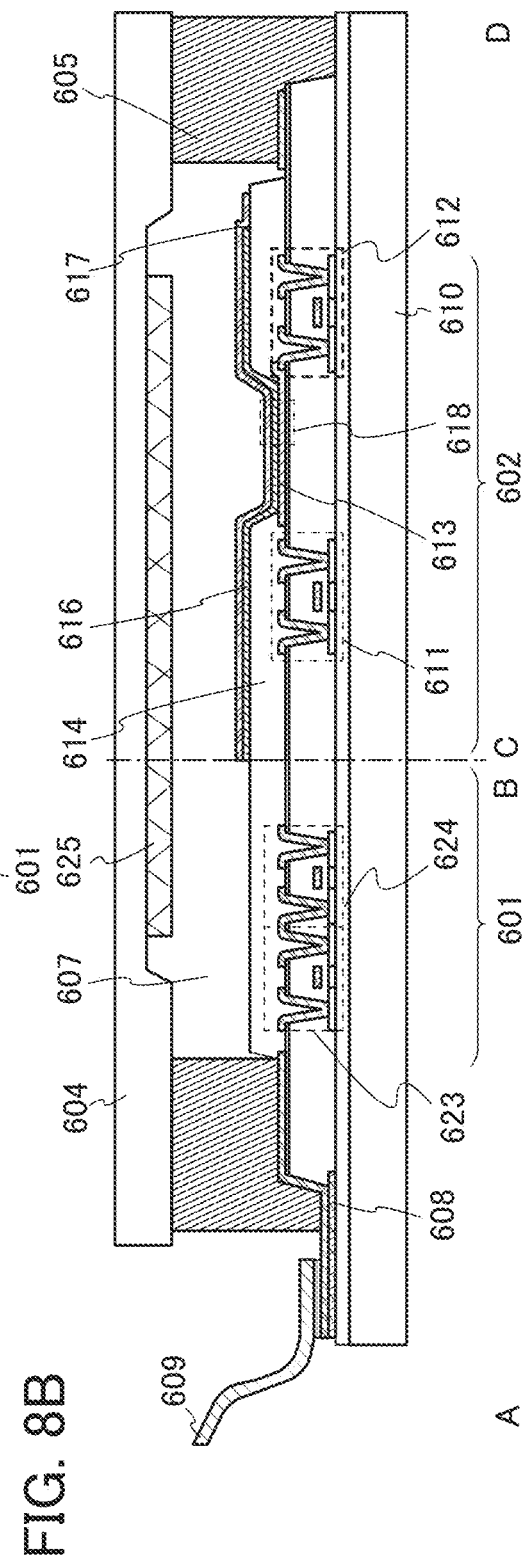

FIG. 8(A) is a top view of a light-emitting apparatus, and FIG. 8(B) is a cross-sectional view taken along A-B and C-D in FIG. 8(A). This light-emitting apparatus includes a driver circuit portion (a source side driver circuit) 601, a pixel portion 602, and a driver circuit portion (a gate side driver circuit) 603, which are indicated by dotted lines, as components controlling light emission from a light-emitting element. Furthermore, 604 denotes a sealing substrate, 625 denotes a desiccant, 605 denotes a sealant, and a portion surrounded by the sealant 605 is a space 607.

Note that a lead wiring 608 is a wiring for transmitting signals to be input to the source side driver circuit 601 and the gate side driver circuit 603 and receives a video signal, a clock signal, a start signal, a reset signal, and the like from an FPC (flexible printed circuit) 609 serving as an external input terminal. Although only the FPC is illustrated here, a printed wiring board (PWB) may be attached to the FPC. The light-emitting apparatus in this specification includes not only the light-emitting apparatus itself but also the state where the FPC or the PWB is attached thereto.

Next, a cross-sectional structure of the above light-emitting apparatus is described with reference to FIG. 8(B). The driver circuit portion and the pixel portion are formed over an element substrate 610; here, the source side driver circuit 601, which is the driver circuit portion, and one pixel in the pixel portion 602 are illustrated.

Note that in the source side driver circuit 601, a CMOS circuit in which an n-channel TFT 623 and a p-channel TFT 624 are combined is formed. The driver circuit may be formed of various CMOS circuits, PMOS circuits, or NMOS circuits. Although a driver-integrated type where the driver circuit is formed over the substrate is described in this embodiment, the driver circuit is not necessarily integrated and can be formed not over the substrate but outside the substrate.

The pixel portion 602 is formed of pixels including a switching TFT 611, a current controlling TFT 612, and a first electrode 613 electrically connected to a drain thereof. Note that an insulator 614 is formed to cover an end portion of the first electrode 613. The insulator 614 can be formed using a positive photosensitive resin film.

In order to improve the coverage with a film formed over the insulator 614, the insulator 614 is formed to have a surface with curvature at its upper end portion or lower end portion. For example, in the case where a photosensitive acrylic is used as a material of the insulator 614, only the upper end portion of the insulator 614 preferably has a curved surface. The radius of curvature of the curved surface is preferably greater than or equal to 0.2 μm and less than or equal to 0.3 μm. Either a negative photosensitive material or a positive photosensitive material can be used as the insulator 614.

An EL layer 616 and a second electrode 617 are formed over the first electrode 613. Here, as a material used for the first electrode 613 functioning as an anode, a material with a high work function is desirably used. For example, a single-layer film of an ITO film, an indium tin oxide film containing silicon, an indium oxide film containing zinc oxide at 2 wt % or higher and 20 wt % or lower, a titanium nitride film, a chromium film, a tungsten film, a Zn film, a Pt film, or the like, a stacked layer of titanium nitride and a film containing aluminum as its main component, a three-layer structure of a titanium nitride film, a film containing aluminum as its main component, and a titanium nitride film, or the like can be used. Note that the stacked-layer structure achieves low wiring resistance, a favorable ohmic contact, and a function as an anode.

The EL layer 616 is formed by any of a variety of methods such as an evaporation method using an evaporation mask, an inkjet method, and a spin coating method. A material included in the EL layer 616 may be a low molecular compound or a high molecular compound (including an oligomer or a dendrimer).

As a material used for the second electrode 617, which is formed over the EL layer 616 and functions as a cathode, a material with a low work function (e.g., Al, Mg, Li, Ca, or an alloy or a compound thereof, MgAg, MgIn, or AlLi) is preferably used. Note that in the case where light generated in the EL layer 616 passes through the second electrode 617, a stacked layer of a thin metal film with a reduced thickness and a transparent conductive film (e.g., ITO, indium oxide containing zinc oxide at 2 wt % or higher and 20 wt % or lower, indium tin oxide containing silicon, or zinc oxide (ZnO)) is preferably used for the second electrode 617.

Note that the first electrode 613, the EL layer 616, and the second electrode 617 constitute a light-emitting element 618. The light-emitting element 618 is preferably the light-emitting element having the structure described in Embodiment 1 and Embodiment 2. In the light-emitting apparatus of this embodiment, the pixel portion, which includes a plurality of light-emitting elements, may include both the light-emitting element with the structure described in Embodiment 1 and Embodiment 2 and a light-emitting element with another structure.

The sealing substrate 604 and the element substrate 610 are attached to each other using the sealant 605, so that a structure in which a light-emitting element 618 is provided in the space 607 surrounded by the element substrate 610, the sealing substrate 604, and the sealant 605 is employed. Note that the space 607 is filled with a filler, and may be filled with an inert gas (nitrogen, argon, or the like) or a resin and/or a desiccant.

Note that an epoxy-based resin or glass frit is preferably used for the sealant 605. Furthermore, these materials are preferably materials that transmit moisture or oxygen as little as possible. As a material used for the sealing substrate 604, in addition to a glass substrate and a quartz substrate, a plastic substrate formed of FRP (Fiber Reinforced Plastics), PVF (polyvinyl fluoride), polyester, acrylic, or the like can be used.

As described above, the light-emitting apparatus using the light-emitting element described in Embodiment 1 and Embodiment 3 can be obtained.

Structure Example 1 of Light-Emitting Apparatus

As an example of a display device, FIG. 9 shows a light-emitting apparatus in which a light-emitting element exhibiting white light emission is formed and a coloring layer (a color filter) is formed.

FIG. 9(A) illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition wall 1026, an EL layer 1028, a second electrode 1029 of the light-emitting elements, a sealing substrate 1031, a sealant 1032, a red pixel 1044R, a green pixel 1044G, a blue pixel 1044B, a white pixel 1044W, and the like.

In FIG. 9(A) and FIG. 9(B), coloring layers (a red coloring layer 1034R, a green coloring layer 1034G, and a blue coloring layer 1034B) are provided on a transparent base material 1033. A black layer (black matrix) 1035 may be additionally provided. The transparent base material 1033 provided with the coloring layers and the black layer is positioned and fixed to the substrate 1001. Note that the coloring layers and the black layer are covered with an overcoat layer 1036. In FIG. 9(A), there is a light-emitting layer from which light is extracted to the outside without passing through the coloring layers and a light-emitting layer from which light is extracted to the outside after passing through the coloring layers of each color. The light that does not pass through the coloring layers is white, and the light that passes through the coloring layers is red, green, and blue, so that an image can be expressed with the pixels of four colors.

FIG. 9(B) shows an example in which the red coloring layer 1034R, the green coloring layer 1034G, and the blue coloring layer 1034B are formed between the gate insulating film 1003 and the first interlayer insulating film 1020. As shown in FIG. 9(B), the coloring layers may be provided between the substrate 1001 and the sealing substrate 1031.

The above-described light-emitting apparatus is a light-emitting apparatus having a structure in which light is extracted from the substrate 1001 side where the TFTs are formed (a bottom emission type), but may be a light-emitting apparatus having a structure in which light is extracted from the sealing substrate 1031 side (a top emission type).

Structure Example 2 of Light-Emitting Apparatus

FIG. 10(A) and FIG. 10(B) each show a cross-sectional view of a top-emission light-emitting apparatus. In this case, a substrate that does not transmit light can be used as the substrate 1001. The process up to the formation of a connection electrode that connects the TFT and the anode of the light-emitting element is performed in a manner similar to that of a bottom-emission-type light-emitting apparatus. Then, a third interlayer insulating film 1037 is formed to cover an electrode 1022. This insulating film may have a planarization function. The third interlayer insulating film 1037 can be formed using a material similar to that of the second interlayer insulating film 1021 or using other various materials.

A lower electrode 1025W, a lower electrode 1025R, a lower electrode 1025G, and a lower electrode 1025B of the light-emitting element are anodes here, but may be cathodes. Furthermore, in the case of the top-emission light-emitting apparatus as illustrated in FIG. 10(A) and FIG. 10(B), the lower electrode 1025W, the lower electrode 1025R, the lower electrode 1025G, and the lower electrode 1025B are preferably reflective electrodes. Note that the second electrode 1029 preferably has a function of reflecting light and a function of transmitting light. It is preferable that a microcavity structure be used between the second electrode 1029, and the lower electrode 1025W, the lower electrode 1025R, the lower electrode 1025G, and the lower electrode 1025B, in which case a function of amplifying light with a specific wavelength is included. The structure of the EL layer 1028 is an element structure similar to the structures described in Embodiment 1 and Embodiment 3, with which white light emission can be obtained.

In FIG. 9(A), FIG. 9(B), FIG. 10(A), and FIG. 10(B), the structure of the EL layer for providing white light emission can be achieved by, for example, using a plurality of light-emitting layers or using a plurality of light-emitting units. Note that the structure for providing white light emission is not limited thereto.

In a top emission structure as shown in FIG. 10(A) and FIG. 10(B), sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer (black matrix) 1030 which is positioned between pixels. The coloring layers (the red coloring layer 1034R, the green coloring layer 1034G, and the blue coloring layer 1034B) and the black layer (black matrix) may be covered with the overcoat layer. Note that a substrate having a light-transmitting property is used as the sealing substrate 1031.

FIG. 10(A) illustrates a structure in which full color display is performed using three colors of red, green, and blue; alternatively, full color display may be performed using four colors of red, green, blue, and white as illustrated in FIG. 10(B). Note that the structure for performing full color display is not limited to them. For example, full color display using four colors of red, green, blue, and yellow may be performed.

In the light-emitting element of one embodiment of the present invention, a fluorescent material is used as a guest material. Since a fluorescent material has a sharper spectrum than a phosphorescent material, light emission with high color purity can be obtained. Accordingly, when the light-emitting element is used for the light-emitting apparatus described in this embodiment, a light-emitting apparatus with high color reproducibility can be obtained.

As described above, the light-emitting apparatus using the light-emitting element described in Embodiment 1 and Embodiment 3 can be obtained.

Note that this embodiment can be combined as appropriate with any of the other embodiments.

Embodiment 5

In this embodiment, electronic devices and display devices of embodiments of the present invention will be described.

In addition, an electronic device and a display device that have a flat surface, high emission efficiency, and high reliability can be manufactured according to one embodiment of the present invention. In addition, an electronic device and a display device that have a curved surface, high emission efficiency, and high reliability can be manufactured according to one embodiment of the present invention. Moreover, a light-emitting element having high color reproducibility can be obtained as described above.

Examples of the electronic devices include a television device, a desktop or laptop personal computer, a monitor of a computer or the like, a digital camera, a digital video camera, a digital photo frame, a mobile phone, a portable game machine, a portable information terminal, an audio reproducing device, and a large game machine such as a pachinko machine.

Figure 11A:
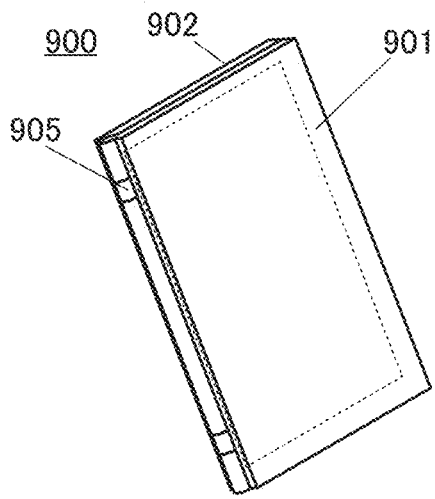
FIGS. 11A to 11D Perspective views illustrating display modules of embodiments of the present invention.
Figure 11B:
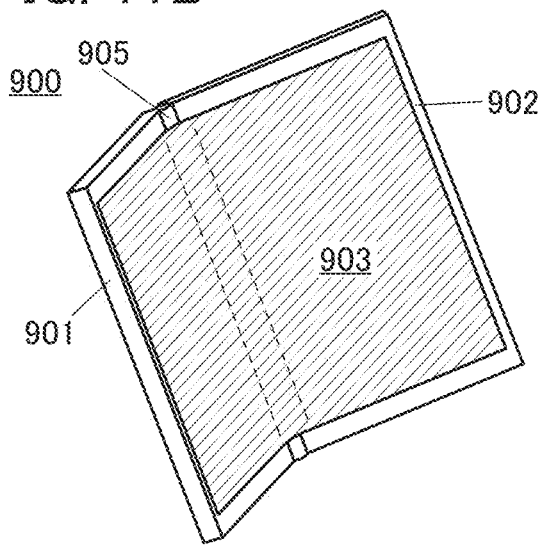

A portable information terminal 900 illustrated in FIGS. 11(A) and 11(B) includes a housing 901, a housing 902, a display portion 903, a hinge portion 905, and the like.

The housing 901 and the housing 902 are joined together by the hinge portion 905. The portable information terminal 900 can be opened as illustrated in FIG. 11(B) from a folded state (FIG. 11(A)). Thus, the portable information terminal 900 has high portability when carried and excellent visibility with its large display region when used.

In the portable information terminal 900, the flexible display portion 903 is provided across the housing 901 and the housing 902 which are joined together by the hinge portion 905.

The light-emitting apparatus manufactured using one embodiment of the present invention can be used for the display portion 903. Thus, a highly reliable portable information terminal can be manufactured.

The display portion 903 can display at least one of text information, a still image, a moving image, and the like. When text information is displayed on the display portion, the portable information terminal 900 can be used as an e-book reader.

When the portable information terminal 900 is opened, the display portion 903 is held in a state with a large radius of curvature. For example, the display portion 903 is held while including a curved portion with a radius of curvature of greater than or equal to 1 mm and less than or equal to 50 mm, preferably greater than or equal to 5 mm and less than or equal to 30 mm. Part of the display portion 903 can display an image while being curved since pixels are continuously arranged from the housing 901 to the housing 902.

The display portion 903 functions as a touch panel and can be controlled with a finger, a stylus, or the like.

The display portion 903 is preferably formed using one flexible display. Thus, a seamless continuous image can be displayed between the housing 901 and the housing 902. Note that each of the housing 901 and the housing 902 may be provided with a display.

The hinge portion 905 preferably includes a locking mechanism so that an angle formed between the housing 901 and the housing 902 does not become larger than a predetermined angle when the portable information terminal 900 is opened. For example, an angle at which they become locked (they are not opened any further) is preferably greater than or equal to 90° and less than 180° and can be typically 90°, 120°, 135°, 150°, 175°, or the like. In this way, the convenience, safety, and reliability of the portable information terminal 900 can be improved.

When the hinge portion 905 includes a locking mechanism, excessive force is not applied to the display portion 903; thus, breakage of the display portion 903 can be prevented. Therefore, a highly reliable portable information terminal can be achieved.

The housing 901 and the housing 902 may be provided with a power button, an operation button, an external connection port, a speaker, a microphone, or the like.

One of the housing 901 and the housing 902 is provided with a wireless communication module, and data can be transmitted and received through a computer network such as the Internet, a LAN (Local Area Network), or Wi-Fi (registered trademark).

Figure 11C:
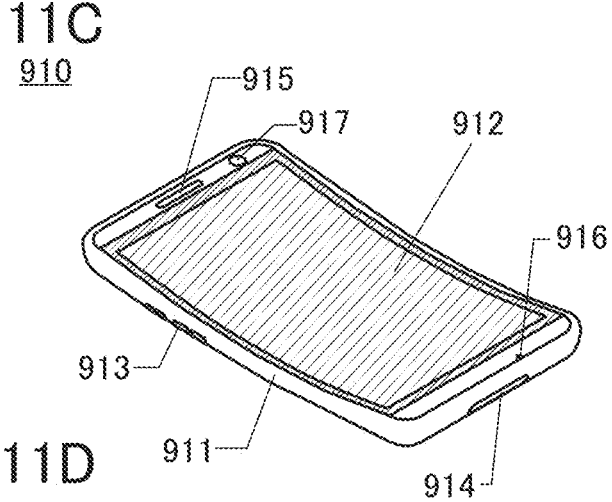

A portable information terminal 910 illustrated in FIG. 11(C) includes a housing 911, a display portion 912, an operation button 913, an external connection port 914, a speaker 915, a microphone 916, a camera 917, and the like.

The light-emitting apparatus fabricated using one embodiment of the present invention can be used for the display portion 912. Thus, the portable information terminal can be fabricated with a high yield.

The portable information terminal 910 includes a touch sensor in the display portion 912. A variety of operations such as making a call and inputting a character can be performed by touch on the display portion 912 with a finger, a stylus, or the like.

In addition, the operation of the operation button 913 can switch the power ON and OFF operations and types of images displayed on the display portion 912. For example, switching from a mail creation screen to a main menu screen can be performed.

When a sensing device such as a gyroscope sensor or an acceleration sensor is provided inside the portable information terminal 910, the direction of display on the screen of the display portion 912 can be automatically switched by determining the orientation (horizontal or vertical) of the portable information terminal 910. Furthermore, the direction of display on the screen can be switched by touch on the display portion 912, operation of the operation button 913, sound input using the microphone 916, or the like.

The portable information terminal 910 has, for example, one or more functions selected from a telephone set, a notebook, an information browsing system, and the like. Specifically, the portable information terminal can be used as a smartphone. The portable information terminal 910 is capable of executing a variety of applications such as mobile phone calls, e-mailing, text viewing and writing, music replay, video replay, Internet communication, and games, for example.

Figure 11D:
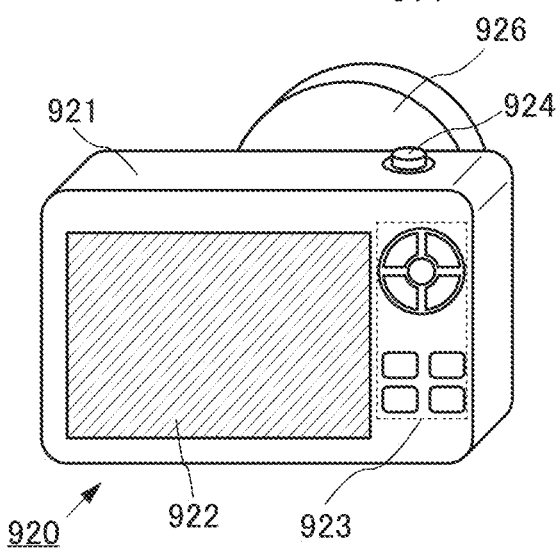

A camera 920 illustrated in FIG. 11(D) includes a housing 921, a display portion 922, operation buttons 923, a shutter button 924, and the like. Furthermore, a detachable lens 926 is attached to the camera 920.

The light-emitting apparatus fabricated using one embodiment of the present invention can be used for the display portion 922. Thus, a highly reliable camera can be fabricated.

Although the camera 920 here is configured such that the lens 926 is detachable from the housing 921 for replacement, the lens 926 may be integrated with the housing 921.

A still image or a moving image can be taken with the camera 920 at the press of the shutter button 924. In addition, the display portion 922 has a function of a touch panel, and images can also be taken by the touch on the display portion 922.

Note that a stroboscope, a viewfinder, or the like can be additionally attached to the camera 920. Alternatively, these may be incorporated into the housing 921.

Figure 12A:
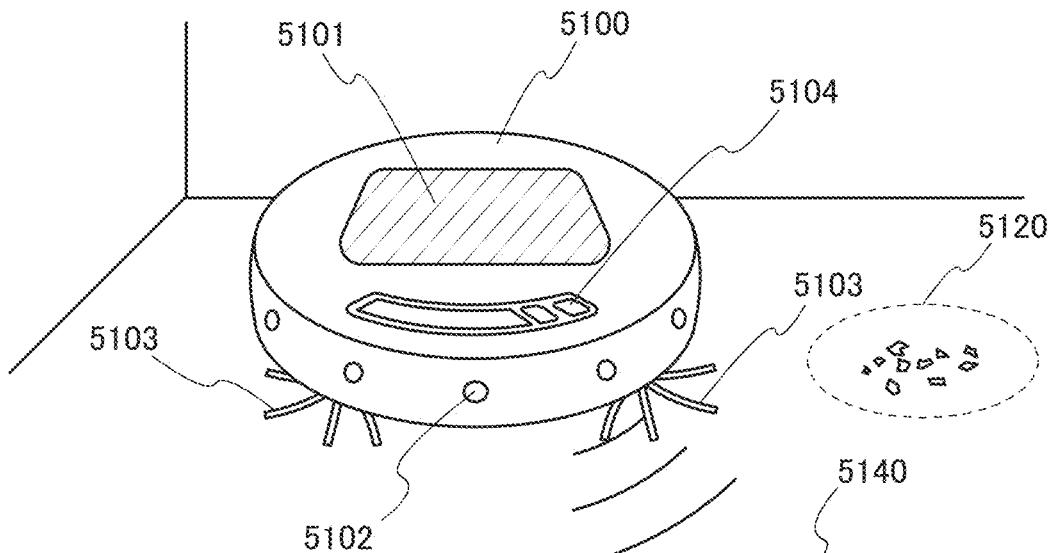
FIGS. 12A to 12C Diagrams illustrating electronic devices of embodiments of the present invention.

FIG. 12(A) is a schematic view showing an example of a cleaning robot.

A cleaning robot 5100 includes a display 5101 placed on its top surface, a plurality of cameras 5102 placed on its side surface, a brush 5103, and an operation button 5104. Although not illustrated, the bottom surface of the cleaning robot 5100 is provided with a tire, an inlet, and the like. Furthermore, the cleaning robot 5100 includes various sensors such as an infrared sensor, an ultrasonic sensor, an acceleration sensor, a piezoelectric sensor, an optical sensor, and a gyroscope sensor. In addition, the cleaning robot 5100 has a wireless communication means.

The cleaning robot 5100 is self-propelled, detects dust 5120, and can suck up the dust through the inlet provided on the bottom surface.

The cleaning robot 5100 can determine whether there is an obstacle such as a wall, furniture, or a step by analyzing images taken by the cameras 5102. When an object that is likely to be caught in the brush 5103, such as a wire, is detected by image analysis, the rotation of the brush 5103 can be stopped.

The display 5101 can display the remaining capacity of a battery, the amount of vacuumed dust, and the like. The display 5101 may display the path on which the cleaning robot 5100 has run. The display 5101 may be a touch panel, and the operation button 5104 may be provided on the display 5101.

The cleaning robot 5100 can communicate with a portable electronic device 5140 such as a smartphone. The portable electronic device 5140 can display images taken by the cameras 5102. Accordingly, an owner of the cleaning robot 5100 can monitor the room even from the outside. The display on the display 5101 can be checked by the portable electronic device 5140 such as a smartphone.

The light-emitting apparatus of one embodiment of the present invention can be used for the display 5101.

Figure 12B:
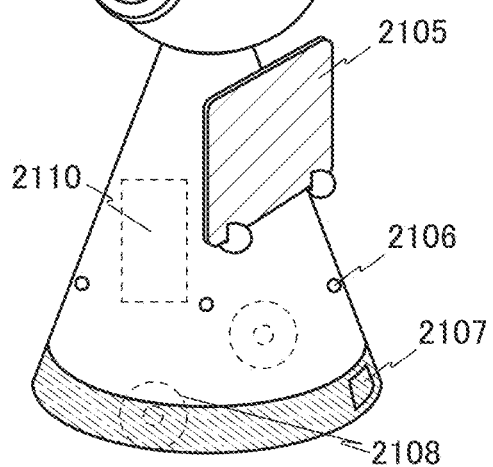

A robot 2100 illustrated in FIG. 12(B) includes an arithmetic device 2110, an illuminance sensor 2101, a microphone 2102, an upper camera 2103, a speaker 2104, a display 2105, a lower camera 2106, an obstacle sensor 2107, and a moving mechanism 2108.

The microphone 2102 has a function of detecting a speaking voice of a user, an environmental sound, and the like. The speaker 2104 has a function of outputting sound. The robot 2100 can communicate with a user using the microphone 2102 and the speaker 2104.

The display 2105 has a function of displaying various kinds of information. The robot 2100 can display information desired by a user on the display 2105. The display 2105 may be provided with a touch panel. Moreover, the display 2105 may be a detachable information terminal, in which case charging and data communication can be performed when the display 2105 is set at the home position of the robot 2100.

The upper camera 2103 and the lower camera 2106 each have a function of taking an image of the surroundings of the robot 2100. The obstacle sensor 2107 can detect the presence of an obstacle in the direction where the robot 2100 advances with the moving mechanism 2108. The robot 2100 can move safely by recognizing the surroundings with the upper camera 2103, the lower camera 2106, and the obstacle sensor 2107.

The light-emitting apparatus of one embodiment of the present invention can be used for the display 2105.

Figure 12C:
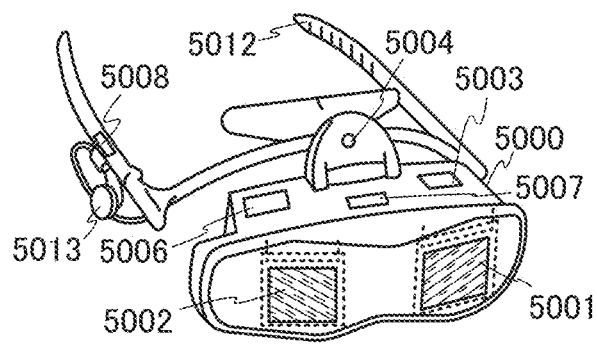

FIG. 12(C) illustrates an example of a goggle-type display. The goggle-type display includes, for example, a housing 5000, a display portion 5001, a speaker 5003, an LED lamp 5004, operation keys 5005 (including a power switch or an operation switch), a connection terminal 5006, a sensor 5007 (a sensor having a function of measuring force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared ray), a microphone 5008, a second display portion 5002, a support 5012, and an earphone 5013.

The light-emitting apparatus of one embodiment of the present invention can be used for the display portion 5001 and the second display portion 5002.

Figure 13A:
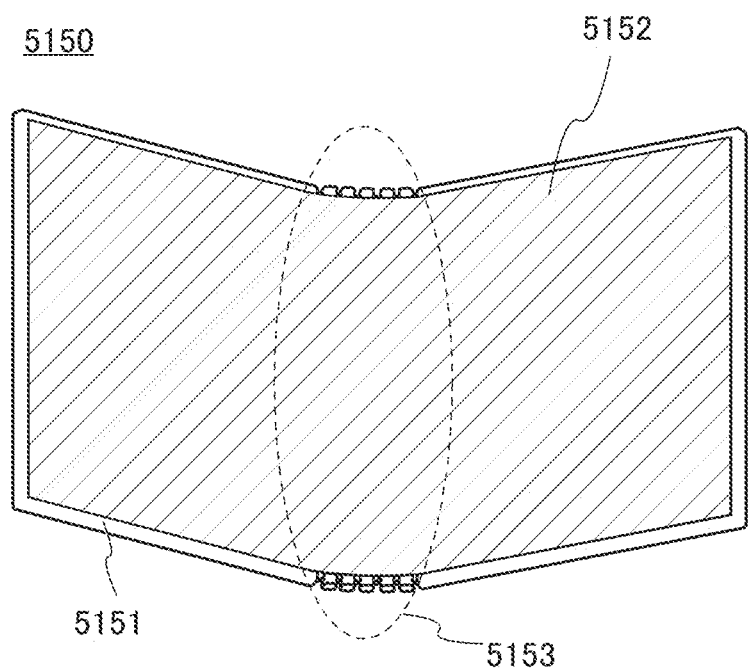
FIGS. 13A and 13B Perspective views illustrating a display device of one embodiment of the present invention.
Figure 13B:
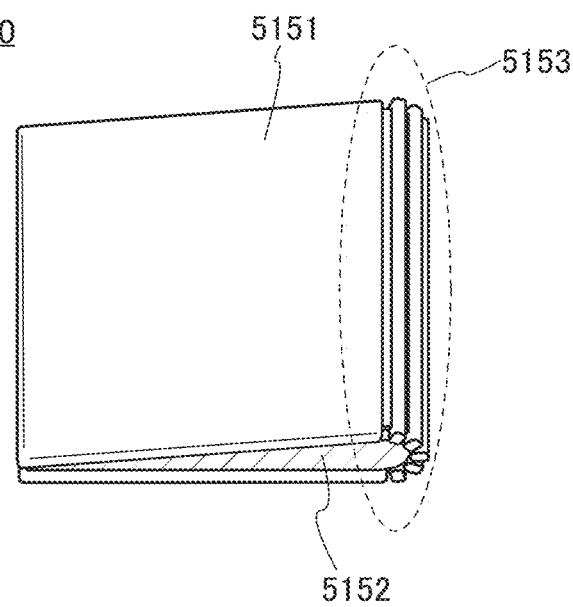

FIGS. 13(A) and 13(B) illustrate a foldable portable information terminal 5150. The foldable portable information terminal 5150 includes a housing 5151, a display region 5152, and a bend portion 5153. FIG. 13(A) illustrates the portable information terminal 5150 that is opened. FIG. 13(B) illustrates the portable information terminal 5150 that is folded. Despite its large display region 5152, the portable information terminal 5150 is compact in size and has excellent portability when folded.

The display region 5152 can be folded in half with the bend portion 5153. The bend portion 5153 is formed of a stretchable member and a plurality of supporting members, and in the case where the display region is folded, the stretchable member stretches and the bend portion 5153 has a radius of curvature of 2 mm or more, preferably 5 mm or more.

Note that the display region 5152 may be a touch panel (an input/output device) including a touch sensor (an input device). The light-emitting apparatus of one embodiment of the present invention can be used for the display region 5152.

This embodiment can be combined with the other embodiments as appropriate.

Embodiment 6

In this embodiment, examples in which the light-emitting element of one embodiment of the present invention is used for various lighting devices will be described with reference to FIG. 14. With the use of the light-emitting element of one embodiment of the present invention, a highly reliable lighting device with high emission efficiency can be manufactured.

Fabricating the light-emitting element of one embodiment of the present invention over a substrate having flexibility enables an electronic device or a lighting device that has a light-emitting region with a curved surface to be obtained.

Furthermore, a light-emitting apparatus in which the light-emitting element of one embodiment of the present invention is used can also be used for lighting for motor vehicles; for example, such lighting can be provided on a windshield, a ceiling, and the like.

Figure 14:
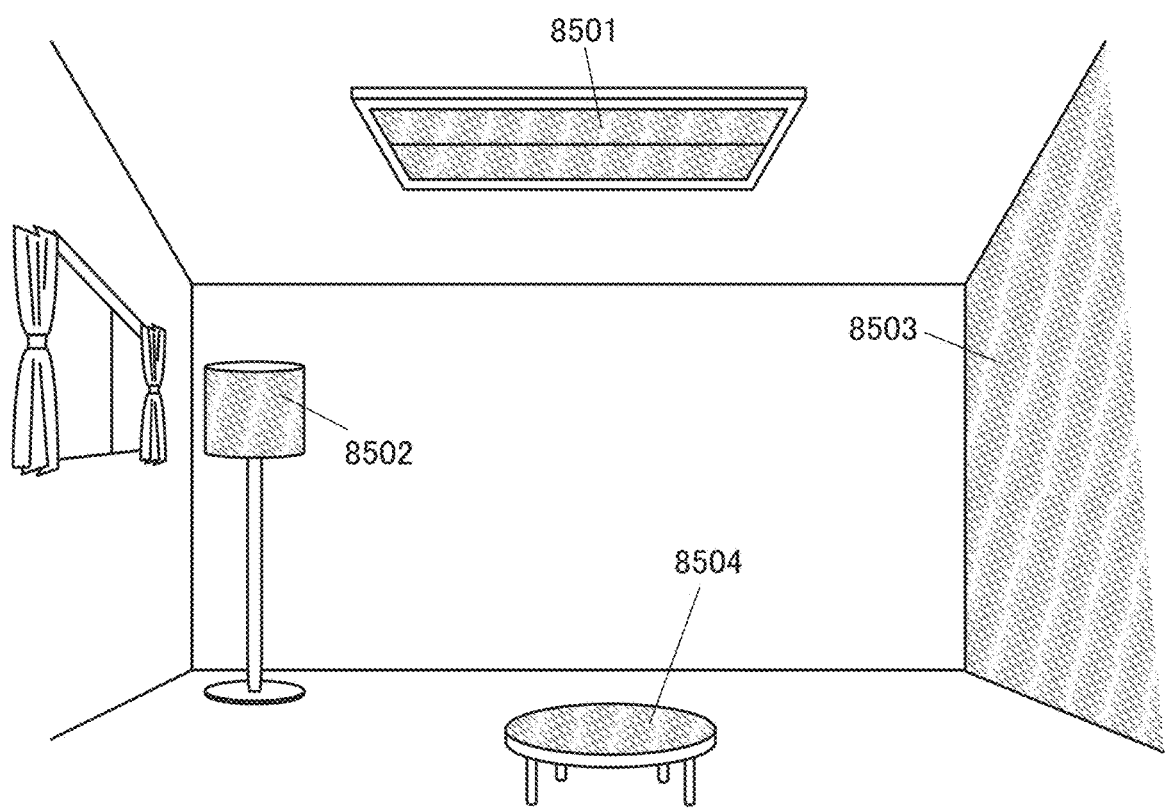
FIG. 14 A diagram illustrating lighting devices of one embodiment of the present invention.

FIG. 14 illustrates an example in which the light-emitting element is used for an indoor lighting device 8501. Since the light-emitting element can have a larger area, a lighting device having a large area can also be formed. In addition, a lighting device 8502 in which a light-emitting region has a curved surface can also be formed with the use of a housing with a curved surface. A light-emitting element described in this embodiment is in the form of a thin film, which allows the housing to be designed more freely. Thus, the lighting device can be elaborately designed in a variety of ways. Furthermore, a wall of the room may be provided with a large-sized lighting device 8503. The lighting devices 8501, 8502, and 8503 may be provided with a touch sensor with which power-on or off is performed.

Moreover, when the light-emitting element is used on the surface side of a table, a lighting device 8504 which has a function as a table can be obtained. When the light-emitting element is used as part of other furniture, a lighting device having a function of the furniture can be obtained.

As described above, lighting devices and electronic devices can be obtained by application of the light-emitting element of one embodiment of the present invention. Note that the light-emitting element can be used for lighting devices and electronic devices in a variety of fields without being limited to the lighting devices and the electronic devices described in this embodiment.

The structure described in this embodiment can be used in appropriate combination with any of the structures described in the other embodiments.

Example 1

In this example, a synthesis method of 2-tert-butyl-N,N,N',N'-tetrakis(4-tert-butylphenyl)-9,10-anthracenediamine (abbreviation: 2tBu-ptBuDPhA2Anth), which is an organic compound represented by Structural Formula (100) of Embodiment 1, will be described. This compound is a guest material having protecting groups, which can be favorably used for a light-emitting element of one embodiment of the present invention.

1.2 g (3.1 mmol) of 2-tert-butylanthracene, 1.8 g (6.4 mmol) of bis(4-tert-butylphenyl)amine, 1.2 g (13 mmol) of sodium t-butoxide, and 60 mg (0.15 mmol) of 2-dicyclohexylphosphino-2',6'-dimethoxy-1,1'-biphenyl (abbreviation: SPhos) were put into a 200 mL three-neck flask, and the air in the flask was replaced with nitrogen. To this mixture was added 35 mL of xylene, and the mixture was degassed under reduced pressure; then, 40 mg (70 μmol) of bis(dibenzylideneacetone)palladium(0) was added to the mixture and the mixture was stirred for 4 hours at 170° C. under a nitrogen stream.

After the stirring, 400 mL of toluene was added to the obtained mixture, which was then subjected to suction filtration through Florisil (Wako Pure Chemical Industries, Ltd., Catalog Number: 066-05265), Celite (Wako Pure Chemical Industries, Ltd., Catalog Number: 537-02305), and aluminum oxide to give a filtrate. The obtained filtrate was concentrated to give a brown solid.

This solid was purified by silica gel column chromatography (developing solvent: hexane:toluene=9:1) to obtain an objective yellow solid. The obtained yellow solid was recrystallized with toluene, hexane, and ethanol to give 1.5 g of an objective yellow solid in a yield of 61%. The synthesis scheme is shown in (A-1) below.

[Chemical Formula 46]

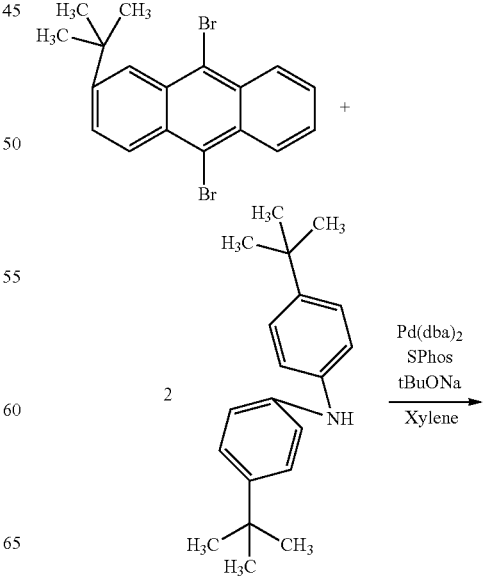

(A-1)

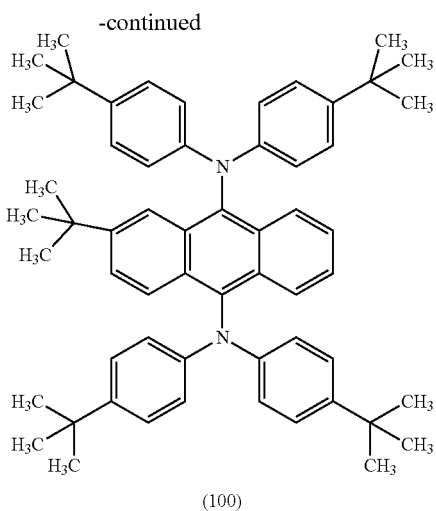

(100)

By a train sublimation method, 1.5 g of the obtained yellow solid was purified by sublimation. In the sublimation purification, the yellow solid was heated at 315° C. under a pressure of 4.5 Pa for 15 hours. After the sublimation purification, 1.3 g of an objective yellow solid was obtained at a collection rate of 89%.

Figure 15A:
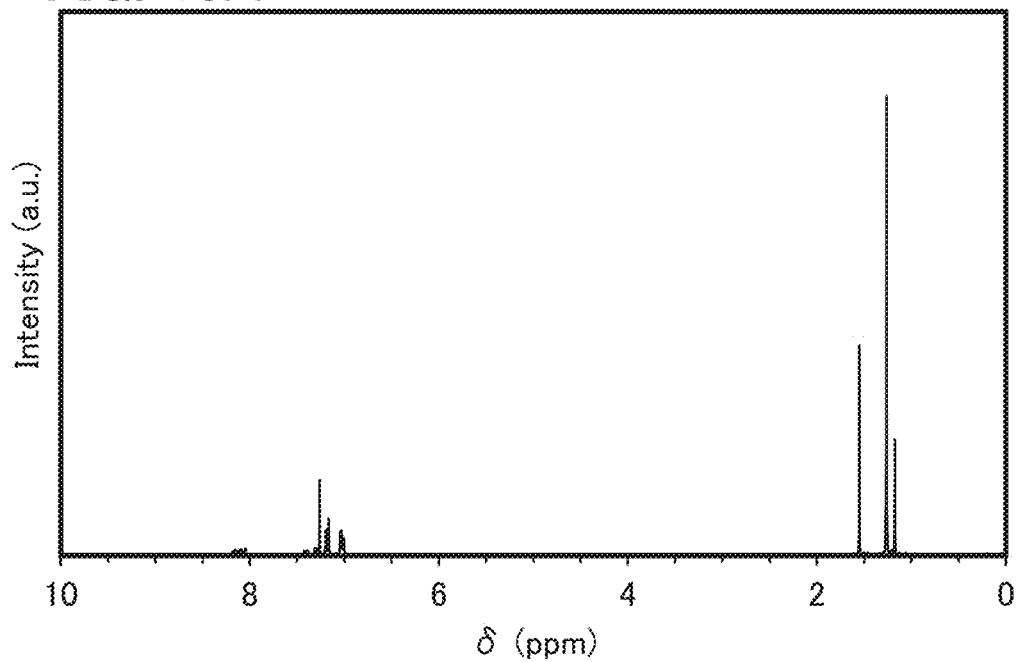
FIGS. 15A and 15B Diagrams showing NMR charts of a compound in Example.
Figure 15B:
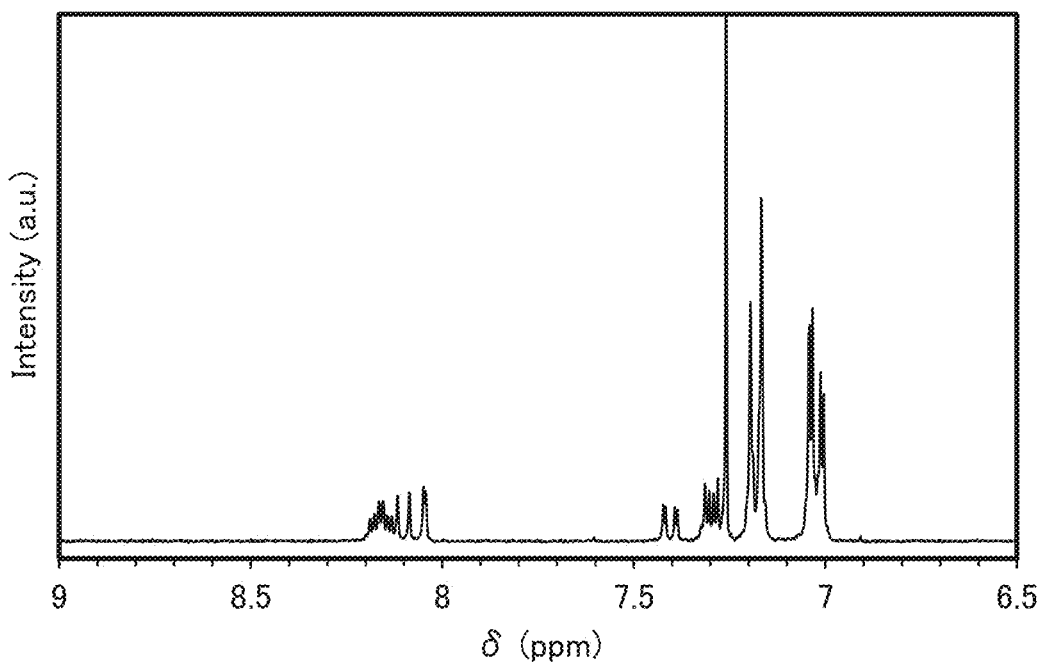
Figure 16:
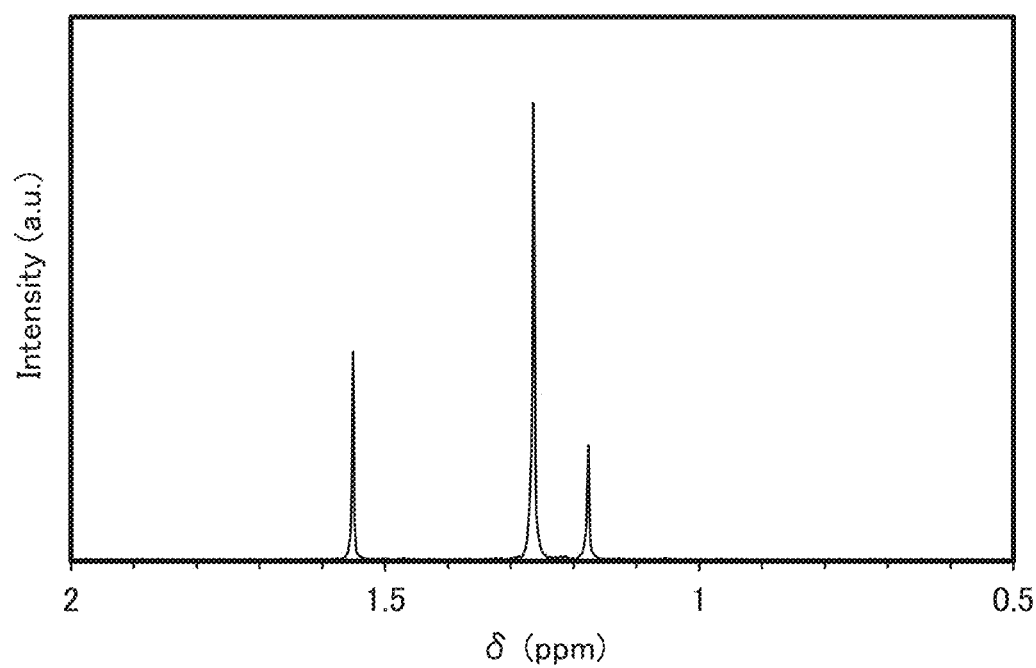
FIG. 16 A diagram showing an NMR chart of a compound in Example.

Results of $^1$H NMR measurement of the yellow solid obtained in this synthesis will be described below. FIG. 15 and FIG. 16 are the $^1$H-NMR charts. Note that FIG. 15(B) is an enlarged diagram of the range of 6.5 ppm to 9.0 ppm of FIG. 15(A). FIG. 16 is an enlarged diagram of the range of 0.5 ppm to 2.0 ppm of FIG. 15(A). The results indicate that 2tBu-ptBuDPhA2Anth, which was the objective substance, was obtained.

$^1$H NMR (CDCl$_3$, 300 MHz): σ=8.20-8.13 (m, 2H), 8.12 (d, J=8.8 Hz, 1H), 8.05 (d, J=2.0 Hz, 1H), 7.42 (dd, J=9.3 Hz, 2.0 Hz, 1H), 7.32-7.26 (m, 2H) 7.20 (d, J=8.8 Hz, 8H), 7.04 (dd, J=8.8 Hz, 2.4 Hz, 8H), 1.26 (s, 36H), 1.18 (s, 9H).

Figure 17:
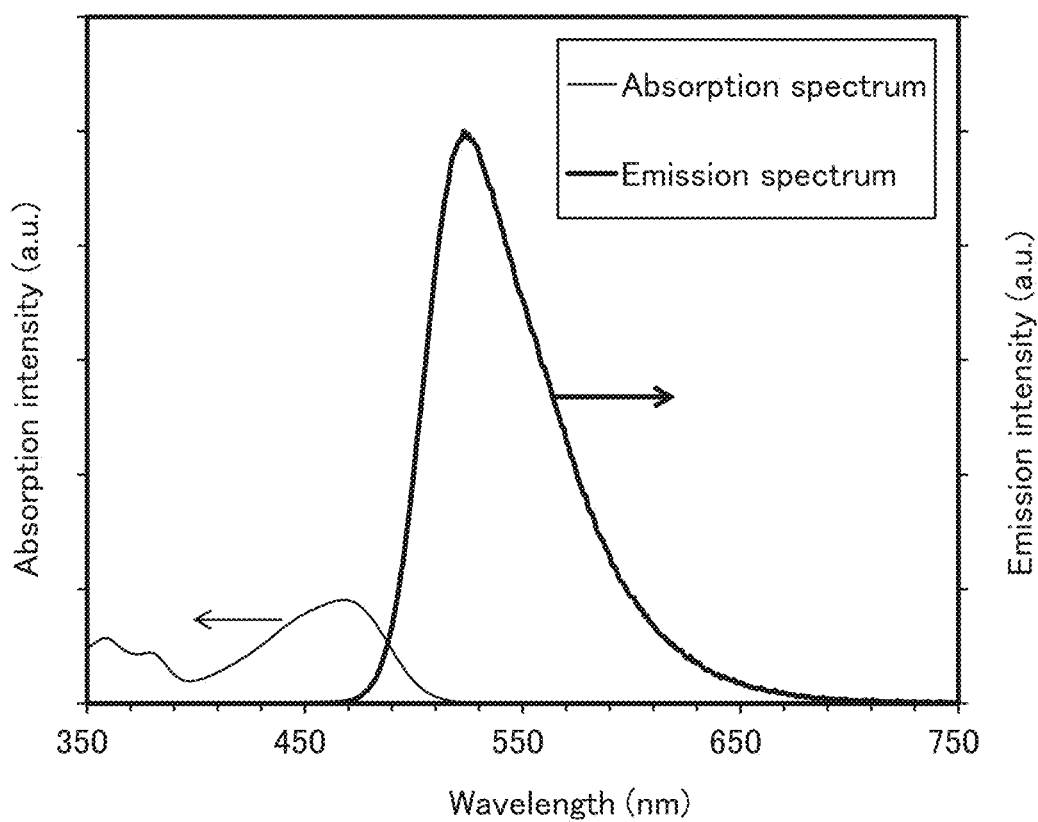
FIG. 17 A diagram showing absorption and emission spectra of a compound in Example.

Next, FIG. 17 shows the measurement results of the absorption spectrum and the emission spectrum of 2tBu-ptBuDPhA2Anth in a toluene solution. For the measurement of the absorption spectrum of the toluene solution, an ultraviolet-visible light spectrophotometer (V550, manufactured by JASCO Corporation) was used, and the spectrum of toluene alone in a quartz cell was subtracted.

As shown in FIG. 17, in the case of 2tBu-ptBuDPhA2Anth in the toluene solution, absorption peaks were observed at around 468 nm, 378 nm, and 359 nm, and an emission wavelength peak was at 523 nm (excitation wavelength: 440 nm).

Example 2

In this example, a synthesis method of 2-tert-butyl-N,N,N',N'-tetrakis(3,5-di-tert-butylphenyl)-9,10-anthracenediamine (abbreviation: 2tBu-mmtBuDPhA2Anth), which is an organic compound of one embodiment of the present invention represented by Structural Formula (102) of Embodiment 1, will be described. This compound is a guest material having protecting groups, which can be favorably used for a light-emitting element of one embodiment of the present invention.

Step 1: Synthesis of bis(3,5-tert-butylphenyl)amine 5.4 g (20 mmol) of 1-bromo-3,5-di-tert-butylbenzene, 5.0 g (24 mmol) of 3,5-di-tert-butylaniline, and 4.7 g (49 mmol) of sodium t-butoxide were put into a 200 mL three-neck flask, and the air in the flask was replaced with nitrogen. To this mixture was added 100 mL of toluene, and the obtained mixture was degassed under reduced pressure. Then, 1.3 mL (1.5 mmol) of tri-tert-butylphosphine (a 10 w % hexane solution) and 0.17 g (0.3 mmol) of bis(dibenzylideneacetone)palladium(0) were added to the mixture and the mixture was stirred for 6 hours at 120° C. under a nitrogen stream.

After the stirring, 300 mL of toluene was added to the obtained mixture, which was then subjected to suction filtration through Florisil, Celite, and aluminum oxide to give a filtrate. The obtained filtrate was concentrated to give a brown solid.

This solid was purified by silica gel column chromatography (developing solvent; hexane:toluene=4:1) to obtain 7.5 g of an objective white solid in a yield of 95%. The synthesis scheme of Step 1 is shown in (B-1) below.

[Chemical Formula 47]

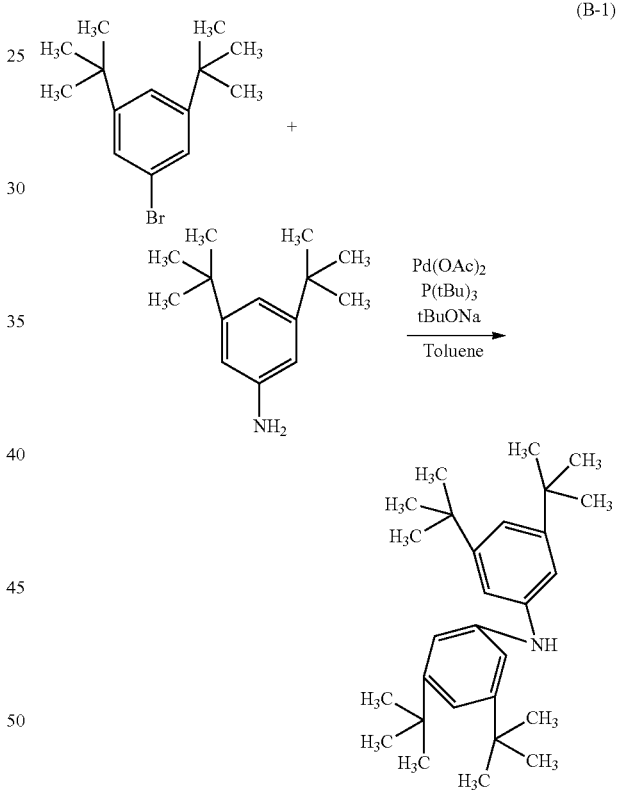

(B-1)

Step 2: Synthesis of 2tBu-mmtBuDPhA2Anth 0.95 g (2.5 mmol) of 2-tert-butylanthracene, 2.0 g (5.1 mmol) of bis(3,5-tert-butylphenyl)amine, 1.0 g (10 mmol) of sodium t-butoxide, and 60 mg (0.15 mmol) of SPhos were put into a 200 mL three-neck flask, and the air in the flask was replaced with nitrogen. To this mixture was added 30 mL of xylene, and the mixture was degassed under reduced pressure; then, 40 mg (70 μmol) of bis(dibenzylideneacetone)palladium(0) was added to the mixture and the mixture was stirred for 5 hours at 170° C. under a nitrogen stream.

After the stirring, 400 mL of toluene was added to the obtained mixture, which was then subjected to suction filtration through Florisil, Celite, and aluminum oxide to give a filtrate. The obtained filtrate was concentrated to give a brown solid.

This solid was purified by silica gel column chromatography (developing solvent; hexane:toluene=9:1) to obtain an objective yellow solid. The obtained yellow solid was recrystallized with hexane and methanol to give 0.30 g of an objective yellow solid in a yield of 12%. The synthesis scheme of Step 2 is shown in (B-2) below.

[Chemical Formula 48]

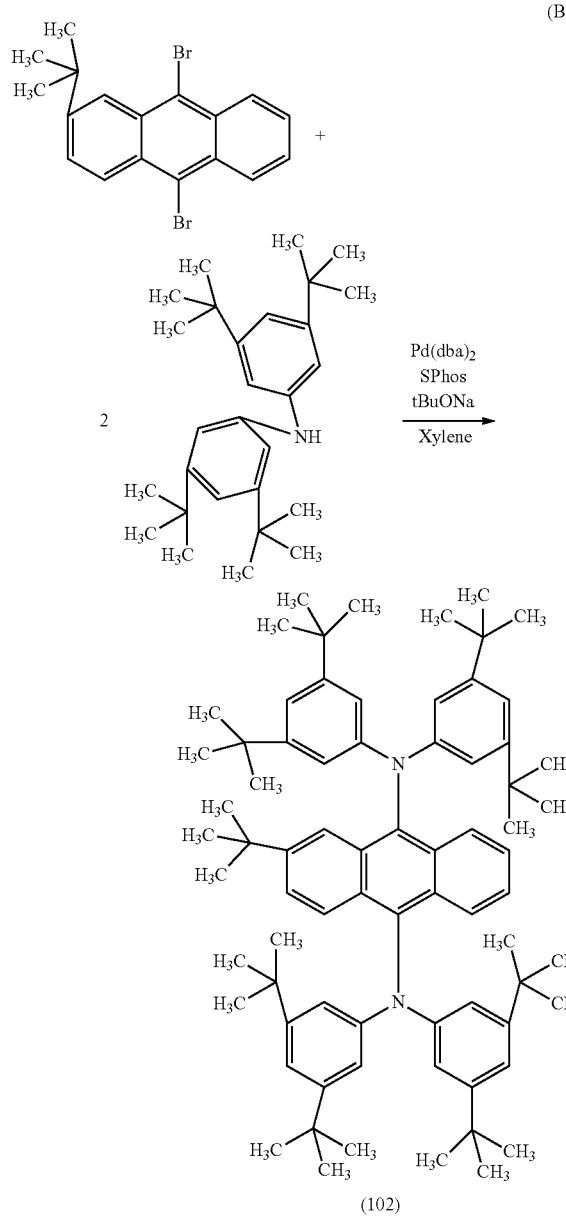

(102)

By a train sublimation method, 0.30 g of the obtained yellow solid was purified by sublimation. In the sublimation purification, the yellow solid was heated at 230° C. under a pressure of 3.6 Pa for 15 hours. After the sublimation purification, 0.15 g of an objective yellow solid was obtained at a collection rate of 50%.

Figure 18A:
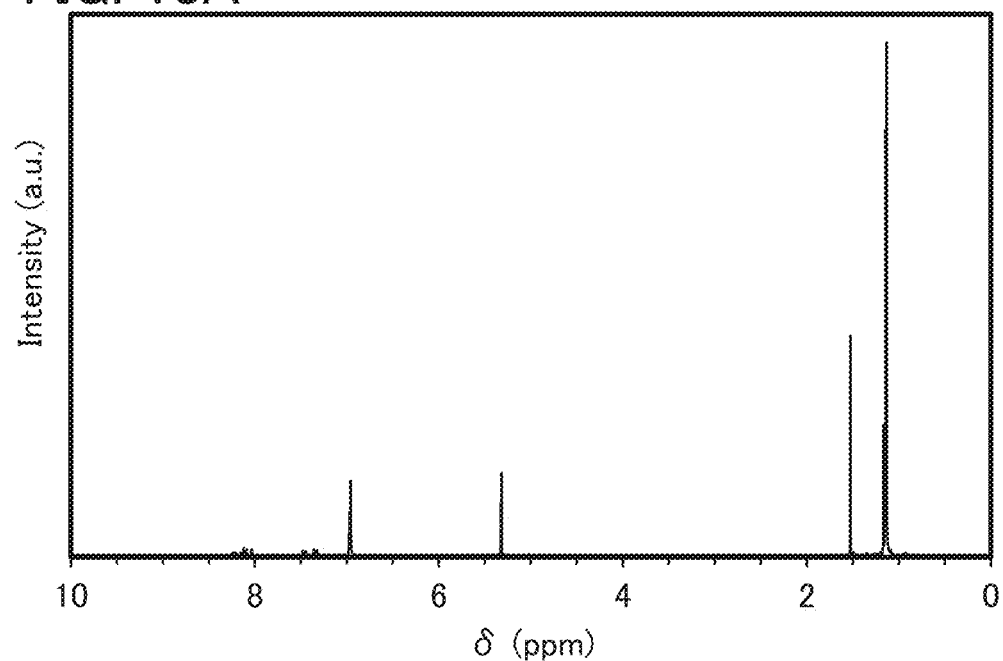
FIGS. 18A and 18B Diagrams showing NMR charts of a compound in Example.
Figure 18B:
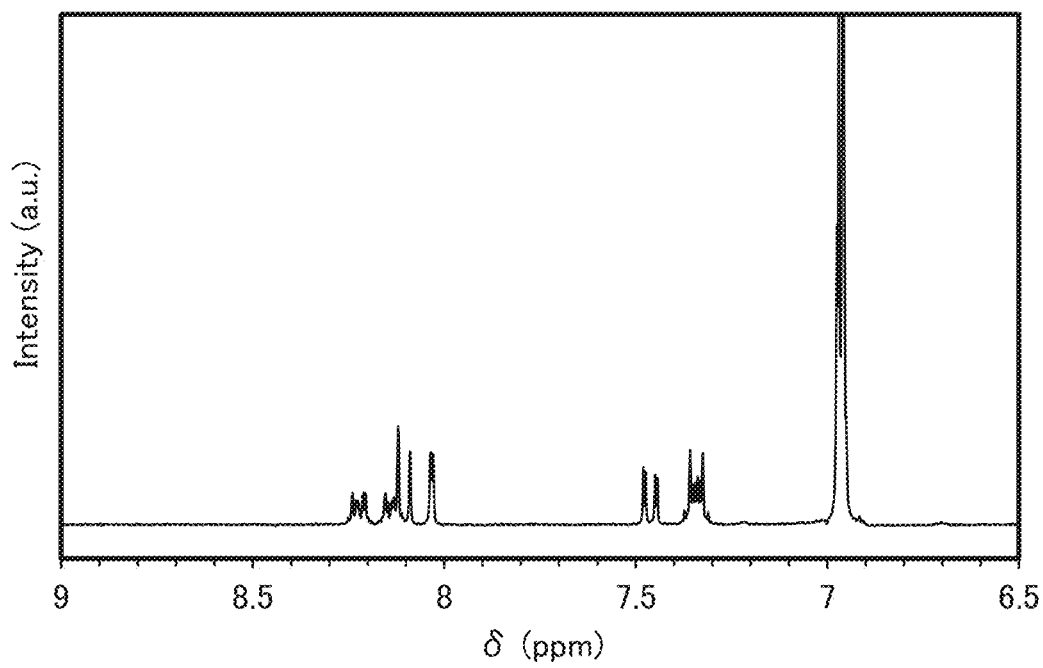
Figure 19:
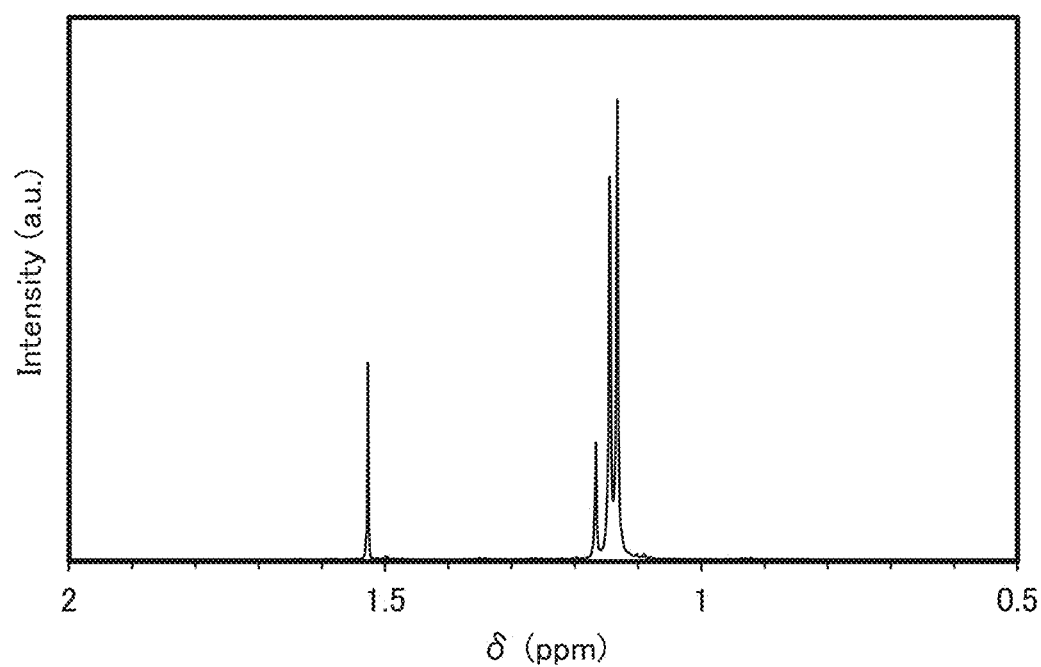
FIG. 19 A diagram showing an NMR chart of a compound in Example.

Results of $^1$H NMR measurement of the yellow solid obtained in Step 2 described above will be described below. FIG. 18 and FIG. 19 are the $^1$H-NMR charts. Note that FIG. 18(B) is an enlarged chart of the range of 6.5 ppm to 9.0 ppm of FIG. 18(A). FIG. 19 is an enlarged chart of the range of 0.5 ppm to 2.0 ppm of FIG. 18(A). The results indicate that 2tBu-mmtBuDPhA2Anth was obtained.

$^1$H NMR (CD$_2$Cl$_2$, 300 MHz): σ=8.25-8.20 (m, 1H), 8.16-8.09 (m, 1H), 8.03 (d, J=1.5 Hz, 1H), 7.48 (dd, J=9.3 Hz, 2.0 Hz, 1H), 7.37-7.31 (m, 2H), 6.97-6.95 (m, 12H), 1.17 (s, 9H), 1.15-1.13 (m, 72H).

Figure 20:
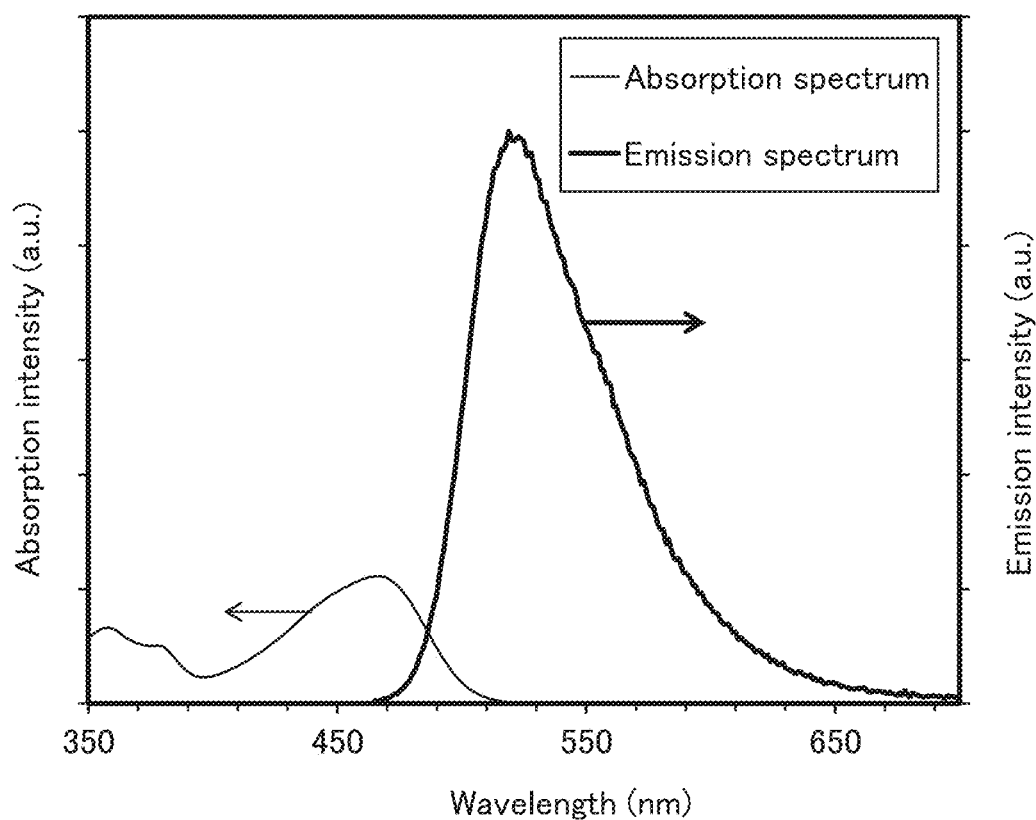
FIG. 20 A diagram showing absorption and emission spectra of a compound in Example.

Next, FIG. 20 shows the measurement results of the absorption spectrum and the emission spectrum of 2tBu-mmtBuDPhA2Anth in a toluene solution. The measurement method is similar to the method described in Example 1.

As shown in FIG. 20, in the case of 2tBu-mmtBuDPhA2Anth in the toluene solution, absorption peaks were observed at around 466 nm, 379 nm, and 358 nm, and an emission wavelength peak was at 519 nm (excitation wavelength: 458 nm).

Example 3

In this example, a synthesis method of 2,6-di-tert-butyl-N,N,N',N'-tetrakis(4-tert-butylphenyl)-9,10-anthracenediamine (abbreviation: 2,6tBu-ptBuDPhA2Anth), which is an organic compound represented by Structural Formula (101) of Embodiment 1, will be described. This compound is a guest material having protecting groups, which can be favorably used for a light-emitting element of one embodiment of the present invention.

1.6 g (3.6 mmol) of 2,6-di-tert-butylanthracene, 3.5 g (13 mmol) of bis(4-tert-butylphenyl)amine, 3.6 g (37 mmol) of sodium t-butoxide, and 0.18 g (1.1 mmol) of SPhos were put into a 200 mL three-neck flask, and the air in the flask was replaced with nitrogen. To this mixture was added 40 mL of xylene, and the mixture was degassed under reduced pressure; then, 0.12 g (0.21 mmol) of bis(dibenzylideneacetone)palladium(0) was added to the mixture and the mixture was stirred for 22 hours at 170° C. under a nitrogen stream.

After the stirring, 400 mL of toluene was added to the obtained mixture, which was then subjected to suction filtration through Florisil, Celite, and aluminum oxide to give a filtrate. The obtained filtrate was concentrated to give a brown solid.

This solid was purified by silica gel column chromatography (developing solvent; hexane:toluene=9:1) to obtain an objective yellow solid. The obtained yellow solid was recrystallized with toluene to give 1.2 g of an objective yellow solid in a yield of 38%. The synthesis scheme of Step 1 is shown in (C-1) below.

[Chemical Formula 49]

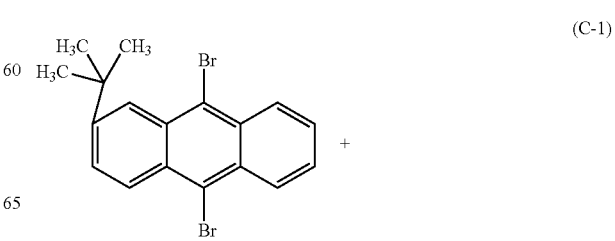

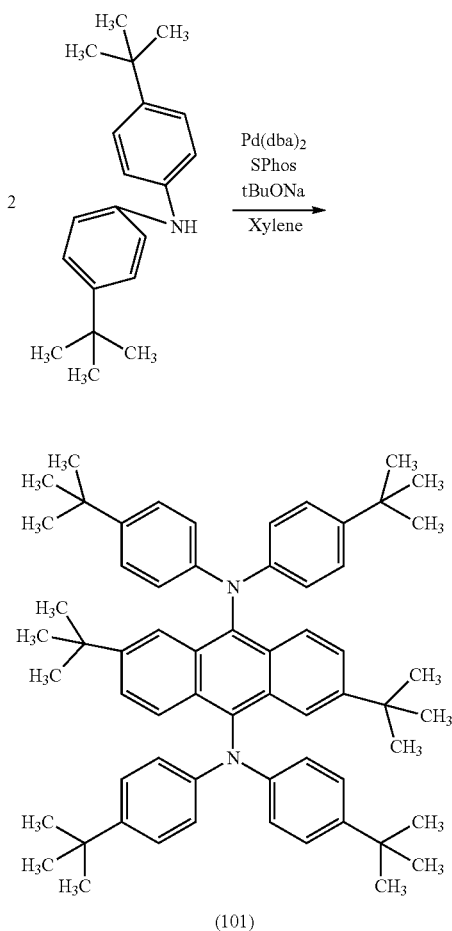

(101)

By a train sublimation method, 1.2 g of the obtained yellow solid was purified by sublimation. In the sublimation purification, the yellow solid was heated at 315° C. under a pressure of 4.0 Pa for 15 hours. After the sublimation purification, 0.94 g of an objective yellow solid was obtained at a collection rate of 82%.

Figure 21A:
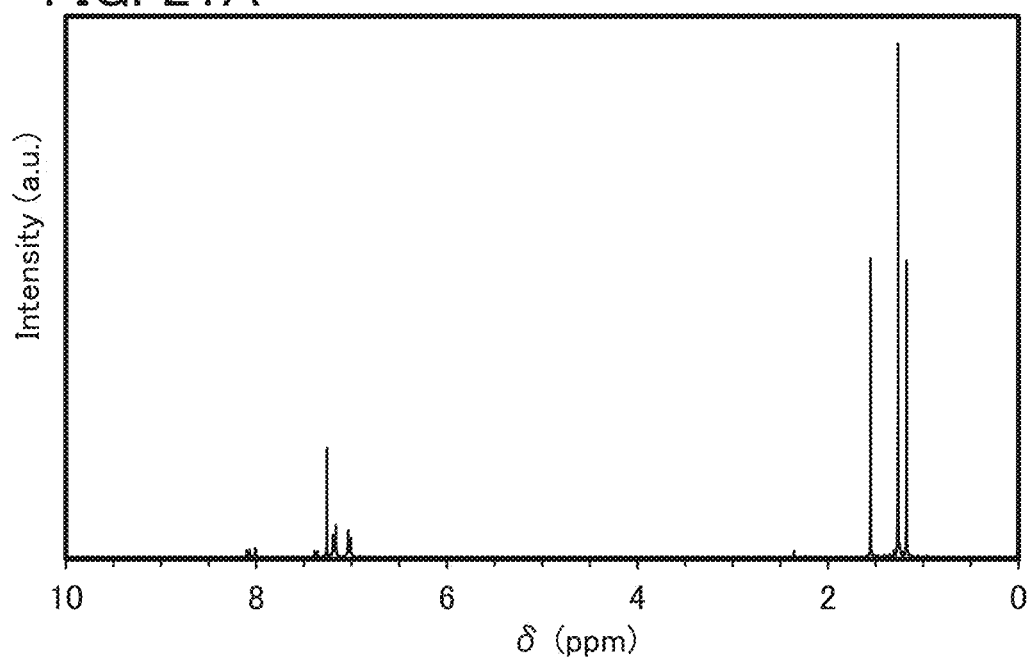
FIGS. 21A and 21B Diagrams showing NMR charts of a compound in Example.
Figure 21B:
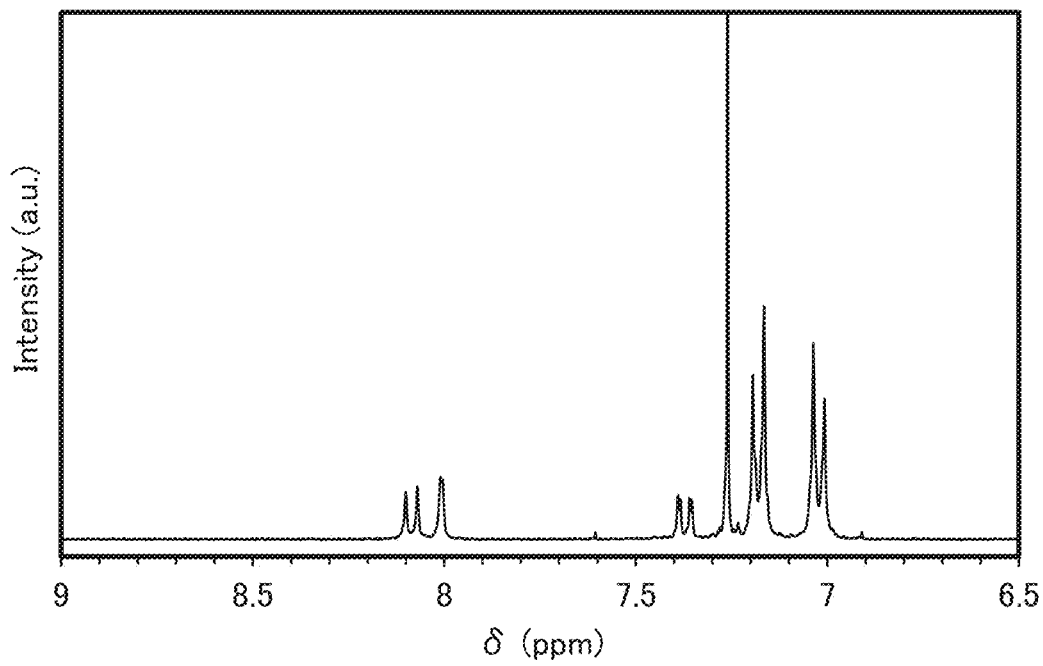
Figure 22:
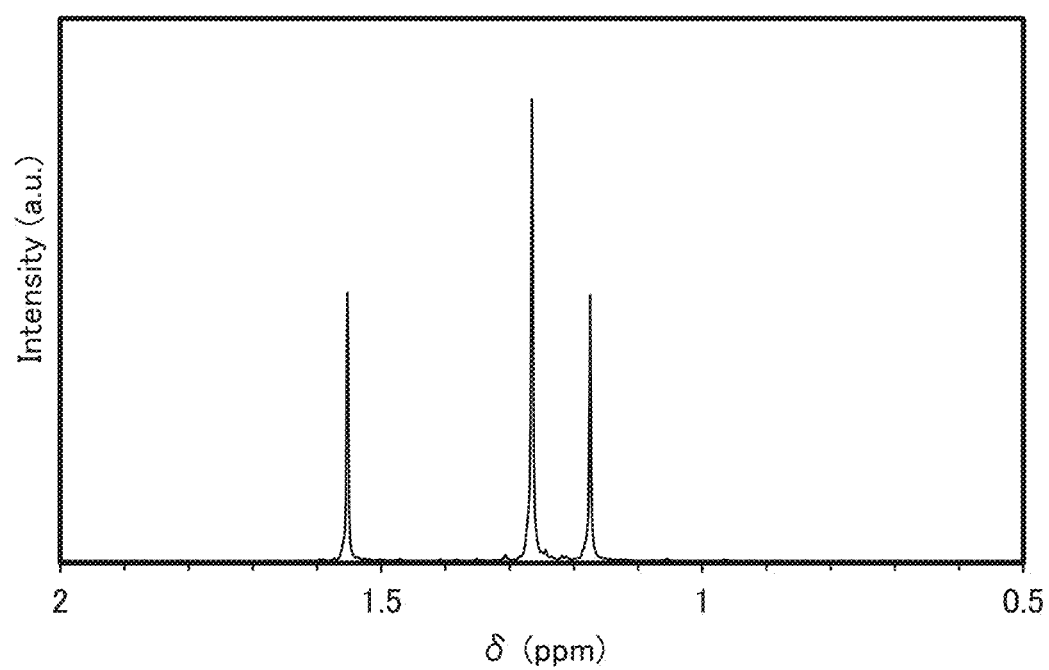
FIG. 22 A diagram showing an NMR chart of a compound in Example.

Results of $^1$H NMR measurement of the yellow solid obtained in Step 1 described above will be described below. FIG. 21 and FIG. 22 are the $^1$H-NMR charts. Note that FIG. 21(B) is an enlarged chart of the range of 6.5 ppm to 9.0 ppm of FIG. 21(A). FIG. 22 is an enlarged chart of the range of 0.5 ppm to 2.0 ppm of FIG. 21(A). The results indicate that 2,6tBu-ptBuDPhA2Anth was obtained.

$^1$H NMR (CDCl$_3$, 300 MHz): σ=8.10 (d, J=9.3 Hz, 2H), 8.01 (d, J=1.5 Hz, 2H), 7.39 (dd, J=9.3 Hz, 2.0 Hz, 2H), 7.19-7.16 (m, 8H) 7.05-7.01 (m, 8H), 1.27 (s, 36H), 1.17 (s, 18H).

Figure 23:
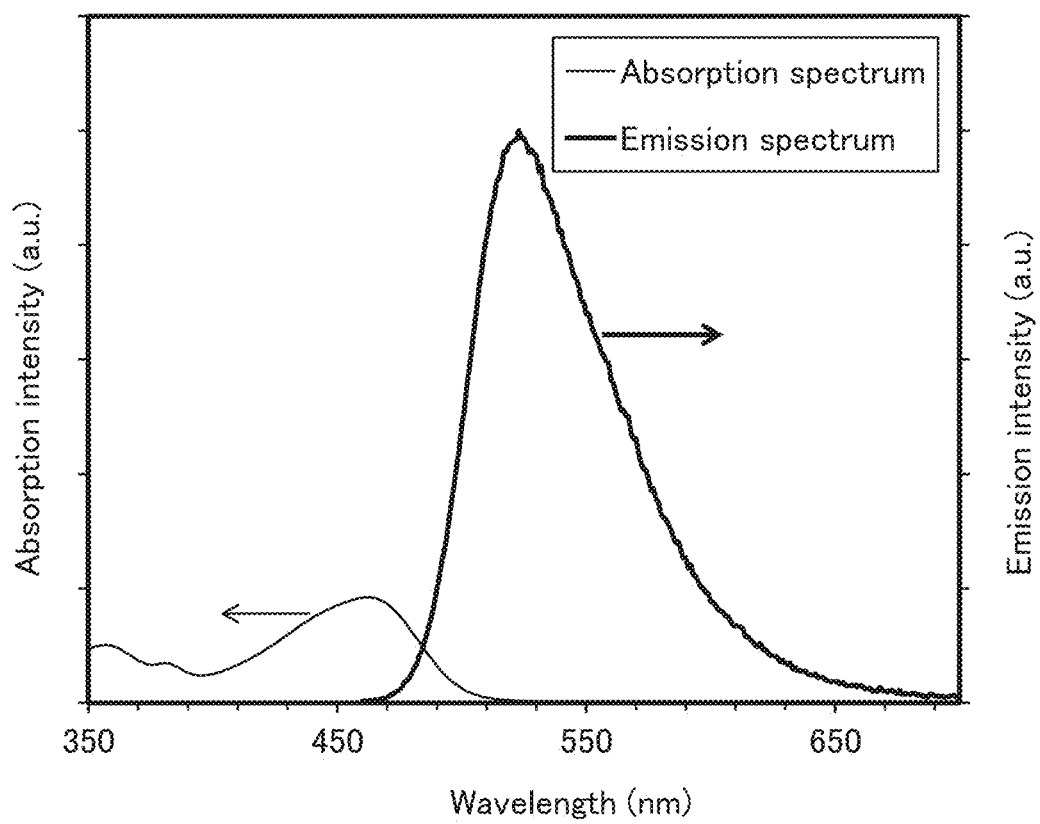
FIG. 23 A diagram showing absorption and emission spectra of a compound in Example.

Next, FIG. 23 shows the measurement results of the absorption spectrum and the emission spectrum of 2,6tBu-ptBuDPhA2Anth in a toluene solution. The measurement method is similar to the method described in Example 1.

As shown in FIG. 23, in the case of 2,6tBu-ptBuDPhA2Anth in the toluene solution, absorption peaks were observed at around 462 nm, 381 nm, and 358 nm, and an emission wavelength peak was at 523 nm (excitation wavelength: 455 nm).

Example 4

In this example, a synthesis method of 2,6-di-tert-butyl-N,N,N',N'-tetrakis(3,5-di-tert-butylphenyl)-9,10-anthracenediamine (abbreviation: 2,6tBu-mmtBuDPhA2Anth), which is an organic compound of one embodiment of the present invention represented by Structural Formula (103) of Embodiment 1, will be described. This compound is a guest material having protecting groups, which can be favorably used for a light-emitting element of one embodiment of the present invention.

1.1 g (2.5 mmol) of 2,6-di-tert-butylanthracene, 2.3 g (5.8 mmol) of bis(3,5-tert-butylphenyl)amine, 1.1 g (11 mmol) of sodium t-butoxide, and 60 mg (0.15 mmol) of SPhos were put into a 200 mL three-neck flask, and the air in the flask was replaced with nitrogen. To this mixture was added 25 mL of xylene, and the mixture was degassed under reduced pressure; then, 40 mg (70 µmol) of bis(dibenzylideneacetone)palladium(0) was added to the mixture and the mixture was stirred for 6 hours at 150° C. under a nitrogen stream.

After the stirring, 400 mL of toluene was added to the obtained mixture, which was then subjected to suction filtration through Florisil, Celite, and aluminum oxide to give a filtrate. The obtained filtrate was concentrated to give a brown solid.

This solid was purified by silica gel column chromatography (developing solvent; hexane:toluene=9:1) to obtain an objective yellow solid. The obtained yellow solid was recrystallized with hexane and methanol to give 0.45 g of an objective yellow solid in a yield of 17%. The synthesis scheme of Step 1 is shown in (D-1) below.

[Chemical Formula 50]

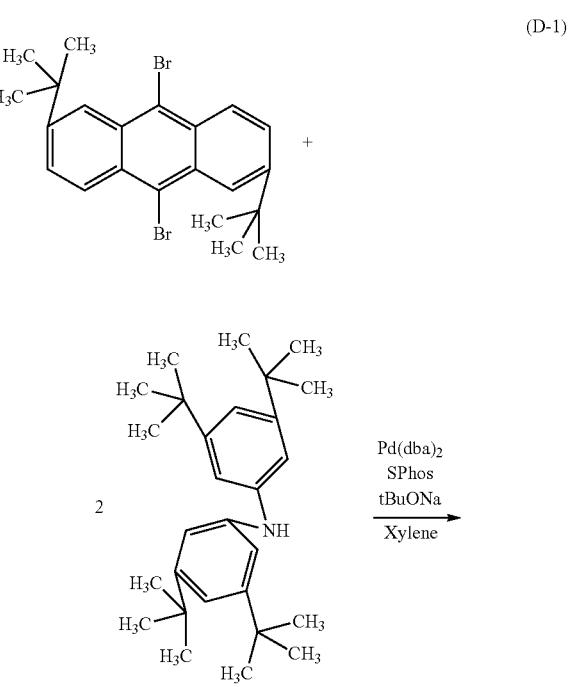

(D-1)

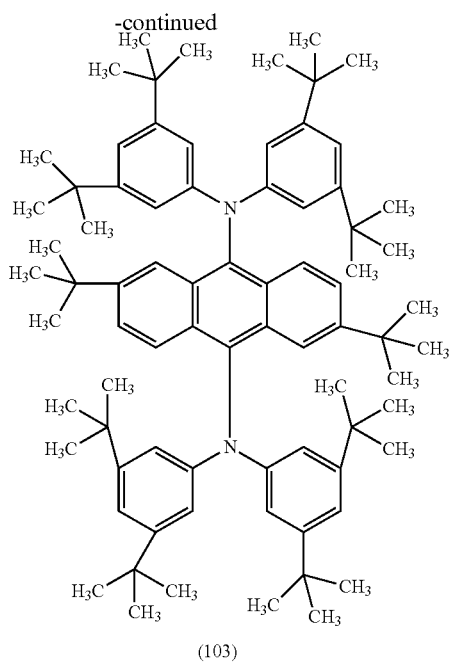

(103)

By a train sublimation method, 0.45 g of the obtained yellow solid was purified by sublimation. In the sublimation purification, the yellow solid was heated at 275° C. under a pressure of 5.0 Pa for 15 hours. After the sublimation purification, 0.37 g of an objective yellow solid was obtained at a collection rate of 82%.

Figure 24A:
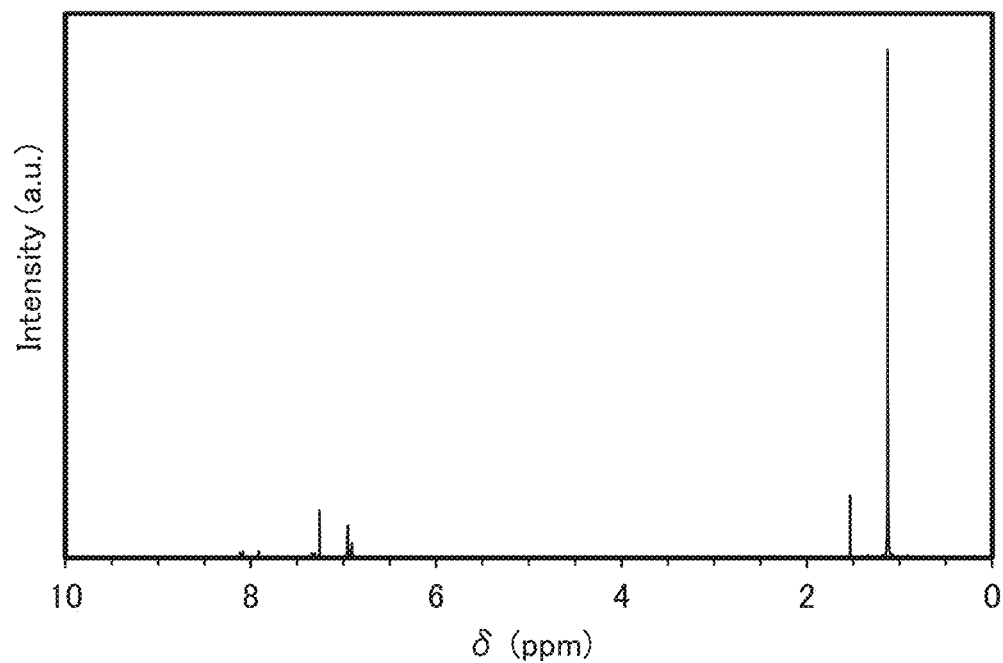
FIGS. 24A and 24B Diagrams showing NMR charts of a compound in Example.
Figure 24B:
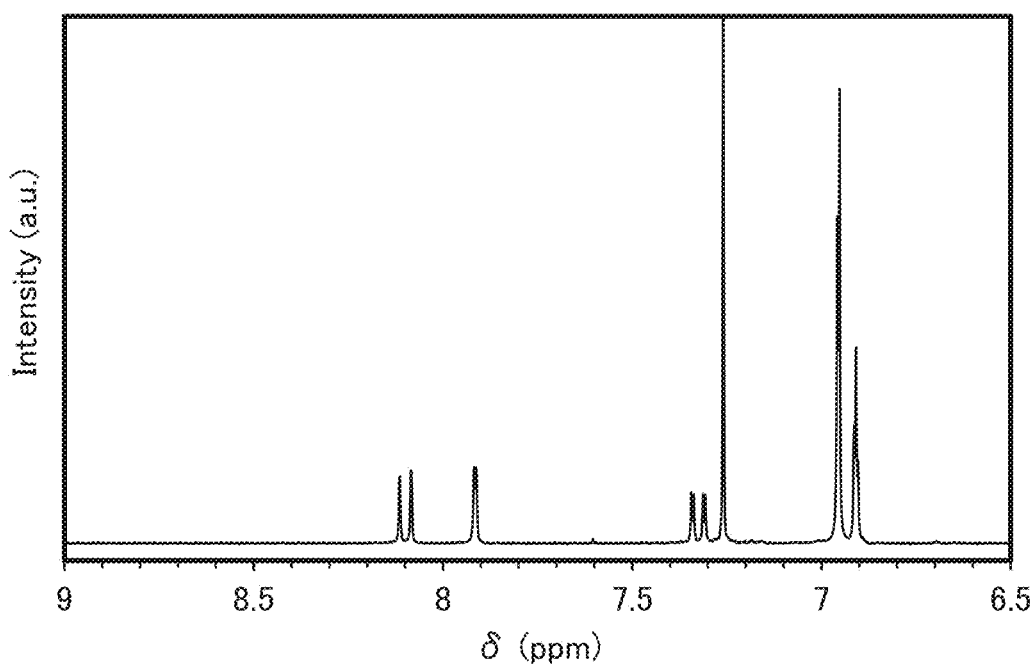
Figure 25:
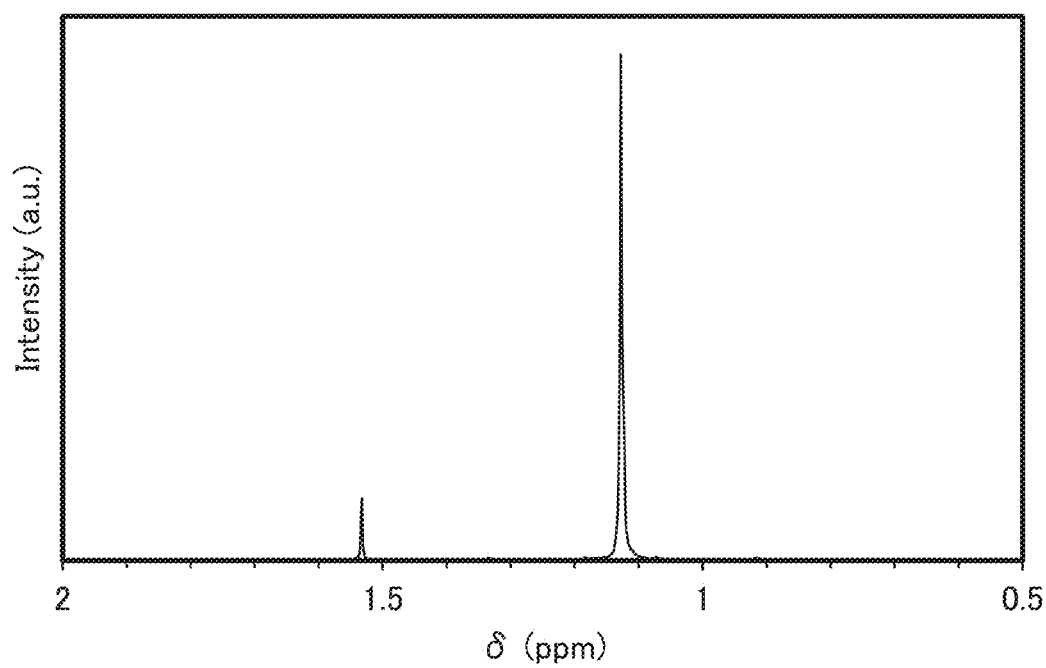
FIG. 25 A diagram showing an NMR chart of a compound in Example.

Results of $^1$H NMR measurement of the yellow solid obtained in Step 1 described above will be described below. FIG. 24 and FIG. 25 are the $^1$H-NMR charts. Note that FIG. 24(B) is an enlarged chart of the range of 6.5 ppm to 9.0 ppm of FIG. 24(A). FIG. 25 is an enlarged chart of the range of 0.5 ppm to 2.0 ppm of FIG. 24(A). The results indicate that 2,6tBu-mmtBuDPhA2Anth was obtained.

$^1$H NMR (CDCl$_3$, 300 MHz): σ=8.11 (d, J=9.3 Hz, 2H), 7.92 (d, J=1.5 Hz, 1H), 7.34 (dd, J=9.3 Hz, 2.0 Hz, 2H), 6.96-6.95 (m, 8H), 6.91-6.90 (m, 4H), 1.13-1.12 (m, 90H).

Figure 26:
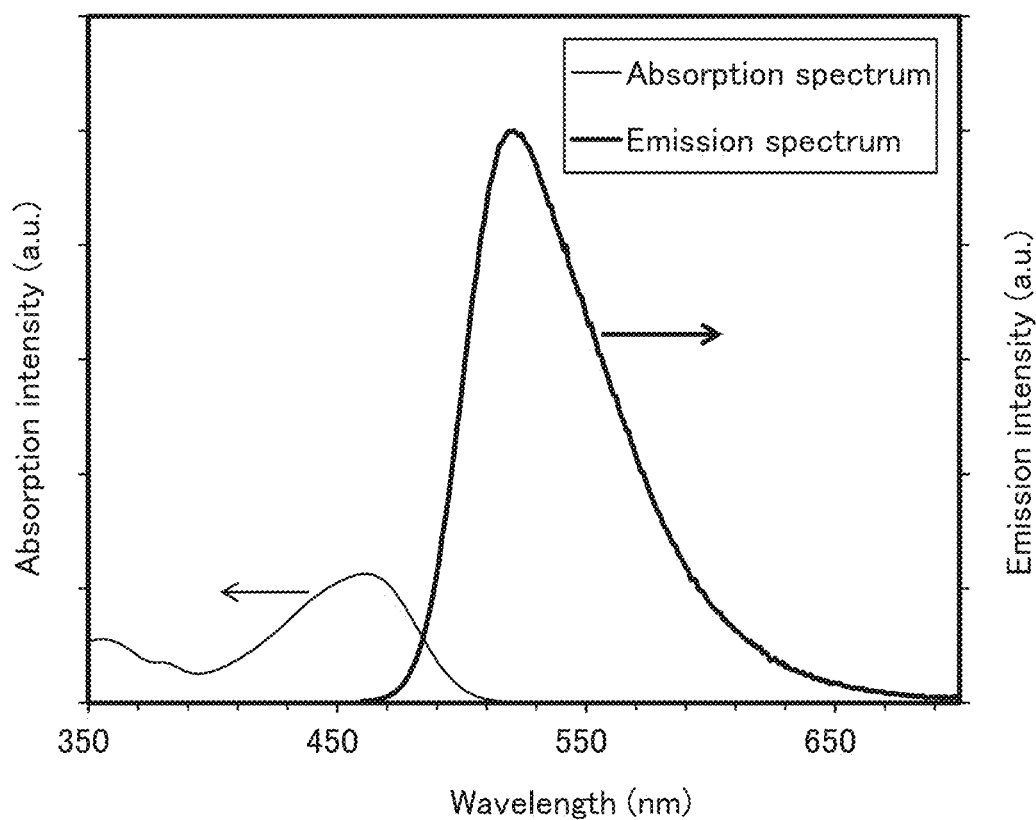
FIG. 26 A diagram showing absorption and emission spectra of a compound in Example.

Next, FIG. 26 shows the measurement results of the absorption spectrum and the emission spectrum of 2,6tBu-mmtBuDPhA2Anth in a toluene solution. The measurement method is similar to the method described in Example 1.

As shown in FIG. 26, in the case of 2,6tBu-mmtBuDPhA2Anth in the toluene solution, absorption peaks were observed at around 461 nm, 379 nm, and 358 nm, and an emission wavelength peak was at 521 nm (excitation wavelength: 455 nm).

Example 5

In this example, a synthesis method of 1,3,8,10-tetra-tert-butyl-7,14-bis(3,5-di-tert-butylphenyl)-5,12-dihydroquino [2,3-b]acridine (abbreviation: Oct-tBuDPQd), which is an organic compound of one embodiment of the present invention represented by Structural Formula (104) of Embodiment 1, will be described. This compound is a guest material having protecting groups, which can be favorably used for a light-emitting element of one embodiment of the present invention.

Step 1: Synthesis of 1,4-cyclohexadiene-1,4-dicarboxylic acid and 2,5-bis{(3,5-di-tert-butylphenyl) amino}-dimethylester 5.6 g (24 mmol) of 1,4-cyclohexanedione-2,5-dicarboxylic dimethyl and 10 g (48 mmol) of 3,5-di-tert-butylaniline were put into a 200 mL three-neck flask equipped with a reflux pipe, and this mixture was stirred at 170° C. for 2 hours. Methanol was added to the obtained reddish-orange solid to form a slurry, and the mixture was collected by suction filtration. The obtained solid was washed with hexane and methanol and dried, so that 12 g of an objective reddish-orange solid was obtained in a yield of 82%. The synthesis scheme of Step 1 is shown in (E-1) below.

[Chemical Formula 51]

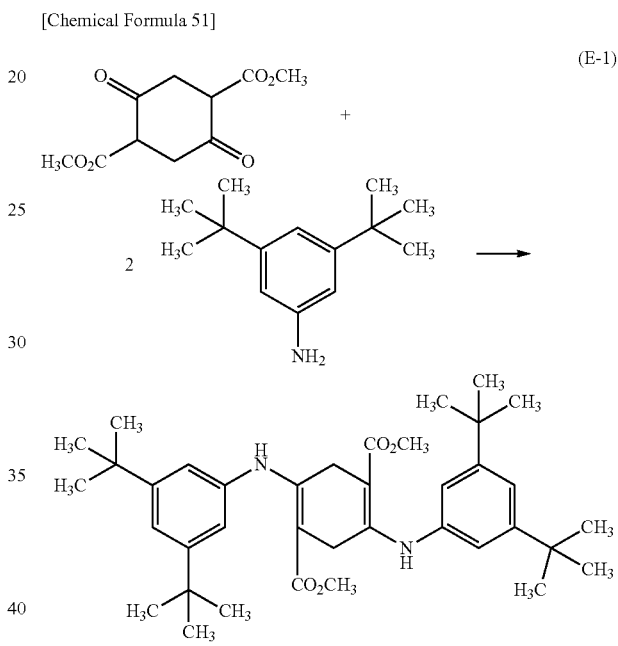

(E-1)

Given below are $^1$H NMR numerical data of the obtained solid. The data reveal that an objective compound was obtained.

$^1$H NMR (chloroform-d, 500 MHz): δ=10.6 (s, 2H), 7.20 (t, J=1.5 Hz, 2H), 6.94 (d, J=2.0 Hz, 4H), 3.65 (s, 6H), 3.48 (s, 4H), 1.33 (s, 36H).

Step 2: Synthesis of 1,4-benzenedicarboxylic acid and 2,5-bis{(3,5-di-tert-butylphenyl)amino}-dimethylester 12 g (20 mmol) of 1,4-cyclohexadiene-1,4-dicarboxylic acid and 2,5-bis{(3,5-di-tert-butylphenyl)amino}-dimethylester, which were obtained in Step 1, and 150 mL of toluene were put into a 300 mL three-neck flask equipped with a reflux pipe. The mixture was refluxed for 15 hours with air bubbles. After stirring, the precipitated solid was collected by suction filtration and the obtained solid was washed with hexane and methanol, so that 7.3 g of an objective red solid was obtained. The obtained filtrate was concentrated and a solid is further obtained. This solid was washed with hexane and methanol and collected by suction filtration, so that 3.1 g of an objective red solid was obtained. Thus, 10.4 g of the objective compounds were obtained in total in a yield of 85%. The synthesis scheme of Step 2 is shown in (E-2) below.

[Chemical Formula 52]

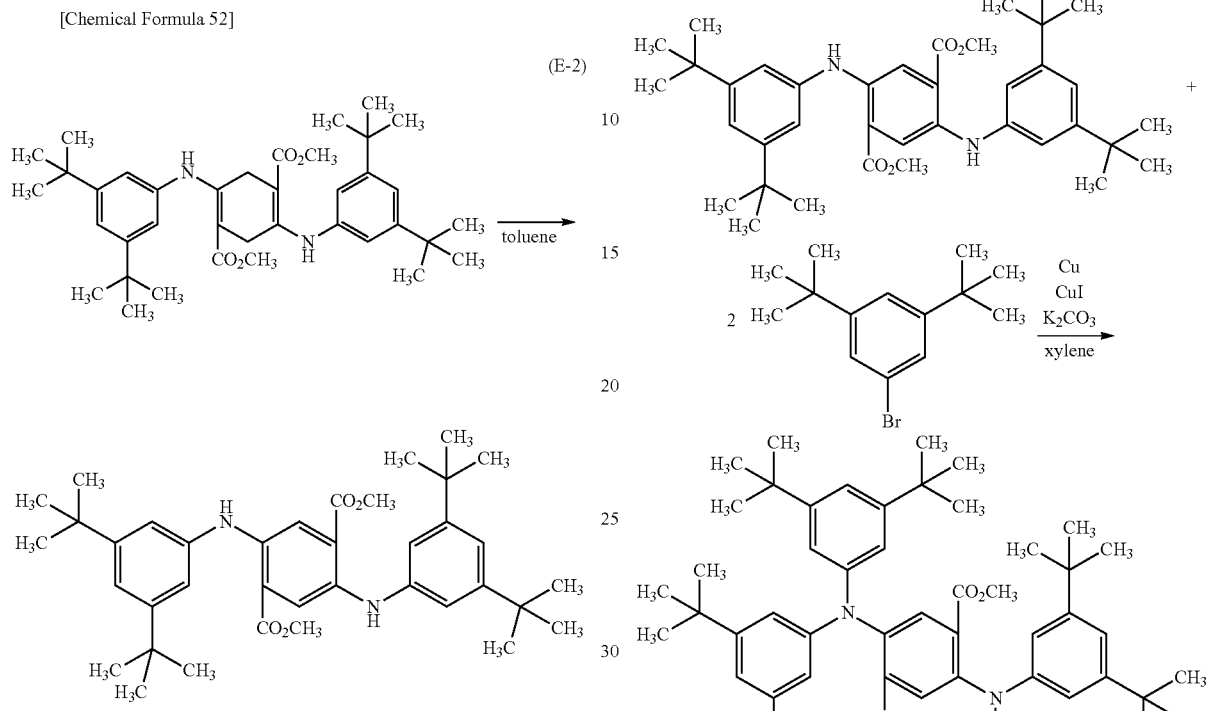

Given below are $^1$H NMR numerical data of the obtained solid. The data reveal that an objective compound was obtained.

$^1$H NMR (chloroform-d, 500 MHz): δ=8.84 (s, 2H), 8.18 (s, 2H), 7.08 (d, J=2.0 Hz, 4H), 7.20 (t, J=1.0 Hz, 2H), 3.83 (s, 6H), 1.34 (s, 36H).

Step 3: Synthesis of 1,4-benzenedicarboxylic acid and 2,5-bis[N,N'-bis(3,5-di-tert-butylphenyl)amino]-dimethylester 4.0 g (6.7 mmol) of 1,4-benzenedicarboxylic acid and 2,5-bis{(3,5-di-tert-butylphenyl)amino}-dimethylester, which were obtained in Step 2, 3.9 g (14.6 mmol) of 1-bromo-3,5-di-tert-butylbenzene, 0.46 g (7.3 mmol) of copper, 50 mg (0.26 mmol) of copper iodide, 1.0 g (7.3 mmol) of potassium carbonate, and 10 mL of xylene were put into a 200 mL three-neck flask equipped with a reflux pipe, the mixture was degassed at reduced pressure, and the air in the flask was replaced with nitrogen. This mixture was refluxed for 20 hours. To the obtained mixture, 0.46 g (7.3 mmol) of copper and 50 mg of copper iodide (0.26 mmol) were added, and the mixture was further refluxed for 16 hours. Dichloromethane was added to the obtained mixture to form a slurry. The solid was removed by suction filtration, and the obtained filtrate was concentrated. The obtained solid was washed with hexane and ethanol. The washed solid was recrystallized with hexane/toluene to give 4.4 g of a yellow solid, which was an objective compound, in a yield of 72%. The synthesis scheme of Step 3 is shown in (E-3) below.

[Chemical Formula 53]

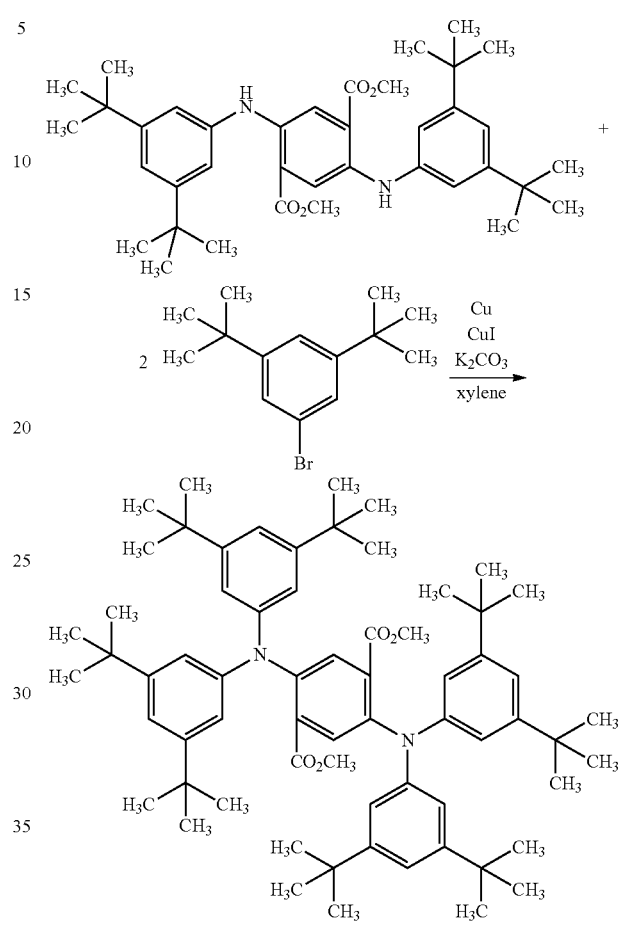

Given below are $^1$H NMR numerical data of the obtained solid. The data reveal that an objective compound was obtained.

$^1$H NMR (chloroform-d, 500 MHz): δ=7.48 (s, 2H), 6.97 (t, J=2.0 Hz, 4H), 7.08 (d, J=1.5 Hz, 8H), 3.25 (s, 6H), 1.23 (s, 72H).

Step 4: Synthesis of 1,3,8,10-tetra-tert-butyl-7,14-bis(3,5-di-tert-butyl phenyl)-5,12-dihydroquino[2,3-b]acridine-7,14-dione (abbreviation: Oct-tBuDPQd)

4.4 g (4.8 mmol) of 1,4-benzenedicarboxylic acid and 2,5-bis[N,N'-bis(3,5-di-tert-butylphenyl)amino]-dimethyl ester, which were obtained in Step 3, and 20 mL of methanesulfonate were put into a 100 mL three-neck flask equipped with a reflux pipe, and the mixture was stirred at 160° C. for 7 hours. The mixture was cooled to room temperature, slowly poured into 300 mL of ice water, and then left until it reached room temperature. This mixture was filtered by gravity filtration, and the obtained solid was washed with water and a saturated aqueous solution of sodium hydrogencarbonate. This solid was dissolved in toluene, the obtained toluene solution was washed with water and saturated saline, and drying was performed with magnesium sulfate. This mixture was filtered through Celite (produced by Wako Pure Chemical Industries, Ltd., Catalog No.: 537-02305) and aluminum oxide. The obtained filtrate was concentrated to give 3.3 g of a blackish-brown solid. The obtained solid was purified by silica gel column chromatography (developing solvent: hexane:ethyl acetate=20:1) to give 150 mg of a reddish-orange solid, which was an objective compound, in a yield of 5%. The synthesis scheme of Step 4 is shown in (E-4) below.

[Chemical Formula 54]

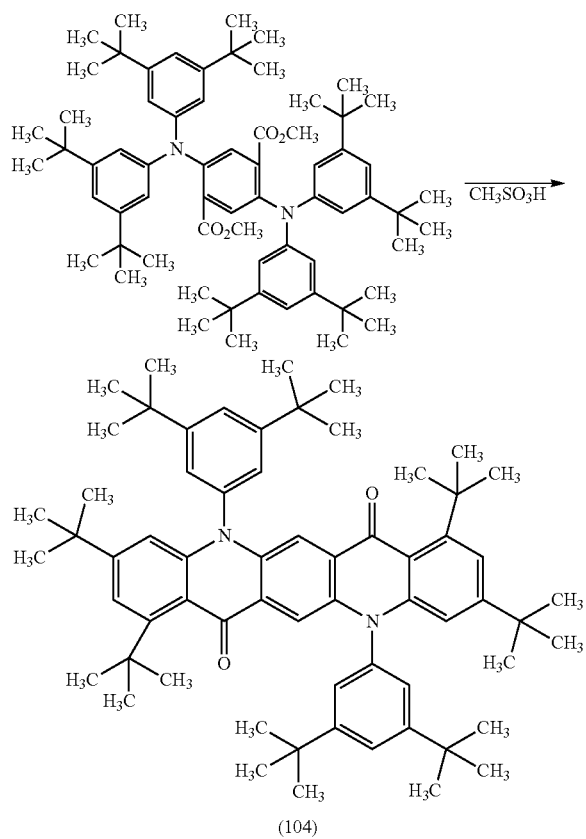

(E-4)

(104)

Figure 27A:
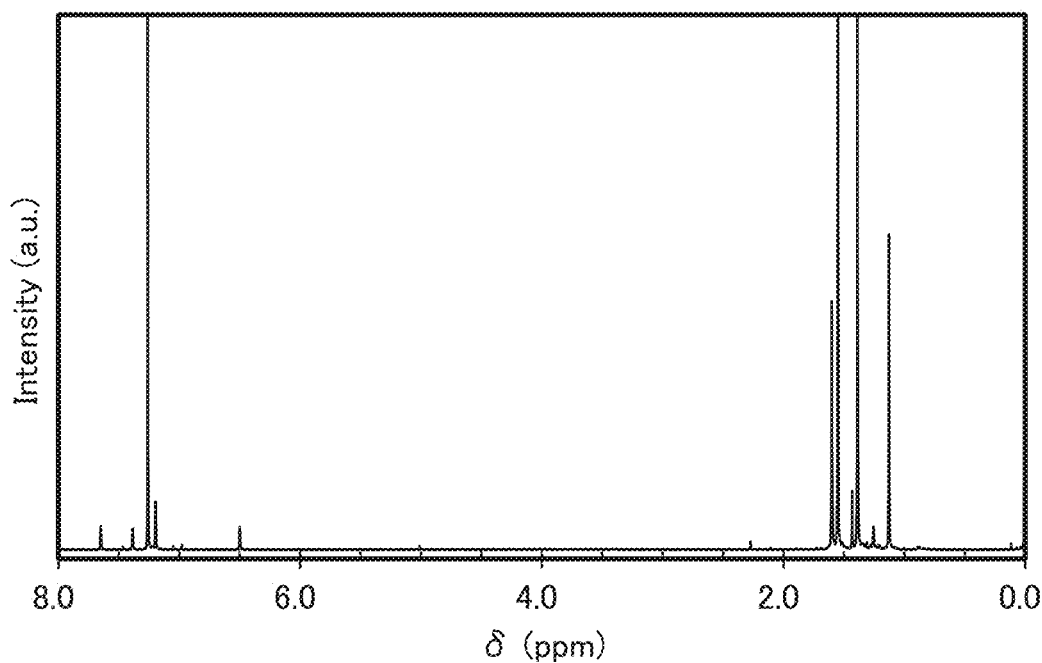
FIGS. 27A and 27B Diagrams showing NMR charts of a compound in Example.
Figure 27B:
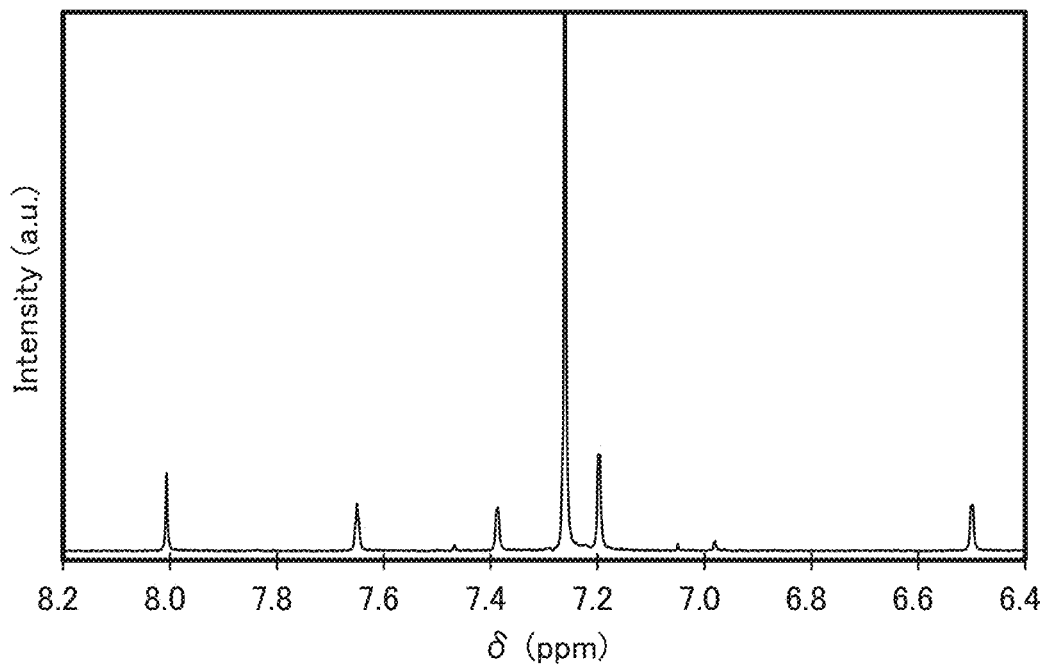
Figure 28:
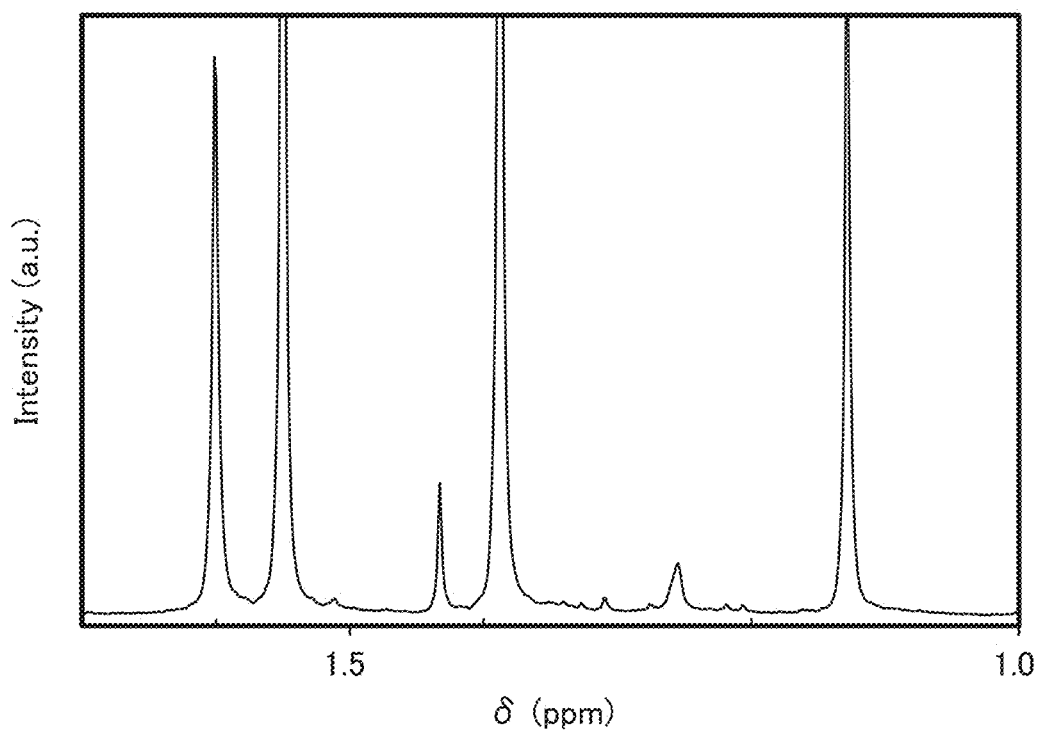
FIG. 28 A diagram showing an NMR chart of a compound in Example.

Results of $^1$H NMR measurement of the yellow solid obtained in Step 4 described above will be described below. FIG. 27 and FIG. 28 are the $^1$H-NMR charts. Note that FIG. 27(B) is an enlarged chart of the range of 6.5 ppm to 9.0 ppm of FIG. 27(A). FIG. 28 is an enlarged chart of the range of 0.5 ppm to 2.0 ppm of FIG. 27(A). The results indicate that Oct-tBuDPQd was obtained.

$^1$H NMR (chloroform-d, 500 MHz): δ=8.00 (s, 2H), 7.65 (t, J=2.0 Hz, 2H), 7.39 (d, J=1.0 Hz, 4H), 7.20 (d, J=2.0 Hz, 2H), 6.50 (d, J=1.0 Hz, 2H), 1.60 (s, 18H), 1.39 (s, 36H), 1.13 (s, 18H).

Figure 29:
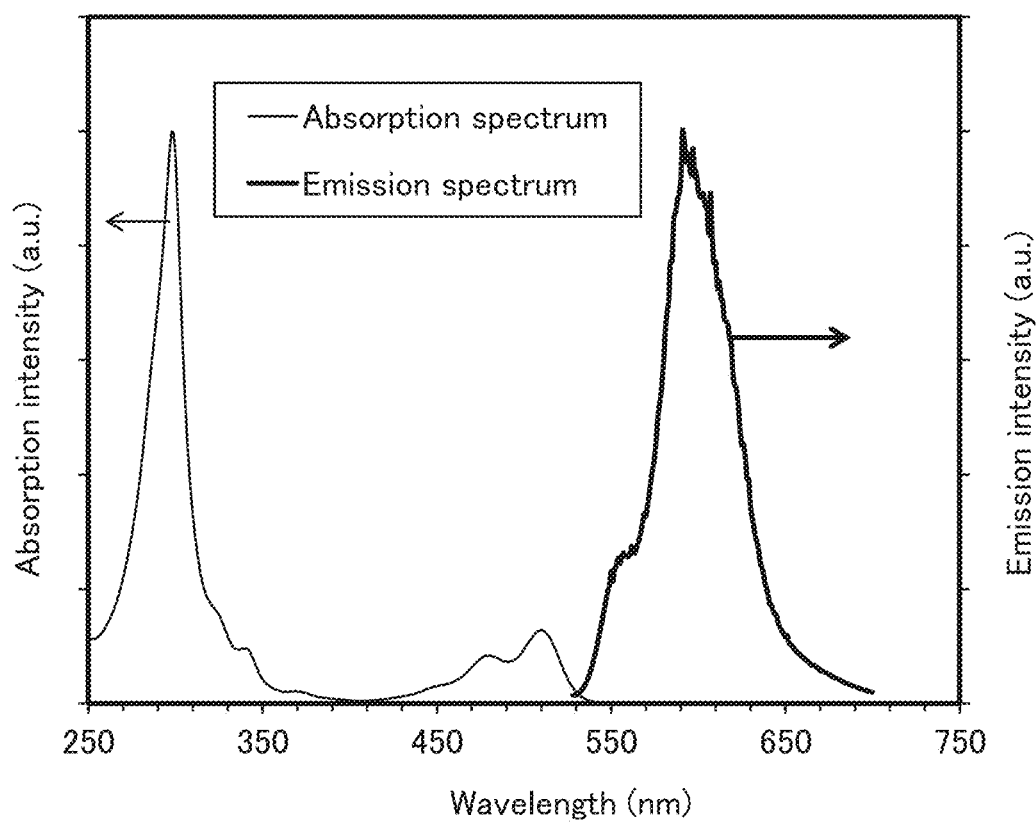
FIG. 29 A diagram showing absorption and emission spectra of a compound in Example.
Figure 30:
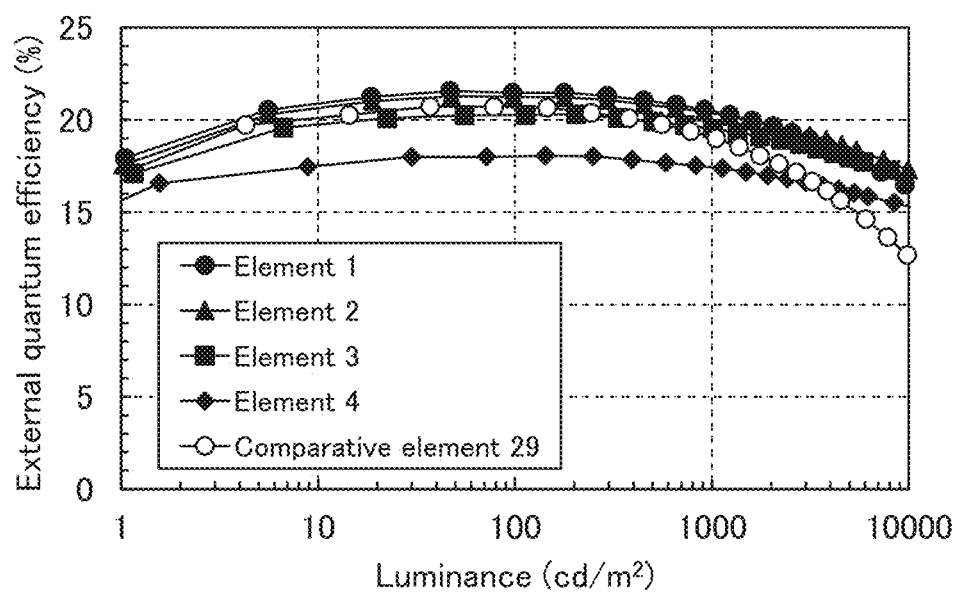
FIG. 30 A diagram showing external quantum efficiency-luminance characteristics of light-emitting elements in Example.
Figure 31:
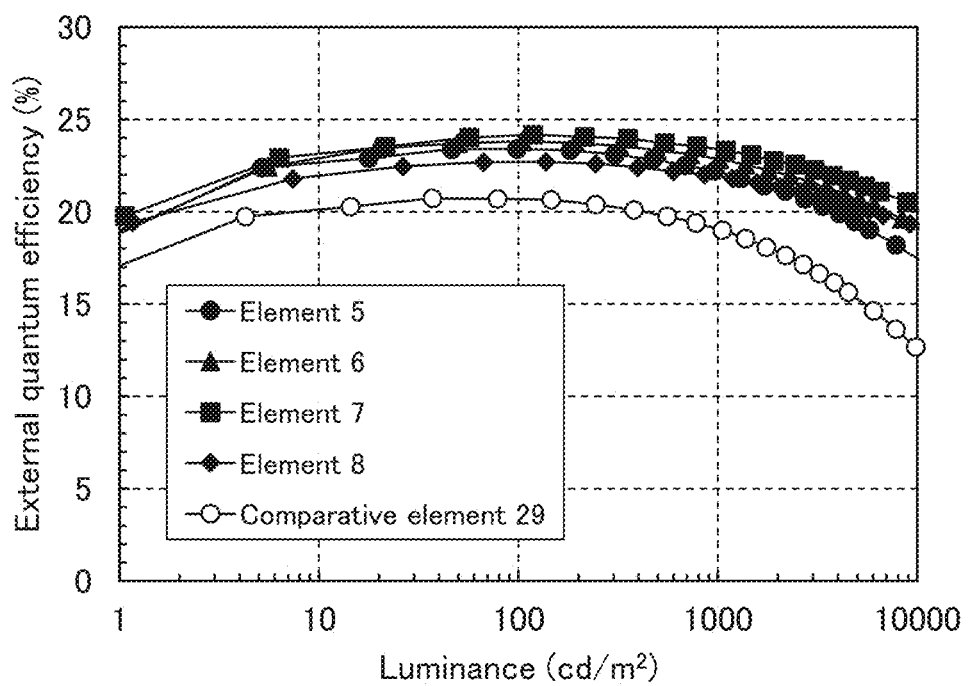
FIG. 31 A diagram showing external quantum efficiency-luminance characteristics of light-emitting elements in Example.
Figure 32:
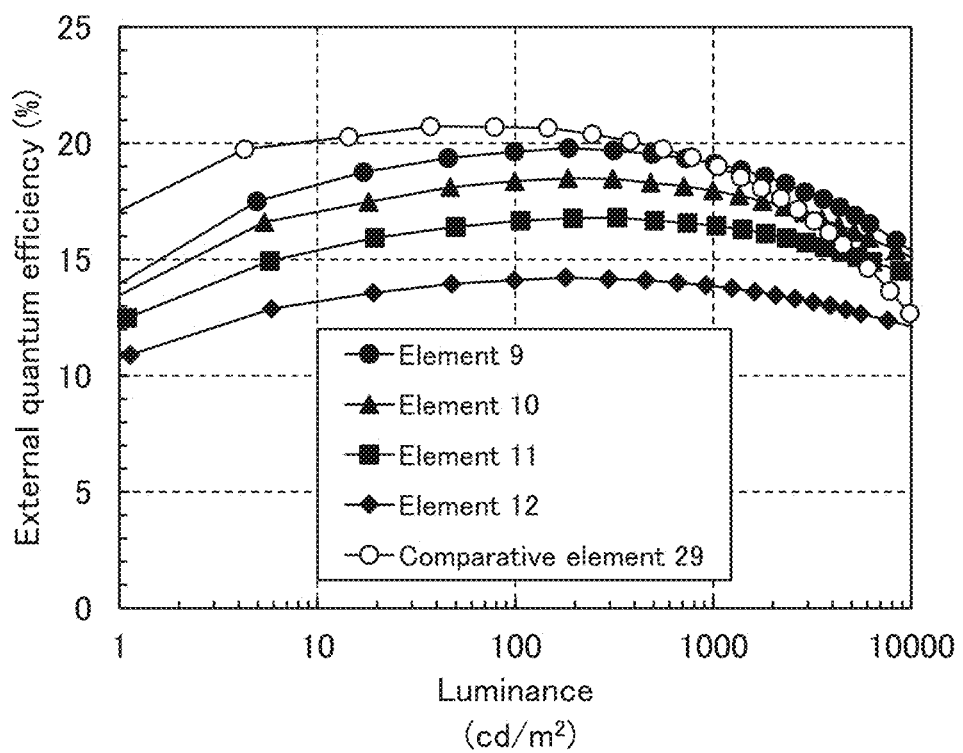
FIG. 32 A diagram showing external quantum efficiency-luminance characteristics of light-emitting elements in Example.
Figure 33:
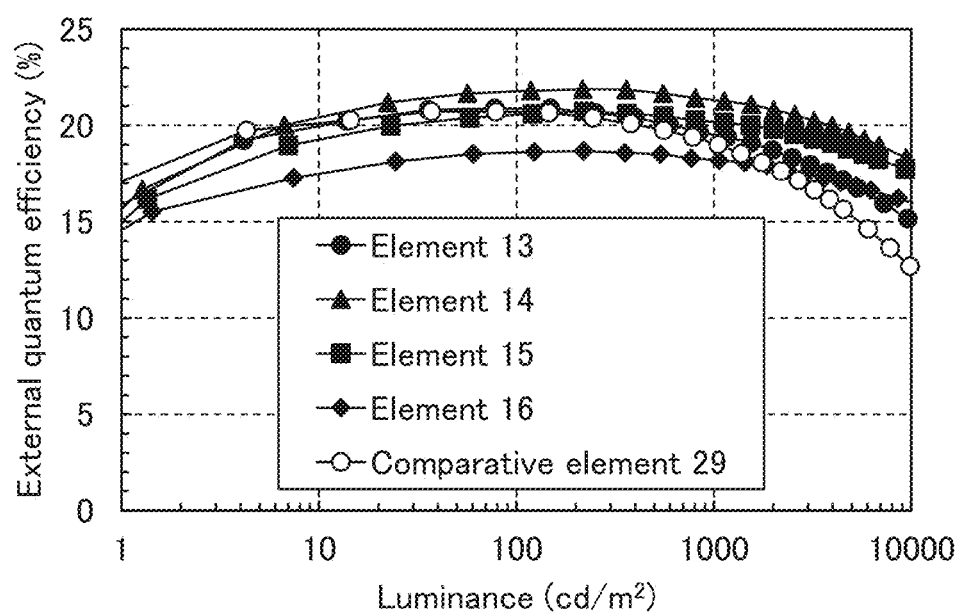
FIG. 33 A diagram showing external quantum efficiency-luminance characteristics of light-emitting elements in Example.
Figure 34:
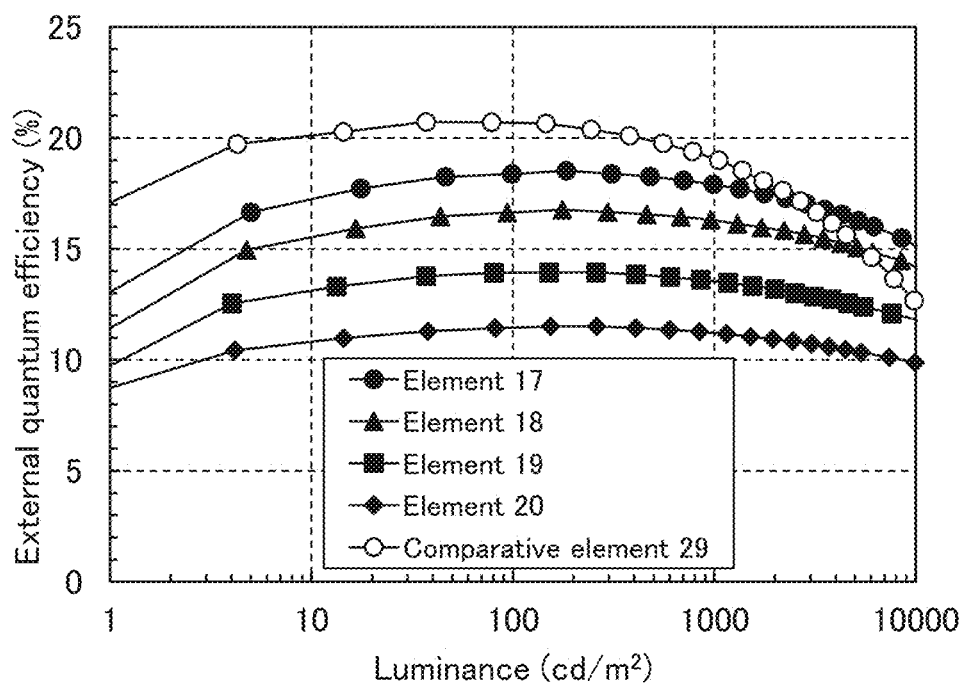
FIG. 34 A diagram showing external quantum efficiency-luminance characteristics of light-emitting elements in Example.
Figure 35:
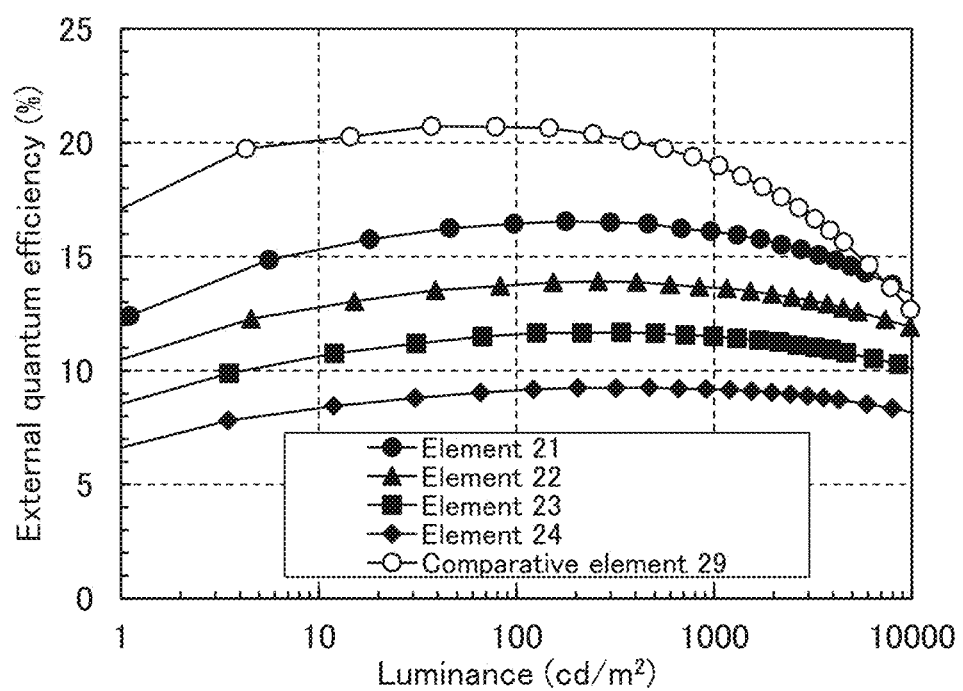
FIG. 35 A diagram showing external quantum efficiency-luminance characteristics of light-emitting elements in Example.
Figure 36:
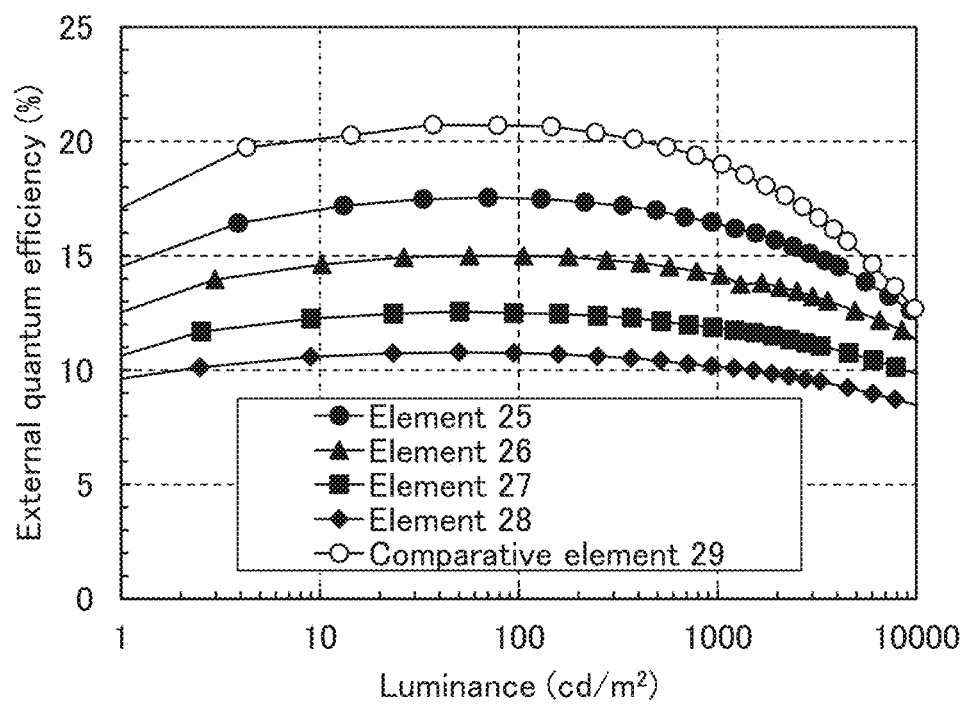
FIG. 36 A diagram showing external quantum efficiency-luminance characteristics of light-emitting elements in Example.

Next, FIG. 29 shows the measurement results of the absorption spectrum and the emission spectrum of Oct-tBuDPQd in a dichloromethane solution. The measurement method is similar to the method described in Example 1.

As shown in FIG. 29, in the case of Oct-tBuDPQd in the dichloromethane solution, absorption peaks were observed at around 510 nm, 480 nm, and 447 nm, and an emission wavelength peak was at 591 nm (excitation wavelength: 510 nm).

Next, the calculation results of the HOMO level and the LUMO level of Oct-tBuDPQd on the basis of a cyclic voltammetry (CV) measurement are shown. The calculation method is shown below.

An electrochemical analyzer (ALS model 600A or 600C, manufactured by BAS Inc.) was used as a measurement apparatus. To prepare a solution for the CV measurement, dehydrated dimethylformamide (DMF) (produced by Sigma-Aldrich Inc., 99.8%, catalog No. 22705-6) was used as a solvent, tetra-n-butylammonium perchlorate (n-Bu$_4$NClO$_4$) (produced by Tokyo Chemical Industry Co., Ltd., catalog No. T0836) as a supporting electrolyte was dissolved at a concentration of 100 mmol/L, and the object to be measured was also dissolved at a concentration of 2 mmol/L. A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an Ag/Ag$^+$ electrode (RE7 reference electrode for non-aqueous solvent, manufactured by BAS Inc.) was used as a reference electrode. Note that the measurement was performed at room temperature (20° C. to 25° C.). In addition, the scan speed in the CV measurement was fixed to 0.1 V/sec, and an oxidation potential Ea [V] and a reduction potential Ec [V] with respect to the reference electrode were measured. Ea was an intermediate potential of an oxidation-reduction wave, and Ec was an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]=−4.94−Ea and LUMO level [eV]=−4.94−Ec.

CV measurement was repeated 100 times, and the oxidation-reduction wave in the hundredth cycle was compared with the oxidation-reduction wave in the first cycle to examine the electrical stability of the compound.

As a result, it was found that the HOMO level of Oct-tBuDPQd was −5.60 eV and the LUMO level thereof was −3.06 eV. In addition, when the oxidation-reduction wave was repeatedly measured and the waveform of the first cycle was compared with that in the hundredth cycle, 74% of the peak intensity was maintained in the measurement of the oxidation potential Ea [V]; thus, resistance to oxidation of Oct-tBuDPQd was found to be high.

Then, thermogravimetry-differential thermal analysis (TG-DTA) of Oct-tBuDPQd was performed. The measurement was performed using a high vacuum differential type differential thermal balance (TG-DTA2410SA, manufactured by Bruker AXS K.K.). The measurement was performed at 10 Pa at a temperature rising rate of 10° C./min under a nitrogen stream (a flow rate of 2.4 mL/min). The thermogravimetry-differential thermal analysis showed that the temperature (decomposition temperature) of Oct-tBuDPQd at which the weight measured by thermogravimetry becomes −5% of the weight at the start of the measurement is 234° C., which means sublimation at a relatively low temperature at 10 Pa.

Example 6

In this example, fabrication examples of light-emitting elements of embodiments of the present invention and comparative light-emitting elements and the characteristics of the light-emitting elements are described. The structure of each of the light-emitting elements fabricated in this example is the same as that in FIG. 1(A). Table 1 to Table 3 show the details of the element structures. The structures and abbreviations of compounds that were used are shown below. Note that the above examples and embodiments can be referred to for other organic compounds.

[Chemical Formula 55]
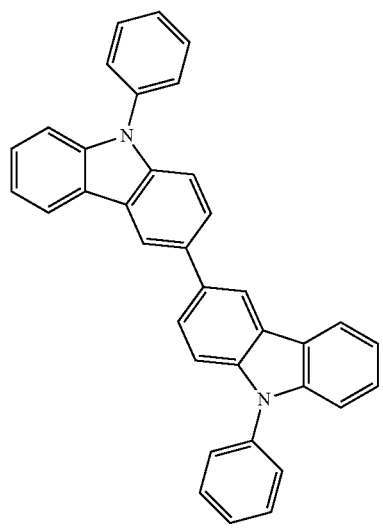
PCCP
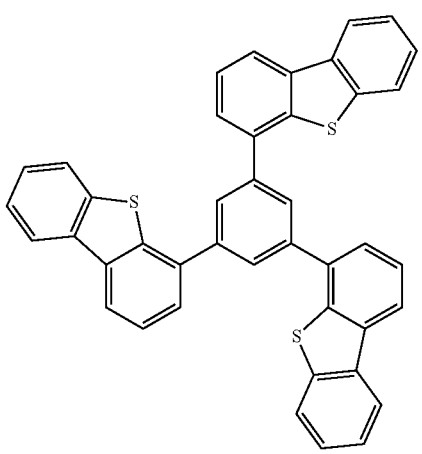
DBT3P-II
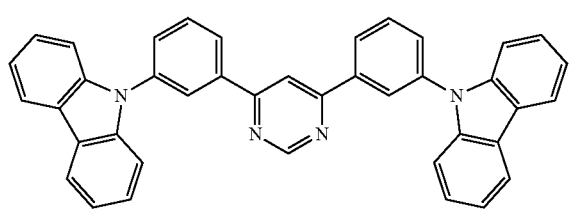
4,6mCzP2Pm
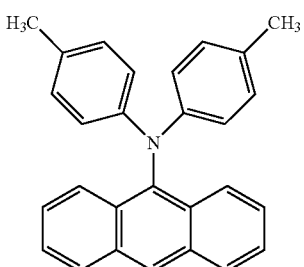
TTPA
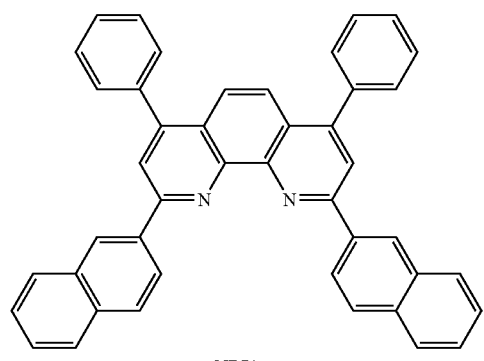
NBPhen
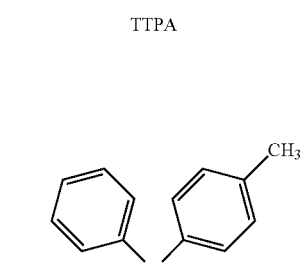
MeDPhA2A
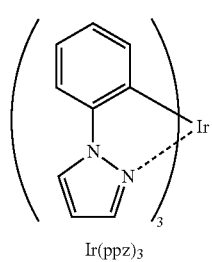
Ir(ppz)₃

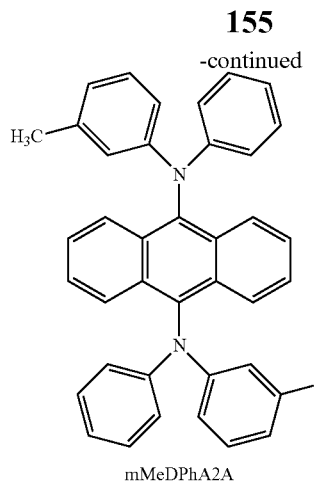

mMeDPhA2A

TABLE 1

| Layer | | Reference numeral | Thickness (nm) | Material | Weight ratio |
|---|---|---|---|---|---|
| Light-emitting elements 1 to 4 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | 4,6mCzP2Pm | — |
| | Light-emitting layer | 130 | 40 | 4,6mCzP2Pm:Ir(ppz)$_3$:2tBu-ptBuDPhA2Anth | 0.8:0.2:$x_1$ |
| | Hole-transport layer | 112 | 20 | PCCP | — |
| | Hole-injection layer | 111 | 40 | DBT3P-II:MoO$_3$ | 1:0.5 |
| | Anode | 101 | 70 | ITSO | — |
| Light-emitting elements 5 to 8 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | 4,6mCzP2Pm | — |
| | Light-emitting layer | 130 | 40 | 4,6mCzP2Pm:Ir(ppz)$_3$:2tBu-mmtBuDPhA2Anth | 0.8:0.2:$x_1$ |
| | Hole-transport layer | 112 | 20 | PCCP | — |
| | Hole-injection layer | 111 | 40 | DBT3P-II:MoO$_3$ | 1:0.5 |
| | Anode | 101 | 70 | ITSO | — |
| Light-emitting elements 9 to 12 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | 4,6mCzP2Pm | — |
| | Light-emitting layer | 130 | 40 | 4,6mCzP2Pm:Ir(ppz)$_3$:2,6tBu-ptBuDPhA2Anth | 0.8:0.2:$x_1$ |
| | Hole-transport layer | 112 | 20 | PCCP | — |
| | Hole-injection layer | 111 | 40 | DBT3P-II:MoO$_3$ | 1:0.5 |
| | Anode | 101 | 70 | ITSO | — |

TABLE 1-continued

| Layer | | Reference numeral | Thickness (nm) | Material | Weight ratio |
|---|---|---|---|---|---|
| Light-emitting elements 13 to 16 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | 4,6mCzP2Pm | — |
| | Light-emitting layer | 130 | 40 | 4,6mCzP2Pm:Ir(ppz)$_3$:2,6tBu-mmtBuDPhA2Anth | 0.8:0.2:$x_1$ |
| | Hole-transport layer | 112 | 20 | PCCP | — |
| | Hole-injection layer | 111 | 40 | DBT3P-II:MoO$_3$ | 1:0.5 |
| | Anode | 101 | 70 | ITSO | — |

TABLE 2

| Layer | | Reference numeral | Thickness (nm) | Material | Weight ratio |
|---|---|---|---|---|---|
| Comparative light-emitting elements 17 to 20 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | 4,6mCzP2Pm | — |
| | Light-emitting layer | 130 | 40 | 4,6mCzP2Pm:Ir(ppz)$_3$:TTPA | 0.8:0.2:$x_1$ |
| | Hole-transport layer | 112 | 20 | PCCP | — |
| | Hole-injection layer | 111 | 40 | DBT3P-II:MoO$_3$ | 1:0.5 |
| | Anode | 101 | 70 | ITSO | — |
| Comparative light-emitting elements 21 to 24 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | 4,6mCzP2Pm | — |
| | Light-emitting layer | 130 | 40 | 4,6mCzP2Pm:Ir(ppz)$_3$:MeDPhA2A | 0.8:0.2:$x_1$ |
| | Hole-transport layer | 112 | 20 | PCCP | — |
| | Hole-injection layer | 111 | 40 | DBT3P-II:MoO$_3$ | 1:0.5 |
| | Anode | 101 | 70 | ITSO | — |
| Comparative light-emitting elements 25 to 28 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | 4,6mCzP2Pm | — |
| | Light-emitting layer | 130 | 40 | 4,6mCzP2Pm:Ir(ppz)$_3$:mMeDPhA2A | 0.8:0.2:$x_1$ |
| | Hole-transport layer | 112 | 20 | PCCP | — |
| | Hole-injection layer | 111 | 40 | DBT3P-II:MoO$_3$ | 1:0.5 |
| | Anode | 101 | 70 | ITSO | — |

TABLE 2-continued

|  | Layer | Reference numeral | Thickness (nm) | Material | Weight ratio |
|---|---|---|---|---|---|
| Comparative light-emitting element 29 | Electrode | 102 | 200 | Al | — |
|  | Electron-injection layer | 119 | 1 | LiF | — |
|  | Electron-transport layer | 118(2) | 10 | NBPhen | — |
|  |  | 118(1) | 20 | 4,6mCzP2Pm | — |
|  | Light-emitting layer | 130 | 40 | 4,6mCzP2Pm:Ir(ppz)$_3$ | 0.8:0.2 |
|  | Hole-transport layer | 112 | 20 | PCCP | — |
|  | Hole-injection layer | 111 | 40 | DBT3P-II:MoO$_3$ | 1:0.5 |
|  | Anode | 101 | 70 | ITSO | — |

TABLE 3

|  | Light-emitting elements 1, 5, 9, and 13 Comparative light-emitting elements 17, 21, and 25 | Light-emitting elements 2, 6, 10, and 14 Comparative light-emitting elements 18, 22, and 26 | Light-emitting elements 3, 7, 11, and 15 Comparative light-emitting elements 19, 23, and 27 | Light-emitting elements 4, 8, 12, and 16 Comparative light-emitting elements 20, 24, and 28 |
|---|---|---|---|---|
| $x_1$ | 0.01 | 0.025 | 0.05 | 0.1 |

<Fabrication of Light-Emitting Elements>

Fabrication methods of the light-emitting elements fabricated in this example will be described below.

<<Fabrication of Light-Emitting Element 1 to Light-Emitting Element 4>>

As the electrode 101, an ITSO film was formed to a thickness of 70 nm over a glass substrate. Note that the electrode area of the electrode 101 was set to 4 mm$^2$ (2 mm×2 mm).

Next, as the hole-injection layer 111, DBT3P-II and molybdenum oxide (MoO$_3$) were deposited over the electrode 101 by co-evaporation in a weight ratio (DBT3P-II: MoO$_3$) of 1:0.5 to a thickness of 40 nm.

Then, as the hole-transport layer 112, PCCP was deposited on the hole-injection layer 111 by evaporation to a thickness of 20 nm.

Next, as the light-emitting layer 130, 4,6mCzP2Pm, tris[2-(1H-pyrazol-1-yl-κN$^2$)phenyl-κC]iridium(III) (abbreviation: Ir(ppz)$_3$), and 2tBu-ptBuDPhA2Anth were deposited over the hole-transport layer 112 by co-evaporation at a weight ratio (4,6mCzP2Pm:Ir(ppz)$_3$:2tBu-ptBuDPhA2Anth) of 0.8:0.2:$x_1$ to a thickness of 40 nm. In the light-emitting layer 130, Ir(ppz)$_3$ is a phosphorescent material containing Ir and 4,6mCzP2Pm and Ir(ppz)$_3$ form an exciplex in combination. Furthermore, 2tBu-ptBuDPhA2Anth is a fluorescent material having protecting groups. Note that the value $x_1$ differs between the light-emitting elements, and Table 3 shows the value $x_1$ in each of the light-emitting elements.

Next, as the electron-transport layer 118, 4,6mCzP2Pm and NBPhen were sequentially deposited by evaporation to a thickness of 20 nm and to a thickness of 10 nm, respectively, over the light-emitting layer 130. Then, as the electron-injection layer 119, LiF was deposited on the electron-transport layer 118 by evaporation to a thickness of 1 nm.

Next, as the electrode 102, aluminum (Al) was formed over the electron-injection layer 119 to a thickness of 200 nm.

Next, in a glove box containing a nitrogen atmosphere, a light-emitting element 1 to a light-emitting element 4 were sealed by fixing a glass substrate for sealing to the glass substrate on which the organic materials were formed using a sealant for organic EL. Specifically, the sealant was applied to the periphery of the organic materials formed on the glass substrate, the glass substrate was bonded to the glass substrate for sealing, irradiation with ultraviolet light having a wavelength of 365 nm at 6 J/cm$^2$ was performed, and heat treatment at 80° C. for one hour was performed. Through the above steps, the light-emitting element 1 to the light-emitting element 4 were obtained.

<<Fabrication of Light-Emitting Element 5 to Light-Emitting Element 16 and Comparative Light-Emitting Element 17 to Comparative Light-Emitting Element 29>>

A light-emitting element 5 to a light-emitting element 16 and a comparative light-emitting element 17 to a comparative light-emitting element 29 are different from the above-described light-emitting element 1 to light-emitting element 4 only in a fluorescent material (guest material) used for the light-emitting layer 130, and other steps of the fabrication method are the same as those for the light-emitting element 1. The details of the element structures are shown in Table 1 to Table 3; thus, the details of the fabrication methods are omitted.

The guest materials used for the light-emitting element 1 to the light-emitting element 16 each have protecting groups around a luminophore, whereas the guest materials used for the comparative light-emitting element 17 to the comparative light-emitting element 28 have no bulky substituent. Moreover, a guest material is not used for a light-emitting layer of the comparative light-emitting element 29. Thus, light emission observed from the comparative light-emitting element 29 is light emission of the exciplex formed by 4,6mCzP2Pm and Ir(ppz)$_3$.

<Characteristics of Light-Emitting Elements>

Next, the characteristics of the fabricated light-emitting element 1 to light-emitting element 16 and comparative light-emitting element 17 to comparative light-emitting element 29 were measured. Luminance and CIE chromaticity were measured with a luminance colorimeter (BM-5A manufactured by TOPCON TECHNOHOUSE CORPORATION), and electroluminescence spectra were measured with a multi-channel spectrometer (PMA-11 manufactured by Hamamatsu Photonics K.K.).

FIG. 30 to FIG. 36 show the external quantum efficiency-luminance characteristics of the light-emitting element 1 to the light-emitting element 16 and the comparative light-emitting element 17 to the comparative light-emitting element 29. FIG. 37 to FIG. 43 show the electroluminescence spectra of the light-emitting element 1 to the light-emitting element 16 and the comparative light-emitting element 17 to the comparative light-emitting element 29 to which a current at a current density of 2.5 mA/cm² was supplied. Note that the measurement of the light-emitting elements was performed at room temperature (in an atmosphere maintained at 23° C.).

Table 4 and Table 5 show the element characteristics of the light-emitting element 1 to the light-emitting element 16 and the comparative light-emitting element 17 to the comparative light-emitting element 29 at around 1000 cd/m².

TABLE 4

|  | Voltage (V) | Current density (mA/cm²) | CIE chromaticity (x, y) | Luminance (cd/m²) | Current efficiency (cd/A) | Power efficiency (lm/W) | External quantum efficiency (%) |
|---|---|---|---|---|---|---|---|
| Light-emitting element 1 | 3.20 | 1.24 | (0.312, 0.637) | 915 | 73.6 | 72.2 | 20.6 |
| Light-emitting element 2 | 3.20 | 1.21 | (0.315, 0.647) | 912 | 75.7 | 74.3 | 20.4 |
| Light-emitting element 3 | 3.20 | 1.37 | (0.319, 0.650) | 1010 | 73.7 | 72.4 | 19.5 |
| Light-emitting element 4 | 3.20 | 1.70 | (0.329, 0.648) | 1129 | 66.6 | 65.4 | 17.4 |
| Light-emitting element 5 | 3.20 | 1.26 | (0.292, 0.636) | 967 | 76.7 | 75.3 | 22.2 |
| Light-emitting element 6 | 3.20 | 1.25 | (0.285, 0.651) | 1014 | 81.0 | 79.6 | 22.8 |
| Light-emitting element 7 | 3.20 | 1.30 | (0.283, 0.660) | 1094 | 84.2 | 82.7 | 23.3 |
| Light-emitting element 8 | 3.10 | 1.05 | (0.287, 0.668) | 859 | 81.7 | 82.8 | 22.0 |
| Light-emitting element 9 | 3.20 | 1.50 | (0.292, 0.643) | 1018 | 68.0 | 66.8 | 19.1 |
| Light-emitting element 10 | 3.20 | 1.51 | (0.293, 0.656) | 997 | 66.1 | 64.9 | 18.0 |
| Light-emitting element 11 | 3.20 | 1.67 | (0.298, 0.661) | 1036 | 62.1 | 61.0 | 16.5 |
| Light-emitting element 12 | 3.20 | 1.72 | (0.305, 0.662) | 919 | 53.4 | 52.5 | 13.9 |
| Light-emitting element 13 | 3.20 | 1.24 | (0.285, 0.629) | 838 | 67.6 | 66.4 | 19.7 |
| Light-emitting element 14 | 3.20 | 1.50 | (0.280, 0.646) | 1127 | 75.1 | 73.7 | 21.3 |
| Light-emitting element 15 | 3.20 | 1.54 | (0.278, 0.657) | 1123 | 72.7 | 71.4 | 20.1 |
| Light-emitting element 16 | 3.20 | 1.58 | (0.282, 0.663) | 1061 | 67.2 | 66.0 | 18.2 |

TABLE 5

|  | Voltage (V) | Current density (mA/cm²) | CIE chromaticity (x, y) | Luminance (cd/m²) | Current efficiency (cd/A) | Power efficiency (lm/W) | External quantum efficiency (%) |
|---|---|---|---|---|---|---|---|
| Comparative light-emitting element 17 | 3.20 | 1.47 | (0.332, 0.635) | 989 | 67.1 | 65.9 | 17.9 |
| Comparative light-emitting element 18 | 3.20 | 1.54 | (0.344, 0.633) | 961 | 62.4 | 61.3 | 16.3 |
| Comparative light-emitting element 19 | 3.20 | 1.63 | (0.356, 0.627) | 857 | 52.7 | 51.7 | 13.6 |
| Comparative light-emitting element 20 | 3.30 | 2.65 | (0.367, 0.620) | 1149 | 43.3 | 41.2 | 11.2 |
| Comparative light-emitting element 21 | 3.20 | 1.65 | (0.302, 0.641) | 957 | 58.1 | 57.0 | 16.1 |
| Comparative light-emitting element 22 | 3.30 | 2.28 | (0.308, 0.650) | 1159 | 50.8 | 48.3 | 13.6 |
| Comparative light-emitting element 23 | 3.30 | 2.26 | (0.314, 0.652) | 988 | 43.7 | 41.6 | 11.5 |

TABLE 5-continued

| | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Comparative light-emitting element 24 | 3.30 | 2.58 | (0.329, 0.645) | 909 | 35.3 | 33.6 | 9.2 |
| Comparative light-emitting element 25 | 3.30 | 1.64 | (0.298, 0.628) | 938 | 57.0 | 54.3 | 16.5 |
| Comparative light-emitting element 26 | 3.40 | 2.06 | (0.291, 0.643) | 1038 | 50.3 | 46.5 | 14.2 |
| Comparative light-emitting element 27 | 3.40 | 2.19 | (0.289, 0.655) | 947 | 43.3 | 40.0 | 11.9 |
| Comparative light-emitting element 28 | 3.40 | 2.50 | (0.291, 0.659) | 939 | 37.6 | 34.8 | 10.2 |
| Comparative light-emitting element 29 | 3.30 | 1.63 | (0.323, 0.610) | 1053 | 64.7 | 61.6 | 19.0 |

Figure 37:
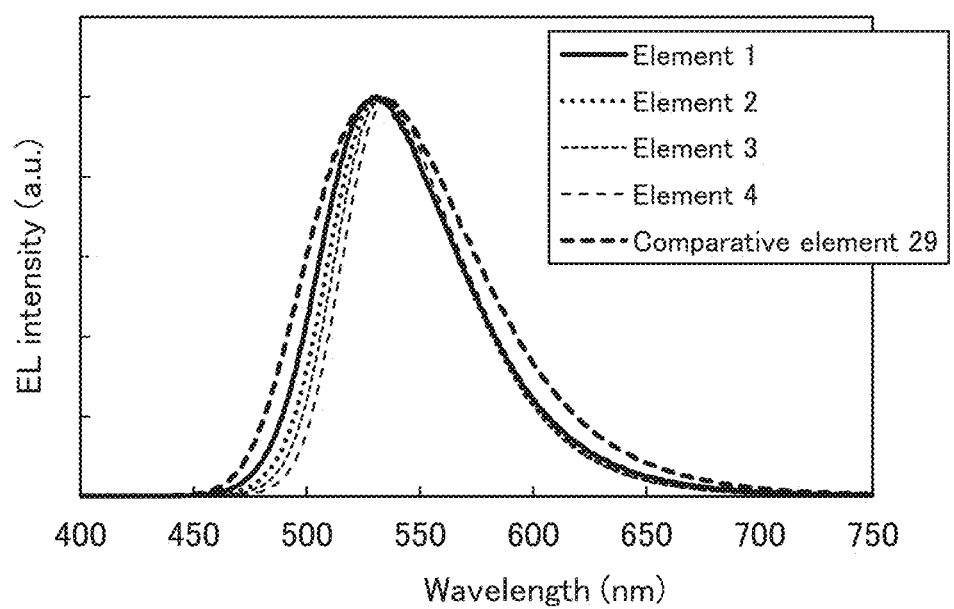
FIG. 37 A diagram showing electroluminescence spectra of light-emitting elements in Example.
Figure 38:
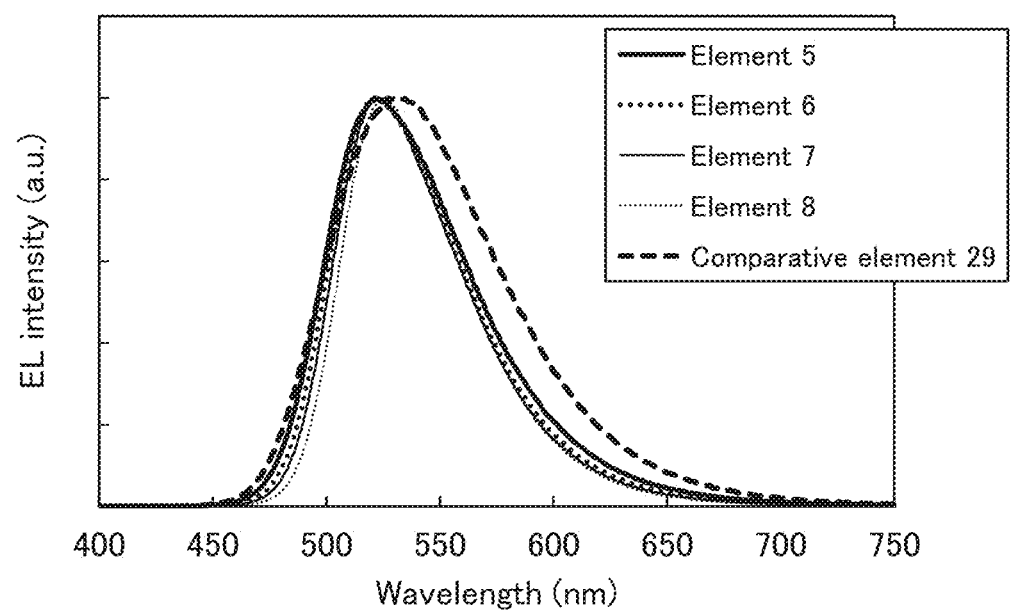
FIG. 38 A diagram showing electroluminescence spectra of light-emitting elements in Example.
Figure 39:
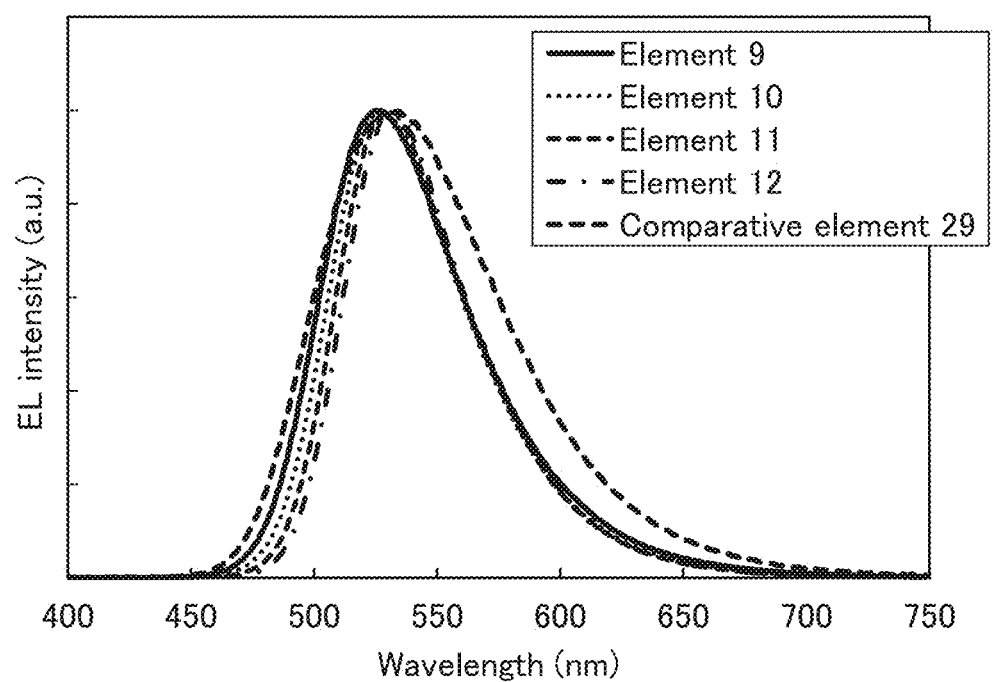
FIG. 39 A diagram showing electroluminescence spectra of light-emitting elements in Example.
Figure 40:
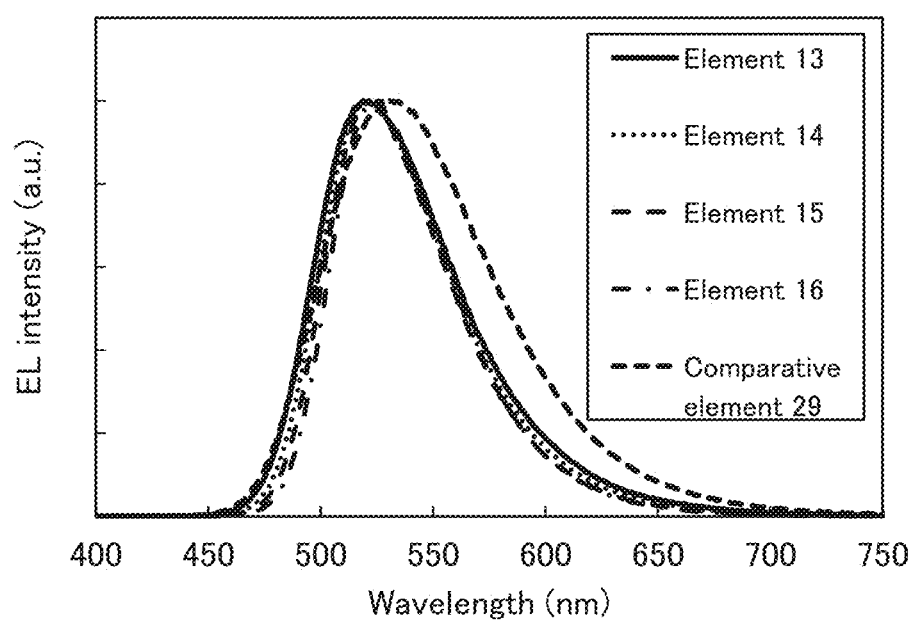
FIG. 40 A diagram showing electroluminescence spectra of light-emitting elements in Example.
Figure 41:
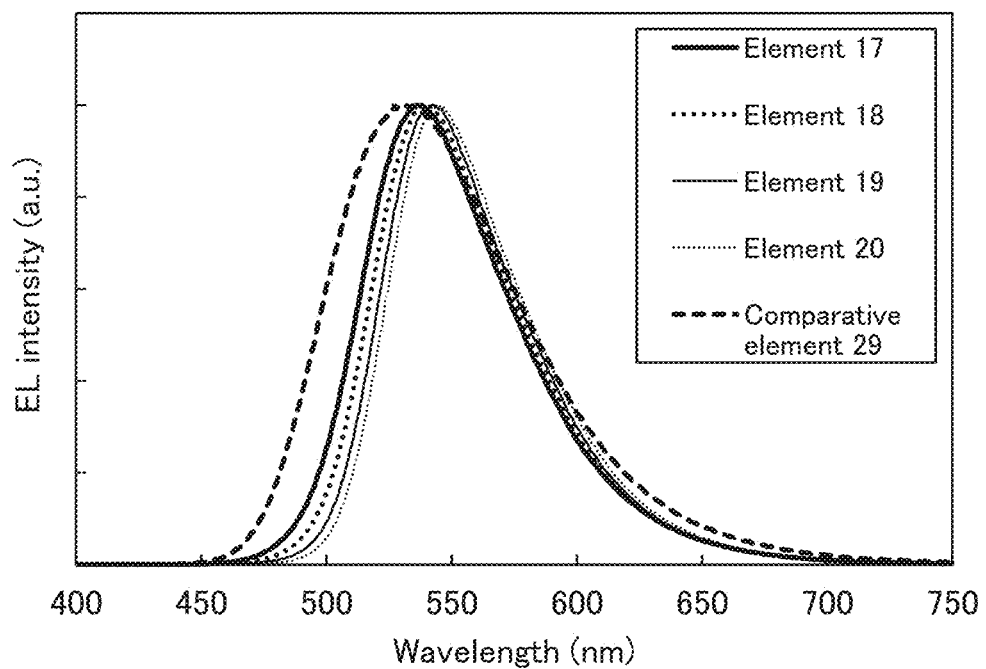
FIG. 41 A diagram showing electroluminescence spectra of light-emitting elements in Example.
Figure 42:
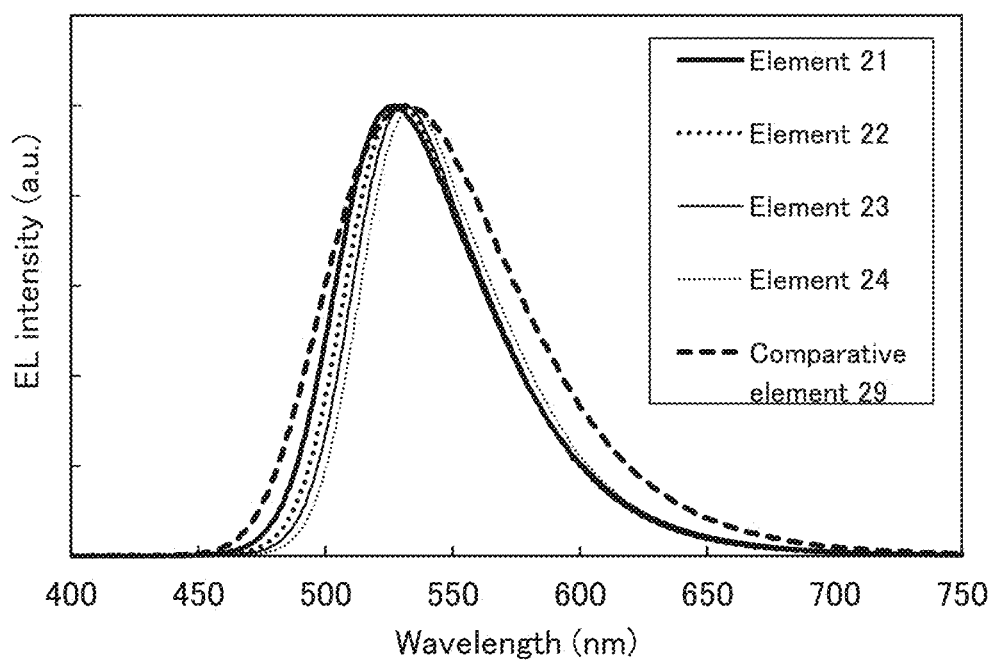
FIG. 42 A diagram showing electroluminescence spectra of light-emitting elements in Example.
Figure 43:
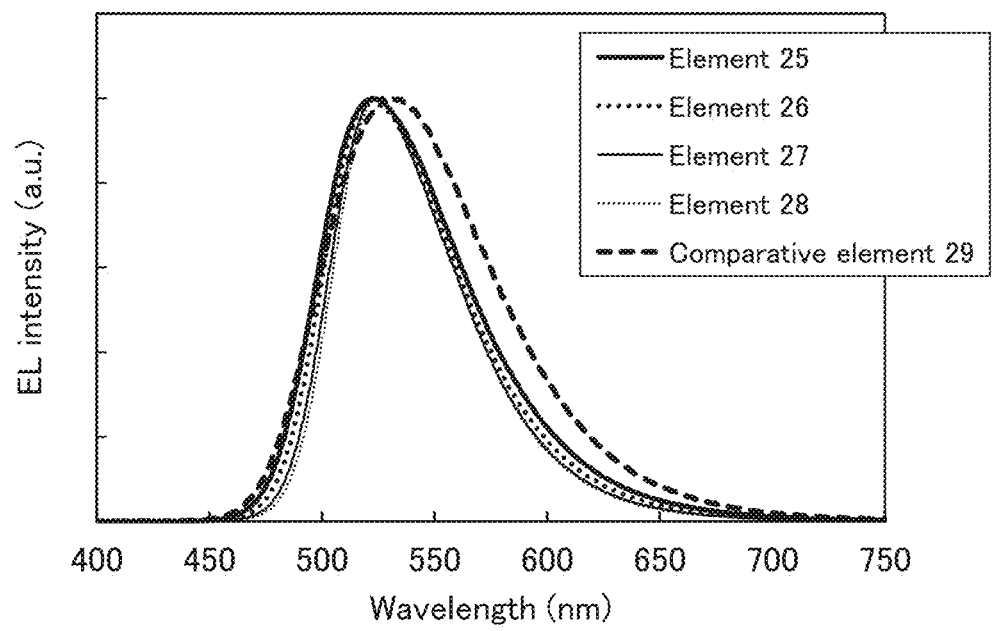
FIG. 43 A diagram showing electroluminescence spectra of light-emitting elements in Example.

As shown in FIG. 37, the emission spectra of the light-emitting element 1 to the light-emitting element 4 had a peak wavelength at approximately 535 nm and a full width at half maximum of approximately 67 nm, i.e., exhibited green light emission originating from 2tBu-ptBuDPhA2Anth. As shown in FIG. 38, the emission spectra of the light-emitting element 5 to the light-emitting element 8 had a peak wavelength at approximately 522 nm and a full width at half maximum of approximately 68 nm, i.e., exhibited green light emission originating from 2tBu-mmtBuDPhA2Anth. As shown in FIG. 39, the emission spectra of the light-emitting element 9 to the light-emitting element 12 had a peak wavelength at approximately 530 nm and a full width at half maximum of approximately 65 nm, i.e., exhibited green light emission originating from 2,6tBu-ptBuDPhA2Anth. As shown in FIG. 40, the emission spectra of the light-emitting element 13 to the light-emitting element 16 had a peak wavelength at approximately 521 nm and a full width at half maximum of approximately 67 nm, i.e., exhibited green light emission originating from 2,6tBu-mmtBuDPhA2Anth. As shown in FIG. 41, the emission spectra of the comparative light-emitting element 17 to the comparative light-emitting element 20 had a peak wavelength at approximately 540 nm and a full width at half maximum of approximately 66 nm, i.e., exhibited green light emission originating from TTPA. As shown in FIG. 42, the emission spectra of the comparative light-emitting element 21 to the comparative light-emitting element 24 had a peak wavelength at approximately 530 nm and a full width at half maximum of approximately 65 nm, i.e., exhibited green light emission originating from MeDPhA2A. As shown in FIG. 43, the emission spectra of the comparative light-emitting element 25 to the comparative light-emitting element 28 had a peak wavelength at approximately 523 nm and a full width at half maximum of approximately 68 nm, i.e., exhibited green light emission originating from mMeDPhA2A. Thus, it was found that light emission originating from the fluorescent material of each element is obtained from the light-emitting element 1 to the light-emitting element 16 and the comparative light-emitting element 17 to the comparative light-emitting element 28. As shown in FIG. 37, the emission spectrum of the comparative light-emitting element 29 had a peak wavelength at 531 nm and a full width at half maximum of approximately 88 nm. This is different from the emission spectra obtained from 4,6mCzP2Pm and Ir(ppz)$_3$, indicating that light emission obtained from the comparative light-emitting element 29 is light emission of the exciplex formed by 4,6mCzP2Pm and Ir(ppz)$_3$.

Note that in some cases, the shapes of the emission spectra of the guest materials contained in the materials are slightly different between in a solution (e.g., a toluene solution) (PL spectra) and in the light-emitting element (EL spectra). This is because in each light-emitting element, light emission of the guest material is affected by a recombination region, an optical path length from the recombination region to the outside, or the like. The shapes of the emission spectra of light-emitting elements using the same guest material are not completely the same in some cases. This is also because influence of a recombination region or an optical path length is slightly different between the light-emitting elements.

Although the light-emitting element 1 to the light-emitting element 16 and the comparative light-emitting element 17 to the comparative light-emitting element 28 exhibit light emission originating from the fluorescent materials, as shown in FIG. 30 to FIG. 36 and Table 4 and Table 5, they exhibited high emission efficiency with an external quantum efficiency exceeding at least 9%. In addition, the light-emitting element 1 to the light-emitting element 16, which are light-emitting elements of embodiments of the present invention, exhibited a higher external quantum efficiency than the comparative light-emitting element 17 to the comparative light-emitting element 28 at any concentration. According to the results, in the light-emitting elements of embodiments of the present invention, non-radiative decay of triplet excitons was inhibited, and both the singlet excitation energy and the triplet excitation energy were efficiently converted into light emission of the fluorescent material.

FIG. 37 to FIG. 40 indicate that light emission from the exciplex of 4,6mCzP2Pm and Ir(ppz)$_3$, which are energy donors, and light emission from each light-emitting element of one embodiment of the present invention, that is, light emission from each energy acceptor (guest material) have similar colors. Thus, although the guest material whose emission color is close to that of the energy donor is used in the light-emitting element of one embodiment of the present invention, the light-emitting element with high efficiency is obtained. When the emission colors of an energy donor and an energy acceptor are close to each other as described above, the rate constant of energy transfer by the Förster mechanism is reduced according to Formula (1); however, in the light-emitting element of one embodiment of the present invention, the concentration of a fluorescent material, which is an energy donor, can be increased. Therefore, a fluorescent material having an emission color close to that of the energy donor can be used as a guest material.

Note that as described above, the peak wavelength of the emission spectrum of 2tBu-mmtBuDPhA2Anth in a toluene solution was 519 nm, and the peak wavelength of the emission spectrum of the exciplex of 4,6mCzP2Pm and Ir(ppz)$_3$ was 531 nm. Thus, the light-emitting element of one embodiment of the present invention can also favorably use a combination of an energy donor and an energy acceptor that have emission colors close to each other.

Since the generation probability of singlet excitons which are generated by recombination of carriers (holes and electrons) injected from the pair of electrodes is at most 25%, the external quantum efficiency of a fluorescent element in the case where the light extraction efficiency to the outside is 30% is at most 7.5%. However, the light-emitting element 1 to the light-emitting element 16 and the comparative light-emitting element 17 to the comparative light-emitting element 28 have external quantum efficiency of higher than 7.5%. This is because, in addition to light emission originating from singlet excitons generated by recombination of carriers (holes and electrons) injected from the pair of electrodes, light emission originating from energy transfer from triplet excitons or light emission originating from singlet excitons generated from triplet excitons by reverse intersystem crossing in the exciplex is obtained from the fluorescent material. That is, the light-emitting element 1 to the light-emitting element 16 and the comparative light-emitting element 17 to the comparative light-emitting element 28 can be regarded as light-emitting elements utilizing ExEF.

<CV Measurement Results>

Then, the electrochemical characteristics (oxidation reaction characteristics and reduction reaction characteristics) of 4,6mCzP2Pm and Ir(ppz)$_3$ used for the light-emitting layers of the light-emitting elements were measured by cyclic voltammetry (CV) measurement. The measurement method is similar to the method described in Example 5.

According to the CV measurement results, the oxidation potential of 4,6mCzP2Pm was 0.95 V and the reduction potential was −2.06 V. In addition, the HOMO level of 4,6mCzP2Pm, which was calculated from the CV measurement, was −5.89 eV and the LUMO level was −2.88 eV. The oxidation potential of Ir(ppz)$_3$ was 0.45 V and the reduction potential was −3.17 V. The HOMO level of Ir(ppz)$_3$, which was calculated from the CV measurement, was −5.39 eV and the LUMO level was −1.77 eV.

As described above, the LUMO level of 4,6mCzP2Pm is lower than the LUMO level of Ir(ppz)$_3$, and the HOMO level of Ir(ppz)$_3$ is higher than the HOMO level of 4,6mCzP2Pm. Thus, in the case where the compounds are used in a light-emitting layer, electrons and holes are efficiently injected into 4,6mCzP2Pm and Ir(ppz)$_3$, respectively, so that 4,6mCzP2Pm and Ir(ppz)$_3$ can form an exciplex.

From comparison between the emission spectrum of the comparative light-emitting element 29 shown in FIG. 37 and the absorption spectra of the guest materials used as the guest materials of the light-emitting element 1 to the light-emitting element 16 shown in FIG. 17, FIG. 20, FIG. 23, and FIG. 26, it is found that an absorption band on the longest wavelength side of the absorption spectrum and the emission spectra overlap with each other. This indicates that the light-emitting element 1 to the light-emitting element 16 emit light by receiving excitation energy of the above-described exciplex. FIG. 161 shows the relation among the EL (emission) spectrum of the comparative light-emitting element 29 and the absorption spectra and the emission spectra of the guest materials in a toluene solution which are used for the light-emitting element 1 to the light-emitting element 12. When the absorption spectra of the guest materials are compared with each other in FIG. 161, absorption bands on the longest wavelength side of the absorption spectra and the emission spectra overlap with each other.

<Change in External Quantum Efficiency Depending on Guest Material Concentration>

Figure 44:
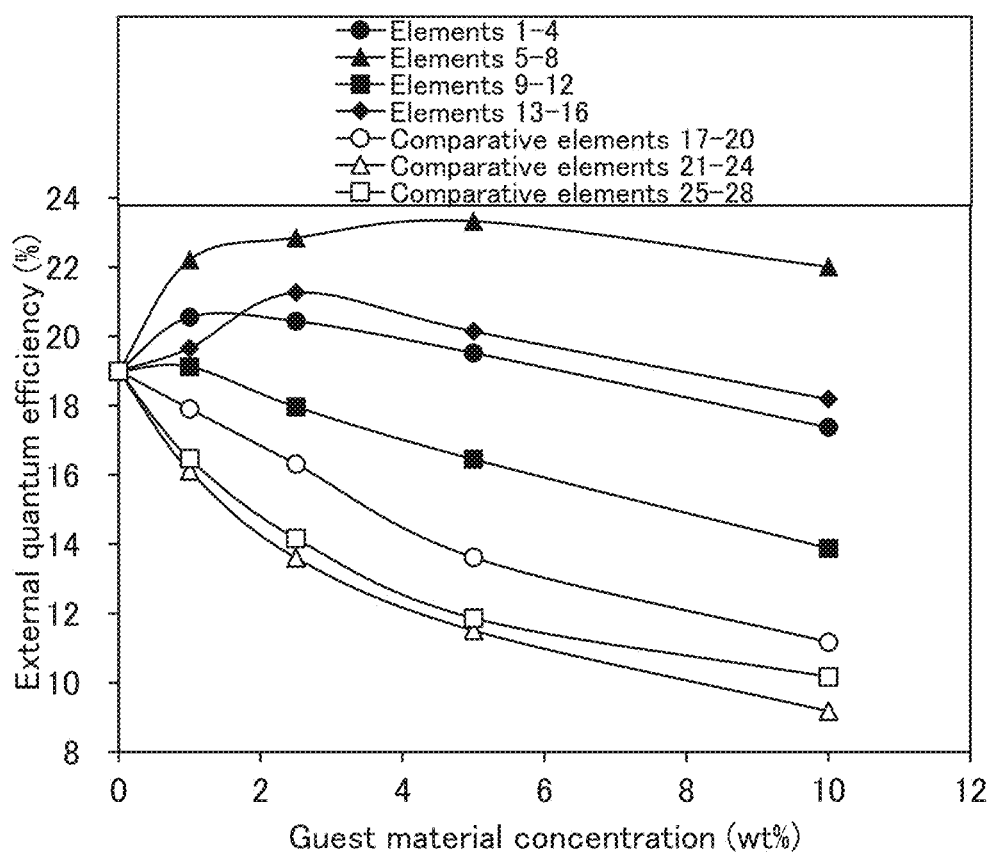
FIG. 44 A diagram showing the relation between external quantum efficiency and guest material concentration in Example.
Figure 45:
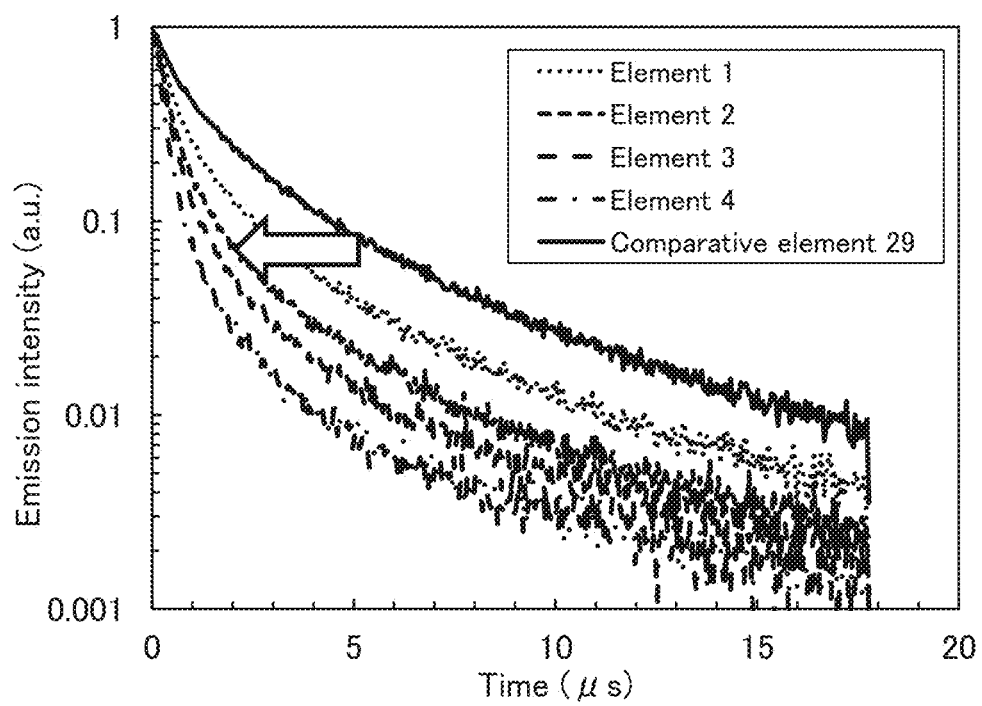
FIG. 45 A diagram showing emission lifetime measurement results of light-emitting elements in Example.
Figure 46:
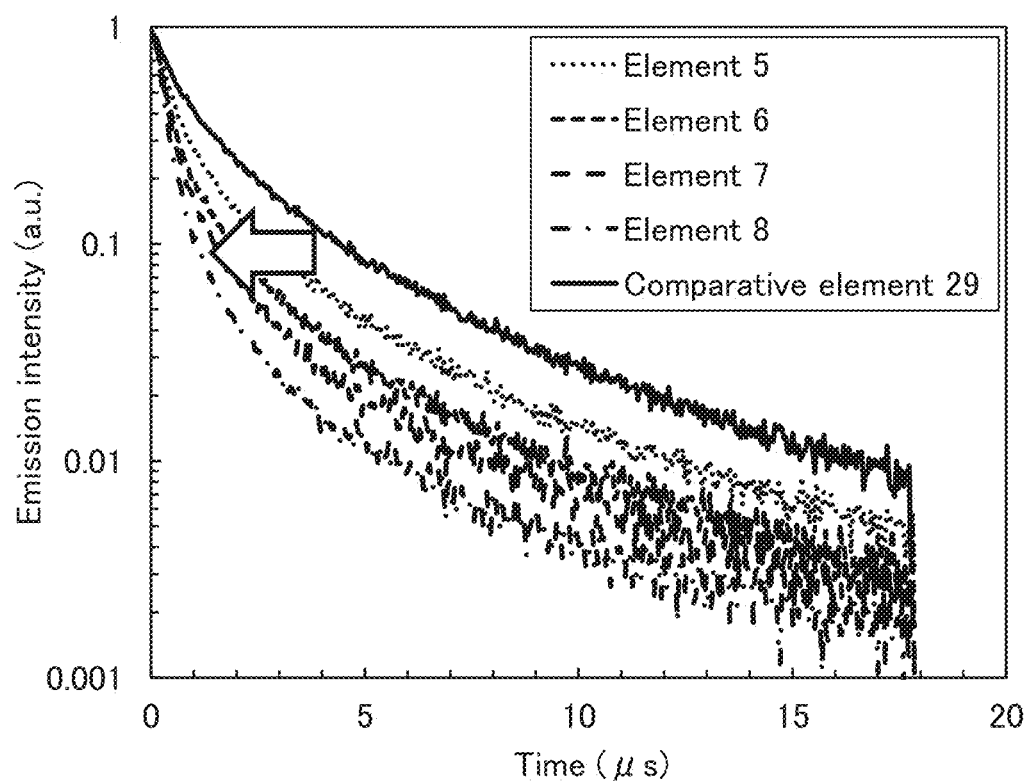
FIG. 46 A diagram showing emission lifetime measurement results of light-emitting elements in Example.
Figure 47:
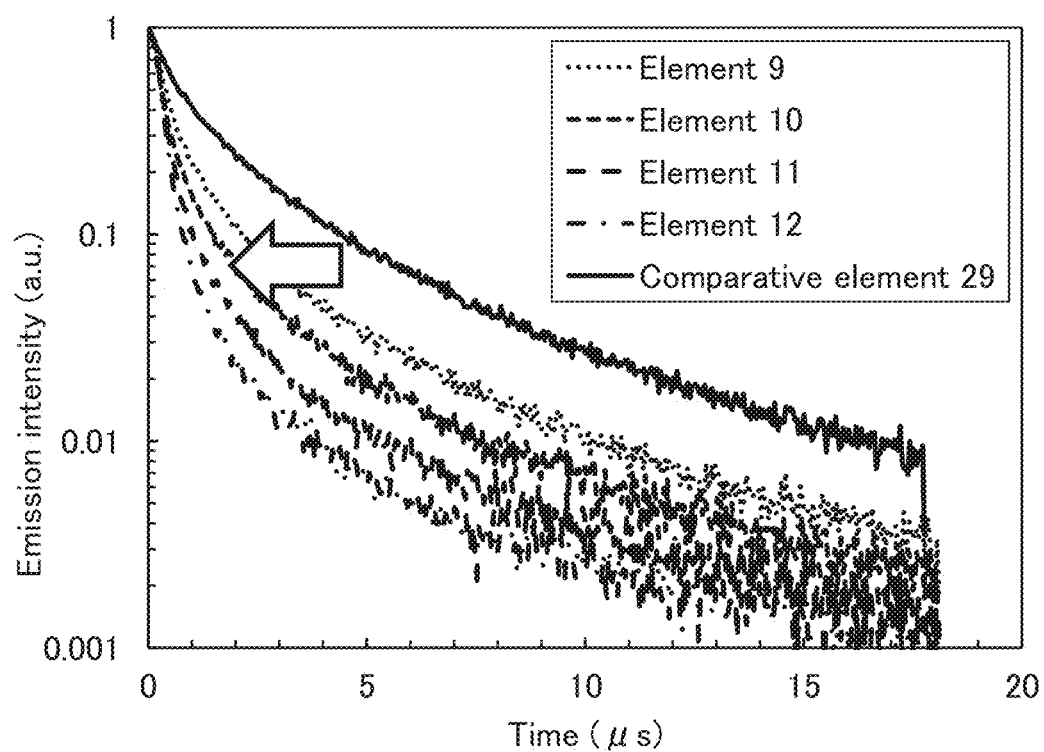
FIG. 47 A diagram showing emission lifetime measurement results of light-emitting elements in Example.
Figure 48:
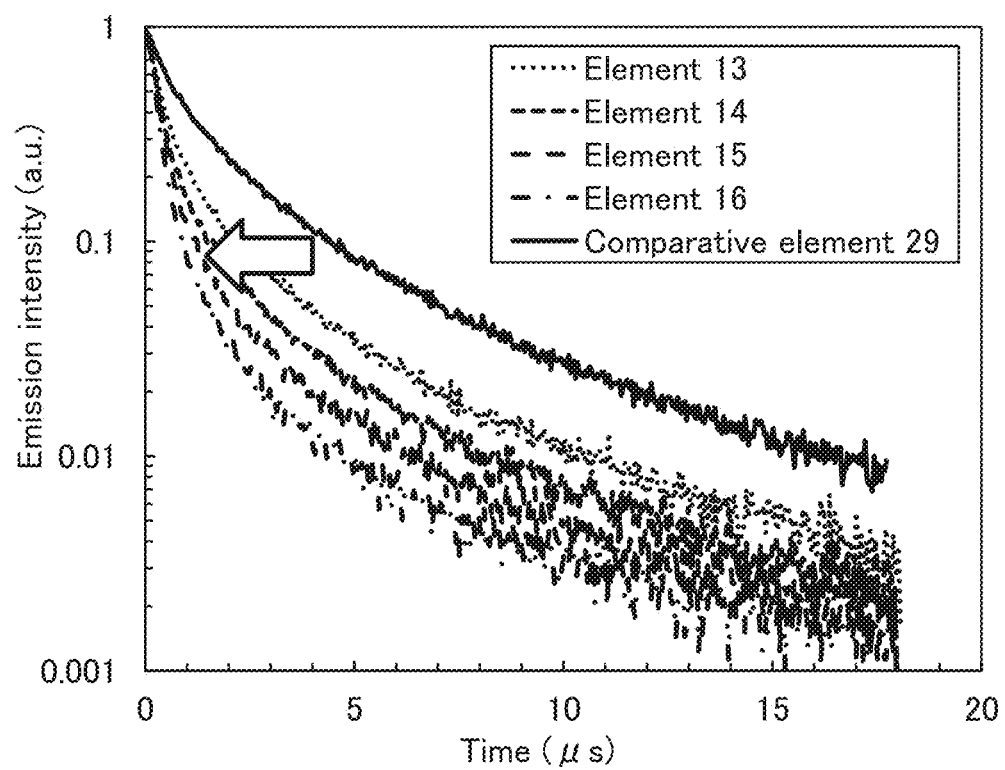
FIG. 48 A diagram showing emission lifetime measurement results of light-emitting elements in Example.
Figure 49:
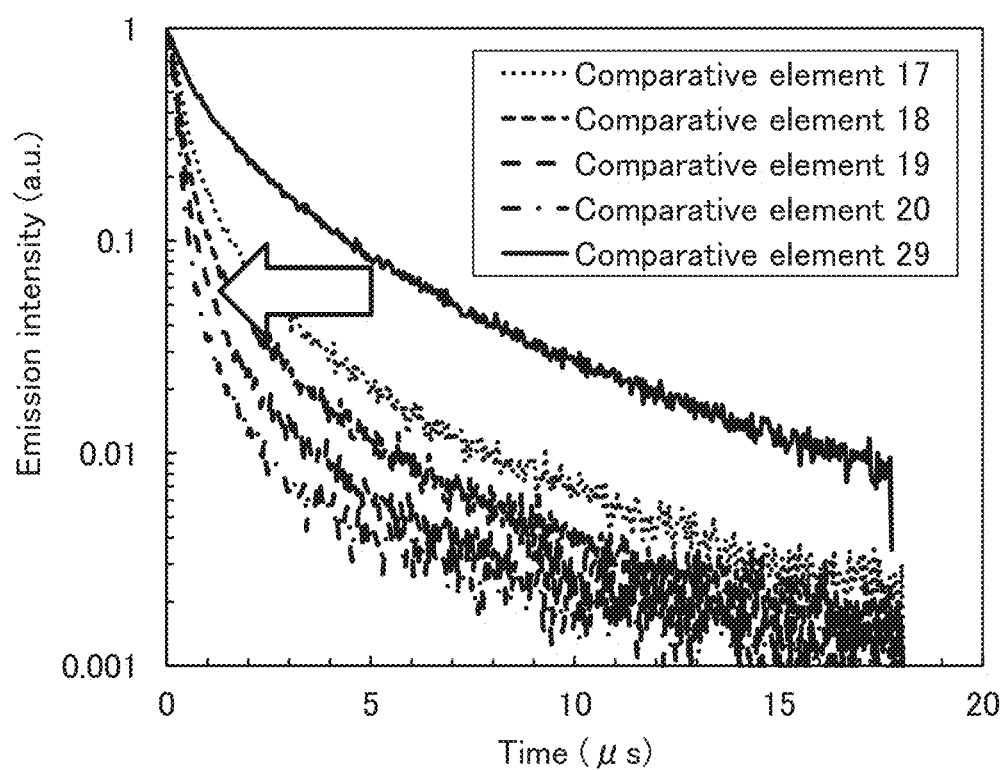
FIG. 49 A diagram showing emission lifetime measurement results of light-emitting elements in Example.
Figure 50:
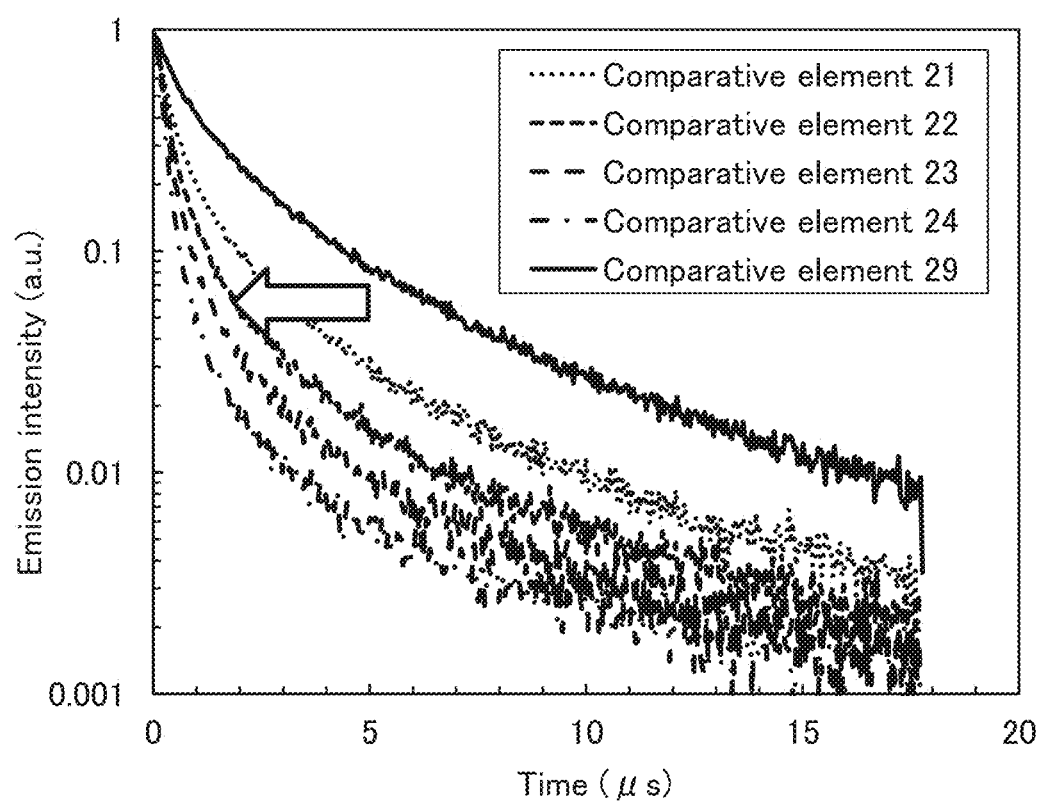
FIG. 50 A diagram showing emission lifetime measurement results of light-emitting elements in Example.
Figure 51:
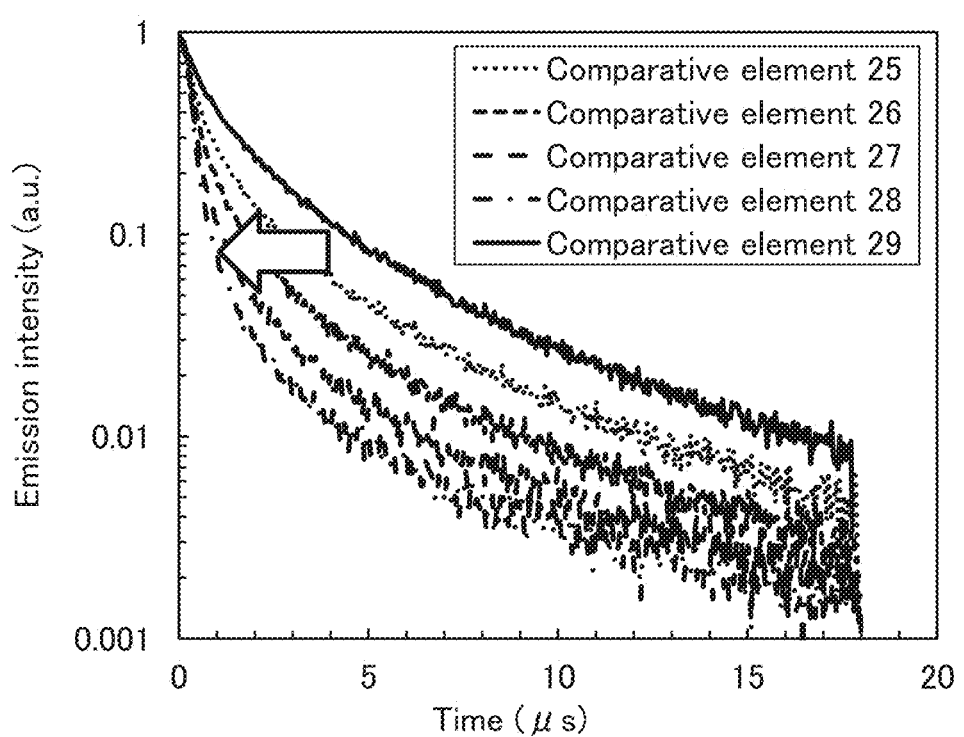
FIG. 51 A diagram showing emission lifetime measurement results of light-emitting elements in Example.
Figure 52:
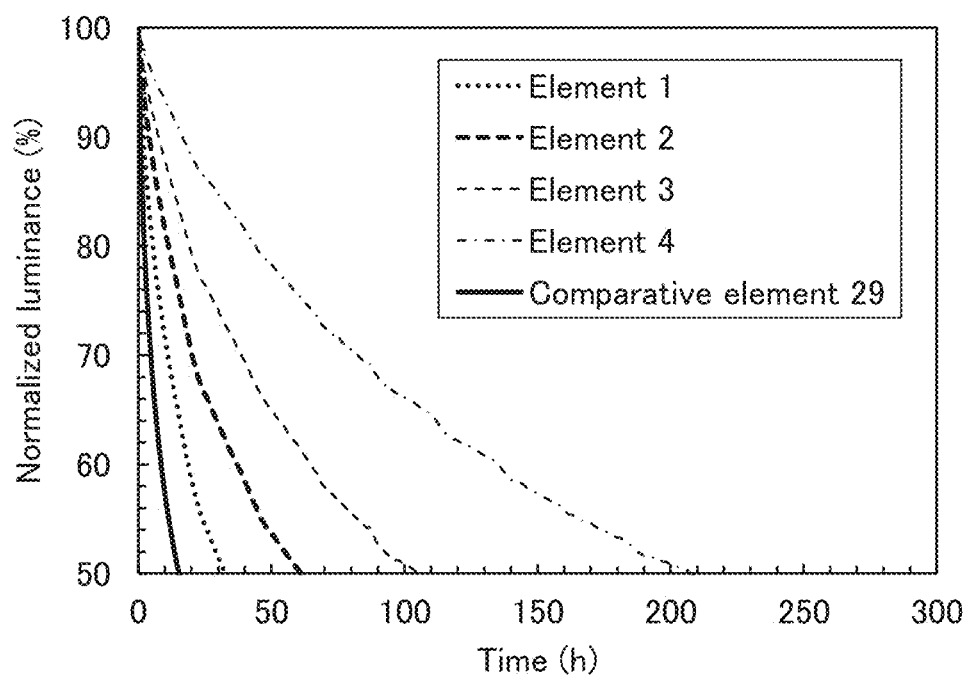
FIG. 52 A diagram showing reliability measurement results of light-emitting elements in Example.
Figure 53:
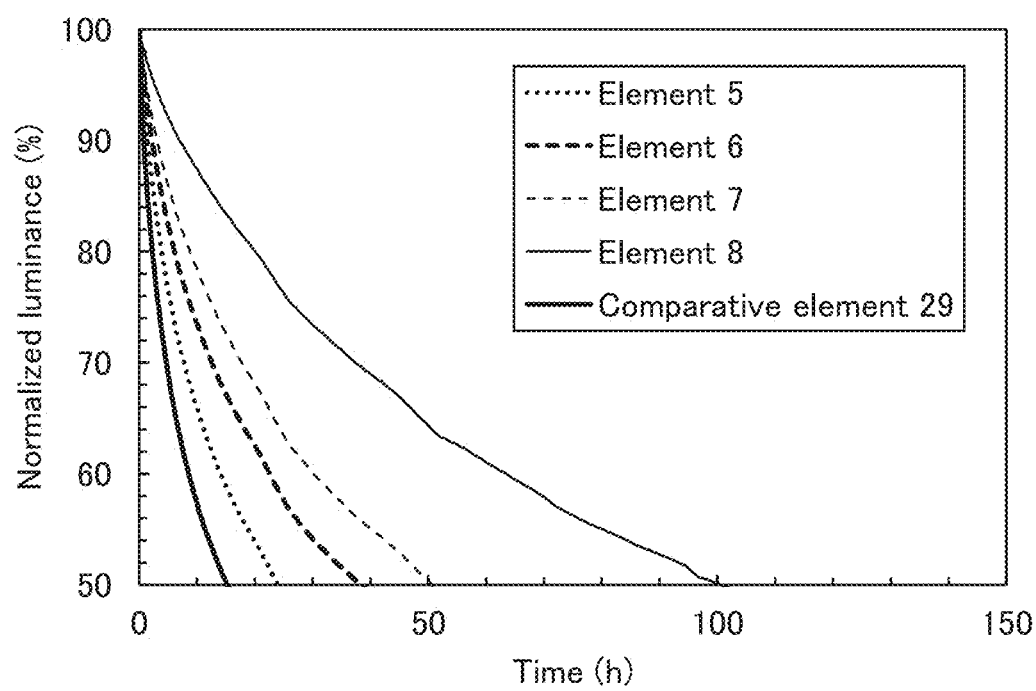
FIG. 53 A diagram showing reliability measurement results of light-emitting elements in Example.
Figure 54:
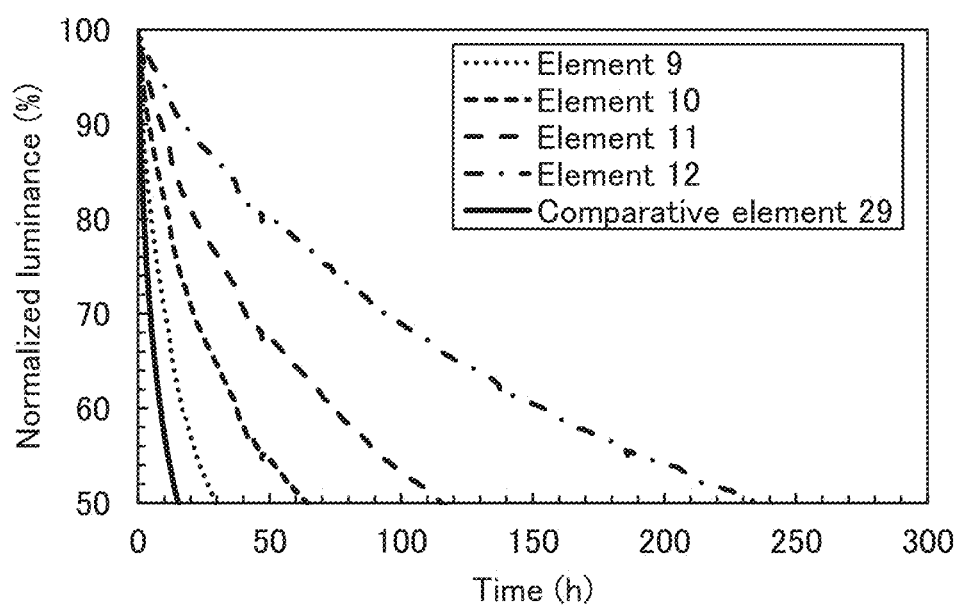
FIG. 54 A diagram showing reliability measurement results of light-emitting elements in Example.
Figure 55:
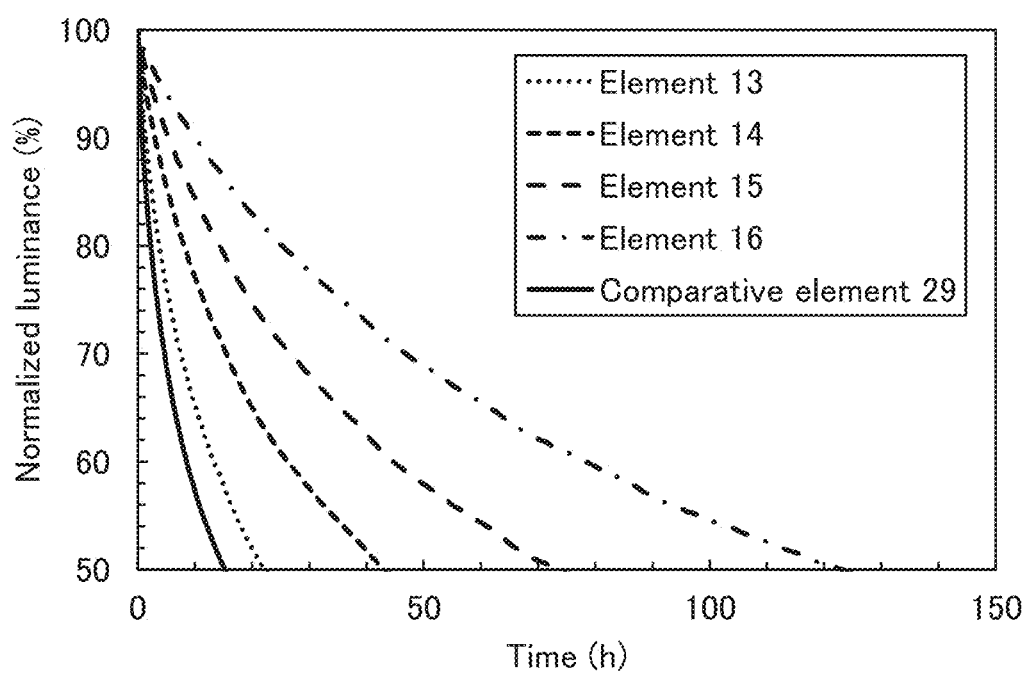
FIG. 55 A diagram showing reliability measurement results of light-emitting elements in Example.

FIG. 44 shows the relation between the guest material concentration and external quantum efficiency of each guest material. It is found from FIG. 44 that a decrease in efficiency due to an increase in the concentration is inhibited in the light-emitting element 1 to the light-emitting element 16 of embodiments of the present invention using the guest materials having protecting groups compared to that in the comparative light-emitting element 17 to the comparative light-emitting element 28. As described above, a fluorescent element using the fluorescent material used in the comparative light-emitting element 17 to the comparative light-emitting element 28 as a guest material and a material having a function of converting triplet excitation energy into light emission as a host material has a problem in that emission efficiency significantly decreases when the guest material concentration increases. In the comparative light-emitting element 17 to the comparative light-emitting element 28, when the guest material concentration is changed from 1 wt % to 10 wt %, external quantum efficiency decreases by approximately 40% to 50%. This means that energy transfer by the Dexter mechanism cannot be inhibited in the comparative light-emitting element 17 to the comparative light-emitting element 28. On the other hand, a reduction in the efficiency can be inhibited in the light-emitting element of one embodiment of the present invention, which uses a fluorescent material having protecting groups as a guest material. It was also found that, depending on the guest material, an increase in the concentration improves emission efficiency. This is because the use of a guest material having protecting groups in a light-emitting layer inhibits energy transfer of triplet excitation energy from a host material to a guest material by the Dexter mechanism and deactivation of the triplet excitation energy. Another reason is that an increase in the guest material concentration enables efficient use of energy transfer of excitation energy from the host material to the guest material by the Förster mechanism, and thus both the triplet excitation energy and the singlet excitation energy can be efficiently converted into light emission of a fluorescent material. This effect was found to be particularly large in the light-emitting elements 5 to 8 and the light-emitting elements 13 to 16 that use 2tBu-mmtBuDPhA2Anth or 2,6tBu-mmtBuDPhA2Anth in which a diphenylamino group is bonded to a luminophore, the phenyl group has two protecting groups, and the two protecting groups are bonded to the 3-position and the 5-position of the phenyl group. It is suggested that the protecting groups included in the bonding positions can effectively make the luminophore away from the host material. Accordingly, it was found that with the light-emitting element of one embodiment of the present invention, a light-emitting element with high guest material concentration and high emission efficiency can be obtained.

<Fluorescence Lifetime Measurement of Light-Emitting Elements>

Next, in order to examine a difference in emission rate with the concentration of each guest material, fluorescence lifetimes of the light-emitting elements were measured. A picosecond fluorescence lifetime measurement system (manufactured by Hamamatsu Photonics K.K.) was used for the measurement. In this measurement, for measurement of the fluorescence lifetimes of the light-emitting elements, a square wave pulse voltage was applied to the light-emitting elements, and time-resolved measurement of light emission, which was attenuated from the falling of the voltage, was performed with a streak camera. The pulse voltage was applied at a frequency of 10 Hz, and data with a high S/N ratio was obtained by integrating data obtained by repeated measurements. The measurement was performed at room temperature (300 K) under the conditions of an applied pulse voltage of approximately 3 V to 4 V, a pulse time width of 100 µsec, a negative bias voltage of −5 V (when the element is not driven), and a measurement time range of 20 µsec so that the luminance of the light-emitting element becomes around 1000 cd/m$^2$. FIG. 45 to FIG. 51 show the measurement results. Note that in the measurement results in FIG. 45 to FIG. 51, the vertical axis represents the emission intensity normalized to that in a state where carriers are steadily injected (the pulse voltage is applied). The horizontal axis represents time elapsed after the falling of the pulse voltage.

Fitting of attenuation curves shown in FIG. 45 to FIG. 51 using an exponential function revealed that the light-emitting element 1 to the light-emitting element 16 and the comparative light-emitting element 17 to the comparative light-emitting element 28 emit light including a prompt fluorescence component of 0.5 µs or less and a delayed fluorescence component of approximately 3 µs. Furthermore, it was also found that when a fluorescent material is added as a guest material, as the fluorescent material concentration is high, the proportion of the prompt fluorescence component increases and the proportion of the delayed fluorescence component decreases regardless of the guest material. The comparative light-emitting element 29 was found to exhibit light emission of the exciplex of 4,6mCzP2Pm and Ir(ppz)$_3$, which are host materials, and exhibit light emission including a prompt fluorescence component of 1 µs or less and a delayed fluorescence component of approximately 3 µs. These facts indicate that when a fluorescent material is added to the light-emitting layer as a guest material, the proportion of the prompt fluorescence component originating from the fluorescent material increases. Here, as described above, the light-emitting element 1 to the light-emitting element 16 of embodiments of the present invention using the guest materials having protecting groups show a high external quantum efficiency even when the light-emitting elements have a high fluorescent material concentration. That is, the light-emitting element of one embodiment of the present invention has high emission efficiency even when the proportion of light emission originating from the fluorescent material increases. Thus, it is suggested that, in the light-emitting element of one embodiment of the present invention, energy transfer of triplet excitation energy from the host material to the guest material by the Dexter mechanism and deactivation of the triplet excitation energy can be inhibited and thus the guest material concentration can be increased, whereby the efficiency of energy transfer of excitation energy by the Förster mechanism can be improved. On the contrary, in the comparative light-emitting element 17 to the comparative light-emitting element 28 using the guest materials having no bulky substituent, influence of energy transfer of triplet excitation energy from the host material to the guest material by the Dexter mechanism and deactivation of the triplet excitation energy is large, so that the emission efficiency decreases while the proportion of light emission originating from the fluorescent material increases. Thus, the light-emitting element of one embodiment of the present invention can utilize both the singlet excitation energy and the triplet excitation energy for light emission efficiently.

<Reliability Measurement of Light-Emitting Elements>

Next, driving tests at a constant current of 0.5 mA were performed on the light-emitting element 1 to the light-emitting element 16. The results are shown in FIG. 52 to FIG. 55. According to FIG. 52 to FIG. 55, as the guest material concentration is increased, reliability becomes favorable. This indicates that when the guest material concentration is increased, excitation energy in the light-emitting layer can be converted into light emission of the guest material efficiently. In other words, it is suggested that the rate of energy transfer of triplet excitation energy by the Förster mechanism from the host material to the guest material can be increased by increasing the guest material concentration. Thus, the guest material concentration can be increased in the light-emitting element of one embodiment of the present invention, so that a light-emitting element with favorable emission efficiency and favorable reliability can be obtained.

<Comparison Between Reliabilities of Light-Emitting Elements and Comparative Light-Emitting Elements>

Figure 69:
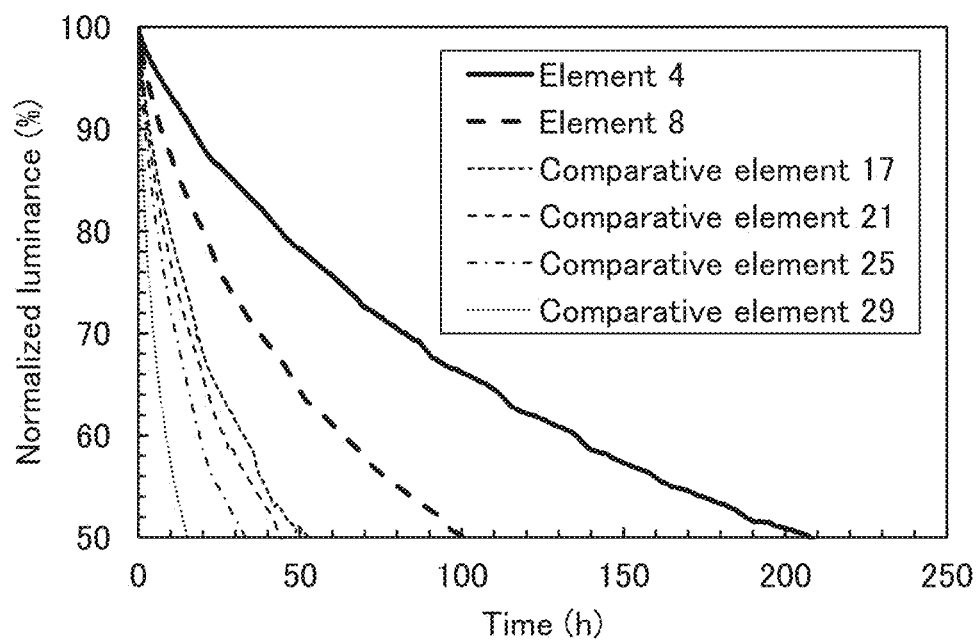
FIG. 69 A diagram showing reliability measurement results of light-emitting elements in Example.

Next, driving tests at a constant current of 0.5 mA were performed on the light-emitting element 4, the light-emitting element 8, the comparative light-emitting element 17, the comparative light-emitting element 21, the comparative light-emitting element 25, and the comparative light-emitting element 29. FIG. 69 shows the results.

In the comparative light-emitting element 17 to the comparative light-emitting element 20, when the guest material concentration is increased, emission efficiency decreases as described above. The comparative light-emitting element 17 has the highest external quantum efficiency among the comparative light-emitting element 17 to the comparative light-emitting element 20. Similarly, the comparative light-emitting element 21 and the comparative light-emitting element 25 have the highest emission efficiency among the comparative light-emitting elements using the same guest material. In other words, they are comparative light-emitting elements having the lowest guest material concentration (1 wt %) among the comparative light-emitting elements using the same guest material. In contrast, the light-emitting element 4 and the light-emitting element 8 have the highest guest material concentration (10 wt %) among the light-emitting elements using the same guest material. The light-emitting element of one embodiment of the present invention with high emission efficiency can be manufactured even when the guest material concentration is high as described above. Therefore, although the light-emitting element 4 and the light-emitting element 8 have high guest material concentration, they have external quantum efficiency higher than or equal to that of the comparative light-emitting element having the highest emission efficiency among the comparative light-emitting elements using the same guest material. Furthermore, FIG. 69 shows that the light-emitting element 4 and the light-emitting element 8 have more favorable reliability than the comparative light-emitting element 17, the comparative light-emitting element 21, the comparative light-emitting element 25, and the comparative light-emitting element 29.

Here, energy transfer from an energy acceptor to a guest material of a light-emitting layer, i.e., energy transfer related to light emission conflicts with a quenching process due to the influence of an impurity or a degraded material. Therefore, in order to obtain a highly reliable light-emitting element, it is important to increase the energy transfer rate related to light emission. The guest material concentration in the light-emitting layer is preferably high in order to increase the energy transfer rate. As described above, when the guest material concentration is increased in the comparative light-emitting element, emission efficiency is significantly lowered. Therefore, it is difficult to manufacture a light-emitting element with favorable emission efficiency and favorable reliability. In contrast, in the light-emitting element of one embodiment of the present invention, the rate of energy transfer by the Förster mechanism can be increased while energy transfer by the Dexter mechanism is inhibited, and a light-emitting element with favorable emission efficiency and favorable reliability can be obtained by reducing the influence of conflict with a quenching process. The results in FIG. 69 show this effect. Thus, the guest material concentration can be increased in the light-emitting element of one embodiment of the present invention, so that a light-emitting element with favorable emission efficiency and favorable reliability can be obtained.

Example 7

In this example, fabrication examples and the characteristics of light-emitting elements of embodiments of the present invention and comparative light-emitting elements, which are different from those in the above examples, are described. The structure of each of the light-emitting elements fabricated in this example is the same as that in FIG. 1(A). Table 6 and Table 7 show the details of the element structures. The structures and abbreviations of compounds that were used are shown below. Note that the above examples and embodiments can be referred to for other organic compounds.

[Chemical Formula 56]

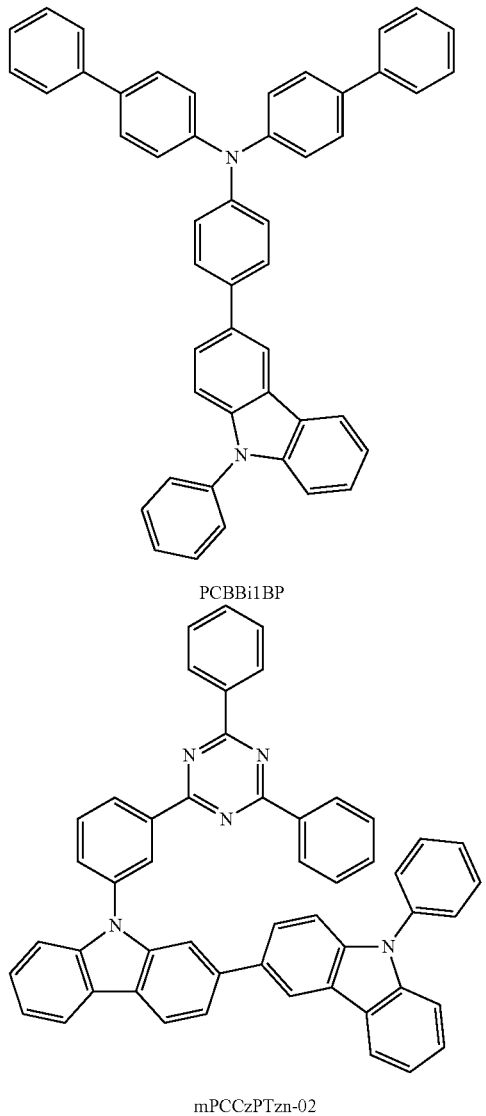

PCBBi1BP mPCCzPTzn-02

TABLE 6

| | Layer | Reference numeral | Thickness (nm) | Material | Weight ratio |
|---|---|---|---|---|---|
| Light-emitting element 30 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | mPCCzPTzn-02 | — |
| | Light-emitting layer | 130 | 40 | mPCCzPTzn-02:PCCP:GD270:2,6tBu-ptBuDPhA2Anth | 0.5:0.5:0.1:0.05 |
| | Hole-transport layer | 112 | 20 | PCBBi1BP | — |
| | Hole-injection layer | 111 | 40 | DBT3P-II:MoO$_3$ | 1:0.5 |
| | Anode | 101 | 70 | ITSO | — |

TABLE 6-continued

| | Layer | Reference numeral | Thickness (nm) | Material | Weight ratio |
|---|---|---|---|---|---|
| Light-emitting element 31 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | mPCCzPTzn-02 | — |
| | Light-emitting layer | 130 | 40 | mPCCzPTzn-02:PCCP:GD270:2,6tBu-mmtBuDPhA2Anth | 0.5:0.5:0.1:0.05 |
| | Hole-transport layer | 112 | 20 | PCBBi1BP | — |
| | Hole-injection layer | 111 | 40 | DBT3P-II:MoO$_3$ | 1:0.5 |
| | Anode | 101 | 70 | ITSO | — |
| Light-emitting element 32 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | mPCCzPTzn-02 | — |
| | Light-emitting layer | 130 | 40 | mPCCzPTzn-02:PCCP:GD270:2tBu-ptBuDPhA2Anth | 0.5:0.5:0.1:0.05 |
| | Hole-transport layer | 112 | 20 | PCBBi1BP | — |
| | Hole-injection layer | 111 | 40 | DBT3P-II:MoO$_3$ | 1:0.5 |
| | Anode | 101 | 70 | ITSO | — |
| Light-emitting element 33 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | mPCCzPTzn-02 | — |
| | Light-emitting layer | 130 | 40 | mPCCzPTzn-02:PCCP:GD270:2tBu-mmtBuDPhA2Anth | 0.5:0.5:0.1:0.05 |
| | Hole-transport layer | 112 | 20 | PCBBi1BP | — |
| | Hole-injection layer | 111 | 40 | DBT3P-II:MoO$_3$ | 1:0.5 |
| | Anode | 101 | 70 | ITSO | — |

TABLE 7

| | Layer | Reference numeral | Thickness (nm) | Material | Weight ratio |
|---|---|---|---|---|---|
| Comparative light-emitting element 34 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | mPCCzPTzn-02 | — |
| | Light-emitting layer | 130 | 40 | mPCCzPTzn-0:PCCP:GD270:TTPA | 0.5:0.5:0.1:0.05 |
| | Hole-transport layer | 112 | 20 | PCBBi1BP | — |
| | Hole-injection layer | 111 | 40 | DBT3P-II:MoO$_3$ | 1:0.5 |
| | Anode | 101 | 70 | ITSO | — |

TABLE 7-continued

| | Layer | Reference numeral | Thickness (nm) | Material | Weight ratio |
|---|---|---|---|---|---|
| Comparative light-emitting element 35 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | 4,6mCzP2Pm | — |
| | Light-emitting layer | 130 | 40 | mPCCzPTzn-02:PCCP:GD270:MeDPhA2A | 0.5:0.5:0.1:0.05 |
| | Hole-transport layer | 112 | 20 | PCCP | — |
| | Hole-injection layer | 111 | 40 | DBT3P-II: $MoO_3$ | 1:0.5 |
| | Anode | 101 | 70 | ITSO | — |
| Comparative light-emitting element 36 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | 4,6mCzP2Pm | — |
| | Light-emitting layer | 130 | 40 | mPCCzPTzn-02:PCCP:GD270:mMeDPhA2A | 0.5:0.5:0.1:0.05 |
| | Hole-transport layer | 112 | 20 | PCCP | — |
| | Hole-injection layer | 111 | 40 | DBT3P-II:$MoO_3$ | 1:0.5 |
| | Anode | 101 | 70 | ITSO | — |

<Fabrication of Light-Emitting Elements>

Fabrication methods of the light-emitting elements fabricated in this example will be described below.

<<Fabrication of light-emitting element 30>>

As the electrode 101, an ITSO film was formed to a thickness of 70 nm over a glass substrate. Note that the electrode area of the electrode 101 was set to 4 $mm^2$ (2 mm×2 mm).

Next, as the hole-injection layer 111, DBT3P-II and molybdenum oxide ($MoO_3$) were deposited over the electrode 101 by co-evaporation in a weight ratio (DBT3P-II: $MoO_3$) of 1:0.5 to a thickness of 40 nm.

Then, as the hole-transport layer 112, PCBBi1BP was deposited on the hole-injection layer 111 by evaporation to a thickness of 20 nm.

Next, as the light-emitting layer 130, mPCCzPTzn-02, PCCP, GD270 (manufactured by Jilin Optical and Electronic Materials Co., Ltd.), and 2tBu-ptBuDPhA2Anth were deposited over the hole-transport layer 112 by co-evaporation at a weight ratio (mPCCzPTzn-02:PCCP:GD270:2tBu-ptBuDPhA2Anth) of 0.5:0.5:0.1:0.05 to a thickness of 40 nm.

Next, as the electron-transport layer 118, mPCCzPTzn-02 and NBPhen were sequentially deposited by evaporation to a thickness of 20 nm and to a thickness of 10 nm, respectively, over the light-emitting layer 130. Then, as the electron-injection layer 119, LiF was deposited on the electron-transport layer 118 by evaporation to a thickness of 1 nm.

Next, as the electrode 102, aluminum (Al) was formed over the electron-injection layer 119 to a thickness of 200 nm.

Next, in a glove box containing a nitrogen atmosphere, a light-emitting element 30 was sealed by fixing a glass substrate for sealing to the glass substrate on which the organic materials were formed using a sealant for organic EL. Specifically, the sealant was applied to the periphery of the organic materials formed on the glass substrate, the glass substrate was bonded to the glass substrate for sealing, irradiation with ultraviolet light having a wavelength of 365 nm at 6 $J/cm^2$ was performed, and heat treatment at 80° C. for one hour was performed. Through the above steps, the light-emitting element 30 was obtained.

<<Fabrication of Light-Emitting Element 31 to Light-Emitting Element 33 and Comparative Light-Emitting Element 34 to Comparative Light-Emitting Element 36>>

A light-emitting element 31 to a light-emitting element 33 and a comparative light-emitting element 34 to a comparative light-emitting element 36 are different from the fabrication method of the above-described light-emitting element 30 only in a fluorescent material (guest material) used for the light-emitting layer 130, and other steps of the fabrication method are the same as those for the light-emitting element 30. The details of the element structures are shown in Table 6 and Table 7; thus, the details of the fabrication methods are omitted.

The guest materials used for the light-emitting element 30 to the light-emitting element 33 each have protecting groups around a luminophore, whereas the guest materials used for the comparative light-emitting element 34 to the comparative light-emitting element 36 have no bulky substituent. In this example, a combination of mPCCzPTzn-02 and PCCP forms an exciplex and GD270 is a phosphorescent material containing Ir. Thus, the light-emitting element 30 to the light-emitting element 33 and the comparative light-emitting element 34 to the comparative light-emitting element 36 can convert triplet excitation energy into fluorescence because the exciplex or the phosphorescent material serves as an energy donor. A light-emitting layer of each light-emitting element can also be regarded as a light-emitting layer obtained by adding a fluorescent material to a light-emitting layer that can utilize ExTET.

<Characteristics of Light-Emitting Elements>

Next, the characteristics of the fabricated light-emitting element 30 to light-emitting element 33 and comparative light-emitting element 34 to comparative light-emitting element 36 were measured. Note that the measurement method is similar to that in Example 6.

Figure 56:
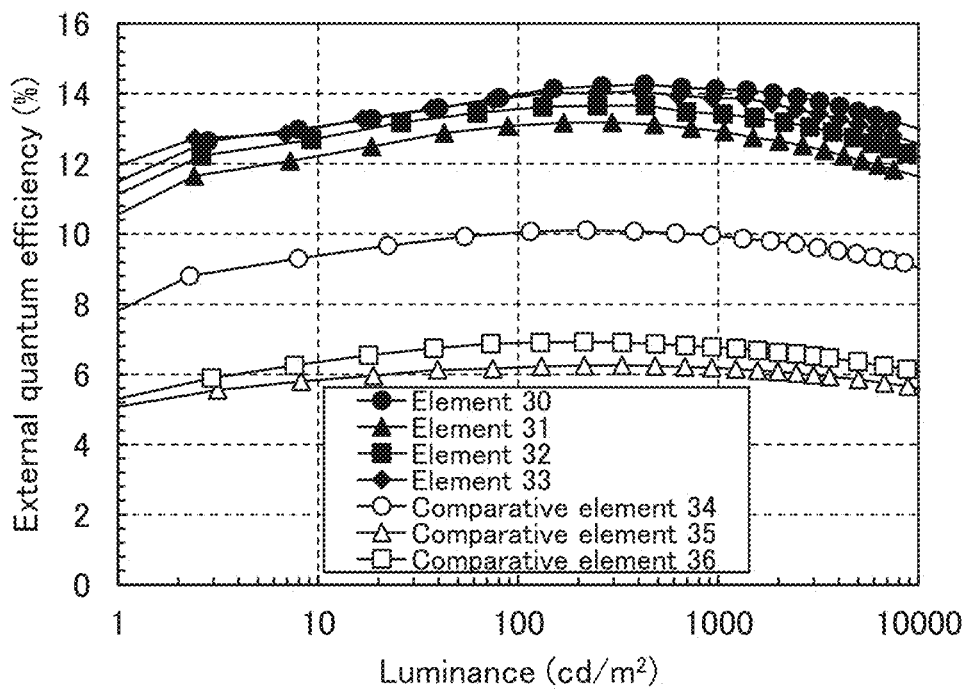
FIG. 56 A diagram showing external quantum efficiency-luminance characteristics of light-emitting elements in Example.
Figure 57:
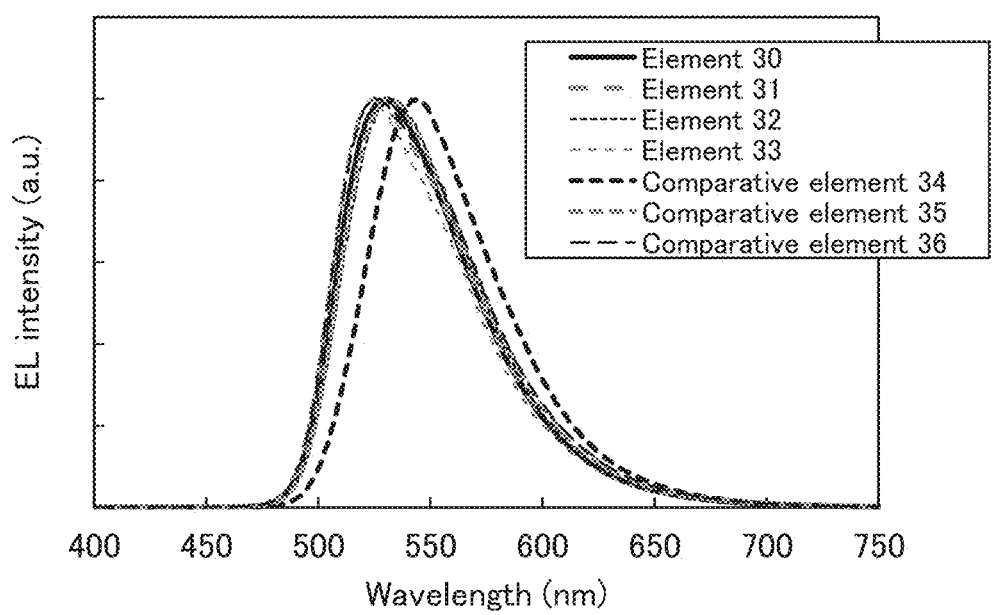
FIG. 57 A diagram showing electroluminescence spectra of light-emitting elements in Example.

FIG. 56 shows the external quantum efficiency-luminance characteristics of the light-emitting element 30 to the light-emitting element 33 and the comparative light-emitting element 34 to the comparative light-emitting element 36. FIG. 57 shows electroluminescence spectra of the light-emitting element 30 to the light-emitting element 33 and the comparative light-emitting element 34 to the comparative light-emitting element 36 to which a current at a current density of 2.5 mA/cm$^2$ was supplied. Note that the measurement of the light-emitting elements was performed at room temperature (in an atmosphere maintained at 23° C.).

Table 8 shows the element characteristics of the light-emitting element 30 to the light-emitting element 33 and the comparative light-emitting element 34 to the comparative light-emitting element 36 at around 1000 cd/m$^2$.

TABLE 8

| | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting element 30 | 3.20 | 1.81 | (0.318, 0.650) | 968 | 53.5 | 52.5 | 14.1 |
| Light-emitting element 31 | 3.20 | 2.22 | (0.311, 0.655) | 1072 | 48.2 | 47.3 | 12.9 |
| Light-emitting element 32 | 3.10 | 2.09 | (0.326, 0.647) | 1057 | 50.5 | 51.2 | 13.4 |
| Light-emitting element 33 | 3.20 | 1.81 | (0.309, 0.654) | 937 | 51.8 | 50.9 | 13.9 |
| Light-emitting element 34 | 3.10 | 2.41 | (0.361, 0.624) | 926 | 38.4 | 39.0 | 10.0 |
| Light-emitting element 35 | 3.40 | 4.00 | (0.324, 0.648) | 928 | 23.2 | 21.5 | 6.2 |
| Light-emitting element 36 | 3.40 | 3.70 | (0.320, 0.647) | 931 | 25.2 | 23.3 | 6.8 |

As shown in FIG. 57, the emission spectrum of the light-emitting element 30 had a peak wavelength at 531 nm and a full width at half maximum of 66 nm, i.e., exhibited green light emission originating from 2,6tBu-ptBuDPhA2Anth. The emission spectrum of the light-emitting element 31 had a peak wavelength at 525 nm and a full width at half maximum of 69 nm, i.e., exhibited green light emission originating from 2,6tBu-mmtBuDPhA2Anth. The emission spectrum of the light-emitting element 32 had a peak wavelength at 533 nm and a full width at half maximum of 66 nm, i.e., exhibited green light emission originating from 2tBu-ptBuDPhA2Anth. The emission spectrum of the light-emitting element 33 had a peak wavelength at 525 nm and a full width at half maximum of 66 nm, i.e., exhibited green light emission originating from 2tBu-mmtBuDPhA2Anth. The emission spectrum of the comparative light-emitting element 34 had a peak wavelength at 544 nm and a full width at half maximum of 66 nm, i.e., exhibited green light emission originating from TTPA. The emission spectrum of the comparative light-emitting element 35 had a peak wavelength at 530 nm and a full width at half maximum of 68 nm, i.e., exhibited green light emission originating from MeDPhA2A. The emission spectrum of the comparative light-emitting element 36 had a peak wavelength at 526 nm and a full width at half maximum of 72 nm, i.e., exhibited green light emission originating from mMeDPhA2A.

Accordingly, light emission originating from the fluorescent materials in the light-emitting elements was obtained from the light-emitting element 30 to the light-emitting element 33 and the comparative light-emitting element 34 to the comparative light-emitting element 36. Thus, the excitation energy of each light-emitting element is found to be transferred to the fluorescent material that is the guest material of each light-emitting element. This indicates that both singlet excitation energy and triplet excitation energy that are generated in the light-emitting layer are transferred to the fluorescent material through the exciplex or the phosphorescent material.

Although the light-emitting element 30 to the light-emitting element 33 exhibit light emission originating from the fluorescent materials, as shown in FIG. 56 and Table 8, they exhibited high emission efficiency with an external quantum efficiency exceeding 10%, and a higher external quantum efficiency than the comparative light-emitting element 34 to the comparative light-emitting element 36. This result indicates that in the light-emitting element of one embodiment of the present invention, non-radiative decay of triplet excitons is inhibited, contributing to efficient conversion into light emission. Thus, it was found that the use of a guest material having protecting groups in a light-emitting layer can inhibit energy transfer of triplet excitation energy from a host material to a guest material by the Dexter mechanism and non-radiative decay of triplet excitation energy.

FIG. 162 shows the relation between the EL (emission) spectrum of the comparative light-emitting element 103 and the absorption spectra and the emission spectra of the guest materials in a toluene solution used for the light-emitting element 31, the light-emitting element 33, the comparative light-emitting element 34, and the comparative light-emitting element 35. Note that the comparative light-emitting element 103 is a phosphorescent element utilizing ExTET, and each of the light-emitting element 30 to the light-emitting element 33 and the comparative light-emitting element 34 to the comparative light-emitting element 36 can be regarded as an element obtained by adding a fluorescent material to the comparative light-emitting element 103. FIG.

162 shows that absorption bands on the longest wavelength side of the absorption spectra of the guest materials and the emission spectra overlap with each other. This indicates that the light-emitting element 31, the light-emitting element 33, the comparative light-emitting element 34, and the comparative light-emitting element 35 emit light by receiving excitation energy of the above-described exciplex. Although not illustrated, the absorption spectra of the guest materials used for the light-emitting element 30, the light-emitting element 32, and the comparative light-emitting element 36 and the emission spectrum of the comparative light-emitting element 103 have a similar relation.

Furthermore, it was found from FIG. 56 and FIG. 57 that even when the energy donor and the guest material exhibit similar emission colors, a light-emitting element with high emission efficiency can be obtained according to one embodiment of the present invention.

<Reliability Measurement of Light-Emitting Elements>

Figure 58:
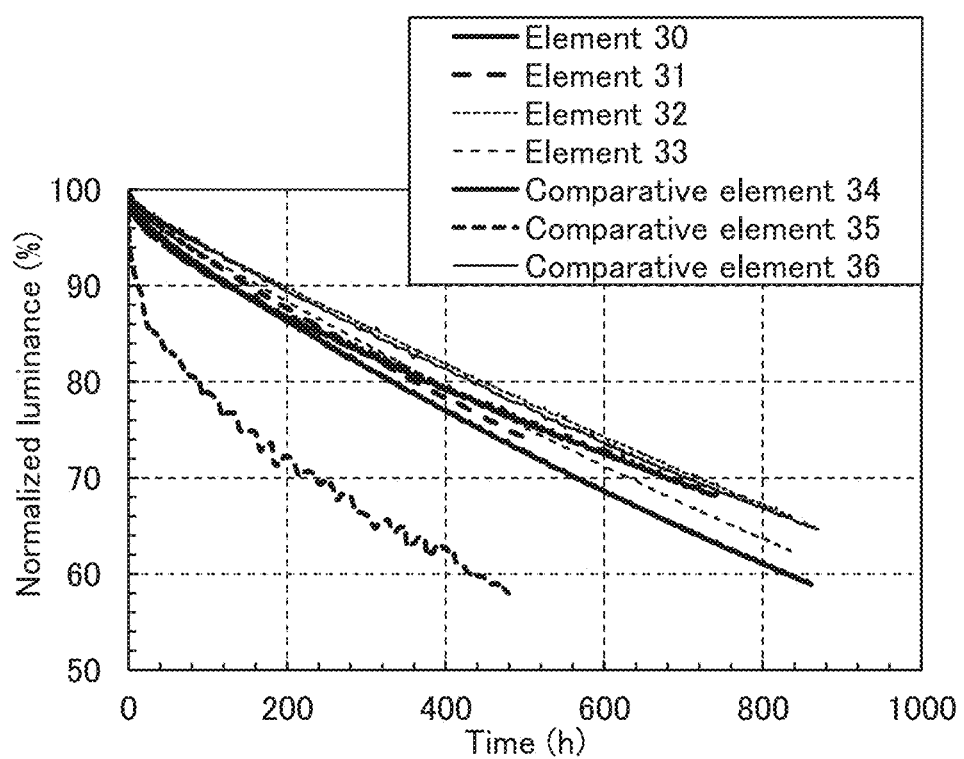
FIG. 58 A diagram showing reliability measurement results of light-emitting elements in Example.

Next, driving tests at a constant current of 2.0 mA were performed on the light-emitting element 30 to the light-emitting element 33 and the comparative light-emitting element 34 to the comparative light-emitting element 36. The results are shown in FIG. 58. It was found from FIG. 58 that the time for which luminance is reduced by 30% exceeds 500 hours in the light-emitting element 30 to the light-emitting element 33 and the comparative light-emitting element 34 and the comparative light-emitting element 36, that is, the light-emitting elements are favorably reliable. In the case where the reliability of the light-emitting elements was evaluated under the same conditions of current application as in this measurement, the light-emitting element 30 to the light-emitting element 33 and the comparative light-emitting element 34 and the comparative light-emitting element 36 had substantially the same reliability. Thus, the light-emitting element of one embodiment of the present invention with high efficiency and high reliability can be obtained.

Here, as a method of constant-current driving test of light-emitting elements, a method of unifying current values for the light-emitting elements and a method of unifying the luminances of the light-emitting elements are given. In the case of unifying the luminances of the light-emitting elements, a light-emitting element with favorable emission efficiency has a lower current load. As described above, the light-emitting element 30 to the light-emitting element 33 have a higher external quantum efficiency than the comparative light-emitting element 34 to the comparative light-emitting element 36. Thus, in the case of unifying the luminances of the light-emitting elements, the light-emitting element of one embodiment of the present invention has a lower current load than the comparative light-emitting element, and thus can be regarded to have favorable reliability.

Accordingly, the light-emitting element of one embodiment of the present invention can favorably use an exciplex or a phosphorescent material as a host material. Moreover, a structure in which a fluorescent material is added to a light-emitting layer which can utilize ExTET is favorably employed.

Example 8

In this example, fabrication examples and the characteristics of light-emitting elements of embodiments of the present invention and comparative light-emitting elements, which are different from those in the above examples, are described. The structure of each of the light-emitting elements fabricated in this example is the same as that in FIG. 1(A). Table 9 and Table 10 show the details of the element structures. The structures and abbreviations of compounds that were used are shown below. Note that the above examples and embodiments can be referred to for other organic compounds.

[Chemical Formula 57]

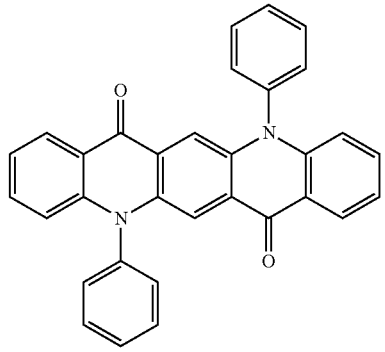

DPQd

TABLE 9

| Layer | | Reference numeral | Thickness (nm) | Material | Weight ratio |
|---|---|---|---|---|---|
| Light-emitting elements 37 to 40 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | 4,6mCzP2Pm | — |
| | Light-emitting layer | 130 | 40 | 4,6mCzP2Pm:Ir(ppz)$_3$:Oct-tBuDPQd | 0.8:0.2:x2 |
| | Hole-transport layer | 112 | 20 | PCCP | — |
| | Hole-injection layer | 111 | 40 | DBT3P-II:MoO$_3$ | 1:0.5 |
| | Anode | 101 | 70 | ITSO | — |

TABLE 9-continued

| | Layer | Reference numeral | Thickness (nm) | Material | Weight ratio |
|---|---|---|---|---|---|
| Comparative light-emitting elements 41 to 44 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | 4,6mCzP2Pm | — |
| | Light-emitting layer | 130 | 40 | 4,6mCzP2Pm:Ir(ppz)$_3$:DPQd | 0.8:0.2:x2 |
| | Hole-transport layer | 112 | 20 | PCCP | — |
| | Hole-injection layer | 111 | 40 | DBT3P-II:MoO$_3$ | 1:0.5 |
| | Anode | 101 | 70 | ITSO | — |

TABLE 10

| | Light-emitting element 37 Comparative light-emitting element 41 | Light-emitting element 38 Comparative light-emitting element 42 | Light-emitting element 39 Comparative light-emitting element 43 | Light-emitting element 40 Comparative light-emitting element 44 |
|---|---|---|---|---|
| $x_2$ | 0.005 | 0.01 | 0.025 | 0.05 |

<Fabrication of Light-Emitting Element 37 to Light-Emitting Element 40>

A light-emitting element 37 to a light-emitting element 40 are different from the fabrication of the above-described light-emitting element 1 only in a guest material of the light-emitting layer 130, and other steps of the fabrication method are the same as those for the light-emitting element 1.

As the light-emitting layer 130, 4,6mCzP2Pm, Ir(ppz)$_3$, and Oct-tBuDPQd were deposited over the hole-transport layer 112 of each of the light-emitting element 37 to the light-emitting element 40 by co-evaporation at a weight ratio (4,6mCzP2Pm:Ir(ppz)$_3$:Oct-tBuDPQd) of 0.8:0.2:$x_2$ to a thickness of 40 nm. In the light-emitting layer 130, Ir(ppz)$_3$ is a phosphorescent material containing Ir and 4,6mCzP2Pm and Ir(ppz)$_3$ form an exciplex in combination.

Furthermore, Oct-tBuDPQd is a fluorescent material having protecting groups. Note that the value $x_2$ differs between the light-emitting elements, and Table 10 shows the value $x_2$ in each of the light-emitting elements.

<<Fabrication of Comparative Light-Emitting Element 41 to Comparative Light-Emitting Element 44>>

A comparative light-emitting element 41 to a comparative light-emitting element 44 are different from the above-described light-emitting element 37 to light-emitting element 40 only in a fluorescent material (guest material) used for the light-emitting layer 130, and other steps of the fabrication method are the same as those for the light-emitting element 1. The details of the element structures are shown in Table 9 and Table 10; thus, the details of the fabrication methods are omitted.

The guest materials used for the light-emitting element 37 to the light-emitting element 40 each have protecting groups around a luminophore, whereas the guest materials used for the comparative light-emitting element 41 to the comparative light-emitting element 44 have no protecting group. Each of the luminophores described in this example is a quinacridone skeleton.

<Characteristics of Light-Emitting Elements>

Next, the characteristics of the fabricated light-emitting element 37 to light-emitting element 40 and comparative light-emitting element 41 to comparative light-emitting element 44 were measured. Note that the measurement method is similar to that in Example 6.

Figure 59:
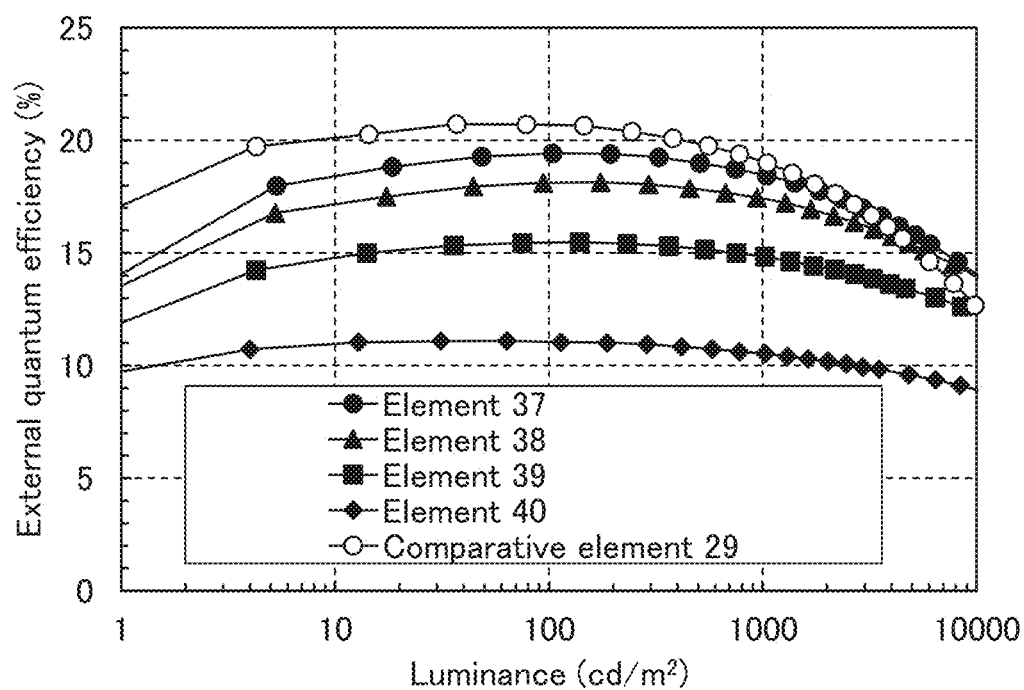
FIG. 59 A diagram showing external quantum efficiency-luminance characteristics of light-emitting elements in Example.
Figure 60:
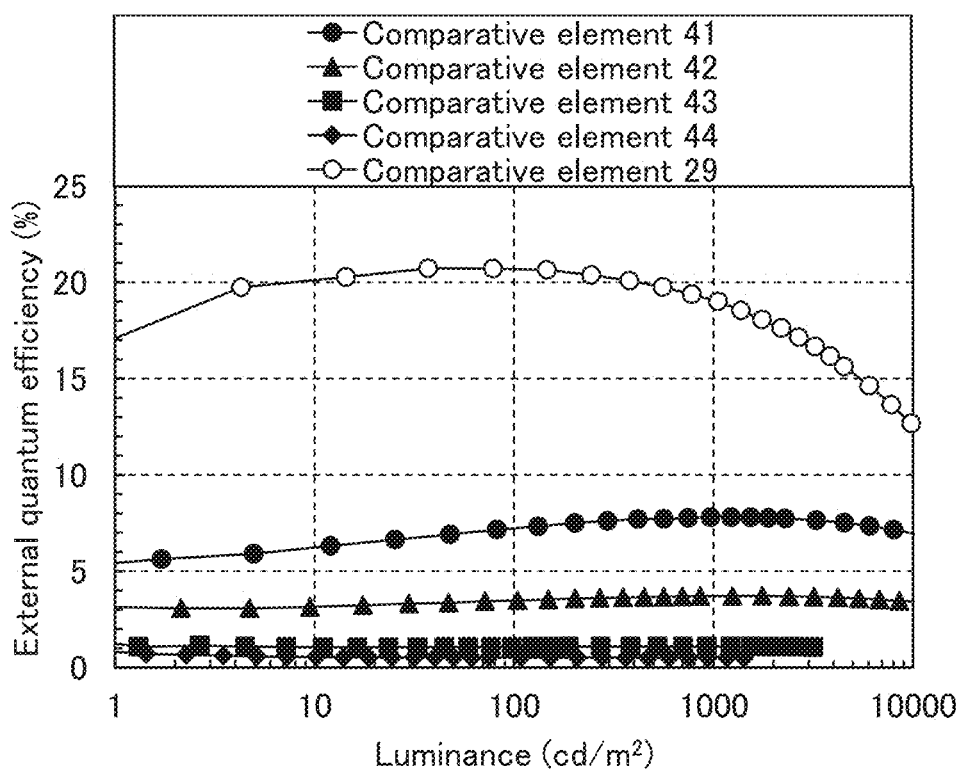
FIG. 60 A diagram showing external quantum efficiency-luminance characteristics of light-emitting elements in Example.
Figure 61:
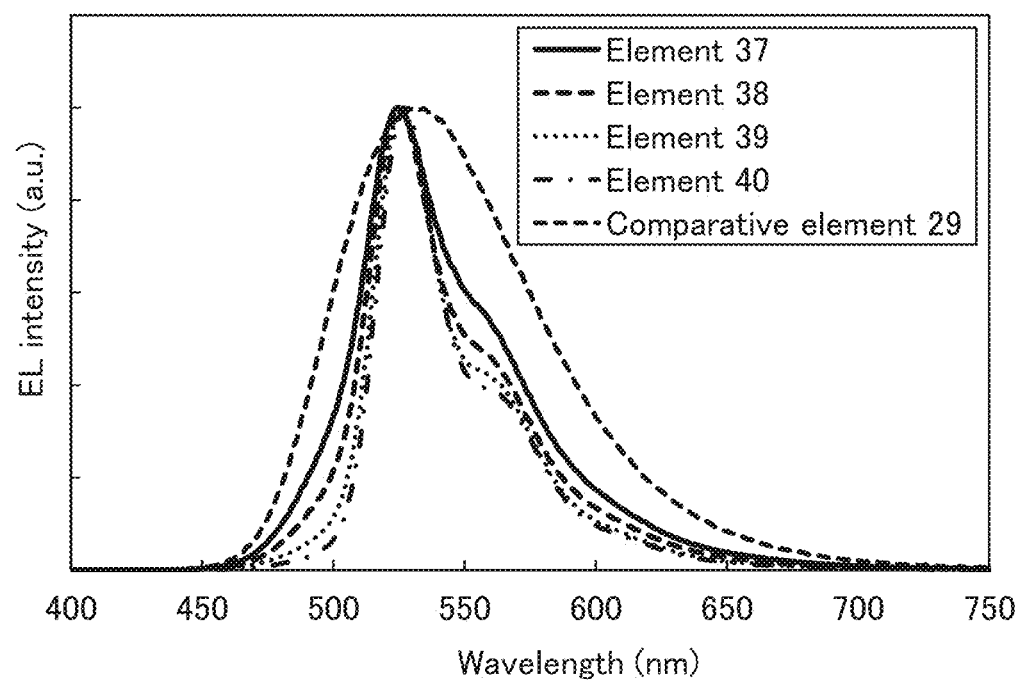
FIG. 61 A diagram showing electroluminescence spectra of light-emitting elements in Example.
Figure 62:
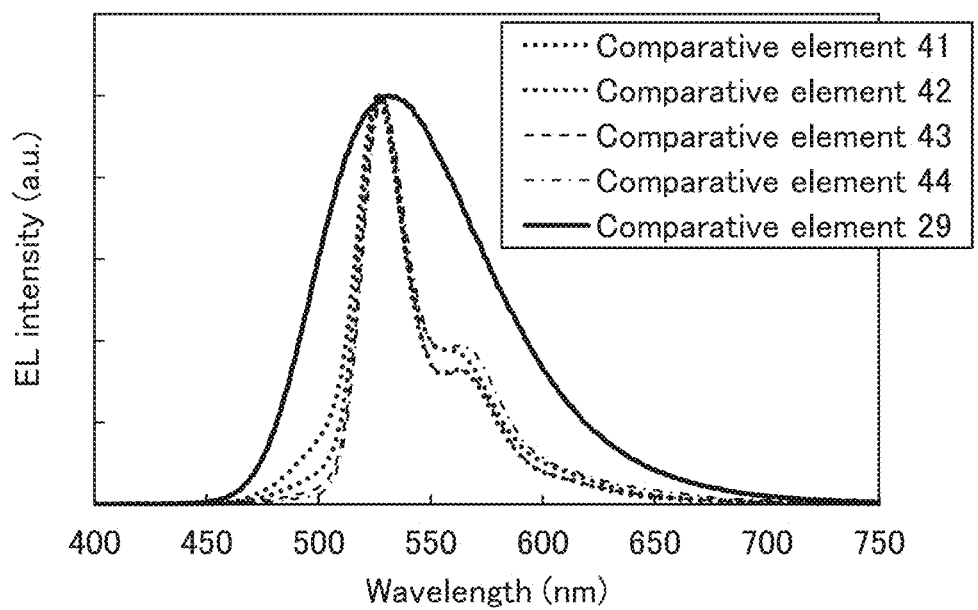
FIG. 62 A diagram showing electroluminescence spectra of light-emitting elements in Example.

FIG. 59 and FIG. 60 show the external quantum efficiency-luminance characteristics of the light-emitting element 37 to the light-emitting element 40 and the comparative light-emitting element 41 to the comparative light-emitting element 44. FIG. 61 and FIG. 62 show the electroluminescence spectra of the light-emitting element 37 to the light-emitting element 40 and the comparative light-emitting element 41 to the comparative light-emitting element 44 to which a current at a current density of 2.5 mA/cm$^2$ was supplied. Note that the measurement of the light-emitting elements was performed at room temperature (in an atmosphere maintained at 23° C.).

Table 11 shows the element characteristics of the light-emitting element 37 to the light-emitting element 40 and the comparative light-emitting element 41 to the comparative light-emitting element 44 at around 1000 cd/m$^2$.

TABLE 11

| | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting element 37 | 3.20 | 1.58 | (0.293, 0.646) | 1046 | 66.3 | 65.1 | 18.4 |
| Light-emitting element 38 | 3.20 | 1.45 | (0.286, 0.664) | 942 | 64.8 | 63.7 | 17.5 |
| Light-emitting element 39 | 3.30 | 1.79 | (0.283, 0.681) | 1025 | 57.3 | 54.6 | 14.8 |

TABLE 11-continued

|  | Voltage (V) | Current density (mA/cm²) | CIE chromaticity (x, y) | Luminance (cd/m²) | Current efficiency (cd/A) | Power efficiency (lm/W) | External quantum efficiency (%) |
|---|---|---|---|---|---|---|---|
| Light-emitting element 40 | 3.40 | 2.46 | (0.283, 0.689) | 1024 | 41.6 | 38.4 | 10.5 |
| Comparative light-emitting element 41 | 3.60 | 3.28 | (0.292, 0.661) | 965 | 29.4 | 25.6 | 7.8 |
| Comparative light-emitting element 42 | 4.00 | 5.93 | (0.288, 0.677) | 857 | 14.5 | 11.4 | 3.7 |
| Comparative light-emitting element 43 | 5.00 | 21.47 | (0.292, 0.681) | 927 | 4.3 | 2.7 | 1.1 |
| Comparative light-emitting element 44 | 5.80 | 48.84 | (0.308, 0.669) | 940 | 1.9 | 1.0 | 0.5 |

As shown in FIG. 61 and FIG. 62, the emission spectra of the light-emitting element 37 to the light-emitting element 40 had peak wavelengths at 525 nm, 525 nm, 526 nm, and 527 nm and full widths at half maximum of 57 nm, 41 nm, 33 nm, and 31 nm, respectively, i.e., exhibited green light emission originating from Oct-tBuDPQd. The emission spectra of the comparative light-emitting element 41 to the comparative light-emitting element 44 had peak wavelengths at 526 nm, 527 nm, 528 nm, and 529 nm and full widths at half maximum of 29 nm, 25 nm, 25 nm, and 26 nm, respectively, i.e., exhibited green light emission originating from DPQd. Thus, the excitation energy of each light-emitting element is found to be transferred to the fluorescent material that is the guest material of each light-emitting element.

Although the light-emitting element 37 to the light-emitting element 40 exhibit light emission originating from the fluorescent materials, as shown in FIG. 59 and Table 11, they exhibited high emission efficiency with an external quantum efficiency exceeding at least 10%. In addition, the light-emitting element 37 to the light-emitting element 40, which are light-emitting elements of embodiments of the present invention, exhibited a higher external quantum efficiency than the comparative light-emitting element 41 to the comparative light-emitting element 44. This result indicates that in the light-emitting element of one embodiment of the present invention, non-radiative decay of triplet excitons is inhibited, contributing to efficient conversion into light emission. Thus, even when the quinacridone skeleton is used as the luminophore of the guest material having protective groups, both the singlet excitation energy and the triplet excitation energy of each light-emitting element are transferred to the fluorescent material, which is the guest material of each light-emitting element. That is, it was found that energy transfer of triplet excitation energy from a host material to a guest material by the Dexter mechanism and deactivation of the triplet excitation energy can be inhibited according to one embodiment of the present invention.

Although not illustrated, absorption bands on the longest wavelength side of the absorption spectra of the guest materials used in this example and the emission spectrum of the comparative light-emitting element 29 overlap with each other. Thus, the excited energy of the exciplex which is formed by 4,6mCzP2Pm and Ir(ppz)₃ and serves as an energy donor is efficiently transferred to each guest material by the Förster mechanism.

Furthermore, it was found from FIG. 59 and FIG. 61 that even when the energy donor and the guest material exhibit similar emission colors, a light-emitting element with high emission efficiency can be obtained according to one embodiment of the present invention. It was found that even when a full width at half maximum of the emission spectrum of the guest material is smaller than that of the energy donor, such a combination can also be favorably used in the light-emitting element of one embodiment of the present invention. Thus, the light-emitting element of one embodiment of the present invention having a color similar to that of the energy donor and high color purity can be obtained.

<Change in External Quantum Efficiency Depending on Guest Material Concentration>

Figure 63:
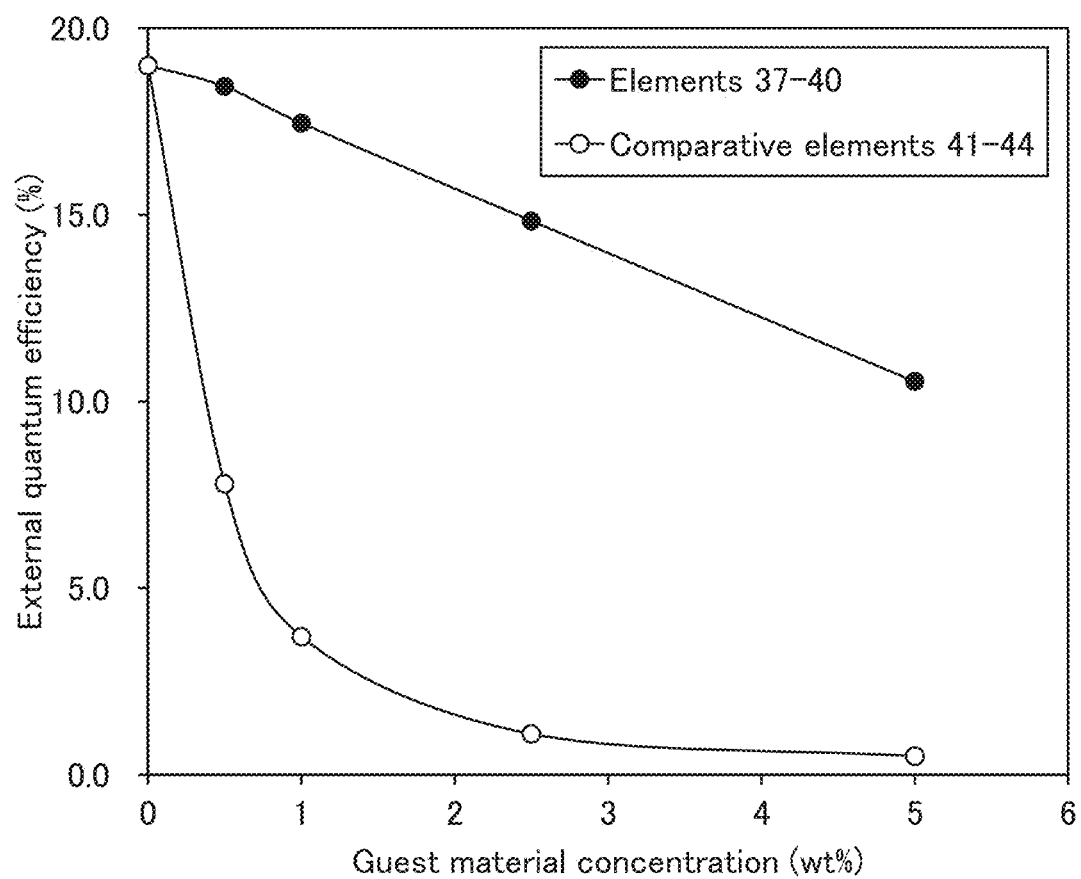
FIG. 63 A diagram showing the relation between external quantum efficiency and guest material concentration in Example.

FIG. 63 shows the relation between the guest material concentration and external quantum efficiency of each guest material. It is found from FIG. 63 that a decrease in efficiency due to an increase in the concentration is inhibited in the light-emitting element 37 to the light-emitting element 40 of embodiments of the present invention each using the guest material having protecting groups compared to that in the comparative light-emitting element 41 to the comparative light-emitting element 44. Therefore, in the light-emitting element of one embodiment of the present invention, as described above, even when the guest material concentration is increased, energy transfer of triplet excitation energy from the host material to the guest material by the Dexter mechanism can be inhibited and deactivation of the triplet excitation energy can be inhibited; thus, a light-emitting element with high emission efficiency can be obtained.

<Fluorescence Lifetime Measurement of Light-Emitting Elements>

Figure 64:
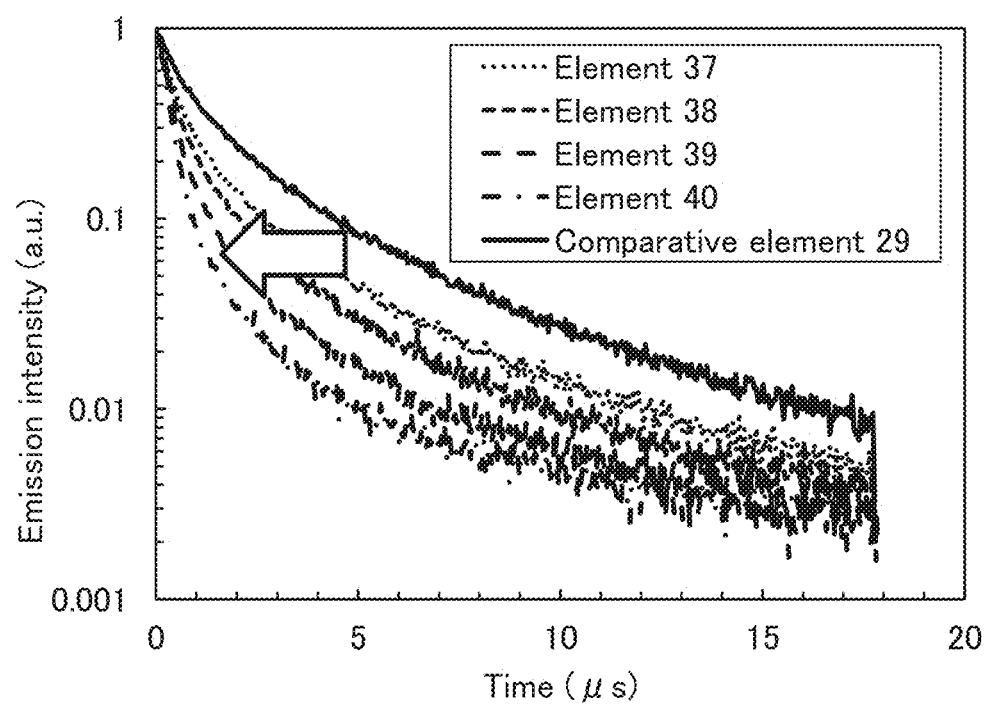
FIG. 64 A diagram showing emission lifetime measurement results of light-emitting elements in Example.
Figure 65:
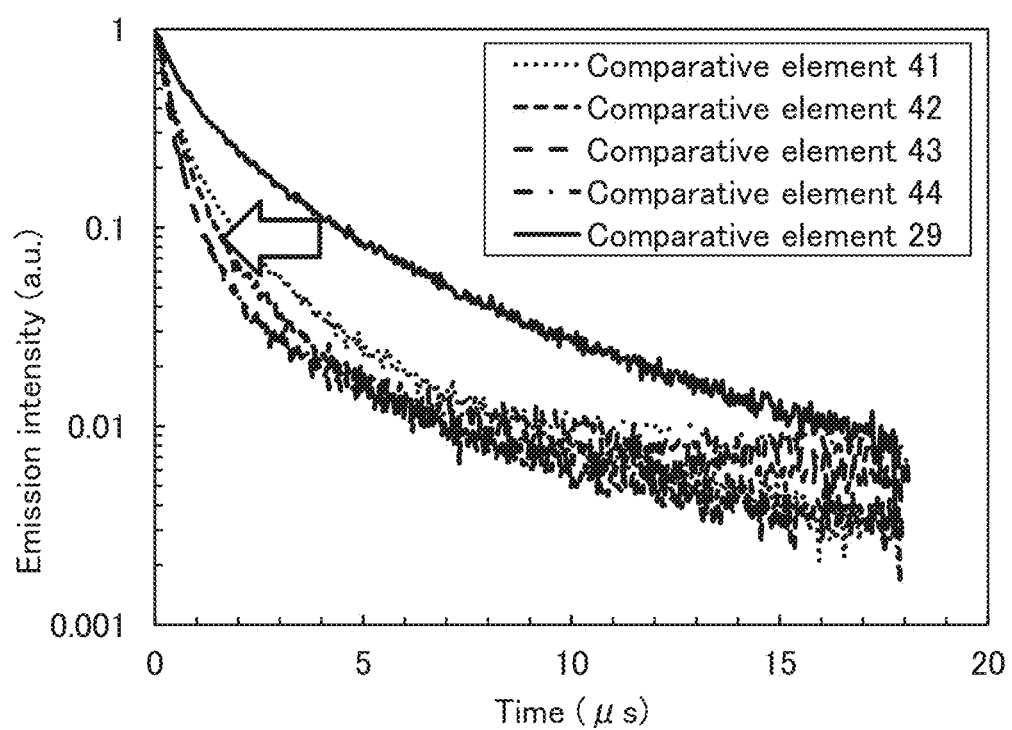
FIG. 65 A diagram showing emission lifetime measurement results of light-emitting elements in Example.

Next, fluorescence lifetimes of the fabricated light-emitting element 37 to light-emitting element 40 and comparative light-emitting element 41 to comparative light-emitting element 44 were measured. Note that the measurement method is similar to that in Example 1. FIG. 64 and FIG. 65 show the results.

Fitting of attenuation curves shown in FIG. 64 and FIG. 65 using an exponential function revealed that the light-emitting element 37 to the light-emitting element 40 and the comparative light-emitting element 41 to the comparative light-emitting element 44 emit light including a prompt fluorescence component of 1 μs or less and a delayed fluorescence component of approximately 3 μs. Furthermore, it was also found that when a fluorescent material is added as a guest material, as the fluorescent material concentration is high, the proportion of the prompt fluorescence component increases and the proportion of the delayed fluorescence component decreases regardless of the guest material. These facts indicate that when a fluorescent material is added to the light-emitting layer as a guest material, the proportion of the prompt fluorescence component originating from the fluorescent material increases. Here, as described above, the light-emitting element 37 to the light-emitting element 40 of embodiments of the present invention each using the guest material having protecting groups show a high external quantum efficiency even when the light-emitting elements have a high fluorescent material concentration. That is, the light-emitting element of one embodiment of the present invention has high emission efficiency even when the proportion of light emission originating from the fluorescent material increases. Thus, it is suggested that, in the light-emitting element of one embodiment of the present invention, energy transfer of triplet excitation energy from the host material to the guest material by the Dexter mechanism and deactivation of the triplet excitation energy can be inhibited and thus the guest material concentration can be increased, whereby the efficiency of energy transfer of excitation energy by the Förster mechanism can be improved. On the contrary, in the comparative light-emitting element 41 to the comparative light-emitting element 44 each using the guest material having no protecting group, influence of energy transfer of triplet excitation energy from the host material to the guest material by the Dexter mechanism and deactivation of the triplet excitation energy is large, so that the emission efficiency decreases while the proportion of light emission originating from the fluorescent material increases. Thus, the light-emitting element of one embodiment of the present invention can utilize both the singlet excitation energy and the triplet excitation energy for light emission efficiently.

From the above, not only the above-described anthracene skeleton but also a quinacridone skeleton can be favorably used as the luminophore of the guest material that can be used for the light-emitting element of one embodiment of the present invention.

Example 9

In this example, fabrication examples and the characteristics of light-emitting elements of embodiments of the present invention and comparative light-emitting elements, which are different from those in the above examples, are described. The structure of each of the light-emitting elements fabricated in this example is the same as that in FIG. 1(A). Table 12 shows the details of the element structures. Note that the above examples and embodiments can be referred to for other organic compounds.

TABLE 12

|  | Layer | Reference numeral | Thickness (nm) | Material | Weight ratio |
|---|---|---|---|---|---|
| Light-emitting element 45 | Electrode | 102 | 200 | Al | — |
|  | Electron-injection layer | 119 | 1 | LiF | — |
|  | Electron-transport layer | 118(2) | 10 | NBPhen | — |
|  |  | 118(1) | 20 | 4,6mCzP2Pm | — |
|  | Light-emitting layer | 130 | 40 | mPCCzPTzn-02:PCCP:GD270:Oct-tBuDPQd | 0.5:0.5:0.1:0.05 |
|  | Hole-transport layer | 112 | 20 | PCCP | — |
|  | Hole-injection layer | 111 | 40 | DBT3P-II:MoO$_3$ | 1:0.5 |
|  | Anode | 101 | 70 | ITSO | — |
| Comparative light-emitting element 46 | Electrode | 102 | 200 | Al | — |
|  | Electron-injection layer | 119 | 1 | LiF | — |
|  | Electron-transport layer | 118(2) | 10 | NBPhen | — |
|  |  | 118(1) | 20 | 4,6mCzP2Pm | — |
|  | Light-emitting layer | 130 | 40 | mPCCzPTzn-02:PCCP:GD270:DPQd | 0.5:0.5:0.1:0.05 |
|  | Hole-transport layer | 112 | 20 | PCCP | — |
|  | Hole-injection layer | 111 | 40 | DBT3P-II:MoO$_3$ | 1:0.5 |
|  | Anode | 101 | 70 | ITSO | — |

<Fabrication of Light-Emitting Element 45>

A light-emitting element 45 is different from the fabrication of the above-described light-emitting element 30 only in a guest material of the light-emitting layer 130, and other steps of the fabrication method are the same as those for the light-emitting element 30.

Next, as the light-emitting layer 130, mPCCzPTzn-02, PCCP, GD270 (manufactured by Jilin Optical and Electronic Materials Co., Ltd.), and Oct-tBuDPQd were deposited over the hole-transport layer 112 of the light-emitting element 45 by co-evaporation at a weight ratio (mPCCzPTzn-02:PCCP:GD270:Oct-tBuDPQd) of 0.5:0.5:0.1:0.05 to a thickness of 40 nm.

<<Fabrication of Comparative Light-Emitting Element 46>>

A comparative light-emitting element 46 is different from the fabrication method of the above-described light-emitting element 45 only in a fluorescent material (guest material) used for the light-emitting layer 130, and other steps of the fabrication method are the same as those for the light-emitting element 45. The details of the element structures are shown in Table 12; thus, the details of the fabrication methods are omitted.

The guest material used for the light-emitting element 45 has protecting groups around a luminophore, whereas the guest material used for the comparative light-emitting element 46 has no protecting group. In this example, a combination of mPCCzPTzn-02 and PCCP forms an exciplex and GD270 is a phosphorescent material containing Ir. Thus, the light-emitting element 45 and the comparative light-emitting element 46 can convert triplet excitation energy into fluorescence because the exciplex or the phosphorescent material serves as an energy donor. A light-emitting layer of each light-emitting element can also be regarded as a light-emitting layer obtained by adding a fluorescent material to a light-emitting layer that can utilize ExTET.

<Characteristics of Light-Emitting Elements>

Next, the characteristics of the fabricated light-emitting element 45 and comparative light-emitting element 46 were measured. Note that the measurement method is similar to that in Example 6.

Figure 66:
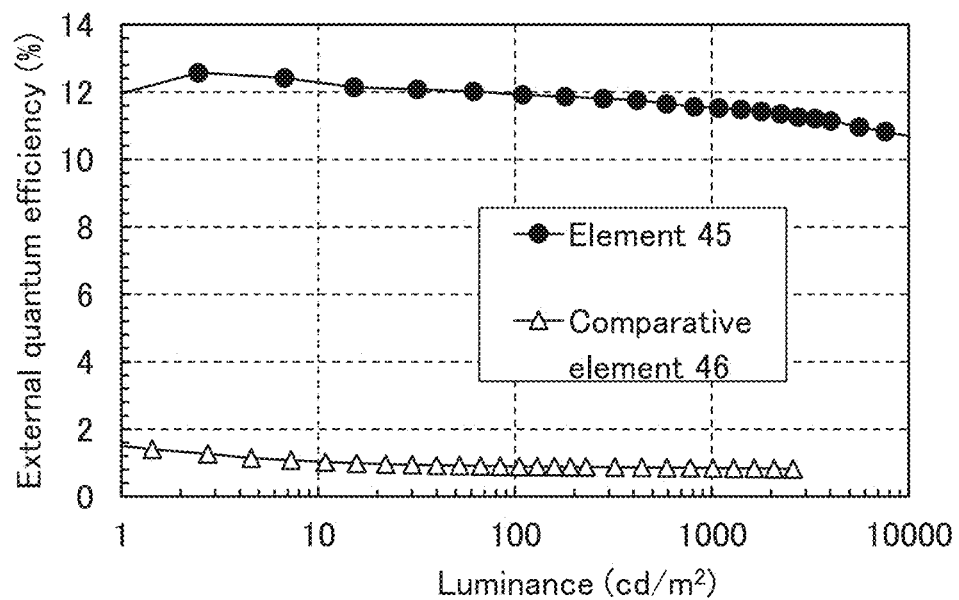
FIG. 66 A diagram showing external quantum efficiency-luminance characteristics of light-emitting elements in Reference example.
Figure 67:
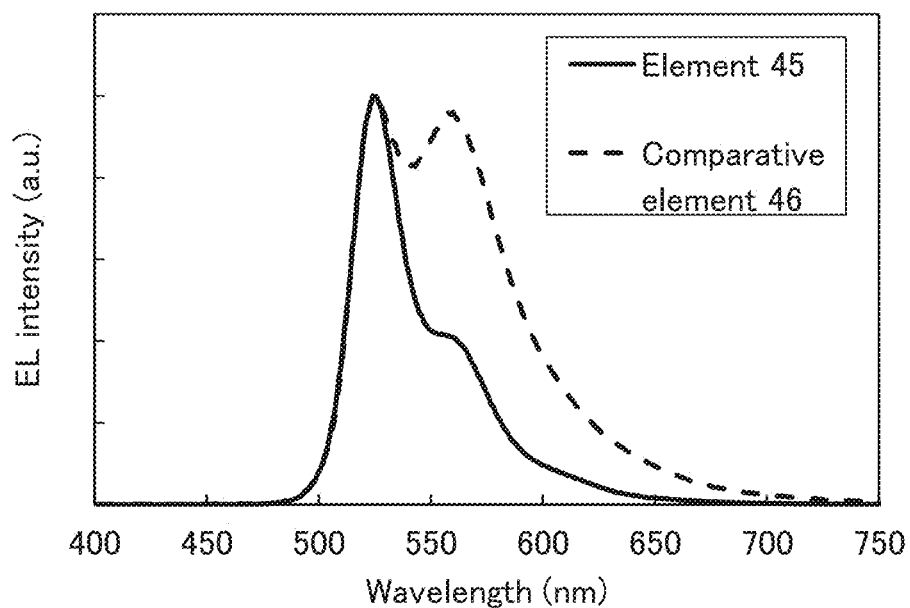
FIG. 67 A diagram showing electroluminescence spectra of light-emitting elements in Reference example.

FIG. 66 shows the external quantum efficiency-luminance characteristics of the light-emitting element 45 and the comparative light-emitting element 46. FIG. 67 shows electroluminescence spectra of the light-emitting element 45 and the comparative light-emitting element 46 to which a current at a current density of 2.5 mA/cm$^2$ was supplied. Note that the measurement of the light-emitting elements was performed at room temperature (in an atmosphere maintained at 23° C.).

Table 13 shows the element characteristics of the light-emitting element 45 and the comparative light-emitting element 46 at around 1000 cd/m$^2$.

Although the light-emitting element 45 exhibits light emission originating from the fluorescent materials, as shown in FIG. 66 and Table 13, they exhibited high emission efficiency with an external quantum efficiency exceeding 10%. This result indicates that in the light-emitting element of one embodiment of the present invention, non-radiative decay of triplet excitons is inhibited, contributing to efficient conversion into light emission. Thus, it was found that the use of a guest material having protecting groups in a light-emitting layer can inhibit energy transfer of triplet excitation energy from a host material to a guest material by the Dexter mechanism and non-radiative decay of triplet excitation energy.

Although not illustrated, absorption bands on the longest wavelength side of the absorption spectra of the guest materials used in this example and the emission spectrum of the comparative light-emitting element 103 overlap with each other. Thus, the energy of GD270, which serves as an energy donor, is efficiently transferred to each guest material by the Förster mechanism.

Furthermore, it was found from FIG. 66 and FIG. 67 that even when the energy donor and the guest material exhibit similar emission colors, a light-emitting element with high emission efficiency can be obtained according to one embodiment of the present invention.

Accordingly, the light-emitting element of one embodiment of the present invention can favorably use an exciplex or a phosphorescent material as a host material. Moreover, a structure in which a fluorescent material is added to a light-emitting layer which can utilize ExTET is favorably employed.

Example 10

In this example, a synthesis method of 2-trimethylsilyl-N,N,N',N'-tetrakis(3,5-di-tert-butylphenyl)-9,10-anthracenediamine (abbreviation: 2TMS-mmtBuDPhA2Anth),

TABLE 13

| | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting element 45 | 3.40 | 2.39 | (0.287, 0.687) | 1085 | 45.4 | 41.9 | 11.5 |
| Comparative light-emitting element 46 | 5.00 | 32.5 | (0.354, 0.628) | 1013 | 3.1 | 2.0 | 0.8 |

As shown in FIG. 67, the light-emitting element 45 exhibited green light emission originating from Oct-tBuDPQd whose emission spectrum has a peak wavelength at 525 nm and a full width at half maximum of 30 nm. The comparative light-emitting element 46 exhibited green light emission originating from DPQd whose emission spectrum has a peak wavelength at 525 nm and a full width at half maximum of 75 nm. Accordingly, light emission originating from the fluorescent materials in the light-emitting elements was obtained from the light-emitting element 45 and the comparative light-emitting element 46. Thus, the excitation energy of each light-emitting element is found to be transferred to the fluorescent material that is the guest material of each light-emitting element. This indicates that both singlet excitation energy and triplet excitation energy that are generated in the light-emitting layer are transferred to the fluorescent material through the exciplex or the phosphorescent material.

which is an organic compound represented by Structural Formula (229) of Embodiment 1, will be described.

Step 1: Synthesis of 9,10-dibromo-2-trimethylsilylanthracene 2.7 g (11 mmol) of 2-trimethylsilylanthracene was put into a 500 mL three-neck flask, and the atmosphere in the flask was replaced with nitrogen. Then, 110 mL of N,N-dimethyl sulfoxide was added thereto, and the mixture was stirred at room temperature. Then, 4.0 g (23 mmol) of N-bromosuccinimide was added thereto, and the mixture was stirred at room temperature for 15 hours. After the stirring, water was added to the reaction mixture to give an aqueous layer and an organic layer. The aqueous layer was subjected to extraction with toluene, and the obtained extracted solution and the organic layer were combined. The mixed solution of the extracted solution and the organic layer was washed with water and a saturated aqueous solution of sodium chloride, and then drying was performed with magnesium sulfate. This mixture was separated by gravity filtration, and the filtrate was concentrated to give a yellow brown solid. After 450 mL of hexane and 50 mL of toluene were added to the obtained yellow brown solid, suction filtration was performed through Florisil, Celite, and aluminum oxide to give a filtrate. The obtained filtrate was concentrated to give a yellow brown solid. The obtained solid was recrystallized with ethyl acetate/ethanol, whereby 2.4 g of a yellow solid was obtained in a yield of 54%. The synthesis scheme of Step 1 is shown in (F-1) below.

[Chemical Formula 58]

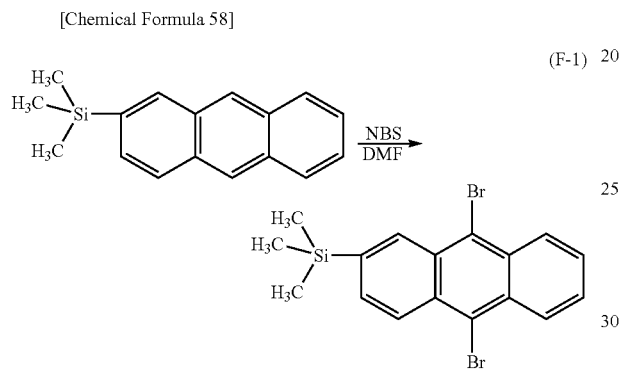

(F-1)

Figure 70A:
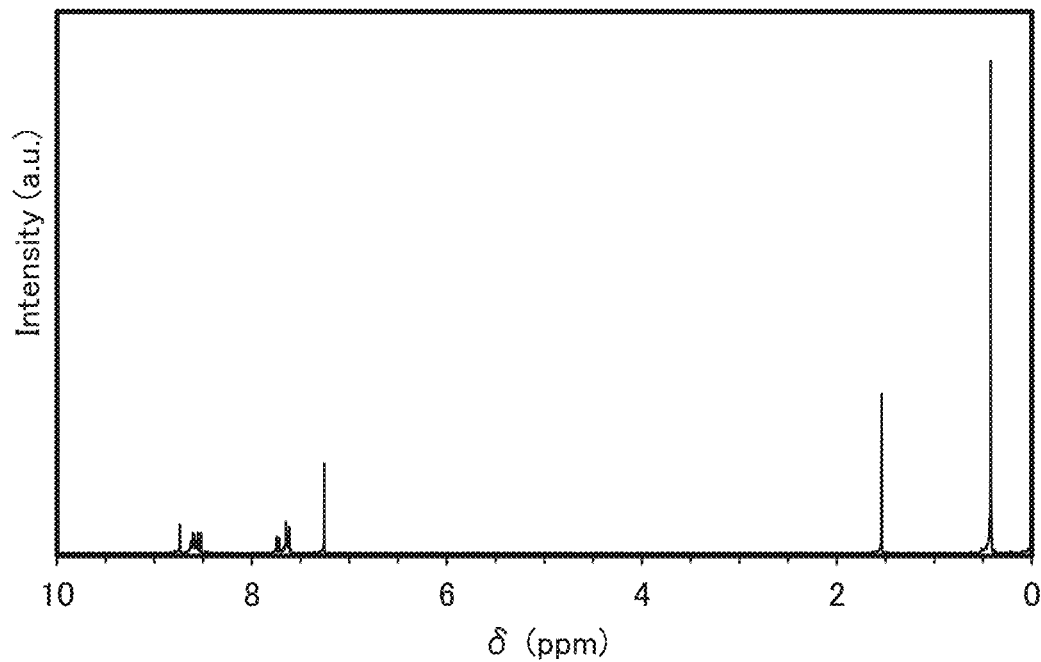
FIGS. 70A and 70B Diagrams showing NMR charts of a compound in Example.
Figure 70B:
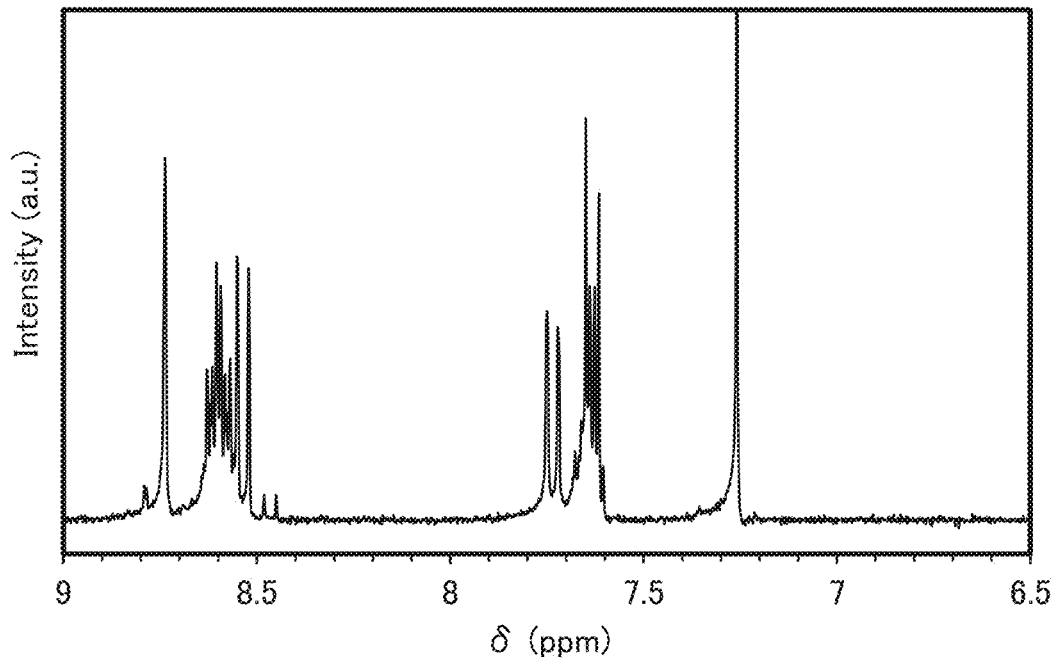
Figure 71:
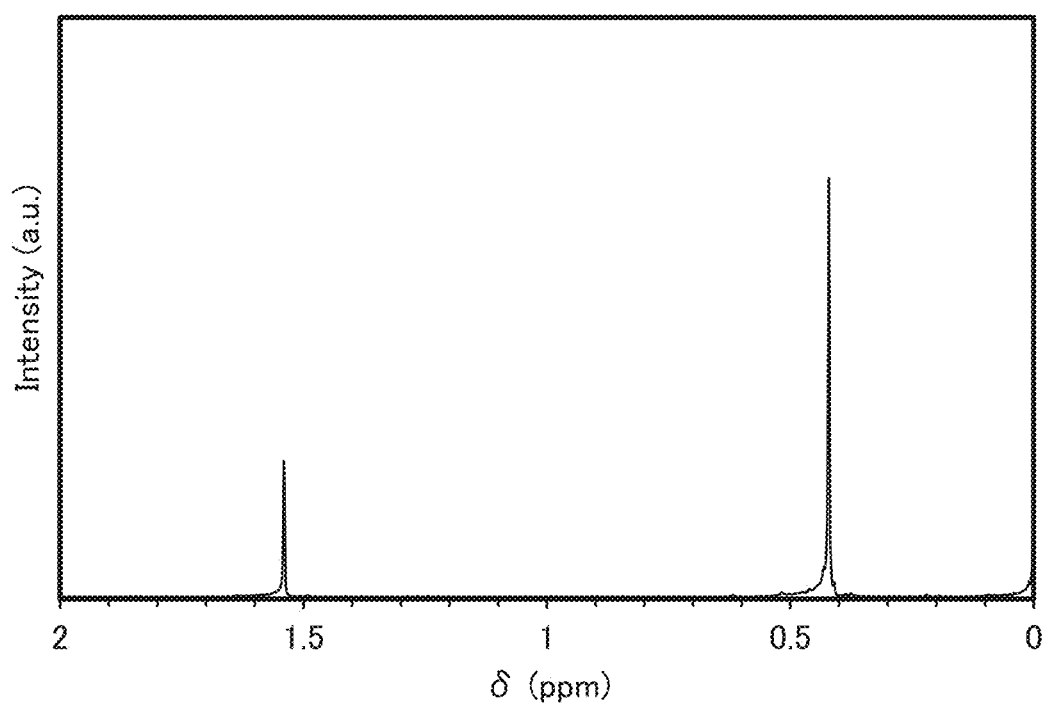
FIG. 71 A diagram showing an NMR chart of a compound in Example.

Results of $^1$H NMR measurement of the yellow solid obtained in Step 1 described above will be described below. FIG. 70 and FIG. 71 are the $^1$H-NMR charts. Note that FIG. 70(B) is an enlarged chart of the range of 6.5 ppm to 9.0 ppm of FIG. 70(A). FIG. 71 is an enlarged chart of the range of 0.0 ppm to 2.0 ppm of FIG. 70(A). The results indicate that 9,10-dibromo-2-trimethylsilylanthracene was obtained.

$^1$H NMR (CDCl$_3$, 300 MHz): σ=8.74 (s, 1H), 8.63-8.56 (m, 2H), 8.55 (d, J=8.8 Hz, 1H), 7.75 (d, J=8.3 Hz, 1H), 7.68-7.61 (m, 2H), 0.42 (s, 9H).

Step 2: Synthesis of 2TMS-mmtBuDPhA2Anth 1.4 g (3.3 mmol) of 9,10-dibromo-2-trimethylsilylanthracene, 2.6 g (6.6 mmol) of bis(3,5-tert-butylphenyl)amine, 1.3 g (14 mmol) of sodium t-butoxide, and 60 mg (0.15 mmol) of SPhos were put into a 200 mL three-neck flask, and the air in the flask was replaced with nitrogen. To this mixture was added 33 mL of xylene, and the mixture was degassed under reduced pressure; then, 40 mg (70 μmol) of bis(dibenzylideneacetone)palladium(0) was added to the mixture and the mixture was stirred for 6 hours at 150° C. under a nitrogen stream. After the stirring, 400 mL of toluene was added to the obtained mixture, which was then subjected to suction filtration through Florisil, Celite, and aluminum oxide to give a filtrate. The obtained filtrate was concentrated to give a brown solid. This solid was purified by silica gel column chromatography (developing solvent: hexane:toluene=9:1) to obtain a yellow solid. The obtained yellow solid was recrystallized with ethyl acetate and ethanol to give 0.40 g of an objective yellow solid in a yield of 12%. The synthesis scheme of Step 2 is shown in (F-2) below.

[Chemical Formula 59]

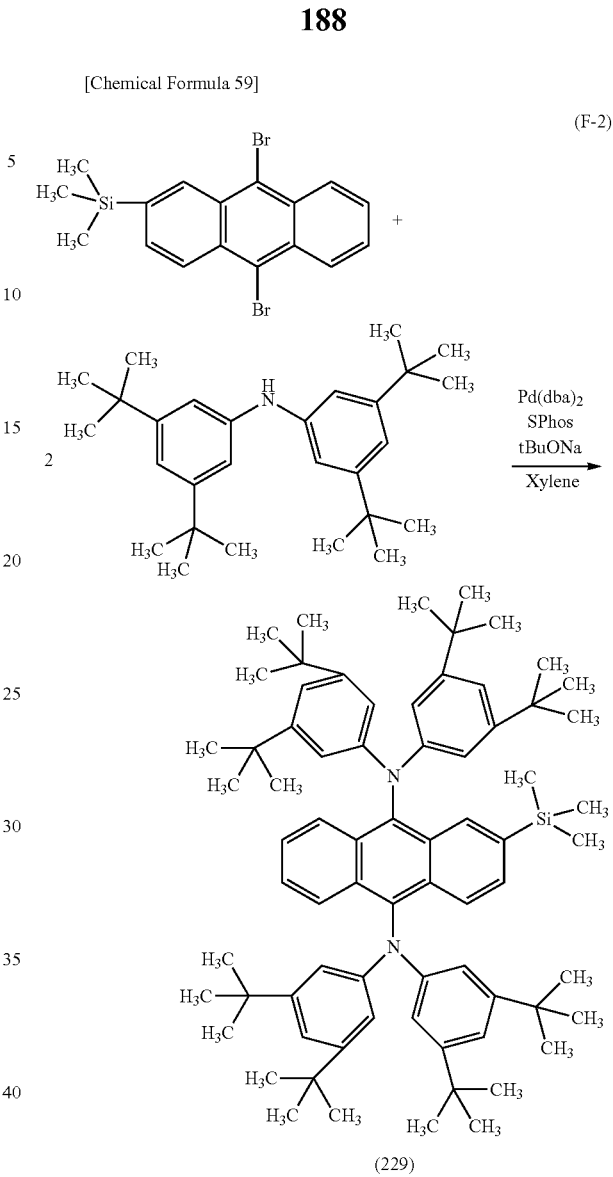

By a train sublimation method, 0.40 g of the obtained yellow solid was purified by sublimation. In the sublimation purification, the yellow solid was heated at 260° C. under a pressure of 3.5 Pa for 15 hours. After the sublimation purification, 0.35 g of an objective yellow solid was obtained at a collection rate of 87%.

Figure 72A:
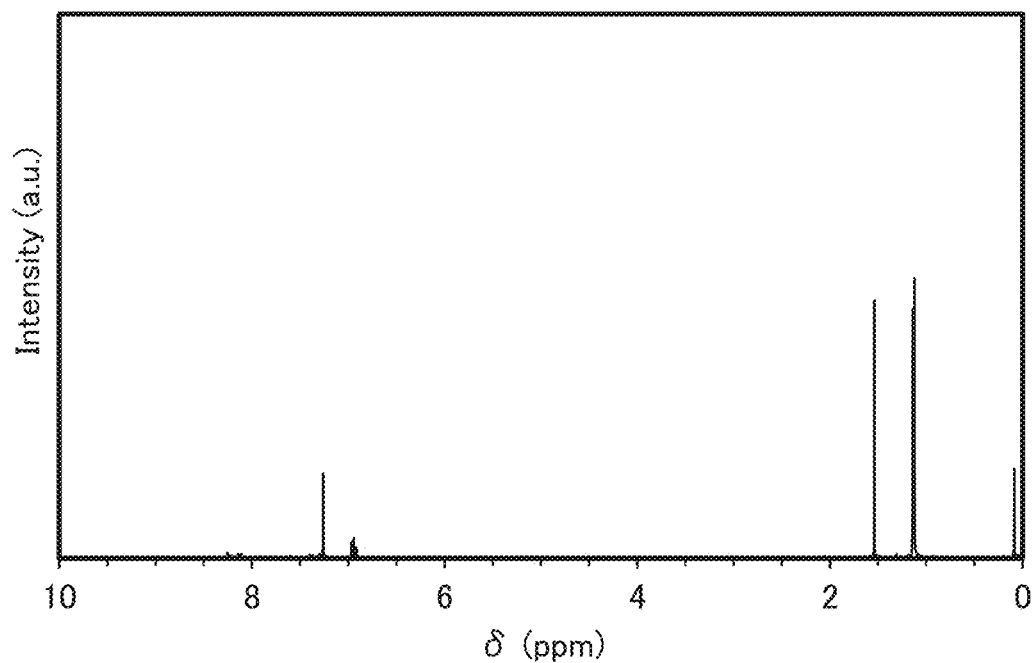
FIGS. 72A and 72B Diagrams showing NMR charts of a compound in Example.
Figure 72B:
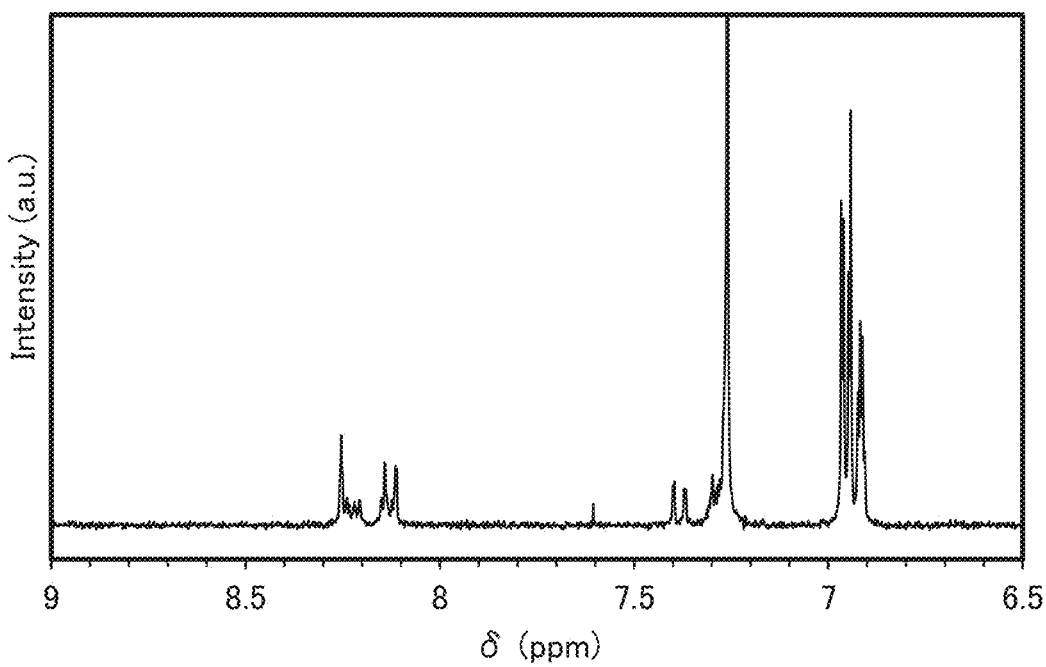
Figure 73:
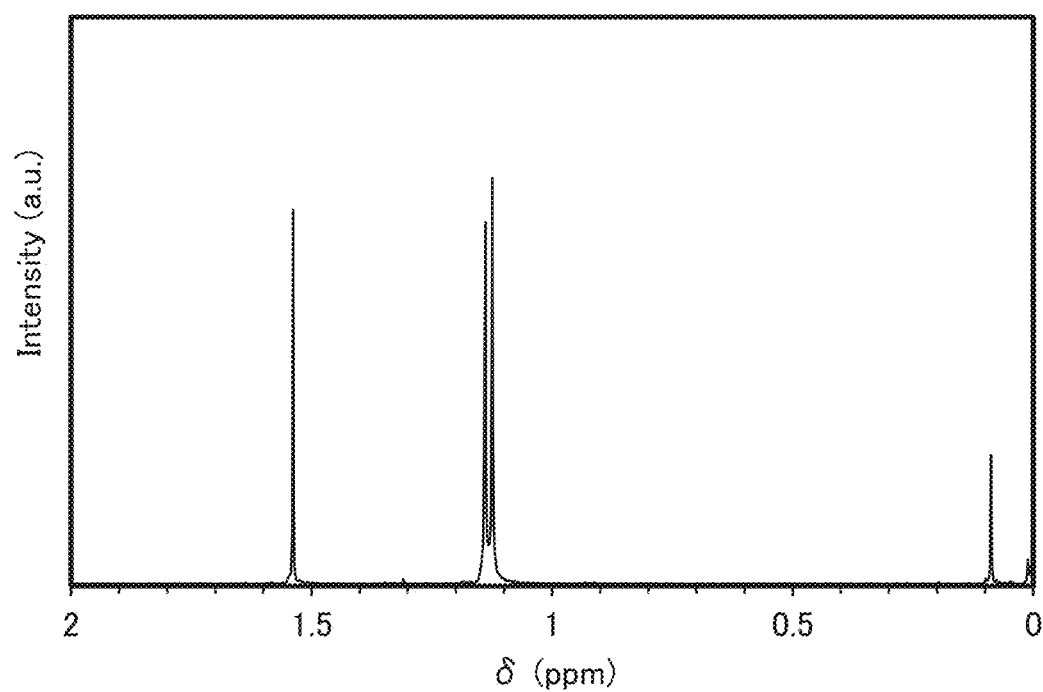
FIG. 73 A diagram showing an NMR chart of a compound in Example.

Results of $^1$H NMR measurement of the yellow solid obtained in Step 2 described above will be described below. FIG. 72 and FIG. 73 are the $^1$H-NMR charts. Note that FIG. 72(B) is an enlarged chart of the range of 6.5 ppm to 9.0 ppm of FIG. 72(A). FIG. 73 is an enlarged chart of the range of 0.0 ppm to 2.0 ppm of FIG. 72(A). The results indicate that 2TMS-mmtBuDPhA2Anth was obtained.

$^1$H NMR (CDCl$_3$, 300 MHz): σ=8.25 (s, 1H), 8.24-8.21 (m, 1H), 8.15-8.11 (m, 2H), 7.40-7.37 (m, 1H), 7.30-7.27 (m, 2H), 6.97-6.94 (m, 8H), 6.92-6.91 (m, 4H), 1.14 (s, 36H), 1.12 (m, 36H), 0.09 (s, 9H).

Example 11

In this example, a synthesis method of N,N'-(2-phenylanthracene-9,10-diyl)-N,N'-bis(3,5-dicyclohexylphenyl)-N, N'-bis(3,5-di-tert-butylphenyl)diamine (abbreviation: 2Ph-mmchtBuDPhA2Anth), which is an organic compound represented by Structural Formula (250) of Embodiment 1, will be described. This organic compound can be favorably used for a light-emitting element of one embodiment of the present invention.

Step 1: Synthesis of 3,5-dicyclohexylphenyl trifluoromethanesulfonate 8.2 g (32 mmol) of 3,5-dicyclohexylphenol was put into a 1 L recovery flask, and the atmosphere in the flask was replaced with nitrogen. Then, 130 mL of dichloromethane and 12 mL (86 mmol) of triethylamine were added thereto, and the mixture was stirred at 0° C. A solution in which 8 mL (48 mmol) of trifluoromethanesulfonic anhydride was dissolved in 50 mL of dichloromethane was dropped thereinto; then, the mixture was stirred for 3 hours while the temperature was returned to room temperature. After the stirring, 1N hydrochloric acid was added to the mixture, and an aqueous layer was subjected to extraction with dichloromethane. The obtained extracted solution and an organic layer were combined, washed with water and saturated saline, and dried with magnesium sulfate. This mixture was separated by gravity filtration, and the filtrate was concentrated to give a brown oily substance. This solid was purified by silica gel column chromatography (developing solvent: hexane) to give 11 g of an objective colorless oily substance in a yield of 84%. The synthesis scheme of Step 1 is shown in (G-1) below.

[Chemical Formula 60]

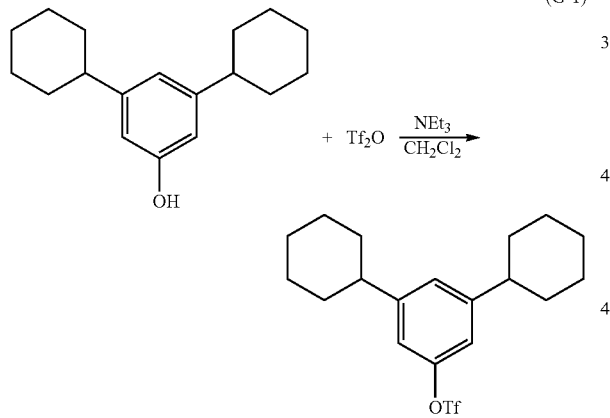

Figure 74A:
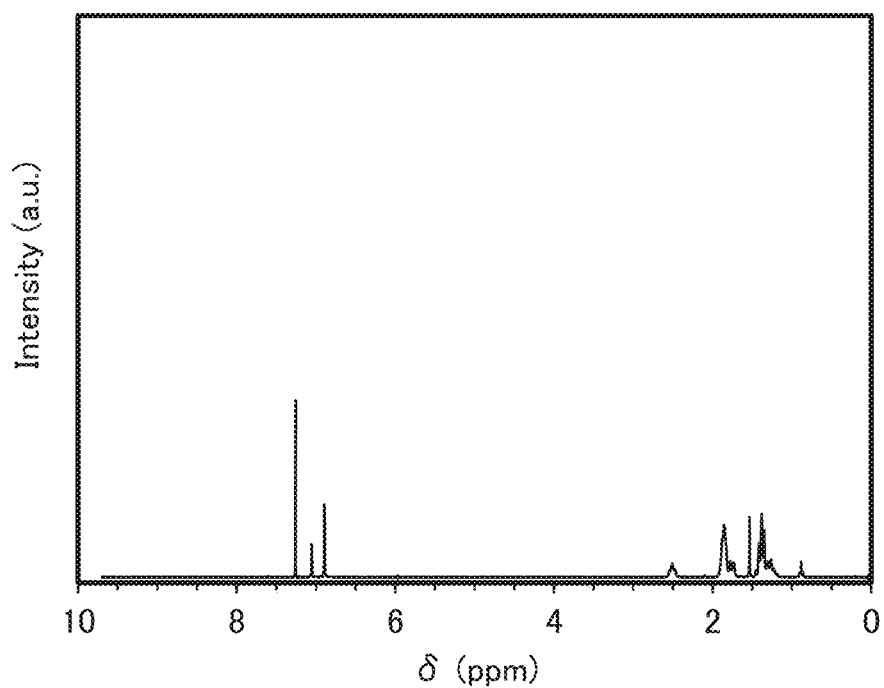
FIGS. 74A and 74B Diagrams showing NMR charts of a compound in Example.
Figure 74B:
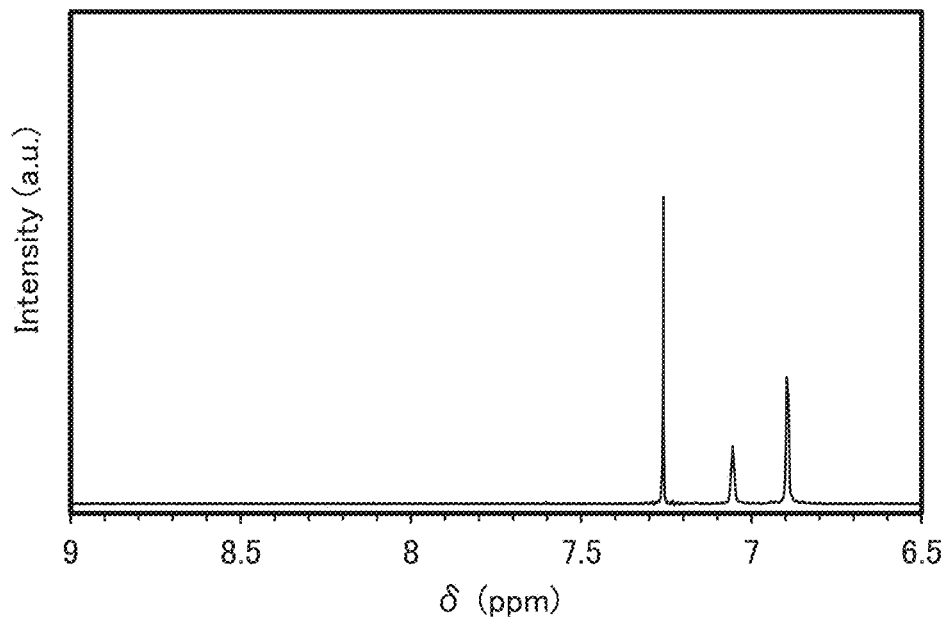
Figure 75:
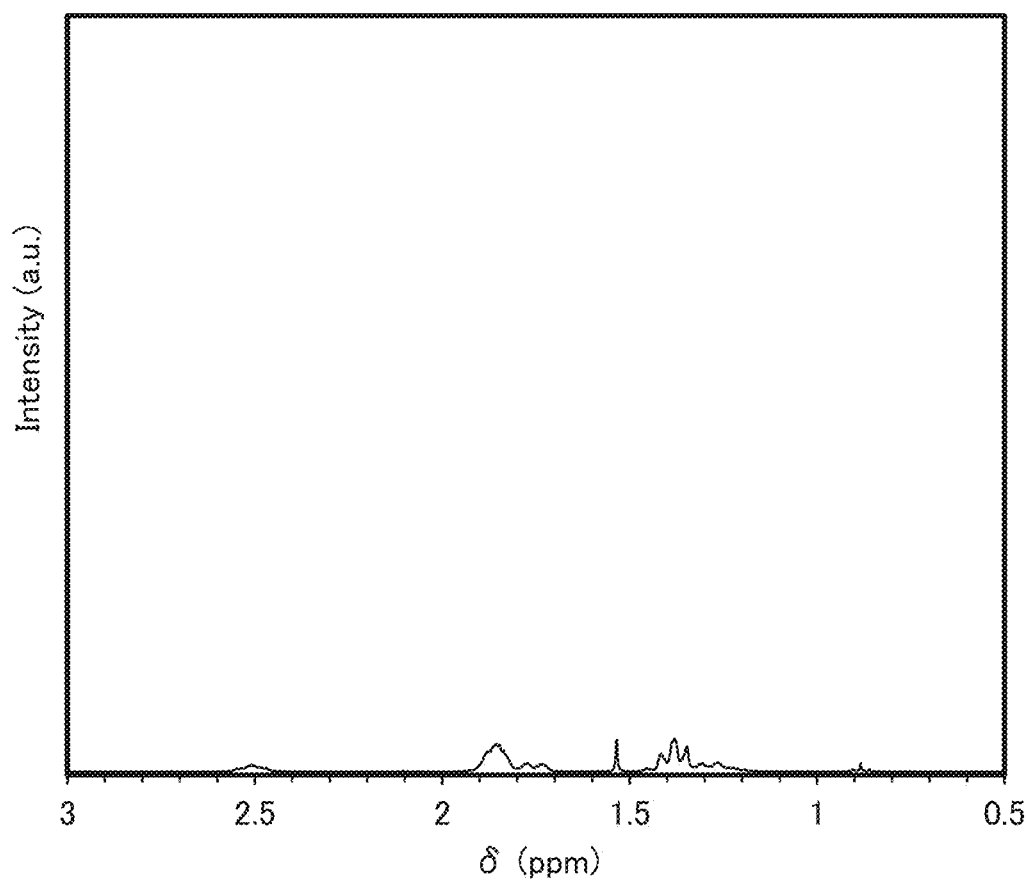
FIG. 75 A diagram showing an NMR chart of a compound in Example.

Results of $^1$H NMR measurement of the colorless oily substance obtained in Step 1 described above will be described below. FIG. 74 and FIG. 75 are the $^1$H-NMR charts. Note that FIG. 74(B) is an enlarged chart of the range of 6.5 ppm to 9.0 ppm of FIG. 74(A). FIG. 75 is an enlarged chart of the range of 0.5 ppm to 3.0 ppm of FIG. 74(A). The results indicate that 3,5-dicyclohexylphenyl trifluoromethanesulfonate was obtained.

$^1$H NMR (CDCl$_3$, 300 MHz): σ=7.06-7.05 (m, 1H), 6.90-6.89 (m, 2H), 2.56-2.46 (m, 2H), 1.88-1.73 (m, 10H), 1.45-1.19 (m, 10H).

Step 2: Synthesis of 3,5-di-cyclohexyl-3',5'-di-tert-butyldiphenylamine 3.9 g (10 mmol) of 3,5-dicyclohexylphenyl trifluoromethanesulfonate was put into a 200 mL three-neck flask, and the air in the flask was replaced with nitrogen. Then, 20 mL of tetrahydrofuran (abbreviation: THF), 2.5 g (12 mmol) of 3,5-di-tert-butylaniline, 4.6 g (14 mmol) of cesium carbonate, and 0.6 g (0.96 mmol) of (±)-2,2'-bis(diphenylphosphino)-1,1'-binaphthyl (abbreviation: (±)-BINAP) were added thereto, and the mixture was degassed under reduced pressure; then, 0.14 g (0.62 mmol) of palladium acetate(II) was added to the mixture and the mixture was stirred for 14 hours at 70° C. under a nitrogen stream. After the stirring, 300 mL of toluene was added to the obtained mixture, which was then subjected to suction filtration through Florisil, Celite, and aluminum oxide to give a filtrate. The obtained filtrate was concentrated to give a reddish-brown solid. This solid was purified by silica gel column chromatography (developing solvent: hexane:toluene=17:3) to obtain 3.2 g of an objective yellow solid in a yield of 72%. The synthesis scheme of Step 2 is shown in (G-2) below.

[Chemical Formula 61]

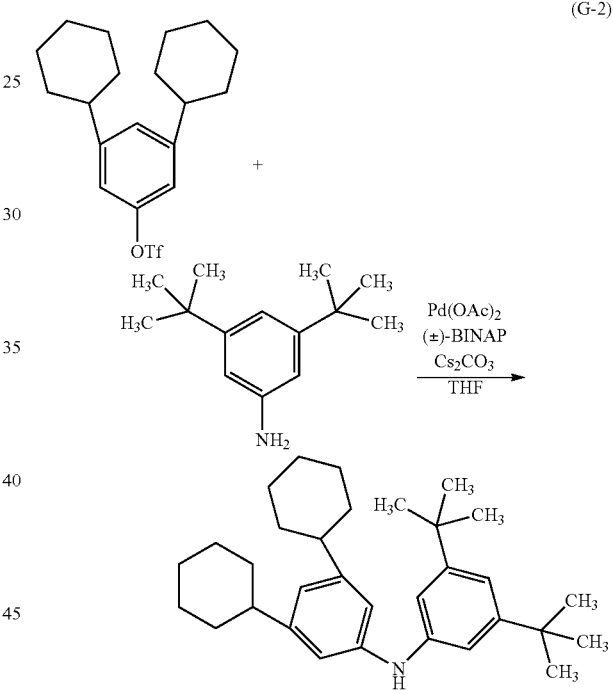

Figure 76A:
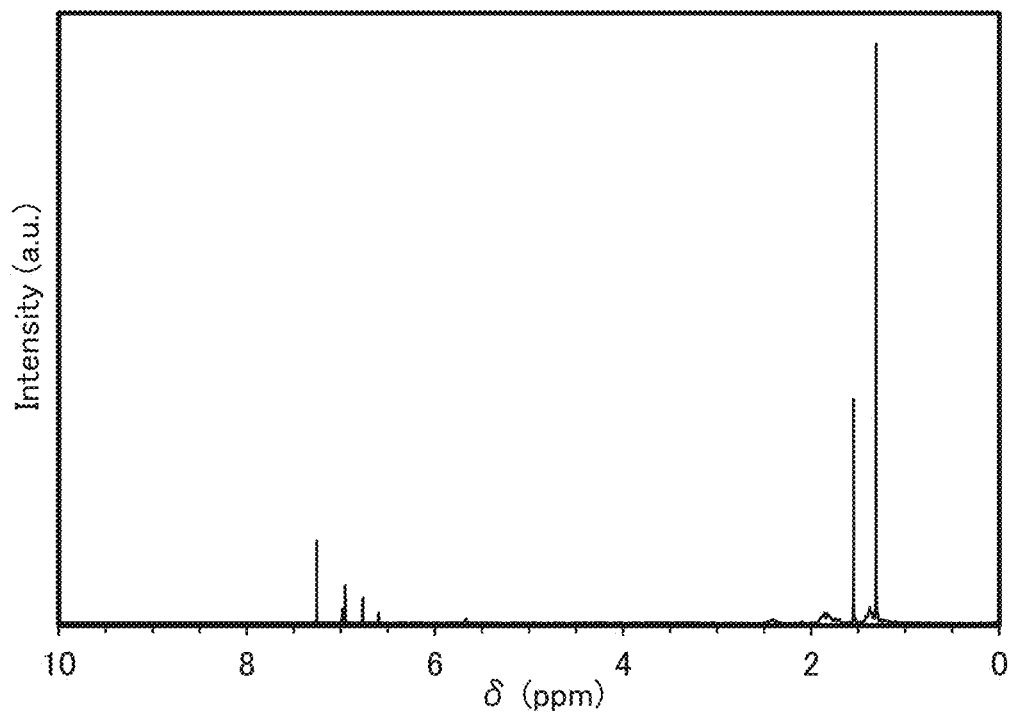
FIGS. 76A and 76B Diagrams showing NMR charts of a compound in Example.
Figure 76B:
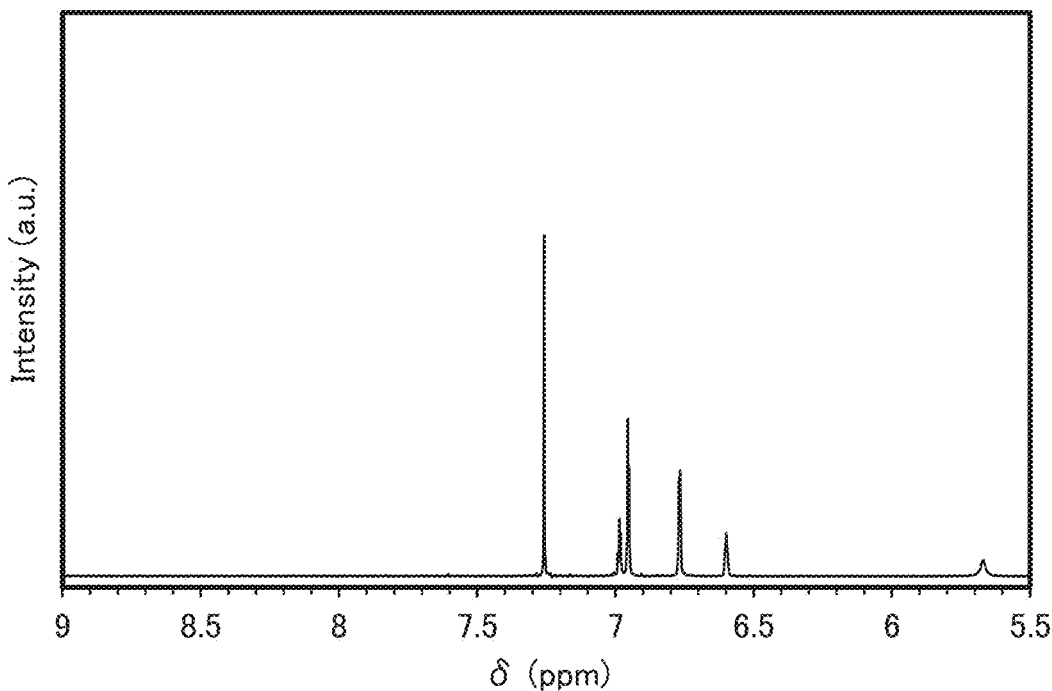
Figure 77:
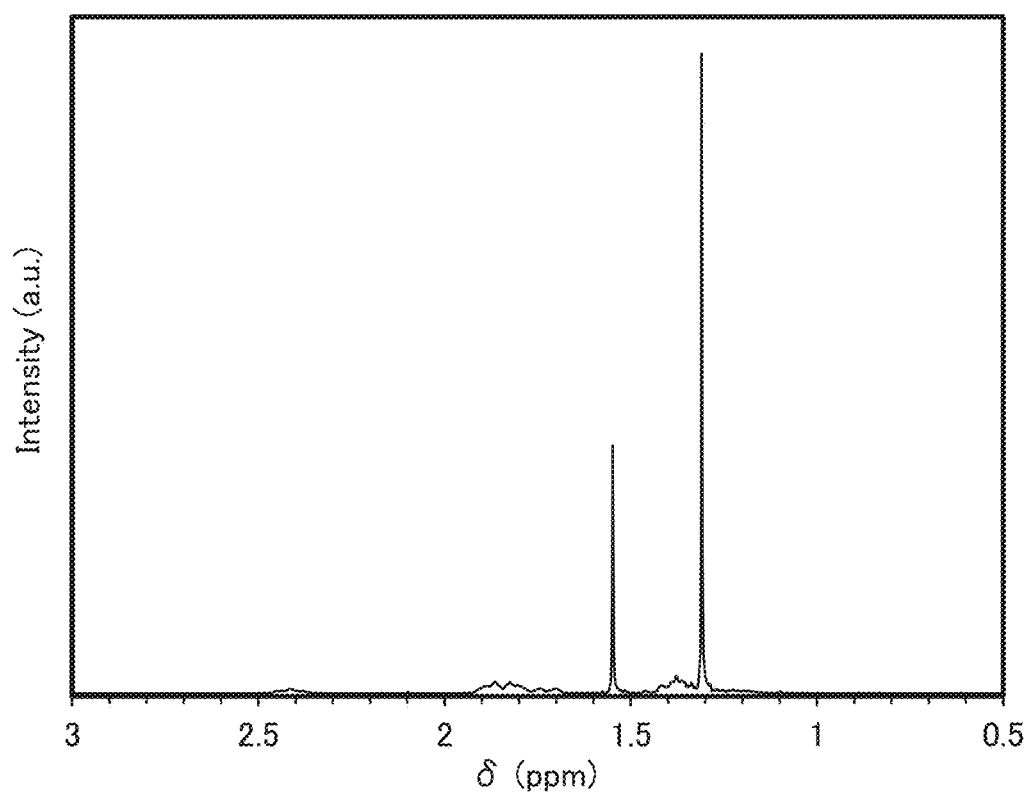
FIG. 77 A diagram showing an NMR chart of a compound in Example.

Results of $^1$H NMR measurement of the yellow solid obtained in Step 2 described above will be described below. FIG. 76 and FIG. 77 are the $^1$H-NMR charts. Note that FIG. 76(B) is an enlarged chart of the range of 5.5 ppm to 9.0 ppm of FIG. 76(A). FIG. 76 is an enlarged chart of the range of 0.5 ppm to 3.0 ppm of FIG. 77(A). The results indicate that 3,5-di-cyclohexyl-3',5'-di-tert-butyldiphenylamine was obtained.

$^1$H NMR (CDCl$_3$, 300 MHz): σ=6.99-6.98 (m, 1H), 6.96-6.95 (m, 2H), 6.77 (m, 2H), 6.60-6.59 (m, 1H), 5.67 (bs, 1H), 2.45-2.37 (m, 2H), 1.89-1.70 (m, 10H), 1.42-1.17 (m, 28H).

Step 3: Synthesis of 2Ph-mmchtBuDPhA2Anth 1.4 g (3.4 mmol) of 9,10-dibromo-2-phenylanthracene, 3.2 g (7.2 mmol) of 3,5-di-cyclohexyl-3',5'-di-tert-butyldiphenylamine, 1.3 g (14 mmol) of sodium t-butoxide, and 60 mg (0.15 mmol) of SPhos were put into a 200 mL three-neck flask, and the air in the flask was replaced with nitrogen. To this mixture was added 35 mL of xylene, and the mixture was degassed under reduced pressure; then, 40 mg (70 μmol) of bis(dibenzylideneacetone)palladium(0) was added to the mixture and the mixture was stirred for 7 hours at 150° C. under a nitrogen stream. After the stirring, 300 mL of toluene was added to the obtained mixture, which was then subjected to suction filtration through Florisil, Celite, and aluminum oxide to give a filtrate. The obtained filtrate was concentrated to give a brown solid.

This solid was purified by silica gel column chromatography (developing solvent: hexane:toluene=9:1) to obtain a yellow solid. The obtained yellow solid was recrystallized with ethyl acetate and ethanol to give an objective yellow solid. The obtained yellow solid was purified by high-performance liquid chromatography (abbreviation: HPLC) (developing solvent: chloroform) to give 0.79 g of an objective yellow solid in a yield of 20%. The synthesis scheme of Step 3 is shown in (G-3) below.

[Chemical Formula 62]

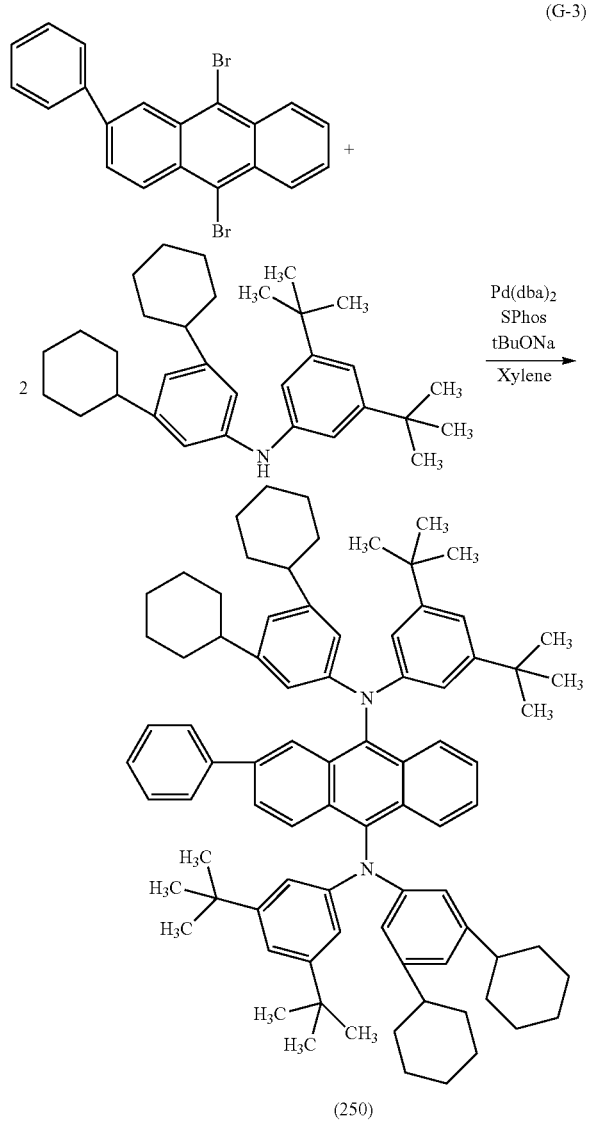

(250)

By a train sublimation method, 0.79 g of the obtained yellow solid was purified by sublimation. In the sublimation purification, the yellow solid was heated at 275° C. under a pressure of 3.5 Pa for 15 hours. After the sublimation purification, 0.72 g of an objective yellow solid was obtained at a collection rate of 91%.

Figure 78A:
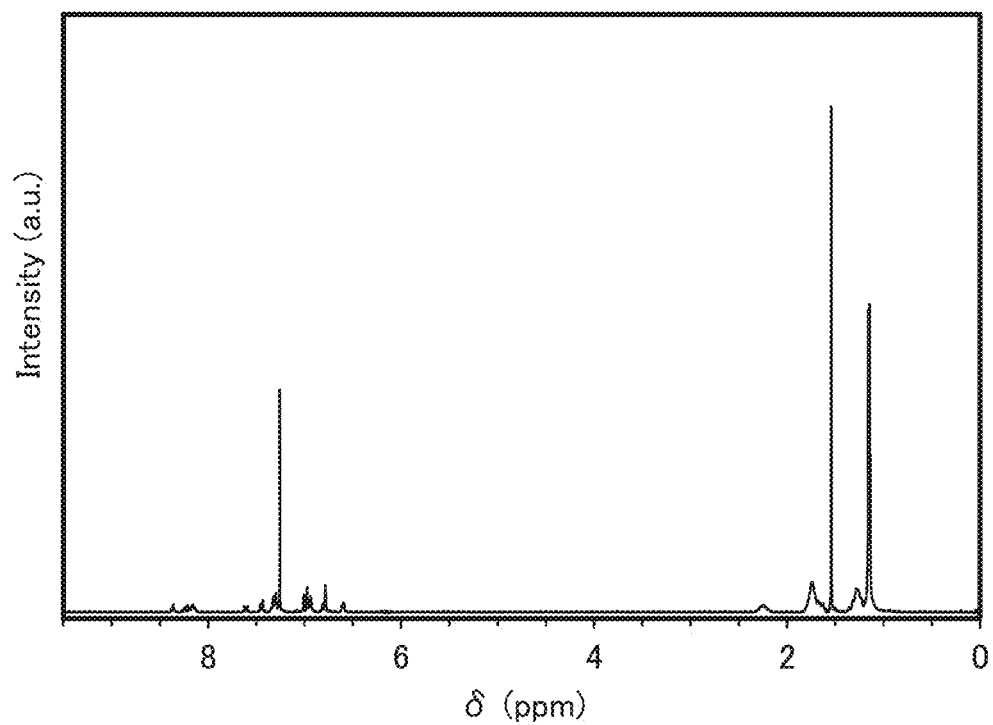
FIGS. 78A and 78B Diagrams showing NMR charts of a compound in Example.
Figure 78B:
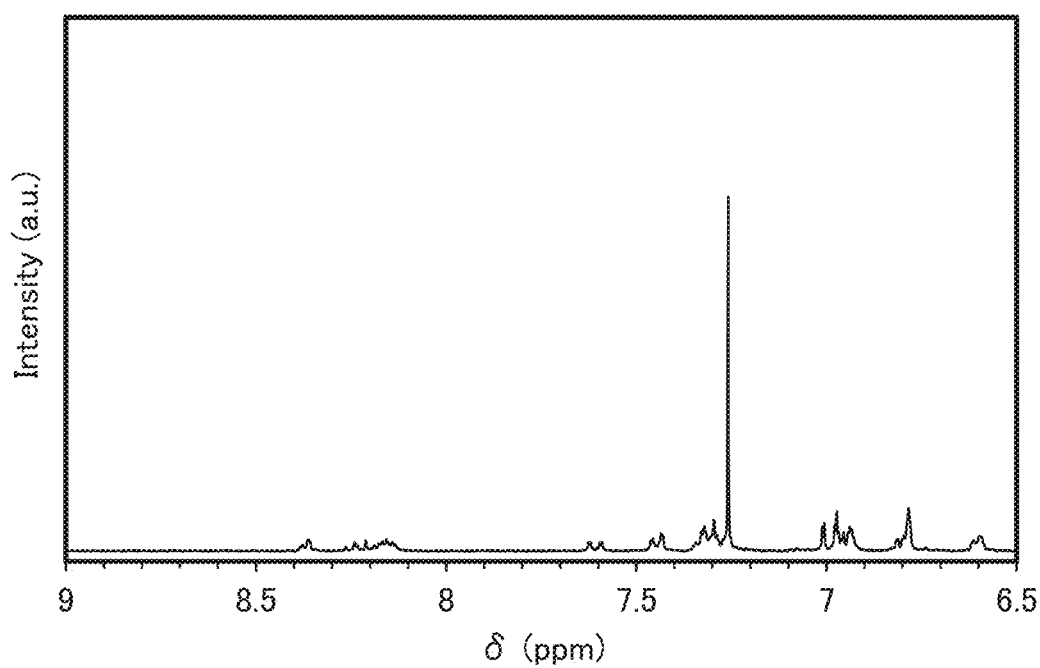
Figure 79:
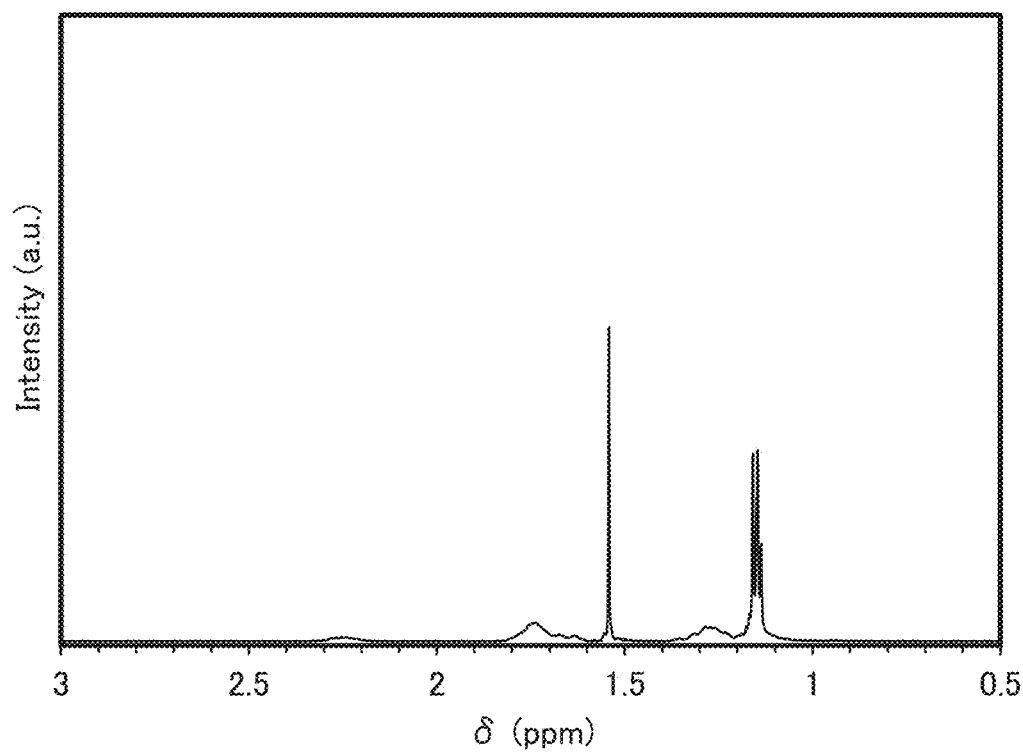
FIG. 79 A diagram showing an NMR chart of a compound in Example.

Results of $^1$H NMR measurement of the yellow solid obtained in Step 3 described above will be described below. FIG. 78 and FIG. 79 are the $^1$H-NMR charts. Note that FIG. 78(B) is an enlarged chart of the range of 6.5 ppm to 9.0 ppm of FIG. 78(A). FIG. 79 is an enlarged chart of the range of 0.5 ppm to 3.0 ppm of FIG. 78(A). The results indicate that 2Ph-mmchtBuDPhA2Anth (Structural Formula (250)) was obtained.

$^1$H NMR (CDCl$_3$, 300 MHz): σ=8.38-8.36 (m, 1H), 8.26-8.13 (m, 3H), 7.63-7.59 (m, 1H), 7.46-7.43 (m, 2H), 7.34-7.29 (m, 5H), 7.01-6.93 (m, 6H), 6.82-6.78 (m, 4H), 6.61-6.59 (m, 2H), 2.28-2.21 (m, 4H), 1.74-1.63 (m, 20H), 1.35-1.14 (m, 56H).

Figure 80:
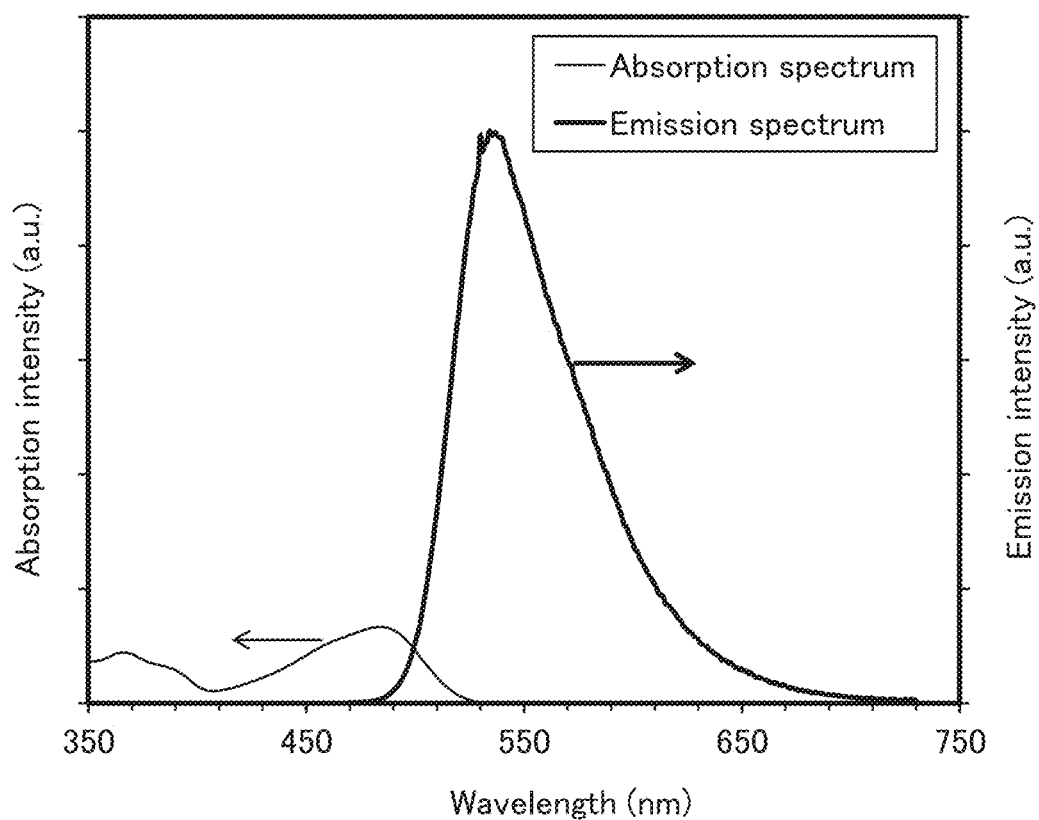
FIG. 80 A diagram showing an absorption spectrum and an emission spectrum of a compound in Example.

Next, FIG. 80 shows the measurement results of the absorption spectrum and the emission spectrum of 2Ph-mmchtBuDPhA2Anth in a toluene solution. The measurement method is similar to the method described in Example 1.

As shown in FIG. 80, in the case of 2Ph-mmchtBuDPhA2Anth in the toluene solution, absorption peaks were observed at around 486 nm, 390 nm, and 367 nm, and an emission wavelength peak was at 534 nm (excitation wavelength: 465 nm).

Example 12

In this example, a synthesis method of 2-phenyl-N,N,N',N'-tetrakis(3,5-dicyclohexylphenyl)-9,10-anthracenediamine (abbreviation: 2Ph-mmchDPhA2Anth), which is an organic compound represented by Structural Formula (222) of Embodiment 1, will be described. This organic compound can be favorably used for a light-emitting element of one embodiment of the present invention.

Step 1: Synthesis of bis(3,5-cyclohexylphenyl)amine 1.4 g (3.5 mmol) of 3,5-dicyclohexylphenyl trifluoromethanesulfonate was put into a 200 mL three-neck flask, and the air in the flask was replaced with nitrogen. To this mixture were added 10 mL of THF, 0.91 g (3.5 mmol) of 3,5-di-cyclohexylaniline, 1.6 g (4.9 mmol) of cesium carbonate, and 0.40 g (0.64 mmol) of (±)-BINAP, and the mixture was degassed under reduced pressure; then, 0.10 g (0.45 mmol) of palladium acetate(II) was added to the mixture and the mixture was stirred for 24 hours at 70° C. under a nitrogen stream. After the stirring, 500 mL of toluene was added to the obtained mixture, which was then subjected to suction filtration through Florisil, Celite, and aluminum oxide to give a filtrate. The obtained filtrate was concentrated to give a brown oily substance. This oily substance was purified by silica gel column chromatography (developing solvent: hexane:toluene=4:1) to obtain 0.90 g of an objective white solid in a yield of 52%. The synthesis scheme of Step 1 is shown in (H-1) below.

[Chemical Formula 63]

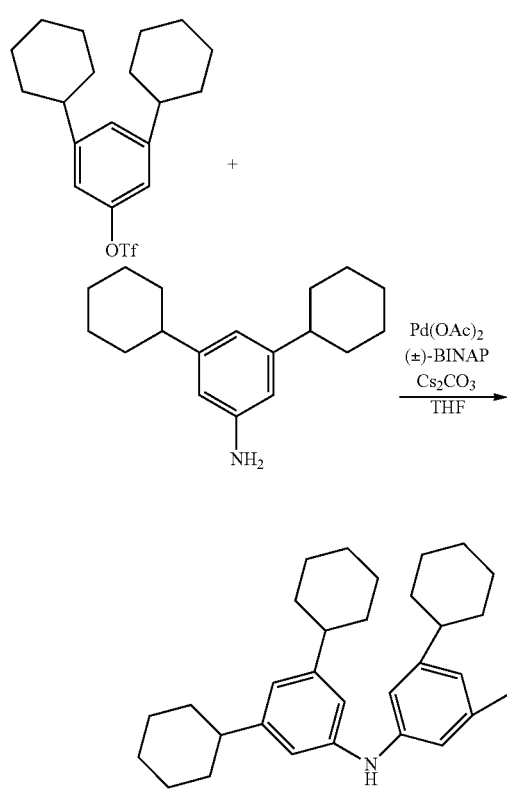

(H-1)

Figure 81A:
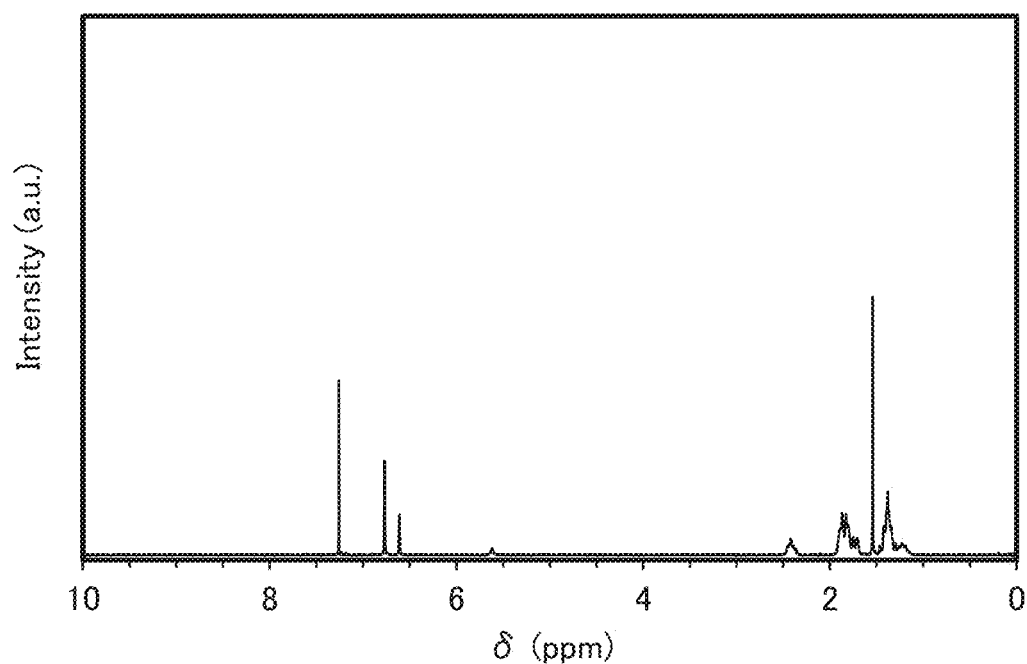
FIGS. 81A and 81B Diagrams showing NMR charts of a compound in Example.
Figure 81B:
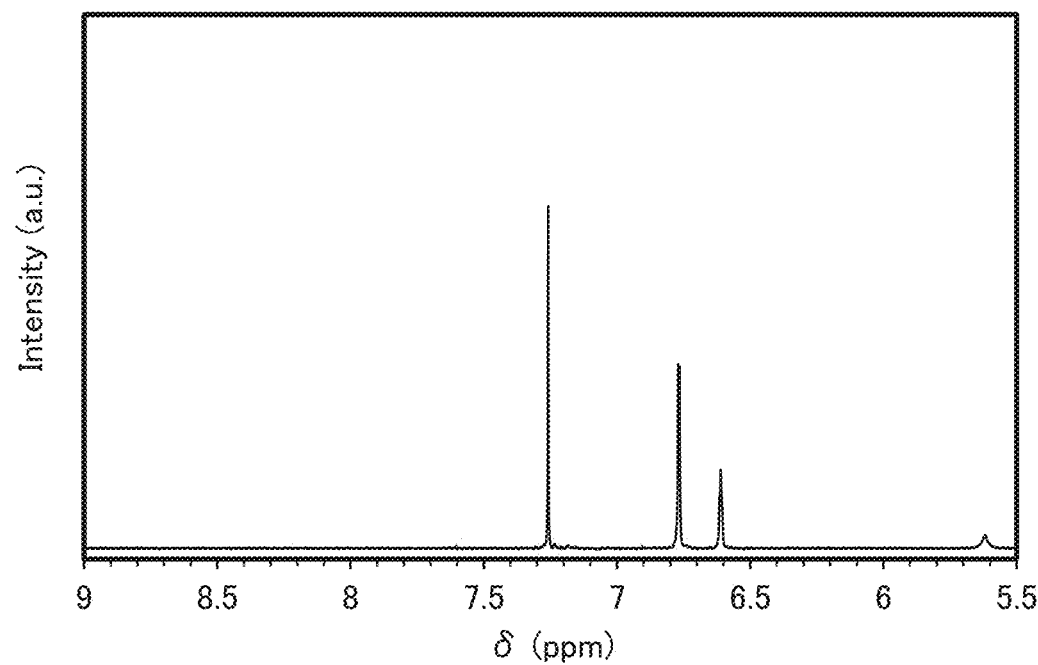
Figure 82:
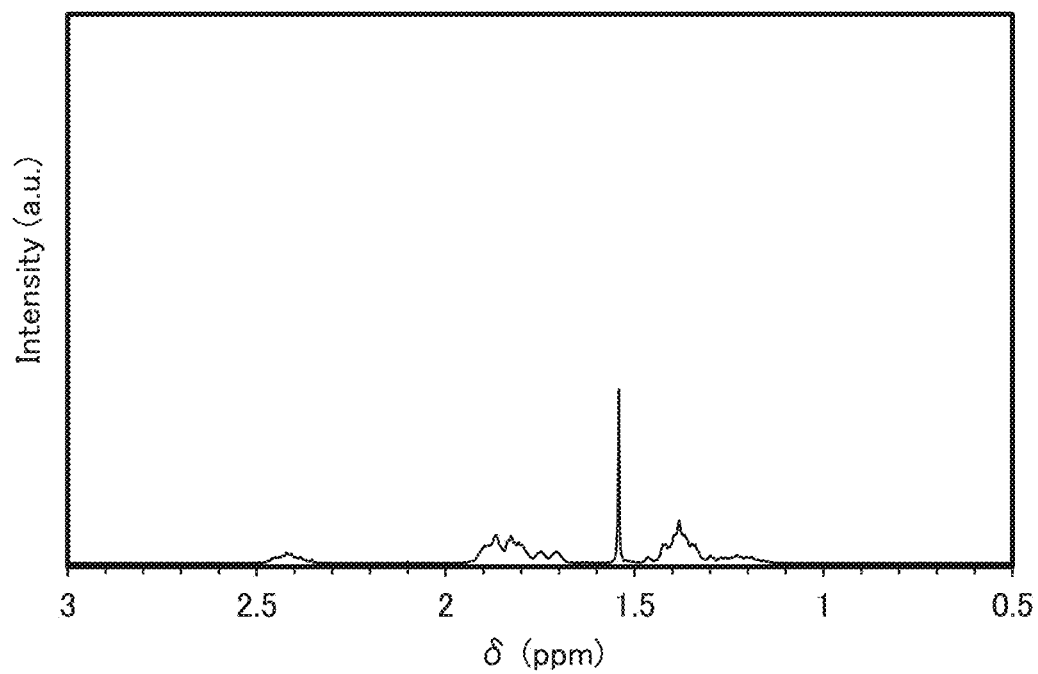
FIG. 82 A diagram showing an NMR chart of a compound in Example.

Results of ¹H NMR measurement of the white solid obtained in Step 1 described above will be described below. FIG. 81 and FIG. 82 are the ¹H-NMR charts. Note that FIG. 81(B) is an enlarged chart of the range of 5.5 ppm to 9.0 ppm of FIG. 81(A). FIG. 82 is an enlarged chart of the range of 0.5 ppm to 3.0 ppm of FIG. 81(A). The results indicate that bis(3,5-cyclohexylphenyl)amine was obtained.

¹H NMR (CDCl$_3$, 300 MHz): σ=6.77 (d, J=1.5 Hz, 4H), 6.62-6.60 (m, 2H), 5.62 (bs, 1H), 2.46-2.36 (m, 4H), 1.90-1.71 (m, 20H), 1.47-1.19 (m, 20H).

Step 2: Synthesis of 2Ph-mmchDPhA2Anth 0.35 g (0.85 mmol) of 9,10-dibromo-2-phenylanthracene, 0.85 g (1.7 mmol) of bis(3,5-cyclohexylphenyl)amine, 0.34 g (3.5 mmol) of sodium t-butoxide, and 60 mg (0.15 mmol) of SPhos were put into a 200 mL three-neck flask, and the air in the flask was replaced with nitrogen. To this mixture was added 10 mL of xylene, and the mixture was degassed under reduced pressure; then, 40 mg (70 μmol) of bis (dibenzylideneacetone)palladium(0) was added to the mixture and the mixture was stirred for 7 hours at 150° C. under a nitrogen stream. After the stirring, 500 mL of toluene was added to the obtained mixture, and then a solid of Florisil and Celite was purified by silica gel column chromatography (developing solvent: hexane:toluene=4:1) to obtain an objective yellow solid. The obtained yellow solid was purified by HPLC (developing solvent: chloroform) to give 0.19 g of an objective yellow solid in a yield of 18%. The synthesis scheme of Step 2 is shown in (H-2) below.

[Chemical Formula 64]

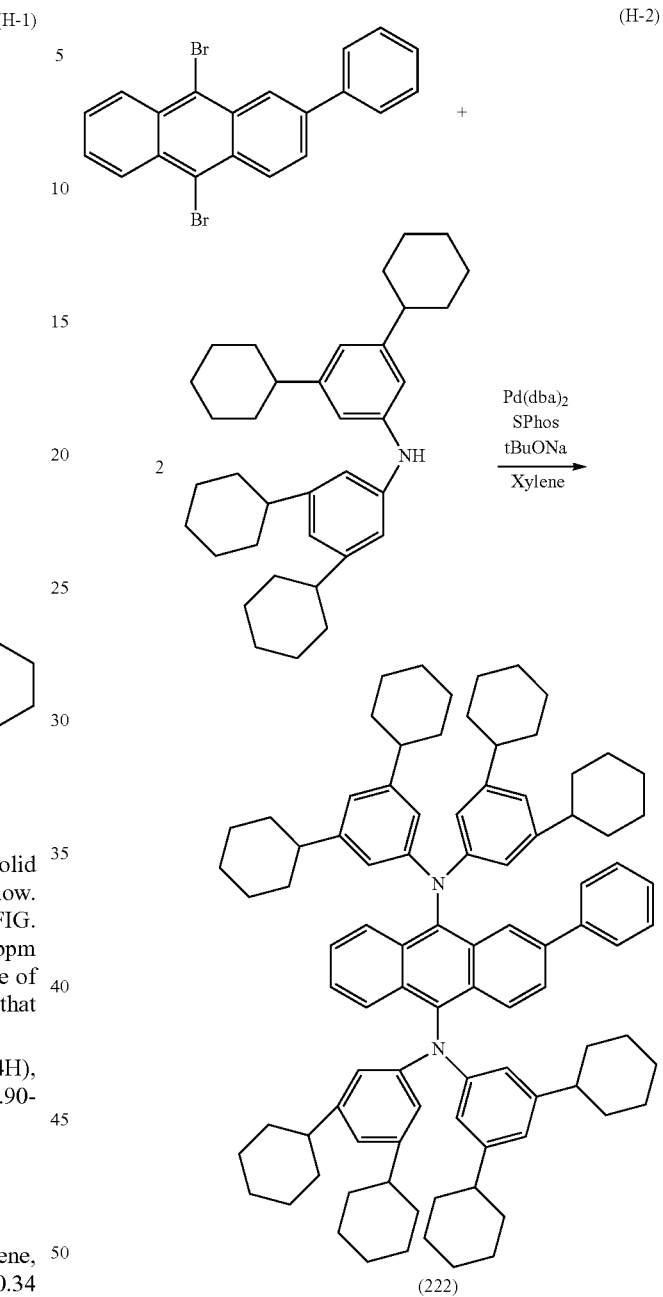

(H-2)

By a train sublimation method, 0.19 g of the obtained yellow solid was purified by sublimation. In the sublimation purification, the yellow solid was heated at 320° C. under a pressure of 3.4 Pa for 15 hours. After the sublimation purification, 0.16 g of an objective yellow solid was obtained at a collection rate of 82%.

Figure 83A:
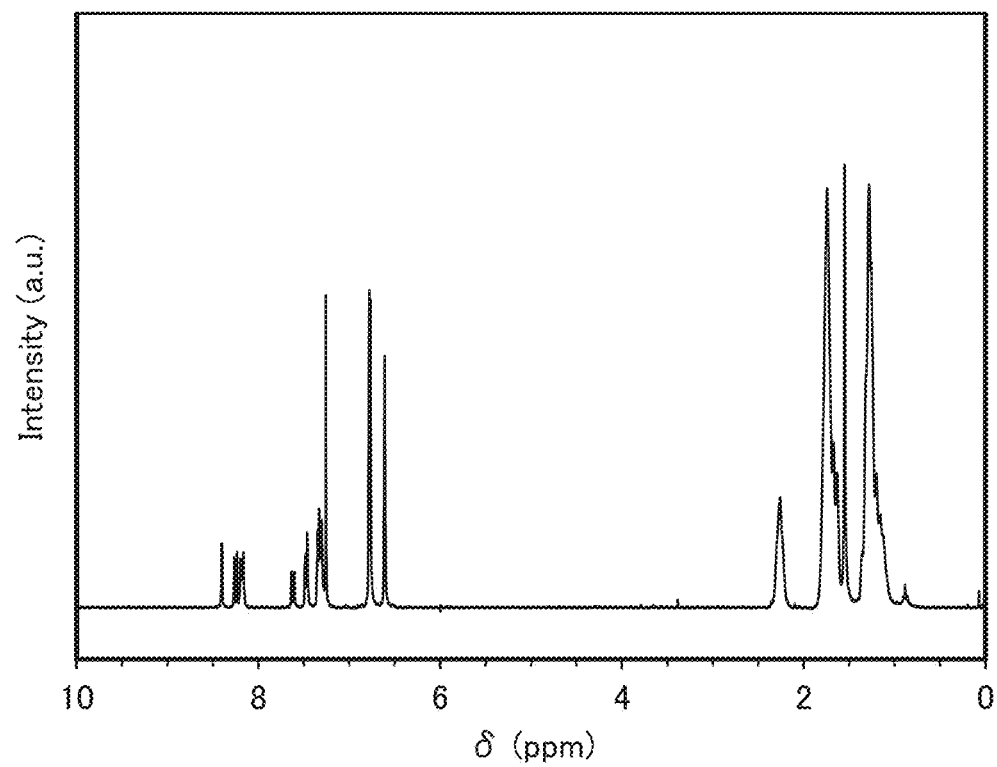
FIGS. 83A and 83B Diagrams showing NMR charts of a compound in Example.
Figure 83B:
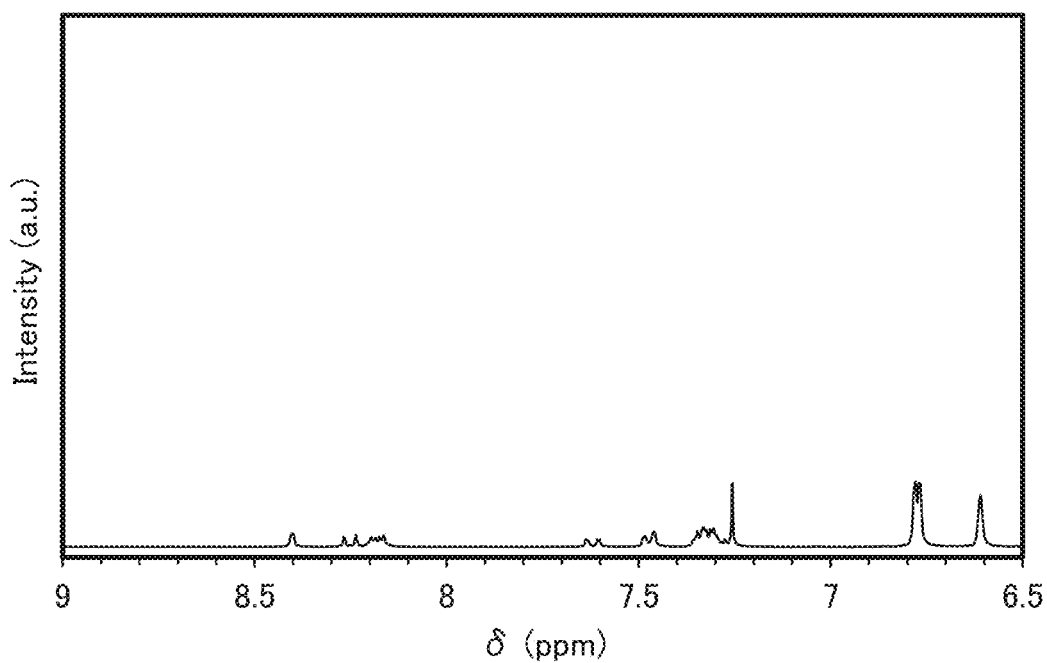
Figure 84:
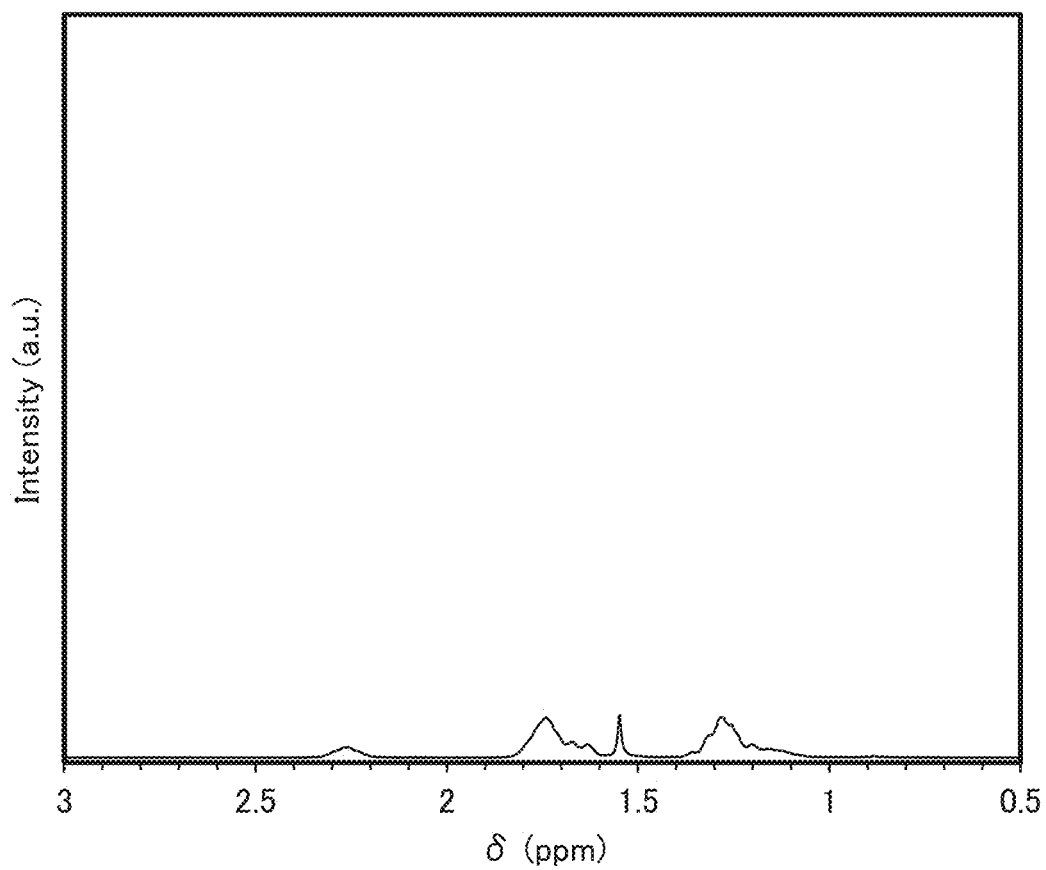
FIG. 84 A diagram showing an NMR chart of a compound in Example.

Results of ¹H NMR measurement of the yellow solid obtained in Step 2 described above will be described below. FIG. 83 and FIG. 84 are the ¹H-NMR charts. Note that FIG. 83(B) is an enlarged chart of the range of 6.5 ppm to 9.0 ppm of FIG. 83(A). FIG. 84 is an enlarged chart of the range of 0.5 ppm to 3.0 ppm of FIG. 83(A). The results indicate that 2Ph-mmchDPhA2Anth, which was the objective substance, was obtained.

$^1$H NMR (CDCl$_3$, 300 MHz): σ=8.40 (d, J=1.5 Hz, 1H), 8.27 (d, J=8.8 Hz, 1H), 8.20-8.16 (m, 2H), 7.60 (dd, J=1.5 Hz, 8.8 Hz, 1H), 7.49-7.46 (m, 2H), 7.35-7.28 (m, 5H), 6.78-6.77 (m, 8H), 6.61 (bs, 4H), 2.32-2.20 (m, 8H), 1.74-1.63 (m, 40H), 1.36-1.12 (m, 40H).

Figure 85:
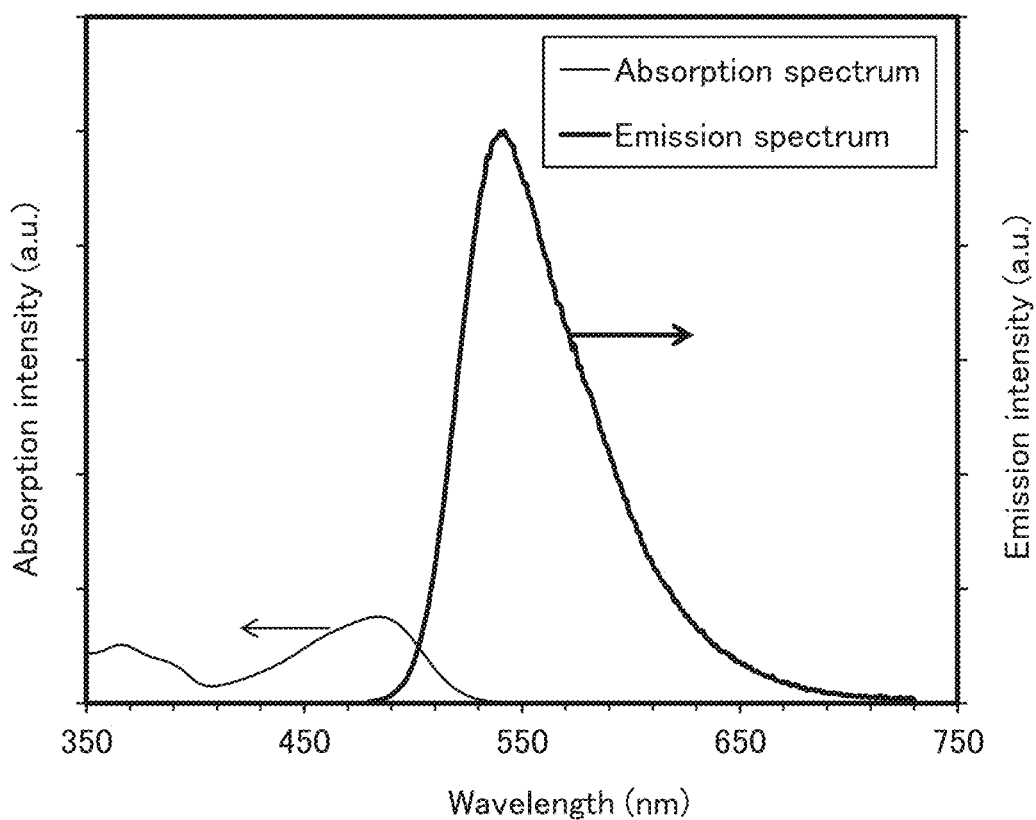
FIG. 85 A diagram showing absorption and emission spectra of a compound in Example.

Next, FIG. 85 shows the measurement results of the absorption spectrum and the emission spectrum of 2Ph-mmchDPhA2Anth in a toluene solution. The measurement method is similar to the method described in Example 1.

As shown in FIG. 85, in the case of 2Ph-mmchDPhA2Anth in the toluene solution, absorption peaks were observed at around 483 nm, 393 nm, and 365 nm, and an emission wavelength peak was at 542 nm (excitation wavelength: 475 nm).

Example 13

In this example, a synthesis method of 2-phenyl-N,N,N',N'-tetrakis(3,5-di-tert-butylphenyl)-9,10-anthracenediamine (abbreviation: 2Ph-mmtBuDPhA2Anth), which is an organic compound represented by Structural Formula (221) of Embodiment 1, will be described. This organic compound can be favorably used for a light-emitting element of one embodiment of the present invention.

1.4 g (3.3 mmol) of 9,10-dibromo-2-phenylanthracene, 2.6 g (6.7 mmol) of bis(3,5-tert-butylphenyl)amine, 1.3 g (14 mmol) of sodium t-butoxide, and 60 mg (0.15 mmol) of SPhos were put into a 200 mL three-neck flask, and the air in the flask was replaced with nitrogen. To this mixture was added 33 mL of xylene, and the mixture was degassed under reduced pressure; then, 40 mg (70 µmol) of bis(dibenzylideneacetone)palladium(0) was added to the mixture and the mixture was stirred for 5 hours at 150° C. under a nitrogen stream. After the stirring, 400 mL of toluene was added to the obtained mixture, which was then subjected to suction filtration through Florisil, Celite, and aluminum oxide to give a filtrate. The obtained filtrate was concentrated to give a brown solid.

This solid was purified by silica gel column chromatography (developing solvent: hexane:toluene=9:1) to obtain an objective yellow solid. The obtained yellow solid was recrystallized with ethyl acetate and ethanol to give 0.51 g of an objective yellow solid in a yield of 15%. The synthesis scheme is shown in (I-1) below.

[Chemical Formula 65]

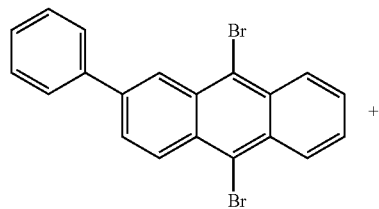

(I-1)

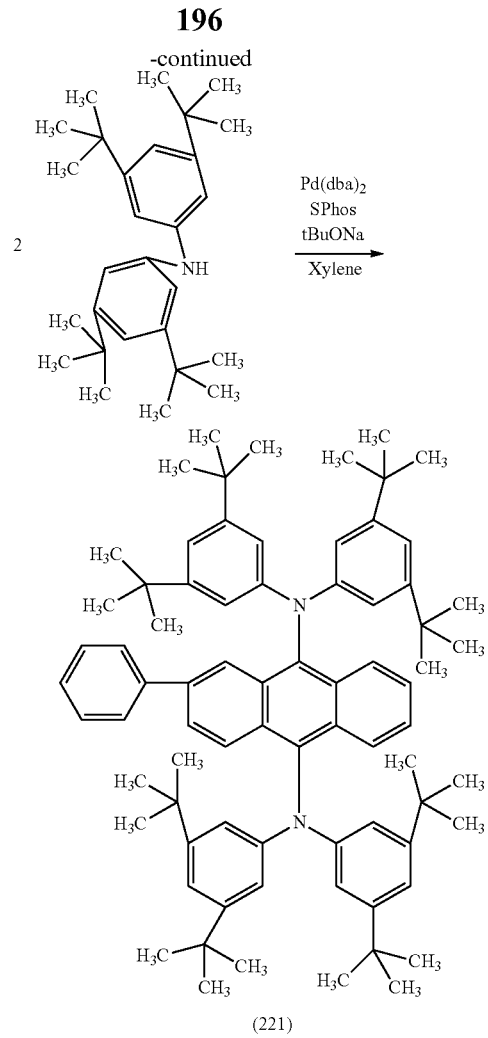

(221)

By a train sublimation method, 0.50 g of the obtained yellow solid was purified by sublimation. In the sublimation purification, the yellow solid was heated at 270° C. under a pressure of 3.6 Pa for 15 hours. After the sublimation purification, 0.38 g of an objective yellow solid was obtained at a collection rate of 77%.

Figure 86A:
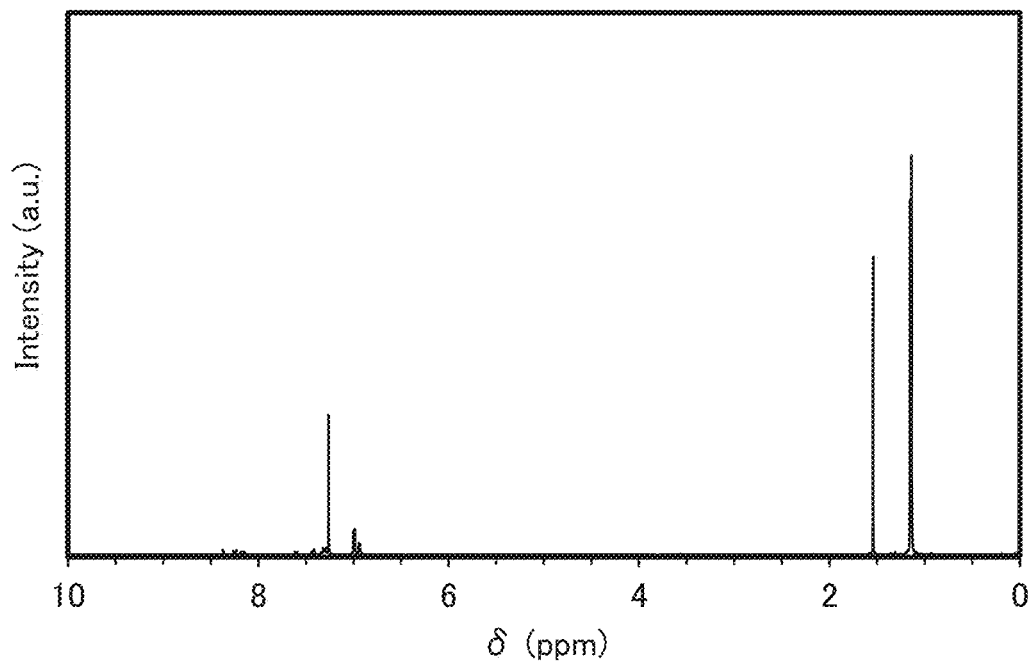
FIGS. 86A and 86B Diagrams showing NMR charts of a compound in Example.
Figure 86B:
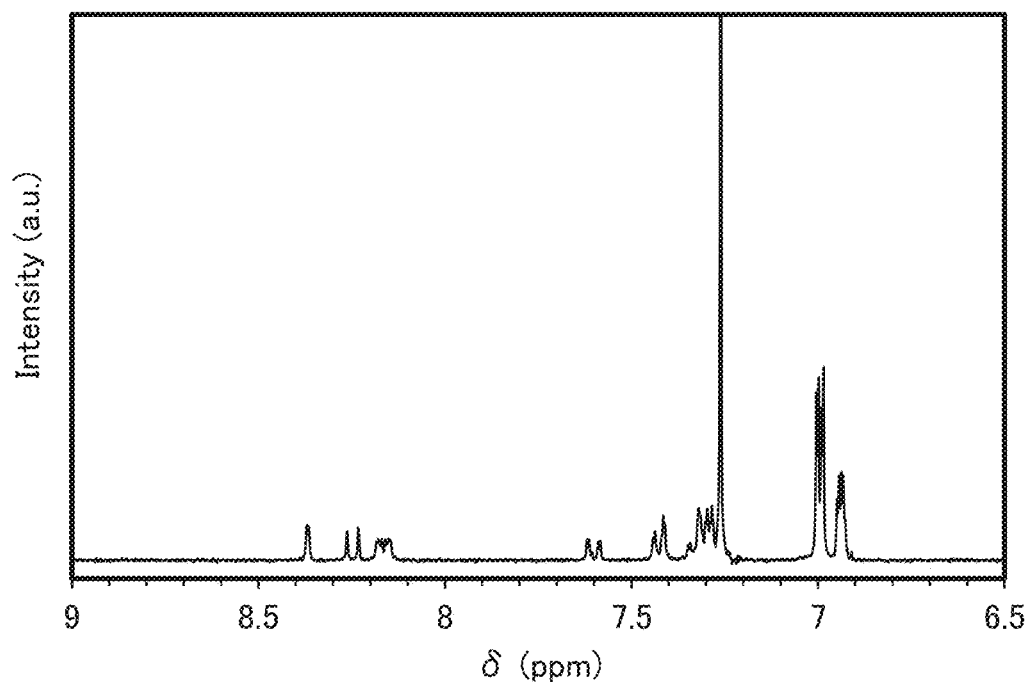
Figure 87:
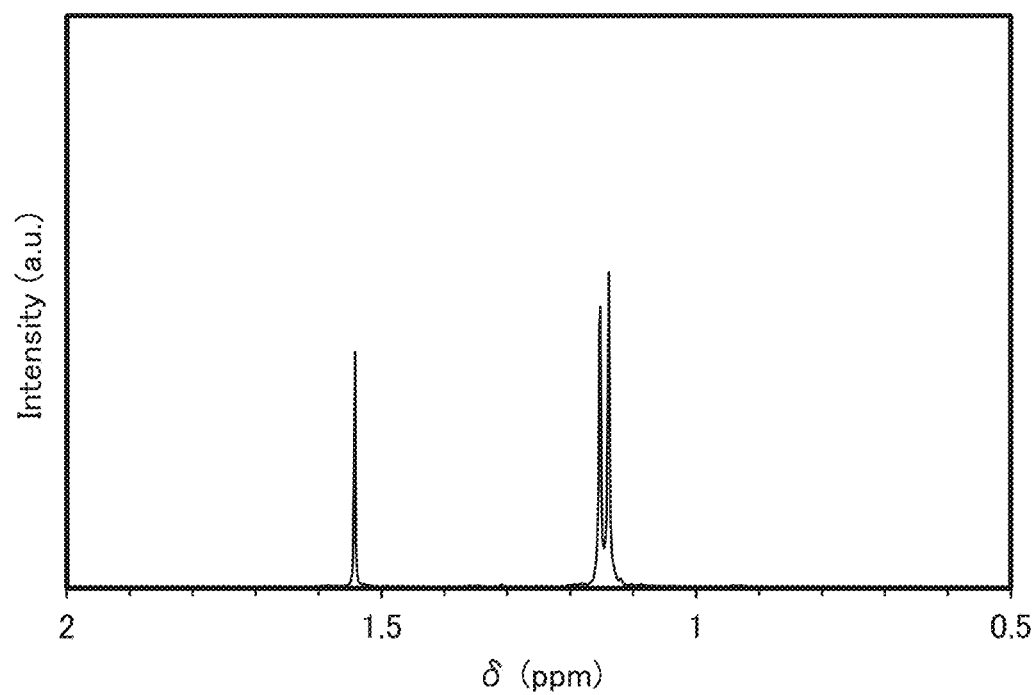
FIG. 87 A diagram showing an NMR chart of a compound in Example.

Results of $^1$H NMR measurement of the yellow solid obtained in Step 1 described above will be described below. FIG. 86 and FIG. 87 are the $^1$H-NMR charts. Note that FIG. 86(B) is an enlarged chart of the range of 6.5 ppm to 9.0 ppm of FIG. 86(A). FIG. 87 is an enlarged chart of the range of 0.5 ppm to 2.0 ppm of FIG. 86(A). The results indicate that 2Ph-mmtBuDPhA2Anth (Structural Formula (221)) was obtained.

$^1$H NMR (CDCl$_3$, 300 MHz): σ=8.37 (d, J=1.5 Hz, 1H), 8.26 (d, J=8.8 Hz, 1H), 8.18-8.14 (m, 2H), 7.62 (dd, J=1.5 Hz, 8.8 Hz, 1H), 7.44-7.41 (m, 2H), 7.35-7.28 (m, 5H), 7.00-6.98 (m, 8H), 6.95-6.93 (m, 4H), 1.15 (s, 36H), 1.14 (s, 36H).

Figure 88:
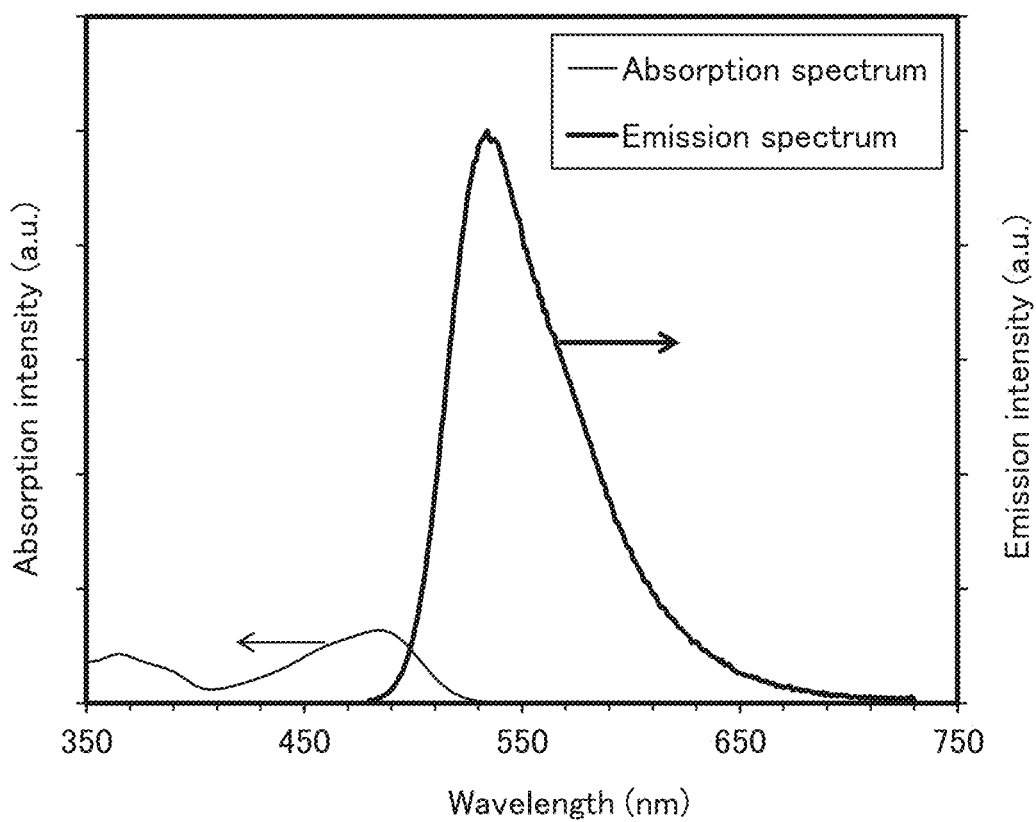
FIG. 88 A diagram showing absorption and emission spectra of a compound in Example.

Next, FIG. 88 shows the measurement results of the absorption spectrum and the emission spectrum of 2Ph-mmtBuDPhA2Anth in a toluene solution. The measurement method is similar to the method described in Example 1.

As shown in FIG. 88, in the case of 2Ph-mmtBuDPhA2Anth in the toluene solution, absorption peaks were observed at around 486 nm, 387 nm, and 366 nm, and an emission wavelength peak was at 534 nm (excitation wavelength: 470 nm).

Example 14

In this example, a synthesis method of N,N'-(2-phenylan-thracene-9,10-diyl)-N,N'-bis(3,5-di-tert-butylphenyl)-N,N'-bis[3,5-bis(3,5-di-tert-butylphenyl)phenyl]diamine (abbreviation: 2Ph-mmtBuDPhA2Anth-02), which is an organic compound represented by Structural Formula (254) of Embodiment 1, will be described. This organic compound can be favorably used for a light-emitting element of one embodiment of the present invention.

Step 1: Synthesis of 3,5-bis(3,5-di-tert-butylphenyl)aniline 2.5 g (10 mmol) of 3,5-dibromoaniline, 4.9 g (21 mmol) of 3,5-di-tert-butylphenylboronic acid, and 0.27 g (0.89 mmol) of tri-o-tolylphosphine were put into a 500 mL three-neck flask, and the air in the flask was replaced with nitrogen. To this mixture were added 75 mL of toluene, 25 mL of ethanol, and 20 mL of a 2M aqueous solution of potassium carbonate, and the mixture was degassed under reduced pressure; then, 40 mg (0.18 mmol) of palladium acetate(II) was added to the mixture and the mixture was stirred for 7 hours at 90° C. under a nitrogen stream. After the stirring, water was added to this mixture, and an aqueous layer was subjected to extraction with toluene. The obtained extracted solution and an organic layer were combined, washed with water and saturated saline, and dried with magnesium sulfate. This mixture was separated by gravity filtration, and the filtrate was concentrated to give a brown oily substance. This solid was purified by silica gel column chromatography (developing solvent: toluene) to give 1.8 g of an objective brownish-white substance in a yield of 37%. The synthesis scheme of Step 1 is shown in (J-1) below.

[Chemical Formula 66]

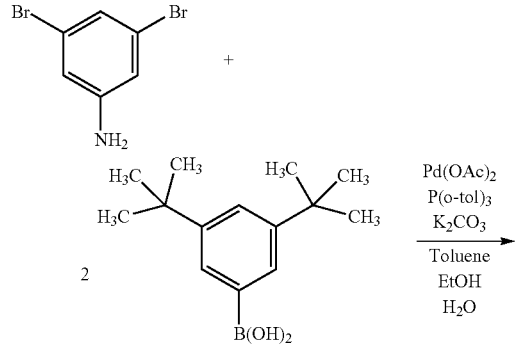

Figure 89A:
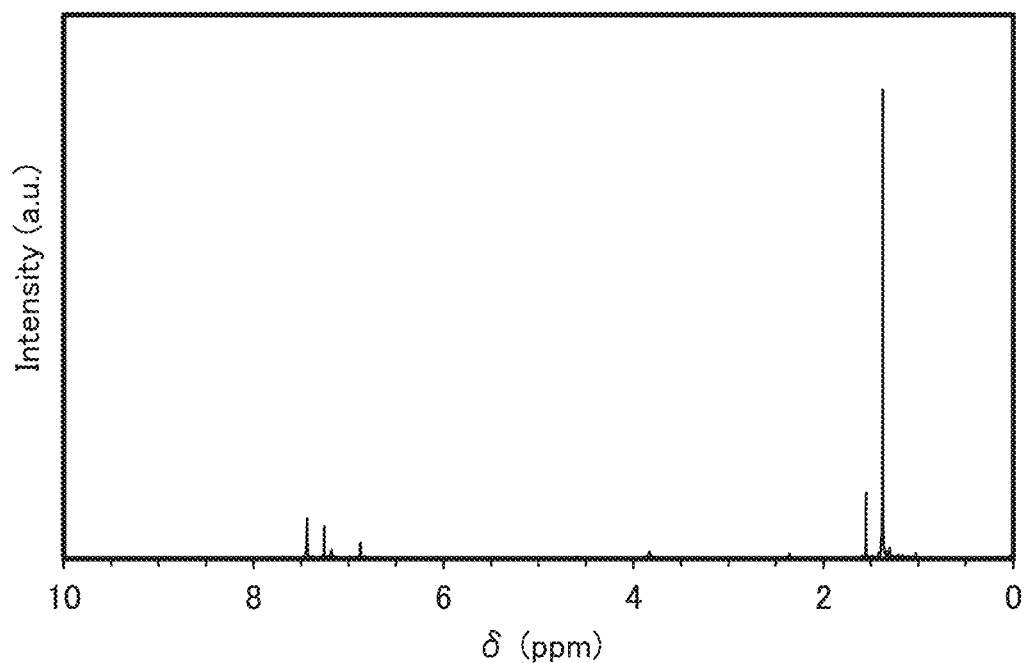
FIGS. 89A and 89B Diagrams showing NMR charts of a compound in Example.
Figure 89B:
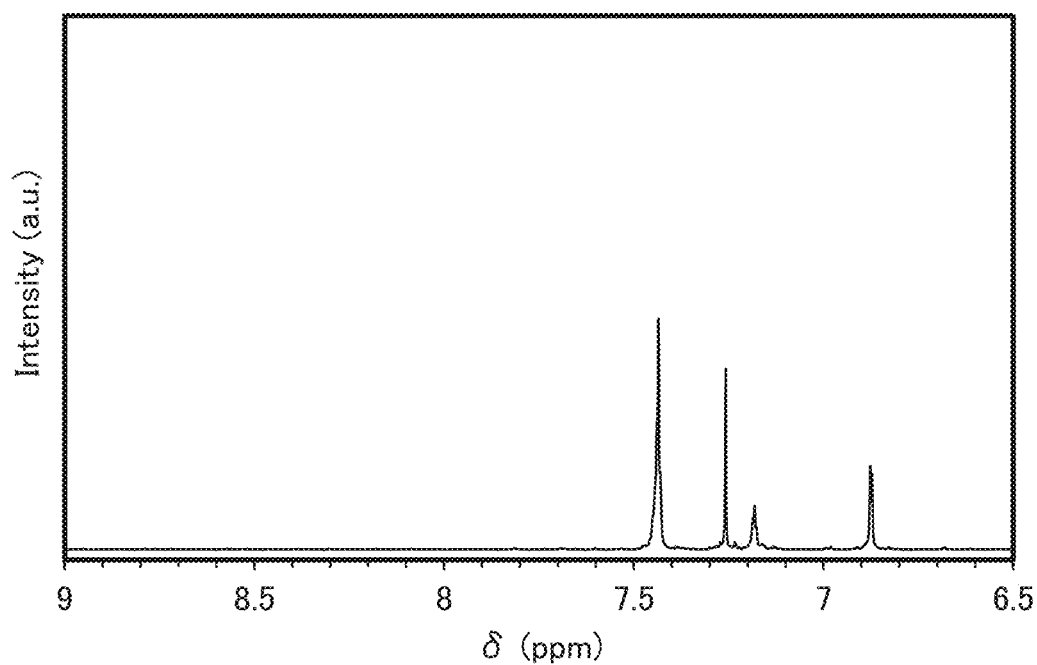
Figure 90:
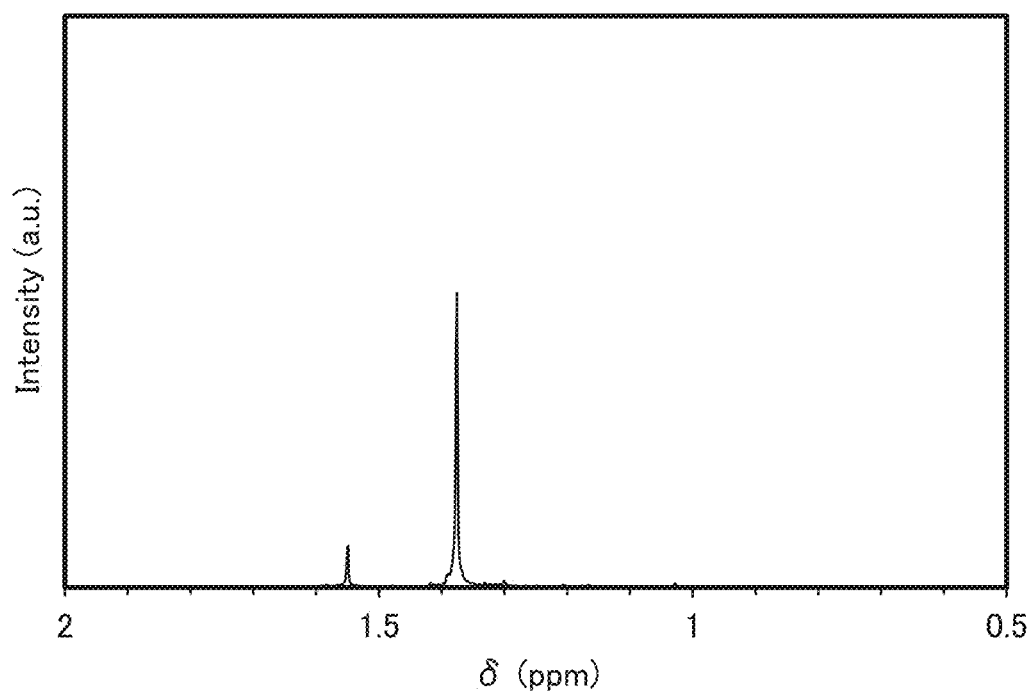
FIG. 90 A diagram showing an NMR chart of a compound in Example.

Results of $^1$H NMR measurement of the brownish-white solid obtained in Step 1 described above will be described below. FIG. 89 and FIG. 90 are the $^1$H-NMR charts. Note that FIG. 89(B) is an enlarged chart of the range of 6.5 ppm to 9.0 ppm of FIG. 89(A). FIG. 90 is an enlarged chart of the range of 0.5 ppm to 2.0 ppm of FIG. 89(A). The results indicate that 3,5-bis(3,5-di-tert-butylphenyl)aniline was obtained.

$^1$H NMR (CDCl$_3$, 300 MHz): σ=7.44-7.33 (m, 6H), 7.19-7.18 (m, 1H), 6.88 (d, J=1.5 Hz, 2H), 3.85 (bs, 2H), 1.37 (s, 36H).

Step 2: Synthesis of 3,5-di-tert-butyl-3',5'-bis(3,5-di-tert-butylphenyl)diphenylamine 0.72 g (2.7 mmol) of 1-bromo-3,5-di-tert-butylbenzene, 1.3 g (2.7 mmol) of 3,5-bis(3,5-di-tert-butylphenyl)aniline, and 0.50 g (5.2 mmol) of sodium t-butoxide were put into a 200 mL three-neck flask, and the air in the flask was replaced with nitrogen. To this mixture was added 30 mL of toluene, and the mixture was degassed under reduced pressure; then, 0.30 mL (97 μmop of tri-tert-butylphosphine (a 10 w % hexane solution) and 40 mg (70 μmop of bis(dibenzylideneacetone)palladium(0) were added to the mixture and the mixture was stirred for 3 hours at 90° C. under a nitrogen stream. After the stirring, 300 mL of toluene was added to the obtained mixture, which was then subjected to suction filtration through Florisil, Celite, and aluminum oxide to give a filtrate. The obtained filtrate was concentrated to give a brown solid. This solid was purified by silica gel column chromatography (developing solvent: hexane:toluene=17:3) to obtain 1.3 g of an objective brownish-white solid in a yield of 71%. The synthesis scheme of Step 2 is shown in (J-2) below.

[Chemical Formula 67]

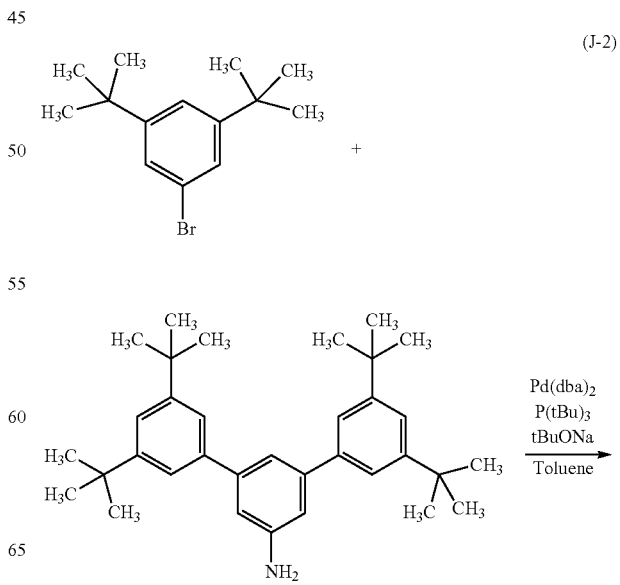

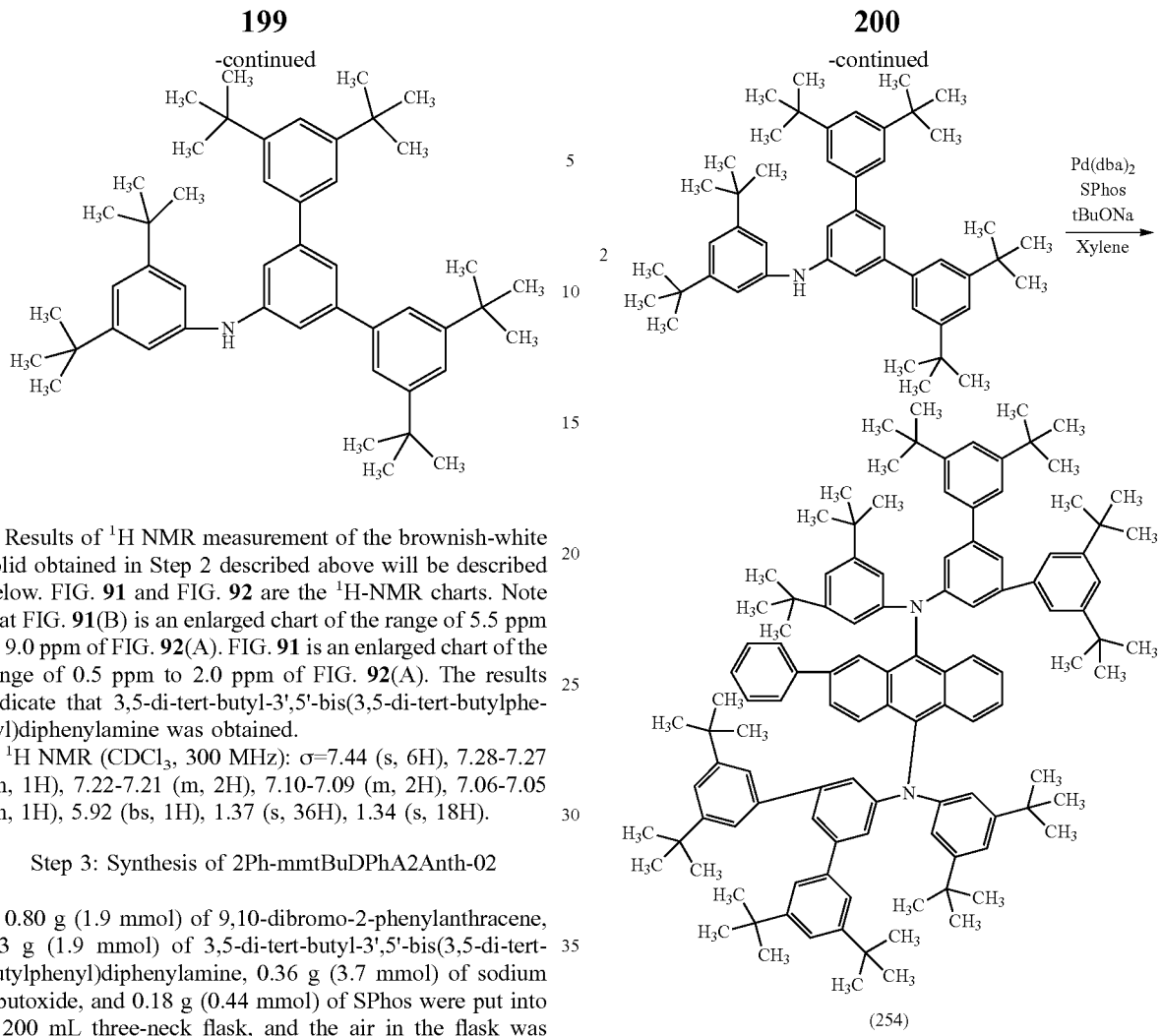

Figure 91A:
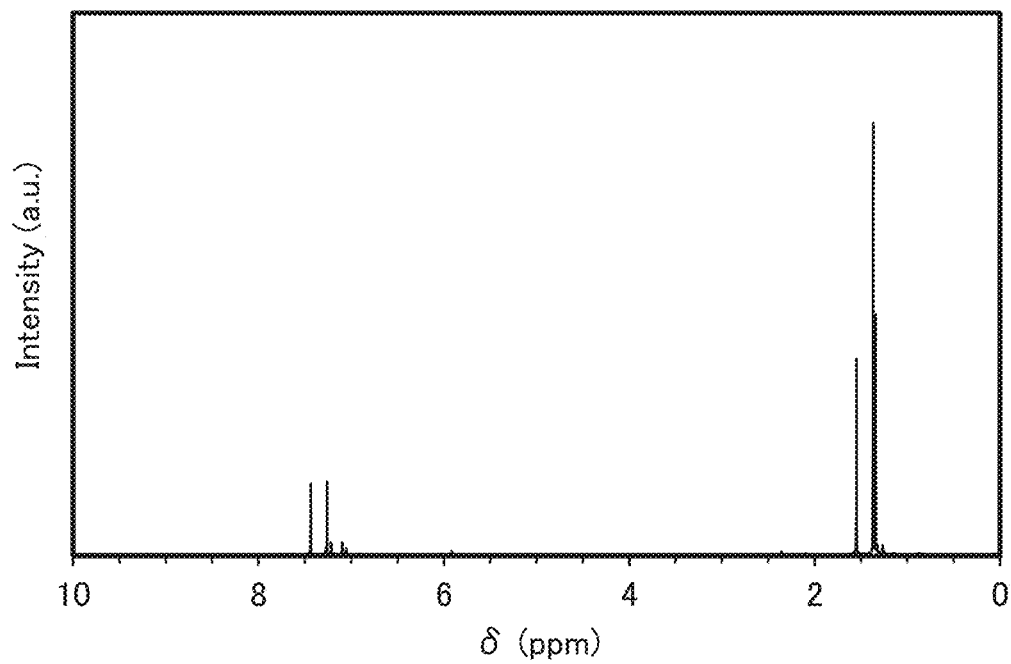
FIGS. 91A and 91B Diagrams showing NMR charts of a compound in Example.
Figure 91B:
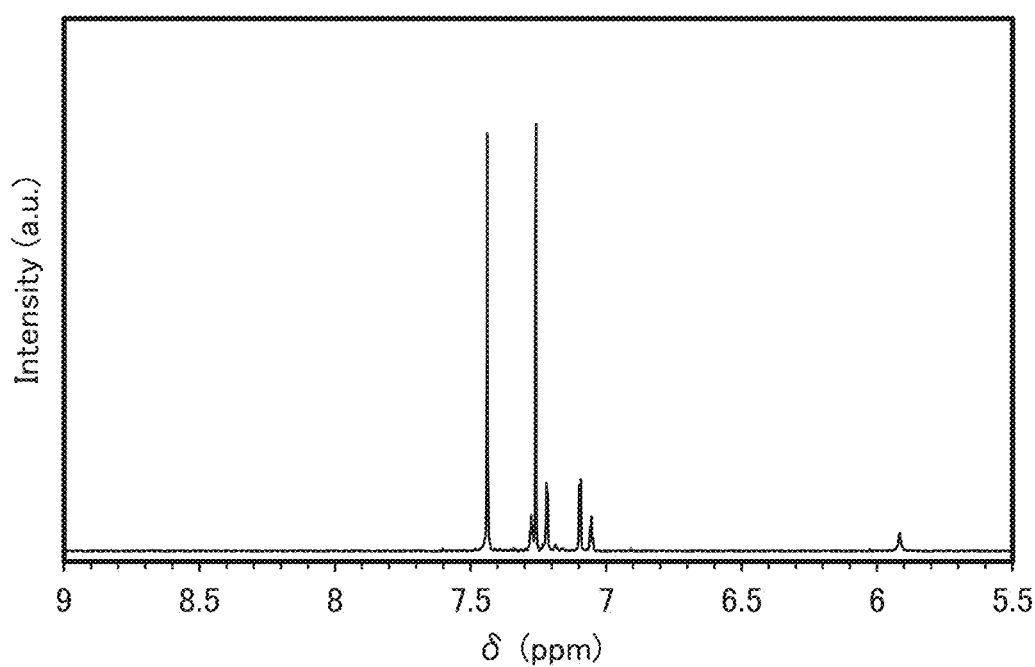
Figure 92:
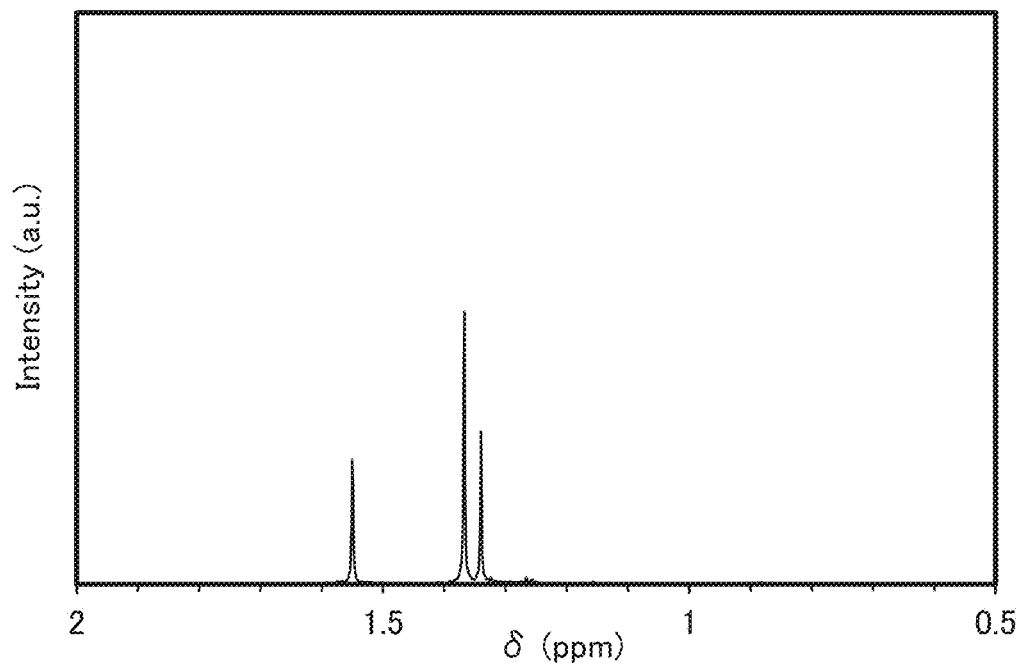
FIG. 92 A diagram showing an NMR chart of a compound in Example.

Results of $^1$H NMR measurement of the brownish-white solid obtained in Step 2 described above will be described below. FIG. 91 and FIG. 92 are the $^1$H-NMR charts. Note that FIG. 91(B) is an enlarged chart of the range of 5.5 ppm to 9.0 ppm of FIG. 92(A). FIG. 91 is an enlarged chart of the range of 0.5 ppm to 2.0 ppm of FIG. 92(A). The results indicate that 3,5-di-tert-butyl-3',5'-bis(3,5-di-tert-butylphenyl)diphenylamine was obtained.

$^1$H NMR (CDCl$_3$, 300 MHz): σ=7.44 (s, 6H), 7.28-7.27 (m, 1H), 7.22-7.21 (m, 2H), 7.10-7.09 (m, 2H), 7.06-7.05 (m, 1H), 5.92 (bs, 1H), 1.37 (s, 36H), 1.34 (s, 18H).

Step 3: Synthesis of 2Ph-mmtBuDPhA2Anth-02

0.80 g (1.9 mmol) of 9,10-dibromo-2-phenylanthracene, 1.3 g (1.9 mmol) of 3,5-di-tert-butyl-3',5'-bis(3,5-di-tert-butylphenyl)diphenylamine, 0.36 g (3.7 mmol) of sodium t-butoxide, and 0.18 g (0.44 mmol) of SPhos were put into a 200 mL three-neck flask, and the air in the flask was replaced with nitrogen. To this mixture was added 10 mL of xylene, and the mixture was degassed under reduced pressure; then, 0.12 g (0.21 mmol) of bis(dibenzylideneacetone)palladium(0) was added to the mixture and the mixture was stirred for 20 hours at 150° C. under a nitrogen stream. After the stirring, 400 mL of toluene was added to the obtained mixture, which was then subjected to suction filtration through Florisil, Celite, and aluminum oxide to give a filtrate. The obtained filtrate was concentrated to give a brown solid. This solid was purified by silica gel column chromatography (developing solvent: hexane:toluene=9:1) to obtain an objective yellow solid. The obtained yellow solid was recrystallized with hexane and methanol to give 0.30 g of an objective yellow solid in a yield of 20%. The synthesis scheme of Step 3 is shown in (J-3) below.

[Chemical Formula 68]

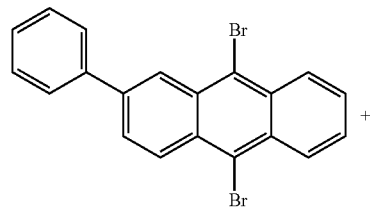

(J-3)

By a train sublimation method, 0.30 g of the obtained yellow solid was purified by sublimation. In the sublimation purification, the yellow solid was heated at 295° C. under a pressure of 3.8 Pa for 15 hours. After the sublimation purification, 0.25 g of an objective yellow solid was obtained at a collection rate of 83%.

Figure 93A:
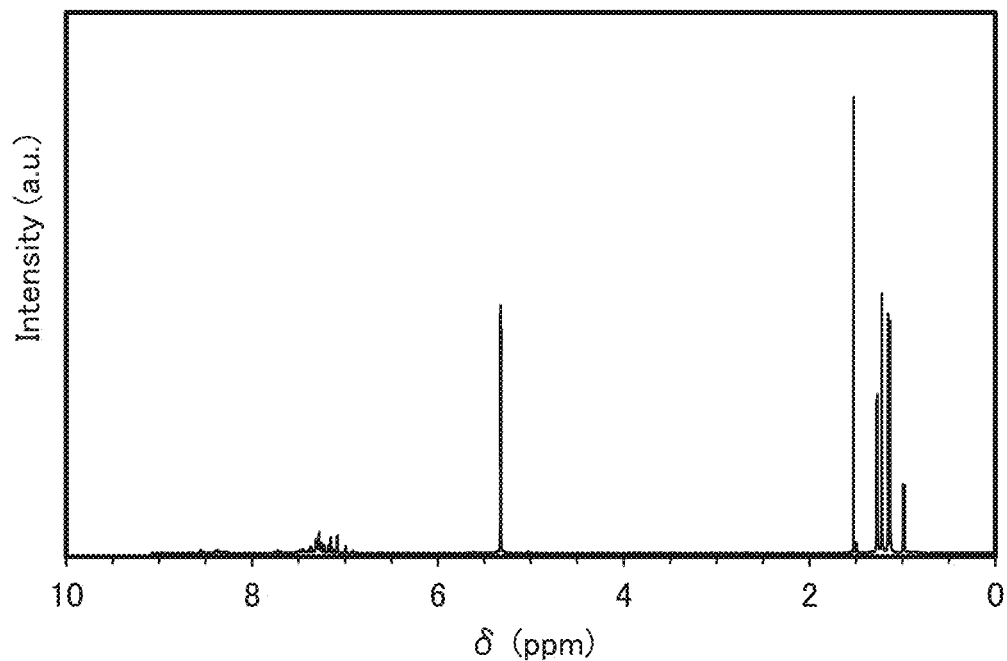
FIGS. 93A and 93B Diagrams showing NMR charts of a compound in Example.
Figure 93B:
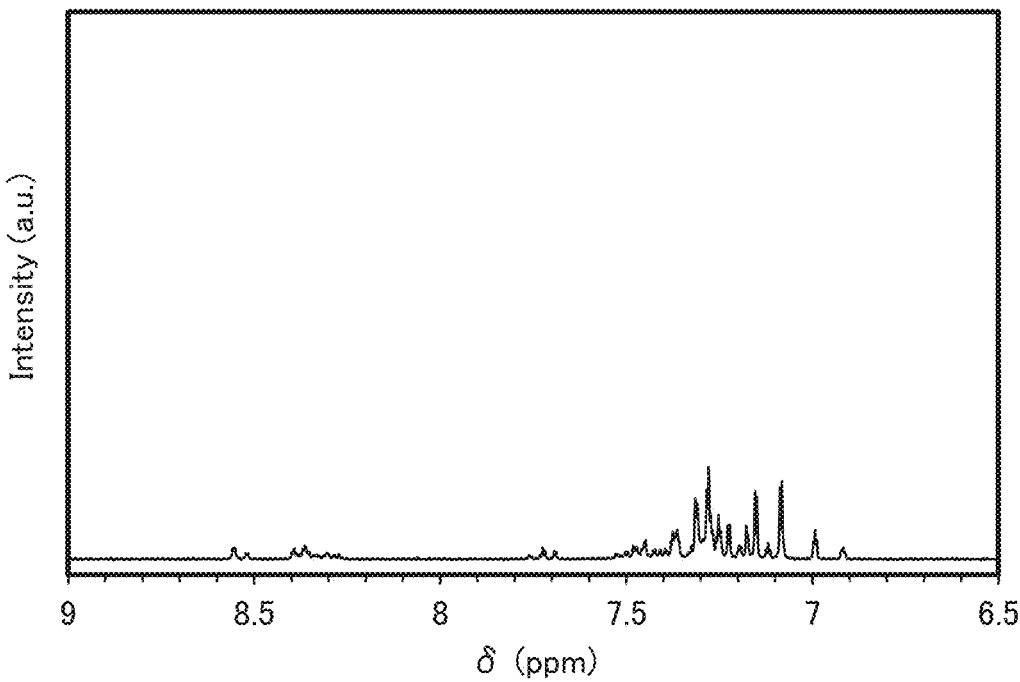
Figure 94:
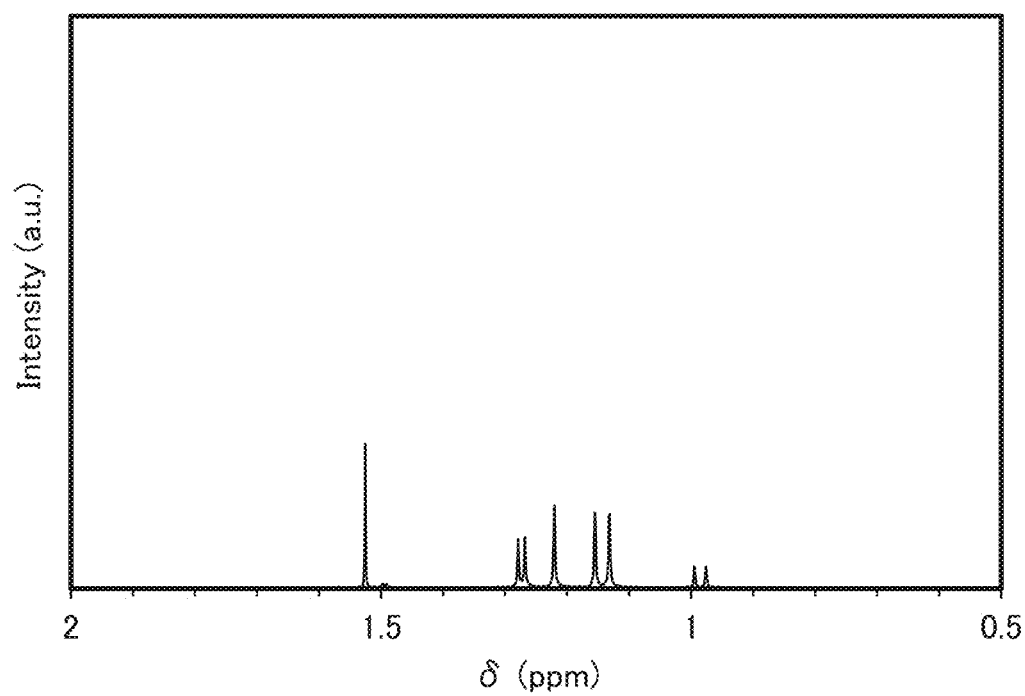
FIG. 94 A diagram showing an NMR chart of a compound in Example.

Results of $^1$H NMR measurement of the yellow solid obtained in Step 3 will be described below. FIG. 93 and FIG. 94 are the $^1$H-NMR charts. Note that FIG. 93(B) is an enlarged chart of the range of 6.5 ppm to 9.0 ppm of FIG. 93(A). FIG. 94 is an enlarged chart of the range of 0.5 ppm to 2.0 ppm of FIG. 93(A). The results indicate that 2Ph-mmtBuDPhA2Anth-02 was obtained.

$^1$H NMR (CD$_2$Cl$_2$, 300 MHz): σ=8.56-8.52 (m, 1H), 8.40-8.27 (m, 3H), 7.76-7.69 (m, 1H), 7.53-7.36 (m, 7H), 7.33-7.11 (m, 19H), 7.09-7.08 (m, 3H), 7.00-6.91 (m, 2H), 1.28-0.98 (m, 108H).

Figure 95:
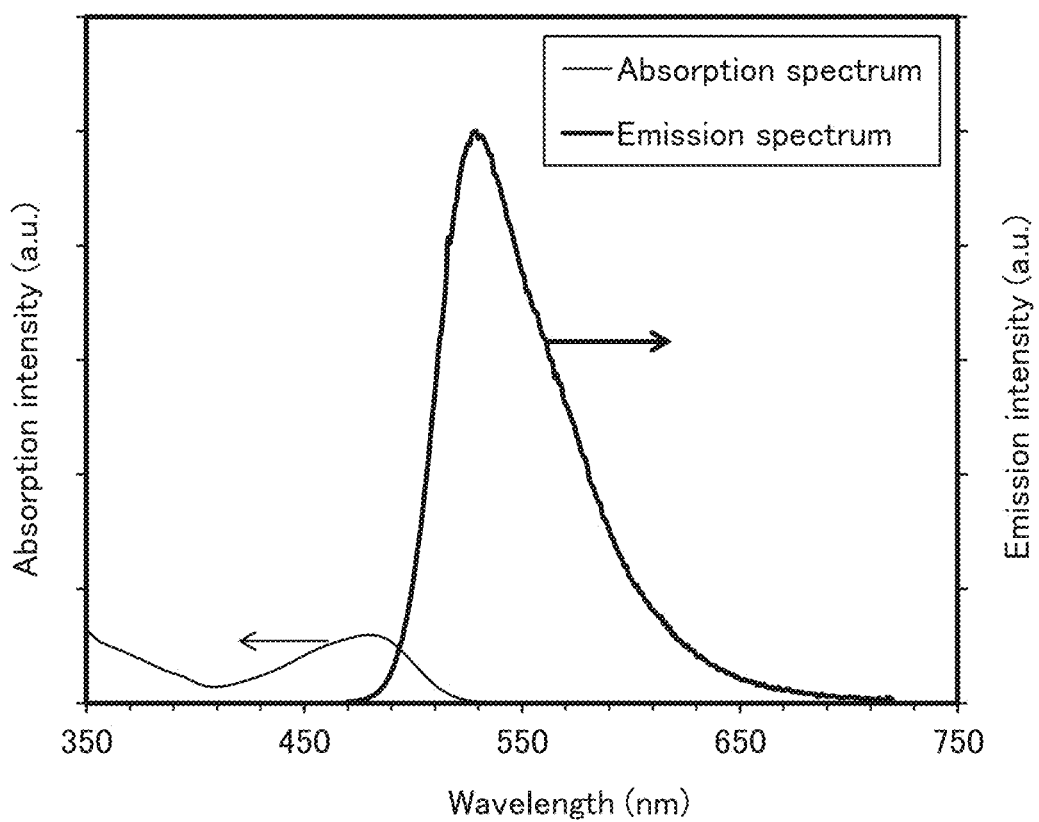
FIG. 95 A diagram showing absorption and emission spectra of a compound in Example.

Next, FIG. 95 shows the measurement results of the absorption spectrum and the emission spectrum of 2Ph-mmtBuDPhA2Anth-02 in a toluene solution. The measurement method is similar to the method described in Example 1.

As shown in FIG. 95, in the case of 2Ph-mmtBuDPhA2Anth-02 in the toluene solution, absorption peaks were observed at around 484 nm, 392 nm, and 343 nm, and an emission wavelength peak was at 529 nm (excitation wavelength: 465 nm).

Example 15

In this example, a synthesis method of 2,6-diphenyl-N,N,N',N'-tetrakis(3,5-di-tert-butylphenyl)-9,10-anthracenediamine (abbreviation: 2,6Ph-mmtBuDPhA2Anth), which is an organic compound represented by Structural Formula (225) of Embodiment 1, will be described. This organic compound can be favorably used for a light-emitting element of one embodiment of the present invention.

Step 1: Synthesis of 2,6Ph-mmtBuDPhA2Anth 1.8 g (3.6 mmol) of 9,10-dibromo-2,6-diphenylanthracene, 2.8 g (7.2 mmol) of bis(3,5-tert-butylphenyl)amine, 1.4 g (15 mmol) of sodium t-butoxide, and 60 mg (0.15 mmol) of SPhos were put into a 200 mL three-neck flask, and the air in the flask was replaced with nitrogen. To this mixture was added 36 mL of xylene, and the mixture was degassed under reduced pressure; then, 40 mg (70 μmol) of bis(dibenzylideneacetone)palladium(0) was added to the mixture and the mixture was stirred for 3 hours at 150° C. under a nitrogen stream. After the stirring, 400 mL of toluene was added to the obtained mixture, which was then subjected to suction filtration through Florisil, Celite, and aluminum oxide to give a filtrate. The obtained filtrate was concentrated to give a brown solid. This solid was purified by silica gel column chromatography (developing solvent: hexane:toluene=9:1) to obtain a yellow solid. The obtained yellow solid was recrystallized with ethyl acetate and ethanol to give 0.61 g of an objective yellow solid in a yield of 15%. The synthesis scheme of Step 1 is shown in (K-1) below.

[Chemical Formula 69]

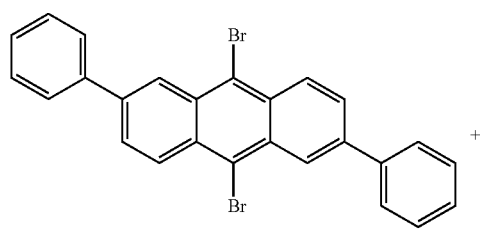

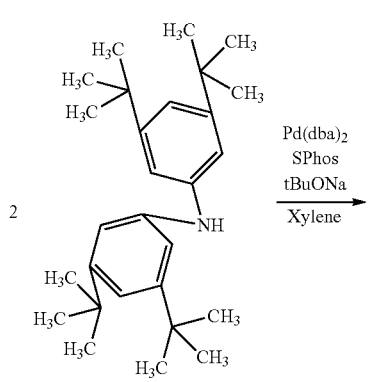

(K-1)

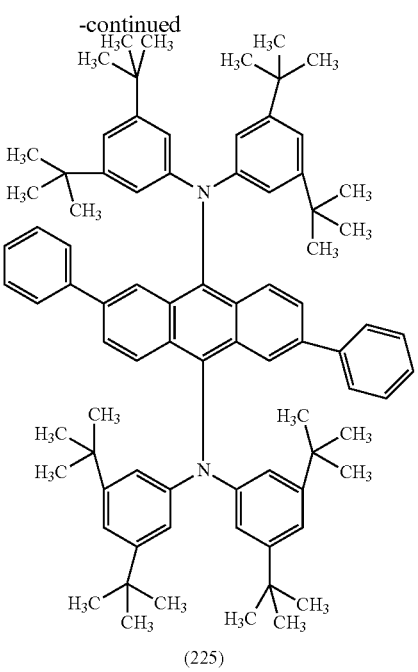

(225)

By a train sublimation method, 0.61 g of the obtained yellow solid was purified by sublimation. In the sublimation purification, the yellow solid was heated at 280° C. under a pressure of 3.8 Pa for 15 hours. After the sublimation purification, 0.56 g of an objective yellow solid was obtained at a collection rate of 91%.

Figure 96A:
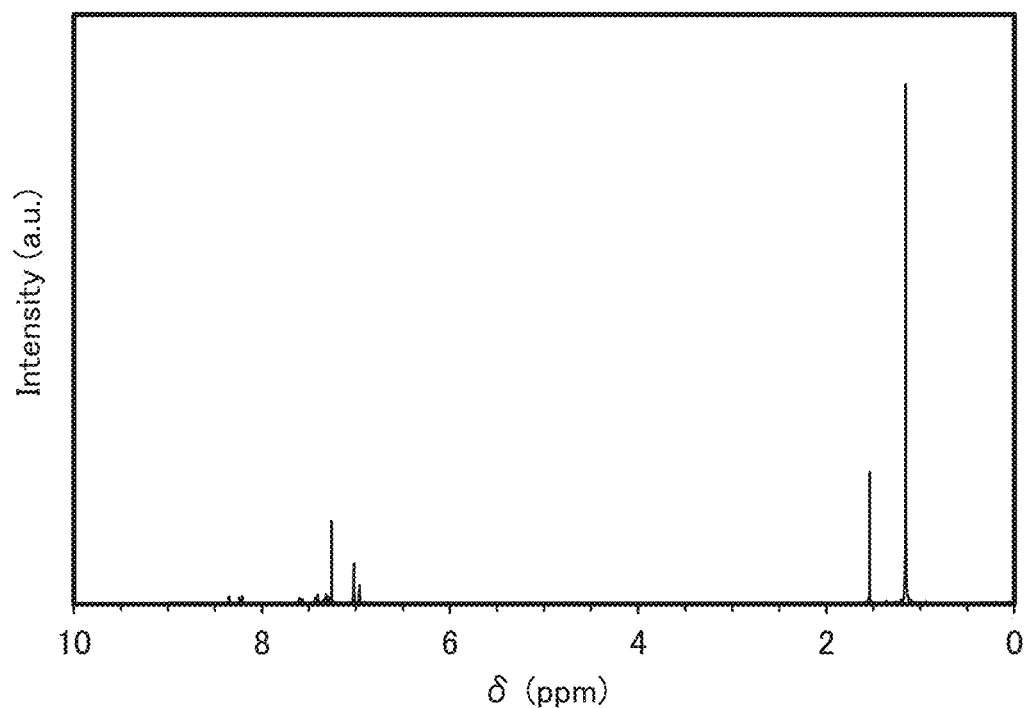
FIGS. 96A and 96B Diagrams showing NMR charts of a compound in Example.
Figure 96B:
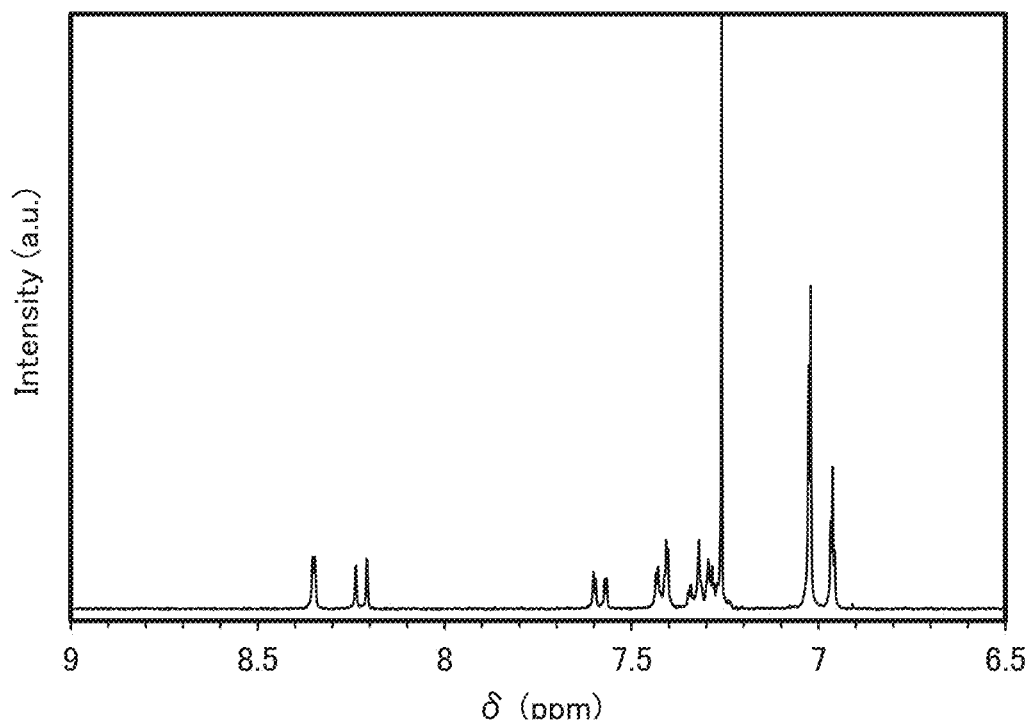
Figure 97:
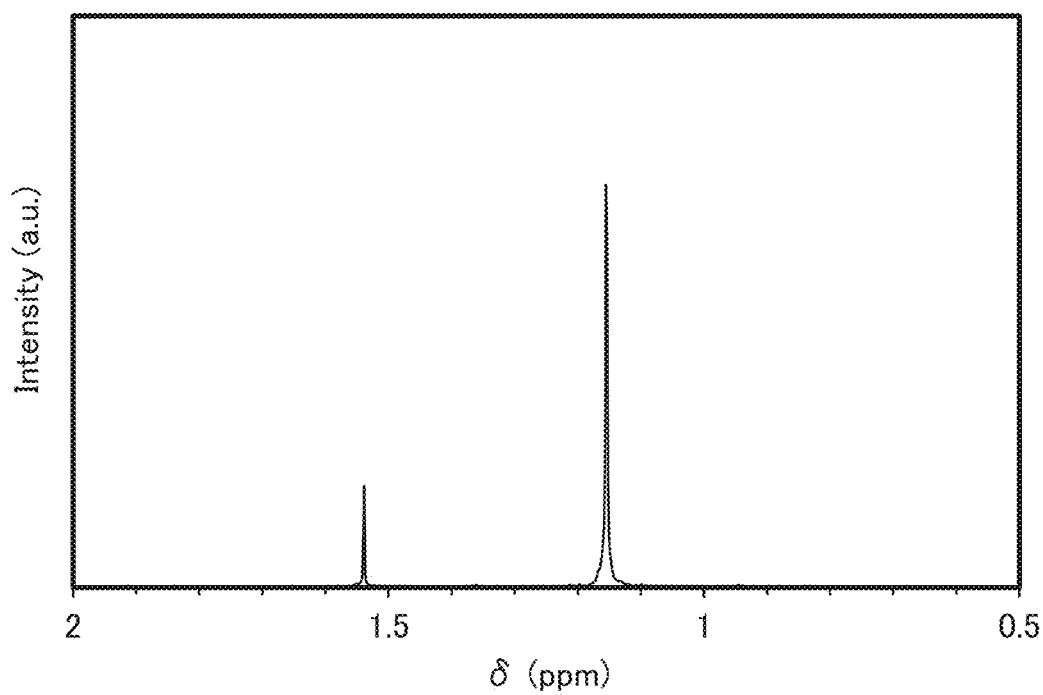
FIG. 97 A diagram showing an NMR chart of a compound in Example.

Results of $^1$H NMR measurement of the yellow solid obtained in Step 1 described above will be described below. FIG. 96 and FIG. 97 are the $^1$H-NMR charts. Note that FIG. 96(B) is an enlarged chart of the range of 6.5 ppm to 9.0 ppm of FIG. 96(A). FIG. 97 is an enlarged chart of the range of 0.5 ppm to 2.0 ppm of FIG. 96(A). The results indicate that 2,6Ph-mmtBuDPhA2Anth was obtained.

$^1$H NMR (CDCl$_3$, 300 MHz): σ=8.35 (d, J=1.5 Hz, 2H), 8.24 (d, J=8.8 Hz, 2H), 7.60 (dd, J=1.5 Hz, 8.8 Hz, 2H), 7.43-7.40 (m, 4H), 7.35-7.24 (m, 6H), 7.03-7.02 (m, 8H), 6.97-6.96 (m, 4H), 1.16 (s, 72H).

Figure 98:
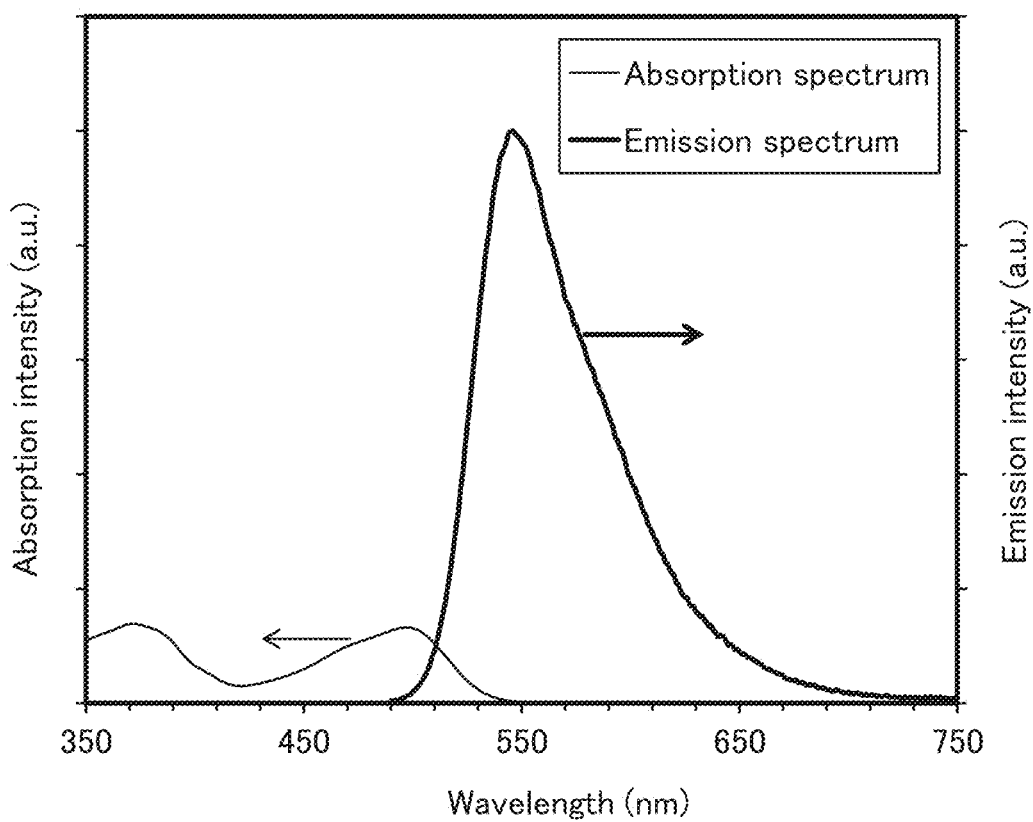
FIG. 98 A diagram showing absorption and emission spectra of a compound in Example.

Next, FIG. 98 shows the measurement results of the absorption spectrum and the emission spectrum of 2,6Ph-mmtBuDPhA2Anth in a toluene solution. The measurement method is similar to the method described in Example 1.

As shown in FIG. 98, in the case of 2,6Ph-mmtBuDPhA2Anth in the toluene solution, absorption peaks were observed at around 498 nm, 373 nm, and 330 nm, and an emission wavelength peak was at 546 nm (excitation wavelength: 480 nm).

Example 16

In this example, a synthesis method of 2-phenyl-N,N,N',N'-tetrakis[3,5-bis(4-cyclohexylphenyl)phenyl]-9,10-anthracenediamine (abbreviation: 2Ph-mmchPDPhA2Anth), which is an organic compound represented by Structural Formula (264) of Embodiment 1, will be described. This organic compound can be favorably used for a light-emitting element of one embodiment of the present invention.

Step 1: Synthesis of 3,5-bis(4-cyclohexylphenyl)aniline 0.87 g (3.5 mmol) of 3,5-dibromoaniline, 2.0 g (7.0 mmol) of 4-cyclohexylphenilboronic acid pinacol ester, and 0.28 g (0.92 mmol) of tri-o-tolylphosphine were put into a 200 mL three-neck flask, and the air in the flask was replaced with nitrogen. To this mixture were added 20 mL of toluene, 5 mL of ethanol, and 7 mL of a 2M aqueous solution of potassium carbonate, and the mixture was degassed under reduced pressure; then, 40 mg (0.18 mmol) of palladium acetate(II) was added to the mixture and the mixture was stirred for 9 hours at 90° C. under a nitrogen stream. After the stirring, water was added to this mixture, and an aqueous layer was subjected to extraction with toluene. The obtained extracted solution and an organic layer were combined, washed with water and saturated saline, and dried with magnesium sulfate. This mixture was separated by gravity filtration, and the filtrate was concentrated to give a brown oily substance. This solid was purified by silica gel column chromatography (developing solvent: toluene) to give 0.95 g of an objective brownish-white substance in a yield of 67%. The synthesis scheme of Step 1 is shown in (L-1) below.

[Chemical Formula 70]

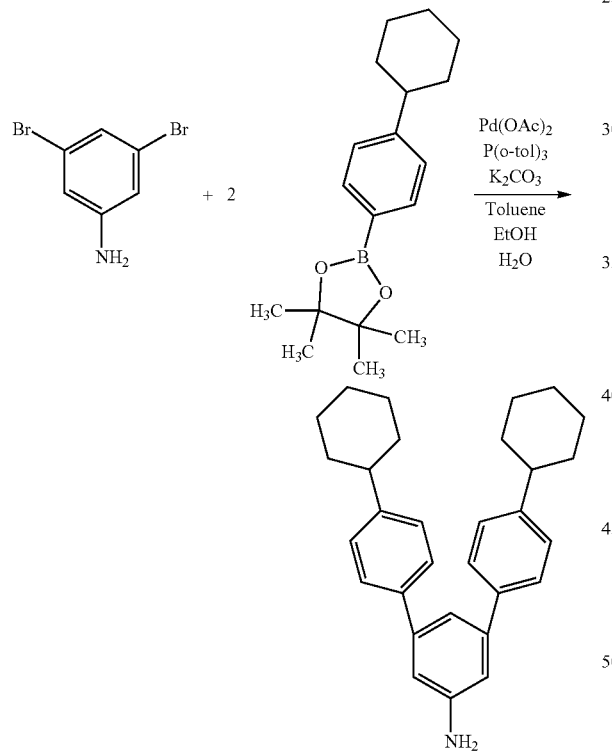

(L-1)

Figure 99A:
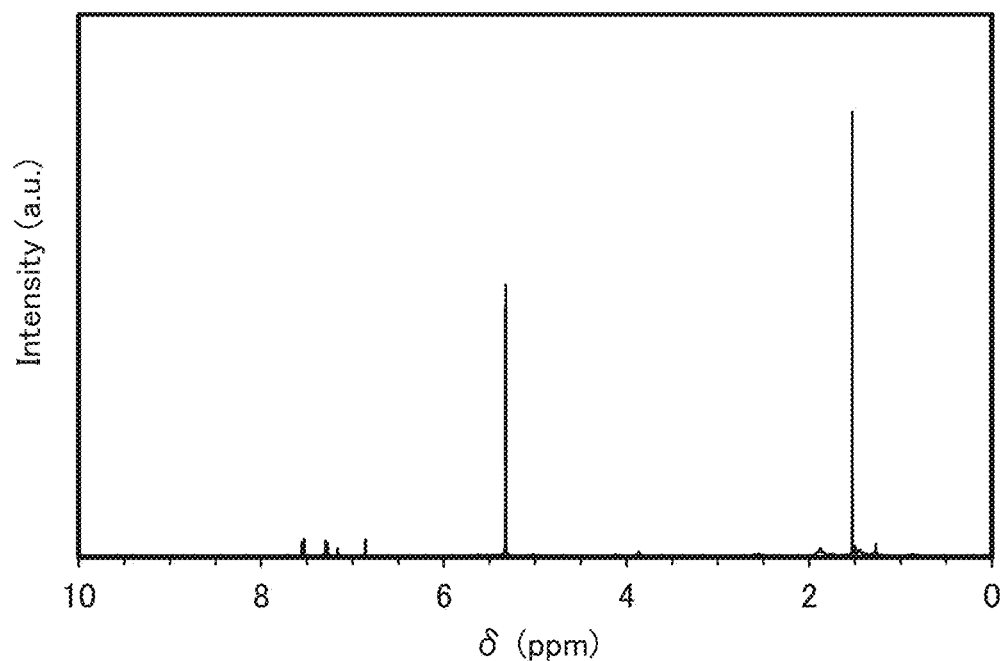
FIGS. 99A and 99B Diagrams showing NMR charts of a compound in Example.
Figure 99B:
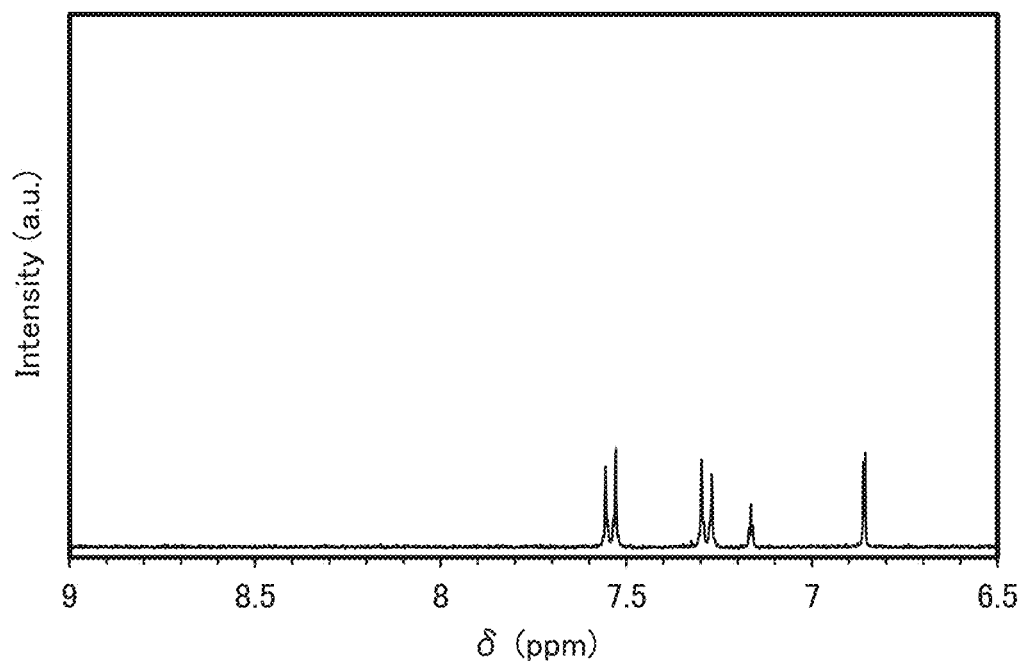
Figure 100:
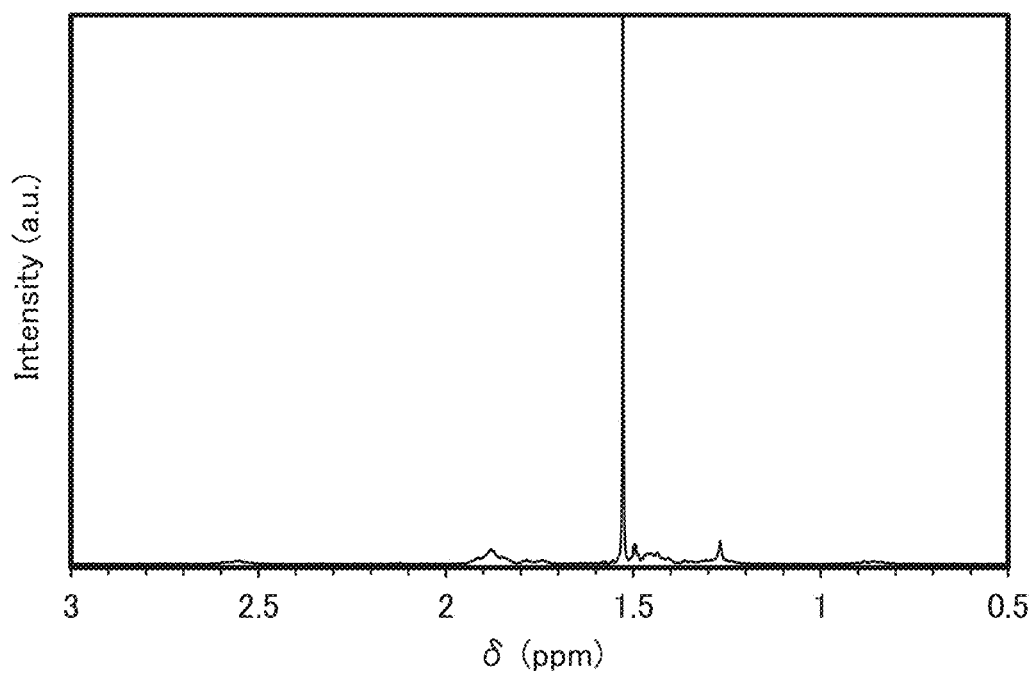
FIG. 100 A diagram showing an NMR chart of a compound in Example.

Results of $^1$H NMR measurement of the brownish-white solid obtained in Step 1 described above will be described below. FIG. 99 and FIG. 100 are the $^1$H-NMR charts. Note that FIG. 99(B) is an enlarged chart of the range of 6.5 ppm to 9.0 ppm of FIG. 99(A). FIG. 100 is an enlarged chart of the range of 0.5 ppm to 3.0 ppm of FIG. 99(A). The results indicate that 3,5-bis(4-cyclohexylphenyl)aniline was obtained.

$^1$H NMR (CD$_2$Cl$_2$, 300 MHz): σ=7.56-7.53 (m, 4H), 7.30-7.27 (m, 4H), 7.17-7.16 (m, 1H), 6.86 (d, J=1.5 Hz, 2H), 3.87 (bs, 2H), 2.59-2.51 (m, 2H), 1.92-1.74 (m, 10H), 1.50-1.23 (m, 10H).

Step 2: Synthesis of 1-chloro-3,5-bis(4-cyclohexylphenyl)benzene 1.4 g (5.2 mmol) of 1,3-dibromo-5-chlorobenzene, 3.0 g (10 mmol) of 4-cyclohexylphenilboronic acid pinacol ester, and 0.28 g (0.92 mmol) of tri-o-tolylphosphine were put into a 200 mL three-neck flask, and the air in the flask was replaced with nitrogen. To this mixture were added 30 mL of toluene, 10 mL of ethanol, and 10 mL of a 2M aqueous solution of potassium carbonate, and the mixture was degassed under reduced pressure; then, 60 mg (0.27 mmol) of palladium acetate(II) was added to the mixture and the mixture was stirred for 13 hours at 90° C. under a nitrogen stream. After the stirring, water was added to this mixture, and an aqueous layer was subjected to extraction with toluene. The obtained extracted solution and an organic layer were combined, washed with water and saturated saline, and dried with magnesium sulfate. This mixture was separated by gravity filtration, and the filtrate was concentrated to give a brown oily substance. This oily substance was purified by silica gel column chromatography (developing solvent: hexane) to give 0.95 g of an objective brownish-white substance in a yield of 43%. The synthesis scheme of Step 2 is shown in (L-2) below.

[Chemical Formula 71]

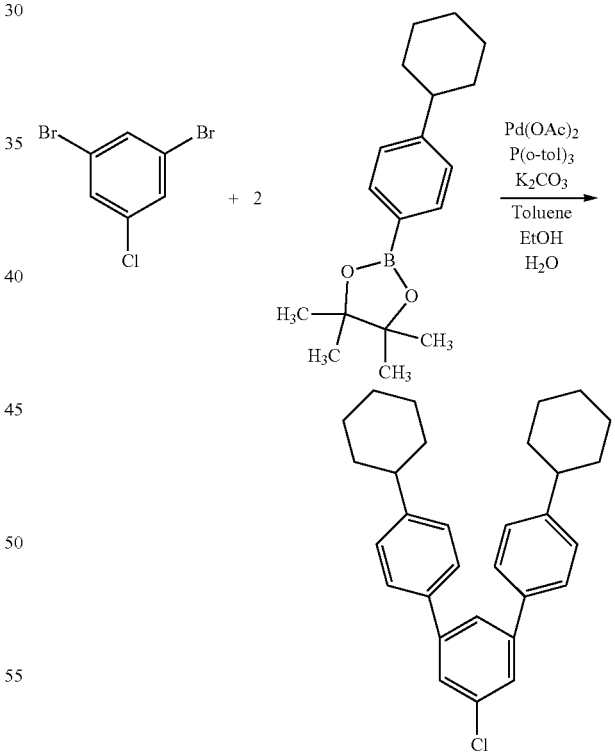

(L-2)

Figure 101A:
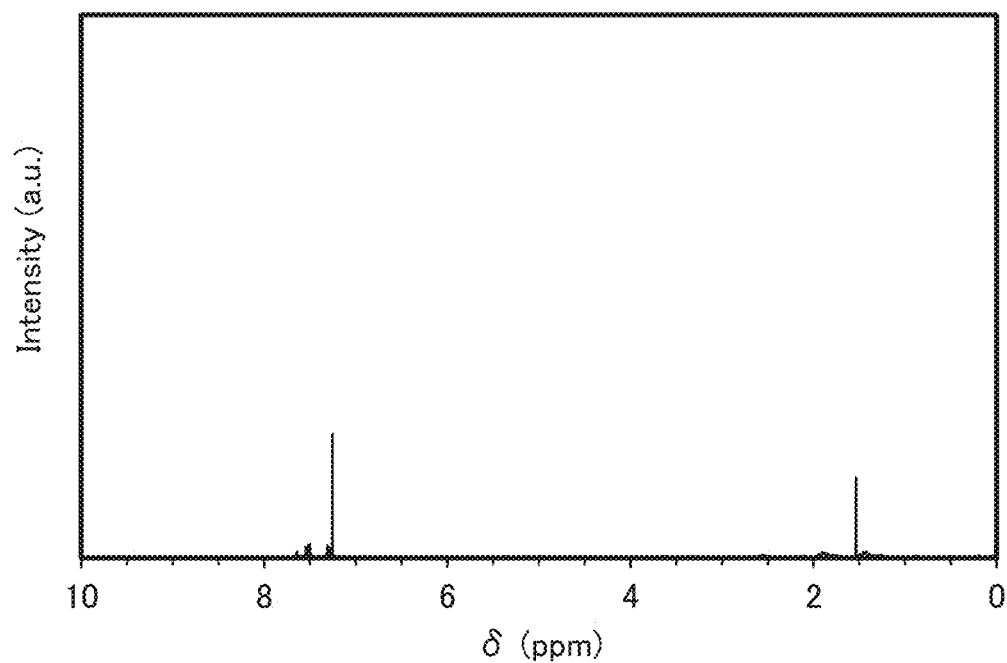
FIGS. 101A and 101B Diagrams showing NMR charts of a compound in Example.
Figure 101B:
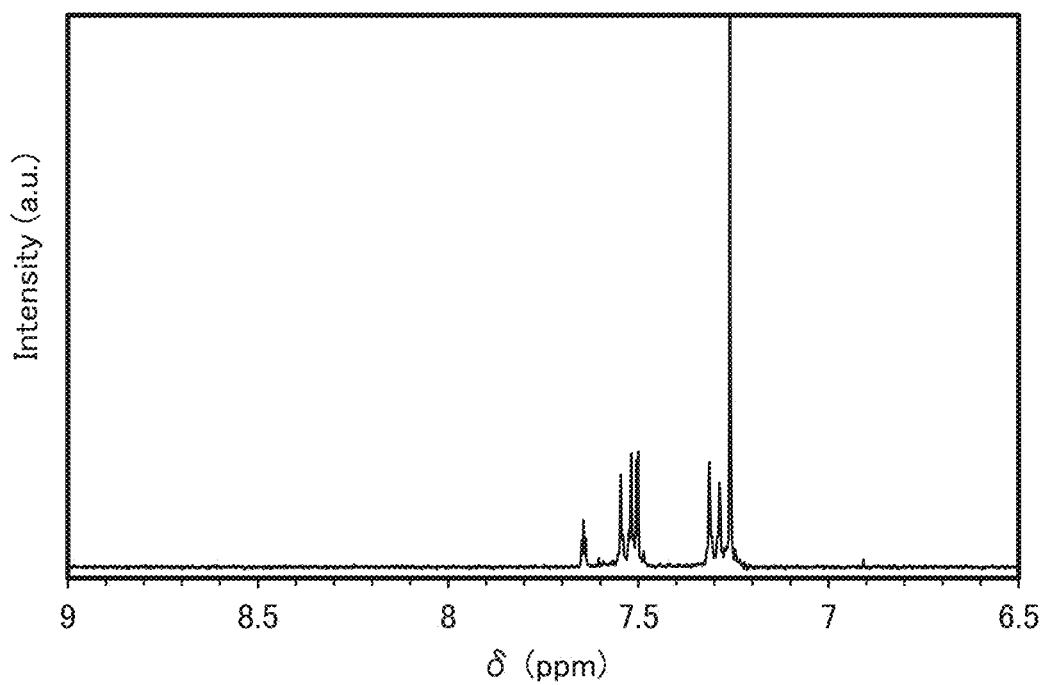
Figure 102:
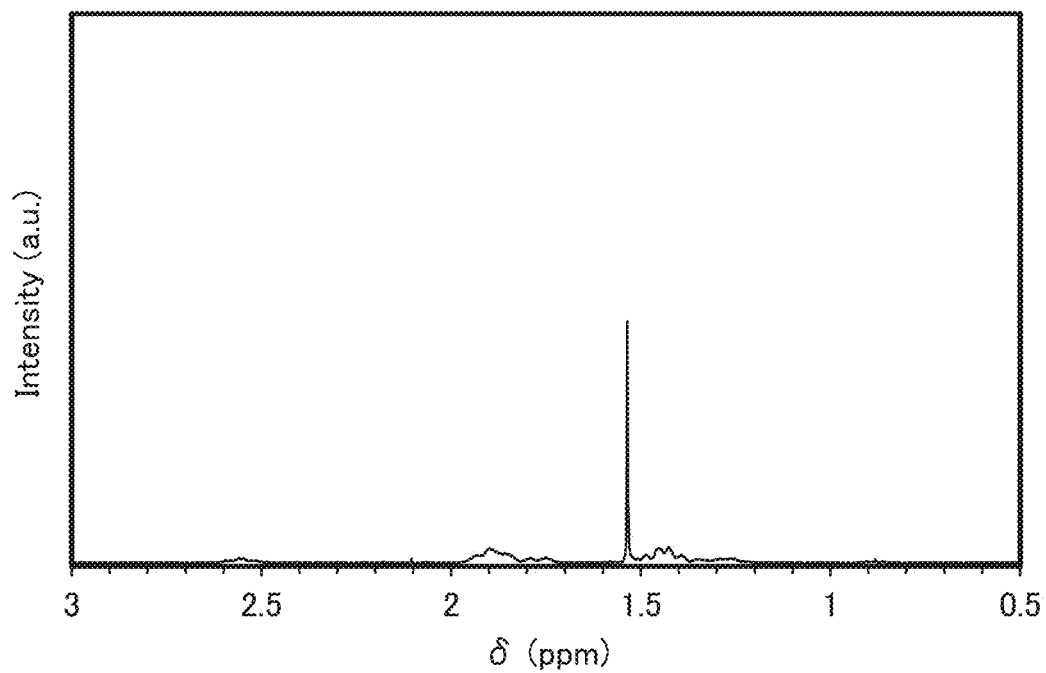
FIG. 102 A diagram showing an NMR chart of a compound in Example.

Results of $^1$H NMR measurement of the white solid obtained in Step 2 described above will be described below. FIG. 101 and FIG. 102 are the $^1$H-NMR charts. Note that FIG. 101(B) is an enlarged chart of the range of 6.5 ppm to 9.0 ppm of FIG. 101(A). FIG. 102 is an enlarged chart of the range of 0.5 ppm to 3.0 ppm of FIG. 101(A). The results indicate that 1-chloro-3,5-bis(4-cyclohexylphenyl)benzene was obtained.

$^1$H NMR (CDCl$_3$, 300 MHz): σ=7.65-7.64 (m, 1H), 7.55-7.50 (m, 6H), 7.31-7.29 (m, 4H), 2.60-2.51 (m, 2H), 1.94-1.73 (m, 10H), 1.49-1.38 (m, 10H).

Step 3: Synthesis of bis[3,5-bis(4-cyclohexylphenyl)phenyl]amine 0.95 g (2.2 mmol) of 1-chloro-3,5-bis(4-cyclohexylphenyl)benzene, 0.95 g (2.3 mmol) of 3,5-bis(4-cyclohexylphenyl)aniline, 0.44 g (4.6 mmol) of sodium t-butoxide, and 50 mg (0.14 mmol) of n-butyldiadamantylphosphine were put into a 100 mL three-neck flask, and the air in the flask was replaced with nitrogen. To this mixture was added 15 mL of toluene, and the mixture was degassed under reduced pressure; then, 30 mg (52 μmol) of bis(dibenzylideneacetone)palladium(0) was added to the mixture and the mixture was stirred for 4 hours at 120° C. under a nitrogen stream. After the stirring, 500 mL of toluene was added to the obtained mixture, which was then subjected to suction filtration through Florisil, Celite, and aluminum oxide to give a filtrate. The obtained filtrate was concentrated to give a brown solid. This solid was purified by silica gel column chromatography (developing solvent: hexane:toluene=3:2) to obtain 1.4 g of an objective white solid in a yield of 79%. The synthesis scheme of Step 3 is shown in (L-3) below.

[Chemical Formula 72]

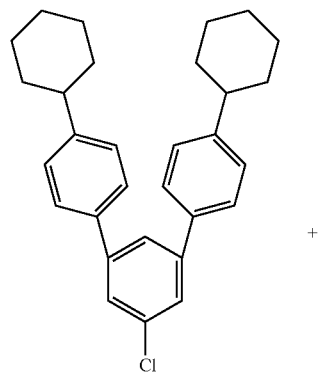

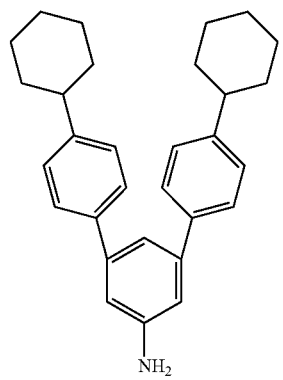

(L-3)

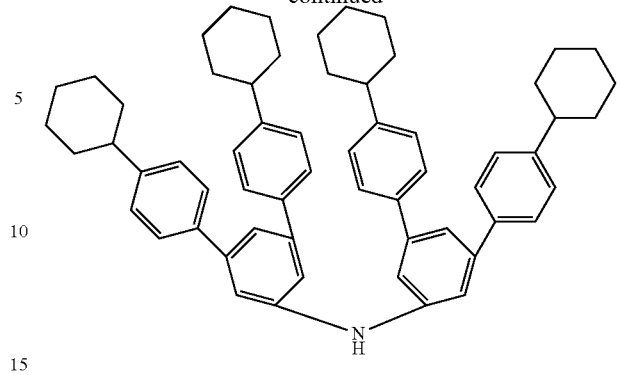

Figure 103A:
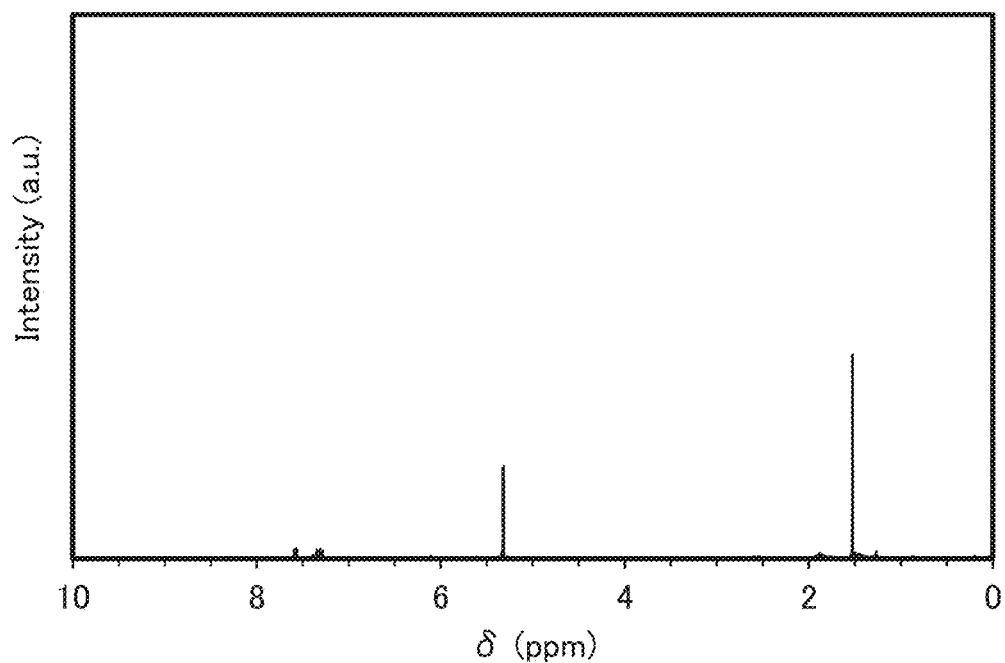
FIGS. 103A and 103B Diagrams showing NMR charts of a compound in Example.
Figure 103B:
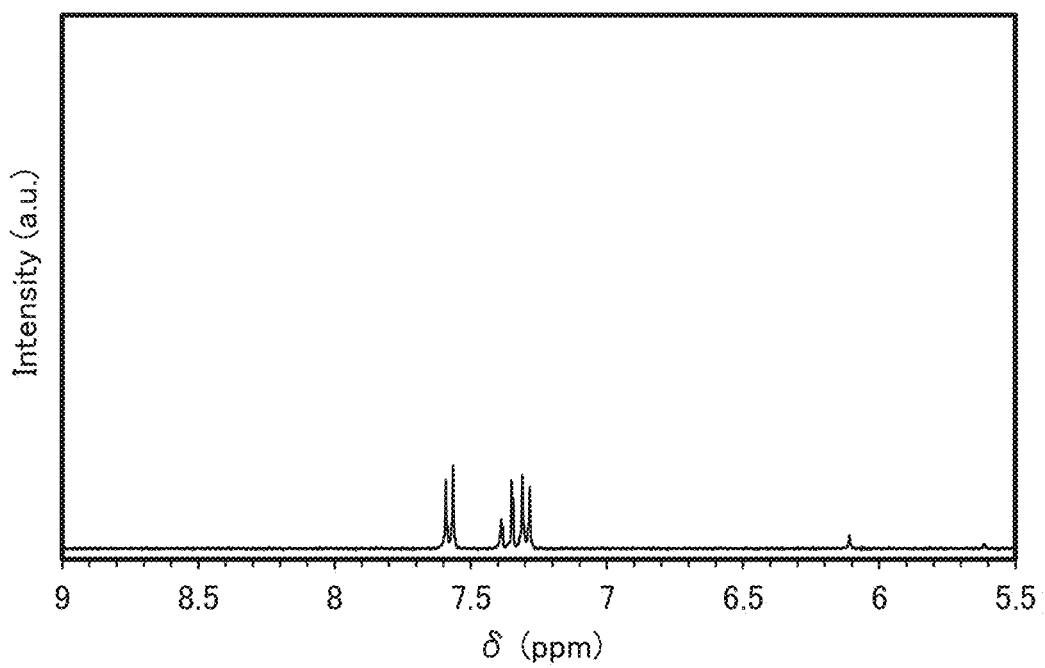
Figure 104:
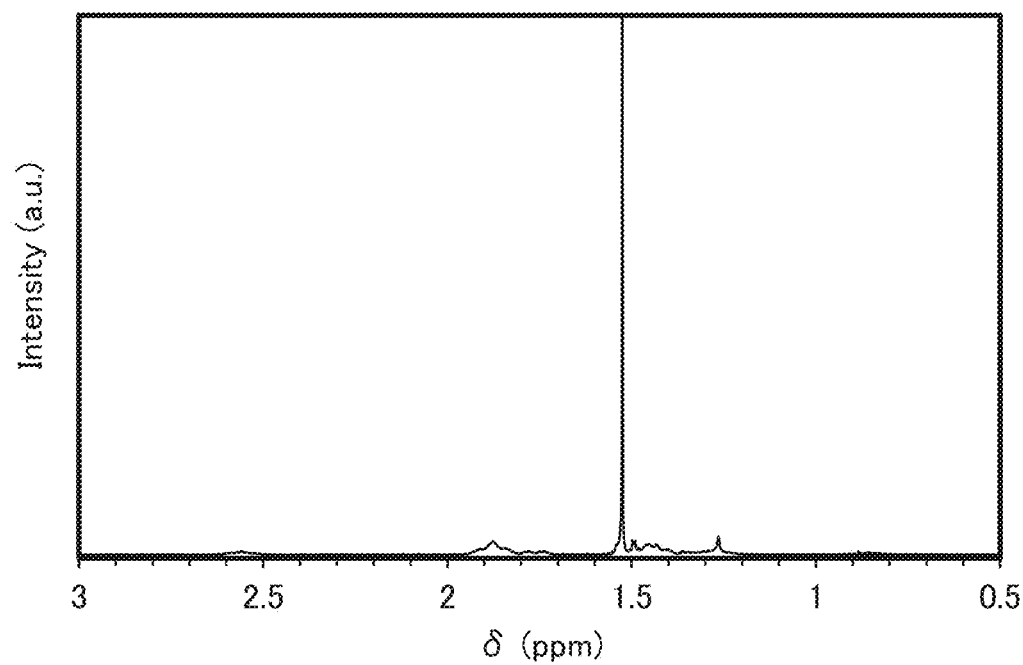
FIG. 104 A diagram showing an NMR chart of a compound in Example.

Results of $^1$H NMR measurement of the brownish-white solid obtained in Step 3 described above will be described below. FIG. 103 and FIG. 104 are the $^1$H-NMR charts. Note that FIG. 103(B) is an enlarged chart of the range of 5.5 ppm to 9.0 ppm of FIG. 103(A). FIG. 104 is an enlarged chart of the range of 0.5 ppm to 3.0 ppm of FIG. 103(A). The results indicate that bis[3,5-bis(4-cyclohexylphenyl)phenyl]amine was obtained.

$^1$H NMR (CD$_2$Cl$_2$, 300 MHz): σ=7.59-7.56 (m, 8H), 7.39-7.38 (m, 2H), 7.35-7.34 (m, 4H), 7.32-7.28 (m, 8H), 6.11 (bs, 1H), 2.60-2.51 (m, 4H), 1.93-1.73 (m, 20H), 1.50-1.24 (m, 20H).

Step 4: Synthesis of 2Ph-mmchPDPhA2Anth 0.35 g (0.85 mmol) of 9,10-dibromo-2-phenylanthracene, 1.4 g (1.8 mmol) of bis[3,5-bis(4-cyclohexylphenyl)phenyl]amine, 0.34 g (3.5 mmol) of sodium t-butoxide, and 60 mg (0.15 mmol) of SPhos were put into a 200 mL three-neck flask, and the air in the flask was replaced with nitrogen. To this mixture was added 10 mL of xylene, and the mixture was degassed under reduced pressure; then, 40 mg (70 μmop of bis(dibenzylideneacetone)palladium(0) was added to the mixture and the mixture was stirred for 6 hours at 150° C. under a nitrogen stream. After the stirring, 500 mL of toluene was added to the obtained mixture, which was then subjected to suction filtration through Florisil, Celite, and aluminum oxide to give a filtrate. The obtained filtrate was concentrated to give a brown solid. This solid was purified by silica gel column chromatography (developing solvent: hexane:toluene=4:1) to obtain a yellow solid-1. The obtained yellow solid-1 was recrystallized with toluene and ethyl acetate to give a yellow solid-2. The obtained yellow solid-2 was purified by HPLC (developing solvent: chloroform) to give 0.68 g of an objective yellow solid in a yield of 43%. The synthesis scheme of Step 3 is shown in (L-4) below.

[Chemical Formula 73]

(L-4)

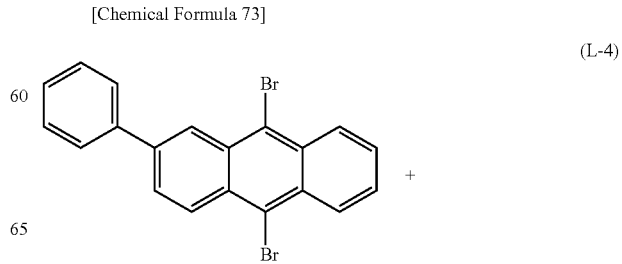

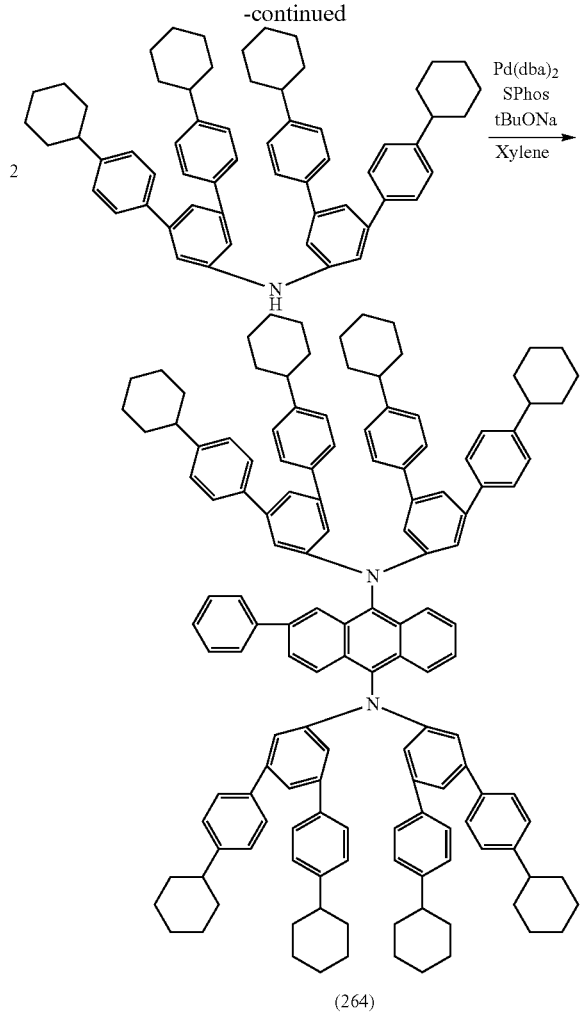

(264)

Figure 105A:
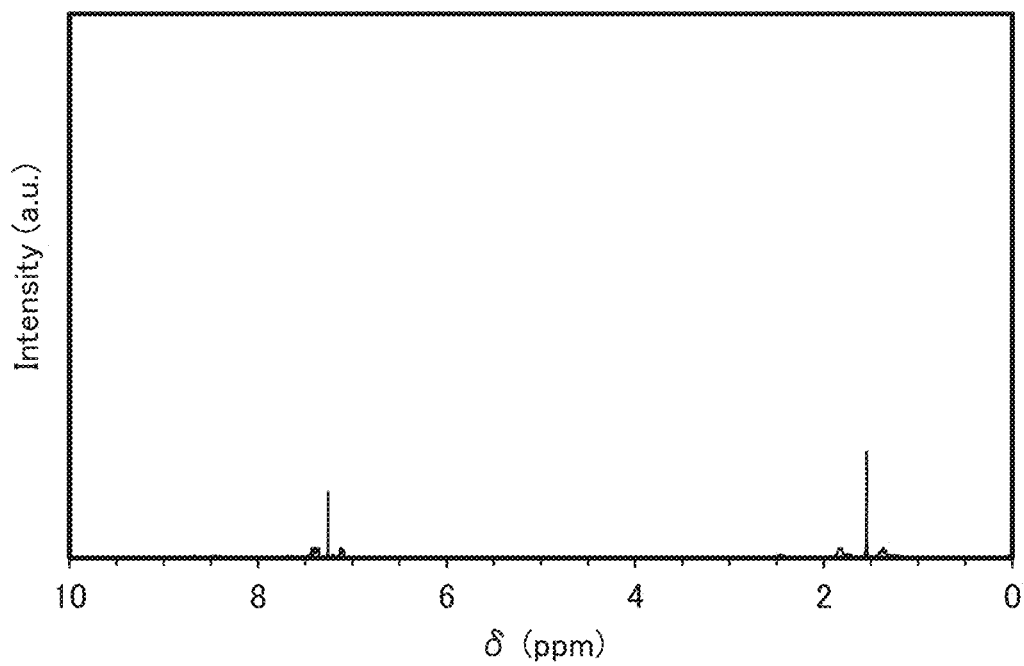
FIGS. 105A and 105B Diagrams showing NMR charts of a compound in Example.
Figure 105B:
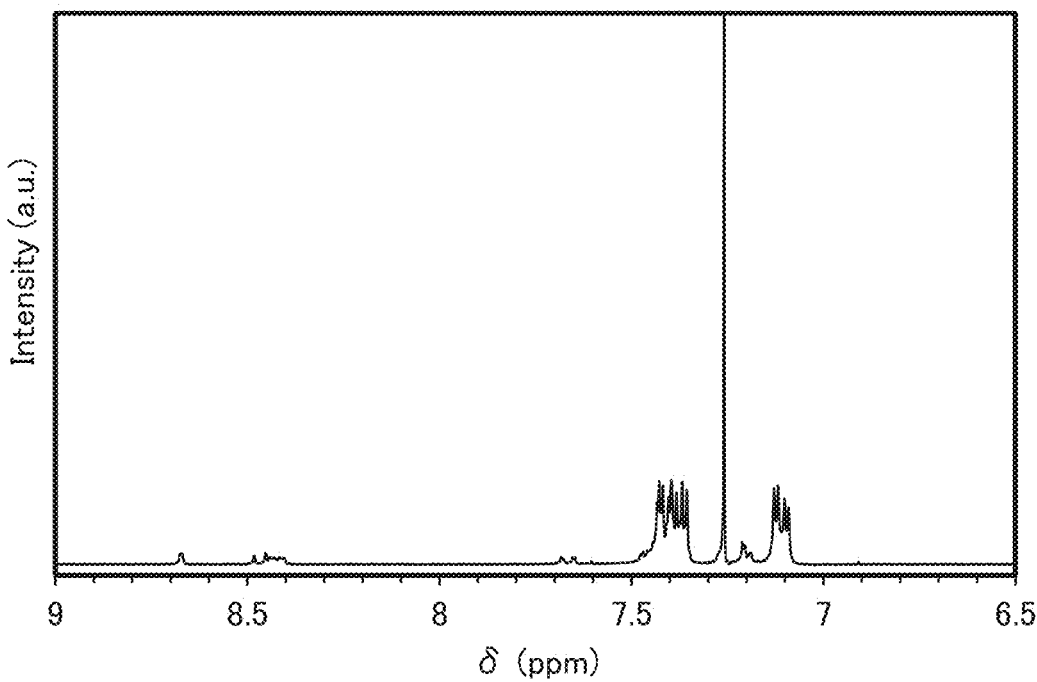
Figure 106:
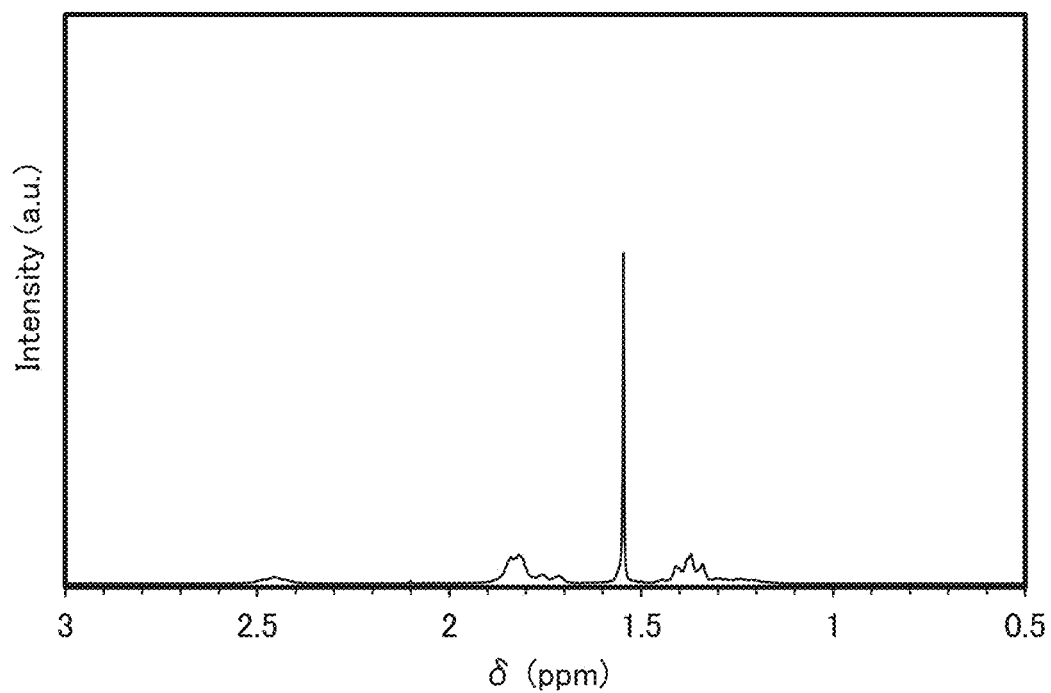
FIG. 106 A diagram showing an NMR chart of a compound in Example.

Results of ¹H NMR measurement of the yellow solid obtained in Step 4 described above will be described below. FIG. 105 and FIG. 106 are the ¹H-NMR charts. Note that FIG. 105(B) is an enlarged chart of the range of 6.5 ppm to 9.0 ppm of FIG. 105(A). FIG. 106 is an enlarged chart of the range of 0.5 ppm to 3.0 ppm of FIG. 105(A). The results indicate that 2Ph-mmchPDPhA2Anth was obtained.

¹H NMR (CD$_2$Cl$_2$, 300 MHz): σ=8.67 (m, 1H), 8.48-8.40 (m, 3H), 7.68-7.65 (m, 1H), 7.48-7.36 (m, 33H), 7.21-7.19 (m, 2H), 7.13-7.09 (m, 16H), 2.49-2.42 (m, 8H), 1.83-1.71 (m, 40H), 1.45-1.20 (m, 40H).

Figure 107:
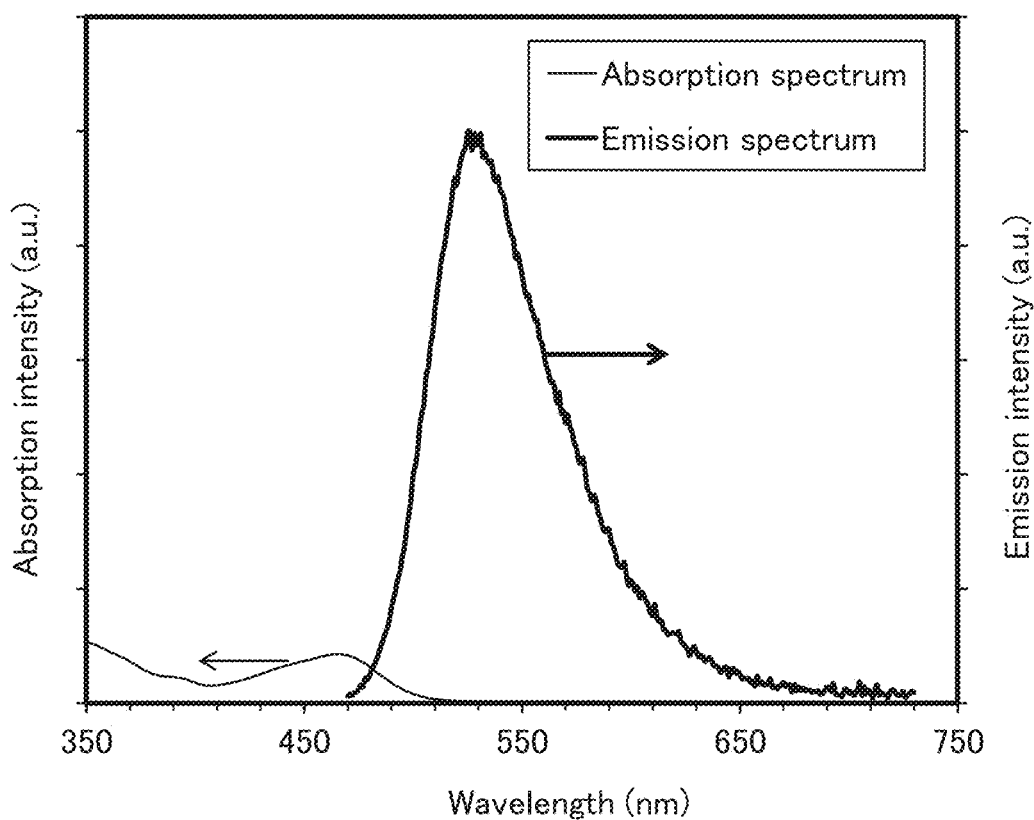
FIG. 107 A diagram showing absorption and emission spectra of a compound in Example.

Next, FIG. 107 shows the measurement results of the absorption spectrum and the emission spectrum of 2Ph-mmchPDPhA2Anth in a toluene solution. The measurement method is similar to the method described in Example 1.

As shown in FIG. 107, in the case of 2Ph-mmchPDPhA2Anth in the toluene solution, absorption peaks were observed at around 467 nm, 393 nm, and 351 nm, and an emission wavelength peak was at 526 nm (excitation wavelength: 455 nm).

Example 17

In this example, a synthesis method of N,N'-(2-phenylanthracene-9,10-diyl)-N,N'-bis(3,5-di-tert-butylphenyl)-N,N'-bis(3,5-di-trimethylsilylphenyl)diamine (abbreviation: 2Ph-mmtBuTMSDPhA2Anth), which is an organic compound represented by Structural Formula (257) of Embodiment 1, will be described. This organic compound can be favorably used for a light-emitting element of one embodiment of the present invention.

Step 1: Synthesis of 3,5-di-tert-butyl-3',5'-di-trimethylsilyldiphenylamine 2.0 g (6.6 mmol) of 3,5-bis(trimethylsilyl)bromobenzene, 1.6 g (7.8 mmol) of 3,5-di-tert-butylaniline, and 1.5 g (16 mmol) of sodium t-butoxide were put into a 200 mL three-neck flask, and the air in the flask was replaced with nitrogen. To this mixture was added 35 mL of toluene, and the mixture was degassed under reduced pressure; then, 0.40 mL (0.13 mmol) of tri-tert-butylphosphine (a 10 w % hexane solution) and 60 mg (0.10 mol) of bis(dibenzylideneacetone)palladium(0) were added to the mixture and the mixture was stirred for one hour at 90° C. under a nitrogen stream. After the stirring, 500 mL of toluene was added to the obtained mixture, which was then subjected to suction filtration through Florisil, Celite, and aluminum oxide to give a filtrate. The obtained filtrate was concentrated to give a brown oily substance. This brown oily substance was purified by silica gel column chromatography (developing solvent: hexane:toluene=9:1) to obtain 2.8 g of an objective colorless oily substance in a yield of 99%. The synthesis scheme of Step 1 is shown in (M-1) below.

[Chemical Formula 74]

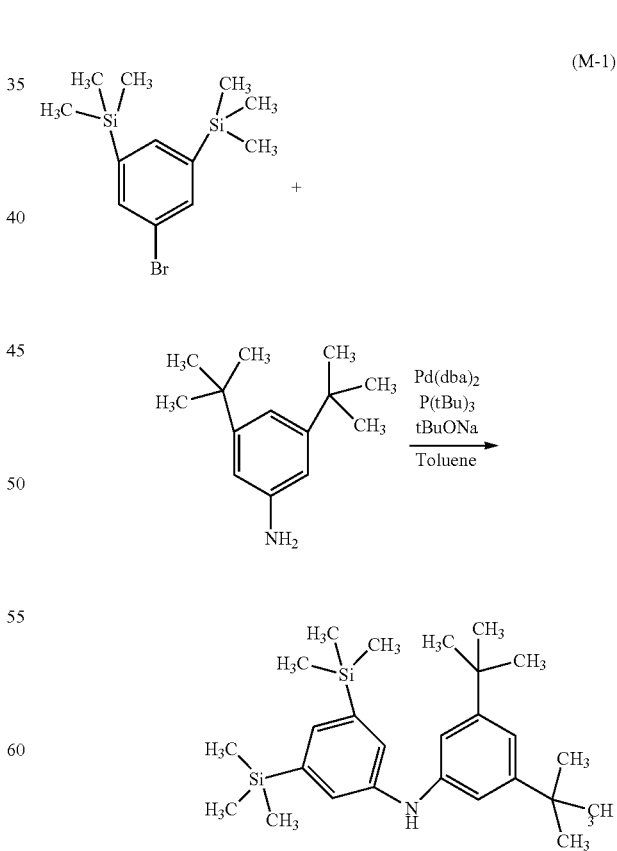

(M-1)

Figure 108A:
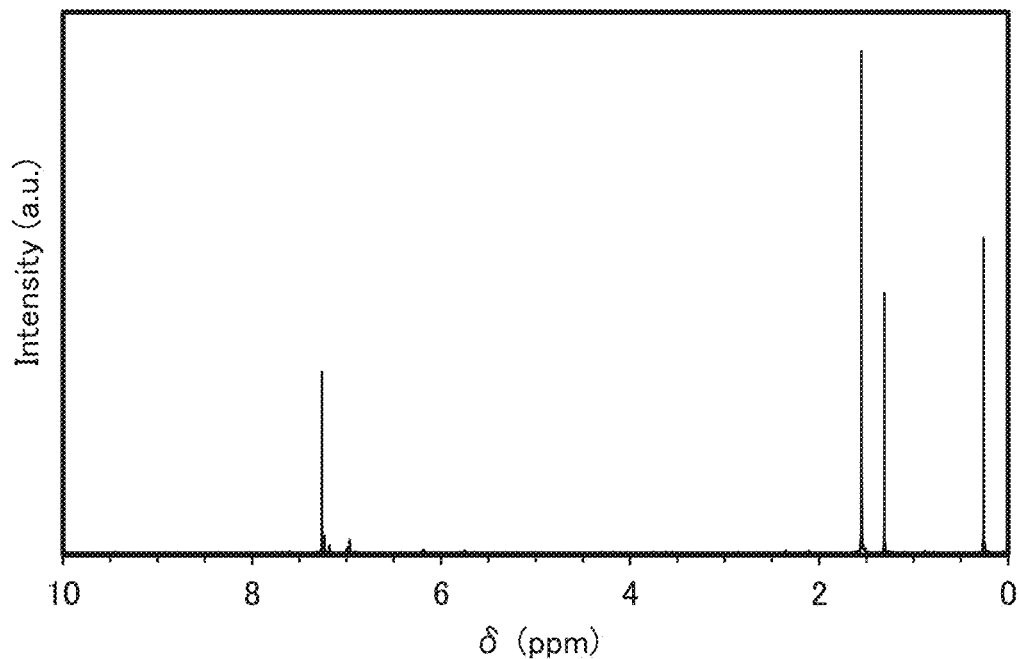
FIGS. 108A and 108B Diagrams showing NMR charts of a compound in Example.
Figure 108B:
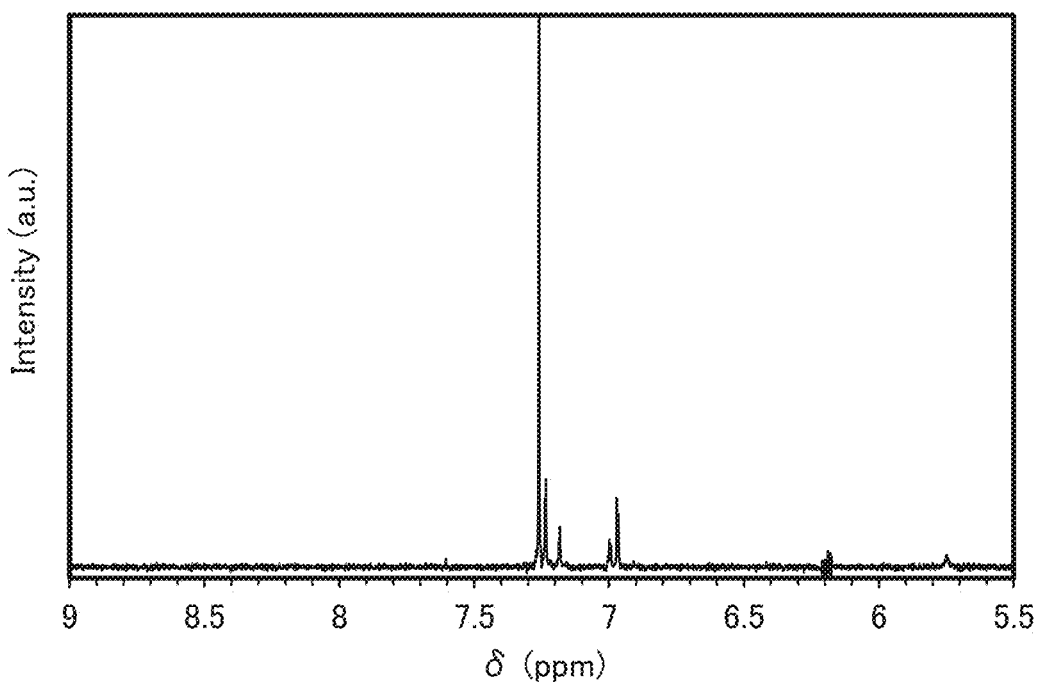
Figure 109:
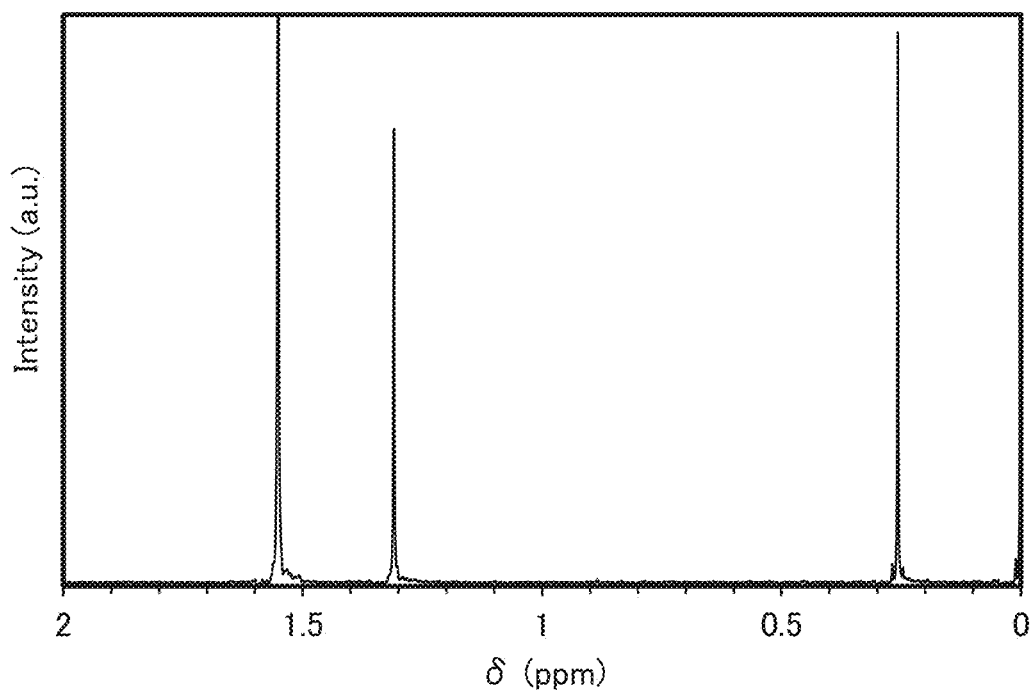
FIG. 109 A diagram showing an NMR chart of a compound in Example.

Results of ¹H NMR measurement of the colorless oily substance obtained in Step 1 described above will be described below. FIG. 108 and FIG. 109 are the ¹H-NMR charts. Note that FIG. 108(B) is an enlarged chart of the range of 5.5 ppm to 9.0 ppm of FIG. 108(A). FIG. 109 is an enlarged chart of the range of 0.0 ppm to 2.0 ppm of FIG. 108(A). The results indicate that 3,5-di-tert-butyl-3',5'-di-trimethylsilyldiphenylamine was obtained.

¹H NMR (CDCl₃, 300 MHz): σ=7.24-7.23 (m, 2H), 7.19-7.18 (m, 1H), 7.00-6.99 (m, 1H), 6.97 (m, 2H), 5.75 (bs, 1H), 1.31 (s, 18H), 0.26 (s, 18H).

Step 2: Synthesis of 2Ph-mmtBuTMSDPhA2Anth 1.3 g (3.1 mmol) of 9,10-dibromo-2-phenylanthracene, 2.8 g (6.5 mmol) of 3,5-di-tert-butyl-3',5'-di-trimethylsilyl-diphenylamine 1.2 g (12 mmol) of sodium t-butoxide, and 60 mg (0.15 mmol) of SPhos were put into a 200 mL three-neck flask, and the air in the flask was replaced with nitrogen. To this mixture was added 35 mL of xylene, and the mixture was degassed under reduced pressure; then, 40 mg (70 μmop of bis(dibenzylideneacetone)palladium(0) was added to the mixture and the mixture was stirred for 7 hours at 150° C. under a nitrogen stream. After the stirring, 500 mL of toluene was added to the obtained mixture, which was then subjected to suction filtration through Florisil, Celite, and aluminum oxide to give a filtrate. The obtained filtrate was concentrated to give a brown solid. This solid was purified by silica gel column chromatography (developing solvent: hexane:toluene=9:1) to obtain an objective yellow solid. The obtained yellow solid was recrystallized with ethyl acetate and ethanol to give 0.31 g of an objective yellow solid in a yield of 9%. The synthesis scheme of Step 2 is shown in (M-2) below.

[Chemical Formula 75]

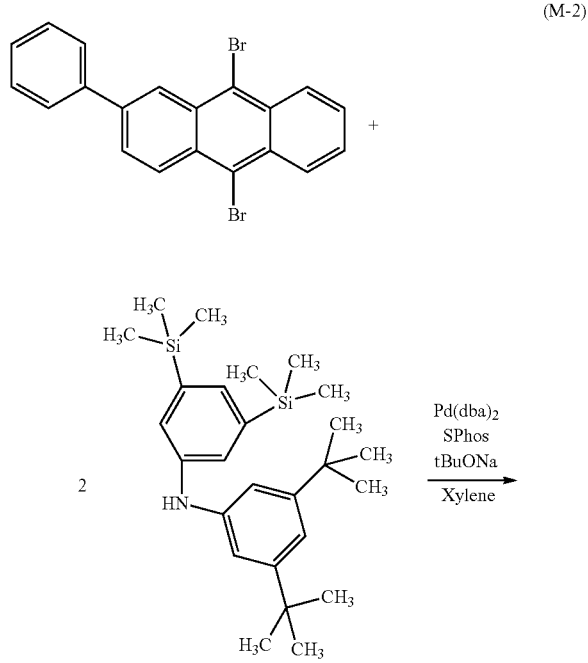

(M-2)

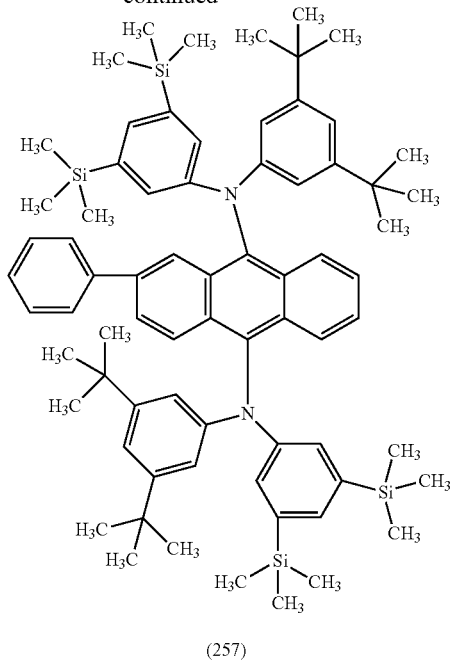

(257)

By a train sublimation method, 0.31 g of the obtained yellow solid was purified by sublimation. In the sublimation purification, the yellow solid was heated at 220° C. under a pressure of 3.6 Pa for 15 hours. After the sublimation purification, 0.27 g of an objective yellow solid was obtained at a collection rate of 87%.

Figure 110A:
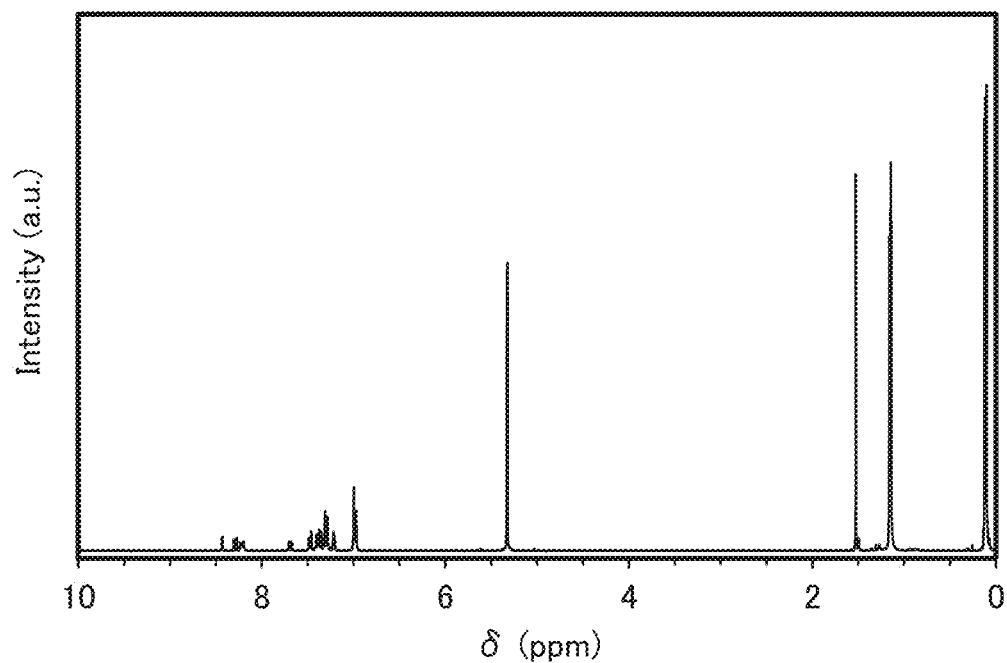
FIGS. 110A and 110B Diagrams showing NMR charts of a compound in Example.
Figure 110B:
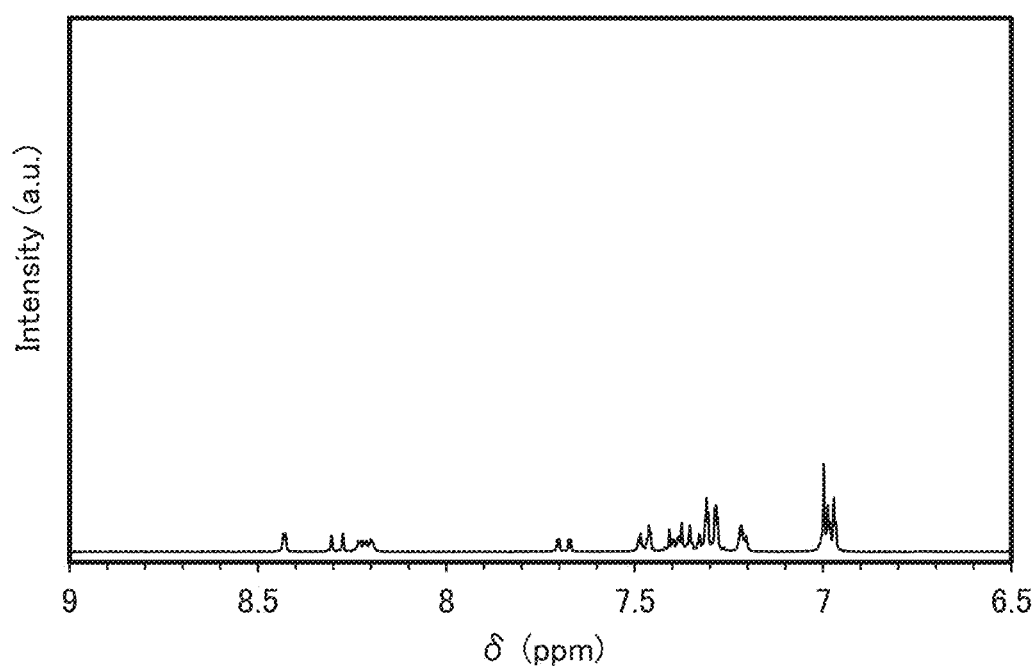
Figure 111:
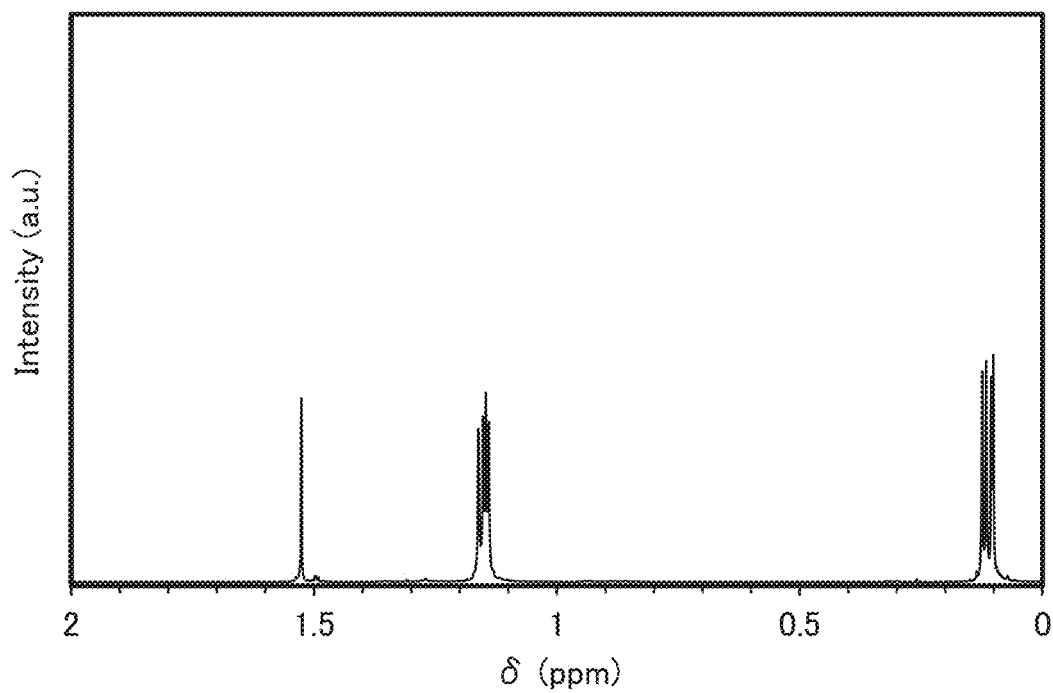
FIG. 111 A diagram showing an NMR chart of a compound in Example.

Results of ¹H NMR measurement of the yellow solid obtained in Step 2 described above will be described below. FIG. 110 and FIG. 111 are the ¹H-NMR charts. Note that FIG. 110(B) is an enlarged chart of the range of 6.5 ppm to 9.0 ppm of FIG. 110(A). FIG. 111 is an enlarged chart of the range of 0.0 ppm to 2.0 ppm of FIG. 110. The results indicate that 2Ph-mmtBuTMSDPhA2Anth was obtained.

¹H NMR (CD₂Cl₂, 300 MHz): σ=8.43 (d, J=1.5 Hz, 1H), 8.27 (d, J=8.8 Hz, 1H), 8.23-8.20 (m, 2H), 7.67 (dd, J=1.5 Hz, 8.8 Hz, 1H), 7.49-7.46 (m, 2H), 7.41-7.26 (m, 9H), 7.22-7.20 (m, 2H), 7.00-6.97 (m, 6H), 1.18-1.14 (m, 36H), 0.12-0.10 (m, 36H).

Figure 112:
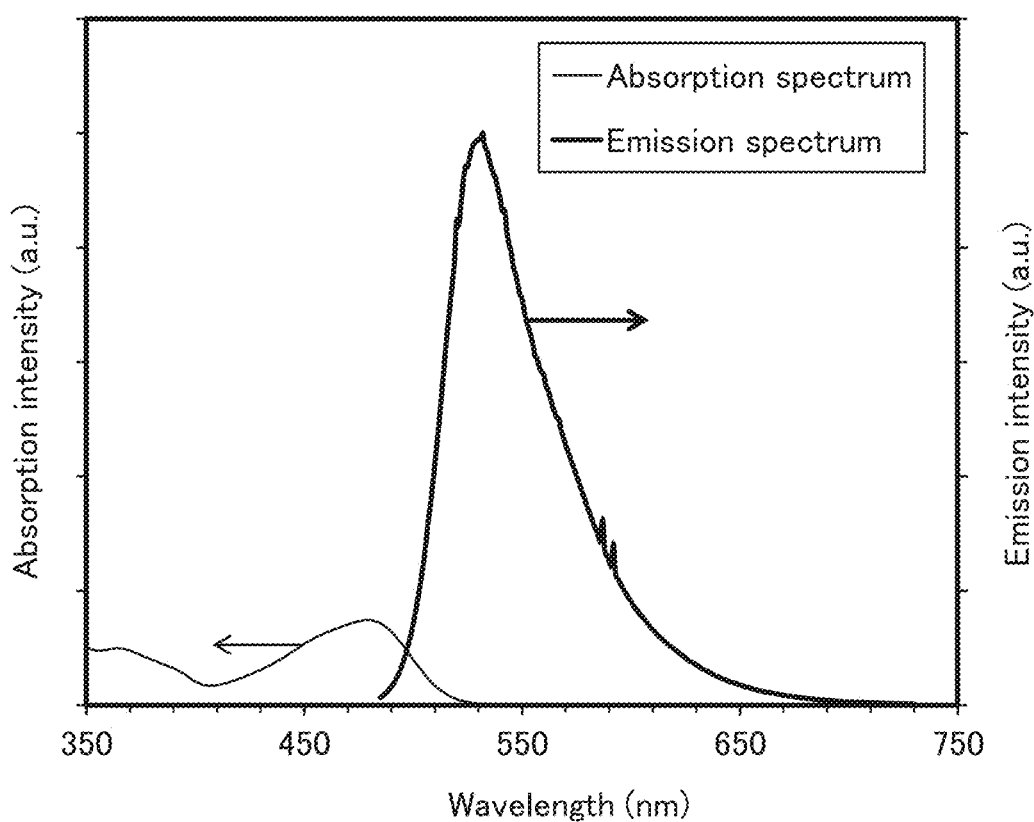
FIG. 112 A diagram showing absorption and emission spectra of a compound in Example.
Figure 113:
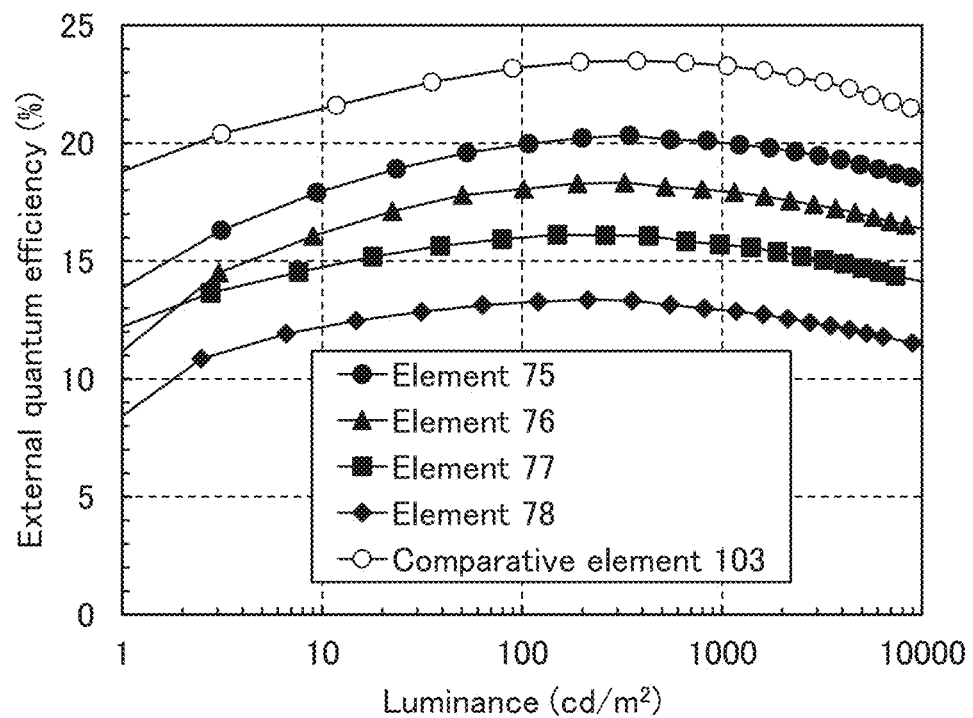
FIG. 113 A diagram showing external quantum efficiency-luminance characteristics of light-emitting elements in Example.

Next, FIG. 112 shows the measurement results of the absorption spectrum and the emission spectrum of 2Ph-mmtBuTMSDPhA2Anth in a toluene solution. The measurement method is similar to the method described in Example 1.

As shown in FIG. 112, in the case of 2Ph-mmtBuTMSDPhA2Anth in the toluene solution, absorption peaks were observed at around 480 nm, 389 nm, and 367 nm, and an emission wavelength peak was at 532 nm (excitation wavelength: 470 nm).

Example 18

In this example, fabrication examples of light-emitting elements of embodiments of the present invention and comparative light-emitting elements and the characteristics of the light-emitting elements are described. The structure of each of the light-emitting elements fabricated in this example is the same as that in FIG. 1(A). Table 14 to Table 17 show the details of the element structures. The structures and abbreviations of fluorescent materials having protecting groups that were used are shown below. Note that the above examples and embodiments can be referred to for other organic compounds.
[Chemical Formula 76]
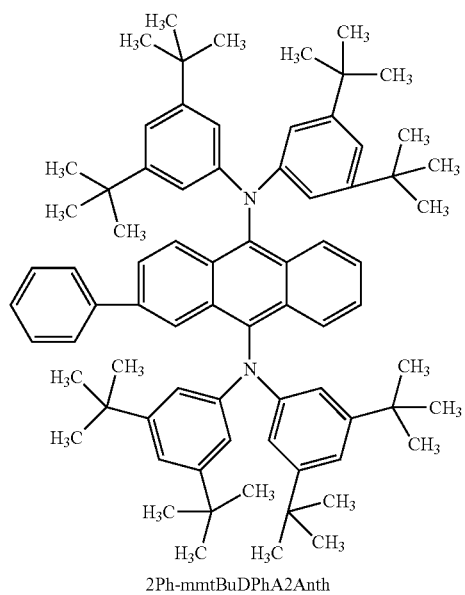
2Ph-mmtBuDPhA2Anth
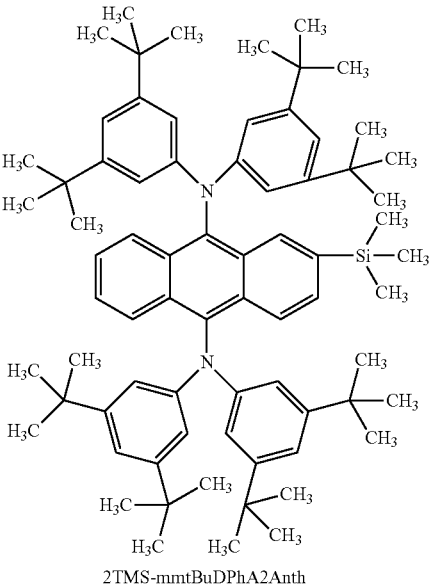
2TMS-mmtBuDPhA2Anth
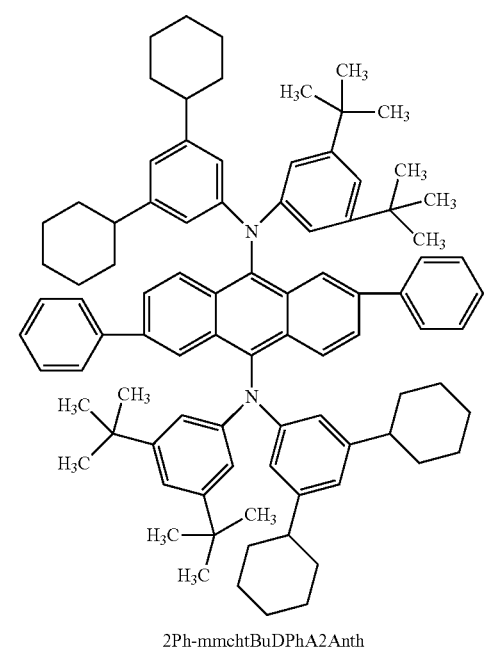
2,6Ph-mmtBuDPhA2Anth
2Ph-mmchtBuDPhA2Anth

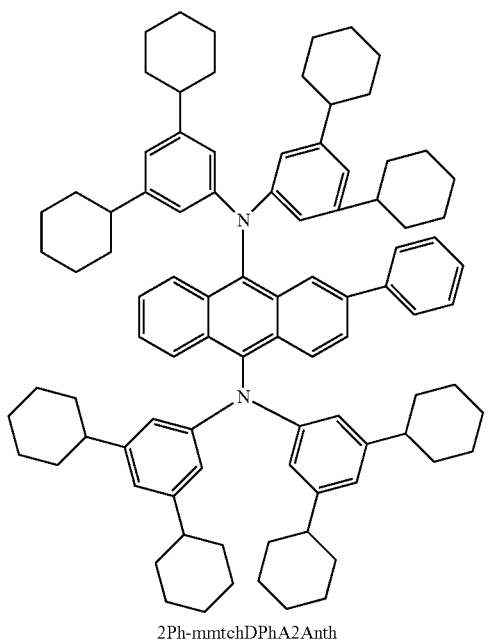

2Ph-mmtchDPhA2Anth

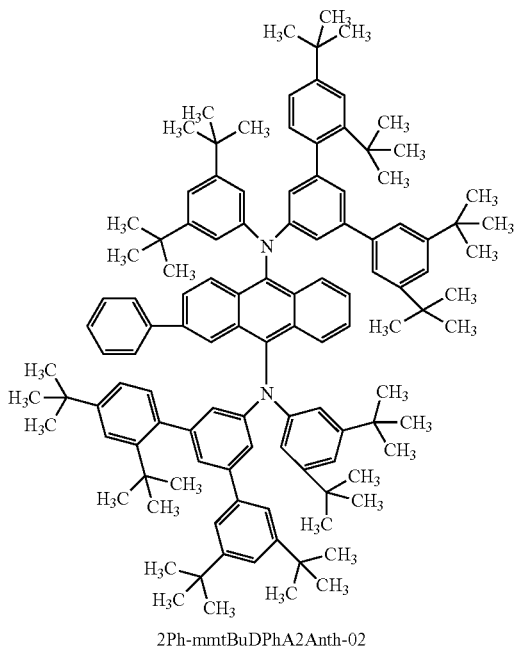 [SMILES: CC(C)(C)c1cc(-c2cc(-c3ccc(C(C)(C)C)cc3C(C)(C)C)cc(N(c3cc(C(C)(C)C)cc(C(C)(C)C)c3)c3c4ccccc4c(N(c4cc(-c5cc(C(C)(C)C)cc(C(C)(C)C)c5)cc(-c5ccc(C(C)(C)C)cc5C(C)(C)C)c4)c4cc(C(C)(C)C)cc(C(C)(C)C)c4)c4cc(-c5ccccc5)ccc34)c2)cc(C(C)(C)C)c1]

2Ph-mmtBuDPhA2Anth-02

TABLE 14

| | Layer | Reference numeral | Thickness (nm) | Material | Weight ratio |
|---|---|---|---|---|---|
| Light-emitting elements 75 to 78 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | mPCCzPTzn-02 | — |
| | Light-emitting layer | 130 | 40 | mPCCzPTzn-02:PCCP:GD270:2Ph-mmtBuDPhA2Anth | 0.5:0.5:0.1:$y_1$ |
| | Hole-transport layer | 112 | 20 | PCBBi1BP | — |
| | Hole-injection layer | 111 | 40 | DBT3P-II:MoO$_3$ | 1:0.5 |
| | Anode | 101 | 70 | ITSO | — |
| Light-emitting elements 79 to 82 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | mPCCzPTzn-02 | — |
| | Light-emitting layer | 130 | 40 | mPCCzPTzn-02:PCCP:GD270:2,6Ph-mmtBuDPhA2Anth | 0.5:0.5:0.1:$y_1$ |
| | Hole-transport layer | 112 | 20 | PCBBi1BP | — |
| | Hole-injection layer | 111 | 40 | DBT3P-II:MoO$_3$ | 1:0.5 |
| | Anode | 101 | 70 | ITSO | — |
| Light-emitting elements 83 to 86 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | mPCCzPTzn-02 | — |

TABLE 14-continued

|  | Layer | Reference numeral | Thickness (nm) | Material | Weight ratio |
|---|---|---|---|---|---|
|  | Light-emitting layer | 130 | 40 | mPCCzPTzn-02:PCCP:GD270:2TMS-mmtBuDPhA2Anth | 0.5:0.5:0.1:y$_1$ |
|  | Hole-transport layer | 112 | 20 | PCBBi1BP | — |
|  | Hole-injection layer | 111 | 40 | DBT3P-II:MoO$_s$ | 1:0.5 |
|  | Anode | 101 | 70 | ITSO | — |
| Light-emitting elements 87 to 90 | Electrode | 102 | 200 | Al | — |
|  | Electron-injection layer | 119 | 1 | LiF | — |
|  | Electron-transport layer | 118(2) | 10 | NBPhen | — |
|  |  | 118(1) | 20 | mPCCzPTzn-02 | — |
|  | Light-emitting layer | 130 | 40 | mPCCzPTzn-02:PCCP:GD270:2Ph-mmchtBuDPhA2Anth | 0.5:0.5:0.1:y$_1$ |
|  | Hole-transport layer | 112 | 20 | PCBBi1BP | — |
|  | Hole-injection layer | 111 | 40 | DBT3P-II:MoO$_3$ | 1:0.5 |
|  | Anode | 101 | 70 | ITSO | — |

TABLE 15

|  | Layer | Reference numeral | Thickness (nm) | Material | Weight ratio |
|---|---|---|---|---|---|
| Light-emitting elements 91 to 94 | Electrode | 102 | 200 | Al | — |
|  | Electron-injection layer | 119 | 1 | LiF | — |
|  | Electron-transport layer | 118(2) | 10 | NBPhen | — |
|  |  | 118(1) | 20 | mPCCzPTzn-02 | — |
|  | Light-emitting layer | 130 | 40 | mPCCzPTzn-02:PCCP:GD270:2Ph-mmchDPhA2Anth | 0.5:0.5:0.1:y$_1$ |
|  | Hole-transport layer | 112 | 20 | PCBBi1BP | — |
|  | Hole-injection layer | 111 | 40 | DBT3P-II:MoO$_3$ | 1:0.5 |
|  | Anode | 101 | 70 | ITSO | — |
| Light-emitting elements 95 to 98 | Electrode | 102 | 200 | Al | — |
|  | Electron-injection layer | 119 | 1 | LiF | — |
|  | Electron-transport layer | 118(2) | 10 | NBPhen | — |
|  |  | 118(1) | 20 | mPCCzPTzn-02 | — |
|  | Light-emitting layer | 130 | 40 | mPCCzPTzn-02:PCCP:GD270:2Ph-mmtBuDPhA2Anth-02 | 0.5:0.5:0.1:y$_2$ |
|  | Hole-transport layer | 112 | 20 | PCBBi1BP | — |
|  | Hole-injection layer | 111 | 40 | DBT3P-II:MoO$_3$ | 1:0.5 |
|  | Anode | 101 | 70 | ITSO | — |
| Comparative light-emitting elements 99 to 102 | Electrode | 102 | 200 | Al | — |
|  | Electron-injection layer | 119 | 1 | LiF | — |
|  | Electron-transport layer | 118(2) | 10 | NBPhen | — |
|  |  | 118(1) | 20 | mPCCzPTzn-02 | — |

TABLE 15-continued

| Layer | | Reference numeral | Thickness (nm) | Material | Weight ratio |
|---|---|---|---|---|---|
| Comparative light-emitting element 103 | Light-emitting layer | 130 | 40 | mPCCzPTzn-02:PCCP:GD270:TTPA | $0.5:0.5:0.1:y_1$ |
| | Hole-transport layer | 112 | 20 | PCBBi1BP | — |
| | Hole-injection layer | 111 | 40 | DBT3P-II:MoO$_3$ | 1:0.5 |
| | Anode | 101 | 70 | ITSO | — |
| | Electrode | 102 | 200 | Al | — |
| | Electron-injection layer | 119 | 1 | LiF | — |
| | Electron-transport layer | 118(2) | 10 | NBPhen | — |
| | | 118(1) | 20 | mPCCzPTzn-02 | — |
| | Light-emitting layer | 130 | 40 | mPCCzPTzn-02:PCCP:GD270 | 0.5:0.5:0.1 |
| | Hole-transport layer | 112 | 20 | PCBBi1BP | — |
| | Hole-injection layer | 111 | 40 | DBT3P-II:MoO$_3$ | 1:0.5 |
| | Anode | 101 | 70 | ITSO | — |

TABLE 16

| | Light-emitting elements 75, 79, 83, 87, and 91 Comparative light-emitting element 99 | Light-emitting elements 76, 80, 84, 88, and 92 Comparative light-emitting element 100 | Light-emitting elements 77, 81, 85, 89, and 93 Comparative light-emitting element 101 | Light-emitting elements 78, 82, 86, 90, and 94 Comparative light-emitting element 102 |
|---|---|---|---|---|
| $y_1$ | 0.01 | 0.025 | 0.05 | 0.1 |

TABLE 17

| | Light-emitting element 95 | Light-emitting element 96 | Light-emitting element 97 | Light-emitting element 98 |
|---|---|---|---|---|
| $y_2$ | 0.01 | 0.033 | 0.066 | 0.1 |

<<Fabrication of Light-Emitting Element 75 to Light-Emitting Element 98 and Comparative Light-Emitting Element 99 to Comparative Light-Emitting Element 103>>

A light-emitting element 75 to a light-emitting element 98 and a comparative light-emitting element 99 to a comparative light-emitting element 103 are different from the fabrication method of the above-described light-emitting element 30 only in a fluorescent material (guest material) used for the light-emitting layer 130, and other steps of the fabrication method are the same as those for the light-emitting element 30. The details of the element structures are shown in Table 14 to Table 17; thus, the details of the fabrication methods are omitted.

Note that GD270 in the light-emitting layer 130 of each of the light-emitting elements and the comparative light-emitting elements is a phosphorescent material containing Ir. Moreover, 2Ph-mmtBuDPhA2Anth in each of the light-emitting element 75 to the light-emitting element 78 is a fluorescent material having protecting groups and has a structure in which a phenyl group is bonded to an anthracene skeleton, which is a luminophore. Similarly, 2,6Ph-mmtBuDPhA2Anth in each of the light-emitting element 79 to the light-emitting element 82 is a fluorescent material having protecting groups and has a structure in which two phenyl groups are bonded to an anthracene skeleton, which is a luminophore. Similarly, 2TMS-mmtBuDPhA2Anth in each of the light-emitting element 83 to the light-emitting element 86 is a fluorescent material having protecting groups and has a structure in which a trimethylsilyl group is bonded to an anthracene skeleton, which is a luminophore. Similarly, 2Ph-mmchtBuDPhA2Anth in each of the light-emitting element 87 to the light-emitting element 90 is a fluorescent material having protecting groups and has a cyclohexyl group and a tertiary butyl group as the protecting groups. Furthermore, a structure in which a phenyl group is bonded to an anthracene skeleton, which is a luminophore, is included. Similarly, 2Ph-mmchDPhA2Anth in each of the light-emitting element 91 to the light-emitting element 94 is a fluorescent material having protecting groups and has cyclohexyl groups as the protecting groups. Furthermore, a structure in which a phenyl group is bonded to an anthracene skeleton, which is a luminophore, is included. Similarly, 2Ph-mmtBuDPhA2Anth-02 in each of the light-emitting element 95 to the light-emitting element 98 is a fluorescent material having protecting groups and has a structure in which a biphenyl group having a tertiary butyl group is bonded to an amino group. Furthermore, a structure in which a phenyl group is bonded to an anthracene skeleton, which is a luminophore, is included. In addition, TTPA in each of the light-emitting element 99 to the light-emitting element 102 is a fluorescent material having an anthracene skeleton and has no bulky substituent. The comparative light-emitting element 103 is a phosphorescent element in which GD270 emits light.

<Characteristics of Light-Emitting Elements>

Next, the characteristics of the fabricated light-emitting element 76 to light-emitting element 98 and comparative light-emitting element 99 to comparative light-emitting element 103 were measured. The measurement was performed in a manner similar to that in Example 6.

FIG. 113 to FIG. 124 show the external quantum efficiency-luminance characteristics of the light-emitting element 75 to the light-emitting element 98 and the comparative light-emitting element 103 and the electroluminescence spectra of those to which a current at a current density of 2.5 mA/cm² was supplied. FIG. 125 shows the electroluminescence spectra of the comparative light-emitting element 99 to the comparative light-emitting element 103 to which a current at a current density of 2.5 mA/cm² was supplied. Note that the measurement of the light-emitting elements was performed at room temperature (in an atmosphere maintained at 23° C.). Each diagram also shows the measurement results of the comparative light-emitting element 103. The comparative light-emitting element 103 is a light-emitting element containing no fluorescent material and is a phosphorescent element from which light emission originating from GD270 is observed. The light-emitting element 76 to the light-emitting element 98 can be regarded as elements obtained by adding a fluorescent material having protecting groups to the comparative light-emitting element 103.

Table 18 and Table 19 show the element characteristics of the light-emitting element 75 to the light-emitting element 98 and the comparative light-emitting element 99 to the comparative light-emitting element 103 at around 1000 cd/m².

TABLE 18

|  | Voltage (V) | Current density (mA/cm²) | CIE chromaticity (x, y) | Luminance (cd/m²) | Current efficiency (cd/A) | Power efficiency (lm/W) | External quantum efficiency (%) |
|---|---|---|---|---|---|---|---|
| Light-emitting element 75 | 3.10 | 1.11 | (0.349, 0.628) | 844 | 75.8 | 76.8 | 20.1 |
| Light-emitting element 76 | 3.20 | 1.69 | (0.354, 0.627) | 1156 | 68.4 | 67.1 | 17.9 |
| Light-emitting element 77 | 3.20 | 1.61 | (0.359, 0.625) | 975 | 60.5 | 59.4 | 15.7 |
| Light-emitting element 78 | 3.30 | 2.37 | (0.366, 0.620) | 1180 | 49.7 | 47.3 | 12.9 |
| Light-emitting element 79 | 3.00 | 1.02 | (0.354, 0.626) | 884 | 86.7 | 90.8 | 22.9 |
| Light-emitting element 80 | 3.00 | 1.11 | (0.370, 0.615) | 960 | 86.2 | 90.3 | 22.6 |
| Light-emitting element 81 | 3.00 | 1.14 | (0.383, 0.605) | 948 | 82.9 | 86.8 | 21.7 |
| Light-emitting element 82 | 3.00 | 1.21 | (0.399, 0.593) | 900 | 74.3 | 77.8 | 19.5 |
| Light-emitting element 83 | 3.10 | 1.28 | (0.332, 0.639) | 975 | 76.2 | 77.2 | 20.4 |
| Light-emitting element 84 | 3.10 | 1.28 | (0.334, 0.639) | 862 | 67.3 | 68.2 | 17.8 |
| Light-emitting element 85 | 3.20 | 1.80 | (0.335, 0.641) | 1030 | 57.2 | 56.1 | 15.0 |
| Light-emitting element 86 | 3.30 | 2.54 | (0.339, 0.640) | 1149 | 45.3 | 43.1 | 11.7 |
| Light-emitting element 87 | 3.10 | 1.19 | (0.339, 0.638) | 977 | 82.4 | 83.5 | 21.9 |
| Light-emitting element 88 | 3.10 | 1.25 | (0.347, 0.635) | 971 | 77.6 | 78.7 | 20.3 |
| Light-emitting element 89 | 3.10 | 1.22 | (0.356, 0.629) | 866 | 70.8 | 71.8 | 18.4 |
| Light-emitting element 90 | 3.20 | 1.78 | (0.363, 0.624) | 1084 | 60.9 | 59.7 | 15.6 |

TABLE 19

|  | Voltage (V) | Current density (mA/cm²) | CIE chromaticity (x, y) | Luminance (cd/m²) | Current efficiency (cd/A) | Power efficiency (lm/W) | External quantum efficiency (%) |
|---|---|---|---|---|---|---|---|
| Light-emitting element 91 | 3.00 | 0.94 | (0.344, 0.636) | 804 | 85.7 | 89.8 | 22.3 |
| Light-emitting element 92 | 3.10 | 1.25 | (0.362, 0.624) | 974 | 77.6 | 78.6 | 19.8 |
| Light-emitting element 93 | 3.10 | 1.21 | (0.369, 0.619) | 865 | 71.4 | 72.3 | 18.2 |
| Light-emitting element 94 | 3.20 | 1.76 | (0.375, 0.615) | 1137 | 64.5 | 63.3 | 16.5 |
| Light-emitting element 95 | 3.10 | 1.51 | (0.314, 0.654) | 1176 | 78.1 | 79.1 | 20.8 |
| Light-emitting element 96 | 3.10 | 1.46 | (0.314, 0.655) | 1040 | 71.0 | 72.0 | 18.8 |
| Light-emitting element 97 | 3.20 | 1.95 | (0.316, 0.657) | 1179 | 60.3 | 59.2 | 15.7 |
| Light-emitting element 98 | 3.20 | 1.72 | (0.317, 0.658) | 887 | 51.6 | 50.7 | 13.4 |

TABLE 19-continued

|  | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Comparative light-emitting element 99 | 3.10 | 1.86 | (0.337, 0.639) | 1163 | 62.4 | 63.2 | 16.4 |
| Comparative light-emitting element 100 | 3.10 | 2.06 | (0.350, 0.631) | 1014 | 49.2 | 49.9 | 12.8 |
| Comparative light-emitting element 101 | 3.10 | 2.41 | (0.361, 0.624) | 926 | 38.4 | 39.0 | 10.0 |
| Comparative light-emitting element 102 | 3.10 | 2.93 | (0.369, 0.618) | 855 | 29.1 | 29.5 | 7.5 |
| Comparative light-emitting element 103 | 3.00 | 1.24 | (0.319, 0.648) | 1064 | 85.8 | 89.9 | 23.3 |

Figure 114:
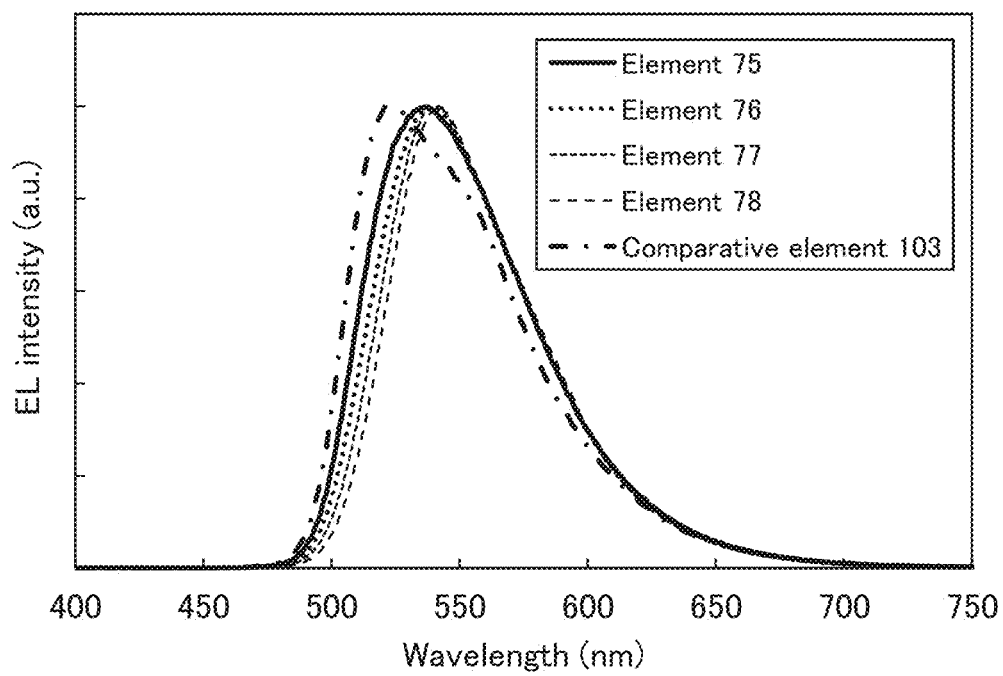
FIG. 114 A diagram showing electroluminescence spectra of light-emitting elements in Example.
Figure 115:
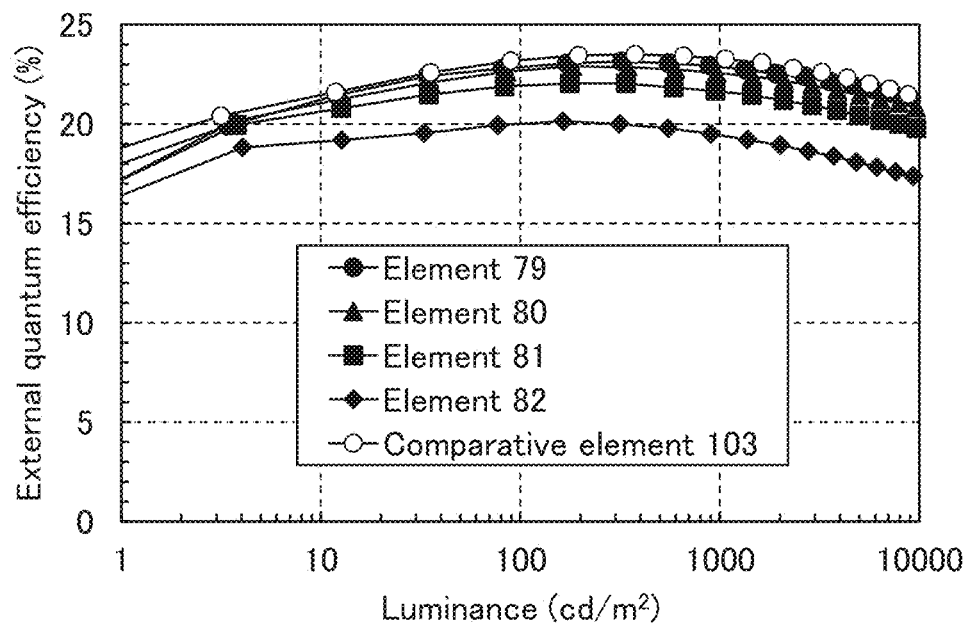
FIG. 115 A diagram showing external quantum efficiency-luminance characteristics of light-emitting elements in Example.
Figure 116:
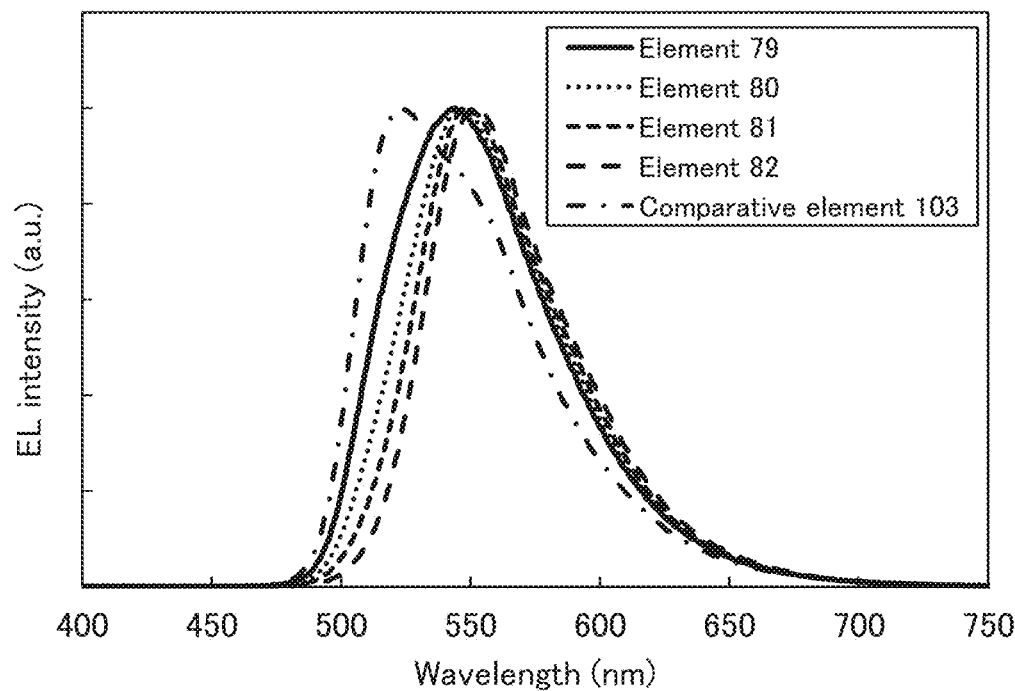
FIG. 116 A diagram showing electroluminescence spectra of light-emitting elements in Example.
Figure 117:
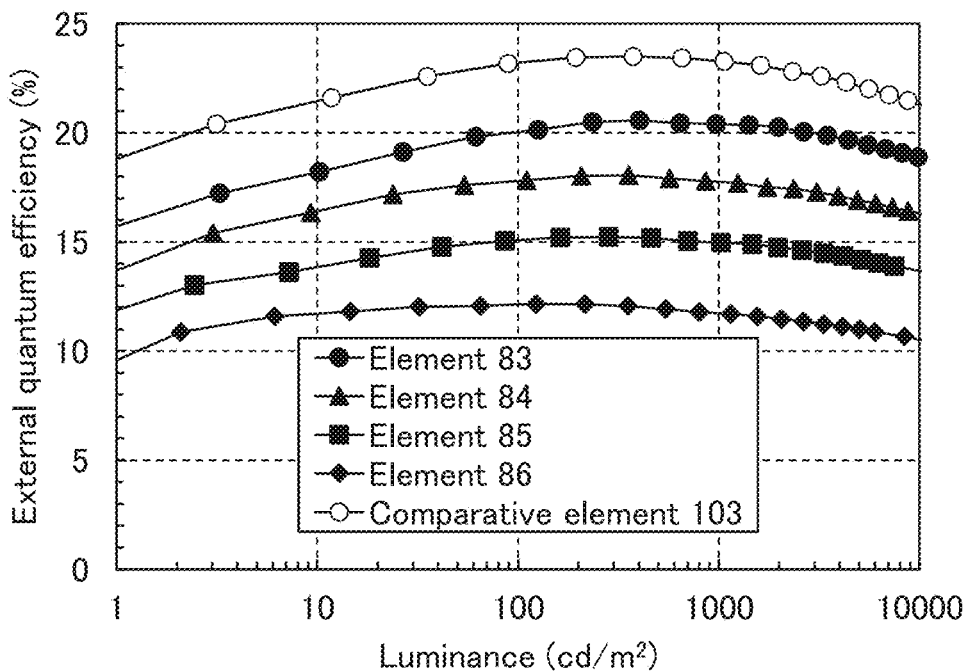
FIG. 117 A diagram showing external quantum efficiency-luminance characteristics of light-emitting elements in Example.
Figure 118:
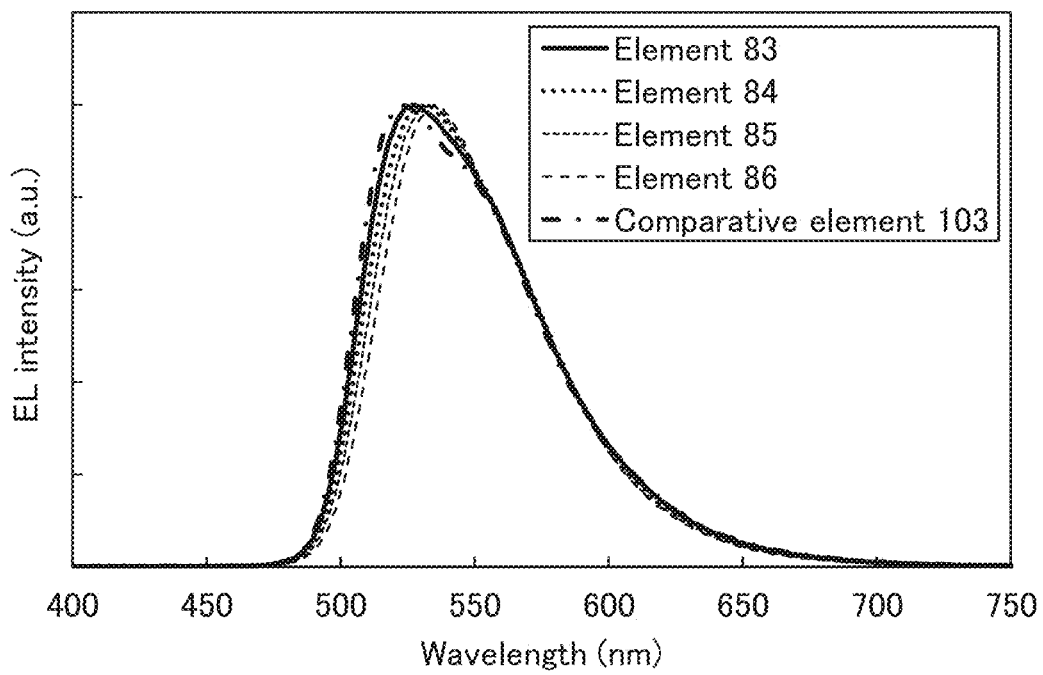
FIG. 118 A diagram showing electroluminescence spectra of light-emitting elements in Example.
Figure 119:
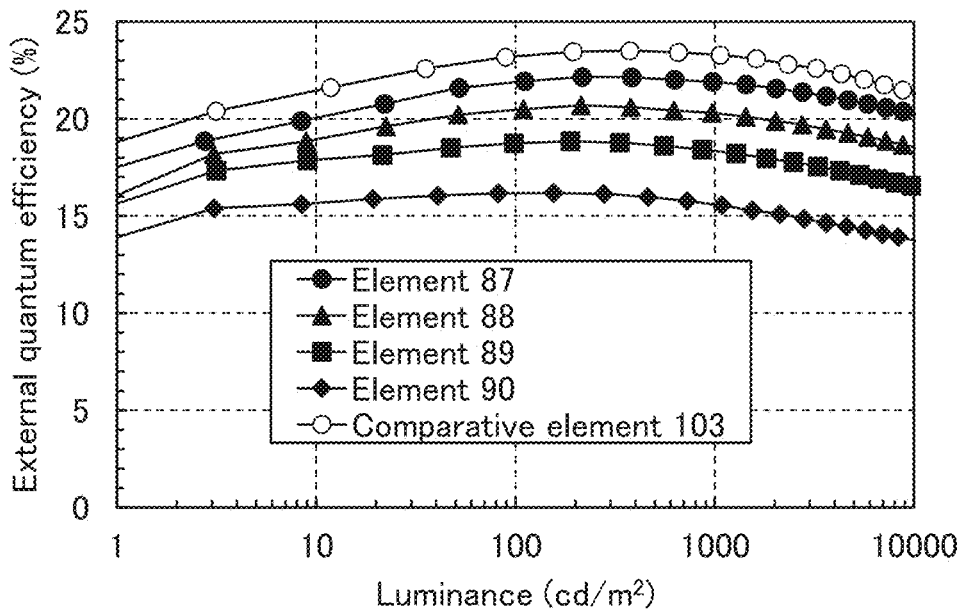
FIG. 119 A diagram showing external quantum efficiency-luminance characteristics of light-emitting elements in Example.

As shown in FIG. 114, the emission spectra of the light-emitting element 75 to the light-emitting element 78 had a peak wavelength at approximately 540 nm and a full width at half maximum of approximately 69 nm, i.e., exhibited green light emission originating from 2Ph-mmtBuDPhA2Anth. As shown in FIG. 116, the emission spectra of the light-emitting element 79 to the light-emitting element 82 had a peak wavelength at approximately 548 nm and a full width at half maximum of approximately 68 nm, i.e., exhibited green light emission originating from 2,6Ph-mmtBuDPhA2Anth. As shown in FIG. 118, the emission spectra of the light-emitting element 83 to the light-emitting element 86 had a peak wavelength at approximately 532 nm and a full width at half maximum of approximately 70 nm, i.e., exhibited green light emission originating from 2TMS-mmtBuDPhA2Anth. As shown in FIG. 120, the emission spectra of the light-emitting element 87 to the light-emitting element 90 had a peak wavelength at approximately 540 nm and a full width at half maximum of approximately 68 nm, i.e., exhibited green light emission originating from 2Ph-mmchtBuDPhA2Anth. As shown in FIG. 122, the emission spectra of the light-emitting element 91 to the light-emitting element 94 had a peak wavelength at approximately 543 nm and a full width at half maximum of approximately 65 nm, i.e., exhibited green light emission originating from 2Ph-mmchDPhA2Anth. As shown in FIG. 124, the emission spectra of the light-emitting element 95 to the light-emitting element 98 had a peak wavelength at approximately 530 nm and a full width at half maximum of approximately 65 nm, i.e., exhibited green light emission originating from 2Ph-mmtBuDPhA2Anth-02. As shown in FIG. 125, the emission spectra of the comparative light-emitting element 99 to the light-emitting element 102 had a peak wavelength at approximately 541 nm and a full width at half maximum of approximately 68 nm, i.e., exhibited green light emission originating from TTPA. Light emission different from that of the comparative light-emitting element 103 was observed from all of the light-emitting elements.

Accordingly, light emission originating from the fluorescent materials in the light-emitting elements was obtained from the light-emitting element 75 to the light-emitting element 98. Thus, the excitation energy of each light-emitting element is found to be transferred to the fluorescent material that is the guest material of each light-emitting element. This indicates that both singlet excitation energy and triplet excitation energy that are generated in the light-emitting layer are transferred to the fluorescent material through the exciplex or the phosphorescent material.

Although the light-emitting element 75 to the light-emitting element 98 exhibit light emission originating from the fluorescent materials, as shown in FIG. 113 to FIG. 124 and Table 18 and Table 19, they exhibited high emission efficiency with an external quantum efficiency exceeding 10%. This result indicates that in the light-emitting element of one embodiment of the present invention, non-radiative decay of triplet excitons is inhibited, contributing to efficient conversion into light emission. Thus, it was found that the use of a guest material having protecting groups in a light-emitting layer can inhibit energy transfer of triplet excitation energy from a host material to a guest material by the Dexter mechanism and non-radiative decay of triplet excitation energy.

FIG. 163 shows the EL (emission) spectrum of the comparative light-emitting element 103 and the absorption spectra of 2tBu-mmtBuDPhA2Anth used for the light-emitting element 33, 2Ph-mmtBuDPhA2Anth used for the light-emitting element 75 to the light-emitting element 78, and 2,6Ph-mmtBuDPhA2Anth used for the light-emitting element 79 to the light-emitting element 82 in a toluene solution. An anthracene skeleton, which is a luminophore, of 2tBu-mmtBuDPhA2Anth, 2Ph-mmtBuDPhA2Anth, and 2,6Ph-mmtBuDPhA2Anth has a tertiary butyl group, one phenyl group, and two phenyl groups, respectively. FIG. 163 shows that as the number of phenyl groups bonded to the luminophore increases, the rising position of the absorption spectrum shifts to a longer wavelength side. Therefore, the absorption spectrum of the energy acceptor having a larger number of phenyl groups bonded to the luminophore overlaps with a larger part of the emission spectrum of GD270 which is an energy donor. According to Formula (1), an energy acceptor whose luminophore has a phenyl group is preferable because the rate of energy transfer by the Förster mechanism is increased.

Although not illustrated, absorption bands on the longest wavelength side of the absorption spectra of the guest materials used in this example and the emission spectrum of the comparative light-emitting element 103 overlap with each other. Thus, the energy of GD270, which serves as an energy donor, is efficiently transferred to each guest material by the Förster mechanism.

Furthermore, according to FIG. 113 to FIG. 124, an emission color similar to a color of the energy donor is efficiently obtained from the guest material of the light-emitting element of one embodiment of the present invention.

It was also found that a variety of bulky alkyl groups such as a tertiary butyl group and a cyclohexyl group can be used as a protecting group. Moreover, a diphenyl group as well as a phenyl group can be favorably used as an aryl group of a diarylamino group bonded to a luminophore. Furthermore, a variety of substituents such as a phenyl group and a trimethylsilyl group can be bonded to the luminophore in addition to a branched-chain alkyl group such as a tertiary butyl group. In addition, a plurality of substituents can be bonded to the luminophore.

<Change in External Quantum Efficiency Depending on Guest Material Concentration>

FIG. 126 shows the relation between the guest material concentration and external quantum efficiency of each guest material. It is found from FIG. 126 that a decrease in efficiency due to an increase in the concentration is inhibited in the light-emitting element 75 to the light-emitting element 98 of embodiments of the present invention each using the guest material having protecting groups compared to that in the comparative light-emitting element 99 to the comparative light-emitting element 102. Therefore, in the light-emitting element of one embodiment of the present invention, as described above, even when the guest material concentration is increased, energy transfer of triplet excitation energy from the host material to the guest material by the Dexter mechanism can be inhibited and deactivation of the triplet excitation energy can be inhibited; thus, a light-emitting element with high emission efficiency can be obtained.

<Reliability Measurement of Light-Emitting Elements>

Next, driving tests at a constant current of 2.0 mA were performed on the light-emitting element 76 to the light-emitting element 98 and the comparative light-emitting element 103. The results are shown in FIG. 127 to FIG. 132. According to FIG. 127 to FIG. 132, as the guest material concentration is increased, reliability becomes favorable. This indicates that when the guest material concentration is increased, excitation energy in the light-emitting layer can be converted into light emission of the guest material efficiently. In other words, it is suggested that the rate of energy transfer of triplet excitation energy by the Förster mechanism from the host material to the guest material can be increased by increasing the guest material concentration.

Thus, the guest material concentration can be increased in the light-emitting element of one embodiment of the present invention, so that a light-emitting element with favorable emission efficiency and favorable reliability can be obtained. FIG. 133 shows the results of driving tests at a constant current of 2.0 mA performed on the comparative light-emitting element 99 to the comparative light-emitting element 102.

<Fluorescence Lifetime Measurement of Light-Emitting Elements>

Next, in order to examine a difference in emission rate with the concentration in the light-emitting element 79 to the light-emitting element 82, the light-emitting element 87 to the light-emitting element 90, and the comparative light-emitting element 99 to the comparative light-emitting element 103, fluorescence lifetimes of the light-emitting elements were measured. The measurement was performed in a manner similar to that in the above example. FIG. 134 to FIG. 136 show the results.

It was found from FIG. 134 to FIG. 136 that when a fluorescent material is added as a guest material, as the fluorescent material concentration is high, the proportion of the prompt fluorescence component increases and the proportion of the delayed fluorescence component decreases regardless of the guest material. The comparative light-emitting element 103 exhibits long-lifetime phosphorescent light emission originating from the light emission of GD270, which is a phosphorescent material. These facts indicate that addition of the fluorescent material as a guest material to the light-emitting layer increases the proportion of the prompt fluorescence component derived from the fluorescent material. Here, as described above, among the light-emitting element 79 to the light-emitting element 82 and the light-emitting element 87 to the light-emitting element 90 of embodiments of the present invention using the guest materials having protecting groups, the light-emitting element with a higher guest material concentration has higher reliability. In other words, there is a correlation between the emission lifetime and the excitation lifetime. This suggests that an increase in the guest material concentration promotes energy transfer by the Förster mechanism between the energy donor and the acceptor. Thus, in the light-emitting element of one embodiment of the present invention, energy transfer by the Dexter mechanism between the energy donor and the acceptor can be inhibited, and thus the light-emitting layer can be doped with a fluorescent material at a high concentration, so that a light-emitting element with high emission efficiency can be obtained and the rate of energy transfer by the Förster mechanism can be increased, whereby the reliability can be improved. The results of the reliability and the emission lifetime of each of the comparative light-emitting element 99 to the comparative light-emitting element 102 have a similar tendency, but the external quantum efficiency significantly decreases. That is, it is difficult for the light-emitting element using TTPA, which is a reference material, to achieve both high emission efficiency and high reliability.

Example 19

In this example, fabrication examples of light-emitting elements of embodiments of the present invention and the characteristics of the light-emitting elements are described. The structure of each of the light-emitting elements fabricated in this example is the same as that in FIG. 1(A). Table 20 to Table 23 show the details of the element structures. Note that the above examples and embodiments can be referred to for organic compounds used.

TABLE 20

| | Layer | Reference numeral | Thickness (nm) | Material | Weight ratio |
|---|---|---|---|---|---|
| Light-emitting elements 104 to 107 | Electrode | 102 | 200 | Al | — |
| | Electron-injection layer | 119 | 1 | LiF | — |

TABLE 20-continued

| Layer | | Reference numeral | Thickness (nm) | Material | Weight ratio |
|---|---|---|---|---|---|
| | Electron-transport layer | 118(2) | 10 | NBPhen | — |
| | | 118(1) | 20 | 4,6mCzP2Pm | — |
| | Light-emitting layer | 130 | 40 | 4,6mCzP2Pm:Ir(ppz)$_3$:2Ph-mmtBuDPhA2Anth | 0.8:0.2:y$_3$ |
| | Hole-transport layer | 112 | 20 | PCCP | — |
| | Hole-injection layer | 111 | 40 | DBT3P-II:MoO$_3$ | 1:0.5 |
| | Anode | 101 | 70 | ITSO | — |
| Light-emitting elements 108 to 111 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | 4,6mCzP2Pm | — |
| | Light-emitting layer | 130 | 40 | 4,6mCzP2Pm:Ir(ppz)$_3$:2,6Ph-mmtBuDPhA2Anth | 0.8:0.2:y$_3$ |
| | Hole-transport layer | 112 | 20 | PCCP | — |
| | Hole-injection layer | 111 | 40 | DBT3P-II:MoO$_3$ | 1:0.5 |
| | Anode | 101 | 70 | ITSO | — |
| Light-emitting elements 112 to 115 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | 4,6mCzP2Pm | — |
| | Light-emitting layer | 130 | 40 | 4,6mCzP2Pm:Ir(ppz)$_3$:2TMS-mmtBuDPhA2Anth | 0.8:0.2:y$_3$ |
| | Hole-transport layer | 112 | 20 | PCCP | — |
| | Hole-injection layer | 111 | 40 | DBT3P-II:MoO$_3$ | 1:0.5 |
| | Anode | 101 | 70 | ITSO | — |
| Light-emitting elements 116 to 119 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | 4,6mCzP2Pm | — |
| | Light-emitting layer | 130 | 40 | 4,6mCzP2Pm:Ir(ppz)$_3$:2Ph-mmchtBuDPhA2Anth | 0.8:0.2:y$_3$ |
| | Hole-transport layer | 112 | 20 | PCCP | — |
| | Hole-injection layer | 111 | 40 | DBT3P-II:MoO$_3$ | 1:0.5 |
| | Anode | 101 | 70 | ITSO | — |

TABLE 21

| Layer | | Reference numeral | Thickness (nm) | Material | Weight ratio |
|---|---|---|---|---|---|
| Light-emitting elements 120 to 123 | Electrode | 102 | 200 | Al | — |
| | Electron-injection layer | 119 | 1 | LiF | — |

TABLE 21-continued

| | Layer | Reference numeral | Thickness (nm) | Material | Weight ratio |
|---|---|---|---|---|---|
| | Electron-transport layer | 118(2)<br>118(1) | 10<br>20 | NBPhen<br>4,6mCzP2Pm | —<br>— |
| | Light-emitting layer | 130 | 40 | 4,6mCzP2Pm:Ir(ppz)$_3$:2Ph-mmchDPhA2Anth | 0.8:0.2:y$_3$ |
| | Hole-transport layer | 112 | 20 | PCCP | — |
| | Hole-injection layer | 111 | 40 | DBT3P-II:MoO$_3$ | 1:0.5 |
| | Anode | 101 | 70 | ITSO | — |
| Light-emitting elements 124 to 127 | Electrode | 102 | 200 | Al | — |
| | Electron-injection layer | 119 | 1 | LiF | — |
| | Electron-transport layer | 118(2)<br>118(1) | 10<br>20 | NBPhen<br>4,6mCzP2Pm | —<br>— |
| | Light-emitting layer | 130 | 40 | 4,6mCzP2Pm:Ir(ppz)$_3$:2Ph-mmtBuDPhA2Anth-02 | 0.8:0.2:y$_4$ |
| | Hole-transport layer | 112 | 20 | PCCP | — |
| | Hole-injection layer | 111 | 40 | DBT3P-II:MoO$_3$ | 1:0.5 |
| | Anode | 101 | 70 | ITSO | — |
| Comparative light-emitting element 29 | Electrode | 102 | 200 | Al | — |
| | Electron-injection layer | 119 | 1 | LiF | — |
| | Electron-transport layer | 118(2)<br>118(1) | 10<br>20 | NBPhen<br>4,6mCzP2Pm | —<br>— |
| | Light-emitting layer | 130 | 40 | 4,6mCzP2Pm:Ir(ppz)$_3$ | 0.8:0.2 |
| | Hole-transport layer | 112 | 20 | PCCP | — |
| | Hole-injection layer | 111 | 40 | DBT3P-II:MoO$_3$ | 1:0.5 |
| | Anode | 101 | 70 | ITSO | — |

TABLE 22

| | Light-emitting elements 104, 108, 112, 116, and 120 | Light-emitting elements 105, 109, 113, 117, and 121 | Light-emitting elements 106, 110, 114, 118, and 122 | Light-emitting elements 107, 111, 115, 119, and 123 |
|---|---|---|---|---|
| y$_3$ | 0.01 | 0.025 | 0.05 | 0.1 |

TABLE 23

| | Light-emitting element 124 | Light-emitting element 125 | Light-emitting element 126 | Light-emitting element 127 |
|---|---|---|---|---|
| y$_4$ | 0.01 | 0.022 | 0.045 | 0.13 |

<<Fabrication of Light-Emitting Element 104 to Light-Emitting Element 127>>

A light-emitting element 104 to a light-emitting element 127 are different from the above-described light-emitting element 1 only in a fluorescent material (guest material) used for the light-emitting layer 130, and other steps of the fabrication method are the same as those for the light-emitting element 1. The details of the element structures are shown in Table 20 to Table 23; thus, the details of the fabrication methods are omitted.

<Characteristics of Light-Emitting Elements>

Next, the characteristics of the fabricated light-emitting element 104 to light-emitting element 127 were measured. The measurement was performed in a manner similar to that in Example 6.

FIG. 137 to FIG. 148 show the external quantum efficiency-luminance characteristics of the light-emitting element 104 to the light-emitting element 127 and the comparative light-emitting element 29 and the electroluminescence spectra of those to which a current at a current density of 2.5 mA/cm$^2$ was supplied. Note that the measurement of the light-emitting elements was performed at room temperature (in an atmosphere maintained at 23° C.).

Table 24 and Table 25 show the element characteristics of the light-emitting element 104 to the light-emitting element 127 and the comparative light-emitting element 29 at around 1000 cd/m$^2$.

TABLE 24

|  | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
| --- | --- | --- | --- | --- | --- | --- | --- |
| Light-emitting element 104 | 3.10 | 1.35 | (0.327, 0.637) | 1160 | 86.2 | 87.3 | 23.0 |
| Light-emitting element 105 | 3.00 | 0.89 | (0.338, 0.638) | 815 | 91.3 | 95.7 | 23.7 |
| Light-emitting element 106 | 3.00 | 0.94 | (0.349, 0.633) | 832 | 88.8 | 93.0 | 22.7 |
| Light-emitting element 107 | 3.10 | 1.47 | (0.357, 0.629) | 1156 | 78.5 | 79.6 | 20.0 |
| Light-emitting element 108 | 3.20 | 1.42 | (0.360, 0.607) | 1163 | 82.0 | 80.5 | 22.2 |
| Light-emitting element 109 | 3.10 | 1.09 | (0.379, 0.601) | 944 | 86.8 | 88.0 | 22.8 |
| Light-emitting element 110 | 3.10 | 1.10 | (0.396, 0.592) | 888 | 80.7 | 81.8 | 21.1 |
| Light-emitting element 111 | 3.10 | 1.22 | (0.410, 0.582) | 871 | 71.5 | 72.5 | 18.8 |
| Light-emitting element 112 | 3.20 | 1.08 | (0.318, 0.635) | 879 | 81.5 | 80.0 | 22.4 |
| Light-emitting element 113 | 3.20 | 1.11 | (0.318, 0.645) | 969 | 87.5 | 85.9 | 23.3 |
| Light-emitting element 114 | 3.20 | 1.19 | (0.323, 0.649) | 1081 | 90.7 | 89.0 | 23.6 |
| Light-emitting element 115 | 3.20 | 1.34 | (0.330, 0.648) | 1152 | 86.1 | 84.5 | 22.1 |

TABLE 25

|  | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
| --- | --- | --- | --- | --- | --- | --- | --- |
| Light-emitting element 116 | 3.10 | 0.98 | (0.332, 0.629) | 855 | 87.0 | 88.1 | 23.4 |
| Light-emitting element 117 | 3.10 | 0.98 | (0.343, 0.631) | 899 | 91.7 | 92.9 | 23.9 |
| Light-emitting element 118 | 3.20 | 1.33 | (0.353, 0.628) | 1159 | 87.1 | 85.5 | 22.4 |
| Light-emitting element 119 | 3.20 | 1.41 | (0.366, 0.621) | 1003 | 71.3 | 70.0 | 18.2 |
| Light-emitting element 120 | 3.10 | 1.13 | (0.336, 0.631) | 1028 | 91.0 | 92.2 | 24.0 |
| Light-emitting element 121 | 3.10 | 1.06 | (0.357, 0.624) | 945 | 88.8 | 90.0 | 22.8 |
| Light-emitting element 122 | 3.10 | 1.11 | (0.365, 0.620) | 962 | 86.6 | 87.8 | 22.0 |
| Light-emitting element 123 | 3.10 | 1.13 | (0.380, 0.609) | 837 | 74.0 | 74.9 | 18.8 |
| Light-emitting element 124 | 3.10 | 1.11 | (0.303, 0.633) | 855 | 77.3 | 78.3 | 21.7 |
| Light-emitting element 125 | 3.10 | 1.07 | (0.301, 0.644) | 856 | 80.2 | 81.3 | 22.0 |
| Light-emitting element 126 | 3.20 | 1.49 | (0.301, 0.654) | 1166 | 78.3 | 76.8 | 20.9 |
| Light-emitting element 127 | 3.20 | 1.35 | (0.316, 0.654) | 1038 | 76.8 | 75.4 | 19.9 |
| Comparative light-emitting element 29 | 3.30 | 1.63 | (0.323, 0.610) | 1053 | 64.7 | 61.6 | 19.0 |

As shown in FIG. 138, the emission spectra of the light-emitting element 104 to the light-emitting element 107 had a peak wavelength at approximately 539 nm and a full width at half maximum of approximately 62 nm, i.e., exhibited green light emission originating from 2Ph-mmtBuDPhA2Anth. As shown in FIG. 140, the emission spectra of the light-emitting element 108 to the light-emitting element 111 had a peak wavelength at approximately 548 nm and a full width at half maximum of approximately 64 nm, i.e., exhibited green light emission originating from 2,6Ph-mmtBuDPhA2Anth. As shown in FIG. 142, the emission spectra of the light-emitting element 112 to the light-emitting element 115 had a peak wavelength at approximately 533 nm and a full width at half maximum of approximately 67 nm, i.e., exhibited green light emission originating from 2TMS-mmtBuDPhA2Anth. As shown in FIG. 144, the emission spectra of the light-emitting element 116 to the light-emitting element 119 had a peak wavelength at approximately 539 nm and a full width at half maximum of approximately 64 nm, i.e., exhibited green light emission originating from 2Ph-mmchtBuDPhA2Anth. As shown in FIG. 146, the emission spectra of the light-emitting element 120 to the light-emitting element 123 had a peak wavelength at approximately 542 nm and a full width at half maximum of approximately 62 nm, i.e., exhibited green light emission originating from 2Ph-mmchDPhA2Anth. As shown in FIG. 148, the emission spectra of the light-emitting element 124 to the light-emitting element 127 had a peak wavelength at approximately 530 nm and a full width at half maximum of approximately 65 nm, i.e., exhibited green light emission originating from 2Ph-mmtBuDPhA2Anth-02. Light emission different from that of the comparative light-emitting element 29 was obtained from all of the light-emitting elements. The comparative light-emitting element 29 emits light originating from the exciplex formed by 4,6mCzP2Pm and Ir(ppz)$_3$.

Accordingly, light emission originating from the fluorescent materials in the light-emitting elements was obtained from the light-emitting element 104 to the light-emitting element 127. Thus, the excitation energy of each light-emitting element is found to be transferred to the fluorescent material that is the guest material of each light-emitting element. This indicates that both singlet excitation energy and triplet excitation energy that are generated in the light-emitting layer are transferred to the fluorescent material through the exciplex or the phosphorescent material.

Although the light-emitting element 104 to the light-emitting element 127 exhibit light emission originating from the fluorescent materials, as shown in FIG. 137 to FIG. 148, Table 24, and Table 25, they exhibited extremely high emission efficiency with an external quantum efficiency exceeding 18%. This result indicates that in the light-emitting element of one embodiment of the present invention, non-radiative decay of triplet excitons is inhibited, contributing to efficient conversion into light emission. Thus, it was found that the use of a guest material having protecting groups in a light-emitting layer can inhibit energy transfer of triplet excitation energy from a host material to a guest material by the Dexter mechanism and non-radiative decay of triplet excitation energy.

Although not illustrated, absorption bands on the longest wavelength side of the absorption spectra of the guest materials used in this example and the emission spectrum of the comparative light-emitting element 29 overlap with each other. Thus, the excited energy of the exciplex which is formed by Ir(ppz)$_3$ and 4,6mCzP2Pm and serves as an energy donor is efficiently transferred to each guest material by the Förster mechanism.

It was also found that a variety of bulky alkyl groups such as a tertiary butyl group and a cyclohexyl group can be used as a protecting group. Moreover, a diphenyl group as well as a phenyl group can be favorably used as an aryl group of a diarylamino group bonded to a luminophore. Furthermore, a variety of substituents such as a phenyl group and a trimethylsilyl group can be bonded to the luminophore in addition to a branched-chain alkyl group such as a tertiary butyl group. In addition, a plurality of substituents can be bonded to the luminophore.

<Change in External Quantum Efficiency Depending on Guest Material Concentration>

FIG. 149 shows the relation between the guest material concentration and external quantum efficiency of each guest material. It is found from FIG. 149 that a decrease in efficiency due to an increase in the concentration is inhibited in the light-emitting element 104 to the light-emitting element 127 of embodiments of the present invention using the guest materials having protecting groups. In addition, emission efficiency is improved by addition of the guest material depending on the concentration. Therefore, in the light-emitting element of one embodiment of the present invention, as described above, even when the guest material concentration is increased, energy transfer of triplet excitation energy from the host material to the guest material by the Dexter mechanism can be inhibited and deactivation of the triplet excitation energy can be inhibited; thus, a light-emitting element with high emission efficiency can be obtained.

<Reliability Measurement of Light-Emitting Elements>

Next, driving tests at a constant current of 2.0 mA were performed on the light-emitting element 104 to the light-emitting element 127. The results are shown in FIG. 150 to FIG. 155. According to FIG. 150 to FIG. 155, as the guest material concentration is increased, reliability becomes favorable. This indicates that when the guest material concentration is increased, excitation energy in the light-emitting layer can be converted into light emission of the guest material efficiently. In other words, it is suggested that the rate of energy transfer of triplet excitation energy by the Förster mechanism from the host material to the guest material can be increased by increasing the guest material concentration. Thus, the guest material concentration can be increased in the light-emitting element of one embodiment of the present invention, so that a light-emitting element with favorable emission efficiency and favorable reliability can be obtained.

<Fluorescence Lifetime Measurement of Light-Emitting Elements>

Next, in order to examine a difference in emission rate with the concentration in the light-emitting element 104 to the light-emitting element 119 and the light-emitting element 124 to the light-emitting element 127, fluorescence lifetimes of the light-emitting elements were measured. The measurement was performed in a manner similar to that in the above example. FIG. 156 to FIG. 160 show the results.

It was found from FIG. 156 to FIG. 160 that when a fluorescent material is added as a guest material, as the fluorescent material concentration is high, the proportion of the prompt fluorescence component increases and the proportion of the delayed fluorescence component decreases regardless of the guest material. The comparative light-emitting element 29 was found to exhibit light emission of the exciplex of 4,6mCzP2Pm and Ir(ppz)$_3$, which are host materials, and exhibit light emission including a prompt fluorescence component of 1 µs or less and a delayed fluorescence component of approximately 3 µs. These facts indicate that when a fluorescent material is added to the light-emitting layer as the guest material, the proportion of a prompt fluorescence component originating from the fluorescent material increases. Here, as described above, the light-emitting element 104 to the light-emitting element 119 and the light-emitting element 124 to the light-emitting element 127 of embodiments of the present invention using the guest materials having protecting groups show a high external quantum efficiency even when the light-emitting elements have a high fluorescent material concentration. That is, the light-emitting element of one embodiment of the present invention has high emission efficiency even when the proportion of light emission originating from the fluorescent material increases. Thus, it is suggested that, in the light-emitting element of one embodiment of the present invention, energy transfer of triplet excitation energy from the host material to the guest material by the Dexter mechanism and deactivation of the triplet excitation energy can be inhibited and thus the guest material concentration can be increased, whereby the efficiency of energy transfer of excitation energy by the Förster mechanism can be improved.

Example 20

In this example, a synthesis method of N,N'-(2-phenylanthracene-9,10-diyl)-N,N'-bis(3,5-di-tert-butylphenyl)-N,N'-bis(3,5-dihexylphenyl)diamine (abbreviation: 2Ph-mmnhtBuDPhA2Anth), which is an organic compound represented by Structural Formula (261) of Embodiment 1, will be described. This compound is a guest material having protecting groups, which can be favorably used for a light-emitting element of one embodiment of the present invention.

Step 1: Synthesis of 3,5-di-tert-butyl-3',5'-dihexyl-diphenylamine 2.0 g (6.1 mmol) of 1-bromo-3,5-dihexylbenzene, 1.3 g (6.3 mmol) of 3,5-di-tert-butylaniline, and 1.2 g (12 mmol) of sodium t-butoxide were put into a 200 mL three-neck flask, and the air in the flask was replaced with nitrogen. To this mixture was added 35 mL of toluene, and the mixture was degassed under reduced pressure; then, 0.40 mL (0.13 mmol) of tri-tert-butylphosphine (a 10 w % hexane solution) and 60 mg (0.10 mol) of bis(dibenzylideneacetone)palladium(0) were added to the mixture and the mixture was stirred for 6 hours at 80° C. under a nitrogen stream. After the stirring, 300 mL of toluene was added to the obtained mixture, which was then subjected to suction filtration through Florisil, Celite, and aluminum oxide to give a filtrate. The obtained filtrate was concentrated to give a brown oily substance. This brown oily substance was purified by silica gel column chromatography (developing solvent: hexane:toluene=9:1) to obtain 2.6 g of an objective colorless oily substance in a yield of 94%. The synthesis scheme of Step 1 is shown in (N-1) below.

Results of $^1$H NMR measurement of the colorless oily substance obtained in Step 1 described above will be described below. FIG. 163 and FIG. 164 are the $^1$H-NMR charts. Note that FIG. 163(B) is an enlarged chart of the range of 5.5 ppm to 9.0 ppm of FIG. 163(A). FIG. 164 is an enlarged chart of the range of 0.0 ppm to 3.0 ppm of FIG. 163(A). The results indicate that 3,5-di-tert-butyl-3',5'-dihexyldiphenylamine was obtained.

$^1$H NMR (CDCl$_3$, 300 MHz): σ=7.00-6.99 (m, 1H), 6.95 (m, 2H), 6.73-6.72 (m, 2H), 6.55-6.54 (m, 1H), 5.64 (bs, 1H), 2.53-2.48 (m, 4H), 1.64-1.57 (m, 4H), 1.38-1.26 (m, 30H), 0.90-0.88 (m, 6H).

Step 2: Synthesis of 2Ph-mmnhtBuDPhA2Anth 1.2 g (2.9 mmol) of 9,10-dibromo-2-phenylanthracene, 2.6 g (5.8 mmol) of 3,5-di-tert-butyl-3',5'-dihexyldiphenylamine, 1.1 g (11 mmol) of sodium t-butoxide, and 60 mg (0.15 mmol) of SPhos were put into a 200 mL three-neck flask, and the air in the flask was replaced with nitrogen. To this mixture was added 30 mL of xylene, and the mixture was degassed under reduced pressure; then, 40 mg (70 μmol) of bis(dibenzylideneacetone)palladium(0) was added to the mixture and the mixture was stirred for 7 hours at 150° C. under a nitrogen stream. After the stirring, 300 mL of toluene was added to the obtained mixture, which was then subjected to suction filtration through Florisil, Celite, and aluminum oxide to give a filtrate. The obtained filtrate was concentrated to give a brown oily substance. This oily substance was purified by silica gel column chromatography (developing solvent: hexane:toluene=10:1) to obtain an objective yellow oily substance. The obtained yellow oily substance was purified by supercritical fluid chromatography (abbreviation: SFC) and high-performance liquid chromatography (abbreviation: HPLC) (developing solvent: chloroform) to give 50 mg of an objective yellow solid in a yield of 1.5%. The synthesis scheme of Step 2 is shown in (N-2) below.

[Chemical Formula 77]

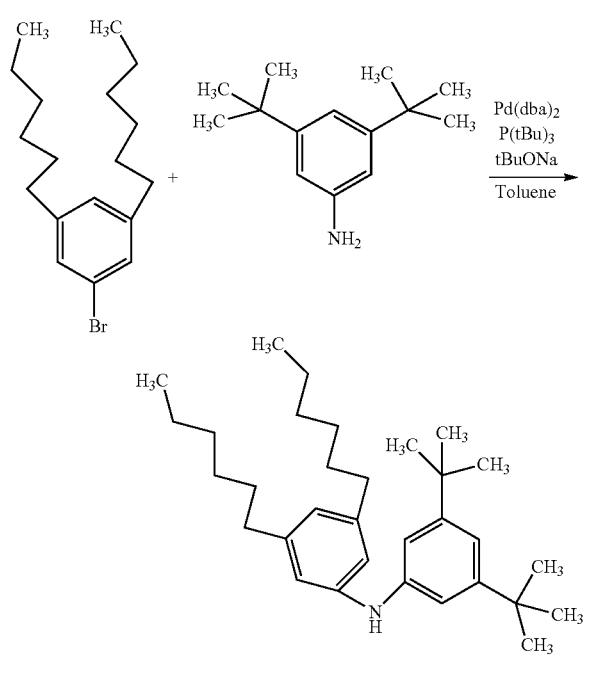

(N-1)

[Chemical Formula 78]

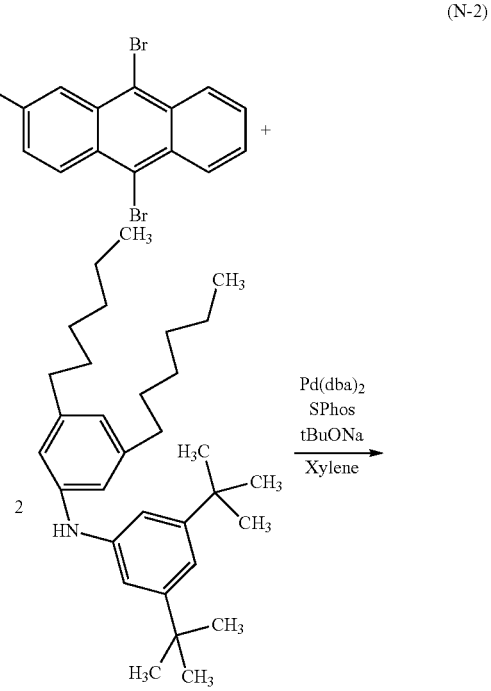

(N-2)

-continued

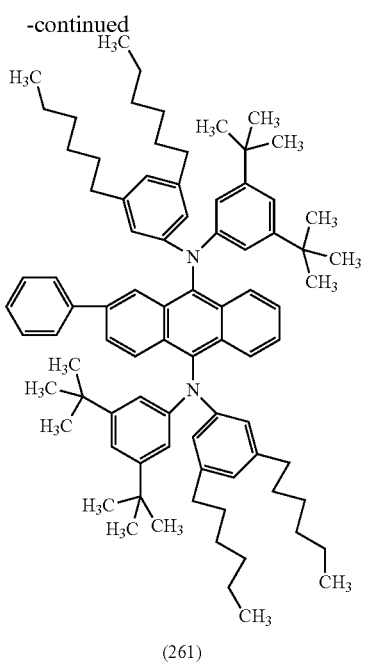

(261)

Results of $^1$H NMR measurement of the yellow solid obtained in Step 2 described above will be described below. FIG. 166 and FIG. 167 are the $^1$H-NMR charts. Note that FIG. 166(B) is an enlarged chart of the range of 6.0 ppm to 9.0 ppm of FIG. 166(A). FIG. 167 is an enlarged chart of the range of 0.0 ppm to 3.0 ppm of FIG. 166(A). The results indicate that 2Ph-mmnhtBuDPhA2Anth was obtained.

$^1$H NMR (CD$_2$Cl$_2$, 300 MHz): σ=8.40-8.38 (m, 1H), 8.24-8.14 (m, 3H), 7.68-7.64 (m, 1H), 7.49-7.45 (m, 2H), 7.38-7.28 (m, 5H), 7.09-7.07 (m, 4H), 7.02-7.00 (m, 2H), 6.70-6.69 (m, 4H), 6.54-6.53 (m, 2H), 2.41-2.33 (m, 8H), 1.53-1.43 (m, 16H), 1.21-1.16 (m, 52H), 0.84-0.79 (m, 12H).

Next, FIG. 168 shows the measurement results of the absorption spectrum and the emission spectrum of 2Ph-mmnhtBuDPhA2Anth in a toluene solution. The measurement method is similar to the method described in Example 1.

As shown in FIG. 168, in the case of 2Ph-mmtBuTMSDPhA2Anth in the toluene solution, absorption peaks were observed at around 485 nm, 388 nm, and 365 nm, and an emission wavelength peak was at 533 nm (excitation wavelength: 475 nm).

Example 21

In this example, fabrication examples of light-emitting elements of embodiments of the present invention and comparative light-emitting elements and the characteristics of the light-emitting elements are described. The structure of each of the light-emitting elements fabricated in this example is the same as that in FIG. 1(A). Table 26 to Table 27 show the details of the element structures. The structures and abbreviations of organic compounds that were used are shown below. Note that the above examples and embodiments can be referred to for other organic compounds.

[Chemical Formula 79]

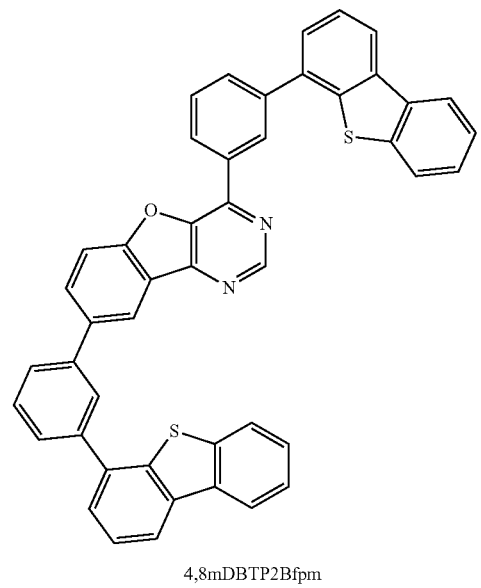

4,8mDBTP2Bfpm

TABLE 26

| Layer | Reference numeral | Thickness (nm) | Material | Weight ratio |
|---|---|---|---|---|
| Light-emitting elements 128 to 130 | | | | |
| Electrode | 102 | 200 | Al | — |
| Electron-injection layer | 119 | 1 | LiF | — |
| Electron-transport layer | 118(2) | 10 | NBPhen | — |
| | 118(1) | 20 | 4,8mDBTP2Bfpm | — |
| Light-emitting layer | 130 | 40 | 4,8mDBTP2Bfpm:PCCP:GD270:2,6Ph-mmtBuDPhA2Anth | 0.5:0.5:0.1:z$_1$ |
| Hole-transport layer | 112 | 20 | PCBBi1BP | — |
| Hole-injection layer | 111 | 40 | DBT3P-II:MoO$_3$ | 1:0.5 |
| Anode | 101 | 70 | ITSO | — |

TABLE 26-continued

| Layer | Reference numeral | Thickness (nm) | Material | Weight ratio |
|---|---|---|---|---|
| Comparative light-emitting element 131 Electrode | 102 | 200 | Al | — |
| Electron-injection layer | 119 | 1 | LiF | — |
| Electron-transport layer | 118(2) | 10 | NBPhen | — |
| | 118(1) | 20 | 4,8mDBTP2Bfpm | — |
| Light-emitting layer | 130 | 40 | 4,8mDBTP2Bfpm:PCCP:GD270 | 0.5:0.5:0.1 |
| Hole-transport layer | 112 | 20 | PCBBi1BP | — |
| Hole-injection layer | 111 | 40 | DBT3P-II:MoO$_3$ | 1:0.5 |
| Anode | 101 | 70 | ITSO | — |

TABLE 27

| | Light-emitting element 128 | Light-emitting element 129 | Light-emitting element 130 |
|---|---|---|---|
| $z_1$ | 0.01 | 0.05 | 0.1 |

<<Fabrication of Light-Emitting Element 128 to Light-Emitting Element 130 and Comparative Light-Emitting Element 131>>

A light-emitting element 128 to a light-emitting element 130 and a comparative light-emitting element 131 are different from the above-described light-emitting element 79 only in a host material of the light-emitting layer 130, the concentration of a guest material, and the material of an electron-transport layer 118(1), and other steps of the fabrication method are the same as those for the light-emitting element 79.

<Fabrication of Light-Emitting Element 128 to Light-Emitting Element 130>

As the light-emitting layer 130, 4,8-bis[3-(dibenzothiophene-4-yl)phenyl]benzofuro[3,2-d]pirymidine (abbreviation: 4,8mDBTP2Bfpm), PCCP, GD270, and 2,6Ph-mmtBuDPhA2Anth were deposited over the hole-transport layer 112 of the light-emitting element 128 to the light-emitting element 130 by co-evaporation at a weight ratio (4,8mDBTP2Bfpm:PCCP:GD270:2,6Ph-mmtBuDPhA2Anthh) of 0.5:0.5:0.1:$z_1$ to a thickness of 40 nm. In the light-emitting layer 130, GD270 is a phosphorescent material containing Ir. Furthermore, 2,6Ph-mmtBuDPhA2Anth is a fluorescent material having protecting groups. Note that the value $z_1$ differs between the light-emitting elements, and Table 27 shows the value $z_1$ in each of the light-emitting elements.

Moreover, as the electron-transport layer 118(1), 4,8mDBTP2Bfpm was deposited over the light-emitting layer 130 by evaporation to a thickness of 20 nm.

<Fabrication of Comparative Light-Emitting Element 131>

As the light-emitting layer 130, 4,8mDBTP2Bfpm, PCCP, and GD270 were deposited over the hole-transport layer 112 of the comparative light-emitting element 131 by co-evaporation at a weight ratio (4,8mDBTP2Bfpm:PCCP:GD270) of 0.5:0.5:0.1 to a thickness of 40 nm. The comparative light-emitting element 131 is a phosphorescent element in which GD270 exhibits phosphorescence. The light-emitting element 128 to the light-emitting element 130 can be regarded as elements obtained by adding a fluorescent material having protecting groups to the light-emitting layer 130 of the comparative light-emitting element 131. Note that a combination of 4,8mDBTP2Bfpm and PCCP forms an exciplex.

Furthermore, as the electron-transport layer 118(1), 4,8mDBTP2Bfpm was deposited over the light-emitting layer 130 by evaporation to a thickness of 20 nm.

<Characteristics of Light-Emitting Elements>

Next, the characteristics of the fabricated light-emitting element 128 to light-emitting element 130 and comparative light-emitting element 131 were measured. The measurement was performed in a manner similar to that in Example 6.

FIG. 169 shows the external quantum efficiency-luminance characteristics of the light-emitting element 128 to the light-emitting element 130 and the comparative light-emitting element 131. FIG. 170 shows electroluminescence spectra of the light-emitting element 128 to the light-emitting element 130 and the comparative light-emitting element 131 to which a current at a current density of 2.5 mA/cm$^2$ was supplied. Note that the measurement of the light-emitting elements was performed at room temperature (in an atmosphere maintained at 23° C.). Each diagram also shows the measurement results of the comparative light-emitting element 131.

Table 28 shows the element characteristics of the light-emitting element 128 to the light-emitting element 130 and the comparative light-emitting element 131 at around 1000 cd/m$^2$.

TABLE 28

| | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting element 128 | 3.30 | 1.00 | (0.356, 0.624) | 829 | 82.5 | 78.5 | 21.9 |
| Light-emitting element 129 | 3.30 | 1.09 | (0.391, 0.599) | 859 | 78.6 | 74.8 | 20.6 |
| Light-emitting element 130 | 3.40 | 1.50 | (0.404, 0.588) | 1059 | 70.8 | 65.4 | 18.7 |
| Comparative light-emitting element 131 | 3.40 | 1.40 | (0.330, 0.639) | 1096 | 78.4 | 72.5 | 21.3 |

As shown in FIG. 170, the emission spectra of the light-emitting element 128 to the light-emitting element 130 had a peak wavelength at approximately 548 nm and a full width at half maximum of approximately 68 nm, i.e., exhibited green light emission originating from 2,6Ph-mmtBuDPhA2Anth. Thus, light emission different from that of the comparative light-emitting element 131 was observed from all of the light-emitting elements. As shown in FIG. 170, the emission spectrum of the comparative light-emitting element 131 had a peak wavelength at 523 nm and a full width at half maximum of approximately 75 nm, i.e., exhibited green light emission originating from GD270.

Accordingly, light emission originating from the fluorescent materials in the light-emitting elements was obtained from the light-emitting element 128 to the light-emitting element 130. Thus, the excitation energy of each light-emitting element is found to be transferred to the fluorescent material that is the guest material of each light-emitting element. This indicates that both singlet excitation energy and triplet excitation energy that are generated in the light-emitting layer are transferred to the fluorescent material through the exciplex or the phosphorescent material.

Although the light-emitting element 128 to the light-emitting element 130 exhibit light emission originating from the fluorescent materials, a high external quantum efficiency exceeding 18% was exhibited as shown in FIG. 169 and Table 28. This result indicates that in the light-emitting element of one embodiment of the present invention, non-radiative decay of triplet excitons is inhibited, contributing to efficient conversion into light emission. Thus, it was found that the use of a guest material having protecting groups in a light-emitting layer can inhibit energy transfer of triplet excitation energy from a host material to a guest material by the Dexter mechanism and non-radiative decay of triplet excitation energy.

Although not illustrated, absorption bands on the longest wavelength side of the absorption spectra of the guest materials used in this example and the emission spectrum of the comparative light-emitting element 103 overlap with each other. Thus, the energy of GD270, which serves as an energy donor, is efficiently transferred to each guest material by the Förster mechanism.

<Change in External Quantum Efficiency Depending on Guest Material Concentration>

FIG. 171 shows the relation between the guest material concentration and external quantum efficiency of each guest material. It is found from FIG. 171 that a decrease in efficiency due to an increase in the concentration is extremely small in the light-emitting element 128 to the light-emitting element 130 of embodiments of the present invention each using the guest material having protecting groups. Therefore, in the light-emitting element of one embodiment of the present invention, even when the guest material concentration is increased, energy transfer of triplet excitation energy from the host material to the guest material by the Dexter mechanism can be inhibited and deactivation of the triplet excitation energy can be inhibited; thus, a light-emitting element with high emission efficiency can be obtained. It was also found that an organic compound having a benzofuropyrimidine skeleton and/or a dibenzothiophene skeleton, such as 4,8mDBTP2Bfpm, can be favorably used for the light-emitting element of one embodiment of the present invention.

<Reliability Measurement of Light-Emitting Elements>

Next, driving tests at a constant current of 2.0 mA were performed on the light-emitting element 128 to the light-emitting element 130. The results are shown in FIG. 172. According to FIG. 172, as the guest material concentration is increased, reliability becomes favorable. This indicates that when the guest material concentration is increased, excitation energy in the light-emitting layer can be converted into light emission of the guest material efficiently. In other words, it is suggested that the rate of energy transfer of triplet excitation energy by the Förster mechanism from the host material to the guest material can be increased by increasing the guest material concentration. Thus, the guest material concentration can be increased in the light-emitting element of one embodiment of the present invention, so that a light-emitting element with favorable emission efficiency and favorable reliability can be obtained.

Here, the light-emitting element 82 and the light-emitting element 130 are different from each other only in the host material having an electron-transport property of the light-emitting layer and the material used for the electron-transport layer 118(1). The time for which luminance is reduced by 10% (LT90) of the light-emitting element 82 and the light-emitting element 130 were approximately 330 hours and approximately 190 hours, respectively, each of which indicates extremely favorable reliability; the light-emitting element 130 had higher reliability. Thus, the organic compound having a benzofuropyrimidine skeleton and/or a dibenzothiophene skeleton, which was used for the light-emitting element 130, can be favorably used for the light-emitting element of one embodiment of the present invention.

Example 22

In this example, fabrication examples of light-emitting elements of embodiments of the present invention and the characteristics of the light-emitting elements are described. The structure of each of the light-emitting elements fabricated in this example is the same as that in FIG. 1(A). Table 29 and Table 30 show the details of the element structures. The structures and abbreviations of organic compounds that were used are shown below. Note that the above examples and embodiments can be referred to for other organic compounds.

[Chemical Formula 80]

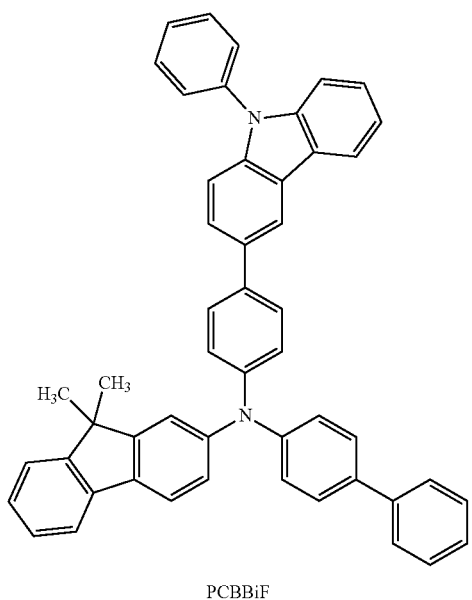

PCBBiF

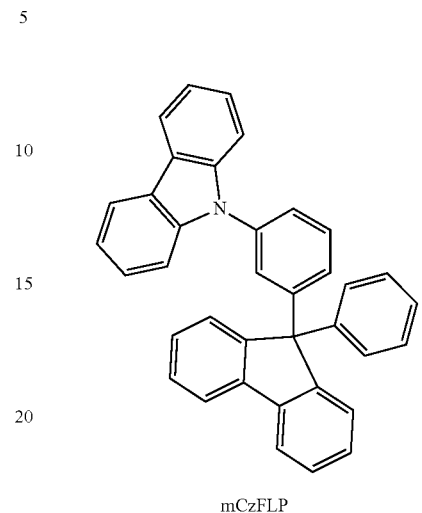

mCzFLP

TABLE 29

| Layer | | Reference numeral | Thickness (nm) | Material | Weight ratio |
|---|---|---|---|---|---|
| Light-emitting elements 132 to 135 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | mPCCzPTzn-02 | — |
| | Light-emitting layer | 130 | 40 | mPCCzPTzn-02:PCBBiF:2tBu-ptBuDPhA2Anth | 0.8:0.2:$w_1$ |
| | Hole-transport layer | 112 | 20 | mCzFLP | — |
| | Hole-injection layer | 111 | 40 | DBT3P-II:MoO$_3$ | 1:0.5 |
| | Anode | 101 | 70 | ITSO | — |
| Comparative light-emitting element 136 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | 4,8mDBTP2Bfpm | — |
| | Light-emitting layer | 130 | 40 | mPCCzPTzn-02:PCBBiF | 0.8:0.2 |
| | Hole-transport layer | 112 | 20 | mCzFLP | — |
| | Hole-injection layer | 111 | 40 | DBT3P-II:MoO$_3$ | 1:0.5 |
| | Anode | 101 | 70 | ITSO | — |

TABLE 30

| | Light-emitting element 132 | Light-emitting element 133 | Light-emitting element 134 | Light-emitting element 135 |
|---|---|---|---|---|
| $w_1$ | 0.01 | 0.025 | 0.05 | 0.1 |

<<Fabrication of Light-Emitting Element 132 to Light-Emitting Element 135 and Comparative Light-Emitting Element 136>>

A light-emitting element 132 to a light-emitting element 135 and a comparative light-emitting element 136 are different from the above-described light-emitting element 79 only in the materials of the light-emitting layer 130 and the hole-transport layer 112, and other steps of the fabrication method are the same as those for the light-emitting element 79.

<Fabrication of Light-Emitting Element 132 to Light-Emitting Element 135>

As the hole-transport layer 112, 9-[3-(9-phenyl-9H-fluoren-9-yl)phenyl]-9H-carbazole (abbreviation: mCzFLP) was deposited over the hole-injection layer 111 of the light-emitting element 132 to the light-emitting element 135 by evaporation to a thickness of 20 nm.

As the light-emitting layer 130, mPCCzPTzn-02, PCBBiF, and 2tBu-ptBuDPhA2Anth were deposited over the hole-transport layer 112 by co-evaporation at a weight ratio (mPCCzPTzn-02:PCBBiF:2tBu-ptBuDPhA2Anth) of 0.8:0.2:$w_1$ to a thickness of 40 nm. In the light-emitting layer 130, mPCCzPTzn-02 and PCBBiF form an exciplex in combination. As described above, the exciplex can convert triplet excitation energy into singlet excitation energy. Thus, the exciplex serves as an energy donor in the light-emitting layer 130. Furthermore, 2tBu-ptBuDPhA2Anth is a fluorescent material having protecting groups and serves as an energy donor. Note that the value iv' differs between the light-emitting elements, and Table 30 shows the value $w_1$ in each of the light-emitting elements.

<Fabrication of Comparative Light-Emitting Element 136>

As the hole-transport layer 112, mCzFLP was deposited over the hole-injection layer 111 of the comparative light-emitting element 136 by evaporation to a thickness of 20 nm.

As the light-emitting layer 130, mPCCzPTzn-02 and PCBBiF were deposited over the hole-transport layer 112 by co-evaporation at a weight ratio (mPCCzPTzn-02:PCBBiF) of 0.8:0.2 to a thickness of 40 nm. As described later, light emission from an exciplex formed by mPCCzPTzn-02 and PCBBiF is observed from the comparative light-emitting element 131. The light-emitting element 132 to the light-emitting element 135 can be regarded as elements obtained by adding 2tBu-ptBuDPhA2Anth to the light-emitting layer of the comparative light-emitting element 136

<Characteristics of Light-Emitting Elements>

Next, the characteristics of the fabricated light-emitting element 132 to light-emitting element 135 and comparative light-emitting element 136 were measured. The measurement was performed in a manner similar to that in Example 6.

FIG. 173 shows the external quantum efficiency-luminance characteristics of the light-emitting element 132 to the light-emitting element 135 and the comparative light-emitting element 136. FIG. 174 shows electroluminescence spectra of the light-emitting element 128 to the light-emitting element 130 and the comparative light-emitting element 136 to which a current at a current density of 2.5 mA/cm² was supplied. Note that the measurement of the light-emitting elements was performed at room temperature (in an atmosphere maintained at 23° C.). Each diagram also shows the measurement results of the comparative light-emitting element 136.

Table 31 shows the element characteristics of the light-emitting element 132 to the light-emitting element 135 and the comparative light-emitting element 136 at around 1000 cd/m².

TABLE 31

| | Voltage (V) | Current density (mA/cm²) | CIE chromaticity (x, y) | Luminance (cd/m²) | Current efficiency (cd/A) | Power efficiency (lm/W) | External quantum efficiency (%) |
|---|---|---|---|---|---|---|---|
| Light-emitting element 132 | 3.40 | 2.90 | (0.331, 0.634) | 1090 | 37.6 | 34.7 | 10.4 |
| Light-emitting element 133 | 3.40 | 3.19 | (0.320, 0.647) | 1129 | 35.4 | 32.7 | 9.5 |
| Light-emitting element 134 | 3.30 | 2.30 | (0.319, 0.653) | 846 | 36.8 | 35.0 | 9.6 |
| Light-emitting element 135 | 3.30 | 2.36 | (0.319, 0.655) | 870 | 36.9 | 35.1 | 9.5 |
| Comparative light-emitting element 136 | 3.20 | 1.73 | (0.355, 0.611) | 834 | 48.3 | 47.5 | 13.9 |

As shown in FIG. 174, the emission spectra of the light-emitting element 132 to the light-emitting element 135 had a peak wavelength at approximately 534 nm and a full width at half maximum of approximately 67 nm, i.e., exhibited green light emission originating from 2tBu-ptBuDPhA2Anth. Thus, light emission different from that of the comparative light-emitting element 136 was observed from all of the light-emitting elements. As shown in FIG. 174, the emission spectrum of the comparative light-emitting element 136 had a peak wavelength at 537 nm and a full width at half maximum of approximately 83 nm, i.e., exhibited green light emission originating from the exciplex formed by mPCCzPTzn-02 and PCBBiF.

Accordingly, light emission originating from the fluorescent materials in the light-emitting elements was obtained from the light-emitting element 132 to the light-emitting element 135. Thus, the excitation energy of each light-emitting element is found to be transferred to the fluorescent material that is the guest material of each light-emitting element. This indicates that both singlet excitation energy and triplet excitation energy that are generated in the light-emitting layer are transferred to the fluorescent material through the exciplex.

Although the light-emitting element 132 to the light-emitting element 135 exhibit light emission originating from the fluorescent materials, high emission efficiency exceeding 9% was exhibited even in the light-emitting element with a high florescent material concentration as shown in FIG. 173 and Table 31. This value exceeds the maximum value of the external quantum efficiency of the fluorescent element. This result indicates that in the light-emitting element of one embodiment of the present invention, non-radiative decay of triplet excitons is inhibited, contributing to efficient conversion into light emission. Thus, it was found that the use of a guest material having protecting groups in a light-emitting layer can inhibit energy transfer of triplet excitation energy from a host material to a guest material by the Dexter mechanism and non-radiative decay of triplet excitation energy. Furthermore, it was found that an exciplex can also be favorably used as the host material.

Note that FIG. 175 shows the relation between the EL (emission) spectrum of the comparative light-emitting element 136 and the absorption spectrum and the emission spectrum of 2tBu-ptBuDPhA2Anth in a toluene solution, which was used for the light-emitting element 132 to the light-emitting element 135. According to FIG. 175, it is found from comparison between the absorption spectra of the guest materials that an absorption band on the longest wavelength side of the absorption spectrum and the emission spectrum overlap with each other. This indicates that energy transfer from GD270 to 2tBu-ptBuDPhA2Anth by the Förster mechanism occurs.

<Change in External Quantum Efficiency Depending on Guest Material Concentration>

FIG. 176 shows the relation between the guest material concentration and external quantum efficiency. It is found from FIG. 176 that a decrease in efficiency due to an increase in the concentration is small in the light-emitting elements of embodiments of the present invention. Therefore, in the light-emitting element of one embodiment of the present invention, even when the guest material concentration is increased, energy transfer of triplet excitation energy from the host material to the guest material by the Dexter mechanism can be inhibited and non-radiative decay of the triplet excitation energy can be inhibited; thus, a light-emitting element with high emission efficiency can be obtained. It was also found that an exciplex is favorably used for the light-emitting element of one embodiment of the present invention.

<Reliability Measurement of Light-Emitting Elements>

Next, driving tests at a constant current of 2.0 mA were performed on the light-emitting element 132 to the light-emitting element 135. The results are shown in FIG. 177. According to FIG. 177, as the guest material concentration is increased, reliability becomes favorable. This indicates that when the guest material concentration is increased, excitation energy in the light-emitting layer can be converted into light emission of the guest material efficiently. In other words, it is suggested that the rate of energy transfer of triplet excitation energy by the Förster mechanism from the host material to the guest material can be increased by increasing the guest material concentration. Thus, the guest material concentration can be increased in the light-emitting element of one embodiment of the present invention, so that a light-emitting element with favorable emission efficiency and favorable reliability can be obtained.

Example 23

In this example, fabrication examples of light-emitting elements of embodiments of the present invention and the characteristics of the light-emitting elements are described. The structure of each of the light-emitting elements fabricated in this example is the same as that in FIG. 1(A). Table 32 and Table 33 show the details of the element structures. The structures and abbreviations of organic compounds that were used are shown below. Note that the above examples and embodiments can be referred to for other organic compounds.

[Chemical Formula 81]

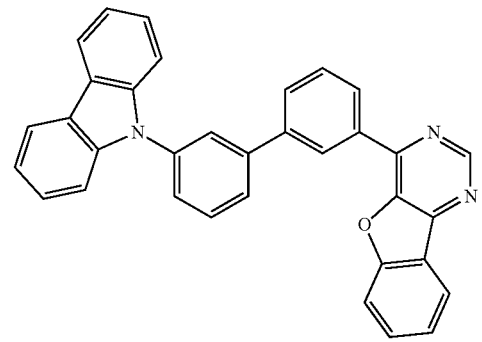

4mCzBPBfpm

TABLE 32

|  | Layer | Reference numeral | Thickness (nm) | Material | Weight ratio |
|---|---|---|---|---|---|
| Light-emitting elements 137 to 141 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | 4mCzBPBfpm | — |
| | Light-emitting layer | 130 | 40 | 4mCzBPBfpm:PCBBiF:guest material | 0.8:0.2:0.05 |
| | Hole-transport layer | 112 | 20 | mCzFLP | — |
| | Hole-injection layer | 111 | 40 | DBT3P-II:MoO$_3$ | 1:0.5 |
| | Anode | 101 | 70 | ITSO | — |

TABLE 32-continued

| Layer | | Reference numeral | Thickness (nm) | Material | Weight ratio |
|---|---|---|---|---|---|
| Comparative light-emitting element 142 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | 4mCzBPBfpm | — |
| | Light-emitting layer | 130 | 40 | 4mCzBPBfpm:PCBBiF | 0.8:0.2 |
| | Hole-transport layer | 112 | 20 | PCBBi1BP | — |
| | Hole-injection layer | 111 | 40 | DBT3P-II:MoO$_3$ | 1:0.5 |
| | Anode | 101 | 70 | ITSO | — |

TABLE 33

| | Guest material |
|---|---|
| Light-emitting element 137 | 2TMS-mmtBuDPhA2Anth |
| Light-emitting element 138 | 2Ph-mmtBuDPhA2Anth |
| Light-emitting element 139 | 2Ph-mmchtBuDPhA2Anth |
| Light-emitting element 140 | 2,6Ph-mmtBuDPhA2Anth |
| Light-emitting element 141 | 2tBu-ptBuDPhA2Anth |

<<Fabrication of Light-Emitting Element 137 to Light-Emitting Element 141 and Comparative Light-Emitting Element 142>>

A light-emitting element 137 to a light-emitting element 141 and a comparative light-emitting element 142 are different from the above-described light-emitting element 132 only in the material of the light-emitting layer 130 and the electron-transport layer 118(1), and other steps of the fabrication method are the same as those for the light-emitting element 132.

<Fabrication of Light-Emitting Elements 137 to Light-Emitting Element 141>

As the light-emitting layer 130, 4-{3-[3'-(9H-carbazol-9-yl)]biphenyl-3-yl}benzofuro[3,2-d]pyrimidine (abbreviation: 4mCzBPBfpm), PCBBiF, and a guest material were deposited over the hole-transport layer 112 by co-evaporation at a weight ratio (4mCzBPBfpm:PCBBiF:the guest material) of 0.8:0.2:0.05 to a thickness of 40 nm. In the light-emitting layer 130, 4mCzBPBfpm and PCBBiF form an exciplex in combination. Thus, the exciplex serves as an energy donor in the light-emitting layer 130. In addition, the guest material was different between the light-emitting elements, and the materials shown in Table 33 were used as the guest materials of the light-emitting elements. All the guest materials shown in Table 33 are fluorescent materials having protecting groups.

Moreover, as the electron-transport layer 118(1), 4mCzBPBfpm was deposited over the light-emitting layer 130 by evaporation to a thickness of 20 nm.

<Fabrication of Comparative Light-Emitting Element 142>

As the light-emitting layer 130, 4mCzBPBfpm and PCBBiF were deposited over the hole-transport layer 112 by co-evaporation at a weight ratio (4mCzBPBfpm:PCBBiF) of 0.8:0.2 to a thickness of 40 nm. As described later, light emission from an exciplex formed by 4mCzBPBfpm and PCBBiF is observed from the comparative light-emitting element 131. The light-emitting element 137 to the light-emitting element 141 can be regarded as elements obtained by adding a guest material to the light-emitting layer of the comparative light-emitting element 142

<Characteristics of Light-Emitting Elements>

Next, the characteristics of the fabricated light-emitting element 137 to light-emitting element 141 and comparative light-emitting element 142 were measured. The measurement was performed in a manner similar to that in Example 6.

FIG. 178 shows the external quantum efficiency-luminance characteristics of the light-emitting element 137 to the light-emitting element 141 and the comparative light-emitting element 142. FIG. 179 shows electroluminescence spectra of the light-emitting element 137 to the light-emitting element 141 and the comparative light-emitting element 142 to which a current at a current density of 2.5 mA/cm$^2$ was supplied. Note that the measurement of the light-emitting elements was performed at room temperature (in an atmosphere maintained at 23° C.). Each diagram also shows the measurement results of the comparative light-emitting element 142.

Table 34 shows the element characteristics of the light-emitting element 137 to the light-emitting element 141 and the comparative light-emitting element 142 at around 1000 cd/m$^2$.

TABLE 34

| | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting element 137 | 3.50 | 2.00 | (0.317, 0.653) | 940 | 46.9 | 42.1 | 12.3 |
| Light-emitting element 138 | 3.50 | 1.89 | (0.335, 0.644) | 861 | 45.5 | 40.8 | 11.7 |

TABLE 34-continued

|  | Voltage (V) | Current density (mA/cm$^2$) | CIE chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting element 139 | 3.50 | 2.01 | (0.335, 0.642) | 953 | 47.4 | 42.6 | 12.3 |
| Light-emitting element 140 | 3.50 | 2.06 | (0.376, 0.611) | 865 | 42.1 | 37.8 | 10.9 |
| Light-emitting element 141 | 3.50 | 2.44 | (0.310, 0.659) | 884 | 36.2 | 32.5 | 9.5 |
| Comparative light-emitting element 142 | 3.40 | 1.84 | (0.327, 0.624) | 1007 | 54.8 | 50.6 | 15.5 |

As shown in FIG. 179, the emission spectrum of the light-emitting element 137 had a peak wavelength at 532 nm and a full width at half maximum of 64 nm, i.e., exhibited green light emission originating from 2TMS-mmtBuDPhA2Anth. The emission spectrum of the light-emitting element 138 had a peak wavelength at 538 nm and a full width at half maximum of 62 nm, i.e., exhibited green light emission originating from 2Ph-mmtBuDPhA2Anth. The emission spectrum of the light-emitting element 139 had a peak wavelength at 539 nm and a full width at half maximum of 62 nm, i.e., exhibited green light emission originating from 2Ph-mmchtBuDPhA2Anth. The emission spectrum of the light-emitting element 140 had a peak wavelength at 548 nm and a full width at half maximum of 60 nm, i.e., exhibited green light emission originating from 2,6Ph-mmtBuDPhA2Anth. The emission spectrum of the light-emitting element 141 had a peak wavelength at 532 nm and a full width at half maximum of 61 nm, i.e., exhibited green light emission originating from 2tBu-ptBuDPhA2Anth. Light emission different from that of the comparative light-emitting element 142 was observed from all of the light-emitting elements. As shown in FIG. 179, the emission spectrum of the comparative light-emitting element 142 had a peak wavelength at 534 nm and a full width at half maximum of approximately 78 nm, i.e., exhibited green light emission originating from the exciplex formed by 4mCzBPBfpm and PCBBiF.

Accordingly, light emission originating from the fluorescent materials in the light-emitting elements was obtained from the light-emitting element 137 to the light-emitting element 141. Thus, the excitation energy of each light-emitting element is found to be transferred to the fluorescent material that is the guest material of each light-emitting element. This indicates that both singlet excitation energy and triplet excitation energy that are generated in the light-emitting layer are transferred to the fluorescent material through the exciplex.

Although the light-emitting element 137 to the light-emitting element 141 exhibit light emission originating from the fluorescent materials, high emission efficiency exceeding 9% was exhibited as shown in FIG. 178 and Table 34. This value exceeds the maximum value of the external quantum efficiency of the fluorescent element. This result indicates that in the light-emitting element of one embodiment of the present invention, non-radiative decay of triplet excitons is inhibited, contributing to efficient conversion into light emission. Thus, it was found that the use of a guest material having protecting groups in a light-emitting layer can inhibit energy transfer of triplet excitation energy from a host material to a guest material by the Dexter mechanism and non-radiative decay of triplet excitation energy. Furthermore, it was found that an exciplex can also be favorably used as the host material.

Although not illustrated, absorption bands on the longest wavelength side of the absorption spectra of the guest materials used in this example and the emission spectrum of the comparative light-emitting element 142 overlap with each other. Thus, the energy of the exciplex, which serves as an energy donor, is efficiently transferred to each guest material by the Förster mechanism.

<Reliability Measurement of Light-Emitting Elements>

Next, driving tests at a constant current of 2.0 mA were performed on the light-emitting element 137 to the light-emitting element 141. The results are shown in FIG. 180. FIG. 180 shows that the light-emitting element of one embodiment of the present invention to which the guest material is added has higher reliability than the comparative light-emitting element 141.

This indicates that when a fluorescent material having protecting groups is added as a guest material, excitation energy in the light-emitting layer can be converted into light emission of the guest material efficiently.

<Fluorescence Lifetime Measurement of Light-Emitting Elements>

Next, fluorescence lifetimes of the light-emitting element 137 to the light-emitting element 141 and the comparative light-emitting element 142 were measured. The measurement was performed in a manner similar to that in the above example. FIG. 181 shows the results.

As shown in FIG. 181, delayed fluorescence is observed from the comparative light-emitting element 142. In the comparative light-emitting element 142, the exciplex is a light-emitting material and triplet excitation energy can be converted into singlet excitation energy by reverse intersystem crossing, thereby being converted into light emission. The delayed fluorescence is observed due to the reverse intersystem crossing. It is found from FIG. 181 that when a fluorescent material having protecting groups is added as a guest material, the proportion of a delayed fluorescence component decreases regardless of the guest material. Here, the light-emitting element of one embodiment of the present invention has a high external quantum efficiency. Accordingly, a decrease in the proportion of a delayed fluorescence component observed in FIG. 181 is not caused by non-radiative decay of triplet excitons in the light-emitting layer and suggests that energy transfer by the Förster mechanism from the exciplex, which is an energy donor, and the guest material, which is an energy acceptor, efficiently occurs.

Example 24

In this example, fabrication examples of light-emitting elements of embodiments of the present invention and the characteristics of the light-emitting elements are described. The structure of each of the light-emitting elements fabricated in this example is the same as that in FIG. 1(A). Table 35 and Table 36 show the details of the element structures. The structures and abbreviations of organic compounds that were used are shown below. Note that the above examples and embodiments can be referred to for other organic compounds.

[Chemical Formula 82]

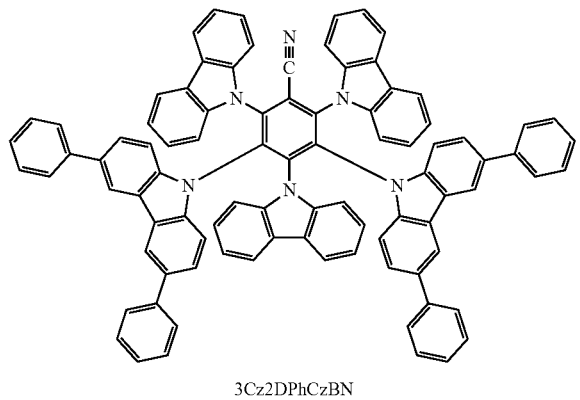

3Cz2DPhCzBN

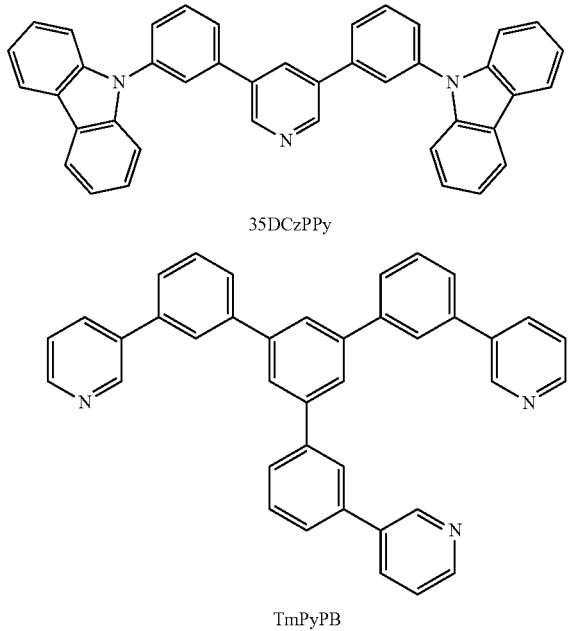

35DCzPPy

TmPyPB

TABLE 35

| | Layer | Reference numeral | Thickness (nm) | Material | Weight ratio |
|---|---|---|---|---|---|
| Light-emitting elements 143 to 145 | Electrode | 102 | 200 | Al | — |
| | Electron-injection layer | 119 | 1 | LiF | — |
| | Electron-transport layer | 118(2) | 10 | TmPyPB | — |
| | | 118(1) | 20 | 35DCzPPy | — |
| | Light-emitting layer | 130 | 40 | 4,6mCzP2Pm:3Cz2DPhCzBN:Oct-tBuDPQd | 1:0.1:$w_2$ |
| | Hole-transport layer | 112 | 20 | mCzFLP | — |
| | Hole-injection layer | 111 | 40 | DBT3P-II:MoO$_3$ | 1:0.5 |
| | Anode | 101 | 70 | ITSO | — |
| Comparative light-emitting elements 146 to 148 | Electrode | 102 | 200 | Al | — |
| | Electron-injection layer | 119 | 1 | LiF | — |
| | Electron-transport layer | 118(2) | 10 | TmPyPB | — |
| | | 118(1) | 20 | 35DCzPPy | — |
| | Light-emitting layer | 130 | 40 | 4,6mCzP2Pm:3Cz2DPhCzBN:DPQd | 1:0.1:$w_2$ |
| | Hole-transport layer | 112 | 20 | mCzFLP | — |
| | Hole-injection layer | 111 | 40 | DBT3P-II:MoO$_3$ | 1:0.5 |
| | Anode | 101 | 70 | ITSO | — |
| Comparative light-emitting element 149 | Electrode | 102 | 200 | Al | — |
| | Electron-injection layer | 119 | 1 | LiF | — |
| | Electron-transport layer | 118(2) | 10 | TmPyPB | — |
| | | 118(1) | 20 | 35DCzPPy | — |

TABLE 35-continued

| Layer | Reference numeral | Thickness (nm) | Material | Weight ratio |
|---|---|---|---|---|
| Light-emitting layer | 130 | 30 | 4,6mCzP2Pm:3Cz2DPhCzBN | 1:0.1 |
| Hole-transport layer | 112 | 20 | mCzFLP | — |
| Hole-injection layer | 111 | 40 | DBT3P-II:MoO$_3$ | 1:0.5 |
| Anode | 101 | 70 | ITSO | — |

TABLE 36

|  | Light-emitting element 143 Comparative light-emitting element 146 | Light-emitting element 144 Comparative light-emitting element 147 | Light-emitting element 145 Comparative light-emitting element 148 |
|---|---|---|---|
| w$_2$ | 0.01 | 0.025 | 0.05 |

<Fabrication of Light-Emitting Elements>

Fabrication methods of the light-emitting elements fabricated in this example will be described below.

<<Fabrication of Light-Emitting Element 143 to Light-Emitting Element 145>>

As the electrode 101, an ITSO film was formed to a thickness of 70 nm over a glass substrate. Note that the electrode area of the electrode 101 was set to 4 mm$^2$ (2 mm×2 mm).

Next, as the hole-injection layer 111, DBT3P-II and molybdenum oxide (MoO$_3$) were deposited over the electrode 101 by co-evaporation in a weight ratio (DBT3P-II: MoO$_3$) of 1:0.5 to a thickness of 40 nm.

Then, as the hole-transport layer 112, mCzFLP was deposited on the hole-injection layer 111 by evaporation to a thickness of 20 nm.

Next, as the light-emitting layer 130, 4,6mCzP2Pm, 2,4, 6-tris(9H-carbazol-9-yl)-3,5-bis(3,6-diphenylcarbazol-9-yl) benzonitrile (abbreviation: 3Cz2DPhCzBN), and Oct-tBuDPQd were deposited over the hole-transport layer 112 by co-evaporation at a weight ratio (4,6mCzP2Pm: 3Cz2DPhCzBN:Oct-tBuDPQd) of 1.0:0.1:w$_2$ to a thickness of 40 nm. In the light-emitting layer 130, 3Cz2DPhCzBN is a material having a TADF property as one molecule. Furthermore, Oct-tBuDPQd is a fluorescent material having protecting groups. In addition, the value w$_2$ differs between the light-emitting elements, and Table 36 shows the value w$_2$ in each of the light-emitting elements. Note that Non-Patent Document 1 discloses that 3Cz2DPhCzBN is a TADF material.

Next, as the electron-transport layer 118, 35DCzPPy and TmPyPB were sequentially deposited by evaporation to a thickness of 20 nm and to a thickness of 10 nm, respectively, over the light-emitting layer 130. Then, as the electron-injection layer 119, LiF was deposited on the electron-transport layer 118 by evaporation to a thickness of 1 nm.

Next, as the electrode 102, aluminum (Al) was formed over the electron-injection layer 119 to a thickness of 200 nm.

Next, in a glove box containing a nitrogen atmosphere, a light-emitting element 143 to a light-emitting element 145 were sealed by fixing a glass substrate for sealing to the glass substrate on which the organic materials were formed using a sealant for organic EL. Specifically, the sealant was applied to the periphery of the organic materials formed on the glass substrate, the glass substrate was bonded to the glass substrate for sealing, irradiation with ultraviolet light having a wavelength of 365 nm at 6 J/cm$^2$ was performed, and heat treatment at 80° C. for one hour was performed. Through the above steps, the light-emitting element 143 to the light-emitting element 145 were obtained.

<<Fabrication of Light-Emitting Element 146 to Light-Emitting Element 149>>

A light-emitting element 146 to a light-emitting element 149 are different from the above-described light-emitting element 143 to light-emitting element 145 only in the component of the light-emitting layer 130, and other steps of the fabrication method are the same as those for the light-emitting element 1. The details of the element structures are shown in Table 35 and Table 36; thus, the details of the fabrication methods are omitted.

The guest material used for the comparative light-emitting element 146 to the comparative light-emitting element 148 does not have protecting groups. The light-emitting layer 130 of the comparative light-emitting element 149 contains 4,6mCzP2Pm and 3Cz2DPhCzBN. Therefore, as described later, from the comparative the light-emitting element 149, light emission originating from 3Cz2DPhCzBN, which serves as an energy donor in the light-emitting element 143 to the light-emitting element 145 and the comparative light-emitting element 146 to the comparative light-emitting element 148, is obtained. In addition, the light-emitting element 143 to the light-emitting element 145 and the comparative light-emitting element 146 to the comparative light-emitting element 148 can be regarded as light-emitting elements obtained by adding a guest material to the comparative light-emitting element 149.

<Characteristics of Light-Emitting Elements>

Next, the characteristics of the fabricated light-emitting element 143 to light-emitting element 145 and comparative light-emitting element 146 to comparative light-emitting element 149 were measured. The measurement was performed in a manner similar to that in Example 6.

FIG. 182 shows the external quantum efficiency-luminance characteristics of the light-emitting element 143 to the light-emitting element 145 and the comparative light-emitting element 146 to the comparative light-emitting element 149. FIG. 183 and FIG. 184 show the electroluminescence spectra of the light-emitting element 143 to the light-emitting element 145 and the comparative light-emitting element 146 to the comparative light-emitting element 149 to which a current at a current density of 2.5 mA/cm$^2$ was supplied. Note that the measurement of the light-emitting elements was performed at room temperature (in an atmosphere maintained at 23° C.).

Table 37 shows the element characteristics of the light-emitting element 143 to the light-emitting element 145 and the comparative light-emitting element 146 to the comparative light-emitting element 149 at around 1000 cd/m².

TABLE 37

|  | Voltage (V) | Current density (mA/cm²) | CIE chromaticity (x, y) | Luminance (cd/m²) | Current efficiency (cd/A) | Power efficiency (lm/W) | External quantum efficiency (%) |
|---|---|---|---|---|---|---|---|
| Light-emitting element 143 | 4.40 | 1.41 | (0.257, 0.645) | 1086 | 77.2 | 55.2 | 21.4 |
| Light-emitting element 144 | 4.60 | 1.58 | (0.276, 0.663) | 1148 | 72.8 | 49.7 | 19.2 |
| Light-emitting element 145 | 5.00 | 1.80 | (0.287, 0.683) | 857 | 47.7 | 30.0 | 12.0 |
| Comparative light-emitting element 146 | 4.00 | 1.78 | (0.264, 0.648) | 938 | 52.8 | 41.5 | 14.3 |
| Comparative light-emitting element 147 | 4.20 | 2.32 | (0.284, 0.672) | 852 | 36.6 | 27.4 | 9.4 |
| Comparative light-emitting element 148 | 4.60 | 4.85 | (0.300, 0.670) | 975 | 20.1 | 13.7 | 5.1 |
| Comparative light-emitting element 149 | 3.80 | 1.35 | (0.224, 0.521) | 853 | 63.2 | 52.2 | 22.5 |

As shown in FIG. 183, the emission spectra of the light-emitting element 143 to the light-emitting element 145 had a peak wavelength at approximately 527 nm and a full width at half maximum of approximately 31 nm, i.e., exhibited green light emission originating from Oct-tBuDPQd. As shown in FIG. 184, the emission spectra of the light-emitting element 146 to the light-emitting element 148 had a peak wavelength at approximately 527 nm and a full width at half maximum of approximately 25 nm, i.e., exhibited green light emission originating from DPQd. Light emission different from that of the comparative light-emitting element 149 was observed from all of the light-emitting elements. As shown in FIG. 183 and FIG. 184, the emission spectrum of the comparative light-emitting element 149 had a peak wavelength at 501 nm and a full width at half maximum of 79 nm, i.e., exhibited green light emission originating from 3Cz2DPhCzBN.

Accordingly, light emission originating from the fluorescent materials in the light-emitting elements was obtained from the light-emitting element 143 to the light-emitting element 145 and the comparative light-emitting element 146 to the comparative light-emitting element 148. Thus, the excitation energy of each light-emitting element is found to be transferred to the fluorescent material that is the guest material of each light-emitting element. This indicates that both singlet excitation energy and triplet excitation energy that are generated in the light-emitting layer are transferred to the fluorescent material through 3Cz2DPhCzBN, which is a TADF material.

Although the light-emitting element 143 to the light-emitting element 145 exhibit light emission originating from the fluorescent materials, a high external quantum efficiency exceeding 10% was exhibited as shown in FIG. 182 and Table 37. This value exceeds the maximum value of the external quantum efficiency of the fluorescent element. This result indicates that in the light-emitting element of one embodiment of the present invention, non-radiative decay of triplet excitons is inhibited, contributing to efficient conversion into light emission. Thus, it was found that the use of a guest material (energy acceptor) having protecting groups in a light-emitting layer can inhibit energy transfer of triplet excitation energy from an energy donor to a guest material by the Dexter mechanism and non-radiative decay of triplet excitation energy.

Note that FIG. 185 shows the relation between the EL (emission) spectrum of the comparative light-emitting element 149 and the absorption spectrum and the emission spectrum of Oct-tBuDPQd in a toluene solution, which was used for the light-emitting element 143 to the light-emitting element 145. According to FIG. 185, it is found that an absorption band on the longest wavelength side of the absorption spectrum and the emission spectrum of the comparative light-emitting element 149 overlap with each other. This indicates that energy transfer from 3Cz2DPhCzBN to Oct-tBuDPQd by the Förster mechanism occurs. The peak wavelength of the emission spectrum of the comparative light-emitting element 149 is 501 nm, and the peak wavelength of the emission spectrum of Oct-tBuDPQd in a toluene solution is 527 nm. Thus, a combination of an energy donor and an energy acceptor that have emission colors close to each other can be favorably used in the light-emitting element of one embodiment of the present invention.

<Change in External Quantum Efficiency Depending on Guest Material Concentration>

FIG. 186 shows the relation between the guest material concentration and external quantum efficiency of each guest material. It is found from FIG. 186 that a decrease in efficiency due to an increase in the concentration is inhibited in the light-emitting element 143 to the light-emitting element 145 of embodiments of the present invention each using the guest material having protecting groups. In contrast, the efficiency of the comparative light-emitting element 146 to the comparative light-emitting element 148 each using the guest material having no protecting group significantly decreases due to an increase in the concentration. Therefore, in the light-emitting element of one embodiment of the present invention, as described above, even when the guest material concentration is increased, energy transfer of triplet excitation energy from an energy donor to the guest material by the Dexter mechanism can be inhibited and deactivation of the triplet excitation energy can be inhibited; thus, a light-emitting element with high emission efficiency can be obtained. In addition, it was found that a TADF material can be also favorably used as an energy donor.

Reference Example

In this reference example, fabrication examples and the characteristics of light-emitting elements, in each of which any of the guest materials used in Example 6 and Example 7 is dispersed in a host material not having a function of converting triplet excitation energy into light emission, that is, general fluorescent elements using the guest materials, are described. The structure of each of the light-emitting elements fabricated in this reference example is the same as that in FIG. 1(A). Table 38 to Table 40 show the details of the element structures. The structures and abbreviations of compounds that were used are shown below. Note that the above examples and embodiments can be referred to for other organic compounds.

[Chemical Formula 83]

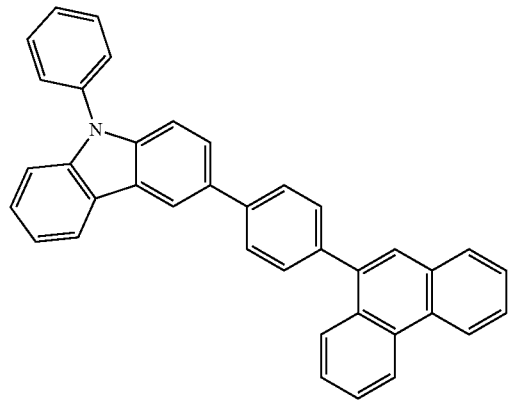

PCPPn

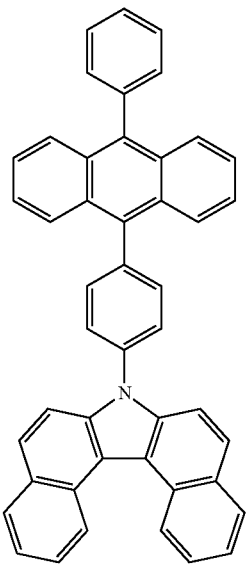

cgDBCzPA

TABLE 38

| | Layer | Reference numeral | Thickness (nm) | Material | Weight ratio |
|---|---|---|---|---|---|
| Reference light-emitting elements 47 to 50 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | cgDBCzPA | — |
| | Light-emitting layer | 130 | 40 | cgDBCzPA:2tBu-ptBuDPhA2Anth | 1:$x_3$ |
| | Hole-transport layer | 112 | 20 | PCPPn | — |
| | Hole-injection layer | 111 | 40 | DBT3P-II:MoO$_3$ | 1:0.5 |
| | Anode | 101 | 70 | ITSO | — |
| Reference light-emitting elements 51 to 54 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | cgDBCzPA | — |
| | Light-emitting layer | 130 | 40 | cgDBCzPA:2tBu-mmtBuDPhA2Anth | 1:$x_3$ |
| | Hole-transport layer | 112 | 20 | PCPPn | — |

TABLE 38-continued

|  | Layer | Reference numeral | Thickness (nm) | Material | Weight ratio |
|---|---|---|---|---|---|
| | Hole-injection layer | 111 | 40 | DBT3P-II:MoO$_3$ | 1:0.5 |
| | Anode | 101 | 70 | ITSO | — |
| Reference light-emitting elements 55 to 58 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | cgDBCzPA | — |
| | Light-emitting layer | 130 | 40 | cgDBCzPA:2,6tBu-ptBuDPhA2Anth | 1:x$_3$ |
| | Hole-transport layer | 112 | 20 | PCPPn | — |
| | Hole-injection layer | 111 | 40 | DBT3P-II:MoO$_3$ | 1:0.5 |
| | Anode | 101 | 70 | ITSO | — |
| Reference light-emitting elements 59 to 62 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | cgDBCzPA | — |
| | Light-emitting layer | 130 | 40 | cgDBCzPA:2,6tBu-mmtBuDPhA2Anth | 1:x$_3$ |
| | Hole-transport layer | 112 | 20 | PCPPn | — |
| | Hole-injection layer | 111 | 40 | DBT3P-II:MoO$_3$ | 1:0.5 |
| | Anode | 101 | 70 | ITSO | — |

TABLE 39

|  | Layer | Reference numeral | Thickness (nm) | Material | Weight ratio |
|---|---|---|---|---|---|
| Reference light-emitting elements 63 to 66 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | cgDBCzPA | — |
| | Light-emitting layer | 130 | 40 | cgDBCzPA:TTPA | 1:x$_3$ |
| | Hole-transport layer | 112 | 20 | PCPPn | — |
| | Hole-injection layer | 111 | 40 | DBT3P-II:MoO$_3$ | 1:0.5 |
| | Anode | 101 | 70 | ITSO | — |
| Reference light-emitting elements 67 to 70 | Electrode | 102 | 200 | Al | — |
| | Electron-injection layer | 119 | 1 | LiF | — |
| | Electron-transport layer | 118(2) | 10 | NBPhen | — |
| | | 118(1) | 20 | cgDBCzPA | — |
| | Light-emitting layer | 130 | 40 | cgDBCzPA:MeDPhA2Anth | 1:x$_3$ |
| | Hole-transport layer | 112 | 20 | PCPPn | — |

TABLE 39-continued

|  | Layer | Reference numeral | Thickness (nm) | Material | Weight ratio |
|---|---|---|---|---|---|
| | Hole-injection layer | 111 | 40 | DBT3P-II:MoO$_3$ | 1:0.5 |
| | Anode | 101 | 70 | ITSO | — |
| Reference light-emitting elements 70 to 74 | Electrode | 102 | 200 | Al | — |
| | Electron-injection layer | 119 | 1 | LiF | — |
| | Electron-transport layer | 118(2) 118(1) | 10 20 | NBPhen cgDBCzPA | — — |
| | Light-emitting layer | 130 | 40 | cgDBCzPA:mMeDPhA2Anth | 1:x$_3$ |
| | Hole-transport layer | 112 | 20 | PCPPn | — |
| | Hole-injection layer | 111 | 40 | DBT3P-II:MoO$_3$ | 1:0.5 |
| | Anode | 101 | 70 | ITSO | — |

TABLE 40

| | Reference light-emitting elements 47, 51, 55, 59, 63, 67, and 71 | Reference light-emitting elements 48, 52, 56, 60, 64, 68, and 72 | Reference light-emitting elements 49, 53, 57, 61, 65, 69, and 73 | Reference light-emitting elements 50, 54, 58, 62, 66, 70, and 74 |
|---|---|---|---|---|
| x$_3$ | 0.01 | 0.025 | 0.05 | 0.1 |

<Fabrication of Reference Light-Emitting Elements>

Fabrication methods of reference light-emitting elements fabricated in this reference example will be described below.

<<Fabrication of Reference Light-Emitting Element 47 to Reference Light-Emitting Element 50>>

As the electrode 101, an ITSO film was formed to a thickness of 70 nm over a glass substrate. Note that the electrode area of the electrode 101 was set to 4 mm$^2$ (2 mm×2 mm).

Next, as the hole-injection layer 111, DBT3P-II and molybdenum oxide (MoO$_3$) were deposited over the electrode 101 by co-evaporation in a weight ratio (DBT3P-II:MoO$_3$) of 1:0.5 to a thickness of 40 nm.

Then, as the hole-transport layer 112, PCPPn was deposited on the hole-injection layer 111 by evaporation to a thickness of 20 nm.

Next, as the light-emitting layer 130, 7-[4-(10-phenyl-9-anthryl)phenyl]-7H-dibenzo[c,g]carbazole (abbreviation: cgDBCzPA) and 2tBu-ptBuDPhA2Anth were deposited over the hole-transport layer 112 by co-evaporation at a weight ratio (cgDBCzPA:2tBu-ptBuDPhA2Anth) of 1:x$_3$ to a thickness of 40 nm. Note that the value x$_3$ differs between the light-emitting elements, and Table 39 shows the value x$_3$ in each of the light-emitting elements.

Next, as the electron-transport layer 118, cgDBCzPA and NBPhen were sequentially deposited by evaporation to a thickness of 20 nm and to a thickness of 10 nm, respectively, over the light-emitting layer 130. Then, as the electron-injection layer 119, LiF was deposited on the electron-transport layer 118 by evaporation to a thickness of 1 nm.

Next, as the electrode 102, aluminum (Al) was formed over the electron-injection layer 119 to a thickness of 200 nm.

Next, in a glove box containing a nitrogen atmosphere, a reference light-emitting element 47 to a reference light-emitting element 50 were sealed by fixing a glass substrate for sealing to the glass substrate on which the organic materials were formed using a sealant for organic EL. Specifically, the sealant was applied to the periphery of the organic materials formed on the glass substrate, the glass substrate was bonded to the glass substrate for sealing, irradiation with ultraviolet light having a wavelength of 365 nm at 6 J/cm$^2$ was performed, and heat treatment at 80° C. for one hour was performed. Through the above steps, the reference light-emitting element 47 to the reference light-emitting element 50 were obtained.

<<Fabrication of Reference Light-Emitting Element 51 to Reference Light-Emitting Element 74>>

A reference light-emitting element 51 to a reference light-emitting element 74 are different from the fabrication method of the above-described reference light-emitting element 47 to reference light-emitting element 50 only in a fluorescent material (guest material) used for the light-emitting layer 130, and other steps of the fabrication method are the same as those for the reference light-emitting element 47 to the reference light-emitting element 50. The details of the element structures are shown in Table 14 to Table 16; thus, the details of the fabrication methods are omitted. Note that the guest materials used for the reference light-emitting element 47 to the reference light-emitting element 62 are the guest materials used for the light-emitting elements of embodiments of the present invention, and the guest materials used for the reference light-emitting element 63 to the reference light-emitting element 74 are the guest materials used for the comparative light-emitting elements.

<Characteristics of Light-Emitting Elements>

Next, the characteristics of the fabricated reference light-emitting element 47 to reference light-emitting element 74 were measured. Note that the measurement method is similar to that in Example 6.

Table 41 and Table 42 show the element characteristics of the reference light-emitting element 47 to the reference light-emitting element 74 at around 1000 cd/m$^2$.

TABLE 41

| | Voltage (V) | Current density (mA/cm²) | CIE chromaticity (x, y) | Luminance (cd/m²) | Current efficiency (cd/A) | Power efficiency (lm/W) | External quantum efficiency (%) |
|---|---|---|---|---|---|---|---|
| Reference light-emitting element 47 | 2.90 | 2.47 | (0.304, 0.632) | 900 | 36.5 | 39.5 | 9.7 |
| Reference light-emitting element 48 | 2.90 | 2.43 | (0.318, 0.646) | 956 | 39.3 | 42.6 | 10.2 |
| Reference light-emitting element 49 | 2.90 | 2.53 | (0.325, 0.647) | 1017 | 40.2 | 43.6 | 10.4 |
| Reference light-emitting element 50 | 2.90 | 2.55 | (0.331, 0.646) | 1012 | 39.7 | 43.0 | 10.2 |
| Reference light-emitting element 51 | 2.90 | 2.40 | (0.255, 0.619) | 787 | 32.7 | 35.5 | 9.5 |
| Reference light-emitting element 52 | 2.90 | 2.17 | (0.271, 0.652) | 803 | 37.1 | 40.1 | 10.2 |
| Reference light-emitting element 53 | 2.90 | 1.95 | (0.279, 0.662) | 760 | 38.9 | 42.1 | 10.5 |
| Reference light-emitting element 54 | 3.00 | 3.43 | (0.285, 0.669) | 1358 | 39.6 | 41.5 | 10.5 |
| Reference light-emitting element 55 | 2.90 | 2.09 | (0.284, 0.648) | 719 | 34.3 | 37.2 | 9.3 |
| Reference light-emitting element 56 | 2.90 | 1.89 | (0.298, 0.659) | 689 | 36.6 | 39.6 | 9.6 |
| Reference light-emitting element 57 | 3.00 | 3.58 | (0.306, 0.659) | 1344 | 37.6 | 39.3 | 9.8 |
| Reference light-emitting element 58 | 3.00 | 2.79 | (0.310, 0.659) | 1042 | 37.3 | 39.1 | 9.7 |
| Reference light-emitting element 59 | 2.90 | 2.07 | (0.258, 0.639) | 683 | 33.0 | 35.7 | 9.4 |
| Reference light-emitting element 60 | 2.90 | 1.71 | (0.270, 0.656) | 608 | 35.5 | 38.5 | 9.8 |
| Reference light-emitting element 61 | 3.00 | 2.83 | (0.276, 0.664) | 1055 | 37.3 | 39.0 | 10.1 |
| Reference light-emitting element 62 | 3.10 | 3.59 | (0.284, 0.665) | 1307 | 36.4 | 36.9 | 9.7 |

TABLE 42

| | Voltage (V) | Current density (mA/cm²) | CIE chromaticity (x, y) | Luminance (cd/m²) | Current efficiency (cd/A) | Power efficiency (lm/W) | External quantum efficiency (%) |
|---|---|---|---|---|---|---|---|
| Reference light-emitting element 63 | 2.95 | 3.22 | (0.342, 0.620) | 1104 | 34.2 | 36.5 | 8.9 |
| Reference light-emitting element 64 | 2.95 | 2.90 | (0.358, 0.624) | 1033 | 35.6 | 38.0 | 9.1 |
| Reference light-emitting element 65 | 2.95 | 2.59 | (0.371, 0.615) | 940 | 36.2 | 38.6 | 9.3 |
| Reference light-emitting element 66 | 3.00 | 3.17 | (0.376, 0.616) | 1131 | 35.7 | 37.4 | 9.2 |
| Reference light-emitting element 67 | 2.95 | 3.68 | (0.292, 0.612) | 1059 | 28.8 | 30.7 | 8.0 |
| Reference light-emitting element 68 | 2.95 | 3.30 | (0.316, 0.635) | 1043 | 31.6 | 33.6 | 8.4 |

TABLE 42-continued

|  | Voltage (V) | Current density (mA/cm²) | CIE chromaticity (x, y) | Luminance (cd/m²) | Current efficiency (cd/A) | Power efficiency (lm/W) | External quantum efficiency (%) |
|---|---|---|---|---|---|---|---|
| Reference light-emitting element 69 | 2.95 | 3.01 | (0.330, 0.640) | 981 | 32.6 | 34.7 | 8.6 |
| Reference light-emitting element 70 | 2.95 | 2.82 | (0.341, 0.634) | 912 | 32.4 | 34.5 | 8.5 |
| Reference light-emitting element 71 | 2.95 | 4.22 | (0.252, 0.583) | 1069 | 25.3 | 27.0 | 7.7 |
| Reference light-emitting element 72 | 2.95 | 4.11 | (0.271, 0.630) | 1190 | 28.9 | 30.8 | 8.2 |
| Reference light-emitting element 73 | 2.90 | 2.21 | (0.287, 0.640) | 666 | 30.2 | 32.7 | 8.3 |
| Reference light-emitting element 74 | 2.90 | 2.14 | (0.298, 0.647) | 667 | 31.2 | 33.9 | 8.4 |

Although the emission spectra obtained from the reference light-emitting element 47 to the reference light-emitting element 74 are not particularly shown, the chromaticities in Table 41 and Table 42 show that light emission originating from the guest materials contained in the light-emitting elements are obtained from the light-emitting elements.

Figure 68:
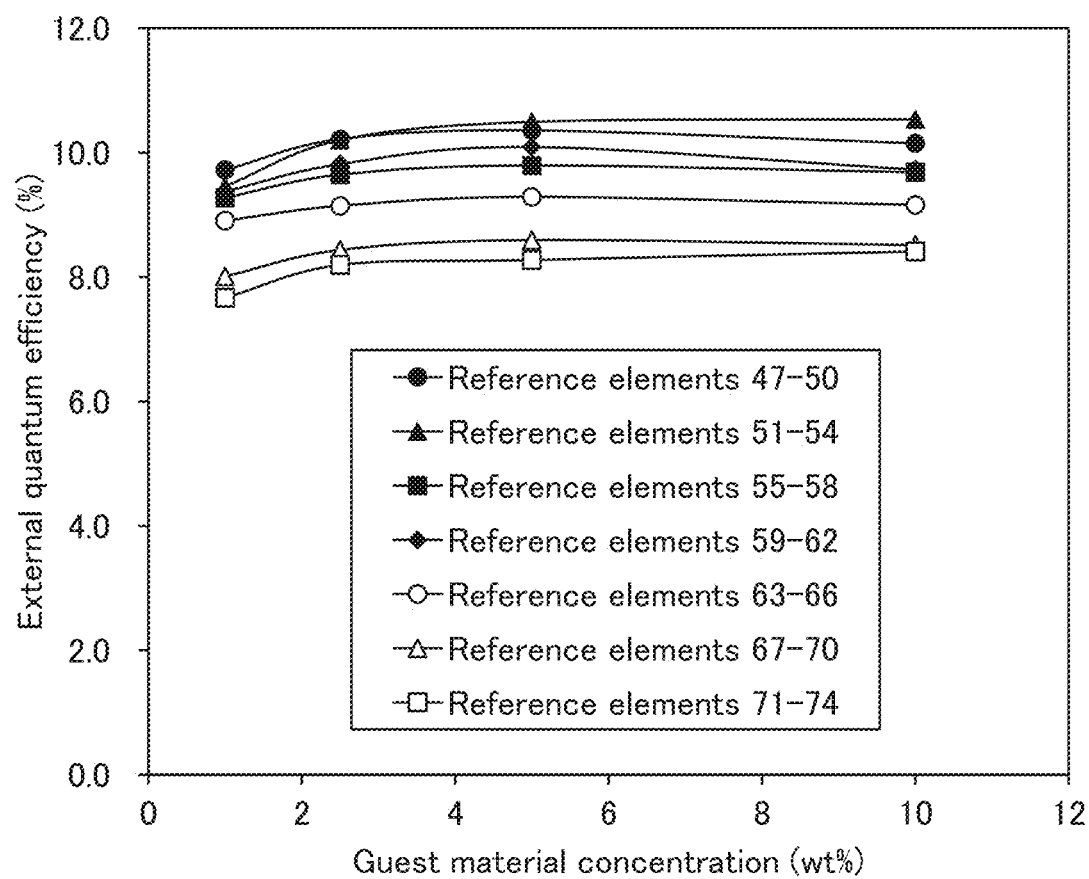
FIG. 68 A diagram showing the relation between external quantum efficiency and guest material concentration in Reference example.

FIG. 68 shows the relation between the guest material concentration and external quantum efficiency of each guest material. FIG. 68 indicates that external quantum efficiency obtained from each of the reference light-emitting element 47 to the reference light-emitting element 74 does not change even when the concentration of each guest material is changed. That is, it was found that the guest material used for the light-emitting element of one embodiment of the present invention does not cause concentration quenching in a concentration range from 1 wt % to 10 wt % when added to a host material not having a function of converting triplet excitation energy into light emission. Accordingly, as shown in FIG. 44, it can be said that a change in the external quantum efficiency due to a change in the guest material concentration in the case where the guest material having no protecting group is added to the host material having a function of converting triplet excitation energy into light emission is caused not by concentration quenching but by non-radiative decay of triplet excitation energy due to energy transfer of triplet excitons in the light-emitting layer by the Dexter mechanism from the host material to the guest material. In contrast, as described above, the light-emitting element of one embodiment of the present invention exhibits a high external quantum efficiency when the guest material having protecting groups is added to the host material having a function of converting triplet excitation energy into light emission. The results suggest that in the light-emitting element of one embodiment of the present invention, energy transfer of triplet excitation energy based on the Dexter mechanism from the host material to the guest material is inhibited and non-radiative decay of triplet excitation energy can be inhibited. Accordingly, in the light-emitting element of one embodiment of the present invention, energy transfer by the Dexter mechanism can be inhibited, so that the rate of energy transfer by the Förster mechanism can be increased by increasing the guest material concentration and both of triplet excitation energy and singlet excitation energy can be converted into light emission, whereby a light-emitting element with high emission efficiency can be obtained.

Note that in the reference light-emitting element, the external quantum efficiency exceeds 7.5% which is the theoretical limit of a fluorescent element. This is caused by TTA (triplet-triplet annihilation) in the light-emitting layer.

REFERENCE NUMERALS

100: EL layer, 101: electrode, 102: electrode, 106: light-emitting unit, 108: light-emitting unit, 111: hole-injection layer, 112: hole-transport layer, 113: electron-transport layer, 114: electron-injection layer, 115: charge-generation layer, 116: hole-injection layer, 117: hole-transport layer, 118: electron-transport layer, 119: electron-injection layer, 120: light-emitting layer, 130: light-emitting layer, 131: compound, 132: compound, 133: compound, 134: compound, 135: compound, 150: light-emitting element, 170: light-emitting layer, 250: light-emitting element, 301: guest material, 302: guest material, 310: luminophore, 320: protecting group, 330: host material, 601: source side driver circuit, 602: pixel portion, 603: gate side driver circuit, 604: sealing substrate, 605: sealant, 607: space, 608: wiring, 609: FPC, 610: element substrate, 611: switching TFT, 612: current controlling TFT, 613: electrode, 614: insulator, 616: EL layer, 617: electrode, 618: light-emitting element, 623: n-channel TFT, 624: p-channel TFT, 625: desiccant, 900: portable information terminal, 901: housing, 902: housing, 903: display portion, 905: hinge portion, 910: portable information terminal, 911: housing, 912: display portion, 913: operation button, 914: external connection port, 915: speaker, 916: microphone, 917: camera, 920: camera, 921: housing, 922: display portion, 923: operation button, 924: shutter button, 926: lens, 1001: substrate, 1002: base insulating film, 1003: gate insulating film, 1006: gate electrode, 1007: gate electrode, 1008: gate electrode, 1020: interlayer insulating film, 1021: interlayer insulating film, 1022: electrode, 1024B: electrode, 1024G: electrode, 1024R: electrode, 1024W: electrode, 1025B: lower electrode, 1025G: lower electrode, 1025R: lower electrode, 1025W: lower electrode, 1026: partition wall, 1028: EL layer, 1029: electrode, 1031: sealing substrate, 1032: sealant, 1033: base material, 1034B: coloring layer, 1034G: coloring layer, 1034R: coloring layer, 1036: overcoat layer, 1037: interlayer insulating film, 1040: pixel portion, 1041: driver circuit portion, 1042: peripheral portion, 1044B: blue pixel, 1044G: green pixel, 1044R: red pixel, 1044W: white pixel, 2100: robot, 2101: illuminance sensor, 2102: microphone, 2103: upper camera, 2104: speaker, 2105: display, 2106: lower camera, 2107: obstacle sensor, 2108: moving mechanism, 2110: arithmetic device, 5000: housing, 5001: display portion, 5002: display portion, 5003: speaker, 5004: LED lamp, 5005: operation key, 5006: connection terminal, 5007: sensor, 5008: microphone, 5012: support, 5013: earphone, 5100: cleaning robot, 5101: display, 5102: camera, 5103: brush, 5104: operation button, 5120: dust, 5140: portable electronic device, 5150: portable information terminal, 5151: housing, 5152: display region, 5153: bend portion, 8501: lighting device, 8502: lighting device, 8503: lighting device, 8504: lighting device

The invention claimed is:

1. A light-emitting element comprising:
a light-emitting layer between a pair of electrodes, the light-emitting layer comprising:
  a first material capable of converting triplet excitation energy into light emission; and
  a second material capable of converting singlet excitation energy into light emission,
  wherein the second material comprises a luminophore and five or more protecting groups,
  wherein the luminophore is a condensed aromatic ring or a condensed heteroaromatic ring,
  wherein each of the five or more protecting groups independently comprises any one of an alkyl group having 1 to 10 carbon atoms, a substituted or unsubstituted cycloalkyl group having 3 to 10 carbon atoms, and a trialkylsilyl group having 3 to 12 carbon atoms,
  wherein light emission is obtained from the second material,
  wherein an emission spectrum of the first material overlaps with an absorption band on the longest wavelength side of an absorption spectrum of the second material, and
  wherein a T1 level of the second material is lower than a T1 level of the first material.

2. The light-emitting element according to claim 1, wherein at least four of the five protecting groups are each independently any one of an alkyl group having 3 to 10 carbon atoms, a substituted or unsubstituted cycloalkyl group having 3 to 10 carbon atoms, and a trialkylsilyl group having 3 to 12 carbon atoms.

3. The light-emitting element according to claim 1, wherein the condensed aromatic ring or the condensed heteroaromatic ring comprises any one of naphthalene, anthracene, fluorene, chrysene, triphenylene, tetracene, pyrene, perylene, coumarin, quinacridone, and naphthobisbenzofuran.

4. The light-emitting element according to claim 1,
wherein the first material comprises a first organic compound and a second organic compound, and
wherein the first organic compound and the second organic compound form an exciplex.

5. The light-emitting element according to claim 1, wherein the first material comprises a compound emitting phosphorescence.

6. The light-emitting element according to claim 1, wherein the first material comprises a compound emitting thermally activated delayed fluorescence.

7. The light-emitting element according to claim 1, wherein concentration of the second material in the light-emitting layer is higher than or equal to 2 wt % and lower than or equal to 30 wt %.

8. A light-emitting apparatus comprising:
the light-emitting element according to claim 1; and
at least one of a color filter and a transistor.

9. An electronic device comprising:
the light-emitting apparatus according to claim 8; and
at least one of a housing and a display portion.

10. A lighting device comprising:
the light-emitting element according to claim 1; and
a housing.

11. A light-emitting element comprising:
a light-emitting layer between a pair of electrodes, the light-emitting layer comprising:
  a first material capable of converting triplet excitation energy into light emission; and
  a second material capable of converting singlet excitation energy into light emission,
  wherein the second material comprises a luminophore and a first protecting group, a second protecting group, a third protecting group and a fourth protecting group,
  wherein the luminophore is a condensed aromatic ring or a condensed heteroaromatic ring,
  wherein each of the first protecting group, the second protecting group, the third protecting group and the fourth protecting group is not directly bonded to the condensed aromatic ring or the condensed heteroaromatic ring,
  wherein each of the first protecting group, the second protecting group, the third protecting group and the fourth protecting group independently comprises any one of an alkyl group having 3 to 10 carbon atoms, a substituted or unsubstituted cycloalkyl group having 3 to 10 carbon atoms, and a trialkylsilyl group having 3 to 12 carbon atoms,
  wherein light emission is obtained from the second material,
  wherein an emission spectrum of the first material overlaps with an absorption band on the longest wavelength side of an absorption spectrum of the second material, and
  wherein a T1 level of the second material is lower than a T1 level of the first material.

12. The light-emitting element according to claim 11,
wherein the second material comprises a first diarylamino group and a second diarylamino group,
wherein the first diarylamino group has a first aryl group and a second aryl group,
wherein the first aryl group is substituted with the first protecting group,
wherein the second aryl group is substituted with the second protecting group,
wherein the second diarylamino group has a third aryl group and a fourth aryl group,
wherein the third aryl group is substituted with the third protecting group, and
wherein the fourth aryl group is substituted with the fourth protecting group.

13. The light-emitting element according to claim 12,
wherein each of the first aryl group, the second aryl group, the third aryl group and the fourth aryl group is independently further substituted with a fifth protecting group comprising any one of an alkyl group having 3 to 10 carbon atoms, a substituted or unsubstituted cycloalkyl group having 3 to 10 carbon atoms, and a trialkylsilyl group having 3 to 12 carbon atoms.

14. The light-emitting element according to claim 11, wherein the condensed aromatic ring or the condensed heteroaromatic ring comprises any one of naphthalene, anthracene, fluorene, chrysene, triphenylene, tetracene, pyrene, perylene, coumarin, quinacridone and naphthobisbenzofuran.

15. The light-emitting element according to claim 11,
wherein the first material comprises a first organic compound and a second organic compound, and
wherein the first organic compound and the second organic compound form an exciplex.

16. The light-emitting element according to claim 11, wherein the first material comprises a compound emitting phosphorescence.

17. The light-emitting element according to claim 11, wherein the first material comprises a compound emitting thermally activated delayed fluorescence.

18. The light-emitting element according to claim 11, wherein concentration of the second material in the light-emitting layer is higher than or equal to 2 wt % and lower than or equal to 30 wt %.

19. A light-emitting apparatus comprising:
the light-emitting element according to claim 11; and
at least one of a color filter and a transistor.

20. An electronic device comprising:
the light-emitting apparatus according to claim 19; and
at least one of a housing and a display portion.

21. A lighting device comprising:
the light-emitting element according to claim 11; and
a housing.

22. A light-emitting element comprising:
a light-emitting layer between a pair of electrodes, the light-emitting layer comprising:
a first material capable of converting triplet excitation energy into light emission; and
a second material capable of converting singlet excitation energy into light emission,
wherein the second material comprises a luminophore and five or more protecting groups,
wherein the luminophore is a condensed aromatic ring or a condensed heteroaromatic ring,
wherein each of the five or more protecting groups independently comprises any one of an alkyl group having 1 to 10 carbon atoms, a substituted or unsubstituted cycloalkyl group having 3 to 10 carbon atoms, and a trialkylsilyl group having 3 to 12 carbon atoms,
wherein light emission is obtained from the second material,
wherein the first material comprises a compound emitting phosphorescence, and
wherein a T1 level of the second material is lower than a T1 level of the first material.

23. The light-emitting element according to claim 22,
wherein at least four of the five protecting groups are each independently any one of an alkyl group having 3 to 10 carbon atoms, a substituted or unsubstituted cycloalkyl group having 3 to 10 carbon atoms, and a trialkylsilyl group having 3 to 12 carbon atoms.

24. The light-emitting element according to claim 22, wherein the condensed aromatic ring or the condensed heteroaromatic ring comprises any one of naphthalene, anthracene, fluorene, chrysene, triphenylene, tetracene, pyrene, perylene, coumarin, quinacridone, and naphthobisbenzofuran.

25. The light-emitting element according to claim 22,
wherein the first material comprises a first organic compound and the compound emitting phosphorescence, and
wherein the first organic compound and the compound emitting phosphorescence form an exciplex.

26. The light-emitting element according to claim 22, wherein an emission spectrum of the first material overlaps with an absorption band on the longest wavelength side of an absorption spectrum of the second material.

27. The light-emitting element according to claim 22, wherein concentration of the second material in the light-emitting layer is higher than or equal to 2 wt % and lower than or equal to 30 wt %.

28. A light-emitting apparatus comprising:
the light-emitting element according to claim 22; and
at least one of a color filter and a transistor.

29. An electronic device comprising:
the light-emitting apparatus according to claim 28; and
at least one of a housing and a display portion.

30. A lighting device comprising:
the light-emitting element according to claim 22; and
a housing.

* * * * *